(12) United States Patent
Allen et al.

(10) Patent No.: US 8,497,265 B2
(45) Date of Patent: Jul. 30, 2013

(54) HETEROARYLOXYHETEROCYCLYL COMPOUNDS AS PDE10 INHIBITORS

(75) Inventors: Jennifer R. Allen, Newbury Park, CA (US); Daniel B. Horne, Simi Valley, CA (US); Essa Hu Harrington, Camarillo, CA (US); Matthew R. Kaller, Ventura, CA (US); Holger Monenschein, Jupiter, FL (US); Thomas T. Nguyen, Newbury Park, CA (US); Andreas Reichelt, Moorpark, CA (US); Robert M. Rzasa, Ventura, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 13/106,718

(22) Filed: May 12, 2011

(65) Prior Publication Data

US 2011/0306588 A1 Dec. 15, 2011

Related U.S. Application Data

(60) Provisional application No. 61/334,520, filed on May 13, 2010.

(51) Int. Cl.
| | |
|---|---|
| C07D 241/18 | (2006.01) |
| C07D 413/14 | (2006.01) |
| C07D 401/14 | (2006.01) |
| A61K 31/5355 | (2006.01) |
| A61K 31/497 | (2006.01) |
| A61P 3/04 | (2006.01) |
| A61P 3/10 | (2006.01) |
| A61P 25/18 | (2006.01) |

(52) U.S. Cl.
USPC .............. 514/235.2; 514/252.11; 514/255.05; 544/357; 544/120; 544/405

(58) Field of Classification Search
USPC ..................... 544/405, 357, 121; 514/255.05, 514/252.11, 235.8
See application file for complete search history.

(56) References Cited

U.S. PATENT DOCUMENTS

| | | | |
|---|---|---|---|
| 4,107,288 A | | 8/1978 | Oppenheim et al. |
| 5,145,684 A | | 9/1992 | Liversidge et al. |
| 2006/0019975 A1 | | 1/2006 | Humphrey et al. |
| 2008/0058339 A1 | * | 3/2008 | Brandt et al. ............ 514/252.03 |
| 2010/0015092 A1 | * | 1/2010 | Nakajima et al. ............ 424/85.6 |
| 2010/0227869 A1 | * | 9/2010 | Peters et al. ............ 514/252.04 |
| 2010/0305065 A1 | * | 12/2010 | Beswick et al. ................ 514/62 |
| 2010/0305133 A1 | * | 12/2010 | Colon et al. ................. 514/249 |
| 2010/0317607 A1 | * | 12/2010 | Wynne et al. .................... 514/40 |
| 2011/0183998 A1 | * | 7/2011 | Zoller et al. ............. 514/255.06 |
| 2011/0263570 A1 | * | 10/2011 | Neustadt et al. ......... 514/217.06 |
| 2011/0306587 A1 | * | 12/2011 | Allen et al. ............. 514/210.16 |
| 2011/0306590 A1 | | 12/2011 | Allen et al. |
| 2011/0306591 A1 | | 12/2011 | Allen et al. |
| 2012/0010212 A1 | * | 1/2012 | Nettekoven et al. ...... 514/252.03 |

FOREIGN PATENT DOCUMENTS

| | | |
|---|---|---|
| EP | 0 039 051 A2 | 4/1981 |
| WO | WO 97/28128 A1 | 8/1997 |
| WO | WO 2004/099201 A1 | 11/2004 |
| WO | WO 2005/012485 A2 | 10/2005 |
| WO | WO 2008/020302 A2 | 2/2008 |
| WO | WO 2009/007115 A1 | 1/2009 |
| WO | WO 2009/025823 A1 | 2/2009 |

OTHER PUBLICATIONS

Weber, et al., Psychopharmacology (Berl). May 2009; 203(4): 723-735, Published online Dec. 9, 2008.*
Ingole, et al., CRIPS vol. 9 No. 3 Jul.-Sep. 2008.*
Kleiman, Treatment of WT or PDE10 KO mice with a selective PDE10 inhibitor, Manuscript EPub on Oct. 5, 2010, http://www.nextbio.com/b/study/ov.nb?id=40612.*
Becker, et al., "Phosphodiesterase inhibitors—Are they potential neuroleptic drugs?" Behavioral Brain Research, 186:155-160, (2007).
Berge, et al., "Pharmaceutical Salts", *JPharmaSciences*, 66:1 (1977).
Bundgaard, et al., "A Novel Solution-Stable, Water-Soluble Prodrug Type for Drugs Containing a Hydroxyl or an NH-Acidic Group", *JMedChem*, 32:12, 2503-2507, (1989).
Celen, et al., "Preclinical Evaluation of $^{18}$F-JNJ41510417 as a Radioligand for PET Imaging of Phosphodiesterase-10A in the Brain," J Nuclear Med., 51(10):1584-1591, (2010).
Fujishige, et al., "Cloning and Characterization of a Novel Human Phosphodiesterase That Hydrolyzes Both cAMP and cGMP ((PDE10A)", *Jour Biol Chem*, 274:26, 18438-18445, (1999).
Giedd, et al., "MRI Assessment of Children With Obsessive-Compulsive Disorder or Tics Associated with Streptococcal Infection", *AmJPsych*, 157:281-283, (2000).
Kung, et al., "Structure—Activity Relationships of Novel 2-Substituted Quinazoline Antibacterial Agents," J. Med. Chem., 42:4705-4713, (1999).
Loughney, et al., "Isolation and characterization of PDE10A, a novel human 3', 5'—cyclic nucleotide phosphodiesterase", *Gene*, 234: 109-117, (1999).
Obeso, et al, "The origin of motor fluctuations in Parkinson's disease", Neurology, 62(Suppl 1): S17-S30 (2004).
Saxena, et al., "Neuroimaging and frontal-subcortical circuitry in obsessive-compulsive disorder", *Br. JPsych.* 173(Suppl. 35):26-37, (1998).
Siuciak, et al., "Inhibition of the striatum-enriched phosphodiesterase PDE10A: A novel approach to the treatment of psychosis," Neuropharmacology, 51:386-396, (2006).
Solderling, et al., "Isolation and characterization of a dual-substrate phosphodiesterase gene family: PDE10A", *Proc. Natl. Acad. Sci.*, 96: 7071-7076, (1999).
Svensson, et al., "The Design and Bioactivation of Presystemically Stable Prodrugs", *Drug Metabolism Rev.*, 19(2), 165-194 (1988).

* cited by examiner

*Primary Examiner* — Susanna Moore
*Assistant Examiner* — Cecilia M Jaisle
(74) *Attorney, Agent, or Firm* — Elsa D. Lemoine

(57) ABSTRACT

Heteroaryloxyheterocyclyl compounds, and compositions containing them, and processes for preparing such compounds. Provided herein also are methods of treating disorders or diseases treatable by inhibition of PDE10, such as obesity, non-insulin dependent diabetes, schizophrenia, Huntington's Disease, bipolar disorder, obsessive-compulsive disorder, and the like.

16 Claims, No Drawings

HETEROARYLOXYHETEROCYCLYL COMPOUNDS AS PDE10 INHIBITORS

CROSS-REFERENCE TO RELATED APPLICATIONS

This application claims the benefit of U.S. Provisional Application No. 61/334,520, filed May 13, 2010, which is hereby incorporated by reference.

FIELD OF THE INVENTION

Provided herein are certain heteroaryloxyheterocyclyl compounds that are PDE10 inhibitors, pharmaceutical compositions containing such compounds, and processes for preparing such compounds. Provided herein also are methods of treating disorders or diseases treatable by inhibition of PDE10, such as obesity, non-insulin dependent diabetes, schizophrenia, bipolar disorder, obsessive-compulsive disorder, and the like.

BACKGROUND

Neurotransmitters and hormones, as well as other types of extracellular signals such as light and odors, create intracellular signals by altering the amounts of cyclic nucleotide monophosphates (cAMP and cGMP) within cells. These intracellular messengers alter the functions of many intracellular proteins. Cyclic AMP regulates the activity of cAMP-dependent protein kinase (PKA). PKA phosphorylates and regulates the function of many types of proteins, including ion channels, enzymes, and transcription factors. Downstream mediators of cGMP signaling also include kinases and ion channels. In addition to actions mediated by kinases, cAMP and cGMP bind directly to some cell proteins and directly regulate their activities.

Cyclic nucleotides are produced from the actions of adenylyl cyclase and guanylyl cyclase, which convert ATP to cAMP and GTP to cGMP. Extracellular signals, often through the actions of G protein-coupled receptors, regulate the activities of the cyclases. Alternatively, the amount of cAMP and cGMP may be altered by regulating the activities of the enzymes that degrade cyclic nucleotides. Cell homeostasis is maintained by the rapid degradation of cyclic nucleotides after stimulus-induced increases. The enzymes that degrade cyclic nucleotides are called 3',5'-cyclic nucleotide-specific phosphodiesterases (PDEs).

Eleven PDE gene families (PDE1-PDE11) have been identified based on their distinct amino acid sequences, catalytic and regulatory characteristics, and sensitivity to small molecule inhibitors. These families are coded for by 21 genes; and further multiple splice variants are transcribed from many of these genes. Expression patterns of each of the gene families are distinct. PDEs differ with respect to their affinity for cAMP and cGMP. Activities of different PDEs are regulated by different signals. For example, PDE1 is stimulated by $Ca^{2+}$/calmodulin. PDE2 activity is stimulated by cGMP. PDE3 is inhibited by cGMP. PDE4 is cAMP specific and is specifically inhibited by rolipram. PDE5 is cGMP-specific. PDE6 is expressed in retina.

PDE10 sequences were identified by using bioinformatics and sequence information from other PDE gene families (Fujishige et al., *J. Biol. Chem.* 274:18438-18445, 1999; Loughney et al., *Gene* 234:109-117, 1999; Soderling et al., *Proc. Natl. Acad. Sci. USA* 96:7071-7076, 1999). The PDE10 gene family is distinguished based on its amino acid sequence, functional properties and tissue distribution. The human PDE10 gene is large, over 200 kilobases, with up to 24 exons coding for each of the splice variants. The amino acid sequence is characterized by two GAF domains (which bind cGMP), a catalytic region, and alternatively spliced N and C termini. Numerous splice variants are possible because at least three alternative exons encode N termini and two exons encode C-termini. PDE10A1 is a 779 amino acid protein that hydrolyzes both cAMP and cGMP. The $K_m$ values for cAMP and cGMP are 0.05 and 3.0 micromolar, respectively. In addition to human variants, several variants with high homology have been isolated from both rat and mouse tissues and sequence banks.

PDE10 RNA transcripts were initially detected in human testis and brain. Subsequent immunohistochemical analysis revealed that the highest levels of PDE10 are expressed in the basal ganglia. Specifically, striatal neurons in the olfactory tubercle, caudate nucleus and nucleus accumbens are enriched in PDE10. Western blots did not reveal the expression of PDE10 in other brain tissues, although immunoprecipitation of the PDE10 complex was possible in hippocampal and cortical tissues. This suggests that the expression level of PDE10 in these other tissues is 100-fold less than in striatal neurons. Expression in hippocampus is limited to the cell bodies, whereas PDE10 is expressed in terminals, dendrites and axons of striatal neurons.

The tissue distribution of PDE10 indicates that PDE10 inhibitors can be used to raise levels of cAMP and/or cGMP within cells that express the PDE10 enzyme, for example, in neurons that comprise the basal ganglia and therefore would be useful in treating a variety of neuropsychiatric conditions involving the basal ganglia such as obesity, non-insulin dependent diabetes, schizophrenia, bipolar disorder, obsessive compulsive disorder, and the like.

Noninvasive, nuclear imaging techniques can be used to obtain basic and diagnostic information about the physiology and biochemistry of a variety of living subjects including experimental animals, normal humans and patients. These techniques rely on the use of sophisticated imaging instrumentation that is capable of detecting radiation emitted from radiotracers administered to such living subjects. The information obtained can be reconstructed to provide planar and tomographic images that reveal distribution of the radiotracer as a function of time. Use of appropriately designed radiotracers can result in images which contain information on the structure, function and most importantly, the physiology and biochemistry of the subject. Much of this information cannot be obtained by other means. The radiotracers used in these studies are designed to have defined behaviors in vivo which permit the determination of specific information concerning the physiology or biochemistry of the subject or the effects that various diseases or drugs have on the physiology or biochemistry of the subject. Currently, radiotracers are available for obtaining useful information concerning such things as cardiac function, myocardial blood flow, lung perfusion, liver function, brain blood flow, regional brain glucose and oxygen metabolism.

Compounds of the invention can be labeled with either positron or gamma emitting radionuclides. For imaging, the most commonly used positron emitting (PET) radionuclides are $^{11}C$, $^{18}F$, $^{15}O$, $^{13}N$, $^{76}Br$, $^{77}Br$, $^{123}I$, or $^{125}I$, wherein $^{11}C$, $^{18}F$, $^{123}I$, or $^{125}I$ are preferred, all of which are accelerator produced. In the two decades, one of the most active areas of nuclear medicine research has been the development of receptor imaging radiotracers. These tracers bind with high affinity and specificity to selective receptors and neuroreceptors. For example, Johnson and Johnson has synthesized and evaluated $^{18}F$-JNJ41510417 as a selective and high-affinity radioligand for in vivo brain imaging of PDE10A using PET (The Journal of Nuclear Medicine; Vol. 51; No. 10; October 2010).

SUMMARY OF THE INVENTION

The present invention comprises a new class of heteroaryloxyheterocyclyl compounds useful in the treatment of diseases, such as PDE10-mediated diseases and other maladies, such as schizophrenia, bipolar disorder, or obsessive-compulsive disorder. Accordingly, the invention also comprises pharmaceutical compositions comprising the compounds, methods for the treatment of PDE10-mediated diseases and other maladies, such as schizophrenia, bipolar disorder, or obsessive-compulsive disorder, using the compounds and compositions of the invention, and intermediates and processes useful for the preparation of the compounds of the invention.

The compounds of the invention are represented by the following general structure:

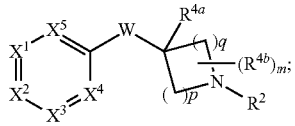

(I)

or a pharmaceutically acceptable salt thereof, wherein W, m, p, q, $R^2$, $R^{4a}$, $R^{4b}$, $X^1$, $X^2$, $X^3$, $X^4$, and $X^5$ are defined below.

Other compounds of the invention are represented by the following general structure:

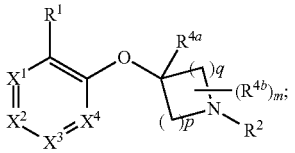

(II)

or a pharmaceutically acceptable salt thereof, wherein m, p, q, $R^1$, $R^2$, $R^{4a}$, $R^{4b}$, $X^1$, $X^2$, $X^3$, and $X^4$ are defined below.

Other compounds of the invention are represented by the following general structure:

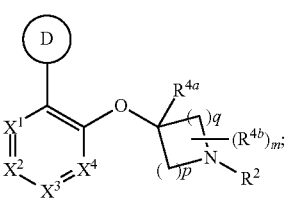

(III)

or a pharmaceutically acceptable salt thereof, wherein m, p, q, Ring D, $R^2$, $R^{4a}$, $R^{4b}$, $X^1$, $X^2$, $X^3$, and $X^4$ are defined below.

Other compounds of the invention are represented by the following general structure:

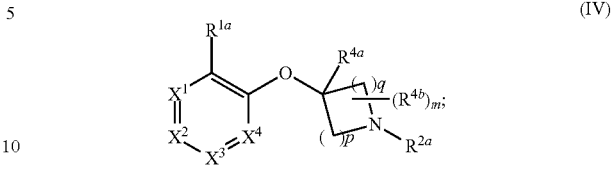

(IV)

or a pharmaceutically acceptable salt thereof, wherein m, p, q, $R^{1a}R^{2a}$, $R^{4a}$, $R^{4b}$, $X^1$, $X^2$, $X^3$, and $X^4$ are defined below.

DETAILED DESCRIPTION OF THE INVENTION

One aspect of the current invention relates to compounds of formula (I):

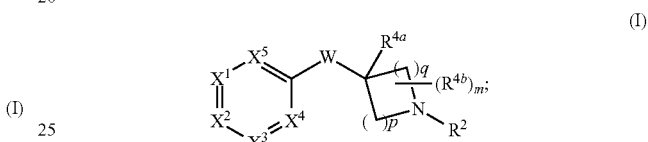

(I)

or a pharmaceutically acceptable salt thereof, wherein:
$X^1$ is N or $CR^6$;
$X^2$ is N or $CR^6$;
$X^3$ is N or $CR^3$;
$X^4$ is N or $CR^6$;
$X^5$ is N or $CR^6$;
1 to 2 of $X^1$, $X^2$, $X^3$, $X^4$ and $X^5$ are N;
the ring containing $X^1$, $X^2$, $X^3$, $X^4$, and $X^5$ can be fused to ring A, ring B, or ring C; each having the formula:

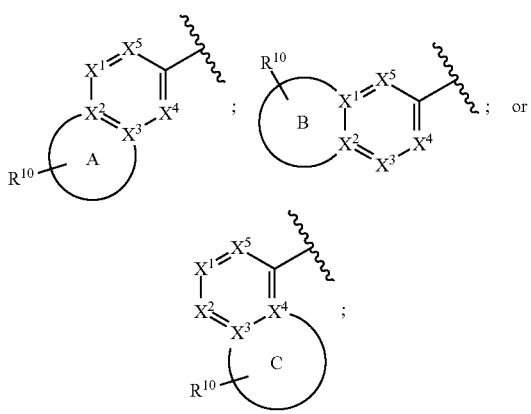

wherein each said ring A, ring B, or ring C is a fused 4- to 6-membered-saturated, -partially saturated, or -unsaturated-carbocyclic or -heterocyclic ring containing 0, 1, 2, or 3 heteroatoms; and is substituted by 0, 1, or 2 $R^{10}$ groups;
W is —O—; —NH—; or —N$C_{1-6}$alk; —CH$_2$—; —CH(CH$_3$)—; or C(CH$_3$)$_2$—;
m is 0, 1, 2, 3, or 4;
each of p and q is independently 0, 1, 2, 3, 4, 5, or 6;
wherein the sum of p and q is 2 to 6;
the ring containing p and q contains 0 or 1 double bond;
$R^1$ is halo, $C_{1-8}$alk, $C_{1-4}$haloalk, —OR$^c$, —N(R$^a$)C(=O)R$^b$, —C(=O)R$^a$, —C(=O)R$^c$, —C(=O)—R$^a$, —NR$^a$R$^c$, —N(R$^c$)C(=O)R$^b$, —N(R$^a$)C(=O)R$^c$, —C(=O)NR$^a$R$^b$, —C(=O)NR$^a$R$^c$, or $C_{0-4}$alk-L$^1$; wherein said $C_{1-8}$alk group is substituted by 0, 1, 2 or 3 groups which are halo, $C_{1-3}$haloalk, —OH, —OC$_{1-4}$alk, —NH$_2$, —NHC$_{1-4}$alk, —OC(=O)C$_{1-4}$alk, or —N(C$_{1-4}$alk)C$_{1-4}$alk;

$R^2$ is —C(=O)R$^5$ or -L$^2$;

each of $R^3$ and $R^6$ is independently $R^1$, H, halo, CN, OH, OC$_{1-4}$alk, C$_{1-4}$alk, or C$_{1-4}$haloalk; wherein 1 or 2 of $R^3$ and $R^6$ must be $R^1$;

$R^{4a}$ is H, C$_{1-4}$alk, or C$_{1-4}$haloalk;

each $R^{4b}$ is independently F, Cl, Br, CN, OH, OC$_{1-4}$alk, C$_{1-4}$alk, or C$_{1-4}$haloalk;

$R^5$ is H, C$_{1-8}$alk, or C$_{0-8}$alk-L$^3$;

$R^a$ is independently H or $R^b$;

$R^b$ is independently phenyl, benzyl, or C$_{1-6}$alk, wherein said phenyl, benzyl, and C$_{1-6}$alk are being substituted by 0, 1, 2 or 3 substituents selected from halo, C$_{1-4}$alk, C$_{1-3}$haloalk, —OH, —OC$_{1-4}$alk, —NH$_2$, —NHC$_{1-4}$alk, —OC(=O)C$_{1-4}$alk, or —N(C$_{1-4}$alk)C$_{1-4}$alk;

$R^c$ is C$_{0-4}$alk-L$^4$; and each of L$^1$, L$^2$, L$^3$, and L$^4$ is independently a carbon-linked or nitrogen-linked saturated, partially-saturated or unsaturated 3-, 4-, 5-, 6-, or 7-membered monocyclic ring or a saturated, partially-saturated or unsaturated 8-, 9-, 10-, 11-, or 12-membered bicyclic ring; each said ring contains 0, 1, 2, 3, or 4 N atoms and 0, 1, or 2 atoms which are O or S; each L$^1$, L$^2$, L$^3$, and L$^4$ is independently substituted by 0, 1, 2 or 3 R$^7$ groups which are independently F, Cl, Br, C$_{1-6}$alk, C$_{1-4}$haloalk, —OR$^a$, —OC$_{1-4}$haloalk, CN, —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —OC$_{1-6}$alkNR$^a$R$^a$, —OC$_{1-6}$alkOR$^a$, —SR$^a$, —S(=O)R$^b$, —S(=O)$_2$R$^b$, —S(=O)$_2$NR$^a$R$^a$, —NR$^a$R$^a$, —NR$^a$R$^c$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{1-6}$alkOR$^a$, —C$_{1-6}$alkNR$^a$R$^a$, —C$_{1-6}$alkOR$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In one embodiment of compound of formula (I), (II), (III), or (IV), or a pharmaceutically acceptable salt thereof, W is —O—.

In another embodiment of compound of formula (I), (II), (III), or (IV), or a pharmaceutically acceptable salt thereof, $R^1$ is a saturated, partially-saturated or unsaturated 4-, 5-, 6-, or 7-membered monocyclic ring, wherein each said ring contains 0, 1, 2, or 3 N atoms and 0, 1, or 2 O atoms, and wherein each said ring is substituted by 0, 1, 2 or 3 R$^7$ groups which are independently F, Cl, Br, C$_{1-6}$alk, C$_{1-4}$haloalk, —OR$^a$, —OC$_{1-4}$haloalk, CN, —C(=O)R$^b$, —C(=O)OR$^a$, —C(=O)NR$^a$R$^a$, —NR$^a$R$^a$, —NR$^a$R$^c$, or —C$_{1-6}$alkOR$^a$.

In another embodiment of compound of formula (I), (II), (III), or (IV), or a pharmaceutically acceptable salt thereof, $R^1$ is a saturated, partially-saturated or unsaturated 5- or 6-membered monocyclic ring, wherein each said ring contains 0, 1, 2, or 3 N atoms and 0, 1, or 2 O atoms, and wherein each said ring is substituted by 0, 1, 2 or 3 R$^7$ groups which are independently F, Cl, Br, C$_{1-6}$alk, C$_{1-4}$haloalk, —OR$^a$, —OC$_{1-4}$haloalk, CN, —C(=O)R$^b$, —C(=O)OR$^a$, —C(=O)NR$^a$R$^a$, —NR$^a$R$^a$, —NR$^a$R$^c$, or —C$_{1-6}$alkOR$^a$.

In another embodiment of compound of formula (I), (II), (III), or (IV), or a pharmaceutically acceptable salt thereof, $R^1$ is a saturated, partially-saturated or unsaturated 8-, 9-, 10-, 11-, or 12-membered bicyclic ring, wherein each said ring contains 0, 1, 2, or 3 N atoms and 0, 1, or 2 O atoms, and wherein each said ring is substituted by 0, 1, 2 or 3 R$^7$ groups which are independently F, Cl, Br, C$_{1-6}$alk, C$_{1-4}$haloalk, —OR$^a$, —OC$_{1-4}$haloalk, CN, —C(=O)R$^b$, —C(=O)OR$^a$, —C(=O)NR$^a$R$^a$, —NR$^a$R$^a$, —NR$^a$R$^c$, or —C$_{1-6}$alkOR$^a$.

In another embodiment of compound of formula (I), (II), (III), or (IV), or a pharmaceutically acceptable salt thereof, $R^1$ is azepanyl, phenyl, 2-pyridyl, 3-pyridyl, 4-pyridyl, morpholinyl, piperidinyl, piperazinyl, dihydropyranyl dihydropyridyl, tetrahydropyranyl, benzothiazolinyl, quinolinyl, or quinazolinyl; each $R^1$ is independently substituted by 0, 1, or 2 R$^7$ groups which are independently F, Cl, Br, methyl, methoxy, —CN, —C(=O)CH$_3$, —C(=O)OC(CH$_3$)$_3$, —C(=O)NH(CH$_3$), —C(=O)N(CH$_3$)$_2$, —NH$_2$, —CH$_2$OH, or —CH$_2$CH$_2$OH.

In another embodiment of compound of formula (I), (II), (III), or (IV), or a pharmaceutically acceptable salt thereof, $R^3$ is $R^1$ or H.

In another embodiment of compound of formula (I), (II), (III), or (IV), or a pharmaceutically acceptable salt thereof, $R^3$ is H.

In another embodiment of compound of formula (I), (II), (III), or (IV), or a pharmaceutically acceptable salt thereof, the ring containing X$^1$, X$^2$, X$^3$, X$^4$, and X$^5$ is pyrimidyl, pyrazinyl, piridazinyl, pyridinyl, quinoxalinyl, or quinolinyl.

In another embodiment of compound of formula (I), (II), (III), or (IV), or a pharmaceutically acceptable salt thereof, the ring containing X$^1$, X$^2$, X$^3$, X$^4$, and X$^5$ is

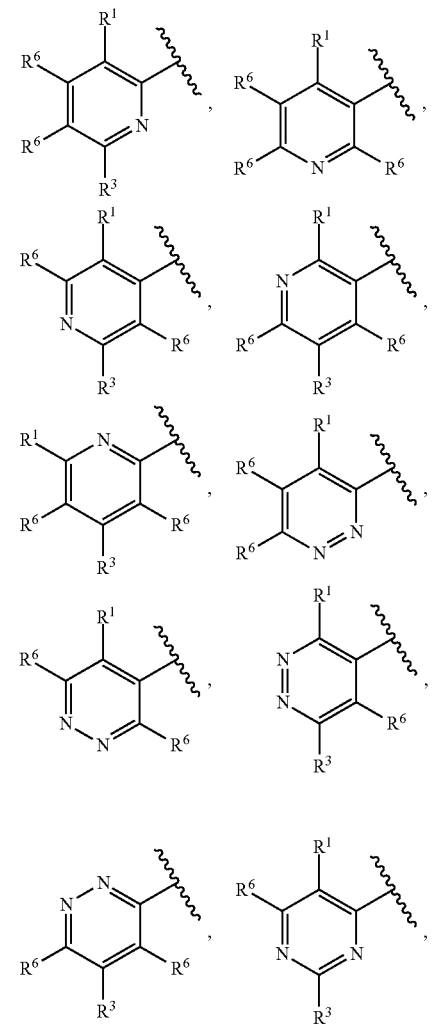

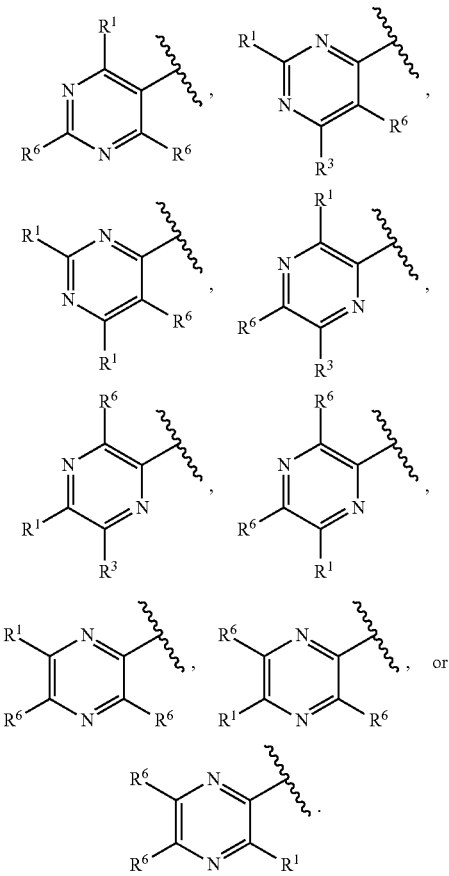
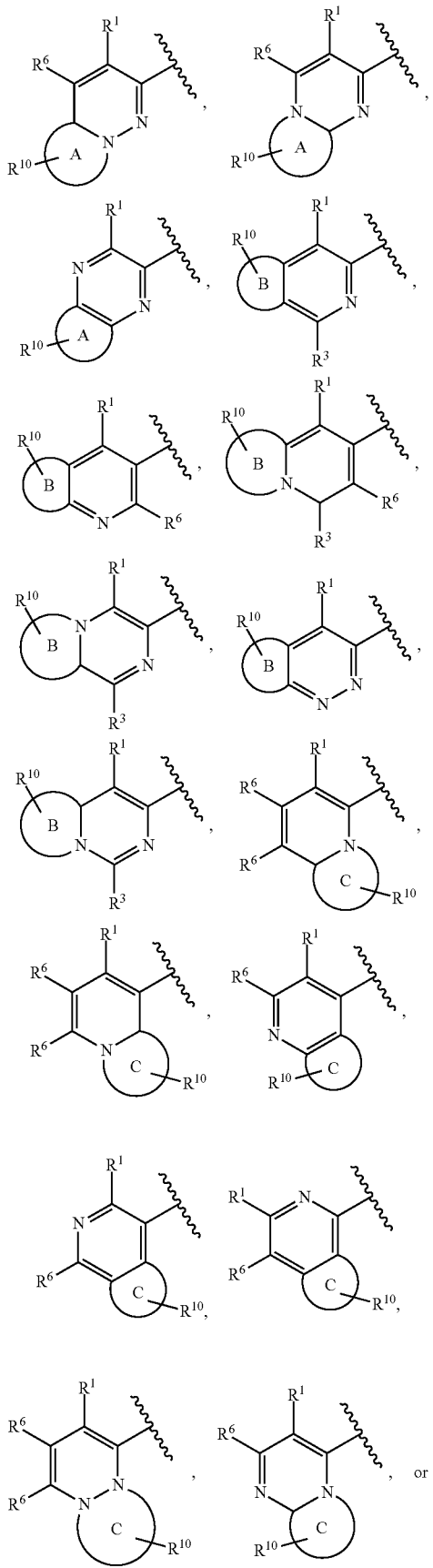
In another embodiment of compound of formula (I), (II), (III), or (IV), or a pharmaceutically acceptable salt thereof,
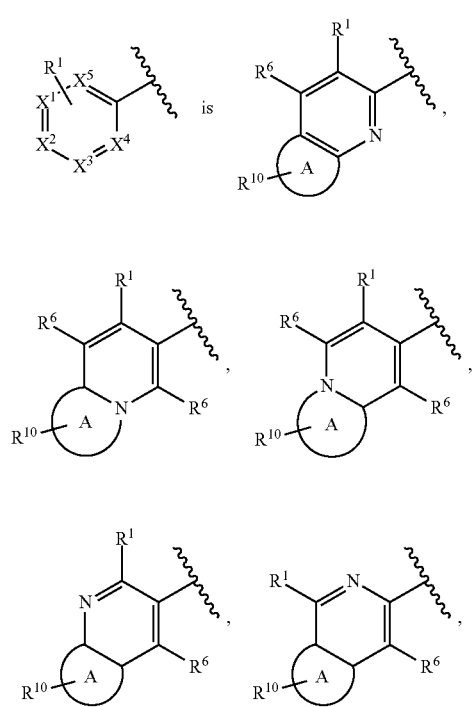

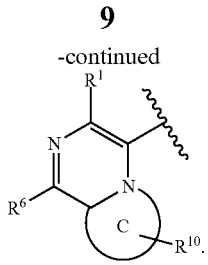

In another embodiment of compound of formula (I), (II), (III), or (IV), or a pharmaceutically acceptable salt thereof, each of said Ring A, Ring B, and Ring C is a fused 4- to 6-membered-saturated, -partially saturated, or -unsaturated-carbocyclic which are fused phenyl, cyclobutyl, cyclopentyl, or cyclohexyl; said Ring A, Ring B, and Ring C is substituted by 0, 1, or 2 $R^{10}$ groups which are oxo, $C_{1-6}$alk, $C_{1-3}$haloalk, —OH, —$OC_{1-4}$alk, —$NH_2$, —$NHC_{1-4}$alk, —OC(=O)$C_{1-4}$alk, or —N($C_{1-4}$alk)$C_{1-4}$alk.

In another embodiment of compound of formula (I), (II), (III), or (IV), or a pharmaceutically acceptable salt thereof, each of said Ring A, Ring B, and Ring C is a fused 5-membered-saturated, -partially saturated, or -unsaturated-heterocyclic ring which are fused furanyl, thiophenyl, pyrrolyl, pyrrolinyl, pyrrolidinyl, dioxolanyl, oxazolyl, thiazolyl, isothiazolyl, imidazolyl, imidazolinyl, imidazolidinyl, pyrazolyl, pyrazolinyl, pyrazolidinyl, isoxazolyl, or isothiazolyl; said Ring A, Ring B, and Ring C is substituted by 0, 1, or 2 $R^{10}$ groups which are oxo, $C_{1-6}$alk, $C_{1-3}$haloalk, —OH, —$OC_{1-4}$alk, —$NH_2$, —$NHC_{1-4}$alk, —OC(=O)$C_{1-4}$alk, or —N($C_{1-4}$alk)$C_{1-4}$alk.

In another embodiment of compound of formula (I), (II), (III), or (IV), or a pharmaceutically acceptable salt thereof, each of said Ring A, Ring B, and Ring C is a fused 6-membered-saturated, -partially saturated, or -unsaturated-heterocyclic ring which are fused pyranyl, pyridinyl, piperidinyl, dioxanyl, morpholinyl, dithianyl, thiomorpholinyl, pyridazinyl, pyrazinyl, or piperazinyl; said Ring A, Ring B, and Ring C is substituted by 0, 1, or 2 $R^{10}$ groups which are oxo, $C_{1-6}$alk, $C_{1-3}$haloalk, —OH, —$OC_{1-4}$alk, —$NH_2$, —$NHC_{1-4}$alk, —OC(=O)$C_{1-4}$alk, or —N($C_{1-4}$alk)$C_{1-4}$alk.

In another embodiment of compound of formula (I), (II), (III), or (IV), or a pharmaceutically acceptable salt thereof, each of p and q is independently 1.

In another embodiment of compound of formula (I), (II), (III), or (IV), or a pharmaceutically acceptable salt thereof, each of p and q is independently 2.

In another embodiment of compound of formula (I), (II), (III), or (IV), or a pharmaceutically acceptable salt thereof, the ring containing p and q contains 0 or 1 double bond.

In another embodiment of compound of formula (I), (II), (III), or (IV), or a pharmaceutically acceptable salt thereof, the sum of p and q is 3; and the ring containing p and q contains 0 or 1 double bond.

In another embodiment of compound of formula (I), (II), (III), or (IV), or a pharmaceutically acceptable salt thereof, m is 0.

In another embodiment of compound of formula (I), (II), (III), or (IV), or a pharmaceutically acceptable salt thereof, the group

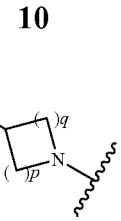

is azetidinyl, pyrrolidinyl, piperidinyl, or azepanyl.

In another embodiment of compound of formula (I), (II), (III), or (IV), or a pharmaceutically acceptable salt thereof, $R^1$ is —C(=O)—O—$R^b$, —C(=O)NR$^a$R$^b$, —OR$^{20}$, or —C(=O)NR$^a$R$^c$.

In another embodiment of compound of formula (I), (II), (III), or (IV), or a pharmaceutically acceptable salt thereof, $R^{4a}$ is H or $C_{1-4}$alk; and m is 0.

In another embodiment of compound of formula (I), (II), (III), or (IV), or a pharmaceutically acceptable salt thereof, $R^5$ is $C_{1-8}$alk or $C_{0-8}$alk-$L^3$.

In another embodiment of compound of formula (I), (II), (III), or (IV), or a pharmaceutically acceptable salt thereof, each $R^6$ is independently H.

In another embodiment of compound of formula (I), (II), (III), or (IV), or a pharmaceutically acceptable salt thereof, $R^a$ is H or $C_{1-6}$alk substituted by 0 or 1 —OH, —$OC_{1-4}$alk, —OC(=O)$C_{1-4}$alk, or —N($C_{1-4}$alk)$C_{1-4}$alk.

In another embodiment of compound of formula (I), (II), (III), or (IV), or a pharmaceutically acceptable salt thereof, $R^c$ is a carbon-linked saturated, partially-saturated or unsaturated 3-, 4-, 5-, or 6-membered monocyclic ring containing 0 or 1 N atom and 0 or 1 atom which is O or S, which is substituted by 0 or 1 $R^7$ groups which are independently F, $C_{1-6}$alk, $C_{1-4}$haloalk, or —OR$^a$.

In another embodiment of compound of formula (I), (II), (III), or (IV), or a pharmaceutically acceptable salt thereof, $R^c$ is a nitrogen-linked saturated, partially-saturated, or unsaturated 4-, 5-, 6- or 7-membered ring heterocycle containing 0, 1 or 2 nitrogen atoms and containing 0 or 1 sulfur or oxygen atom, the heterocycle is substituted by 0, 1, 2 or 3 $R^7$ groups which are independently oxo, F, Cl, Br, Cl, $C_{1-4}$alk, $C_{1-4}$haloalk, —$OC_{1-4}$alk, —$NH_2$, —$NHC_{1-4}$alk, or —N($C_{1-4}$alk)$C_{1-4}$alk.

In another embodiment of compound of formula (I), (II), (III), or (IV), or a pharmaceutically acceptable salt thereof,

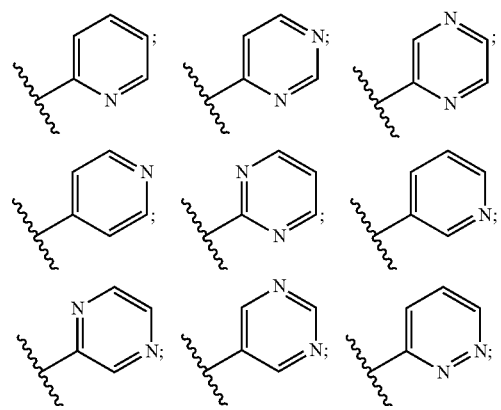

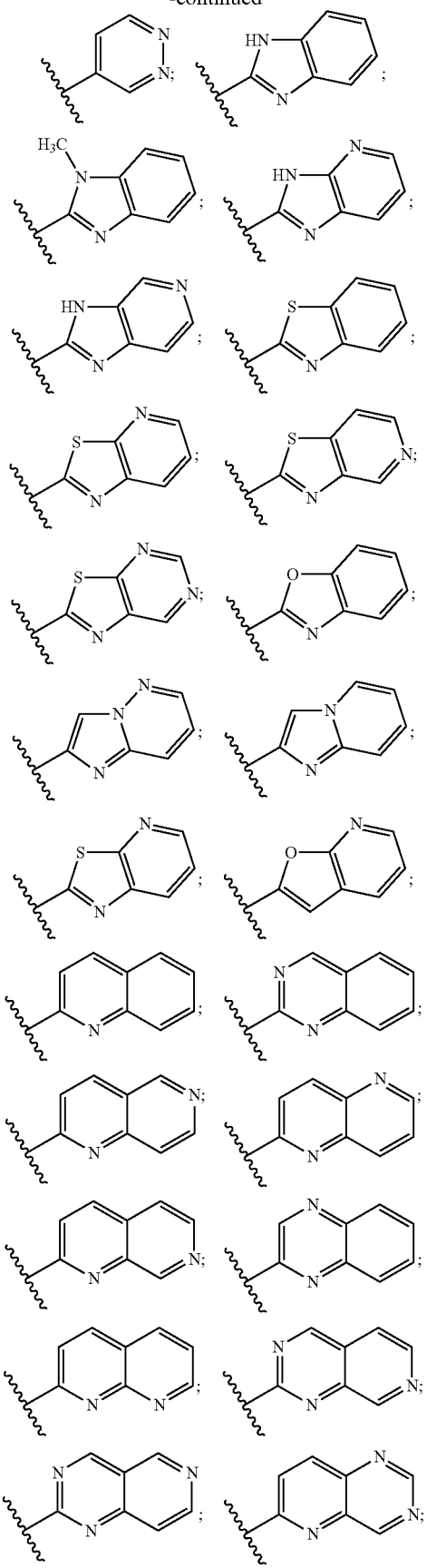

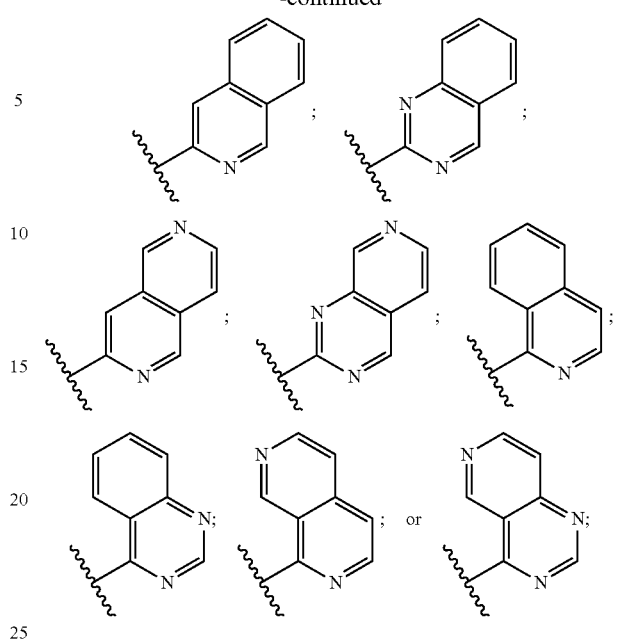

wherein each $R^2$ is substituted by 0, 1 or 2 $R^7$ groups.

In another embodiment of compound of formula (I), (II), (III), or (IV), or a pharmaceutically acceptable salt thereof, $R^2$ is —C(=O)$R^5$ wherein $R^5$ is: H, $C_{1-8}$alk, $C_{0-8}$alk-phenyl, $C_{0-8}$alk-benzimidazolyl, $C_{0-8}$alk-pyrimidinyl, $C_{0-8}$alk-pyridinyl, $C_{0-8}$alk-imidazolyl, $C_{0-8}$alk-benzthiazolyl, $C_{0-8}$alk-pyrrolyl, $C_{0-8}$alk-quinolinyl, $C_{0-8}$alk-quinazolinyl, $C_{0-8}$alk-pyrrolyl, or $C_{0-8}$alk-indolyl; wherein each $R^5$ is substituted by 0, 1 or 2 $R^7$ groups.

In another embodiment of compound of formula (I), (II), (III), or (IV), or a pharmaceutically acceptable salt thereof, W is —O—; $R^1$ is azepanyl, phenyl, 2-pyridyl, 3-pyridyl, 4-pyridyl, morpholinyl, piperidinyl, piperazinyl, dihydropyranyl dihydropyridyl, tetrahydropyranyl, benzothiazolinyl, quinolinyl, or quinazolinyl; each $R^1$ is independently substituted by 0, 1, or 2 $R^7$ groups which are independently F, Cl, Br, methyl, methoxy, —CN, —C(=O)CH$_3$, —C(=O)OC(CH$_3$)$_3$, —C(=O)NH(CH$_3$), —C(=O)N(CH$_3$)$_2$, —NH$_2$, —CH$_2$OH, or —CH$_2$CH$_2$OH; $R^2$ is benzamidazolyl, quinolinyl, or quinazolinyl; each of p and q is independently 1 or 2; and $R^3$ is $R^1$ or H.

Another aspect of the current invention relates to compounds of formula (II):

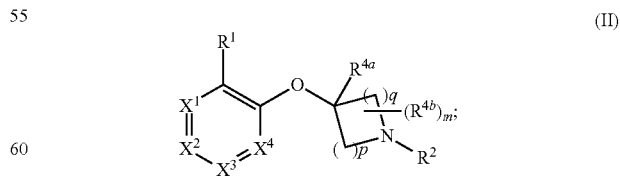

or a pharmaceutically acceptable salt thereof, wherein:
each of $X^1$, $X^2$, and $X^3$ is independently N or $CR^3$; and $X^4$ is N; wherein no more than one of $X^1$, $X^2$, and $X^3$ are N; and wherein any adjacent $X^1$, $X^2$, and $X^3$ may optionally form an optionally substituted-saturated, -partially saturated, or -unsaturated-heterocyclic or -heteroaryl ring fused to the ring containing $X^1$, $X^2$, $X^3$, and $X^4$;

m is 1, 2, 3, or 4;

each of p and q is independently 0, 1, 2, 3, 4, 5, or 6; wherein the sum of p and q is 2 to 6;

$R^1$ is $C_{2-8}$alk, $C_{1-4}$haloalk, —OR$^c$, —N(R$^a$)C(=O)R$^b$, —C(=O)R$^a$, —C(=O)R$^c$, —C(=O)—O—R$^b$, —NR$^a$R$^c$, —N(R$^c$)C(=O)R$^b$, —N(R$^a$)C(=O)R$^c$, —C(=O)NR$^a$R$^b$, —C(=O)NR$^a$R$^c$, or $C_{0-4}$alk-L$^1$; wherein said $C_{2-8}$alk group is substituted by 0, 1, 2 or 3 groups selected from halo, $C_{1-3}$haloalk, —OH, —OC$_{1-4}$alk, —NH$_2$, —NHC$_{1-4}$alk, —OC(=O)C$_{1-4}$alk, or —N(C$_{1-4}$alk)C$_{1-4}$alk;

$R^2$ is —C(=O)R$^5$ or -L$^2$;

$R^3$ is H, F, Cl, Br, CN, OH, OC$_{1-4}$alk, C$_{1-4}$alk or C$_{1-4}$haloalk;

$R^{4a}$ is H, C$_{1-4}$alk or C$_{1-4}$haloalk;

each $R^{4b}$ is independently H, F, Cl, Br, CN, OH, OC$_{1-4}$alk, C$_{1-4}$alk, or C$_{1-4}$haloalk;

$R^5$ is H, C$_{1-8}$alk, or C$_{0-8}$alk-L$^3$;

$R^a$ is independently H or R$^b$;

$R^b$ is independently phenyl, benzyl, or C$_{1-6}$alk, wherein said phenyl, benzyl, and C$_{1-6}$alk are being substituted by 0, 1, 2 or 3 substituents selected from halo, C$_{1-4}$alk, C$_{1-3}$haloalk, —OH, —OC$_{1-4}$alk, —NH$_2$, —NHC$_{1-4}$alk, —OC(=O)C$_{1-4}$alk, or —N(C$_{1-4}$alk)C$_{1-4}$alk;

$R^c$ is C$_{0-4}$alk-L$^4$; and each of L$^1$, L$^2$, L$^3$, and L$^4$ is independently a carbon-linked or nitrogen-linked saturated, partially-saturated or unsaturated 3-, 4-, 5-, 6-, or 7-membered monocyclic ring or a saturated, partially-saturated or unsaturated 8-, 9-, 10-, 11-, or 12-membered bicyclic ring, wherein each said ring contains 0, 1, 2, 3, or 4 N atoms and 0, 1, or 2 atoms selected from O or S; wherein each L$^1$, L$^2$, L$^3$, and L$^4$ is independently substituted by 0, 1, 2 or 3 R$^6$ groups selected from F, Cl, Br, C$_{1-6}$alk, C$_{1-4}$haloalk, —OR$^a$, —OC$_{1-4}$haloalk, CN, —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$ or oxo.

In another embodiment of compound of formula (I), (II), (III), or (IV), or a pharmaceutically acceptable salt thereof, $X^1$ is N or C, and each of $X^2$ and $X^3$ is C.

In another embodiment of compound of formula (I), (II), (III), or (IV), or a pharmaceutically acceptable salt thereof, $X^1$ and $X^2$ form an optionally substituted 5- to 6-membered-saturated, -partially saturated, or -unsaturated-heterocyclic or -heteroaryl ring fused to the ring containing $X^1$, $X^2$, $X^3$, and $X^4$.

In another embodiment of compound of formula (I), (II), (III), or (IV), or a pharmaceutically acceptable salt thereof, $X^2$ and $X^3$ form an optionally substituted 5- to 6-membered-saturated, -partially saturated, or -unsaturated-heterocyclic or -heteroaryl ring fused to the ring containing $X^1$, $X^2$, $X^3$, and $X^4$.

In another embodiment of compound of formula (I), (II), (III), or (IV), or a pharmaceutically acceptable salt thereof, the group:

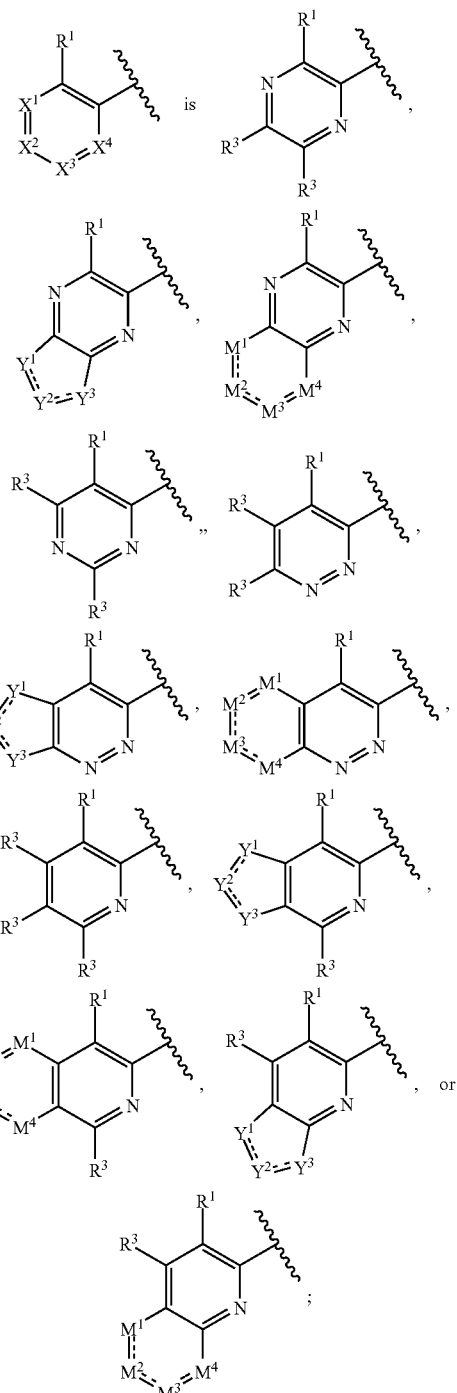

wherein each of $Y^1$, $Y^2$, $Y^3$, $M^1$, $M^2$, $M^3$, and $M^4$ is independently CR$^7$ or a heteroatom selected from S, O, or NR$^8$; wherein no more than one of $Y^1$, $Y^2$, $Y^3$, $M^1$, $M^2$, $M^3$, and $M^4$ are N; wherein $R^7$ is H, halo, C$_{1-4}$alk, C$_{1-3}$haloalk, —OH, —OC$_{1-4}$alk, —NH$_2$, —NHC$_{1-4}$alk, —OC(=O)C$_{1-4}$alk, or —N(C$_{1-4}$alk)C$_{1-4}$alk; and $R^8$ is H, C$_{1-4}$alk, or C$_{1-3}$haloalk.

In another embodiment of compound of formula (I), (II), (III), or (IV), or a pharmaceutically acceptable salt thereof, the group

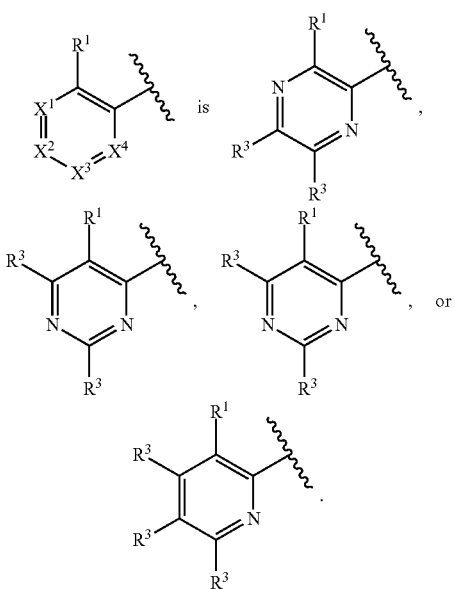

In another embodiment of compound of formula (I), (II), (III), or (IV), or a pharmaceutically acceptable salt thereof, m is 1.

In another embodiment of compound of formula (I), (II), (III), or (IV), or a pharmaceutically acceptable salt thereof, p is 0, 1, or 2.

In another embodiment of compound of formula (I), (II), (III), or (IV), or a pharmaceutically acceptable salt thereof, q is 0, 1, or 2.

In another embodiment of compound of formula (I), (II), (III), or (IV), or a pharmaceutically acceptable salt thereof, $R^1$ is —C(=O)—O—$R^b$, —C(=O)N$R^a R^b$, —O$R^c$, or —C(=O)N$R^a R^c$.

In another embodiment of compound of formula (I), (II), (III), or (IV), or a pharmaceutically acceptable salt thereof, $R^1$ is a saturated, partially-saturated or unsaturated 4-, 5-, 6-, or 7-membered monocyclic ring, wherein each said ring contains 0, 1, 2, or 3 N atoms and 0, 1, or 2 O atoms, and wherein each said ring is substituted by 0, 1, 2 or 3 $R^6$ groups selected from F, Cl, Br, $C_{1-6}$alk, $C_{1-4}$haloalk, —O$R^a$, —O$C_{1-4}$haloalk, CN, —C(=O)$R^b$, —C(=O)O$R^a$, —N$R^a R^a$, —N$R^a R^c$, or oxo.

In another embodiment of compound of formula (I), (II), (III), or (IV), or a pharmaceutically acceptable salt thereof, $R^1$ is a saturated, partially-saturated or unsaturated 5- or 6-membered monocyclic ring, wherein each said ring contains 0, 1, 2, or 3 N atoms and 0, 1, or 2 O atoms, and wherein each said ring is substituted by 0, 1, 2 or 3 $R^6$ groups selected from F, Cl, Br, $C_{1-6}$alk, $C_{1-4}$haloalk, —O$R^a$, —O$C_{1-4}$haloalk, CN, —C(=O)$R^b$, —C(=O)O$R^a$, —N$R^a R^a$, —N$R^a R^c$, or oxo.

In another embodiment of compound of formula (I), (II), (III), or (IV), or a pharmaceutically acceptable salt thereof, $R^1$ is a saturated, partially-saturated or unsaturated 8-, 9-, 10-, 11-, or 12-membered bicyclic ring, wherein each said ring contains 0, 1, 2, or 3 N atoms and 0, 1, or 2 O atoms, and wherein each said ring is substituted by 0, 1, 2 or 3 $R^6$ groups selected from F, Cl, Br, $C_{1-6}$alk, $C_{1-4}$haloalk, —O$R^a$, —O$C_{1-4}$haloalk, CN, —C(=O)$R^b$, —C(=O)O$R^a$, —N$R^a R^c$, $R^c$ or oxo.

In another embodiment of compound of formula (I), (II), (III), or (IV), or a pharmaceutically acceptable salt thereof, $R^1$ is not methyl.

In another embodiment of compound of formula (I), (II), (III), or (IV), or a pharmaceutically acceptable salt thereof, $R^1$ is cyclohexyl, cyclopentyl, cyclopentenyl, cyclohexenyl, cycloheptyl, azetidinyl, phenyl, 2-pyridyl, 3-pyridyl, pyrazolyl, morpholinyl, pyrimidyl, piperazinyl, piperidinyl, dihydropyranyl, tetrahydropyranyl, tetrahydrofuranyl, tetrahydropyridinyl, tetrahydrothiopyranyl, oxaspiro[3.5]nonyl, azepanyl, oxepanyl, or quinolinyl, all of which are substituted by 0, 1, 2 or 3 $R^6$ groups selected from F, Cl, Br, $C_{1-6}$alk, $C_{1-4}$haloalk, —O$R^a$, CN, —C(=O)$R^b$, —C(=O)O$R^a$, —S$R^a$, or oxo.

In another embodiment of compound of formula (I), (II), (III), or (IV), or a pharmaceutically acceptable salt thereof, $R^1$ is $C_{2-6}$alk substituted by 0, 1, 2 or 3 groups selected from halo, $C_{1-3}$haloalk, —OH, —O$C_{1-4}$alk, —$NH_2$, —NH$C_{1-4}$alk, —OC(=O)$C_{1-4}$alk, or —N($C_{1-4}$alk)$C_{1-4}$alk.

In another embodiment of compound of formula (I), (II), (III), or (IV), or a pharmaceutically acceptable salt thereof, $R^1$ is:

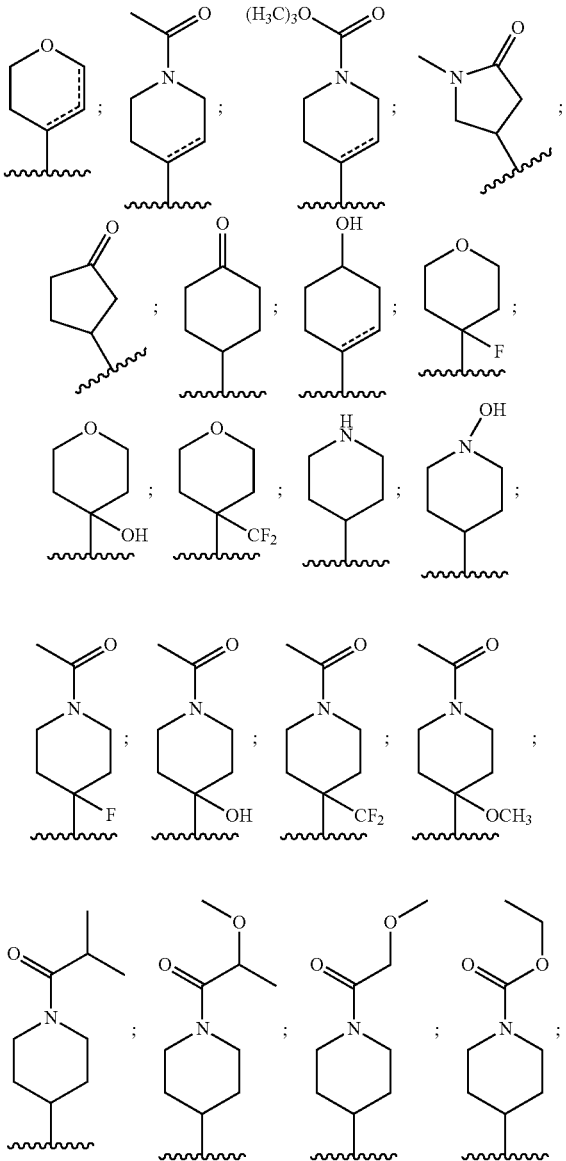

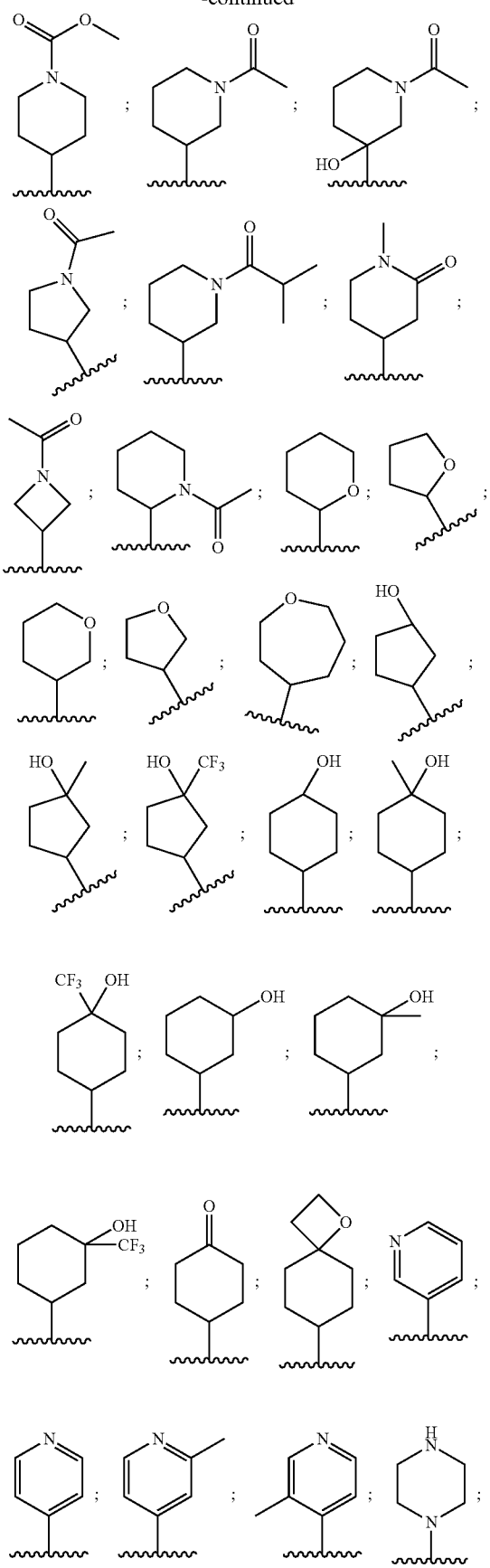
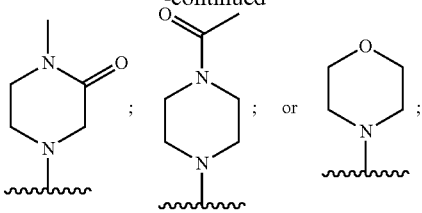

wherein the dotted bond is an optional double bond.

In another embodiment of compound of formula (I), (II), (III), or (IV), or a pharmaceutically acceptable salt thereof, $R^3$ is independently H, F, Cl, Br, CN, OH, $OC_{1-4}$alk, $C_{1-4}$alk or $C_{1-4}$haloalk.

In another embodiment of compound of formula (I), (II), (III), or (IV), or a pharmaceutically acceptable salt thereof, $R^3$ is H, $C_{1-4}$alk, or $C_{1-4}$haloalk.

In another embodiment of compound of formula (I), (II), (III), or (IV), or a pharmaceutically acceptable salt thereof, $R^{4a}$ is H or $C_{1-4}$alk.

In another embodiment of compound of formula (I), (II), (III), or (IV), or a pharmaceutically acceptable salt thereof, each of $R^{4a}$ and $R^{4b}$ is H.

In another embodiment of compound of formula (I), (II), (III), or (IV), or a pharmaceutically acceptable salt thereof, $R^5$ is $C_{1-8}$alk or $C_{0-8}$alk-$L^3$.

In another embodiment of compound of formula (I), (II), (III), or (IV), or a pharmaceutically acceptable salt thereof, $R^6$ is H.

In another embodiment of compound of formula (I), (II), (III), or (IV), or a pharmaceutically acceptable salt thereof, $R^a$ is H or $C_{1-6}$alk substituted by 0 or 1 -OH, —$OC_{1-4}$alk, —OC(=O)Cl_4alk, or —N($C_{1-4}$alk)$C_{1-4}$alk.

In another embodiment of compound of formula (I), (II), (III), or (IV), or a pharmaceutically acceptable salt thereof, $R^c$ is a carbon-linked saturated, partially-saturated or unsaturated 3-, 4-, 5-, or 6-membered monocyclic ring containing 0 or 1 N atom and 0 or 1 atom selected from O or S, which is substituted by 0 or 1 $R^7$ groups selected from F, $C_{1-6}$alk, $C_{1-4}$haloalk, or —$OR^a$.

In another embodiment of compound of formula (I), (II), (III), or (IV), or a pharmaceutically acceptable salt thereof, $R^c$ is a nitrogen-linked saturated, partially-saturated, or unsaturated 4-, 5-, 6- or 7-membered ring heterocycle containing the linking nitrogen and 0, 1 or 2 additional nitrogen atoms and containing 0 or 1 sulfur or oxygen atom, the heterocycle being substituted by 0, 1, 2 or 3 $R^7$ groups selected from F, Cl, Br, $C_1$, $C_{1-4}$alk, $C_{1-4}$haloalk, —$OC_{1-4}$alk, —$NH_2$, —$NHC_{1-4}$alk, —N($C_{1-4}$alk)$C_{1-4}$alk, or oxo.

In another embodiment of compound of formula (I), (II), (III), or (IV), or a pharmaceutically acceptable salt thereof, $R^c$ is a $C_{0-4}$alk-saturated, partially-saturated or unsaturated 3-, 5-, or 6-membered monocyclic ring containing 0 or 1 N atom and 0 or 1 atom selected from O and S, which is substituted by 0 or 1 $R^7$ groups selected from F, $C_{1-6}$alk, $C_{1-4}$haloalk, or —$OR^a$.

In another embodiment of compound of formula (I), (II), (III), or (IV), or a pharmaceutically acceptable salt thereof, $R^2$ is —C(=O)$R^5$.

In another embodiment of compound of formula (I), (II), (III), or (IV), or a pharmaceutically acceptable salt thereof, $R^2$ is —C(=O)$R^5$ or -$L^2$; wherein each of said $R^5$ or -$L^2$ is independently:

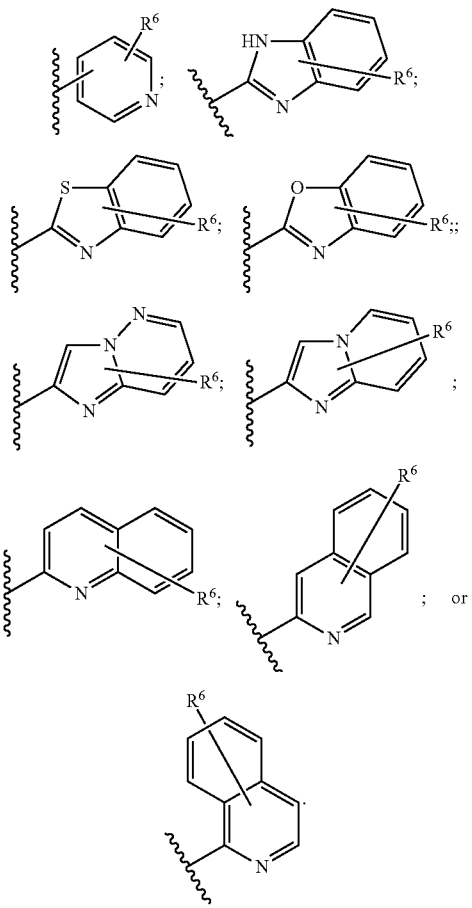

In another embodiment of compound of formula (I), (II), (III), or (IV), or a pharmaceutically acceptable salt thereof, each of said $R^5$ or -$L^2$ is:

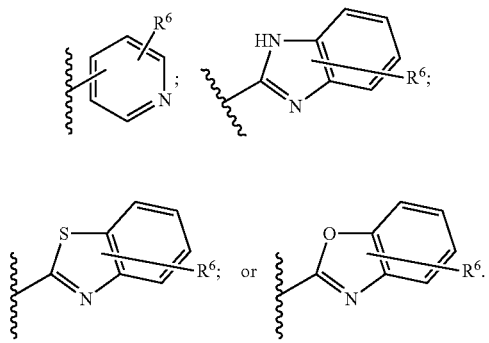

In another embodiment of compound of formula (I), (II), (III), or (IV), or a pharmaceutically acceptable salt thereof, $R^2$ is —C(═O)$R^5$ wherein $R^5$ is: H, $C_{1-8}$alk, $C_{0-8}$alk-phenyl, $C_{0-8}$alk-benzimidazolyl, $C_{0-8}$alk-pyrimidinyl, $C_{0-8}$alk-pyridinyl, $C_{0-8}$alk-imidazolyl, $C_{0-8}$alk-benzthiazolyl, $C_{0-8}$alk-pyrrolyl, $C_{0-8}$alk-quinolinyl, $C_{0-8}$alk-pyrrolyl, or $C_{0-8}$alk-indolyl.

Another aspect of the current invention relates to compounds of formula (III):

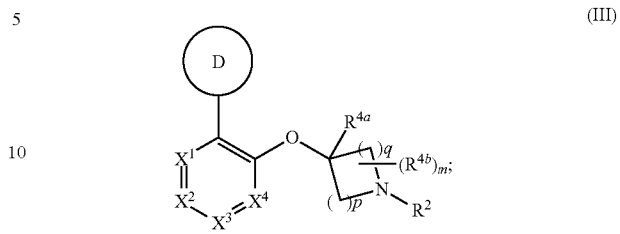

or any pharmaceutically-acceptable salt thereof, wherein:
Ring D is -$L^1$;
each of $X^1$, $X^2$, and $X^3$ is independently N or $CR^3$; and $X^4$ is N; wherein no more than one of $X^1$, $X^2$, and $X^3$ are N; and wherein any adjacent $X^1$, $X^2$, and $X^3$ may optionally form an optionally substituted-saturated, -partially saturated, or -unsaturated-heterocyclic or -heteroaryl ring fused to the ring containing $X^1$, $X^2$, $X^3$, and $X^4$;
m is 1, 2, 3, or 4;
each of p and q is independently 0, 1, 2, 3, 4, 5, or 6; wherein the sum of p and q is 2 to 6;
$R^2$ is —C(═O)$R^5$ or -$L^2$;
$R^3$ is H, F, Cl, Br, CN, OH, O$C_{1-4}$alk, $C_{1-4}$alk or $C_{1-4}$haloalk;
$R^{4a}$ is H, $C_{1-4}$alk, or $C_{1-4}$haloalk;
each $R^{4b}$ is independently H, F, Cl, Br, CN, OH, O$C_{1-4}$alk, $C_{1-4}$alk, or $C_{1-4}$haloalk;
$R^5$ is H, $C_{1-8}$alk, or $C_{0-8}$alk-$L^3$;
$R^a$ is independently H or $R^b$;
$R^b$ is independently phenyl, benzyl, or $C_{1-6}$alk, wherein said phenyl, benzyl, and $C_{1-6}$alk are being substituted by 0, 1, 2 or 3 substituents selected from halo, $C_{1-4}$alk, $C_{1-3}$haloalk, —OH, —O$C_{1-4}$alk, —NH$_2$, —NH$C_{1-4}$alk, —OC(═O)$C_{1-4}$alk, or —N($C_{1-4}$alk)$C_{1-4}$alk; and
each of $L^1$, $L^2$, $L^3$, and $L^4$ is independently a carbon-linked or nitrogen-linked saturated, partially-saturated or unsaturated 3-, 4-, 5-, 6-, or 7-membered monocyclic ring or a saturated, partially-saturated or unsaturated 8-, 9-, 10-, 11-, or 12-membered bicyclic ring, wherein each said ring contains 0, 1, 2, 3, or 4 N atoms and 0, 1, or 2 atoms selected from O or S; wherein each $L^1$, $L^2$, $L^3$, and $L^4$ is independently substituted by 0, 1, 2 or 3 $R^6$ groups selected from F, Cl, Br, $C_{1-6}$alk, $C_{1-4}$haloalk, —O$R^a$, —O$C_{1-4}$haloalk, CN, —C(═O)$R^b$, —C(═O)O$R^a$, —C(═O)N$R^aR^a$, —C(═N$R^a$)N$R^aR^a$, —OC(═O)$R^b$, —OC(═O)N$R^aR^a$, —O$C_{2-6}$alkN$R^aR^a$, —O$C_{2-6}$alkO$R^a$, —S$R^a$, —S(═O)$R^b$, —S(═O)$_2R^b$, —S(═O)$_2$N$R^aR^a$, —N$R^aR^a$, —N($R^a$)C(═O)$R^b$, —N($R^a$)C(═O)O$R^b$, —N($R^a$)C(═O)N$R^aR^a$, —N($R^a$)C(═N$R^a$)N$R^aR^a$, —N($R^a$)S(═O)$_2R^b$, —N($R^a$)S(═O)$_2$N$R^aR^a$, —N$R^aC_{2-6}$alkN$R^aR^a$, —N$R^aC_{2-6}$alkO$R^a$, —$C_{1-6}$alkN$R^aR^a$, —$C_{1-6}$alkO$R^a$, —$C_{1-6}$alkN($R^a$)C(═O)$R^b$, —$C_{1-6}$alkOC(═O)$R^b$, —$C_{1-6}$alkC(═O)N$R^aR^a$, —$C_{1-6}$alkC(═O)O$R^a$ or oxo.

In another embodiment of compound of formula (I), (II), (III), or (IV), or a pharmaceutically acceptable salt thereof, the group

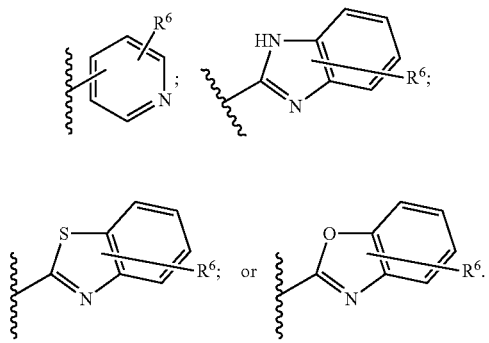

is azetidinyl, pyrrolidinyl, piperidinyl, or azepanyl.

In another embodiment of compound of formula (I), (II), (III), or (IV), or a pharmaceutically acceptable salt thereof, the group

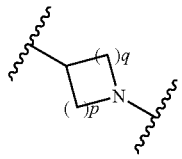

is azetidinyl.

In another embodiment of compound of formula (I), (II), (III), or (IV), or a pharmaceutically acceptable salt thereof, the group

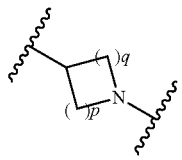

is pyrrolidinyl.

In another embodiment of compound of formula (I), (II), (III), or (IV), or a pharmaceutically acceptable salt thereof, the group

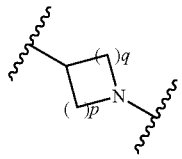

is piperidinyl.

In another embodiment of compound of formula (I), (II), (III), or (IV), or a pharmaceutically acceptable salt thereof, the group

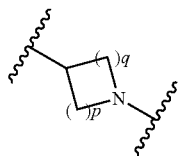

is azepanyl.

In another embodiment of compound of formula (I), (II), (III), or (IV), or a pharmaceutically acceptable salt thereof, ring D is a carbon-linked saturated, partially-saturated or unsaturated 4-, 5-, 6-, or 7-membered monocyclic ring, wherein each said ring contains 0, 1, 2, 3, or 4 N atoms and 0, 1, or 2 atoms selected from O or S; independently substituted by 0, 1, 2 or 3 $R^7$ groups selected from F, Cl, Br, $C_{1-6}$alk, $C_{1-4}$haloalk, —$OR^a$, —$OC_{1-4}$haloalk, CN, —C(=O)$R^b$, —C(=O)$OR^a$, —C(=O)$NR^aR^a$, —C(=$NR^a$)$NR^aR^a$, —OC(=O)$R^b$, —OC(=O)$NR^aR^a$, —$OC_{2-6}$alkNR$^a$R$^a$, —$OC_{2-6}$alkOR$^a$, —$SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —NR$^a$C$_{2-6}$alkNR$^a$R$^a$, —NR$^a$C$_{2-6}$alkOR$^a$, —$C_{1-6}$alkNR$^a$R$^a$, —$C_{1-6}$alkOR$^a$, —$C_{1-6}$alkN($R^a$)C(=O)$R^b$, —$C_{1-6}$alkOC(=O)$R^b$, —$C_{1-6}$alkC(=O)$NR^aR^a$, —$C_{1-6}$alkC(=O)$OR^a$ or oxo.

In another embodiment of compound of formula (I), (II), (III), or (IV), or a pharmaceutically acceptable salt thereof, ring D is a carbon-linked-saturated, partially-saturated or unsaturated 8-, 9-, 10-, 11-, or 12-membered bicyclic ring, wherein each said ring contains 0, 1, 2, 3, or 4 N atoms and 0, 1, or 2 atoms selected from O or S; independently substituted by 0, 1, 2 or 3 $R^7$ groups selected from F, Cl, Br, $C_{1-6}$alk, $C_{1-4}$haloalk, —$OR^a$, —$OC_{1-4}$haloalk, CN, —C(=O)$R^b$, —C(=O)$OR^a$, —C(=O)$NR^aR^a$, —C(=$NR^a$)$NR^aR^a$, —OC(=O)$R^b$, —OC(=O)$NR^aR^a$, —$OC_{2-6}$alkNR$^a$R$^a$, —$OC_{2-6}$alkOR$^a$, —$SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —NR$^a$C$_{2-6}$alkNR$^a$R$^a$, —NR$^a$C$_{2-6}$alkOR$^a$, —$C_{1-6}$alkNR$^a$R$^a$, —$C_{1-6}$alkOR$^a$, —$C_{1-6}$alkN($R^a$)C(=O)$R^b$, —$C_{1-6}$alkOC(=O)$R^b$, —$C_{1-6}$alkC(=O)$NR^aR^a$, —$C_{1-6}$alkC(=O)$OR^a$ or oxo.

In another embodiment of compound of formula (I), (II), (III), or (IV), or a pharmaceutically acceptable salt thereof, ring D is a nitrogen-linked saturated, partially-saturated or unsaturated 4-, 5-, 6-, or 7-membered monocyclic ring, wherein each said ring contains 0, 1, 2, 3, or 4 N atoms and 0, 1, or 2 atoms selected from O or S; independently substituted by 0, 1, 2 or 3 $R^7$ groups selected from F, Cl, Br, $C_{1-6}$alk, $C_{1-4}$haloalk, —$OR^a$, —$OC_{1-4}$haloalk, CN, —C(=O)$R^b$, —C(=O)$OR^a$, —C(=O)$NR^aR^a$, —C(=$NR^a$)$NR^aR^a$, —OC(=O)$R^b$, —OC(=O)$NR^aR^a$, —$OC_{2-6}$alkNR$^a$R$^a$, —$OC_{2-6}$alkOR$^a$, —$SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —NR$^a$C$_{2-6}$alkNR$^a$R$^a$, —NR$^a$C$_{2-6}$alkOR$^a$, —$C_{1-6}$alkNR$^a$R$^a$, —$C_{1-6}$alkOR$^a$, —$C_{1-6}$alkN($R^a$)C(=O)$R^b$, —$C_{1-6}$alkOC(=O)$R^b$, —$C_{1-6}$alkC(=O)$NR^aR^a$, —$C_{1-6}$alkC(=O)$OR^a$ or oxo.

In another embodiment of compound of formula (I), (II), (III), or (IV), or a pharmaceutically acceptable salt thereof, ring D is a nitrogen-linked-saturated, partially-saturated or unsaturated 8-, 9-, 10-, 11-, or 12-membered bicyclic ring, wherein each said ring contains 0, 1, 2, 3, or 4 N atoms and 0, 1, or 2 atoms selected from O or S; independently substituted by 0, 1, 2 or 3 $R^7$ groups selected from F, Cl, Br, $C_{1-6}$alk, $C_{1-4}$haloalk, —$OR^a$, —$OC_{1-4}$haloalk, CN, —C(=O)$R^b$, —C(=O)$OR^a$, —C(=O)$NR^aR^a$, —C(=$NR^a$)$NR^aR^a$, —OC(=O)$R^b$, —OC(=O)$NR^aR^a$, —$OC_{2-6}$alkNR$^a$R$^a$, —$OC_{2-6}$alkOR$^a$, —$SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —NR$^a$C$_{2-6}$alkNR$^a$R$^a$, —NR$^a$C$_{2-6}$alkOR$^a$, —$C_{1-6}$alkNR$^a$R$^a$, —$C_{1-6}$alkOR$^a$, —$C_{1-6}$alkN($R^a$)C(=O)$R^b$, —$C_{1-6}$alkOC(=O)$R^b$, —$C_{1-6}$alkC(=O)$NR^aR^a$, —$C_{1-6}$alkC(=O)$OR^a$ or oxo.

In another embodiment of compound of formula (I), (II), (III), or (IV), or a pharmaceutically acceptable salt thereof, ring D is cyclohexyl, cyclopentyl, cyclopentenyl, cyclohexenyl, or cycloheptyl.

In another embodiment of compound of formula (I), (II), (III), or (IV), or a pharmaceutically acceptable salt thereof, ring D is azetidinyl, phenyl, 2-pyridyl, 3-pyridyl, pyrazolyl, morpholinyl, pyrimidyl, piperazinyl, piperidinyl, dihydropyranyl, tetrahydropyranyl, tetrahydrofuranyl, tetrahydropyridinyl, or tetrahydrothiopyranyl.

In another embodiment of compound of formula (I), (II), (III), or (IV), or a pharmaceutically acceptable salt thereof, ring D is oxaspiro[3.5]nonyl, azepanyl, oxepanyl, or quinolinyl.

In another embodiment of compound of formula (I), (II), (III), or (IV), or a pharmaceutically acceptable salt thereof, ring D is cyclohexyl, cyclopentyl, cyclopentenyl, cyclohexenyl, cycloheptyl, azetidinyl, phenyl, 2-pyridyl, 3-pyridyl, pyrazolyl, morpholinyl, pyrimidyl, piperazinyl, piperidinyl, dihydropyranyl, tetrahydropyranyl, tetrahydrofuranyl, tetrahydropyridinyl, tetrahydrothiopyranyl, oxaspiro[3.5]nonyl, azepanyl, oxepanyl, or quinolinyl, all of which are substituted by 0, 1, 2 or 3 $R^7$ groups selected from F, Cl, Br, $C_{1-6}$alk, $C_{1-4}$haloalk, —$OR^a$, CN, —C(=O)$R^b$, —C(=O)$OR^a$, —$NR^aR^a$, —$SR^a$, or oxo.

In another embodiment of compound of formula (I), (II), (III), or (IV), or a pharmaceutically acceptable salt thereof, each of $X_1$, $X_2$, and $X_3$ is C; the group

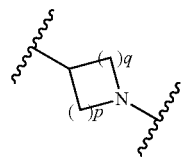

is piperidinyl; and $R^2$ is —C(=O)$R^5$; wherein $R^5$ is phenyl or pyridinyl; wherein said $R^5$ is being substituted by 0, 1, 2 or 3 $R^7$ groups selected from F, Cl, Br, $C_1$, $C_{1-4}$alk, $C_{1-4}$haloalk, —$OC_{1-4}$alk, —$NH_2$, —$NHC_{1-4}$alk, or —$N(C_{1-4}$alk$)C_{1-4}$alk.

Another aspect of the current invention relates to compounds of formula (IV):

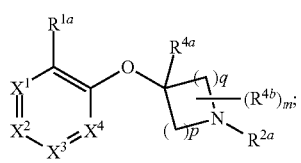

or a pharmaceutically-acceptable salt thereof, wherein:
each of $X^1$, $X^2$, and $X^3$ is independently N or $CR^3$; and $X^4$ is N; wherein no more than one of $X^1$, $X^2$, and $X^3$ are N; and wherein any adjacent $X^1$, $X^2$, and $X^3$ may optionally form an optionally substituted-saturated, -partially saturated, or -unsaturated-heterocyclic or -heteroaryl ring fused to the ring containing $X^1$, $X^2$, $X^3$, and $X^4$;
m is 1, 2, 3, or 4;
each of p and q is independently 0, 1, 2, 3, 4, 5, or 6; wherein the sum of p and q is 2 to 6;
$R^{1a}$ is F, Cl, Br, I, —$OR^a$, or —C(=O)—O—$R^b$;
$R^{2a}$ is —C(=O)$OR^6$;
$R^3$ is H, F, Cl, Br, CN, OH, $OC_{1-4}$alk, $C_{1-4}$alk or $C_{1-4}$haloalk;
$R^{4a}$ is H, $C_{1-4}$alk or $C_{1-4}$haloalk;
each $R^{4b}$ is independently H, F, Cl, Br, CN, OH, $OC_{1-4}$alk, $C_{1-4}$alk, or $C_{1-4}$haloalk;
$R^5$ is H, $C_{1-8}$alk, or $C_{0-8}$alk-$L^3$;
$R^a$ is independently H or $R^b$;

$R^b$ is independently phenyl, benzyl, or $C_{1-6}$alk, wherein said phenyl, benzyl, and $C_{1-6}$alk are being substituted by 0, 1, 2 or 3 substituents selected from halo, $C_{1-4}$alk, $C_{1-3}$haloalk, —OH, —$OC_{1-4}$alk, —$NH_2$, —$NHC_{1-4}$alk, —OC(=O)$C_{1-4}$alk, or —$N(C_{1-4}$alk$)C_{1-4}$alk; and
$L^3$ is independently a carbon-linked or nitrogen-linked saturated, partially-saturated or unsaturated 3-, 4-, 5-, 6-, or 7-membered monocyclic ring or a saturated, partially-saturated or unsaturated 8-, 9-, 10-, 11-, or 12-membered bicyclic ring, wherein each said ring contains 0, 1, 2, 3, or 4 N atoms and 0, 1, or 2 atoms selected from O or S; wherein each $L^1$, $L^2$, $L^3$, and $L^4$ is independently substituted by 0, 1, 2 or 3 $R^2$ groups selected from F, Cl, Br, $C_{1-6}$alk, $C_{1-4}$haloalk, —$OR^a$, —$OC_{1-4}$haloalk, CN, —C(=O)$R^b$, —C(=O)$OR^a$, —C(=O)$NR^aR^a$, —C(=$NR^a$)$NR^aR^a$, —OC(=O)$R^b$, —OC(=O)$NR^aR^a$, —$OC_{2-6}$alk$NR^aR^a$, —$OC_{2-6}$alk$OR^a$, —$SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{2-6}$alk$NR^aR^a$, —$NR^aC_{2-6}$alk$OR^a$, —$C_{1-6}$alk$NR^aR^a$, —$C_{1-6}$alk$OR^a$, —$C_{1-6}$alkN($R^a$)C(=O)$R^b$, —$C_{1-6}$alkOC(=O)$R^b$, —$C_{1-6}$alkC(=O)$NR^aR^a$, —$C_{1-6}$alkC(=O)$OR^a$ or oxo; provided that the compound is not

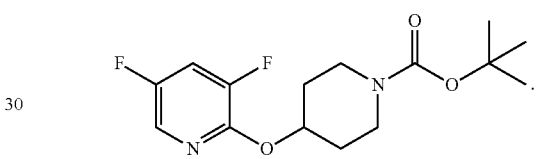

In another embodiment of the compound of formula (III), $R^2$ is —C(=O)$OR^5$ wherein $R^5$ is H, $C_{1-8}$alk, $C_{0-8}$alk-phenyl, $C_{0-8}$alk-benzimidazolyl, $C_{0-8}$alk-pyrimidinyl, $C_{0-8}$alk-pyridinyl, $C_{0-8}$alk-imidazolyl, $C_{0-8}$alk-benzthiazolyl, $C_{0-8}$alk-pyrrolyl, $C_{0-8}$alk-quinolinyl, $C_{0-8}$alk-pyrrolyl, or $C_{0-8}$alk-indolyl.

Another aspect of the invention relates to a method of treating conditions that may be treated with PDE10 inhibitors comprising the step of administering to a patient in need thereof a therapeutically effective amount of any one of the above compounds, or a pharmaceutically acceptable salt thereof.

In one embodiment of the method, said conditions is psychoses, Parkinson's disease, dementias, obsessive compulsive disorder, tardive dyskinesia, choreas, depression, mood disorders, impulsivity, drug addiction, attention deficit/hyperactivity disorder (ADHD), depression with parkinsonian states, personality changes with caudate or putamen disease, dementia and mania with caudate and pallidal diseases, or compulsions with pallidal disease.

In another embodiment of the method, said condition is schizophrenia, Huntington's disease, bipolar disorder, or obsessive-compulsive disorder.

In another embodiment of the method, said condition is schizophrenia.

Another aspect of the invention relates to a pharmaceutical composition comprising any one of the above compounds, or a pharmaceutically acceptable salt thereof, and a pharmaceutically-acceptable excipient.

Another aspect of the invention relates to the use of any one of the above compounds, or a pharmaceutically acceptable salt thereof, as a medicament.

Another aspect of the invention relates to the use of any one of the above compounds, or a pharmaceutically acceptable salt thereof in the manufacture of a medicament for the treatment of schizophrenia, bipolar disorder, or obsessive-compulsive disorder.

Another aspect of the invention relates to a compound, or a pharmaceutically acceptable salt thereof, which is listed below:

1H-Benzo[d]imidazol-2-yl)(4-(3-(pyridine-4-yl)pyrazin-2-yloxy)piperidin-1-yl)methanone;
1-(4-(3-(1-(1H-Benzo[d]imidazol-2-carbonyl)piperidin-4-yloxy)pyrazin-2-yl)-5,6-dihydropyridin-1(2H)-yl)ethanone;
1-(4-(3-(1-(1H-benzo[d]imidazole-2-carbonyl)piperidin-4-yloxy)pyrazin-2-yl)piperidin-1-yl)ethanone;
1-(4-(3-(1-(1H-benzo[d]imidazole-2-carbonyl)azetidin-3-yloxy)pyrazin-2-yl)-5,6-dihydropyridin-1(2H)-yl)ethanone;
1-(4-(3-(1-(1H-benzo[d]imidazole-2-carbonyl)azetidin-3-yloxy)pyrazin-2-yl)piperidin-1-yl)ethanone;
1-(4-(3-(1-(1H-pyrrole-2-carbonyl)azetidin-3-yloxy)pyrazin-2-yl)piperidin-1-yl)ethanone;
1-(3-(2-(1-picolinoylazetidin-3-yloxy)pyridin-3-yl)piperidin-1-yl)ethanone;
(R) and (S)-1-(3-(2-(1-(1H-benzo[d]imidazole-2-carbonyl)azetidin-3-yloxy)pyridin-3-yl)piperidin-1-yl)ethanone;
(1H-benzo[d]imidazol-2-yl)(3-(pyrazin-2-yloxy)azetidin-1-yl)methanone;
(1H-benzo[d]imidazol-2-yl)(3-((3-chloropyrazin-2-yl)oxy)azetidin-1-yl)methanone;
(R) and (S)-1-(3-(2-(1-(1H-benzo[d]imidazole-2-carbonyl)azetidin-3-yloxy)pyridin-3-yl)piperidin-1-yl)-2-methylpropan-1-one;
(1H-benzo[d]imidazol-2-yl)(3-((3-(3,6-dihydro-2H-pyran-4-yl)pyrazin-2-yl)oxy)azetidin-1-yl)methanone;
benzyl 3-((3-chloropyrazin-2-yl)oxy)azetidine-1-carboxylate;
tert-butyl 3-((3-((1r,4r)-4-hydroxycyclohexyl)pyridin-2-yl)oxy)azetidine-1-carboxylate;
(1H-benzo[d]imidazol-2-yl)(3-(3-(tetrahydro-2H-pyran-4-yl)pyridin-2-yloxy)azetidin-1-yl)methanone;
(1H-benzo[d]imidazol-2-yl)(3-(3-(tetrahydro-2H-pyran-4-yl)pyrazin-2-yloxy)azetidin-1-yl)methanone;
benzyl 3-((3-(1-acetyl-4-hydroxypiperidin-4-yl)pyrazin-2-yl)oxy)azetidine-1-carboxylate;
(1H-benzo[d]imidazol-2-yl)(3-((3-morpholinopyrazin-2-yl)oxy)azetidin-1-yl)methanone;
tert-butyl 3-(3-((1-(1H-benzo[d]imidazole-2-carbonyl)azetidin-3-yl)oxy)pyrazin-2-yl)-5,6-dihydropyridine-1(2H)-carboxylate;
tert-butyl 5-(3-((1-(1H-benzo[d]imidazole-2-carbonyl)azetidin-3-yl)oxy)pyrazin-2-yl)-3,4-dihydropyridine-1(2H)-carboxylate;
1-(4-(3-(1-(1H-benzo[d]imidazole-2-carbonyl)azetidin-3-yloxy)pyrazin-2-yl)piperazin-1-yl)ethanone;
(1H-benzo[d]imidazol-2-yl)(3-((3-((1r,4r)-4-hydroxycyclohexyl)pyridin-2-yl)oxy)azetidin-1-yl)methanone;
(1H-benzo[d]imidazol-2-yl)(3-((3-((1s,4s)-4-hydroxycyclohexyl)pyridin-2-yl)oxy)azetidin-1-yl)methanone;
benzyl 3-((3-(3,6-dihydro-2H-pyran-4-yl)quinoxalin-2-yl)oxy)azetidine-1-carboxylate;
(1H-benzo[d]imidazol-2-yl)(3-(3-(2-methylpyridin-4-yl)pyrazin-2-yloxy)azetidin-1-yl)methanone;
1-(4-(3-(1-(1H-pyrrole-2-carbonyl)azetidin-3-yloxy)pyrazin-2-yl)-5,6-dihydropyridin-1(2H)-yl)ethanone;
benzyl 3-((3-(pyridin-4-yl)pyrazin-2-yl)oxy)azetidine-1-carboxylate;

(1H-benzo[d]imidazol-2-yl)(3-(3-(4-(tert-butyldimethylsilyloxy)cyclohex-1-enyl)pyrazin-2-yloxy)azetidin-1-yl)methanone;
(S)-1-(3-(2-((1-(1H-benzo[d]imidazole-2-carbonyl)azetidin-3-yl)oxy)pyridin-3-yl)piperidin-1-yl)-2-methylpropan-1-one OR(R)-1-(3-(2-((1-(1H-benzo[d]imidazole-2-carbonyl)azetidin-3-yl)oxy)pyridin-3-yl)piperidin-1-yl)-2-methylpropan-1-one;
(S)-1-(3-(2-((1-(1H-benzo[d]imidazole-2-carbonyl)azetidin-3-yl)oxy)pyridin-3-yl)piperidin-1-yl)-2-methylpropan-1-one OR(R)-1-(3-(2-((1-(1H-benzo[d]imidazole-2-carbonyl)azetidin-3-yl)oxy)pyridin-3-yl)piperidin-1-yl)-2-methylpropan-1-one;
(1H-benzo[d]imidazol-2-yl)(3-((3-(tetrahydro-2H-pyran-4-yl)quinoxalin-2-yl)oxy)azetidin-1-yl)methanone;
(1H-benzo[d]imidazol-2-yl)(3-(3-(pyridin-3-yl)pyrazin-2-yloxy)azetidin-1-yl)methanone;
1-(3-(2-((1-(1H-indole-2-carbonyl)azetidin-3-yl)oxy)pyridin-3-yl)piperidin-1-yl)ethanone;
(R) and (S)-1-(3-(2-(1-(6-methylnicotinoyl)azetidin-3-yloxy)pyridin-3-yl)piperidin-1-yl)ethanone;
benzyl 3-(3'-methoxy-3,4'-bipyridin-2-yloxy)azetidine-1-carboxylate;
1-(3-(3-((1-(1H-benzo[d]imidazole-2-carbonyl)azetidin-3-yl)oxy)pyrazin-2-yl)-5,6-dihydropyridin-1(2H)-yl)ethanone;
tert-butyl 3-(3-(1-acetylpiperidin-4-yl)pyridin-2-yloxy)azetidine-1-carboxylate;
tert-butyl 3-(3-(3,6-dihydro-2H-pyran-4-yl)pyridin-2-yloxy)azetidine-1-carboxylate;
(R) and (S)-1-(3-(3-(1-acetylpiperidin-3-yl)pyridin-2-yloxy)azetidin-1-yl)-3,3-dimethylbutan-1-one;
1-(3-(2-((1-(4-methyl-1H-pyrrole-2-carbonyl)azetidin-3-yl)oxy)pyridin-3-yl)piperidin-1-yl)ethanone;
1-(4-(3-(1-(4-methyl-1H-pyrrole-2-carbonyl)azetidin-3-yloxy)pyrazin-2-yl)-5,6-dihydropyridin-1(2H)-yl)ethanone;
(1H-benzo[d]imidazol-2-yl)(3-((3-(3,6-dihydro-2H-pyran-4-yl)pyridin-2-yl)oxy)azetidin-1-yl)methanone;
1-(4-(2-(1-(1H-benzo[d]imidazole-2-carbonyl)azetidin-3-yloxy)pyridin-3-yl)piperidin-1-yl)ethanone;
1-(4-(2-((1-(1H-benzo[d]imidazole-2-carbonyl)azetidin-3-yl)oxy)pyridin-3-yl)-4-methoxypiperidin-1-yl)ethanone;
1-(4-(2-((1-(1H-benzo[d]imidazole-2-carbonyl)azetidin-3-yl)oxy)pyridin-3-yl)-3-methoxypiperidin-1-yl)ethanone;
(1H-benzo[d]imidazol-2-yl)(3-((3-(4-hydroxypiperidin-1-yl)pyrazin-2-yl)oxy)azetidin-1-yl)methanone;
4-(3-(1-(1H-benzo[d]imidazole-2-carbonyl)azetidin-3-yloxy)pyrazin-2-yl)cyclohexanone;
tert-butyl 3-(3-(4-hydroxycyclohex-1-enyl)pyridin-2-yloxy)azetidine-1-carboxylate;
(1H-benzo[d]imidazol-2-yl)(3-(3-(4-hydroxycyclohex-1-enyl)pyridin-2-yloxy)azetidin-1-yl)methanone;
1-(4-(3-(1-(5-methylpicolinoyl)azetidin-3-yloxy)pyrazin-2-yl)-5,6-dihydropyridin-1(2H)-yl)ethanone;
1-(4-(3-(1-(benzo[d]thiazol-2-yl)azetidin-3-yloxy)pyrazin-2-yl)-5,6-dihydropyridin-1(2H)-yl)ethanone;
1-(4-(2-(1-(1H-benzo[d]imidazole-2-carbonyl)azetidin-3-yloxy)pyridin-3-yl)-5,6-dihydropyridin-1(2H)-yl)ethanone;
Benzyl 3-(3-(1-acetyl-1,2,3,6-tetrahydropyridin-4-yl)pyrazin-2-yloxy)azetidine-1-carboxylate;
1-(4-(3-(1-(quinolin-2-yl)azetidin-3-yloxy)pyrazin-2-yl)-5,6-dihydropyridin-1(2H)-yl)ethanone;

(S)-1-(3-(2-((1-(1H-indole-2-carbonyl)azetidin-3-yl)oxy)pyridin-3-yl)piperidin-1-yl)ethanone OR(R)-1-(3-(2-((1-(1H-indole-2-carbonyl)azetidin-3-yl)oxy)pyridin-3-yl)piperidin-1-yl)ethanone;

(S)-1-(3-(2-((1-(1H-indole-2-carbonyl)azetidin-3-yl)oxy)pyridin-3-yl)piperidin-1-yl)ethanone OR(R)-1-(3-(2-((1-(1H-indole-2-carbonyl)azetidin-3-yl)oxy)pyridin-3-yl)piperidin-1-yl)ethanone;

1-(4-(2-(1-(benzo[d]thiazol-2-yl)azetidin-3-yloxy)pyridin-3-yl)-5,6-dihydropyridin-1(2H)-yl)ethanone;

1-(4-(2-(1-(quinolin-2-yl)azetidin-3-yloxy)pyridin-3-yl)-5,6-dihydropyridin-1(2H)-yl)ethanone;

(S)-(1H-benzo[d]imidazol-2-yl)(3-(3-(3,6-dihydro-2H-pyran-4-yl)pyridin-2-yloxy)pyrrolidin-1-yl)methanone;

(S)-(1H-benzo[d]imidazol-2-yl)(3-(3-(3,6-dihydro-2H-pyran-4-yl)pyrazin-2-yloxy)pyrrolidin-1-yl)methanone;

(S)-1-(3-(2-((1-(1H-benzo[d]imidazole-2-carbonyl)azetidin-3-yl)oxy)pyridin-3-yl)piperidin-1-yl)ethanone OR(R)-1-(3-(2-((1-(1H-benzo[d]imidazole-2-carbonyl)azetidin-3-yl)oxy)pyridin-3-yl)piperidin-1-yl)ethanone;

(S)-1-(3-(2-((1-(1H-benzo[d]imidazole-2-carbonyl)azetidin-3-yl)oxy)pyridin-3-yl)piperidin-1-yl)ethanone OR(R)-1-(3-(2-((1-(1H-benzo[d]imidazole-2-carbonyl)azetidin-3-yl)oxy)pyridin-3-yl)piperidin-1-yl)ethanone;

(3-((3-(3,6-dihydro-2H-pyran-4-yl)pyridin-2-yl)oxy)azetidin-1-yl)(pyrimidin-4-yl)methanone;

(3-methylpyridin-2-yl)(4-(3-(tetrahydro-2H-pyran-4-yl)pyridin-2-yloxy)piperidin-1-yl)methanone;

1-(4-(3-(1-(1H-benzo[d]imidazol-2-yl)azetidin-3-yloxy)pyrazin-2-yl)piperidin-1-yl)ethanone;

1-(4-(3-(1-(quinolin-2-yl)azetidin-3-yloxy)pyrazin-2-yl)piperidin-1-yl)ethanone;

pyridin-2-yl(4-(3-(tetrahydro-2H-pyran-4-yl)pyridin-2-yloxy)piperidin-1-yl)methanone;

(S)-(1H-benzo[d]imidazol-2-yl)(3-(3-(tetrahydro-2H-pyran-4-yl)pyridin-2-yloxy)pyrrolidin-1-yl)methanone;

(5-methylpyridin-2-yl)(4-(3-(tetrahydro-2H-pyran-4-yl)pyridin-2-yloxy)piperidin-1-yl)methanone;

(6-methylpyridin-2-yl)(4-(3-(tetrahydro-2H-pyran-4-yl)pyridin-2-yloxy)piperidin-1-yl)methanone;

(R)-(1H-benzo[d]imidazol-2-yl)(3-(3-(3,6-dihydro-2H-pyran-4-yl)pyrazin-2-yloxy)pyrrolidin-1-yl)methanone;

(1H-imidazol-2-yl)(4-(3-(tetrahydro-2H-pyran-4-yl)pyridin-2-yloxy)piperidin-1-yl)methanone;

(4-methylpyridin-2-yl)(4-(3-(tetrahydro-2H-pyran-4-yl)pyridin-2-yloxy)piperidin-1-yl)methanone;

benzo[d]thiazol-2-yl(4-(3-(tetrahydro-2H-pyran-4-yl)pyridin-2-yloxy)piperidin-1-yl)methanone;

(1H-benzo[d]imidazol-2-yl)(4-((3-(tetrahydro-2H-pyran-4-yl)pyridin-2-yl)oxy)piperidin-1-yl)methanone;

(R)-(1H-benzo[d]imidazol-2-yl)(3-((3-(tetrahydro-2H-pyran-4-yl)pyridin-2-yl)oxy)pyrrolidin-1-yl)methanone;

(1H-pyrrol-2-yl)(4-(3-(tetrahydro-2H-pyran-4-yl)pyridin-2-yloxy)piperidin-1-yl)methanone;

isoquinolin-3-yl(4-(3-(tetrahydro-2H-pyran-4-yl)pyridin-2-yloxy)piperidin-1-yl)methanone;

2-(1-(4-methylpyridin-2-yl)piperidin-4-yloxy)-3-(tetrahydro-2H-pyran-4-yl)pyridine;

2-(1-(5-methylpyridin-2-yl)piperidin-4-yloxy)-3-(tetrahydro-2H-pyran-4-yl)pyridine;

2-(1-(6-methylpyridin-2-yl)piperidin-4-yloxy)-3-(tetrahydro-2H-pyran-4-yl)pyridine;

(R)-(1H-benzo[d]imidazol-2-yl)(3-(3-(3,6-dihydro-2H-pyran-4-yl)pyridin-2-yloxy)pyrrolidin-1-yl)methanone;

2-(1-(pyridin-2-yl)piperidin-4-yloxy)-3-(tetrahydro-2H-pyran-4-yl)pyridine;

2-(1-(pyridin-2-yl)piperidin-4-yloxy)-3-(tetrahydro-2H-pyran-4-yl)pyrazine;

3-methyl-2-(4-(3-(tetrahydro-2H-pyran-4-yl)pyridin-2-yloxy)piperidin-1-yl)pyridine;

2-(4-(3-(tetrahydro-2H-pyran-4-yl)pyridin-2-yloxy)piperidin-1-yl)quinoline;

(R)-(1H-benzo[d]imidazol-2-yl)(3-(3-(tetrahydro-2H-pyran-4-yl)pyrazin-2-yloxy)pyrrolidin-1-yl)methanone;

2-(1-(3-methylpyridin-2-yl)piperidin-4-yloxy)-3-(tetrahydro-2H-pyran-4-yl)pyrazine;

2-(1-(4-methylpyridin-2-yl)piperidin-4-yloxy)-3-(tetrahydro-2H-pyran-4-yl)pyrazine;

2-(1-(6-methylpyridin-2-yl)piperidin-4-yloxy)-3-(tetrahydro-2H-pyran-4-yl)pyrazine;

2-(4-(3-(tetrahydro-2H-pyran-4-yl)pyrazin-2-yloxy)piperidin-1-yl)quinoline;

1-(3-(3-(tetrahydro-2H-pyran-4-yl)pyrazin-2-yloxy)azetidin-1-yl)isoquinoline;

2-(3-((3-(tetrahydro-2H-pyran-4-yl)pyridin-2-yl)oxy)azetidin-1-yl)quinoline;

1-(4-(3-(tetrahydro-2H-pyran-4-yl)pyrazin-2-yloxy)piperidin-1-yl)isoquinoline;

1-(4-(3-(tetrahydro-2H-pyran-4-yl)pyridin-2-yloxy)piperidin-1-yl)isoquinoline;

(R)-1-(3-(3-(tetrahydro-2H-pyran-4-yl)pyridin-2-yloxy)pyrrolidin-1-yl)isoquinoline;

(R)-2-(3-(3-(tetrahydro-2H-pyran-4-yl)pyridin-2-yloxy)pyrrolidin-1-yl)quinoline;

(S)-3-(3-(3-(tetrahydro-2H-pyran-4-yl)pyrazin-2-yloxy)pyrrolidin-1-yl)isoquinoline;

3-(4-(3-(tetrahydro-2H-pyran-4-yl)pyrazin-2-yloxy)piperidin-1-yl)isoquinoline;

2-(4-(3-(tetrahydro-2H-pyran-4-yl)pyrazin-2-yloxy)piperidin-1-yl)-1H-indole;

(S)-2-(3-(3-(tetrahydro-2H-pyran-4-yl)pyridin-2-yloxy)pyrrolidin-1-yl)quinoline;

(R)-1-(3-(3-(tetrahydro-2H-pyran-4-yl)pyrazin-2-yloxy)pyrrolidin-1-yl)isoquinoline;

(S)-1-(3-(3-(tetrahydro-2H-pyran-4-yl)pyridin-2-yloxy)pyrrolidin-1-yl)isoquinoline;

3-(3-(3-(tetrahydro-2H-pyran-4-yl)pyrazin-2-yloxy)azetidin-1-yl)isoquinoline;

3-(4-(3-(tetrahydro-2H-pyran-4-yl)pyridin-2-yloxy)piperidin-1-yl)isoquinoline;

(S)-3-(3-(3-(tetrahydro-2H-pyran-4-yl)pyridin-2-yloxy)pyrrolidin-1-yl)isoquinoline;

(S)-2-(3-(3-(tetrahydro-2H-pyran-4-yl)pyridin-2-yloxy)pyrrolidin-1-yl)-1H-benzo[d]imidazole;

(R)-2-(3-(3-(tetrahydro-2H-pyran-4-yl)pyrazin-2-yloxy)pyrrolidin-1-yl)quinoline;

(R)-2-(3-((3-(tetrahydro-2H-pyran-4-yl)pyridin-2-yl)oxy)pyrrolidin-1-yl)quinoline;

(R)-2-(3-(3-(tetrahydro-2H-pyran-4-yl)pyridin-2-yloxy)pyrrolidin-1-yl)-1H-benzo[d]imidazole;

(4-chloropyridin-2-yl)(4-(3-(tetrahydro-2H-pyran-4-yl)pyridin-2-yloxy)piperidin-1-yl)methanone;

(5-chloropyridin-2-yl)(4-(3-(tetrahydro-2H-pyran-4-yl)pyridin-2-yloxy)piperidin-1-yl)methanone;

(S)-2-(3-(3-(tetrahydro-2H-pyran-4-yl)pyrazin-2-yloxy)pyrrolidin-1-yl)quinoline;

2-(3-(3-(tetrahydro-2H-pyran-4-yl)pyrazin-2-yloxy)azetidin-1-yl)-1H-benzo[d]imidazole;

2-(4-(3-(tetrahydro-2H-pyran-4-yl)pyridin-2-yloxy)piperidin-1-yl)-1H-benzo[d]imidazole;

(R)-2-(3-(3-(tetrahydro-2H-pyran-4-yl)pyrazin-2-yloxy)pyrrolidin-1-yl)-1H-benzo[d]imidazole;

(S)-1-(3-(3-(tetrahydro-2H-pyran-4-yl)pyrazin-2-yloxy)pyrrolidin-1-yl)isoquinoline;
2-(3-(3-(tetrahydro-2H-pyran-4-yl)pyridin-2-yloxy)azetidin-1-yl)quinoline;
(R)-3-(3-(3-(tetrahydro-2H-pyran-4-yl)pyridin-2-yloxy)pyrrolidin-1-yl)isoquinoline;
1-(4-(2-(1-(quinolin-2-yl)piperidin-4-yloxy)pyridin-3-yl)piperidin-1-yl)ethanone;
2-(4-(3-(piperidin-4-yl)pyridin-2-yloxy)piperidin-1-yl)quinoline;
2-methoxy-1-(4-(3-(1-(quinolin-2-yl)piperidin-4-yloxy)pyrazin-2-yl)piperidin-1-yl)ethanone;
1-(4-(2-((1-(6-chloropyridin-2-yl)piperidin-4-yl)oxy)pyridin-3-yl)piperidin-1-yl)ethanone;
(S)-2-(3-((3-(tetrahydro-2H-pyran-4-yl)pyrazin-2-yl)oxy)pyrrolidin-1-yl)-1H-benzo[d]imidazole;
2-(4-((3-(2-methoxypyridin-3-yl)pyrazin-2-yl)oxy)piperidin-1-yl)quinoline;
1-(4-(2-((1-(pyridin-2-yl)piperidin-4-yl)oxy)pyridin-3-yl)piperidin-1-yl)ethanone;
1-(4-(2-((1-(6-methylpyridin-2-yl)piperidin-4-yl)oxy)pyridin-3-yl)piperidin-1-yl)ethanone;
1-(4-(3-((1-(6-chloropyridin-2-yl)piperidin-4-yl)oxy)pyrazin-2-yl)piperidin-1-yl)ethanone;
1-(4-(2-((1-(4-chloropyridin-2-yl)piperidin-4-yl)oxy)pyridin-3-yl)piperidin-1-yl)ethanone;
2-(4-((3-(pyridin-3-yl)pyrazin-2-yl)oxy)piperidin-1-yl)quinoline;
2-(4-((3-(pyridin-4-yl)pyrazin-2-yl)oxy)piperidin-1-yl)quinoline;
1-(4-(3-((1-(pyridin-2-yl)piperidin-4-yl)oxy)pyrazin-2-yl)piperidin-1-yl)ethanone;
1-(4-(2-((1-(4-methylpyridin-2-yl)piperidin-4-yl)oxy)pyridin-3-yl)piperidin-1-yl)ethanone;
1-(4-(2-((1-(3-methylpyridin-2-yl)piperidin-4-yl)oxy)pyridin-3-yl)piperidin-1-yl)ethanone;
1-(4-(2-((1-(5-chloropyridin-2-yl)piperidin-4-yl)oxy)pyridin-3-yl)piperidin-1-yl)ethanone;
1-(4-(2-((1-(3-chloropyridin-2-yl)piperidin-4-yl)oxy)pyridin-3-yl)piperidin-1-yl)ethanone;
1-(3-((1-(quinolin-2-yl)piperidin-4-yloxy)pyrazin-2-yl)piperidin-4-ol;
2-(4-((3-(4-methoxypiperidin-1-yl)pyrazin-2-yl)oxy)piperidin-1-yl)quinoline;
1-methyl-4-(3-((1-(quinolin-2-yl)azetidin-3-yl)oxy)pyrazin-2-yl)piperazin-2-one;
(1-(3-((1-(quinolin-2-yl)azetidin-3-yl)oxy)pyrazin-2-yl)piperidin-3-yl)methanol;
(1-(3-((1-(quinolin-2-yl)azetidin-3-yl)oxy)pyrazin-2-yl)piperidin-4-yl)methanol;
2-(1-(3-((1-(2-quinolinyl)-3-azetidinyl)oxy)-2-pyrazinyl)-4-piperidinyl)ethanol;
1-(3-((1-(quinolin-2-yl)azetidin-3-yl)oxy)pyrazin-2-yl)piperidine-4-carbonitrile;
((2S)-1-(3-((1-(2-quinolinyl)-3-azetidinyl)oxy)-2-pyrazinyl)-2-pyrrolidinyl)methanol;
1-(3-((1-(quinolin-2-yl)azetidin-3-yl)oxy)pyrazin-2-yl)pyrrolidin-3-ol;
2-(4-(3-((1-(2-quinolinyl)-3-azetidinyl)oxy)-2-pyrazinyl)-1-piperazinyl)ethanol;
2-(3-((3-(4-(1-pyrrolidinyl)-1-piperidinyl)-2-pyrazinyl)oxy)-1-azetidinyl)quinoline;
N,N-dimethyl-1-(3-((1-(2-quinolinyl)oxy)-2-pyrazinyl)-4-piperidinamine;
2-methyl-4-(3-((1-(quinolin-2-yl)azetidin-3-yl)oxy)pyrazin-2-yl)morpholine;
(4-(3-((1-(quinolin-2-yl)azetidin-3-yl)oxy)pyrazin-2-yl)morpholin-2-yl)methanol;
2-(3-((3-(4-(trifluoromethyl)piperidin-1-yl)pyrazin-2-yl)oxy)azetidin-1-yl)quinoline;
1-(3-((1-(2-quinolinyl)-3-azetidinyl)oxy)-2-pyrazinyl)-3-azetidinol;
isoquinolin-1-yl(4-((3-(tetrahydro-2H-pyran-4-yl)pyridin-2-yl)oxy)piperidin-1-yl)methanone;
quinolin-2-yl(4-((3-(tetrahydro-2H-pyran-4-yl)pyrazin-2-yl)oxy)piperidin-1-yl)methanone;
1-(4-(3-((1-(4-methylpyridin-2-yl)piperidin-4-yl)oxy)pyrazin-2-yl)piperidin-1-yl)ethanone;
1-(4-(3-((1-(5-chloropyridin-2-yl)piperidin-4-yl)oxy)pyrazin-2-yl)piperidin-1-yl)ethanone;
1-(4-(3-((1-(4-chloropyridin-2-yl)piperidin-4-yl)oxy)pyrazin-2-yl)piperidin-1-yl)ethanone;
1-(4-(3-((1-(3-chloropyridin-2-yl)piperidin-4-yl)oxy)pyrazin-2-yl)piperidin-1-yl)ethanone;
(S)-1-(3-((1-(quinolin-2-yl)piperidin-4-yl)oxy)pyrazin-2-yl)pyrrolidin-3-ol;
(R)-1-(3-((1-(quinolin-2-yl)piperidin-4-yl)oxy)pyrazin-2-yl)pyrrolidin-3-ol;
2-{4-[3-(2-Methyl-pyridin-4-yl)-pyrazin-2-yloxy]-piperidin-1-yl}-quinoline;
2-(3-((3-(3,6-dihydro-2H-pyran-4-yl)pyrazin-2-yl)oxy)azetidin-1-yl)quinoline;
2-(3-((3-(5-benzyl-1-benzofuran-2-yl)-2-pyrazinyl)oxy)-1-azetidinyl)quinoline;
6-(3-((1-(2-quinolinyl)-3-azetidinyl)oxy)-2-pyrazinyl)-2-quinazolinamine;
2-(3-((3-(6-methoxy-3-pyridinyl)-2-pyrazinyl)oxy)-1-azetidinyl)quinoline;
2-(3-((3-(1,3-benzothiazol-5-yl)-2-pyrazinyl)oxy)-1-azetidinyl)quinoline;
2-(3-((3-(6-chloro-3-pyridinyl)-2-pyrazinyl)oxy)-1-azetidinyl)quinoline;
2-(3-((3-(3-bromophenyl)-2-pyrazinyl)oxy)-1-azetidinyl)quinoline;
(3-(3-((1-(2-quinolinyl)-3-azetidinyl)oxy)-2-pyrazinyl)phenyl)methanol;
(4-(3-((1-(2-quinolinyl)-3-azetidinyl)oxy)-2-pyrazinyl)phenyl)methanol;
2-(3-((3-(5-quinolinyl)-2-pyrazinyl)oxy)-1-azetidinyl)quinoline;
2-(3-((3-(5-phenyl-2-thiophenyl)-2-pyrazinyl)oxy)-1-azetidinyl)quinoline;
2-(3-((3-(3-pyridinyl)-2-pyrazinyl)oxy)-1-azetidinyl)quinoline;
2-(3-((3-(3-quinolinyl)-2-pyrazinyl)oxy)-1-azetidinyl)quinoline;
methyl 4-(3-((1-(2-quinolinyl)-3-azetidinyl)oxy)-2-pyrazinyl)benzoate;
2-(3-((3-(3-fluoro-5-(1-methylethoxy)phenyl)-2-pyrazinyl)oxy)-1-azetidinyl)quinoline;
2-(3-((3-(5-pyrimidinyl)-2-pyrazinyl)oxy)-1-azetidinyl)quinoline;
2-(3-((3-(2-methylpyridin-4-yl)pyrazin-2-yl)oxy)azetidin-1-yl)quinoline;
2-(3-((3-(2-methyl-4-pyridinyl)-2-pyrazinyl)oxy)-1-azetidinyl)quinoline;
2-(3-((3-(6-(cyclopropylmethoxy)-3-pyridinyl)-2-pyrazinyl)oxy)-1-azetidinyl)quinoline;
2-(3-((3-(6-methyl-3-pyridinyl)-2-pyrazinyl)oxy)-1-azetidinyl)quinoline;
2-(3-(3-((3-methyloxetan-3-yl)ethynyl)pyrazin-2-yloxy)azetidin-1-yl)quinoline;

4-(2-((1-(quinolin-2-yl)azetidin-3-yl)oxy)pyridin-3-yl)morpholine;
2-((1-(5-nitropyridin-2-yl)piperidin-4-yl)oxy)-3-(tetrahydro-2H-pyran-4-yl)pyridine;
6-(4-((3-(tetrahydro-2H-pyran-4-yl)pyridin-2-yl)oxy)piperidin-1-yl)pyridin-3-amine;
2-((1-(5-chloropyridin-2-yl)piperidin-4-yl)oxy)-3-(tetrahydro-2H-pyran-4-yl)pyridine;
2-((1-(5-bromopyridin-2-yl)piperidin-4-yl)oxy)-3-(tetrahydro-2H-pyran-4-yl)pyridine;
4-(3-((1-(quinolin-2-yl)piperidin-4-yl)oxy)pyrazin-2-yl)morpholine;
2-(4-((3-(azetidin-1-yl)pyrazin-2-yl)oxy)piperidin-1-yl)quinoline;
(6-(4-((3-(tetrahydro-2H-pyran-4-yl)pyridin-2-yl)oxy)piperidin-1-yl)pyridin-3-yl)methanol;
2-((1-(5-fluoropyridin-2-yl)piperidin-4-yl)oxy)-3-(tetrahydro-2H-pyran-4-yl)pyridine;
6-(4-((3-(tetrahydro-2H-pyran-4-yl)pyridin-2-yl)oxy)piperidin-1-yl)nicotinonitrile;
3-(tetrahydro-2H-pyran-4-yl)-2-((1-(5-(trifluoromethyl)pyridin-2-yl)piperidin-4-yl)oxy)pyridine;
1-(6-(4-((3-(tetrahydro-2H-pyran-4-yl)pyridin-2-yl)oxy)piperidin-1-yl)pyridin-3-yl)ethanone;
4-methyl-2-(4-((3-(tetrahydro-2H-pyran-4-yl)pyrazin-2-yl)oxy)piperidin-1-yl)quinoline;
quinolin-2-yl(4-((3-(tetrahydro-2H-pyran-4-yl)pyridin-2-yl)oxy)piperidin-1-yl)methanone;
1-(4-(3-((1-(6-methylpyridin-2-yl)piperidin-4-yl)oxy)pyrazin-2-yl)piperidin-1-yl)ethanone;
1-(4-(3-((1-(3-methylpyridin-2-yl)piperidin-4-yl)oxy)pyrazin-2-yl)piperidin-1-yl)ethanone;
1-(4-(3-((1-(quinolin-2-yl)piperidin-4-yl)oxy)pyrazin-2-yl)piperazin-1-yl)ethanone;
2-(4-((3-(piperidin-1-yl)pyrazin-2-yl)oxy)piperidin-1-yl)quinoline;
2-(4-((3-(pyrrolidin-1-yl)pyrazin-2-yl)oxy)piperidin-1-yl)quinoline;
2-(4-((3-(3-methylpyridin-4-yl)pyrazin-2-yl)oxy)piperidin-1-yl)quinoline;
6-methyl-2-(4-((3-(tetrahydro-2H-pyran-4-yl)pyrazin-2-yl)oxy)piperidin-1-yl)quinoline;
isoquinolin-1-yl(4-((3-(tetrahydro-2H-pyran-4-yl)pyrazin-2-yl)oxy)piperidin-1-yl)methanone;
1-(3-((1-(quinolin-2-yl)piperidin-4-yl)oxy)pyrazin-2-yl)azetidin-3-ol;
2-(4-((3-(3-chloropyridin-4-yl)pyrazin-2-yl)oxy)piperidin-1-yl)quinoline;
6-(3-((1-(quinolin-2-yl)piperidin-4-yl)oxy)pyrazin-2-yl)-2-oxa-6-azaspiro[3.3]heptane;
6-methyl-2-(4-((3-(tetrahydro-2H-pyran-4-yl)pyridin-2-yl)oxy)piperidin-1-yl)quinoline;
4-methyl-2-(4-((3-(tetrahydro-2H-pyran-4-yl)pyridin-2-yl)oxy)piperidin-1-yl)quinoline;
1-(4-(3-((1-(5-methylpyridin-2-yl)piperidin-4-yl)oxy)pyrazin-2-yl)piperidin-1-yl)ethanone;
(1-(3-((1-(quinolin-2-yl)piperidin-4-yl)oxy)pyrazin-2-yl)piperidin-4-yl)methanol;
1-(4-(3-((1-(quinolin-2-yl)azetidin-3-yl)oxy)pyrazin-2-yl)piperazin-1-yl)ethanone;
7-methyl-2-(4-((3-(tetrahydro-2H-pyran-4-yl)pyridin-2-yl)oxy)piperidin-1-yl)quinoline;
methyl 6-(4-((3-(tetrahydro-2H-pyran-4-yl)pyridin-2-yl)oxy)piperidin-1-yl)nicotinate;
1-(4-(2-((1-(5-methylpyridin-2-yl)piperidin-4-yl)oxy)pyridin-3-yl)piperidin-1-yl)ethanone;
1-(3-((1-(quinolin-2-yl)azetidin-3-yl)oxy)pyrazin-2-yl)piperidin-4-ol;
2-(3-((3-(piperidin-1-yl)pyrazin-2-yl)oxy)azetidin-1-yl)quinoline;
4-(3-((1-(quinolin-2-yl)azetidin-3-yl)oxy)pyrazin-2-yl)morpholine;
8-methyl-2-(4-((3-(tetrahydro-2H-pyran-4-yl)pyridin-2-yl)oxy)piperidin-1-yl)quinoline;
7-methyl-2-(4-((3-(tetrahydro-2H-pyran-4-yl)pyrazin-2-yl)oxy)piperidin-1-yl)quinoline;
8-methyl-2-(4-((3-(tetrahydro-2H-pyran-4-yl)pyrazin-2-yl)oxy)piperidin-1-yl)quinoline;
(4-((3-morpholinopyrazin-2-yl)oxy)piperidin-1-yl)(quinolin-2-yl)methanone;
(4-((3-(2-methylpyridin-4-yl)pyrazin-2-yl)oxy)piperidin-1-yl)(quinolin-2-yl)methanone;
isoquinolin-1-yl(4-((3-(2-methylpyridin-4-yl)pyrazin-2-yl)oxy)piperidin-1-yl)methanone;
1-(6-(3-((1-(quinolin-2-yl)piperidin-4-yl)oxy)pyrazin-2-yl)-2,6-diazaspiro[3.3]heptan-2-yl)ethanone;
1-(3-((1-(quinolin-2-yl)piperidin-4-yl)oxy)pyrazin-2-yl)piperidin-4-one;
1-(3-((1-(quinolin-2-yl)azetidin-3-yl)oxy)pyrazin-2-yl)piperidin-4-one;
1-(4-(5-fluoro-2-((1-(quinolin-2-yl)azetidin-3-yl)oxy)pyridin-3-yl)piperidin-1-yl)ethanone;
(4-((3-morpholinopyridin-2-yl)oxy)piperidin-1-yl)(quinolin-2-yl)methanone;
isoquinolin-1-yl(4-((3-morpholinopyridin-2-yl)oxy)piperidin-1-yl)methanone;
isoquinolin-1-yl(4-((3-morpholinopyrazin-2-yl)oxy)piperidin-1-yl)methanone;
(4-((2'-methyl-[3,4'-bipyridin]-2-yl)oxy)piperidin-1-yl)(quinolin-2-yl)methanone;
isoquinolin-1-yl(4-((2'-methyl-[3,4'-bipyridin]-2-yl)oxy)piperidin-1-yl)methanone;
2-(3-((3-(p-tolyl)pyrazin-2-yl)oxy)azetidin-1-yl)quinoline;
2-(1-(3-((1-(quinolin-2-yl)piperidin-4-yl)oxy)pyrazin-2-yl)piperidin-4-yl)propan-2-ol;
2-(1-(3-((1-(quinolin-2-yl)azetidin-3-yl)oxy)pyrazin-2-yl)piperidin-4-yl)propan-2-ol;
6-(4-((3-(tetrahydro-2H-pyran-4-yl)pyridin-2-yl)oxy)piperidin-1-yl)nicotinaldehyde;
2-((1-(5-chloropyridin-2-yl)piperidin-4-yl)oxy)-3-(tetrahydro-2H-pyran-4-yl)pyridine;
2-(3-((3-(4-(methoxymethyl)piperidin-1-yl)pyrazin-2-yl)oxy)azetidin-1-yl)quinoline;
2-(3-((3-(4,4-difluoropiperidin-1-yl)pyrazin-2-yl)oxy)azetidin-1-yl)quinoline;
2-(3-((3-(2-methoxypyridin-3-yl)pyrazin-2-yl)oxy)azetidin-1-yl)quinoline;
2-(3-((3-(o-tolyl)pyrazin-2-yl)oxy)azetidin-1-yl)quinoline;
2-(3-((3-(2-methoxyphenyl)pyrazin-2-yl)oxy)azetidin-1-yl)quinoline;
2-(4-((3-(4-(methoxymethyl)piperidin-1-yl)pyrazin-2-yl)oxy)piperidin-1-yl)quinoline;
2-(3-((3-(pyridin-4-yl)pyrazin-2-yl)oxy)azetidin-1-yl)quinoline;
2-(3-((3-(4-fluoro-2-methylphenyl)pyrazin-2-yl)oxy)azetidin-1-yl)quinoline;
2-(3-((3-phenylpyrazin-2-yl)oxy)azetidin-1-yl)quinoline;
2-(3-((3-(3-chloropyridin-4-yl)pyrazin-2-yl)oxy)azetidin-1-yl)quinoline;
2-(3-((1-(quinolin-2-yl)azetidin-3-yl)oxy)pyrazin-2-yl)benzonitrile;
2-(3-((3-(m-tolyl)pyrazin-2-yl)oxy)azetidin-1-yl)quinoline;

4-(3-((1-(quinolin-2-yl)azetidin-3-yl)oxy)pyrazin-2-yl)benzonitrile;
2-(3-((3-(3-methylpyridin-4-yl)pyrazin-2-yl)oxy)azetidin-1-yl)quinoline;
2-(3-((3-(pyridin-2-yl)pyrazin-2-yl)oxy)azetidin-1-yl)quinoline;
2-(3-((3-(2-fluoropyridin-4-yl)pyrazin-2-yl)oxy)azetidin-1-yl)quinoline;
3-(3-((1-(quinolin-2-yl)azetidin-3-yl)oxy)pyrazin-2-yl)benzonitrile;
N,N-dimethyl-4-(3-((1-(quinolin-2-yl)azetidin-3-yl)oxy)pyrazin-2-yl)benzamide;
1-(4-(2-((1-(quinolin-2-yl)azetidin-3-yl)oxy)pyridin-3-yl)piperidin-1-yl)ethanone;
1-(2-((1-(quinolin-2-yl)azetidin-3-yl)oxy)pyridin-3-yl)piperidine-4-carbonitrile;
2-(3-((3-(4,4-difluoropiperidin-1-yl)pyridin-2-yl)oxy)azetidin-1-yl)quinoline;
1-(5-fluoro-2-((1-(quinolin-2-yl)azetidin-3-yl)oxy)pyridin-3-yl)piperidine-4-carbonitrile;
2-(3-((3-(4,4-difluoropiperidin-1-yl)-5-fluoropyridin-2-yl)oxy)azetidin-1-yl)quinoline;
2-(3-((3-(4-methylpiperidin-1-yl)pyrazin-2-yl)oxy)azetidin-1-yl)quinoline;
2-(3-((3-(5,6-dihydropyridin-1(2H)-yl)pyrazin-2-yl)oxy)azetidin-1-yl)quinoline;
1-(4-(4-((1-(quinolin-2-yl)azetidin-3-yl)oxy)pyrimidin-5-yl)piperidin-1-yl)ethanone;
7-(3-((1-(quinolin-2-yl)azetidin-3-yl)oxy)pyrazin-2-yl)-2-oxa-7-azaspiro[3.5]nonane;
2-methoxy-1-(4-(3-((1-(quinolin-2-yl)azetidin-3-yl)oxy)pyrazin-2-yl)piperidin-1-yl)ethanone;
2-(3-((3-(2-azabicyclo[2.2.1]heptan-2-yl)pyrazin-2-yl)oxy)azetidin-1-yl)quinoline;
2-(3-((3-(3,3-difluoropyrrolidin-1-yl)pyrazin-2-yl)oxy)azetidin-1-yl)quinoline;
2-(3-((3-(azetidin-1-yl)pyrazin-2-yl)oxy)azetidin-1-yl)quinoline;
2-(3-((3-(azepan-1-yl)pyrazin-2-yl)oxy)azetidin-1-yl)quinoline;
2-(3-((3-(pyrrolidin-1-yl)pyrazin-2-yl)oxy)azetidin-1-yl)quinoline;
(R)-(1-(3-((1-(quinolin-2-yl)azetidin-3-yl)oxy)pyrazin-2-yl)pyrrolidin-2-yl)methanol;
1-(4-(3-((1-(quinolin-2-yl)azetidin-3-yl)oxy)pyridazin-4-yl)piperidin-1-yl)ethanone;
(1-(5-bromo-4-((1-(quinolin-2-yl)azetidin-3-yl)oxy)pyrimidin-2-yl)piperidin-4-yl)methanol;
2-(3-((3-(3,3-difluoropiperidin-1-yl)pyrazin-2-yl)oxy)azetidin-1-yl)quinoline;
1-(3-(3-((1-(quinolin-2-yl)azetidin-3-yl)oxy)pyrazin-2-yl)phenyl)ethanone;
(S)-(1-(3-((1-(quinolin-2-yl)pyrrolidin-3-yl)oxy)pyrazin-2-yl)piperidin-4-yl)methanol;
(1-(3-((1-(quinolin-2-yl)azetidin-3-yl)oxy)quinoxalin-2-yl)piperidin-4-yl)methanol;
(1-(3-((1-(quinolin-2-yl)azetidin-3-yl)oxy)pyridazin-4-yl)piperidin-4-yl)methanol;
(1-(6-((1-(quinolin-2-yl)azetidin-3-yl)oxy)pyridazin-4-yl)piperidin-4-yl)methanol;
(R)-(1-(3-((1-(quinolin-2-yl)pyrrolidin-3-yl)oxy)pyrazin-2-yl)piperidin-4-yl)methanol;
1-(4-(3-((1-(quinolin-2-yl)azetidin-3-yl)oxy)pyrazin-2-yl)phenyl)ethanone;
N,N-dimethyl-3-(3-((1-(quinolin-2-yl)azetidin-3-yl)oxy)pyrazin-2-yl)benzamide;
2-(3-((3-(1-(methylsulfonyl)piperidin-4-yl)pyrazin-2-yl)oxy)azetidin-1-yl)quinoline;
3-(3-((3-bromopyridin-2-yl)oxy)azetidin-1-yl)pyridazine;
methyl 4-(3-((1-(quinolin-2-yl)azetidin-3-yl)oxy)pyrazin-2-yl)piperidine-1-carboxylate;
4-(3-((3-bromopyridin-2-yl)oxy)azetidin-1-yl)pyrimidine;
1-(4-(3-((1-(quinolin-2-yl)azetidin-3-yl)oxy)quinoxalin-2-yl)piperidin-1-yl)ethanone;
1-(3-(3-((1-(quinolin-2-yl)azetidin-3-yl)oxy)pyrazin-2-yl)phenyl)ethanol;
4-(3-((1-(quinolin-2-yl)azetidin-3-yl)oxy)pyrazin-2-yl)-1,4-oxazepane;
(1-(3-((1-(quinolin-2-yl)azetidin-3-yl)oxy)pyrazin-2-yl)pyrrolidin-3-yl)methanol;
2-(3-((3-(3-(methoxymethyl)phenyl)pyrazin-2-yl)oxy)azetidin-1-yl)quinoline;
N-methyl-4-(3-((1-(quinolin-2-yl)azetidin-3-yl)oxy)pyrazin-2-yl)benzamide;
(S)-(1-(3-((1-(quinolin-2-yl)piperidin-3-yl)oxy)pyrazin-2-yl)piperidin-4-yl)methanol;
(R)-(1-(3-((1-(quinolin-2-yl)piperidin-3-yl)oxy)pyrazin-2-yl)piperidin-4-yl)methanol;
2-(3-((3-(4-methyl-1,4-diazepan-1-yl)pyrazin-2-yl)oxy)azetidin-1-yl)quinoline;
1-(4-(3-((1-(quinolin-2-yl)azetidin-3-yl)oxy)pyrazin-2-yl)-1,4-diazepan-1-yl)ethanone;
1-(4-(3-((1-(quinolin-2-yl)azetidin-3-yl)oxy)pyrazin-2-yl)phenyl)ethanol;
(S)-2-(3-((3-(2-methylpyridin-4-yl)pyrazin-2-yl)oxy)piperidin-1-yl)quinoline OR (R)-2-(3-((3-(2-methylpyridin-4-yl)pyrazin-2-yl)oxy)piperidin-1-yl)quinoline;
(S)-2-(3-((3-(2-methylpyridin-4-yl)pyrazin-2-yl)oxy)piperidin-1-yl)quinoline OR (R)-2-(3-((3-(2-methylpyridin-4-yl)pyrazin-2-yl)oxy)piperidin-1-yl)quinoline;
2-(3-((3-chloropyrazin-2-yl)oxy)azetidin-1-yl)quinoline;
2-(3-((3-chloropyrazin-2-yl)oxy)piperidin-1-yl)quinoline;
1-(4-(5-methyl-2-((1-(quinolin-2-yl)azetidin-3-yl)oxy)pyridin-3-yl)piperidin-1-yl)ethanone;
1-(3-((1-(quinolin-2-yl)azetidin-3-yl)oxy)pyrazin-2-yl)azepan-4-ol;
(R)-2-(3-((3-(2-methylpyridin-4-yl)pyrazin-2-yl)oxy)pyrrolidin-1-yl)quinoline;
(S)-2-(3-((3-(2-methylpyridin-4-yl)pyrazin-2-yl)oxy)pyrrolidin-1-yl)quinoline;
4-(3-((1-(quinolin-2-yl)azetidin-3-yl)oxy)pyrazin-2-yl)but-3-yn-2-ol;
2-(3-((3-(3-methoxyprop-1-yn-1-yl)pyrazin-2-yl)oxy)azetidin-1-yl)quinoline;
3-(3-((1-(quinolin-2-yl)azetidin-3-yl)oxy)pyrazin-2-yl)prop-2-yn-1-ol;
(1-(5-bromo-4-((1-(quinolin-2-yl)azetidin-3-yl)oxy)pyrimidin-2-yl)piperidin-3-yl)methanol;
(1-(4-((1-(quinolin-2-yl)azetidin-3-yl)oxy)pyrimidin-2-yl)piperidin-4-yl)methanol;
(1-(5-(piperidin-1-yl)-4-((1-(quinolin-2-yl)azetidin-3-yl)oxy)pyrimidin-2-yl)piperidin-4-yl)methanol;
(1-(5-methyl-2-((1-(quinolin-2-yl)azetidin-3-yl)oxy)pyridin-3-yl)piperidin-4-yl)methanol;
(1-(6-((1-(quinolin-2-yl)azetidin-3-yl)oxy)pyrazin-2-yl)piperidin-4-yl)methanol;
(1-(5-(3-methoxyphenyl)-4-((1-(quinolin-2-yl)azetidin-3-yl)oxy)pyrimidin-2-yl)piperidin-4-yl)methanol;
(1-(3-((1-(quinolin-2-yl)azetidin-3-yl)amino)pyrazin-2-yl)piperidin-4-yl)methanol;
(1-(3-((1-(quinoxalin-2-yl)azetidin-3-yl)oxy)pyrazin-2-yl)piperidin-4-yl)methanol;

5-(3-((1-(quinolin-2-yl)azetidin-3-yl)oxy)pyrazin-2-yl)picolinonitrile;
1-(3-((1-(quinolin-2-yl)azetidin-3-yl)oxy)pyrazin-2-yl)piperidine-4-carboxamide;
(1-(5-bromo-4-((1-(quinolin-2-yl)azetidin-3-yl)oxy)pyrimidin-2-yl)piperidin-2-yl)methanol;
(1-(5-bromo-4-((1-(quinoxalin-2-yl)azetidin-3-yl)oxy)pyrimidin-2-yl)piperidin-4-yl)methanol;
1-(1-(3-((1-(quinolin-2-yl)azetidin-3-yl)oxy)pyrazin-2-yl)piperidin-4-yl)ethanol;
(1-(3-((1-(quinazolin-2-yl)azetidin-3-yl)oxy)pyrazin-2-yl)piperidin-4-yl)methanol;
(1-(5-bromo-6-((1-(quinolin-2-yl)azetidin-3-yl)oxy)pyridin-2-yl)piperidin-4-yl)methanol;
methyl 1-(5-bromo-4-((1-(quinolin-2-yl)azetidin-3-yl)oxy)pyrimidin-2-yl)piperidine-4-carboxylate;
(1-(5-fluoro-4-((1-(quinolin-2-yl)azetidin-3-yl)oxy)pyrimidin-2-yl)piperidin-4-yl)methanol;
(1-(5-fluoro-2-((1-(quinolin-2-yl)azetidin-3-yl)oxy)pyridin-3-yl)piperidin-4-yl)methanol;
1-(1-(5-bromo-4-((1-(quinolin-2-yl)azetidin-3-yl)oxy)pyrimidin-2-yl)piperidin-4-yl)ethanol;
(1-(5-bromo-4-((1-(quinazolin-2-yl)azetidin-3-yl)oxy)pyrimidin-2-yl)piperidin-4-yl)methanol;
1-(1-(3-((1-(quinolin-2-yl)azetidin-3-yl)oxy)pyridazin-4-yl)piperidin-4-yl)ethanol;
1-(5-bromo-4-((1-(quinolin-2-yl)azetidin-3-yl)oxy)pyrimidin-2-yl)piperidin-4-ol;
(1-(5-chloro-4-((1-(quinolin-2-yl)azetidin-3-yl)oxy)pyrimidin-2-yl)piperidin-4-yl)methanol;
2-(3-((5-bromo-2-(4-methylpiperidin-1-yl)pyrimidin-4-yl)oxy)azetidin-1-yl)quinoline;
(1-(5-bromo-4-((1-(quinolin-2-yl)azetidin-3-yl)oxy)pyrimidin-2-yl)pyrrolidin-3-yl)methanol;
(1-(5-(2-methoxypyridin-3-yl)-4-((1-(quinolin-2-yl)azetidin-3-yl)oxy)pyrimidin-2-yl)piperidin-4-yl)methanol;
2,3-bis((1-(quinolin-2-yl)azetidin-3-yl)oxy)quinoxaline;
(1-(2-((1-(quinolin-2-yl)piperidin-4-yl)oxy)pyridin-3-yl)piperidin-4-yl)methanol;
(1-(5-(2-methylpyridin-4-yl)-4-((1-(quinolin-2-yl)azetidin-3-yl)oxy)pyrimidin-2-yl)piperidin-4-yl)methanol;
(1-(5-(6-methylpyridin-3-yl)-4-((1-(quinolin-2-yl)azetidin-3-yl)oxy)pyrimidin-2-yl)piperidin-4-yl)methanol;
tert-butyl 4-(3-((1-(quinolin-2-yl)azetidin-3-yl)oxy)quinoxalin-2-yl)piperidine-1-carboxylate;
benzyl 4-(3-((1-(quinolin-2-yl)azetidin-3-yl)oxy)quinoxalin-2-yl)piperidine-1-carboxylate;
(1-(5-(3,6-dihydro-2H-pyran-4-yl)-4-((1-(quinolin-2-yl)azetidin-3-yl)oxy)pyrimidin-2-yl)piperidin-4-yl)methanol;
(1-(4-((1-(quinolin-2-yl)azetidin-3-yl)oxy)pyridin-3-yl)piperidin-4-yl)methanol;
(1-(4-((1-(quinolin-2-yl)azetidin-3-yl)oxy)-5-(tetrahydro-2H-pyran-4-yl)pyrimidin-2-yl)piperidin-4-yl)methanol;
2-(3-((3-(4-methylpiperazin-1-yl)pyrazin-2-yl)oxy)azetidin-1-yl)quinoline;
tert-butyl 4-(2-(4-(hydroxymethyl)piperidin-1-yl)-4-((1-(quinolin-2-yl)azetidin-3-yl)oxy)pyrimidin-5-yl)-5,6-dihydropyridine-1(2H)-carboxylate;
2-(3-((3-(6-fluoropyridin-3-yl)pyrazin-2-yl)oxy)azetidin-1-yl)quinoline;
2-(3-((2-(pyridin-3-yl)pyrimidin-4-yl)oxy)azetidin-1-yl)quinoline;
2-(3-((2-(pyridin-4-yl)pyrimidin-4-yl)oxy)azetidin-1-yl)quinoline;
4-(4-((1-(quinolin-2-yl)azetidin-3-yl)oxy)pyrimidin-2-yl)aniline;
2-(3-((3-(2-methylpyridin-3-yl)pyrazin-2-yl)oxy)azetidin-1-yl)quinoline;
2-(3-((3-(3-methoxyphenyl)pyrazin-2-yl)oxy)azetidin-1-yl)quinoline;
2-(3-((3-(4-methylpyridin-3-yl)pyrazin-2-yl)oxy)azetidin-1-yl)quinoline;
2-(3-((3-(2-methoxypyridin-3-yl)pyrazin-2-yl)oxy)azetidin-1-yl)quinazoline;
2-(3-methoxyphenyl)-3-((1-(quinolin-2-yl)azetidin-3-yl)oxy)quinoxaline;
2-(3-((3-(3-methoxyphenyl)pyrazin-2-yl)oxy)azetidin-1-yl)quinazoline;
2-((1-(quinolin-2-yl)azetidin-3-yl)oxy)-3-(m-tolyl)quinoxaline;
(1-(5-(2-methoxypyridin-3-yl)-4-((1-(quinazolin-2-yl)azetidin-3-yl)oxy)pyrimidin-2-yl)piperidin-4-yl)methanol;
1-(3-((1-(quinolin-2-yl)azetidin-3-yl)oxy)quinoxalin-2-yl)piperidine-4-carbonitrile;
1-(4-(2-(4-(hydroxymethyl)piperidin-1-yl)-4-((1-(quinolin-2-yl)azetidin-3-yl)oxy)pyrimidin-5-yl)piperidin-1-yl)ethanone;
2-(3-((2-(pyridin-2-yl)pyrimidin-4-yl)oxy)azetidin-1-yl)quinoline;
(4-(4-((1-(quinolin-2-yl)azetidin-3-yl)oxy)pyrimidin-2-yl)phenyl)methanol; or
2-(2-methoxypyridin-3-yl)-3-((1-(quinolin-2-yl)azetidin-3-yl)oxy)quinoxaline.

Another aspect of the invention relates to a compound, or a pharmaceutically acceptable salt thereof, which is listed below:
(3-(3-(3,6-dihydro-2H-pyran-4-yl)pyridin-2-yloxy)azetidin-1-yl)(pyrimidin-4-yl)methanone;
2-(3-(3-(tetrahydro-2H-pyran-4-yl)pyrazin-2-yloxy)azetidin-1-yl)quinoline;
(1H-benzo[d]imidazol-2-yl)(4-(3-(tetrahydro-2H-pyran-4-yl)pyridin-2-yloxy)piperidin-1-yl)methanone;
(R)-(1H-benzo[d]imidazol-2-yl)(3-(3-(tetrahydro-2H-pyran-4-yl)pyridin-2-yloxy)pyrrolidin-1-yl)methanone;
(1H-imidazol-2-yl)(4-(3-(tetrahydro-2H-pyran-4-yl)pyridin-2-yloxy)piperidin-1-yl)methanone;
(1H-pyrrol-2-yl)(4-(3-(tetrahydro-2H-pyran-4-yl)pyridin-2-yloxy)piperidin-1-yl)methanone;
pyridin-2-yl(4-(3-(tetrahydro-2H-pyran-4-yl)pyridin-2-yloxy)piperidin-1-yl)methanone;
(6-methylpyridin-2-yl)(4-(3-(tetrahydro-2H-pyran-4-yl)pyridin-2-yloxy)piperidin-1-yl)methanone;
(5-methylpyridin-2-yl)(4-(3-(tetrahydro-2H-pyran-4-yl)pyridin-2-yloxy)piperidin-1-yl)methanone;
(4-methylpyridin-2-yl)(4-(3-(tetrahydro-2H-pyran-4-yl)pyridin-2-yloxy)piperidin-1-yl)methanone;
(3-methylpyridin-2-yl)(4-(3-(tetrahydro-2H-pyran-4-yl)pyridin-2-yloxy)piperidin-1-yl)methanone;
benzo[d]thiazol-2-yl(4-(3-(tetrahydro-2H-pyran-4-yl)pyridin-2-yloxy)piperidin-1-yl)methanone;
isoquinolin-3-yl(4-(3-(tetrahydro-2H-pyran-4-yl)pyridin-2-yloxy)piperidin-1-yl)methanone;
3-(3-(3-(tetrahydro-2H-pyran-4-yl)pyrazin-2-yloxy)azetidin-1-yl)isoquinoline;
1-(3-(3-(tetrahydro-2H-pyran-4-yl)pyrazin-2-yloxy)azetidin-1-yl)isoquinoline;
2-(3-(3-(tetrahydro-2H-pyran-4-yl)pyrazin-2-yloxy)azetidin-1-yl)-1H-benzo[d]imidazole;
2-(3-(3-(tetrahydro-2H-pyran-4-yl)pyridin-2-yloxy)azetidin-1-yl)quinoline;
2-(1-(pyridin-2-yl)piperidin-4-yloxy)-3-(tetrahydro-2H-pyran-4-yl)pyrazine;

2-(1-(3-methylpyridin-2-yl)piperidin-4-yloxy)-3-(tetrahydro-2H-pyran-4-yl)pyrazine;
2-(1-(4-methylpyridin-2-yl)piperidin-4-yloxy)-3-(tetrahydro-2H-pyran-4-yl)pyrazine;
2-(1-(pyridin-2-yl)piperidin-4-yloxy)-3-(tetrahydro-2H-pyran-4-yl)pyridine;
2-(1-(6-methylpyridin-2-yl)piperidin-4-yloxy)-3-(tetrahydro-2H-pyran-4-yl)pyrazine;
3-methyl-2-(4-(3-(tetrahydro-2H-pyran-4-yl)pyridin-2-yloxy)piperidin-1-yl)pyridine;
2-(1-(4-methylpyridin-2-yl)piperidin-4-yloxy)-3-(tetrahydro-2H-pyran-4-yl)pyridine;
2-(1-(5-methylpyridin-2-yl)piperidin-4-yloxy)-3-(tetrahydro-2H-pyran-4-yl)pyridine;
2-(1-(6-methylpyridin-2-yl)piperidin-4-yloxy)-3-(tetrahydro-2H-pyran-4-yl)pyridine;
1-(4-(3-(tetrahydro-2H-pyran-4-yl)pyrazin-2-yloxy)piperidin-1-yl)isoquinoline;
3-(4-(3-(tetrahydro-2H-pyran-4-yl)pyrazin-2-yloxy)piperidin-1-yl)isoquinoline;
2-(4-(3-(tetrahydro-2H-pyran-4-yl)pyrazin-2-yloxy)piperidin-1-yl)quinoline;
2-(4-(3-(tetrahydro-2H-pyran-4-yl)pyrazin-2-yloxy)piperidin-1-yl)-1H-indole;
1-(4-(3-(tetrahydro-2H-pyran-4-yl)pyridin-2-yloxy)piperidin-1-yl)isoquinoline;
3-(4-(3-(tetrahydro-2H-pyran-4-yl)pyridin-2-yloxy)piperidin-1-yl)isoquinoline;
2-(4-(3-(tetrahydro-2H-pyran-4-yl)pyridin-2-yloxy)piperidin-1-yl)quinoline;
2-(4-(3-(tetrahydro-2H-pyran-4-yl)pyridin-2-yloxy)piperidin-1-yl)-1H-benzo[d]imidazole;
(5-chloropyridin-2-yl)(4-(3-(tetrahydro-2H-pyran-4-yl)pyridin-2-yloxy)piperidin-1-yl)methanone;
(4-chloropyridin-2-yl)(4-(3-(tetrahydro-2H-pyran-4-yl)pyridin-2-yloxy)piperidin-1-yl)methanone;
(S)-(1H-benzo[d]imidazol-2-yl)(3-(3-(3,6-dihydro-2H-pyran-4-yl)pyridin-2-yloxy)pyrrolidin-1-yl)methanone;
(S)-(1H-benzo[d]imidazol-2-yl)(3-(3-(3,6-dihydro-2H-pyran-4-yl)pyrazin-2-yloxy)pyrrolidin-1-yl)methanone;
(S)-(1H-benzo[d]imidazol-2-yl)(3-(3-(tetrahydro-2H-pyran-4-yl)pyridin-2-yloxy)pyrrolidin-1-yl)methanone;
(R)-(1H-benzo[d]imidazol-2-yl)(3-(3-(3,6-dihydro-2H-pyran-4-yl)pyridin-2-yloxy)pyrrolidin-1-yl)methanone;
(R)-(1H-benzo[d]imidazol-2-yl)(3-(3-(3,6-dihydro-2H-pyran-4-yl)pyrazin-2-yloxy)pyrrolidin-1-yl)methanone;
(R)-(1H-benzo[d]imidazol-2-yl)(3-(3-(tetrahydro-2H-pyran-4-yl)pyrazin-2-yloxy)pyrrolidin-1-yl)methanone;
(S)-2-(3-(3-(tetrahydro-2H-pyran-4-yl)pyridin-2-yloxy)pyrrolidin-1-yl)quinoline;
(S)-3-(3-(3-(tetrahydro-2H-pyran-4-yl)pyridin-2-yloxy)pyrrolidin-1-yl)isoquinoline;
(S)-1-(3-(3-(tetrahydro-2H-pyran-4-yl)pyridin-2-yloxy)pyrrolidin-1-yl)isoquinoline;
(S)-2-(3-(3-(tetrahydro-2H-pyran-4-yl)pyridin-2-yloxy)pyrrolidin-1-yl)-1H-benzo[d]imidazole;
(R)-2-(3-(3-(tetrahydro-2H-pyran-4-yl)pyridin-2-yloxy)pyrrolidin-1-yl)quinoline;
(R)-3-(3-(3-(tetrahydro-2H-pyran-4-yl)pyridin-2-yloxy)pyrrolidin-1-yl)isoquinoline;
(R)-1-(3-(3-(tetrahydro-2H-pyran-4-yl)pyridin-2-yloxy)pyrrolidin-1-yl)isoquinoline;
(R)-2-(3-(3-(tetrahydro-2H-pyran-4-yl)pyridin-2-yloxy)pyrrolidin-1-yl)-1H-benzo[d]imidazole;
(S)-2-(3-(3-(tetrahydro-2H-pyran-4-yl)pyrazin-2-yloxy)pyrrolidin-1-yl)quinoline;
(S)-3-(3-(3-(tetrahydro-2H-pyran-4-yl)pyrazin-2-yloxy)pyrrolidin-1-yl)isoquinoline;
(S)-1-(3-(3-(tetrahydro-2H-pyran-4-yl)pyrazin-2-yloxy)pyrrolidin-1-yl)isoquinoline;
(R)-2-(3-(3-(tetrahydro-2H-pyran-4-yl)pyrazin-2-yloxy)pyrrolidin-1-yl)quinoline;
(R)-1-(3-(3-(tetrahydro-2H-pyran-4-yl)pyrazin-2-yloxy)pyrrolidin-1-yl)isoquinoline;
(R)-2-(3-(3-(tetrahydro-2H-pyran-4-yl)pyrazin-2-yloxy)pyrrolidin-1-yl)-1H-benzo[d]imidazole;
1-(4-(2-(1-(benzo[d]thiazol-2-yl)azetidin-3-yloxy)pyridin-3-yl)-5,6-dihydropyridin-1(2H)-yl)ethanone;
1-(4-(2-(1-(quinolin-2-yl)azetidin-3-yloxy)pyridin-3-yl)-5,6-dihydropyridin-1(2H)-yl)ethanone;
(1H-benzo[d]imidazol-2-yl)(3-(3-(tetrahydro-2H-pyran-4-yl)pyrazin-2-yloxy)azetidin-1-yl)methanone;
tert-butyl 3-(3-(1-acetylpiperidin-4-yl)pyridin-2-yloxy)azetidine-1-carboxylate;
tert-butyl 3-(3-(3,6-dihydro-2H-pyran-4-yl)pyridin-2-yloxy)azetidine-1-carboxylate;
1-(4-(2-(1-(1H-benzo[d]imidazole-2-carbonyl)azetidin-3-yloxy)pyridin-3-yl)piperidin-1-yl)ethanone;
(1H-benzo[d]imidazol-2-yl)(3-(3-(4-hydroxypiperidin-1-yl)pyrazin-2-yloxy)azetidin-1-yl)methanone;
(1H-benzo[d]imidazol-2-yl)(3-(3-(pyridin-3-yl)pyrazin-2-yloxy)azetidin-1-yl)methanone;
1-(4-(3-(1-(1H-benzo[d]imidazol-2-yl)azetidin-3-yloxy)pyrazin-2-yl)piperidin-1-yl)ethanone;
1-(4-(3-(1-(quinolin-2-yl)azetidin-3-yloxy)pyrazin-2-yl)piperidin-1-yl)ethanone;
1-(4-(3-(1-(quinolin-2-yl)azetidin-3-yloxy)pyrazin-2-yl)-5,6-dihydropyridin-1(2H)-yl)ethanone;
1-(4-(3-(1-(5-methylpicolinoyl)azetidin-3-yloxy)pyrazin-2-yl)-5,6-dihydropyridin-1(2H)-yl)ethanone;
1-(4-(3-(1-(benzo[d]thiazol-2-yl)azetidin-3-yloxy)pyrazin-2-yl)-5,6-dihydropyridin-1(2H)-yl)ethanone;
(R)-1-(3-(2-(1-(6-methylnicotinoyl)azetidin-3-yloxy)pyridin-3-yl)piperidin-1-yl)ethanone;
(S)-1-(3-(2-(1-(6-methylnicotinoyl)azetidin-3-yloxy)pyridin-3-yl)piperidin-1-yl)ethanone;
(R)-1-(3-(3-(1-acetylpiperidin-3-yl)pyridin-2-yloxy)azetidin-1-yl)-3,3-dimethylbutan-1-one;
(S)-1-(3-(3-(1-acetylpiperidin-3-yl)pyridin-2-yloxy)azetidin-1-yl)-3,3-dimethylbutan-1-one;
1-(4-(3-(1-(1H-benzo[d]imidazole-2-carbonyl)azetidin-3-yloxy)pyrazin-2-yl)piperidin-1-yl)ethanone;
1-(4-(3-(1-(1H-pyrrole-2-carbonyl)azetidin-3-yloxy)pyrazin-2-yl)piperidin-1-yl)ethanone;
1-(4-(3-(1-(1H-benzo[d]imidazole-2-carbonyl)piperidin-4-yloxy)pyrazin-2-yl)piperidin-1-yl)ethanone;
(1H-benzo[d]imidazol-2-yl)(3-(3-(3,6-dihydro-2H-pyran-4-yl)pyridin-2-yloxy)azetidin-1-yl)methanone;
1-(4-(2-(1-(1H-benzo[d]imidazole-2-carbonyl)azetidin-3-yloxy)pyridin-3-yl)-5,6-dihydropyridin-1(2H)-yl)ethanone;
4-(3-(1-(1H-benzo[d]imidazole-2-carbonyl)azetidin-3-yloxy)pyrazin-2-yl)cyclohexanone;
tert-butyl 3-(3-((trans)-4-hydroxycyclohexyl)pyridin-2-yloxy)azetidine-1-carboxylate;
(1H-benzo[d]imidazol-2-yl)(3-(3-(tetrahydro-2H-pyran-4-yl)pyridin-2-yloxy)azetidin-1-yl)methanone;
(1H-benzo[d]imidazol-2-yl)(3-(3-((trans)-4-hydroxycyclohexyl)pyridin-2-yloxy)azetidin-1-yl)methanone;
(1H-benzo[d]imidazol-2-yl)(3-(3-((cis)-4-hydroxycyclohexyl)pyridin-2-yloxy)azetidin-1-yl)methanone;
tert-butyl 3-(3-(4-hydroxycyclohex-1-enyl)pyridin-2-yloxy)azetidine-1-carboxylate;

(1H-benzo[d]imidazol-2-yl)(3-(3-(4-hydroxycyclohex-1-enyl)pyridin-2-yloxy)azetidin-1-yl)methanone;
(R)-1-(3-(2-(1-(4-methyl-1H-pyrrole-2-carbonyl)azetidin-3-yloxy)pyridin-3-yl)piperidin-1-yl)ethanone;
(S)-1-(3-(2-(1-(4-methyl-1H-pyrrole-2-carbonyl)azetidin-3-yloxy)pyridin-3-yl)piperidin-1-yl)ethanone;
1-(4-(3-(1-(4-methyl-1H-pyrrole-2-carbonyl)azetidin-3-yloxy)pyrazin-2-yl)-5,6-dihydropyridin-1(2H)-yl)ethanone;
(R)-1-(3-(2-(1-(1H-indole-2-carbonyl)azetidin-3-yloxy)pyridin-3-yl)piperidin-1-yl)ethanone;
(S)-1-(3-(2-(1-(1H-indole-2-carbonyl)azetidin-3-yloxy)pyridin-3-yl)piperidin-1-yl)ethanone;
benzyl 3-(3-chloropyrazin-2-yloxy)azetidine-1-carboxylate;
(1H-benzo[d]imidazol-2-yl)(3-(pyrazin-2-yloxy)azetidin-1-yl)methanone;
(1H-benzo[d]imidazol-2-yl)(3-(3-chloropyrazin-2-yloxy)azetidin-1-yl)methanone;
(1H-benzo[d]imidazol-2-yl)(3-(3-morpholinopyrazin-2-yloxy)azetidin-1-yl)methanone;
(1H-benzo[d]imidazol-2-yl)(3-(3-(2-methylpyridin-4-yl)pyrazin-2-yloxy)azetidin-1-yl)methanone;
(1H-benzo[d]imidazol-2-yl)(3-(3-(4-hydroxycyclohex-1-enyl)pyrazin-2-yloxy)azetidin-1-yl)methanone;
(1H-benzo[d]imidazol-2-yl)(3-(3-(tetrahydro-2H-pyran-4-yl)pyrazin-2-yloxy)azetidin-1-yl)methanone;
benzyl 3-(3-(pyridin-4-yl)pyrazin-2-yloxy)azetidine-1-carboxylate;
(1H-benzo[d]imidazol-2-yl)(3-(3-(3,6-dihydro-2H-pyran-4-yl)pyrazin-2-yloxy)azetidin-1-yl)methanone;
1-(4-(3-(1-(1H-benzo[d]imidazole-2-carbonyl)azetidin-3-yloxy)pyrazin-2-yl)piperazin-1-yl)ethanone;
benzyl 3-(3'-methoxy-3,4'-bipyridin-2-yloxy)azetidine-1-carboxylate;
Benzyl 3-(3-(1-acetyl-1,2,3,6-tetrahydropyridin-4-yl)pyrazin-2-yloxy)azetidine-1-carboxylate;
(1H-Benzo[d]imidazol-2-yl)(4-(3-(pyridine-4-yl)pyrazin-2-yloxy)piperidin-1-yl)methanone;
2-(4-(3-(piperidin-4-yl)pyridin-2-yloxy)piperidin-1-yl)quinoline;
1-(4-(2-(1-(quinolin-2-yl)piperidin-4-yloxy)pyridin-3-yl)piperidin-1-yl)ethanone;
2-methoxy-1-(4-(3-(1-(quinolin-2-yl)piperidin-4-yloxy)pyrazin-2-yl)piperidin-1-yl)ethanone;
1-(4-(3-(1-(1H-Benzo[d]imidazol-2-ylcarbonyl)piperidin-4-yloxy)pyrazin-2-yl)-5,6-dihydropyridin-1(2H)-yl)ethanone;
1-(4-(3-(1-(1H-benzo[d]imidazole-2-carbonyl)azetidin-3-yloxy)pyrazin-2-yl)-5,6-dihydropyridin-1(2H)-yl)ethanone;
1-(3-(2-(1-picolinoylazetidin-3-yloxy)pyridin-3-yl)piperidin-1-yl)ethanone;
(R)-1-(3-(2-(1-(1H-benzo[d]imidazole-2-carbonyl)azetidin-3-yloxy)pyridin-3-yl)piperidin-1-yl)ethanone;
(S)-1-(3-(2-(1-(1H-benzo[d]imidazole-2-carbonyl)azetidin-3-yloxy)pyridin-3-yl)piperidin-1-yl)ethanone;
(R)-1-(3-(2-(1-(1H-benzo[d]imidazole-2-carbonyl)azetidin-3-yloxy)pyridin-3-yl)piperidin-1-yl)-2-methylpropan-1-one;
(S)-1-(3-(2-(1-(1H-benzo[d]imidazole-2-carbonyl)azetidin-3-yloxy)pyridin-3-yl)piperidin-1-yl)-2-methylpropan-1-one;
1-(4-(3-(1-(1H-pyrrole-2-carbonyl)azetidin-3-yloxy)pyrazin-2-yl)-5,6-dihydropyridin-1(2H)-yl)ethanone;
(S)-1-(3-(2-(1-(1H-benzo[d]imidazole-2-carbonyl)azetidin-3-yloxy)pyridin-3-yl)piperidin-1-yl)-2-methylpropan-1-one;
(R)-1-(3-(2-(1-(1H-benzo[d]imidazole-2-carbonyl)azetidin-3-yloxy)pyridin-3-yl)piperidin-1-yl)-2-methylpropan-1-one;
(S)-1-(3-(2-(1-(1H-indole-2-carbonyl)azetidin-3-yloxy)pyridin-3-yl)piperidin-1-yl)ethanone;
(R)-1-(3-(2-(1-(1H-indole-2-carbonyl)azetidin-3-yloxy)pyridin-3-yl)piperidin-1-yl)ethanone;
(S)-1-(3-(2-(1-(1H-benzo[d]imidazole-2-carbonyl)azetidin-3-yloxy)pyridin-3-yl)piperidin-1-yl)ethanone; or
(R)-1-(3-(2-(1-(1H-benzo[d]imidazole-2-carbonyl)azetidin-3-yloxy)pyridin-3-yl)piperidin-1-yl)ethanone.

The compounds of this invention may have in general several asymmetric centers and are typically depicted in the form of racemic mixtures. This invention is intended to encompass racemic mixtures, partially racemic mixtures and separate enantiomers and diasteromers.

The present invention includes all pharmaceutically acceptable isotopically-labelled compounds of the present invention wherein one or more atoms are replaced by atoms having the same atomic number, but an atomic mass or mass number different from the atomic mass or mass number which predominates in nature.

Examples of isotopes suitable for inclusion in the compounds of the invention include, but are not limited to, isotopes of hydrogen, such as $^2H$ and $^3H$, carbon, such as $^{11}C$, $^{13}C$ and $^{14}C$, chlorine, such as $^{38}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of the present invention, for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of the present invention can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g. $D_2O$, $d_6$-acetone, $d_o$-DMSO.

Specific embodiments of the present invention include the compounds exemplified in the Examples below and their pharmaceutically acceptable salts, complexes, solvates, polymorphs, stereoisomers, metabolites, prodrugs, and other derivatives thereof, Unless otherwise specified, the following definitions apply to terms found in the specification and The term "$C_{\alpha-\beta}$alk" means an alkyl group comprising a minimum of $\alpha$ and a maximum of $\beta$ carbon atoms in a branched, cyclical or linear relationship or any combination of the three, wherein $\alpha$ and $\beta$ represent integers. The alkyl groups described in this section may also contain one or two double or triple bonds. A designation of $C_0$alk indicates a direct bond. Examples of $C_{1-6}$alkyl include, but are not limited to the following:

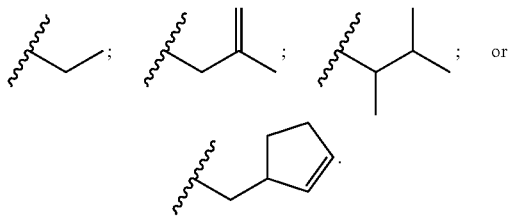

The term "benzo group", alone or in combination, means the divalent radical $C_4H_4=$, one representation of which is —CH=CH—CH=CH—, that when vicinally attached to another ring forms a benzene-like ring—for example tetrahydronaphthylene, indole and the like.

The terms "oxo" and "thioxo" represent the groups =O (as in carbonyl) and =S (as in thiocarbonyl), respectively.

The term "halo" or "halogen" means a halogen atoms selected from F, Cl, Br or I.

The term "$C_{\alpha-\beta}$haloalk" means an alk group, as described above, wherein one or more hydrogen atom of the alk group is replaced by F, Cl, Br or I.

The term "carbon-linked" means a substituent is linked to another group through a carbon atom. Examples of "carbon-linked" substituents include, but are not limited to the following:

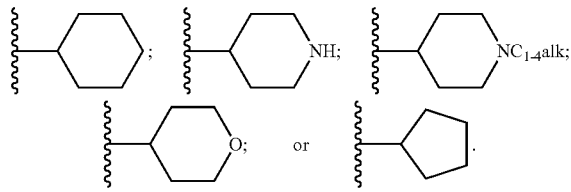

The term "nitrogen-linked" means a substituent is linked to another group through a nitrogen atom. Examples of "nitrogen-linked" substituents include, but are not limited to the following:

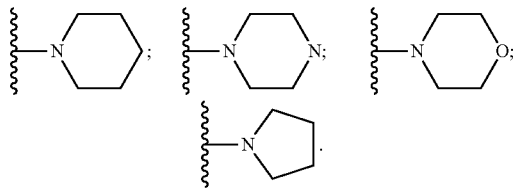

The group $N(R^a)R^a$ and the like include substituents where the two $R^a$ groups together form a ring, optionally including a N, O or S atom, and include groups such as:

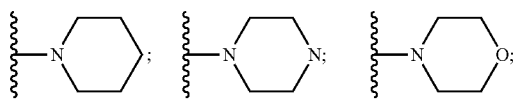

-continued

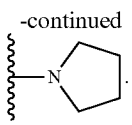

The group $N(C_{\alpha-\beta}alk) C_{\alpha-\beta}alk$, wherein $\alpha$ and $\beta$ are as defined above, include substituents where the two $C_{\alpha-\beta}alk$ groups together form a ring, optionally including a N, O or S atom, and include groups such as:

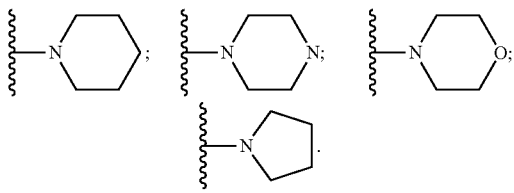

The term "carbocyclyl" means a ring comprising by itself or in combination with other terms, represents, unless otherwise stated, cyclic version of "$C_{\alpha-\beta}alk$". Thus, the term "carbocyclyl" is meant to be included in the terms "$C_{\alpha-\beta}alk$". Examples of carbocycle include cyclopentyl, cyclohexyl, or partially unsaturated ring such as 1-cyclohexenyl, 3-cyclohexenyl, cycloheptyl, cyclobutylene, cyclohexylene and the like. Unless otherwise stated, carbocycle can include fully saturated ring such as phenyl or naphthyl.

The term "heteroatom" means N, O and S.

The term "heterocyclyl" means a ring comprising at least one carbon atom and at least one other atom selected from N, O or S. "Heterocyclyl" includes aromatic heterocyclic ring which is commonly known as heteroaryl. Thus, the term "heteroaryl" is meant to be included in the terms "heterocyclyl". Examples of heterocycles that may be found in the claims include, but are not limited to, the following:

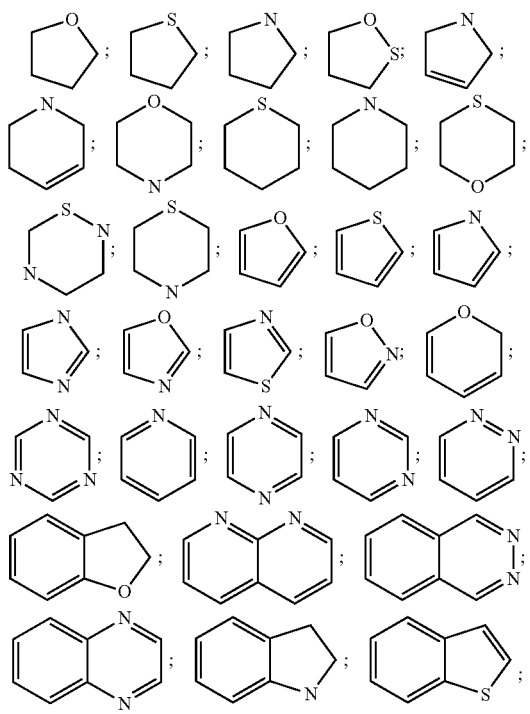

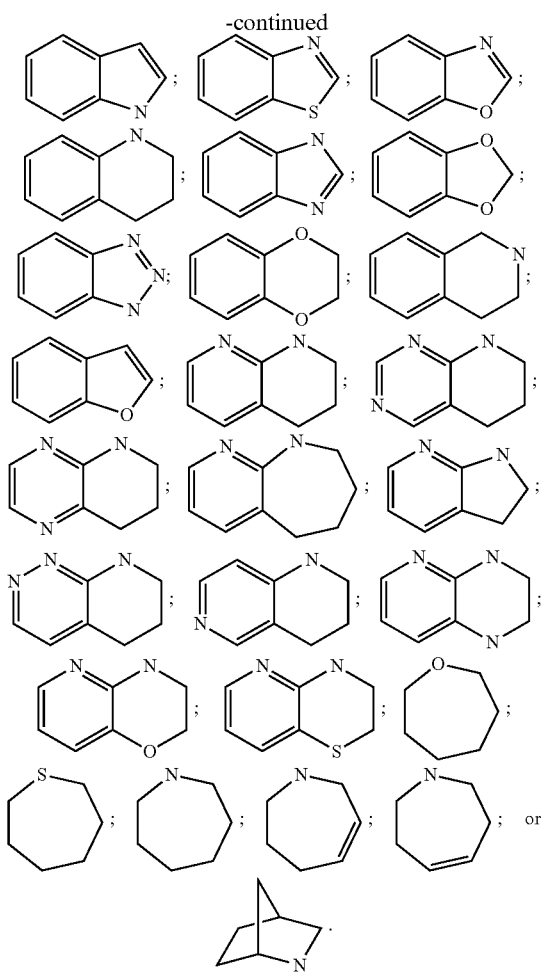

The term "pharmaceutically acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," and Berge et al., J. Pharm. Sci. 66:1 (1977).

The term "saturated, partially-saturated or unsaturated" includes substituents saturated with hydrogens, substituents completely unsaturated with hydrogens and substituents partially saturated with hydrogens.

Representative examples of "saturated, partially-saturated or unsaturated" five to eight membered rings, optionally having one to three heteroatoms, are cyclopentyl, cyclohexyl, cycloheptyl, cyclooctyl and phenyl. Further exemplary five membered rings are furyl, thienyl, pyrrolyl, 2-pyrrolinyl, 3-pyrrolinyl, pyrrolidinyl, 1,3-dioxolanyl, oxazolyl, thiazolyl, imidazolyl, 2H-imidazolyl, 2-imidazolinyl, imidazolidinyl, pyrazolyl, 2-pyrazolinyl, pyrazolidinyl, isoxazolyl, isothiazolyl, 1,2-dithiolyl, 1,3-dithiolyl, 3H-1,2-oxathiolyl, 1,2,3-oxadizaolyl, 1,2,4-oxadiazolyl, 1,2,5-oxadiazolyl, 1,3,4oxadiazolyl, 1,2,3-triazolyl, 1,2,4-trizaolyl, 1,3,4-thiadiazolyl, 3H-1,2,3-dioxazolyl, 1,2,4-dioxazolyl, 1,3,2-dioxazolyl, 1,3,4-dioxazolyl, 5H-1,2,5-oxathiazolyl, and 1,3-oxathiolyl.

Further exemplary six membered rings are 2H-pyranyl, 4H-pyranyl, pyridinyl, piperidinyl, 1,2-dioxinyl, 1,3-dioxinyl, 1,4-dioxanyl, morpholinyl, 1,4-dithianyl, thiomorpholinyl, pyndazinyl, pyrimidinyl, pyrazinyl, piperazinyl, 1,3,5-triazinyl, 1,2,4-triazinyl, 1,2,3-triazinyl, 1,3,5-trithianyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2,5-oxathiazinyl, 1,2,6-(3 oxathiazinyl, and 1,4,2-oxadiazinyl.

Further exemplary seven membered rings are azepinyl, oxepinyl, thiepinyl and 1,2,4-triazepinyl.

Further exemplary eight membered rings are cyclooctyl, cyclooctenyl and cyclooctadienyl.

The term "monocyclic" means a group having a single saturated, partially-saturated, or unsaturated ring system. Typically a monocyclic ring system can have from 3- to 8 atoms in the ring system. The term includes, but is not limited to, cyclopropyl, cyclopropyl, cyclobutyl, cyclopentyl, cyclohexyl, cycloheptyl, phenyl, and the like.

The term "bicyclic" means a group having two interconnected saturated, partially-saturated, or unsaturated rings that include stable bridged, fused, or spiro rings. The bicyclic ring may be attached at any carbon or heteroatom which affords a stable group. Typically a bicyclic ring system can have from 6- to 14 atoms in the ring system. The term includes, but is not limited to, benzimidazole, naphthyl, bicyclo[3.1.0]hexane, bicyclo[4.1.0]heptane, spiro[2.4]heptane, spiro[2.5]octane, bicyclo[4.4.0]decane, bicyclo[4.3.0]nonane, bicyclo[3.3.1] nonane, bicyclo[3.2.1]octane, spiro[4.5]decane, spiro[3.5] nonane, norbornane, bicyclo[2.1.0]pentane, bicyclo[3.3.0] octane, bicyclo[2.2.2]octane, bicyclo[3.3.3]undecane, and the like.

The term "tricyclic" means a group having three interconnected saturated, partially-saturated, or unsaturated rings that include stable bridged, fused, or spirorings. Typically a tricyclic ring system can have from 11 to 18 ring atoms in the ring system. The term includes, but is not limited to, adamantyl, tricyclo[5.2.1.0.sup.2,6]decane, and the like.

Exemplary bicyclic rings consisting of two fused partially saturated, fully saturated or fully unsaturated five and/or six membered rings, optionally having one to four heteroatoms, are indolizinyl, indolyl, isoindolyl, indolinyl, cyclopenta(b) pyridinyl, pyrano(3,4-b)pyrrolyl, benzofuryl, isobenzofuryl, benzo[b]thienyl, benzo[c]thienyl, 1H-indazolyl, indoxazinyl, benzoxazolyl, anthranilyl, benzimidazolyl, benzthiazolyl, purinyl, quinolinyl, isoquinolinyl, cinnolinyl, phthalazinyl, quinazolinyl, quinoxalinyl, 1,8-naphthyridinyl, pteridinyl, indenyl, isoindenyl, naphthyl, tetralinyl, decalinyl, 2H-1-benzopyranyl, pyrido(3,4-b)pyridinyl, pyrido(3,2-b) pyridinyl, pyrido(4,3-b)-pyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl and 4H-1,4-benzoxazinyl.

A cyclic ring group may be bonded to another group in more than one way. If no particular bonding arrangement is specified, then all possible arrangements are intended. For example, the term "pyridyl" includes 2-, 3-, or 4-pyridyl, and the term "thienyl" includes 2-, or 3-thienyl.

The term "substituted" means that a hydrogen atom on a molecule or group is replaced with a group or atom. Typical substitutents include: halogen, $C_{1-8}$alkyl, hydroxyl, C$_{1-8}$alkoxy, —NR$^x$R$^x$, nitro, cyano, halo or perhaloC$_{1-8}$alkyl, C$_{2-8}$alkenyl, C$_{2-8}$alkynyl, —SR$^x$, —S(=O)$_2$R$^x$, —C(=O)OR$^x$, —C(=O)R$^x$, wherein each R$^x$ is independently hydrogen or C$_1$-C$_8$ alkyl. It is noted that when the substituent is —NR$^x$R$^x$, the R$^x$ groups may be joined together with the nitrogen atom to form a ring.

A group or atom that replaces a hydrogen atom is also called a substituent.

Any particular molecule or group can have one or more substituent depending on the number of hydrogen atoms that can be replaced.

The symbol "—" represents a covalent bond and can also be used in a radical group to indicate the point of attachment to another group. In chemical structures, the symbol is commonly used to represent a methyl group in a molecule.

The term "leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

The term "protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, trifluoroacetyl, trichloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl.

The term "silyl protecting groups" means silicon atoms optionally substituted by one or more alkyl, aryl and aralkyl groups. Suitable silyl protecting groups include, but are not limited to, trimethylsilyl, triethylsilyl, triisopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-trisilyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted aromatic heterocyclyl groups (Y'=O, S, NR), and the like, which are illustrated in the following examples:

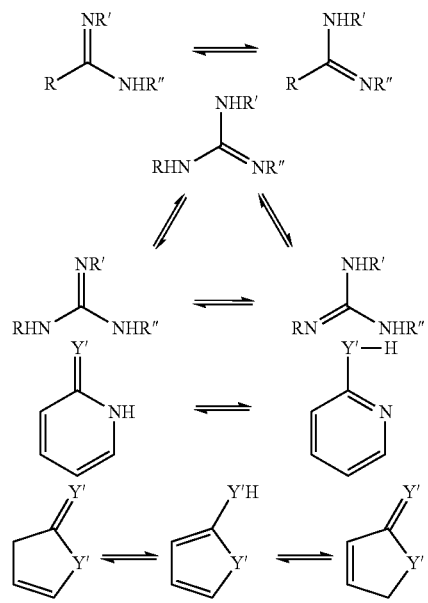

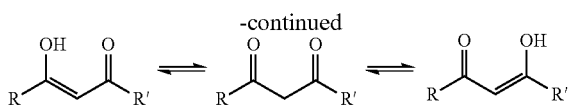

and though one form is named, described, displayed and/or claimed herein, all the tautomeric forms are intended to be inherently included in such name, description, display and/or claim.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

The term "therapeutically effective amount" means an amount of a compound that ameliorates, attenuates or eliminates one or more symptom of a particular disease or condition, or prevents or delays the onset of one of more symptom of a particular disease or condition.

The term "patient" means animals, such as dogs, cats, cows, horses, sheep and humans. Particular patients are mammals. The term patient includes males and females.

The term "pharmaceutically acceptable" means that the referenced substance, such as a compound of Formula I, or a salt of a compound of Formula I, or a formulation containing a compound of Formula I, or a particular excipient, are suitable for administration to a patient.

The terms "treating", "treat" or "treatment" and the like include preventative (e.g., prophylactic) and palliative treatment.

The term "excipient" means any pharmaceutically acceptable additive, carrier, diluent, adjuvant, or other ingredient, other than the active pharmaceutical ingredient (API), which is typically included for formulation and/or administration to a patient.

UTILITY AND METHODS OF USE

Provided herein are methods for treating a disorder or disease by inhibiting PDE10 enzyme. The methods, in general, comprises the step of administering a therapeutically effective amount of a compounds of the present invention, or an individual stereoisomer, a mixture of stereoisomers, or a pharmaceutically acceptable salt or solvate thereof, to a patient in need thereof to treat the disorder or disease.

In certain embodiments, this invention provides a use of a compound as described herein in the manufacture of a medicament for treating a disorder or disease treatable by inhibition of PDE10.

The compounds of the present invention inhibit PDE10 enzyme activity, and hence raise the levels of cAMP or cGMP within cells that express PDE10. Accordingly, inhibition of PDE10 enzyme activity would be useful in the treatment of diseases caused by deficient amounts of cAMP or cGMP in cells. PDE10 inhibitors would also be of benefit in cases wherein raising the amount of cAMP or cGMP above normal levels results in a therapeutic effect. Inhibitors of PDE10 may be used to treat disorders of the peripheral and central nervous system, cardiovascular diseases, cancer, gastro-enterological diseases, endocrinological diseases and urological diseases.

Indications that may be treated with PDE10 inhibitors, either alone or in combination with other drugs, include, but are not limited to, those diseases thought to be mediated in part by the basal ganglia, prefrontal cortex, and hippocampus. These indications include psychoses, Parkinson's disease, dementias, obsessive compulsive disorder, tardive dyskinesia, choreas, depression, mood disorders, impulsivity, drug addiction, attention deficit/hyperactivity disorder (ADHD), depression with parkinsonian states, personality changes with caudate or putamen disease, dementia and mania with caudate and pallidal diseases, and compulsions with pallidal disease.

Psychoses are disorders that affect an individual's perception of reality. Psychoses are characterized by delusions and hallucinations. The compounds of the present invention are suitable for use in treating patients suffering from all forms of psychoses, including, but not limited to, schizophrenia, late-onset schizophrenia, schizoaffective disorders, prodromal schizophrenia, and bipolar disorders. Treatment can be for the positive symptoms of schizophrenia as well as for the cognitive deficits and negative symptoms. Other indications for PDE10 inhibitors include psychoses resulting from drug abuse (including amphetamines and PCP), encephalitis, alcoholism, epilepsy, Lupus, sarcoidosis, brain tumors, multiple sclerosis, dementia with Lewy bodies, or hypoglycemia. Other psychiatric disorders, like posttraumatic stress disorder (PTSD), and schizoid personality can also be treated with PDE10 inhibitors.

Obsessive-compulsive disorder (OCD) has been linked to deficits in the frontal-striatal neuronal pathways (Saxena et al., Br. J. Psychiatry Suppl, 35:26-37, 1998). Neurons in these pathways project to striatal neurons that express PDE10. PDE10 inhibitors cause cAMP to be elevated in these neurons; elevations in cAMP result in an increase in CREB phosphorylation and thereby improve the functional state of these neurons. The compounds of the present invention are therefore suitable for use in the indication of OCD. OCD may result, in some cases, from streptococcal infections that cause autoimmune reactions in the basal ganglia (Giedd et al., Am J Psychiatry. 157:281-283, 2000). Because PDE10 inhibitors may serve a neuroprotective role, administration of PDE10 inhibitors may prevent the damage to the basal ganglia after repeated streptococcal infections and thereby prevent the development of OCD.

In the brain, the level of cAMP or cGMP within neurons is believed to be related to the quality of memory, especially long term memory. Without wishing to be bound to any particular mechanism, it is proposed that, since PDE10 degrades cAMP or cGMP, the level of this enzyme affects memory in animals, for example, in humans. A compound that inhibits cAMP phosphodiesterase (PDE) can thereby increase intracellular levels of cAMP, which in turn activate a protein kinase that phosphorylates a transcription factor (cAMP response binding protein). The phosphorylated transcription factor then binds to a DNA promoter sequence to activate genes that are important in long term memory. The more active such genes are, the better is long-term memory. Thus, by inhibiting a phosphodiesterase, long term memory can be enhanced.

Dementias are diseases that include memory loss and additional intellectual impairment separate from memory. The compounds of the present invention are suitable for use in treating patients suffering from memory impairment in all forms of dementia. Dementias are classified according to their cause and include: neurodegenerative dementias (e.g., Alzheimer's, Parkinson's disease, Huntington's disease, Pick's disease), vascular (e.g., infarcts, hemorrhage, cardiac disorders), mixed vascular and Alzheimer's, bacterial meningitis, Creutzfeld-Jacob Disease, multiple sclerosis, traumatic (e.g., subdural hematoma or traumatic brain injury), infectious (e.g., HIV), genetic (down syndrome), toxic (e.g., heavy metals, alcohol, some medications), metabolic (e.g., vitamin B12 or folate deficiency), CNS hypoxia, Cushing's disease, psychiatric (e.g., depression and schizophrenia), and hydrocephalus.

The condition of memory impairment is manifested by impairment of the ability to learn new information and/or the inability to recall previously learned information. The present invention includes methods for dealing with memory loss separate from dementia, including mild cognitive impairment (MCI) and age-related cognitive decline. The present invention includes methods of treatment for memory impairment as a result of disease. Memory impairment is a primary symptom of dementia and can also be a symptom associated with such diseases as Alzheimer's disease, schizophrenia, Parkinson's disease, Huntington's disease, Pick's disease, Creutzfeld-Jakob disease, HIV, cardiovascular disease, and head trauma as well as age-related cognitive decline. The compounds of the present invention are suitable for use in the treatment of memory impairment due to, for example, Alzheimer's disease, multiple sclerosis, amylolaterosclerosis (ALS), multiple systems atrophy (MSA), schizophrenia, Parkinson's disease, Huntington's disease, Pick's disease, Creutzfeld-Jakob disease, depression, aging, head trauma, stroke, spinal cord injury, CNS hypoxia, cerebral senility, diabetes associated cognitive impairment, memory deficits from early exposure of anesthetic agents, multiinfarct dementia and other neurological conditions including acute neuronal diseases, as well as HIV and cardiovascular diseases.

The compounds of the present invention are also suitable for use in the treatment of a class of disorders known as polyglutamine-repeat diseases. These diseases share a common pathogenic mutation. The expansion of a CAG repeat, which encodes the amino acid glutamine, within the genome leads to production of a mutant protein having an expanded polyglutamine region. For example, Huntington's disease has been linked to a mutation of the protein huntingtin. In individuals who do not have Huntington's disease, huntingtin has a polyglutamine region containing about 8 to 31 glutamine residues. For individuals who have Huntington's disease, huntingtin has a polyglutamine region with over 37 glutamine residues. Aside from Huntington's disease (HD), other known polyglutamine-repeat diseases and the associated proteins include dentatorubral-pallidoluysian atrophy, DRPLA (atrophin-1); spinocerebellar ataxia type-1 (ataxin-1); spinocerebellar ataxia type-2 (ataxin-2); spinocerebellar ataxia type-3 (also called Machado-Joseph disease or MJD) (ataxin-3); spinocerebellar ataxia type-6 (alpha 1a-voltage dependent calcium channel); spinocerebellar ataxia type-7 (ataxin-7); and spinal and bulbar muscular atrophy (SBMA, also know as Kennedy disease).

The basal ganglia are important for regulating the function of motor neurons; disorders of the basal ganglia result in movement disorders. Most prominent among the movement disorders related to basal ganglia function is Parkinson's disease (Obeso et al., Neurology. 62(1 Suppl 1):S17-30, 2004). Other movement disorders related to dysfunction of the basal ganglia include tardive dyskinesia, progressive supranuclear palsy and cerebral palsy, corticobasal degeneration, multiple system atrophy, Wilson disease, dystonia, tics, and chorea. The compounds of the invention are also suitable for use to treat movement disorders related to dysfunction of basal ganglia neurons.

PDE10 inhibitors are useful in raising cAMP or cGMP levels and prevent neurons from undergoing apoptosis. PDE10 inhibitors may be anti-inflammatory by raising cAMP in glial cells. The combination of anti-apoptotic and anti-inflammatory properties, as well as positive effects on synaptic plasticity and neurogenesis, make these compounds useful to treat neurodegeneration resulting from any disease or injury, including stroke, spinal cord injury, Alzheimer's disease, multiple sclerosis, amylolaterosclerosis (ALS), and multiple systems atrophy (MSA).

Autoimmune diseases or infectious diseases that affect the basal ganglia may result in disorders of the basal ganglia including ADHD, OCD, tics, Tourette's disease, Sydenham chorea. In addition, any insult to the brain can potentially damage the basal ganglia including strokes, metabolic abnormalities, liver disease, multiple sclerosis, infections, tumors, drug overdoses or side effects, and head trauma. Accordingly, the compounds of the invention can be used to stop disease progression or restore damaged circuits in the brain by a combination of effects including increased synaptic plasticity, neurogenesis, anti-inflammatory, nerve cell regeneration and decreased apoptosis.

The growth of some cancer cells is inhibited by cAMP and cGMP. Upon transformation, cells may become cancerous by expressing PDE10 and reducing the amount of cAMP or cGMP within cells. In these types of cancer cells, inhibition of PDE10 activity inhibits cell growth by raising cAMP. In some cases, PDE10 may be expressed in the transformed, cancerous cell but not in the parent cell line. In transformed renal carcinoma cells, PDE10 is expressed and PDE10 inhibitors reduce the growth rate of the cells in culture. Similarly, breast cancer cells are inhibited by administration of PDE10 inhibitors. Many other types of cancer cells may also be sensitive to growth arrest by inhibition of PDE10. Therefore, compounds disclosed in this invention can be used to stop the growth of cancer cells that express PDE10.

The compounds of the invention are also suitable for use in the treatment of diabetes and related disorders such as obesity, by focusing on regulation of the cAMP signaling system. By inhibiting PDE-10, especially PDE-10A, intracellular levels of cAMP are increased, thereby increasing the release of insulin-containing secretory granules and, therefore, increasing insulin secretion. See, for example, WO 2005/012485. The compounds of Formula (I) can also be used to treat diseases disclosed in US Patent application publication No. 2006/019975.

Testing

The PDE10 inhibitory activities of the compounds of the present invention can be tested, for example, using the in vitro and in vivo assays described in the Biological Examples below.

Administration and Pharmaceutical Compositions

In general, the compounds of this invention can be administered in a therapeutically effective amount by any of the accepted modes of administration for agents that serve similar utilities. The actual amount of a compound of this invention, i.e., the active ingredient, depends upon numerous factors, such as the severity of the disease to be treated, the age and relative health of the subject, the potency of the compound used, the route and form of administration, and other factors.

Therapeutically effective amounts of compounds of formula (I) may range from approximately 0.1-1000 mg per day; preferably 0.5 to 250 mg/day, more preferably 3.5 mg to 70 mg per day.

In general, compounds of this invention can be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors, such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area, i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of, in general, a compounds of the present invention in combination with at least one pharmaceutically acceptable excipient. Acceptable excipients are non-toxic, aid administration, and do not adversely affect the therapeutic benefit of the compounds of the present invention. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in Remington's Pharmaceutical Sciences, Gennaro, A. R. (Mack Publishing Company, 18th ed., 1995).

The level of the compound in a formulation can vary within the full range employed by those skilled in the art. Typically, the formulation contains, on a weight percent (wt %) basis, from about 0.01-99.99 wt % of a compounds of the present invention based on the total formulation, with the balance being one or more suitable pharmaceutical excipients. Preferably, the compound is present at a level of about 1-80 wt %.

The compounds can be administered as the sole active agent or in combination with other pharmaceutical agents such as other agents used in the treatment of psychoses, especially schizophrenia and bipolar disorder, obsessive-compulsive disorder, Parkinson's disease, Alzheimer's disease, cognitive impairment and/or memory loss, e.g., nicotinic α-7 agonists, PDE4 inhibitors, other PDE10 inhibitors, calcium channel blockers, muscarinic m1 and m2 modulators, adenosine receptor modulators, ampakines, NMDA-R modulators, mGluR modulators, dopamine modulators, serotonin modulators, canabinoid modulators, and cholinesterase inhibitors (e.g., donepezil, rivastigimine, and galanthanamine) In such combinations, each active ingredient can be administered either in accordance with their usual dosage range or a dose below their usual dosage range, and can be administered either simultaneously or sequentially.

Drugs suitable in combination with the compounds of the present invention include, but are not limited to, other suitable schizophrenia drugs such as Clozaril, Zyprexa, Risperidone, and Seroquel; bipolar disorder drugs, including, but not limited to, Lithium, Zyprexa, and Depakote; Parkinson's disease drugs, including, but not limited to, Levodopa, Parlodel, Permax, Mirapex, Tasmar, Contan, Kemadin, Artane, and Cogentin; agents used in the treatment of Alzheimer's disease, including, but not limited to, Reminyl, Cognex, Aricept, Exelon, Akatinol, Neotropin, Eldepryl, Estrogen and Cliquinol; agents used in the treatment of dementia, including, but not limited to, Thioridazine, Haloperidol, Risperidone, Cognex, Aricept, and Exelon; agents used in the treatment of epilepsy, including, but not limited to, Dilantin, Luminol, Tegretol, Depakote, Depakene, Zarontin, Neurontin, Barbita, Solfeton, and Felbatol; agents used in the treatment of multiple sclerosis, including, but not limited to, Detrol, Ditropan XL, OxyContin, Betaseron, Avonex, Azothioprine, Methotrexate, and Copaxone; agents used in the treatment of Huntington's disease, including, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone; agents useful in the treatment of diabetes, including, but not limited to, PPAR ligands (e.g. agonists, antagonists, such as Rosiglitazone, Troglitazone and Pioglitazone), insulin secretagogues (e.g., sulfonylurea drugs, such as Glyburide, Glimepiride, Chlorpropamide, Tolbutamide, and Glipizide, and non-sulfonyl secretagogues), α-glucosidase inhibitors (such as Acarbose, Miglitol, and Voglibose), insulin sensitizers (such as the PPAR-γ agonists, e.g., the glitazones; biguanides, PTP-1B inhibitors, DPP-IV inhibitors, and 11beta-HSD inhibitors), hepatic glucose output lowering compounds (such as glucagon antagonists and metaformin, e.g., Glucophage and Glucophage XR), insulin and insulin derivatives (both long and short acting forms and formulations of insulin); and anti-obesity drugs, including, but not limited to, β-3 agonists, CB-1 agonists, neuropeptide Y5 inhibitors, Ciliary Neurotrophic Factor and derivatives (e.g., Axokine), appetite suppressants (e.g., Sibutramine), and lipase inhibitors (e.g., Orlistat).

EXPERIMENTAL

Unless otherwise noted, all materials were purchased from Sinopharm Chemical Reagent Co., Ltd and used without further purification. All microwave assisted reactions were conducted with a Initiator Synthesizer® from Biotage®. All compounds showed NMR spectra consistent with their assigned structures. Melting points were determined on a Buchi apparatus and are uncorrected. Mass spectral data was determined by electrospray ionization technique. All examples were purified to >90% purity as determined by high-performance liquid chromatography. Unless otherwise stated, reactions were run at room temperature.

The following abbreviations are commonly used:

| | |
|---|---|
| Ac | the group $CH_3$—(CO)— |
| AcOH or HOAc | acetic acid |
| $Ac_2O$ | acetic anhydride |
| BINAP | 2,2'-bis(diphenylphosphino)-1,1'-binaphthalene |
| BnO | Benzyloxy |
| $Boc_2O$ | di-tert-butyl dicarbonate |
| BTEA-Cl | benzyltriethylammonium chloride |
| Bz | Benzyl group |
| Cbz | carboxylic acid benzyl ester |
| CDI | 1,1'-carbonyldiimidazole |
| d | Day |
| DCM | Dichloromethane |
| DIAD | $(CH_3)_2CHOOCN=NCOOCH(CH_3)_2$ |
| DIEA | N,N-diisopropylethylamine |
| Diox | Dioxane |
| DIPEA | diisopropylethyl amine |
| DMA | Dimethylamine |
| DMAP | 4-(dimethylamino)pyridine |
| DME | Dimethoxyethane |
| DMF | N, N-dimethylformamide |
| Dess martin Periodinane | 1,1,1-Tris(acetyloxy)-1,1-dihydro-1,2-benziodoxol-3-(1H)-one |
| DMSO | dimethyl sulfoxide |
| DPPA | diphenyl phosphoryl azide |
| EDCl | N-(3-Dimethylaminopropyl)-N'-ethylcarbodiimide hydrochloride |
| ESI-MS | electrospray ionization mass spectrometry |
| $Et_2O$ | diethyl ether |
| EtOAc | ethyl acetate |
| EtOH | ethyl alcohol |
| $Et_3N$ | triethyl amine |
| g | Grams |
| h | hour or hours |
| HATU | O-(7-Azobenzotriazol-1-yl)-1,1,3,3-tetramethyluronium hexafluorophosphate |
| HBTU | 2-(1H-Benzotriazole-1-yl)-1,1,3,3-tetramethylaminium hexafluorophosphate |
| HCl | Hydrochloric acid |
| HPLC | high pressure liquid chromatography |
| IPA | isopropyl alcohol |
| i $Pr_2NEt$ | Diisopropylethylamine |
| i PrOH | Isopropyl alcohol |
| ISCO | in-situ chemical oxidation |
| Lawesson reagent | 4-Methoxyphenylthiophosphoric cyclic di(thioanhydride), LR, 2,4-Bis(4-methoxyphenyl)-2,4-dithioxo-1,3,2,4-dithiadiphosphetane, 2,4-Bis-(4-methoxyphenyl)-1,3-dithia-2,4-diphosphetane 2,4-disulfide |
| LCMS | liquid chromatography mass spectrometry |
| LDA | Lithium diisopropyl amide |
| LiHMDS | Lithium bis(trimethylsilyl)amide |
| Me | Methyl |
| MeCN | Acetonitrile |
| MeI | Iodomethane |
| MeOH | methyl alcohol |
| MeOD | deuterated methyl alcohol |
| mg | Milligrams |
| min | Min |
| mL | Milliliters |
| $Mo-(CO)_6$ | molybdenum hexacarbonyl |
| MTBE | methyl tert-butyl ether |
| NBS | N-bromosuccinimide |
| NMP | 1-methyl-2-pyrrolidinone |
| NMR | nuclear magnetic resonance |
| NOESY | nuclear Overhauser effect spectroscopy |
| $Pd(dppf)Cl_2$ | [1,1'-Bis(diphenylphosphino)ferrocene]dichloropalladium(II), complex with dichloromethane |
| PMBCl | 1-(chloromethyl)-4-methoxybenzene |
| PTSA | p-toluenesulfonic acid |
| Py | Pyridine |
| RT | RT |
| sat. | Saturated |
| t-bu | tert-butyl group |
| TFA | trifluoroacetic acid |
| THF | Tetrahydrofuran |
| TLC | thin layer chromatography |
| TMSCl | Trimethylsilyl chloride |
| TBDPS | Tert-Butylchlorodiphenyl |
| Tol | Toluene |
| TsCl | 4-toluenesulfonyl chloride ($CH_3C_6H_4SO_2Cl$) |
| Xantphos | 4,5-bis(diphenylphosphino)-9,9-dimethylxanthene |

General Synthetic Methodology:

The compounds of the present invention can be prepared from commercially available starting materials and by using general synthetic techniques known to those of skill in the art. Outlined below are general reaction schemes suitable for preparing the compounds of the invention claimed herein. Further exemplification is found in the specific examples provided. One skilled in the art will understand that similar or related methods can be used for the synthesis of the compounds. One skilled in the art will also appreciate that in several instances it is possible to change the order of the steps used in the preparation of these compounds and obtain similar results

GENERAL SCHEME 1

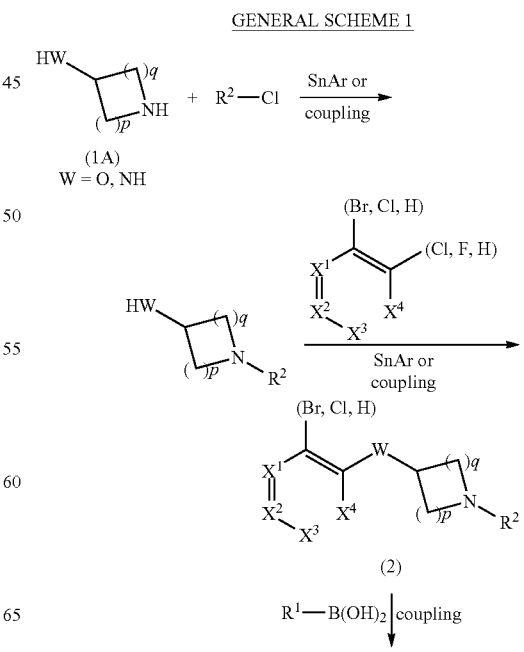

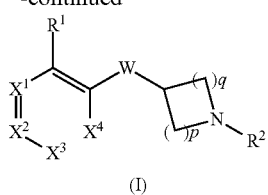

(I)

General Scheme 1 above shows a general method for preparing compounds of formula I as defined herein via key intermediate compound (2). More specific examples of General Scheme 1 are depicted below in General Schemes 1A-1B

GENERAL SCHEMES 1A-1B:

1A. (2) 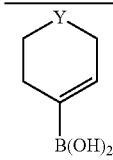

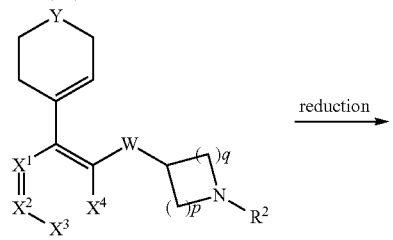

1B. (2) 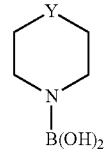

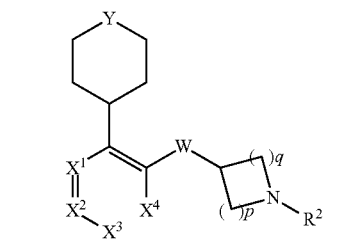

GENERAL SCHEME 2

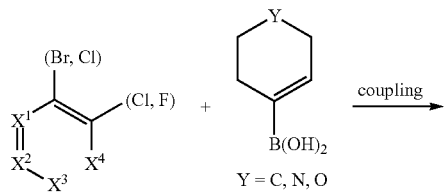

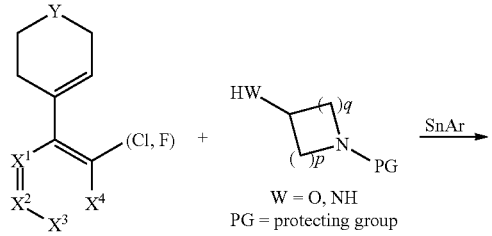

(3)

General Scheme 2 shows a general method for preparing an intermediate compound (3) which is useful in the preparation of compounds of formula (I). More specific examples of General Scheme 2 are depicted below in General Schemes 2A-2B.

It will be appreciated that in the general schemes, other reagents, such as

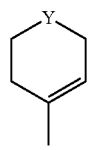

(a) halo; wherein halo can be iodo; or (b) boronic esters, such as or

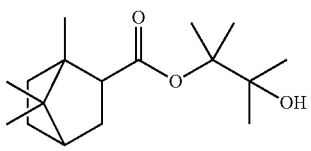 [SMILES: CC(C)(O)C(C)(C)OC(=O)C1CC2CCC1(C)C2(C)C]

(pinacol boronic ester); methyl boronic ester; or ethyl boronic ester; may be used in place of reagent

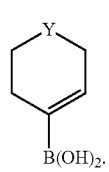

GENERAL SCHEMES 2A-2B:

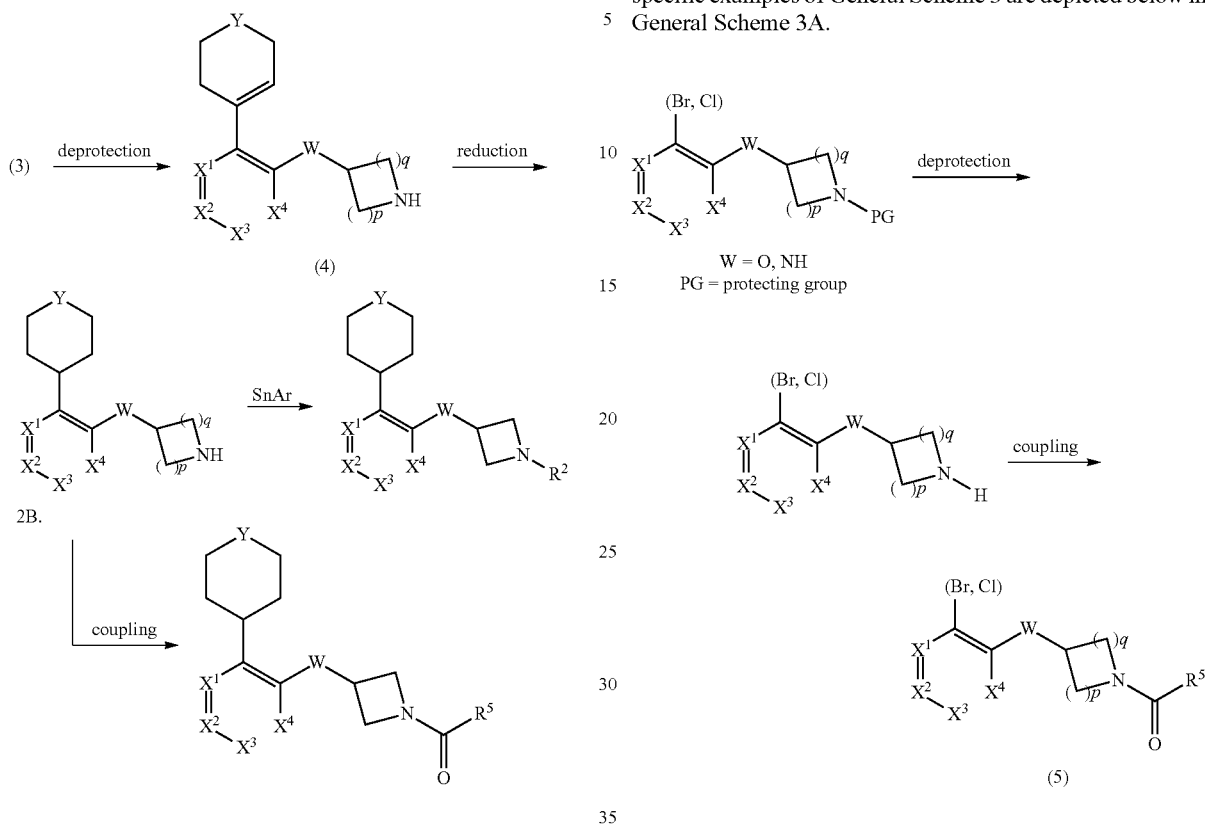

Alternatively, compound (4) may be prepared as follows:

General Scheme 3 shows a further alternative general method for preparing an intermediate compound (5) which is useful in the preparation of compounds of formula (I). More specific examples of General Scheme 3 are depicted below in General Scheme 3A.

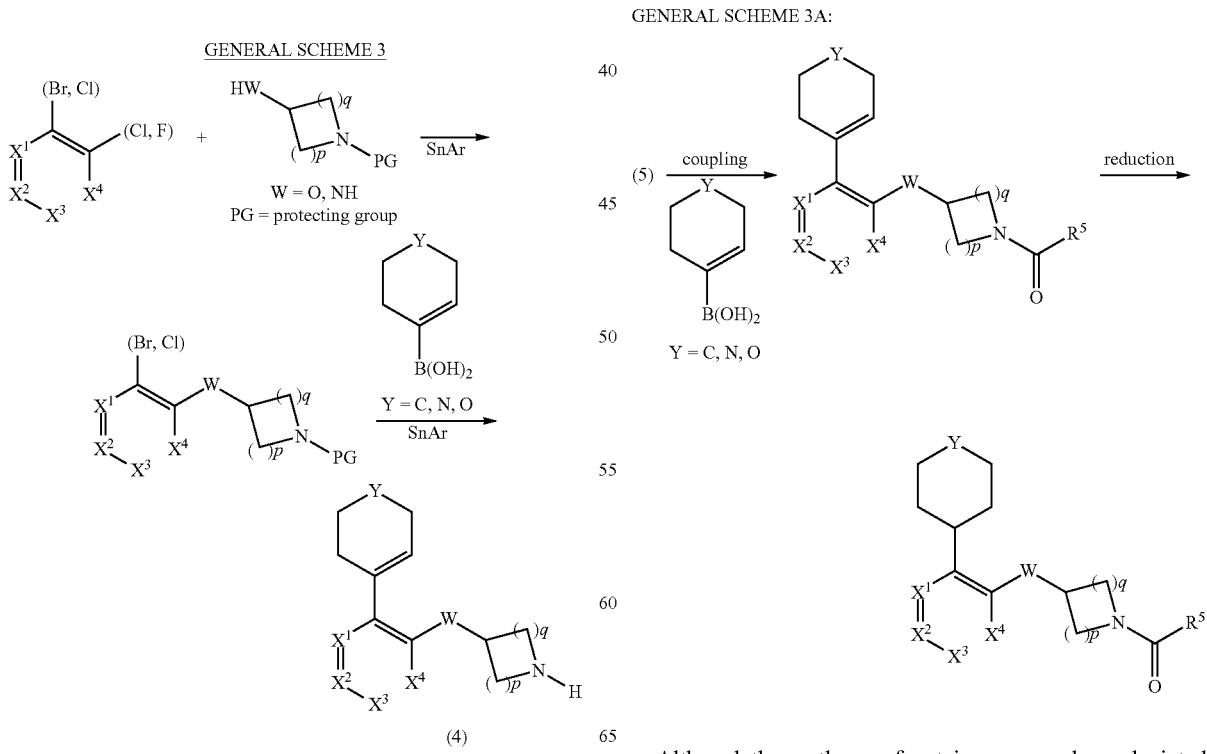

Although the syntheses of certain compounds are depicted above, it will be appreciated that compounds of formula I having other group R¹; for example, a 6-membered heterocyclic ring, can be prepared according to the above General Scheme 3A.

Preparation P1.1: 1-(Quinolin-2-yl)Piperidin-4-ol

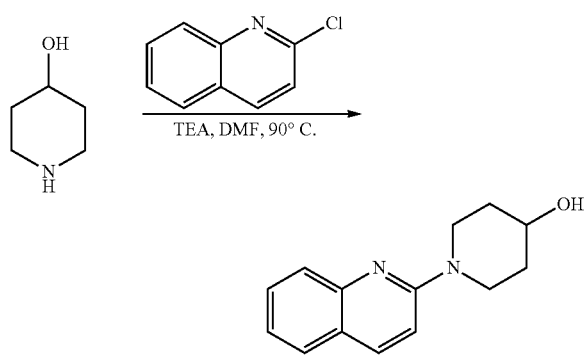

Triethylamine (2.9 g, 29.6 mmol), 2-chloro-quinoline (purchased from Alfa Aesar™) (2.4 g, 14.8 mmol) and piperidin-4-ol (1.5 g, 14.8 mmol) were dissolved in DMF (20 mL). The resulting mixture was heated to 100° C. overnight. The mixture was then diluted with water (20 mL) and extracted with EtOAc (2×50 mL). The combined organic extracts were combined and washed with water (20 mL) and brine (20 mL), dried over Na₂SO₄, and filtered. The filtrate was evaporated in vacuo and the residue was purified by flash column chromatography on silica gel (20% to 70% EtOAc in petroleum ether) to give 1-(quinolin-2-yl)piperidin-4-ol (2.0 g, 8.7 mmol, 60% yield) as white solid. ESI-MS (M+1): 229 calc. for $C_{14}H_{16}N_2O$ 228.

TABLE P1

EXAMPLES P1.1-P1.7 PREPARED ANALOGOUS TO PREPARATION P1.1

| Example | Structure | Chemical Name | M+1 |
|---|---|---|---|
| P1.1 | | 1-(quinolin-2-yl)piperidin-4-ol | 229 |
| P1.2 | | 1-(quinolin-2-yl)azetidin-3-ol | 201 |
| P1.3 | | (racemic mixture) 1-(quinolin-2-yl)piperidin-3-ol | 229 |
| P1.4 | 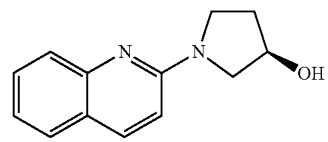 [SMILES: O[C@@H]1CCN(c2ccc3ccccc3n2)C1] | (R)-1-(quinolin-2-yl)pyrrolidin-3-ol | 215 |
| P1.5 | 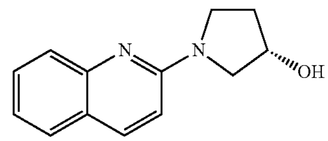 [SMILES: O[C@H]1CCN(c2ccc3ccccc3n2)C1] | (S)-1-(quinolin-2-yl)pyrrolidin-3-ol | 215 |
| P1.6 | 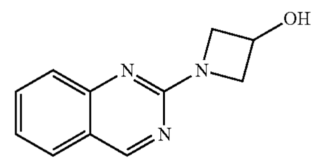 [SMILES: OC1CN(c2ncc3ccccc3n2)C1] | 1-(quinazolin-2-yl)azetidin-3-ol | 202 |
| P1.7 | 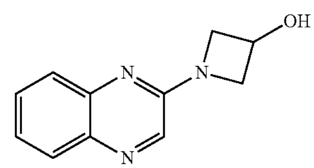 [SMILES: OC1CN(c2cnc3ccccc3n2)C1] | 1-(quinoxalin-2-yl)azetidin-3-ol | 202 |

Preparation P2.1: 2-(4-((3-Chloropyrazin-2-yl)Oxy) Piperidin-1-yl) Quinoline

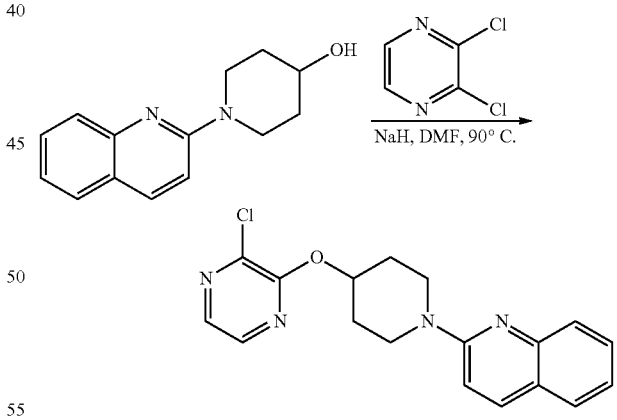

To a solution of 1-(quinolin-2-yl)piperidin-4-ol (see PREPARATION P1.1; 2.0 g, 8.7 mmol) in DMF (30 mL) at room temperature was added sodium hydride (60% wt in mineral oil) (0.47 g, 17.4 mmol) at 0° C. The mixture was stirred at room temperature for 60 min and then 2,3-dichloropyrazine (1.2 g, 8.7 mmol) was added. The reaction mixture was heated to 90° C. overnight and then diluted with water (60 mL) and extracted with EtOAc (2×50 mL). The combined organic extracts were washed with water (40 mL) and brine (40 mL), dried over Na₂SO₄, and filtered. The filtrate was evaporated in vacuo and the residue was purified by flash column chromatography on silica gel (10% to 30% EtOAc in petroleum ether) to give the title product (2.0 g, 5.8 mmol, 70% yield) as white solid. ESI-MS (M+1): 341 calc. for $C_{18}H_{12}ClN_4O$ 340.

TABLE P2

EXAMPLES P2.1-P2.15 PREPARED ANALOGOUS TO PREPARATION P2.1

| Example | Structure | Chemical Name | M + 1 |
|---|---|---|---|
| P2.1 | 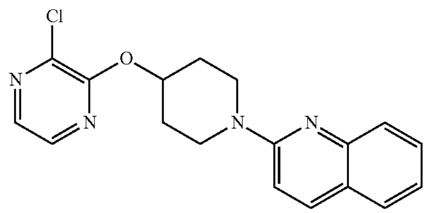 [SMILES: Clc1nccnc1OC1CCN(c2ccc3ccccc3n2)CC1] | 2-(4-((3-chloropyrazin-2-yl)oxy)piperidin-1-yl)quinoline | 341 |
| P2.2 | 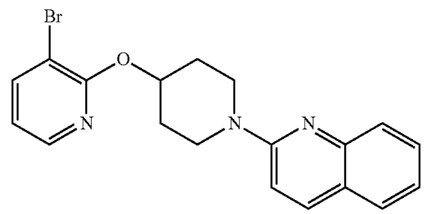 [SMILES: Brc1cccnc1OC1CCN(c2ccc3ccccc3n2)CC1] | 2-(4-((3-bromopyridin-2-yl)oxy)piperidin-1-yl)quinoline | 384 |
| P2.3 | (racemic mixture) | (racemix mixture) 2-(3-((3-chloropyrazin-2-yl)oxy)piperidin-1-yl)quinoline | 341 |
| P2.4 | 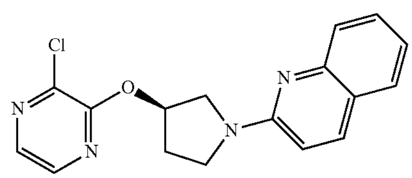 [SMILES: Clc1nccnc1O[C@@H]1CCN(c2ccc3ccccc3n2)C1] | (R)-2-(3-((3-chloropyrazin-2-yl)oxy)pyrrolidin-1-yl)quinoline | 327 |
| P2.5 | 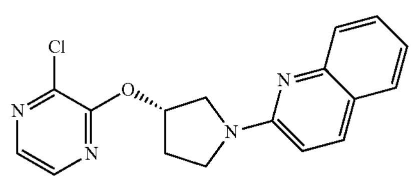 [SMILES: Clc1nccnc1O[C@H]1CCN(c2ccc3ccccc3n2)C1] | (S)-2-(3-((3-chloropyrazin-2-yl)oxy)pyrrolidin-1-yl)quinoline | 327 |
| P2.6 | 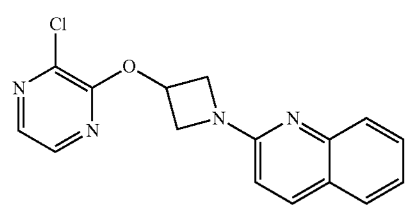 [SMILES: Clc1nccnc1OC1CN(c2ccc3ccccc3n2)C1] | 2-(3-((3-chloropyrazin-2-yl)oxy)azetidin-1-yl)quinoline | 313 |

TABLE P2-continued

EXAMPLES P2.1-P2.15 PREPARED ANALOGOUS TO PREPARATION P2.1

| Example | Structure | Chemical Name | M + 1 |
|---|---|---|---|
| P2.7 | 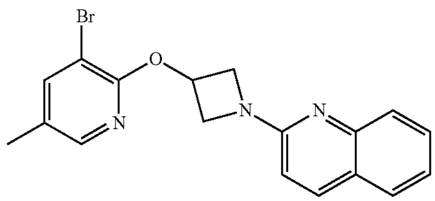 [SMILES: Cc1cnc(OC2CN(c3ccc4ccccc4n3)C2)c(Br)c1] | 2-(3-((3-bromo-5-methylpyridin-2-yl)oxy)azetidin-1-yl)quinoline | 370 |
| P2.8 | 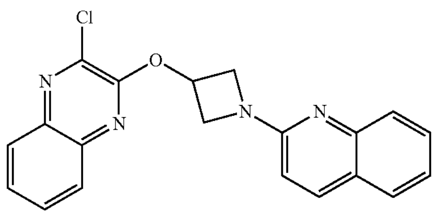 [SMILES: Clc1nc2ccccc2nc1OC1CN(c2ccc3ccccc3n2)C1] | 2-chloro-3-((1-(quinolin-2-yl)azetidin-3-yl)oxy)quinozaline | 363 |
| P2.9 | 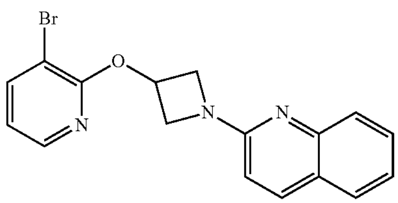 [SMILES: Brc1cccnc1OC1CN(c2ccc3ccccc3n2)C1] | 2-(3-((3-bromopyridin-2-yl)oxy)azetidin-1-yl)quinoline | 356 |
| P2.10 | 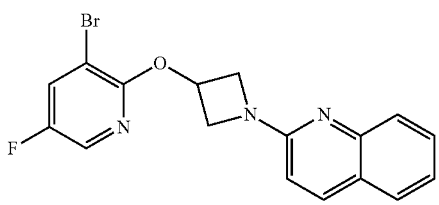 [SMILES: Fc1cnc(OC2CN(c3ccc4ccccc4n3)C2)c(Br)c1] | 2-(3-((3-bromo-5-fluoropyridin-2-yl)oxy)azetidin-1-yl)quinoline | 374 |
| P2.11 | 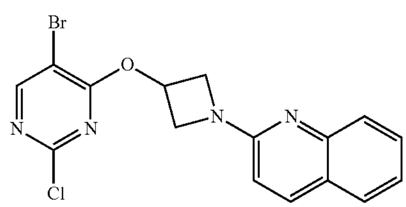 [SMILES: Clc1ncc(Br)c(OC2CN(c3ccc4ccccc4n3)C2)n1] | 2-(3-((5-bromo-2-chloropyrimidin-4-yl)oxy)azetidin-1-yl)quinoline | 393 |
| P2.12 | 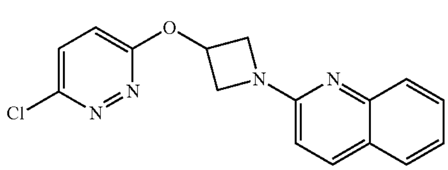 [SMILES: Clc1ccc(OC2CN(c3ccc4ccccc4n3)C2)nn1] | 2-(3-((6-chloropyridazin-3-yl)oxy)azetidin-1-yl)quinoline | 313 |
| P2.13 | 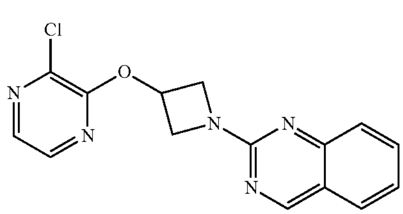 [SMILES: Clc1nccnc1OC1CN(c2ncc3ccccc3n2)C1] | 2-(3-((3-chloropyrazin-2-yl)oxy)azetidin-1-yl)quinazoline | 314 |

TABLE P2-continued

EXAMPLES P2.1-P2.15 PREPARED ANALOGOUS TO PREPARATION P2.1

| Example | Structure | Chemical Name | M + 1 |
|---|---|---|---|
| P2.14 | 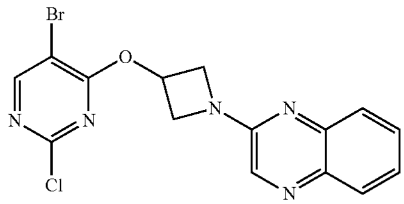 [SMILES: Clc1ncc(Br)c(OC2CN(c3cnc4ccccc4n3)C2)n1] | 2-(3-((5-bromo-2-chloropyrimidin-4-yl)oxy)azetidin-1-yl)quinoxaline | 391, 393 |
| P2.15 | 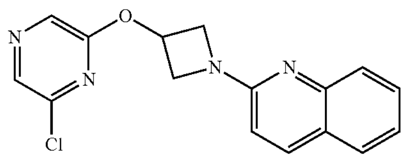 [SMILES: Clc1cncc(OC2CN(c3ccc4ccccc4n3)C2)n1] | 2-(3-((6-chloropyrazin-2-yl)oxy)azetidin-1-yl)quinoline | 313 |

Preparation P3.1: 2-(3-((3-Bromopyridin-4-yl)Oxy)Azetidin-1-yl) Quinoline

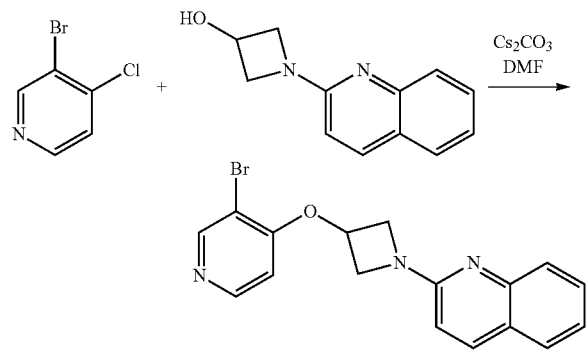

To a solution of 1-(quinolin-2-yl)azetidin-3-ol (see PREPARATION P1.2, step 1; 320 mg, 1.60 mmol) in DMF (10 mL) was added $Cs_2CO_3$ (1.04 g, 3.2 mmol) and 3-bromo-4-chloropyridine (307 mg, 1.60 mmol). The mixture was stirred at 90° C. overnight and then diluted with water (20 mL) and extracted with EtOAc (2×30 mL). The combined organic extracts were washed with water (30 mL) and brine (30 mL), dried over $Na_2SO_4$, and filtered. The filtrate was evaporated in vacuo and the residue was purified by flash column chromatography on silica gel (5% to 30% EtOAc in petroleum ether) to give the title product (350 mg, 0.98 mmol, 61% yield) as white solid. ESI-MS (M+1): 356 calc. for $C_{17}H_{14}BrN_3O$ 355.

TABLE P3

EXAMPLES P3.1-P3.7 PREPARED ANALOGOUS TO PREPARATION P3.1

| Example | Structure | Chemical Name | M + 1 |
|---|---|---|---|
| P3.1 | 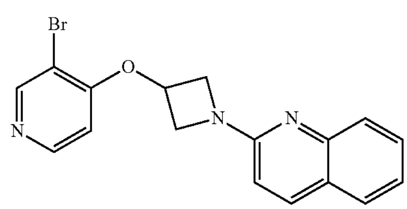 [SMILES: Brc1cnccc1OC1CN(c2ccc3ccccc3n2)C1] | 2-(3-((3-bromopyridin-4-yl)oxy)azetidin-1-yl)quinoline | 356 |
| P3.2 | 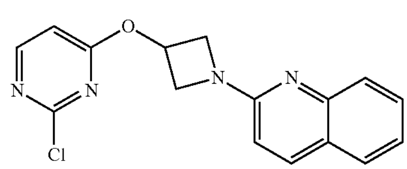 [SMILES: Clc1nccc(OC2CN(c3ccc4ccccc4n3)C2)n1] | 2-(3-((2-chloropyrimidin-4-yl)oxy)azetidin-1-yl)quinoline | 313 |

TABLE P3-continued

EXAMPLES P3.1-P3.7 PREPARED ANALOGOUS TO PREPARATION P3.1

| Example | Structure | Chemical Name | M + 1 |
|---|---|---|---|
| P3.3 | 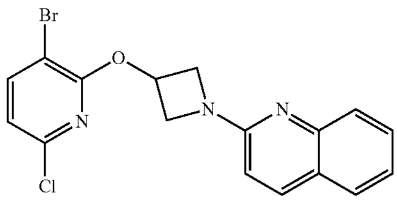 [SMILES: Clc1ccc(Br)c(OC2CN(c3ccc4ccccc4n3)C2)n1] | 2-(3-((3-bromo-6-chloropyridin-2-yl)oxy)azetidin-1-yl)quinoline | 391 |
| P3.4 | 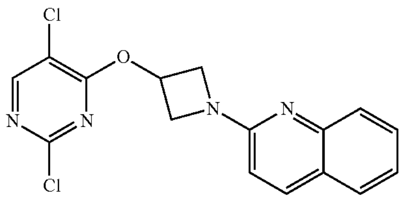 [SMILES: Clc1ncc(Cl)c(OC2CN(c3ccc4ccccc4n3)C2)n1] | 2-(3-((2,5-dichloropyrimidin-4-yl)oxy)azetidin-1-yl)quinoline | 348 |
| P3.5 | 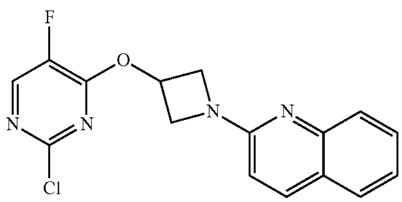 [SMILES: Fc1cnc(Cl)nc1OC1CN(c2ccc3ccccc3n2)C1] | 2-(3-((2-chloro-5-fluoropyrimidin-4-yl)oxy)azetidin-1-yl)quinoline | 331 |
| P3.6 | 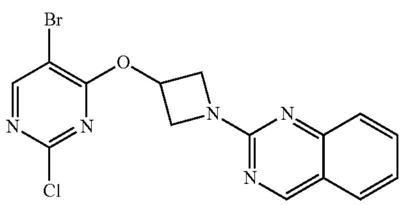 [SMILES: Clc1ncc(Br)c(OC2CN(c3ncc4ccccc4n3)C2)n1] | 2-(3-((5-bromo-2-chloropyrimidin-4-yl)oxy)azetidin-1-yl)quinazoline | 393, 395 |
| P3.7 | 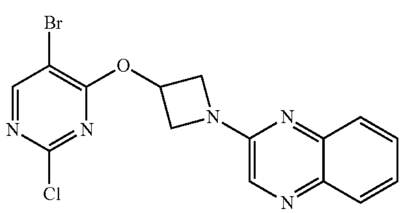 [SMILES: Clc1ncc(Br)c(OC2CN(c3cnc4ccccc4n3)C2)n1] | 2-(3-((5-bromo-2-chloropyrimidin-4-yl)oxy)azetidin-1-yl)quinoxaline | 393 |

Preparation P4.1: 2-(3-((3-(Piperidin-4-yl)Pyrazin-2-yl)Oxy)Azetidin-1-yl)Quinoline Hydrochloride

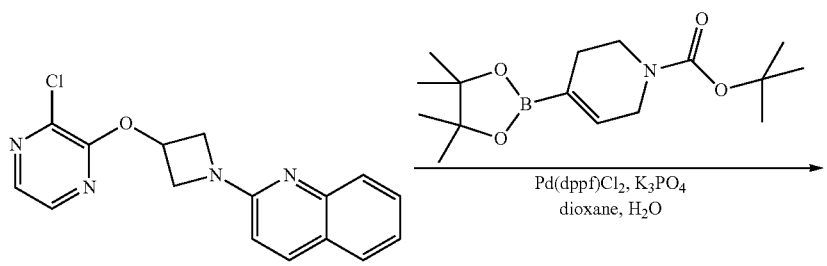

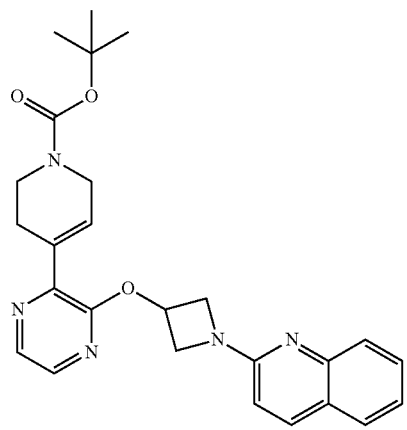

-continued

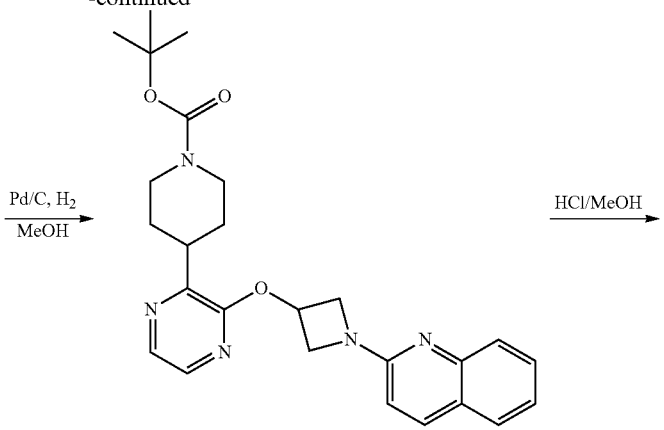

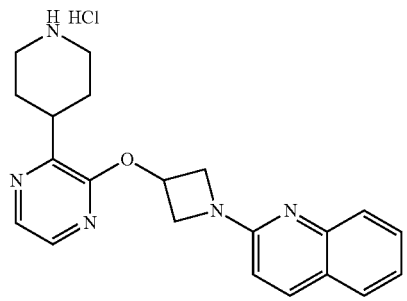

Step 1: Tert-Butyl 4-(3-((1-(Quinolin-2-yl)Azetidin-3-yl)Oxy)Pyrazin-2-yl)-5,6-Dihydropyridine-1(2H)-Carboxylate To a solution of 2-(3-((3-chloropyrazin-2-yl)oxy)azetidin-1-yl)quinoline (see PREPARATION P2.6; 624 mg, 2.0 mmol), tert-butyl 4-(4,4,5,5-tetramethyl-1,3,2-dioxaborolan-2-yl)-5,6-dihydropyridine-1(2H)-carboxylate (618 mg, 2.0 mmol) and $K_3PO_4$ (848 mg, 4.0 mmol) in 1,4-dioxane (20 mL) and $H_2O$ (4 mL) was added Pd(dppf)Cl$_2$ (146 mg, 0.2 mmol) then the reaction mixture was stirred at 110° C. under $N_2$ atmosphere overnight. The reaction mixture was filtered through CELITE® and washed with $CH_2Cl_2$ (50 mL). The filtrate was concentrated and the crude product was purified by silica gel column to give tert-butyl 4-(3-((1-(quinolin-2-yl)azetidin-3-yl)oxy)pyrazin-2-yl)-5,6-dihydropyridine-1(2H)-carboxylate (600 mg, 1.3 mmol, yield 65%). ESI-MS (M+1): 460 calc. for $C_{26}H_{29}N_5O_3$ 459.

Step 2: Tert-Butyl 4-(3-((1-(Quinolin-2-yl)Azetidin-3-yl)Oxy)Pyrazin-2-yl)Piperidine-1-Carboxylate A mixture of tert-butyl 4-(3-((1-(quinolin-2-yl)azetidin-3-yl)oxy)pyrazin-2-yl)-5,6-dihydropyridine-1(2H)-carboxylate (459 mg, 1.0 mmol) and wet Pd—C (50%, 300 mg) in MeOH (20 mL) was stirred under $H_2$ (30 psi) at room temperature overnight then the reaction mixture was filtered through and washed with MeOH. The filtrate was concentrated in vacuo to give tert-butyl 4-(3-((1-(quinolin-2-yl)azetidin-3-yl)oxy)pyrazin-2-yl)piperidine-1-carboxylate (400 mg, 0.86 mmol, yield 86%). ESI-MS (M+1): 463 calc. for $C_{26}H_{31}N_5O_3$ 462.

Step 3: 2-(3-((3-(Piperidin-4-yl)Pyrazin-2-yl)Oxy) Azetidin-1-yl)Quinoline Hydrochloride To tert-butyl 4-(3-((1-(quinolin-2-yl)azetidin-3-yl)oxy)pyrazin-2-yl)piperidine-1-carboxylate (400 mg, 0.86 mmol) was added 4 M HCl in MeOH (20 mL). The reaction mixture was stirred at room temperature for 30 min and concentrated. The residue was dried under high vacuum to give 2-(3-((3-(piperidin-4-yl)pyrazin-2-yl)oxy)azetidin-1-yl)quinoline hydrochloride (310 mg, 0.86 mmol, 100% yield) as a white solid. ESI-MS (M+1): 362 calc. for $C_{21}H_{23}N_5O$ 361.

TABLE P4

EXAMPLES P4.1-P4.9 PREPARED ANALOGOUS TO PREPARATION P4.1

| Example | Structure | Chemical Name | M + 1 |
|---|---|---|---|
| P4.1 | 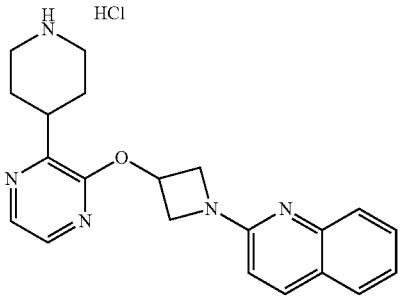 [SMILES: Cl ; c1ccc2nc(N3CC(Oc4nccnc4C4CCNCC4)C3)ccc2c1] | 2-(3-((3-(piperidin-4-yl)pyrazin-2-yl)oxy)azetidin-1-yl)quinoline hydrochloride | 362 |
| P4.2 | 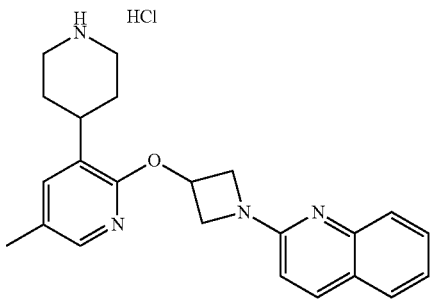 [SMILES: Cl ; Cc1cnc(OC2CN(c3ccc4ccccc4n3)C2)c(C2CCNCC2)c1] | 2-(3-((5-methyl-3-(piperidin-4-yl)pyridin-2-yl)oxy)azetidin-1-yl)quinoline hydrochloride | 375 |
| P4.3 | 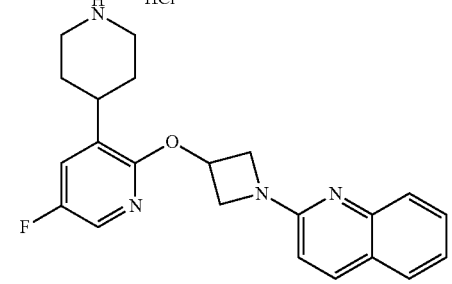 | 2-(3-((5-fluoro-3-(piperidin-4-yl)pyridin-2-yl)oxy)azetidin-1-yl)quinoline hydrochloride | 371 |
| P4.4 | 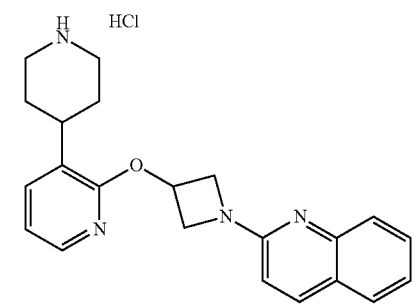 [SMILES: Cl ; c1cnc(OC2CN(c3ccc4ccccc4n3)C2)c(C2CCNCC2)c1] | 2-(3-((3-(piperidin-4-yl)pyridin-2-yl)oxy)azetidin-1-yl)quinoline hydrochloride | 361 |
| P4.5 | 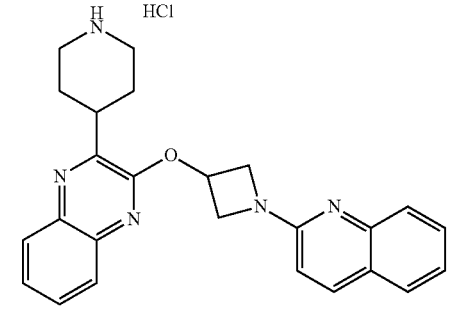 [SMILES: Cl ; c1ccc2nc(N3CC(Oc4nc5ccccc5nc4C4CCNCC4)C3)ccc2c1] | 2-(piperidin-4-yl)-3-((1-(quinolin-2-yl)azetidin-3-yl)oxy)quinoxaline hydrochloride | 412 |

TABLE P4-continued

EXAMPLES P4.1-P4.9 PREPARED ANALOGOUS TO PREPARATION P4.1

| Example | Structure | Chemical Name | M + 1 |
|---|---|---|---|
| P4.6 | 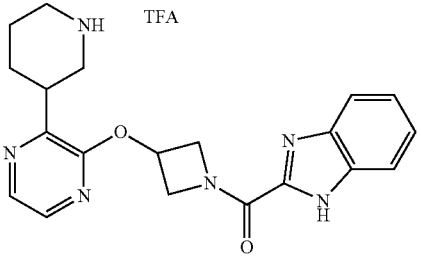 [SMILES: O=C(c1nc2ccccc2[nH]1)N1CC(Oc2nccnc2C2CCCNC2)C1] | (1H-benzo[d]imidazol-2-yl)(3-((3-(piperidin-3-yl)pyrazin-2-yl)oxy)azetidin-1-yl)methanone | |
| P4.7 | 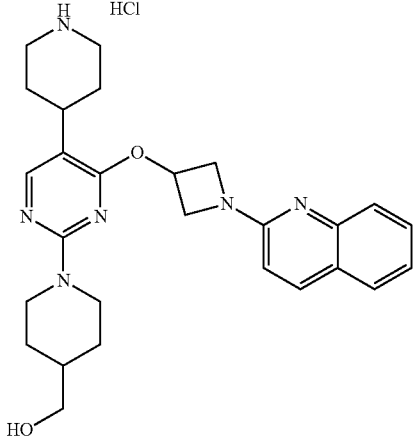 [SMILES: Cl ; OCC1CCN(c2ncc(C3CCNCC3)c(OC3CN(c4ccc5ccccc5n4)C3)n2)CC1] | (1-(5-(piperidin-4-yl)-4-((1-(quinolin-2-yl)azetidin-3-yl)oxy)pyrimidin-2-yl)piperidin-4-yl)methanol hydrochloride | 475 |
| P4.8 | 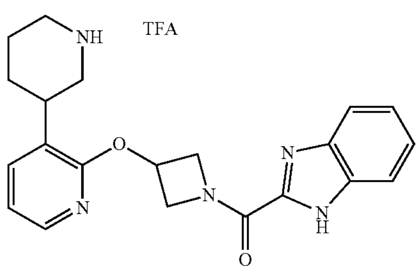 [SMILES: O=C(c1nc2ccccc2[nH]1)N1CC(Oc2ncccc2C2CCCNC2)C1] | (1H-benzo[d]imidazol-2-yl)(3-((3-(piperidin-3-yl)pyridin-2-yl)oxy)azetidin-1-yl)methanone | |
| P4.9 | 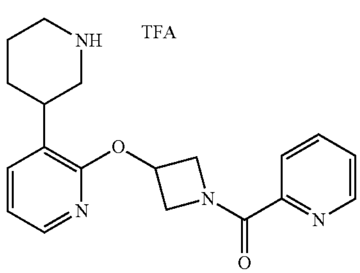 [SMILES: O=C(c1ccccn1)N1CC(Oc2ncccc2C2CCCNC2)C1] | (3-((3-(piperidin-3-yl)pyridin-2-yl)oxy)azetidin-1-yl)(pyridin-2-yl)methanone | |

Preparation P5.1: (1H-Benzo[D]Imidazol-2-yl)(3-((3-(1,2,5,6-Tetrahydropyridin-3-yl)Pyrazin-2-yl)Oxy)Azetidin-1-yl)Methanone

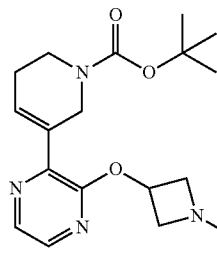

→ 2,2,2-trifluoroacetic acid →

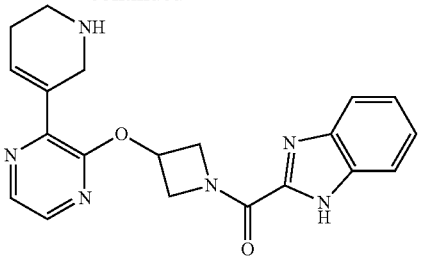

To a solution of tert-butyl 3-(3-(1-(1H-benzo[d]imidazole-2-carbonyl)azetidin-3-yloxy)pyrazin-2-yl)-5,6-dihydropyridine-1(2H)-carboxylate (see EXAMPLE 10.72; 120 mg, 0.252 mmol) in DCM (2 mL) is added 2,2,2-trifluoroacetic acid (116 μL, 1.511 mmol). The reaction was stirred at room temperature 24 hours. The reaction was concentrated, and the residue dissolved in MeOH (2 mL) and applied to a Varian SCX ion exchange column (1 g). The salt was eluted with MeOH (2×5 mL) and the product eluted with 2.0 M $NH_3$ in MeOH (2×5 mL). The $NH_3$ containing fractions were concentrated to give the crude amine which was carried on to the next step without further purification.

TABLE P5

EXAMPLES 5.1-5.4 PREPARED ANALOGOUS TO PREPARATION 5

| Example | Structure | Chemical Name |
|---|---|---|
| P5.1 | 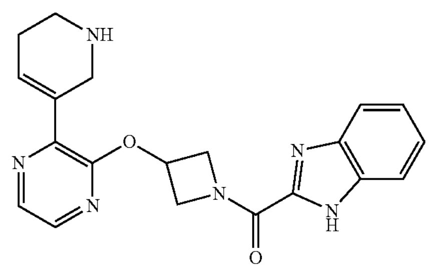 [SMILES: O=C(c1nc2ccccc2[nH]1)N1CC(Oc2nccnc2C2=CCCNC2)C1] | (1H-benzo[d]imidazol-2-yl)(3-((3-(1,2,5,6-tetrahydropyridin-3-yl)pyrazin-2-yl)oxy)azetidin-1-yl)methanone |
| P5.2 | 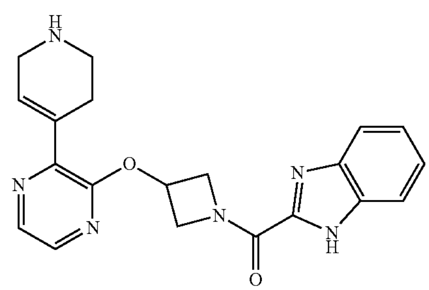 [SMILES: O=C(c1nc2ccccc2[nH]1)N1CC(Oc2nccnc2C2=CCNCC2)C1] | (1H-benzo[d]imidazol-2-yl)(3((3-(1,2,3,6-tetrahydropyridin-4-yl)pyrazin-2-yl)oxy)azetidin-1-yl)methanone |
| P5.3 | 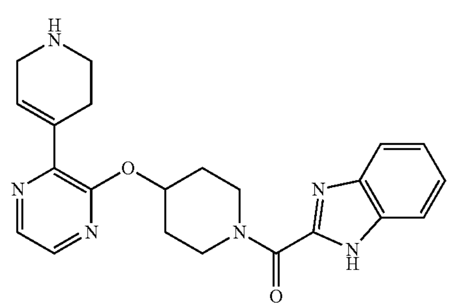 [SMILES: O=C(c1nc2ccccc2[nH]1)N1CCC(Oc2nccnc2C2=CCNCC2)CC1] | (1H-benzo[d]imidazol-2-yl)(4((3-(1,2,3,6-tetrahydropyridin-4-yl)pyrazin-2-yl)oxy)piperidin-1-yl)methanone |

TABLE P5-continued

EXAMPLES 5.1-5.4 PREPARED ANALOGOUS TO PREPARATION 5

| Example | Structure | Chemical Name |
|---|---|---|
| P5.4 | 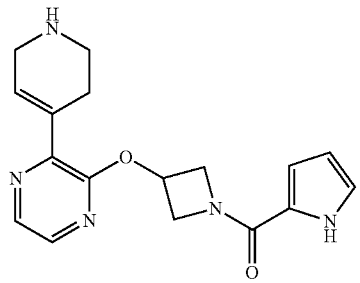 [SMILES: O=C(c1ccc[nH]1)N1CC(Oc2nccnc2C2=CCNCC2)C1] | (1H-pyrrol-2-yl)(3-((3-(1,2,3,6-tetrahydropyridin-4-yl)pyrazin-2-yl)oxy)azetidin-1-yl)methanone |

Preparation P6.1: 2-(3-((6-Chloro-5-Iodopyridazin-3-yl)Oxy)Azetidin-1-yl)Quinoline and 2-(3-((6-Chloro-4-Iodopyridazin-3-yl)Oxy)Azetidin-1-yl)Quinoline

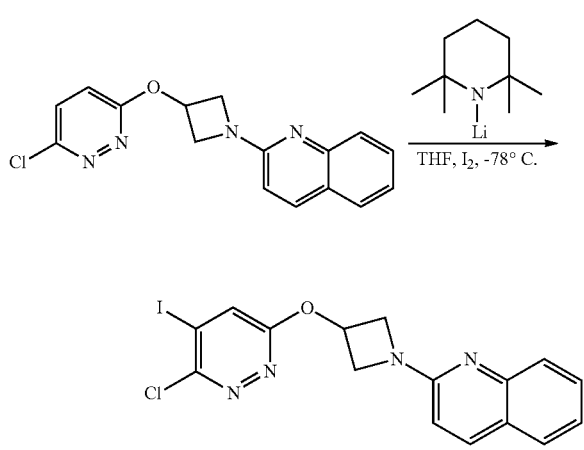

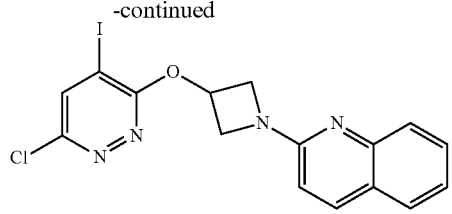

To a solution of 2,2,6,6-tetramethylpiperidin-1-ide (1.12 mg, 7.8 mmol) in THF (20 mL) at −78° C. was added dropwise n-BuLi (3.3 mL, 7.8 mmol). The mixture was stirred at −78° C. for 15 minutes and 2-(3-((6-chloropyridazin-3-yl)oxy)azetidin-1-yl)quinoline (2.02 g, 6.6 mmol) was added. The reaction mixture was stirred at −78° C. for 1 hour. Then $I_2$ (3.3 g, 13.2 mmol) was added at −78° C. The reaction mixture was stirred at −78° C. for 1 hour, and warmed to room temperature, stirred for 1 hour, and neutralized with saturated $NH_4Cl$ (20 mL), diluted with EtOAc (50 mL) and water (80 mL). The aqueous layer was extracted with EtOAc (3×50 mL) and the combined organic extracts were washed with aqueous $Na_2S_2O_3$ (3×50 mL) and brine (40 mL), dried over $MgSO_4$, filtered, and concentrated. The residue was purified by flash column chromatography on silica gel (20% to 70% EtOAc in petroleum ether) to give the title product (1.56 g, 3.6 mmol, yield: 55%); without further separation.

TABLE P6

EXAMPLES P6.1-P6.3 PREPARED ANALOGOUS TO PREPARATION P6.1

| Example | Structure | | Chemical Name | M + 1 |
|---|---|---|---|---|
| P6.1 | | AND | 2-(3-((6-chloro-5-iodopyridazin-3-yl)oxy)azetidin-1-yl)quinoline AND 2-(3-((6-chloro-4-iodopyridazin-3-yl)oxy)azetidin-1-yl)quinoline as isomeric mixture | 439 |

TABLE P6-continued

EXAMPLES P6.1-P6.3 PREPARED ANALOGOUS TO PREPARATION P6.1

| Example | Structure | Chemical Name | M + 1 |
|---|---|---|---|
| P6.2 | 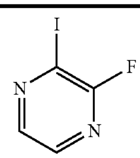 | 2-fluoro-3-iodopyrazine | |
| P6.3 | 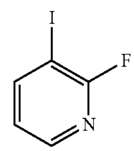 | 2-fluoro-3-iodopyridine | |

Preparation P7.1: (1-(5-Bromo-4-((1-(Quinolin-2-yl)Azetidin-3-yl)Oxy)Pyrimidin-2-yl)Piperidin-4-yl)Methanol

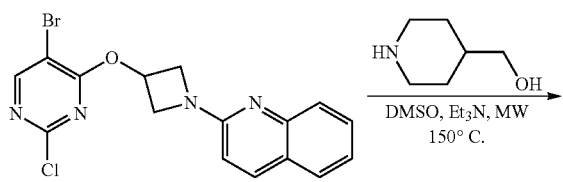

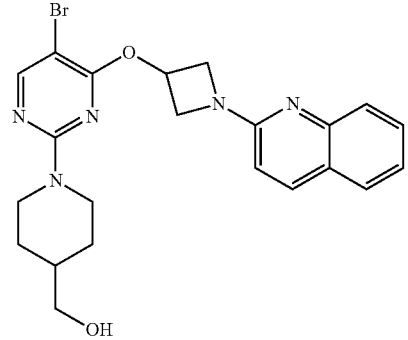 [SMILES: OCC1CCN(c2ncc(Br)c(OC3CN(c4ccc5ccccc5n4)C3)n2)CC1]

To a mixture of 2-(3-((5-bromo-2-chloropyrimidin-4-yl)oxy)azetidin-1-yl)quinoline (see PREPARATION P2.11; 0.1 g, 0.25 mmol) and piperidin-4-yl-methanol (0.028 g, 0.25 mmol) was added DMSO (2 mL) and triethylamine (0.05 g, 0.50 mmol). The solution was heated to 150° C. under microwave for 3 hours. The mixture was then extracted with EtOAc (2×20 mL). The combined organic extracts were washed with water (10 mL) and brine (10 mL), dried over $Na_2SO_4$, and filtered. The filtrate was evaporated in vacuo and the residue was purified by flash column chromatography on silica gel (20% to 60% EtOAc in hexanes) to give the title product (0.02 g, 0.04 mmol, 17% yield) as white solid. ESI-MS (M+1): 471 calc. for $C_{22}H_{24}BrN_5O_2$ 470.

TABLE P7

EXAMPLES P7.1-P7.2 PREPARED ANALOGOUS TO PREPARATION P7.1

| Example | Structure | Chemical Name | M + 1 |
|---|---|---|---|
| P7.1 | 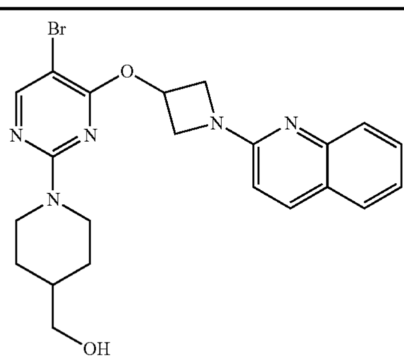 | (1-(5-bromo-4-((1-(quinolin-2-yl)azetidin-3-yl)oxy)pyrimidin-2-yl)piperidin-4-yl)methanol | 470, 472 |

TABLE P7-continued

EXAMPLES P7.1-P7.2 PREPARED ANALOGOUS TO PREPARATION P7.1

| Example | Structure | Chemical Name | M + 1 |
|---|---|---|---|
| P7.2 | 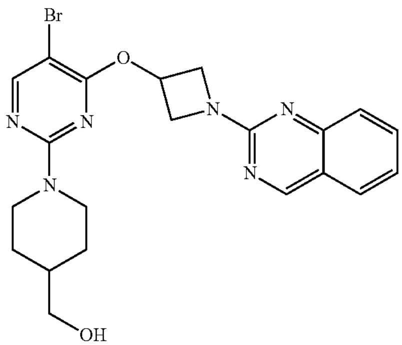 | (1-(5-bromo-4-((1-(quinazolin-2-yl)azetidin-3-yl)oxy)pyrimidin-2-yl)piperidin-4-yl)methanol | 472, 474 |

Preparation P8.1: 1-(3-((1-(Quinolin-2-yl)Azetidin-3-yl)Oxy)Pyrazin-2-yl)Piperidin-4-One

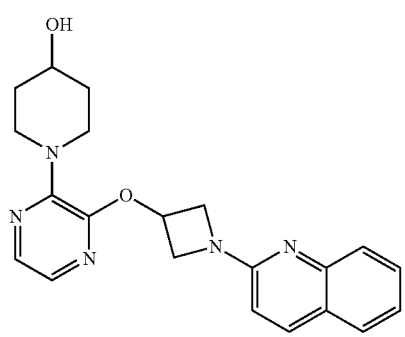

DMP / DCM →

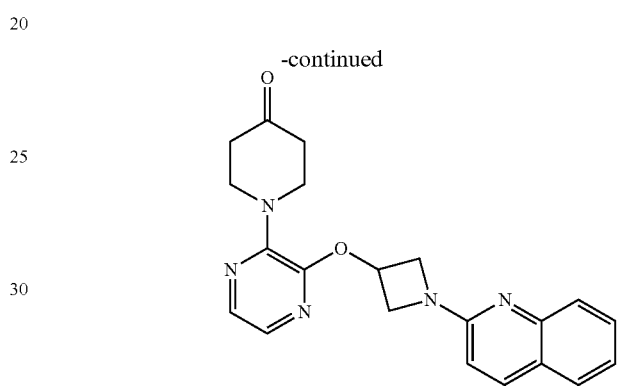

-continued 1-(3-((1-(quinolin-2-yl)azetidin-3-yl)oxy)pyrazin-2-yl)piperidin-4-ol (see EXAMPLE 1.1; 94 mg, 0.25 mmol) was dissolved in anhydrous $CH_2Cl_2$ (10 mL), treated with Dess-Martin periodinane (DMP) (195 mg, 0.50 mmol, 2.0 equiv) and stirred at room temperature until complete conversion. The organic layer was washed with an aqueous solution of $NaHCO_3/Na_2S_2O_3$ (3×10 mL)), dried over $Na_2SO_4$, filtered and evaporated. The resulting residue was purified by flash chromatography (20% to 40% EtOAc in petroleum ether) to 1-(3-((1-(quinolin-2-yl)azetidin-3-yl)oxy)pyrazin-2-yl)piperidin-4-one (75 mg, 0.20 mmol, 80% yield) as a white solid. ESI-MS (M+1): 376 calc. for $C_{21}H_{21}N_5O_2$ 375.

TABLE P8

EXAMPLES P8.1-P8.5 PREPARED ANALOGOUS TO PREPARATION P8.1

| Example | Structure | Chemical Name | M + 1 |
|---|---|---|---|
| P8.1 | 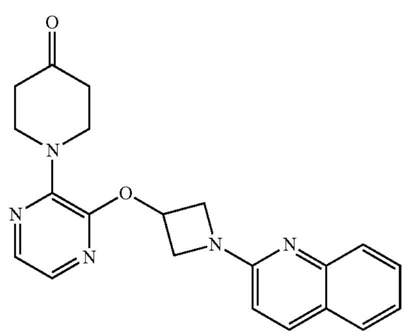 [SMILES: O=C1CCN(c2nccnc2OC2CN(c3ccc4ccccc4n3)C2)CC1] | 1-(3-((1-(quinolin-2-yl)azetidin-3-yl)oxy)pyrazin-2-yl)piperidin-4-one | 376 |

TABLE P8-continued
EXAMPLES P8.1-P8.5 PREPARED ANALOGOUS TO PREPARATION P8.1
| Example | Structure | Chemical Name | M + 1 |
|---|---|---|---|
| P8.2 | 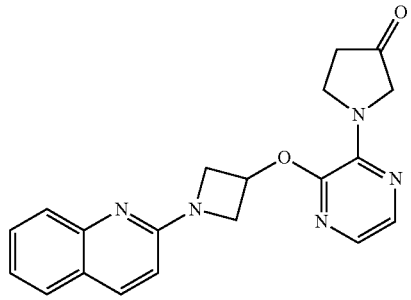 [SMILES: O=C1CCN(c2nccnc2OC2CN(c3ccc4ccccc4n3)C2)C1] | 1-(3-((1-(quinolin-2-yl)azetidin-3-yl)oxy)pyrazin-2-yl)pyrrolidin-3-one | 362 |
| P8.3 | 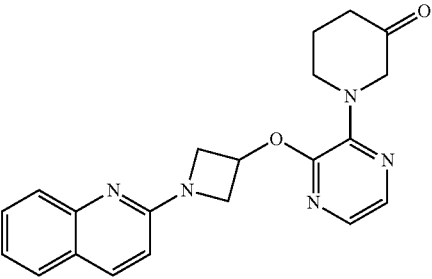 [SMILES: O=C1CCCN(c2nccnc2OC2CN(c3ccc4ccccc4n3)C2)C1] | 1-[3-(1-Quinolin-2-yl-azetidin-3-yloxy)-pyrazin-2-yl]-piperidin-3-one | 376 |
| P8.4 | 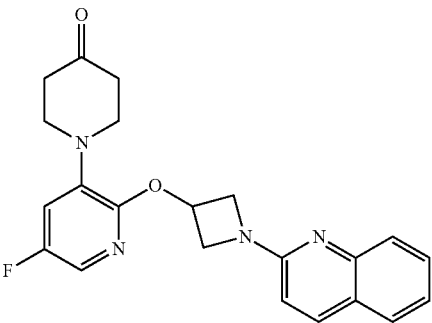 [SMILES: O=C1CCN(c2cc(F)cnc2OC2CN(c3ccc4ccccc4n3)C2)CC1] | 1-(5-fluoro-2-((1-(quinolin-2-yl)azetidin-3-yl)oxy)pyridin-3-yl)piperidin-4-one | |
| P8.5 | 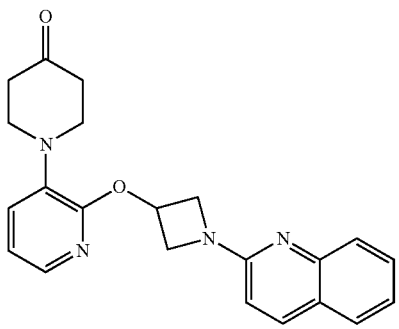 [SMILES: O=C1CCN(c2cccnc2OC2CN(c3ccc4ccccc4n3)C2)CC1] | 1-(2-((1-(quinolin-2-yl)azetidin-3-yl)oxy)pyridin-3-yl)piperidin-4-one | |

Preparation P9.1: 3-Chloro-N-(1-(Quinolin-2-yl)Azetidin-3-yl)Pyrazin-2-Amine

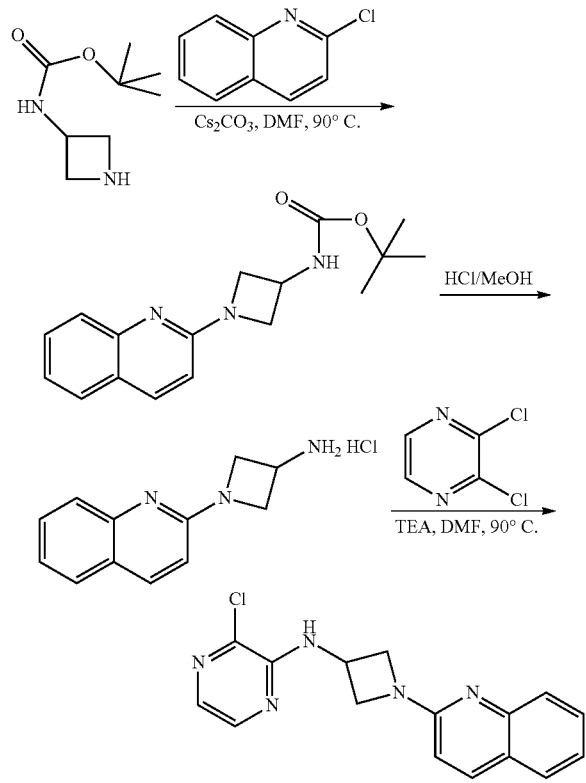

Step 1. Tert-Butyl (1-(Quinolin-2-yl)Azetidin-3-yl)Carbamate

A mixture of $Cs_2CO_3$ (3.2 g, 10.0 mmol), 2-chloro-quinoline (0.8 g, 5.0 mmol) and tert-butyl azetidin-3-ylcarbamate (0.8 g, 5.0 mmol) was dissolved in DMF (20 mL) and the resulting mixture was heated to 100° C. overnight. Then the mixture was diluted with water (20 mL) and extracted with EtOAc (2×50 mL). The combined organic extracts were combined and washed with water (20 mL) and brine (20 mL), dried over $Na_2SO_4$, and filtered. The filtrate was evaporated in vacuo and the residue was purified by flash column chromatography on silica gel (20% to 70% EtOAc in petroleum ether) to give tert-butyl (1-(quinolin-2-yl)azetidin-3-yl)carbamate (0.8 g, 2.9 mmol, 53% yield) as white solid. ESI-MS (M+1): 300 calc. for $C_{17}H_{21}N_3O_2$ 299.

Step 2. 1-(Quinolin-2-yl)Azetidin-3-Amine Hydrochloride

To tert-butyl (1-(quinolin-2-yl)azetidin-3-yl)carbamate (0.8 g, 2.9 mmol) was added 4 M HCl in MeOH (20 mL). The reaction mixture was stirred at room temperature for 30 min and concentrated. The remained solid was dried under high vacuum to give 1-(quinolin-2-yl)azetidin-3-amine hydrochloride (557 mg, 2.8 mmol, 96% yield) as a white solid. ESI-MS (M+1): 200 calc. for $C_{12}H_{13}N_3$ 199.

Step 3. 3-Chloro-N-(1-(Quinolin-2-yl)Azetidin-3-yl)Pyrazin-2-Amine

Triethylamine (560 mg, 5.6 mmol), 1-(quinolin-2-yl)azetidin-3-amine hydrochloride (557 mg, 2.8 mmol) and 2,3-dichloro-pyrazine (414 mg, 2.8 mmol) were dissolved in DMF (20 mL). The resulting mixture was heated to 90° C. overnight. The mixture was then diluted with water (20 mL) and extracted with EtOAc (2×50 mL). The combined organic extracts were combined and washed with water (20 mL) and brine (20 mL), dried over $Na_2SO_4$, and filtered. The filtrate was evaporated in vacuo and the residue was purified by flash column chromatography on silica gel (20% to 50% EtOAc in petroleum ether) to give 3-chloro-N-(1-(quinolin-2-yl)azetidin-3-yl)pyrazin-2-amine (479 mg, 1.5 mmol, 55% yield) as white solid. ESI-MS (M+1): 312 calc. for $C_{16}H_{14}ClN_5$ 311.

Preparation P10.1: 3-Methyl-4-(4,4,5,5-Tetramethyl-1,3,2-Dioxaborolan-2-yl)Pyridine

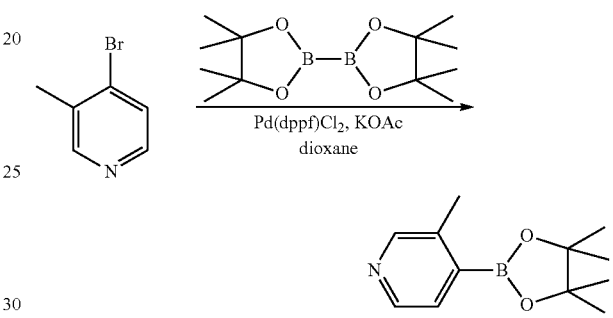

To a solution of 4-bromo-3-methyl-pyridine (170 mg, 1.0 mmol), 4,4,4',4',5,5,5',5'-octamethyl-2,2'-bi(1,3,2-dioxaborolane) (254 mg, 1.0 mmol) and KOAc (180 mg, 2.0 mmol) in 1,4-dioxane (10 mL) was added $Pd(dppf)Cl_2$ (73 mg, 0.1 mmol) then the reaction mixture was stirred at 110° C. under $N_2$ atmosphere overnight. The reaction mixture was filtered through CELITE® and washed with $CH_2Cl_2$ (30 mL). The filtrate was concentrated and the crude product was purified by silica gel column to give the product (105 mg, 0.50 mmol, yield 60%). ESI-MS (M+1): 220 calc. for $C_{12}H_{18}BNO_2$ 219.

TABLE P10

EXAMPLES P10.1-P10.2 PREPARED ANALOGOUS TO PREPARATION P8.1

| Example | Structure | Chemical Name | M + 1 |
|---|---|---|---|
| P10.1 | 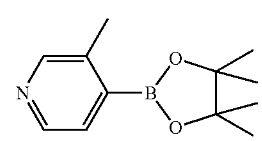 [SMILES: Cc1cnccc1B1OC(C)(C)C(C)(C)O1] | 3-methyl-4-(4,4,5,5-tetramethyl-1,3,2-dioxaborolan-2-yl)pyridine | 220 |
| P10.2 | 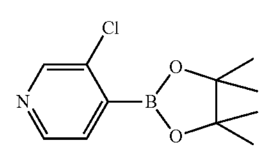 [SMILES: CC1(C)OB(c2ccncc2Cl)OC1(C)C] | 3-chloro-4-(4,4,5,5-tetramethyl-1,3,2-dioxaborolan-2-yl)pyridine | 240 |

Preparation P11.1: Tert-Butyl 3-(4,4,5,5-Tetramethyl-1,3,2-Dioxaborolan-2-yl)-5,6-Dihydropyridine-1(2H)-Carboxylate and Tert-Butyl 5-(4,4,5,5-Tetramethyl-1,3,2-Dioxaborolan-2-yl)-3,4-Dihydropyridine-1(2H)—Carboxylate as Isomeric Mixture

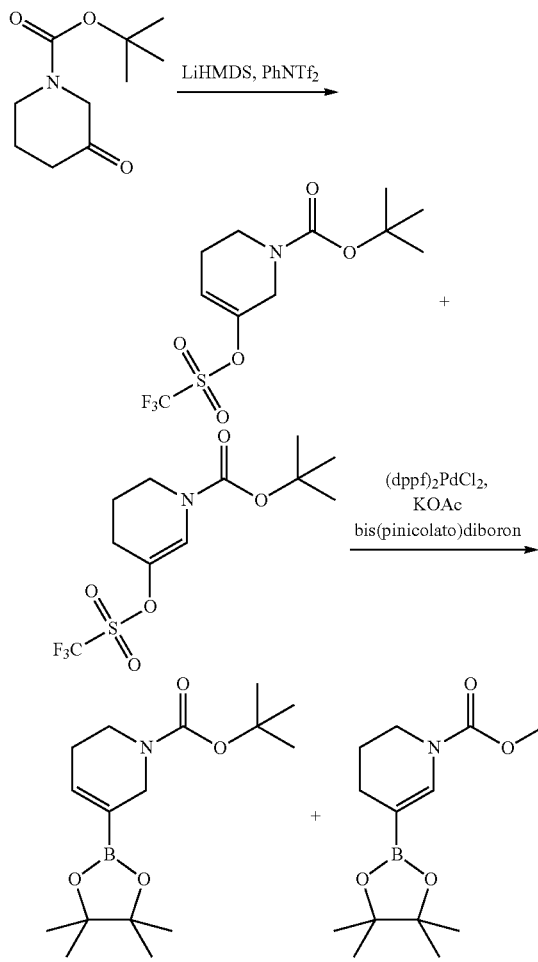

Step 1. Tert-Butyl 3-(Trifluoromethylsulfonyloxy)-5,6-Dihydropyridine-1(2H)-Carboxylate and Tert-Butyl 5-(Trifluoromethylsulfonyloxy)-3,4-Dihydropyridine-1(2H)-Carboxylate as Isomeric Mixture To a solution of tert-butyl 3-oxopiperidine-1-carboxylate (10.00 g, 50.2 mmol) in THF (50 mL) at −78° C. is added dropwise LiHMDS (55.2 mL, 55.2 mmol) (1.0 M in THF). After 20 min, a solution of 1,1,1-trifluoro-N-phenyl-N-(trifluoromethylsulfonyl)methanesulfonamide (PhNTf$_2$) (18.83 g, 52.7 mmol) in THF (50 mL) was added and the reaction warmed to 0° C. and stirred 3 hours. The reaction was quenched with saturated aqueous NaHCO$_3$ solution (1 mL) and the reaction mixture concentrated. The residue was purified through a plug of neutral Al$_2$O$_3$ (10% EtOAc/Hexane eluant) to give a 1:1 mixture of tert-butyl 5-(trifluoromethylsulfonyloxy)-3,4-dihydropyridine-1(2H)-carboxylate (6.28 g, 18.96 mmol, 37.8% yield) and tert-butyl 3-(trifluoromethylsulfonyloxy)-5,6-dihydropyridine-1(2H)-carboxylate (12.56 g, 37.92 mmol, 75.6% yield), an inseparable mixture, as a clear, light yellow oil.

Step 2. Tert-Butyl 3-(4,4,5,5-Tetramethyl-1,3,2-Dioxaborolan-2-yl)-5,6-Dihydropyridine-1(2H)-Carboxylate and Tert-Butyl 5-(4,4,5,5-Tetramethyl-1,3,2-Dioxaborolan-2-yl)-3,4-Dihydropyridine-1(2H)-Carboxylate as Isomeric Mixture A flask with 4,4,4',4',5,5,5'-heptamethyl-2,2'-bi(1,3,2-dioxaborolane) (10.48 g, 43.7 mmol), (dppf)PdCl$_2$ (0.930 g, 1.139 mmol), and potassium acetate (11.18 g, 114 mmol) was flushed with N$_2$ (3×), then 1,4-dioxane (100 mL) was added followed by a solution of tert-butyl 5-(trifluoromethylsulfonyloxy)-3,4-dihydropyridine-1(2H)-carboxylate and tert-butyl 3-(trifluoromethylsulfonyloxy)-5,6-dihydropyridine-1(2H)-carboxylate (1:1 ratio, 12.58 g, 38.0 mmol) in 1,4-dioxane (100 mL). The solution was heated in an 80° C. oil bath for 20 hours. The reaction was quenched with water (100 mL) and the aqueous layer extracted with EtOAc (3×100 mL). The combined organic layers were washed with saturated aqueous NaCl (100 mL), dried with magnesium sulfate (MgSO$_4$), and concentrated. The residue was purified by silica gel chromatography using ISCO™ (330 g SiO$_2$, O-20% EtOAc/hexane) to give tert-butyl 3-(4,4,5,5-tetramethyl-1,3,2-dioxaborolan-2-yl)-5,6-dihydropyridine-1(2H)-carboxylate and tert-butyl 5-(4,4,5,5-tetramethyl-1,3,2-dioxaborolan-2-yl)-3,4-dihydropyridine-1(2H)-carboxylate (7.29 g, 23.58 mmol, 62.1% yield) (inseparable 2:1 mixture of olefin regioisomers) as a white solid.

Preparation P12.1: 1-(4-(4,4,5,5-Tetramethyl-1,3,2-Dioxaborolan-2-yl)-5,6-Dihydropyridin-1(2H)-yl)Ethanone

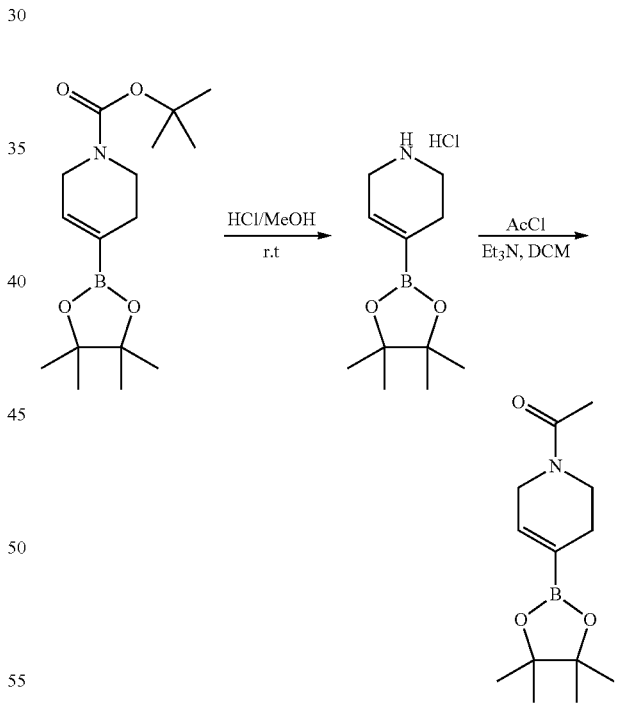

Step 1. 4-(4,4,5,5-Tetramethyl-1,3,2-Dioxaborolan-2-yl)-1,2,3,6-Tetrahydropyridine Hydrochloride The mixture of tert-butyl 4-(4,4,5,5-tetramethyl-1,3,2-dioxaborolan-2-yl)-5,6-dihydropyridine-1(2H)-carboxylate (4.0 g, 12.9 mmol) in HCl/MeOH (20 mL) was stirred at room temperature for 1 hour. Then it was concentrated to give 4-(4,4,5,5-Tetramethyl-[1,3,2]dioxaborolan-2-yl)-1,2,3,6-tetrahydro-pyridine hydrochloride (2.9 g, 11.8 mmol, yield: 91.4%) which was used in the next step without further purification. ESI-MS (M+1): 210 calc. for C$_{11}$H$_{20}$BNO$_2$ 209.

Step 2. 1-(4-(4,4,5,5-Tetramethyl-1,3,2-Dioxaborolan-2-yl)-5,6-Dihydropyridin-1(2H)-yl)Ethanone To a solution of 4-(4,4,5,5-tetramethyl-1,3,2-dioxaborolan-2-yl)-1,2,3,6-tetrahydropyridine hydrochloride (2.9 g, 11.8 mmol) in DCM (30 mL) were added Et$_3$N (3.6 g, 35.4 mmol) and acetyl chloride (AcCl) (932 mg, 11.8 mmol). The reaction mixture was stirred at room temperature for 1 hour, then diluted with DCM (20 mL), washed with H$_2$O (2.0 mL). The organic layer was washed with brine (20 mL), dried over Na$_2$SO$_4$, and filtered, evaporated to give the crude product (3.2 g, crude). ESI-MS (M+1): 252 calc. for C$_{13}$H$_{22}$BNO$_3$ 251.

Preparation 13.1:
2-Chloro-3-(3,6-Dihydro-2H-Pyran-4-yl)Pyridine

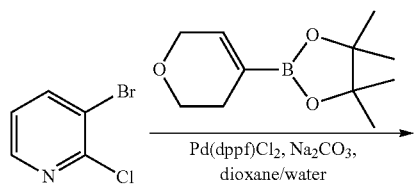

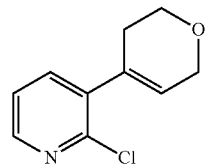

To a solution of 3-bromo-2-chloropyridine (4 g, 10.8 mmol), 4-(3,3,4,4-tetramethyl-borolan-1-yl)-3,6-dihydro-2H-pyran (5.7 g, 13.1 mmol) and Na$_2$CO$_3$ (2.28 g, 21.6 mmol) in 1,4-dioxane (60 mL) and H$_2$O (6 mL) was added Pd(dppf)Cl$_2$ (410 mg, 0.56 mmol). The reaction mixture was stirred at 110° C. under N$_2$ for overnight. The reaction mixture was filtered through CELITE® and washed CH$_2$Cl$_2$. The organic layers were concentrated to give the crude product which was purified by silica gel column chromatography to give the title compound (3.5 g, 14.2 mmol, 70% yield).

TABLE P13

EXAMPLES P13.1-P13.5 PREPARED ANALOGOUS TO PREPARATION P13.1

| Example | Structure | Chemical Name | M + 1 |
|---|---|---|---|
| P13.1 | 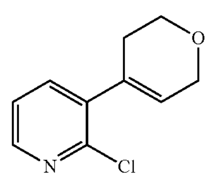 [SMILES: Clc1ncccc1C1=CCOCC1] | 2-chloro-3-(3,6-dihydro-2H-pyran-4-yl)pyridine | 196 |
| P13.2 | 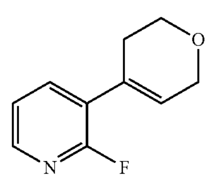 [SMILES: Fc1ncccc1C1=CCOCC1] | 3-(3,6-dihydro-2H-pyran-4-yl)-2-fluoropyridine | |
| P13.3 | 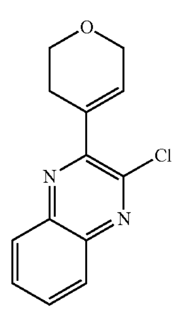 [SMILES: Clc1nc2ccccc2nc1C1=CCOCC1] | 2-chloro-3-(3,6-dihydro-2H-pyran-4-yl)quinoxaline | 247 |

TABLE P13-continued

EXAMPLES P13.1-P13.5 PREPARED ANALOGOUS TO PREPARATION P13.1

| Example | Structure | Chemical Name | M + 1 |
|---|---|---|---|
| P13.4 | 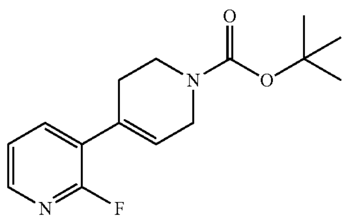 [SMILES: CC(C)(C)OC(=O)N1CC=C(c2cccnc2F)CC1] | tert-butyl 2-fluoro-5',6'-dihydro-[3,4'-bipyridine]-1'(2'H)-carboxylate | 279 |
| P13.5 | 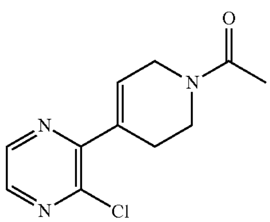 [SMILES: CC(=O)N1CC=C(c2nccnc2Cl)CC1] | 1-(4-(3-chloropyrazin-2-yl)-5,6-dihydropyridin-1(2H)-yl)ethanone | |

Preparation P14.1: 1-(2-Fluoro-5',6'-Dihydro-[3,4'-Bipyridin]-1'(2'H)-yl) Ethanone

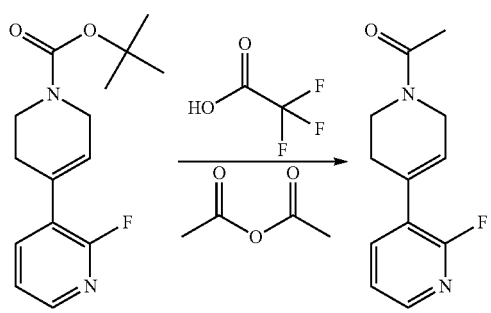

To a solution of tert-butyl 4-(2-fluoropyridin-3-yl)-5,6-dihydropyridine-1(2H)-carboxylate (see PREPARATION P13.4; 3.72 g, 13.37 mmol) in DCM (50 mL) at 0° C. is added 2,2,2-trifluoroacetic acid (2.059 mL, 26.7 mmol, 2.0 eq.). The reaction was warmed to room temperature and stirred 3 hours. Additional 2,2,2-trifluoroacetic acid (4.059 mL, 53 mmol, 4.0 eq.) was added and the reaction stirred an additional 3 hours. The reaction was concentrated, and the residue dissolved in $CH_2Cl_2$ (50 mL) and partioned with saturated aqueous $NaHCO_3$ (25 mL). The aqueous layer was extracted with EtOAc (3×50 mL). The organic layers were combined, dried with magnesium sulfate ($MgSO_4$), and concentrated to give the crude piperidine (1.20 g, 50%). The aqueous layer also contained product, the aqueous layer was concentrated and the solid diluted with 50 mL 50% MeOH/$CH_2Cl_2$ and sonicated 10 min. The solid was filtered and the filtrate concentrated to give 2.80 g crude product.

To the two crude products from above were added acetic anhydride (1.364 g, 13.37 mmol). The solutions were stirred at room temperature for 40 hours. The reaction mixtures were combined, and concentrated. The residue was diluted with $CH_2Cl_2$ and saturated aqueous $NaHCO_3$ and extracted. The aqueous layer was extracted with $CH_2Cl_2$ (2×50 mL), and the organic layers combined, dried over magnesium sulfate ($MgSO_4$), and concentrated. The product was isolated as a brown solid and used in the next step without purification.

TABLE P14

EXAMPLES P14.1-P14.2 PREPARED ANALOGOUS TO PREPARATION 14

| Example | Structure | Chemical Name |
|---|---|---|
| P14.1 | 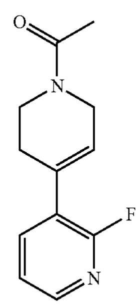 [SMILES: CC(=O)N1CC=C(c2cccnc2F)CC1] | 1-(2-fluoro-5',6'-dihydro-[3,4'-bipyridin]-1'(2'H)-yl)ethanone |
| P14.2 | 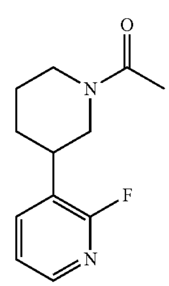 [SMILES: CC(=O)N1CCCC(c2cccnc2F)C1] | 1-(3-(2-fluoropyridin-3-yl)piperidin-1-yl)ethanone |

Preparation P15.1: 1-(4-(2-Fluoropyridin-3-yl)Piperidin-1-yl)Ethanone

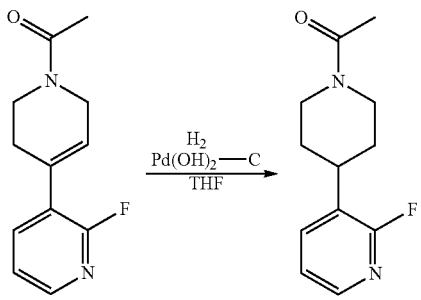

A 2 L Parr shaker bottle was charged with 1-(2-fluoro-5', 6'-dihydro-[3,4'-bipyridin]-1'(2'H)-yl)ethanone (see PREPARATION P14.1; 44.7 g, 0.203 mol), THF (600 mL), and palladium hydroxide on carbon, 20% wet type (22 g, 50 wt %). The bottle was purged three times with $H_2$ and was shaken at room temperature under 50 psi of $H_2$. At 1 hour, crude $^1$HNMR indicated full conversion (aliquot syringe filtered and concentrated). This reaction was filtered (along with another 44.7 g batch) through a CELITE® pad. The pad was washed with THF (2×250 mL). The filtrate was concentrated under vacuum to afford 88.5 g white solid (98% yield, >99% purity by LCMS, excellent purity by $^1$HNMR).

TABLE P15

EXAMPLES P15.1-15.2 PREPARED ANALOGOUS TO PREPARATION 15

| Example | Structure | Chemical Name | M + 1 |
|---|---|---|---|
| P15.1 | 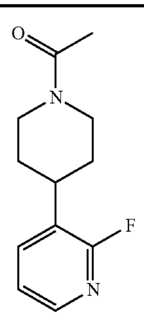 | 1-(4-(2-fluoropyridin-3-yl)piperidin-1-yl)ethanone | 223 |
| P15.2 | 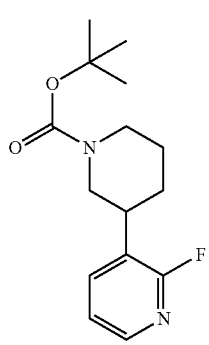 [SMILES: CC(C)(C)OC(=O)N1CCCC(c2cccnc2F)C1] | tert-butyl 3-(2-fluoropyridin-3-yl)piperidine-1-carboxylate | 281 |

Preparation P16.1: Tert-Butyl 4-(3-Chloropyrazin-2-yl)Piperidine-1-Carboxylate

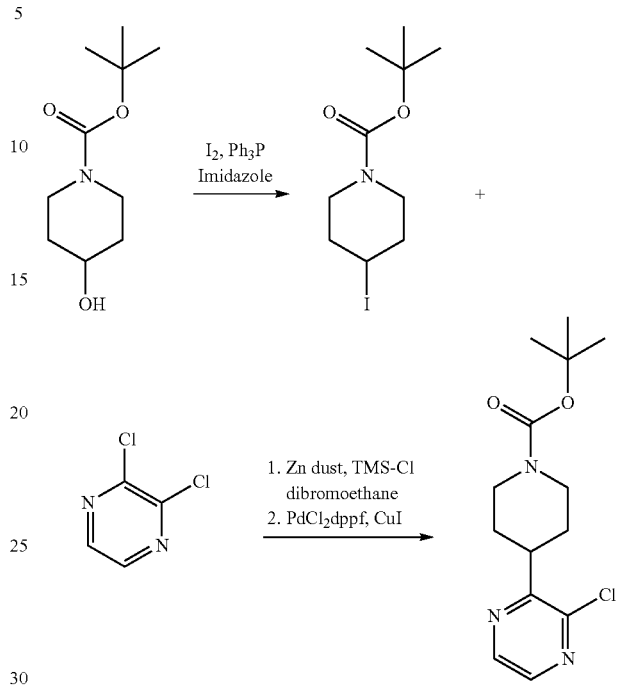

Step 1. Tert-Butyl 4-Iodopiperidine-1-Carboxylate

A solution of tert-butyl 4-hydroxypiperidine-1-carboxylate (246 g, 1.224 mol), imidazole (100 g, 1.469 mol, 1.2 eq.) and triphenylphosphine (385 g, 1.469 mol, 1.2 eq.) in THF (750 mL) was cooled using an ice bath. Then a solution of iodine (373 g, 1.469 mol, 1.2 eq.) in THF (750 mL) was added slowly over a period of 1 hour while keeping the internal temperature below 18° C. The resulting mixture was allowed to stir at room temperature for 5 hours and the mixture was diluted with ethyl acetate (2 L), brine (1 L) and water (500 mL). The organic layer was separated and the aqueous layer was extracted with ethyl acetate (1 L×2). The organic layers were combined, washed with 15% aqueous sodium sulfite (1 L), brine (1 L), dried and concentrated. The resulting residue was stirred with hexanes (2 L) and the solid was removed by filtration. The solid was stirred with hexanes (2 L×2) and filtered. The filtrate was concentrated to give 363 g of crude oil which was purified by column chromatography (eluting with hexanes/ethyl acetate=50:1 to 20:1) to afford 319 g of tert-butyl 4-iodopiperidine-1-carboxylate.

Step 2. Tert-Butyl 4-(3-Chloropyrazin-2-yl)Piperidine-1-Carboxylate

To a suspension of activated zinc dust (84.4 g, 1.29 mol, 1.94 eq.) in anhydrous DMA (270 mL) was added 1,2-dibromoethane (9.1 mL, 0.106 mol, 0.16 eq.), followed by the slow addition of chlorotrimethylsilane (13.5 mL, 0.106 mol, 0.16 eq.) over a period of 5 min. The resulting mixture was stirred for 15 min under nitrogen. Then a solution of tert-butyl 4-iodopiperidine-1-carboxylate (329 g, 1.06 mol, 1.59 eq.) in anhydrous DMA (670 mL) was added to the above suspension over a period of 45 min keeping the internal temperature below 65° C. The resulting mixture was stirred for 1 hour while cooling back to room temperature. The prepared zinc reagent was allowed to stand and the upper clear solution was transferred to a degassed and well stirred solution of 2,3-dichloropyrazine (99 g, 0.664 mol, 1 eq.), PdCl$_2$(dppf) CH$_2$Cl$_2$ (16.3 g, 19.9 mmol, 0.03 eq.) and CuI (7.8 g, 41.2 mmol, 0.062 eq.) in anhydrous DMA (670 mL) using a cannula. DMA (400 mL) was used to rinse the remaining zinc dust and added to the above mixture. The resulting mixture was heated to 80° C. under nitrogen and stirred overnight (19 hours). The mixture was cooled to room temperature and diluted with brine (1 L) and ethyl acetate (6 L). The aqueous phase was extracted with ethyl acetate (4 L) and organic extracts were combined, washed with brine (1 L), dried and concentrated. The resulting residue was purified by column chromatography (eluting with hexanes/ethyl acetate=9:1 to 6:1) to give 92 g of tert-butyl 4-(3-chloropyrazin-2-yl)piperidine-1-carboxylate.

Preparation P17.1:
4-(2-Fluoropyridin-3-yl)Morpholine

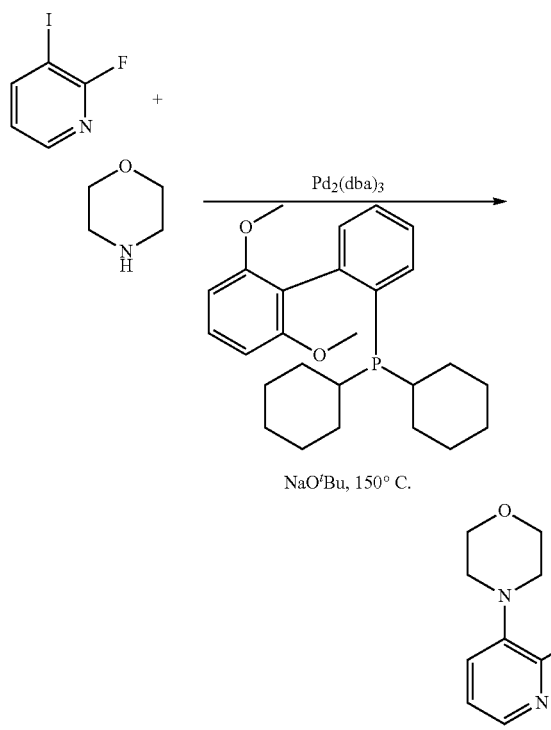

A microwave reaction vessel was charged with 2-fluoro-3-iodopyridine (purchased from Maybridge™) (0.565 g, 2.53 mmol), morpholine (purchased from Aldrich™) (0.221 ml, 2.53 mmol), Pd$_2$(dba)$_3$ (purchased from Strem™) (0.154 g, 0.152 mmol), 2-dicyclohexylphosphino-2',6'-dimethoxy-1,1'-biphenyl (purchased from Strem™) (0.135 g, 0.304 mmol), and sodium t-butoxide (0.8 g, 7.6 mmol). The reaction mixture was stirred and heated in a Discover® model microwave reactor (CEM, Matthews, N.C.) at 150° C. for 20 min (125 watts, Powermax feature on, ramp time 5 min). Solvent was evaporated. The crude product was adsorbed onto a plug of silica gel and chromatographed through a Biotage prepacked silica gel column, eluting with a gradient of 1% to 5% MeOH in CH$_2$Cl$_2$, to provide 4-(2-fluoropyridin-3-yl)morpholine (0.311 g, 67.5% yield).

Preparation P18.1:
4-(3-Fluoropyrazin-2-yl)Cyclohexanone

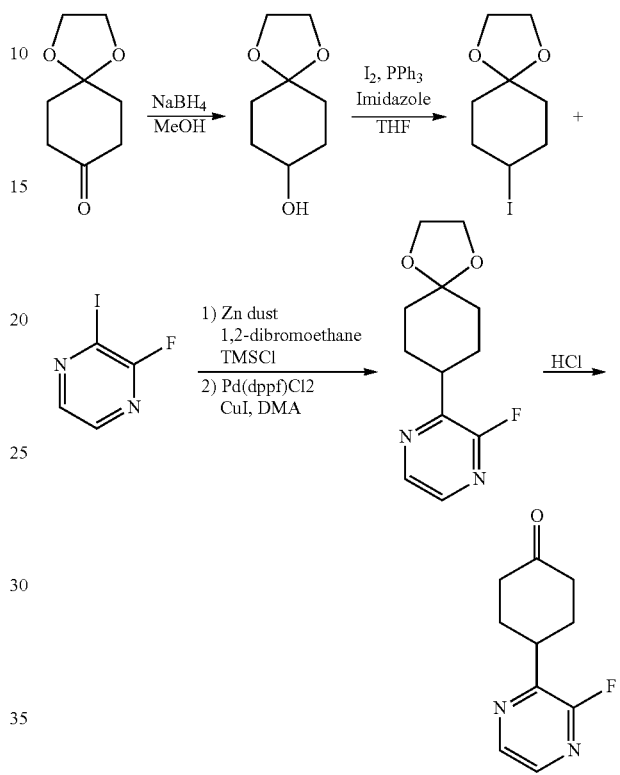

Step 1. 1,4-Dioxaspiro[4.5]Decan-8-Ol

To a solution of 1,4-dioxaspiro[4.5]decan-8-one (244 g, 1.56 mol, 1.0 eq.) in MeOH (5 L) was slowly added NaBH$_4$ (59 g, 1.56 mol, 1.0 eq.) keeping the internal temperature <10° C. using an ice bath. The ice bath was removed and the mixture was stirred for 30 min at room temperature. The solvent was then removed under reduced pressure and the resulting solid was dissolved in 50% diethyl ether in EtOAc (5 L), washed with saturated aqueous NH$_4$Cl (800 mL×3), brine (800 mL), dried over Na$_2$SO$_4$, filtered, and evaporated to give 215 g (87% yield) of 1,4-dioxaspiro[4.5]decan-8-ol. GC-MS: 159 (M+1).

Step 2. 8-Iodo-1,4-Dioxaspiro[4.5]Decane

A mixture of imidazole (111 g, 1.63 mol, 1.2 eq.), PPh$_3$ (428 g, 1.63 mol, 1.2 eq.) and 1,4-dioxaspiro[4.5]decan-8-ol (215 g, 1.36 mol, 1.0 eq.) in THF (1.5 L) was cooled using an ice bath under N$_2$. To this reaction mixture was added slowly a solution of I$_2$ (414 g, 1.63 mol, 1.2 eq.) in THF (1 L) keeping the internal temperature <12° C. After the addition was complete, the reaction mixture was allowed to warm to room temperature and stirred overnight. The reaction mixture was partitioned between H$_2$O (2 L), EtOAc (3 L), and brine (2 L). The aqueous layer was extracted with EtOAc (1 L×2). The combined organic layer was washed with 10% aqueous NaHSO$_3$ (800 mL, organic layer turned light yellow), brine (1

L), dried over Na$_2$SO$_4$, filtered, and evaporated. The crude product was dissolved in diethyl ether (6 L), filtered, and the solid was washed with diethyl ether (300 mL×3). The filtrate was concentrated and purified by column chromatography (100% hexanes to 5% EtOAc in hexanes, R$_f$=0.3 in 5% EtOAc in hexanes) to give 340 g (93.4% yield) of 8-iodo-1,4-dioxaspiro[4.5]decane. GC-MS: 269 (M+1).

Step 3.
2-Fluoro-3-(1,4-Dioxaspiro[4.5]Decan-8-yl)Pyrazine

To a suspension of activated zinc dust (51 g, 0.78 mol, 1.94 eq.) in anhydrous DMA (100 mL) was added 1,2-dibromoethane (5.5 mL, 0.064 mol, 0.16 eq.), followed by the slow addition of chlorotrimethylsilane (8.1 mL, 0.064 mol, 0.16 eq.) over 5 min. The resulting mixture was stirred for 15 min under nitrogen. Then a solution of 8-iodo-1,4-dioxaspiro[4.5]decane (172 g, 0.639 mol, 1.59 eq.) in anhydrous DMA (300 mL) was added to the above suspension over 30 min keeping the internal temperature below 65° C. The resulting mixture was stirred for 1 hour and cooled to room temperature. The prepared zinc reagent was allowed to stand and the upper clear solution was transferred to a degassed and well stirred solution of 2-fluoro-3-iodopyrazine (see PREPARATION P6.2; 90 g, 0.402 mol, 1.0 eq.), PdCl$_2$(dppf)CH$_2$Cl$_2$ (9.8 g, 0.012 mol, 0.03 eq.), and CuI (4.75 g, 0.025 mol, 0.062 eq.) in anhydrous DMA (300 mL) using a cannula. DMA (100 mL) was used to rinse the remaining zinc dust and the solution was added to the above mixture. The resulting mixture was heated to 80° C. under nitrogen and stirred overnight.

Similarly, two other batches were carried out on 10 g (0.045 mol) and 75 g (0.335 mol) scale and the crude from three batches was combined together for work up and purification.

The mixture was diluted with brine (1.5 L) and EtOAc (10 L). The aqueous phase was extracted with EtOAc (6 L) and organic extracts were combined, washed with brine (1 L), dried over Na$_2$SO$_4$, filtered, and concentrated. The crude product was purified by column chromatography (hexanes to 40% EtOAc in hexanes, R$_f$=0.4 in 30% EtOAc in hexanes, UV active) to give 92 g of 2-fluoro-3-(1,4-dioxaspiro[4.5]decan-8-yl). GC-MS: 239 (M+1).

Step 4. 4-(3-Fluoropyrazin-2-yl)Cyclohexanone

A solution of 2-fluoro-3-(1,4-dioxaspiro[4.5]decan-8-yl)pyrazine (91 g, 0.382 mol, 1.0 eq.) in 1N aqueous HCl (573 mL) and acetone (4 L) was heated to 37° C. overnight. The reaction mixture was cooled to room temperature and most of acetone was removed under reduced pressure. The crude material was diluted with EtOAc (4 L) and the solution was washed with aqueous saturated NaHCO$_3$ (500 mL×2), water (500 mL), brine (500 mL), dried over Na$_2$SO$_4$, filtered, and evaporated. The crude product was purified by column chromatography (100% hexanes to 50% EtOAc in hexanes, R$_f$=0.3 in 30% EtOAc in hexanes) to give 52 g (70% yield) of 4-(3-fluoropyrazin-2-yl)cyclohexanone. GC-MS: 195 (M+1); calcd for C$_{10}$H$_{11}$FN$_2$O: 194.21

$^1$H NMR (300 mHz, DMSO-d$_6$) δ 8.60-8.27 (m, 1H), 8.25-8.24 (m, 1H), 3.57-3.48 (m, 1H), 2.69-2.58 (m, 2H), 2.36-2.31 (m, 2H), 2.21-2.14 (m, 2H), 2.07-1.91 (m, 2H)

TABLE P18.1

EXAMPLES P18.1-P18.2 PREPARED ANALOGOUS TO PREPARATION P18.1

| Example | Structure | Chemical Name | M + 1 |
|---|---|---|---|
| P18.1 | ![structure] | 4-(3-fluoropyrazin-2-yl)cyclohexanone | 195 |
| P18.2 | ![structure] | 4-(2-fluoropyridin-3-yl)cyclohexanone | |

Preparation 19.1: (1S,4S)-4-(2-Fluoropyridin-3-yl)Cyclohexanol and (1R,4R)-4-(2-Fluoropyridin-3-yl)Cyclohexanol as Diastereomeric Mixture

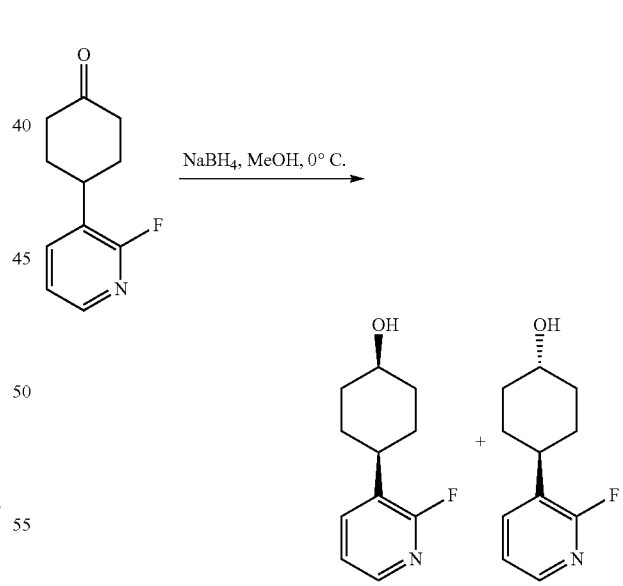

4-(2-fluoropyridin-3-yl)cyclohexanone (see PREPARATION P18.2; 0.420 g, 2.174 mmol) was dissolved in 20 mL MeOH and cooled to 0° C. Sodium boron hydrate (0.123 g, 3.26 mmol) was added slowly portion wise and stirring was continued for 7 hours. The mixture was evaporated and 3 mL of DCM was added to the residue. The mixture was purified and separated via silica gel column chromatography (10-100% EtOAc in hexanes) providing diasteromeric mixture (1s,4s)-4-(2-fluoropyridin-3-yl)cyclohexanol and (1r,4r)-4-(2-fluoropyridin-3-yl)cyclohexanol as white solid.

Preparation P20.1: Benzyl 3-(3-Chloropyrazin-2-yloxy)Azetidine-1-Carboxylate

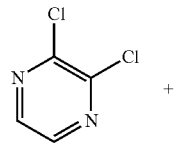

+

To a solution of 3-hydroxy-azetidine-1-carboxylic acid benzyl ester (5.19 g, 27.4 mmol, purchased from Ace Synthesis), 2,3-dichloropyrazine (4.116 g, 27.6 mmol, Oakwood) and DMSO (40 mL) was added sodium tert-butoxide (2.64 g, 27.4 mmol) in three portions. The solution was allowed to stir at room temperature. After 2 hours, the reaction was poured into water (200 mL) and the aqueous solution was extracted with ether (3×50 mL). The combined ether layers were washed with water (50 mL), brine (50 mL), and then concentrated in vacuo. The crude product was adsorbed onto a plug of silica gel and chromatographed through a Redi-Sep® prepacked silica gel column (80 g), eluting with 0% to 20% EtOAc in hexane, to provide benzyl 3-(3-chloropyrazin-2-yloxy)azetidine-1-carboxylate (5.4 g, 61.6% yield), as a yellow oil. MS (ESI) m/z 320.1 (MH+). IC50 (uM): 1.33.

TABLE P20.1

EXAMPLES P20.1-P20.4 PREPARED ANALOGOUS TO PREPARATION P20.1

| Example | Structure | Chemical Name | M + 1 |
|---|---|---|---|
| P20.1 | 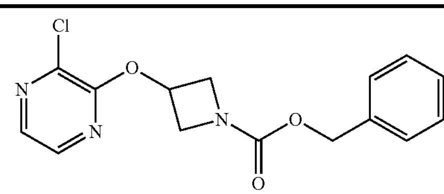 | benzyl 3-(3-chloropyrazin-2-yloxy)azetidine-1-carboxylate | 320 |
| P20.2 | 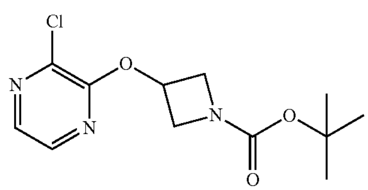 [SMILES: CC(C)(C)OC(=O)N1CC(Oc2nccnc2Cl)C1] | tert-butyl 3-(3-chloropyrazin-2-yloxy)azetidine-1-carboxylate | 308 |
| P20.3 | 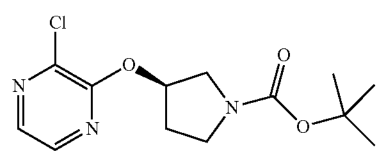 [SMILES: CC(C)(C)OC(=O)N1CC[C@@H](Oc2nccnc2Cl)C1] | (R)-tert-butyl 3-((3-chloropyrazin-2-yl)oxy)pyaolidine-1-carboxylate | 300 |
| P20.4 | 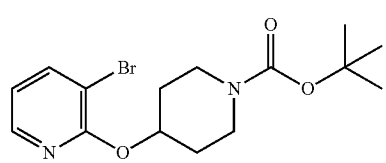 [SMILES: CC(C)(C)OC(=O)N1CCC(Oc2ncccc2Br)CC1] | tert-butyl 4-(3-bromopyridin-2-yloxy)piperidine-1-carboxylate | |

Preparation P21.1: 2-(Azetidin-3-yloxy)Pyrazine

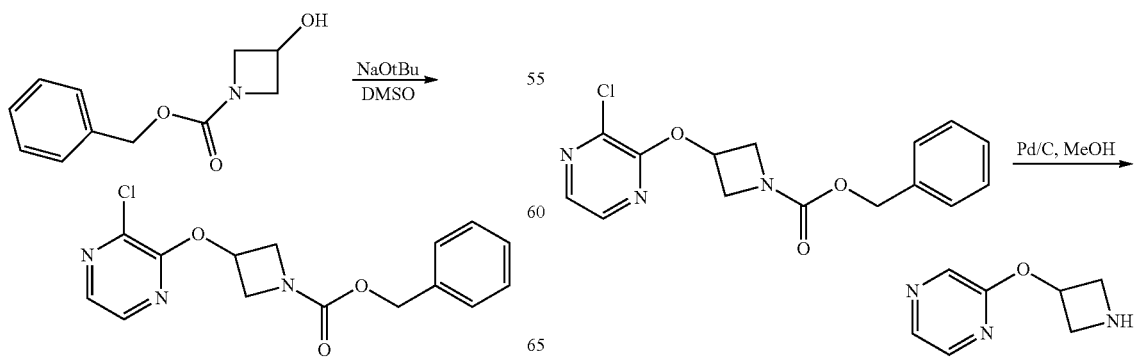

To a nitrogen-purged round bottomed flask was added benzyl 3-(3-chloropyrazin-2-yloxy)azetidine-1-carboxylate (see PREPARATION P20.1; 0.400 g, 0.688 mmol) and Pd/C (0.10 g, 0.094 mmol) and EtOH (10 mL). Hydrogen gas was bubbled through the solution for 1 minute, then a balloon of hydrogen gas was placed atop the round bottomed flask. After 30 minutes, the balloon was removed and the round bottomed flask sealed with a rubber septum. After 16 hours, the reaction was filtered through CELITE® and the cake was washed liberally with EtOAc. The filtrate was concentrated in vacuo to give crude 2-(azetidin-3-yloxy)pyrazine (0.188 g, 181% yield), as a off-white solid. The product was carried forward in the next step without further purification. MS (ESI) m/z 152.1 (MH+).

Preparation P22.1:
2-(Azetidin-3-yloxy)-3-Chloropyrazine Hydrochloride

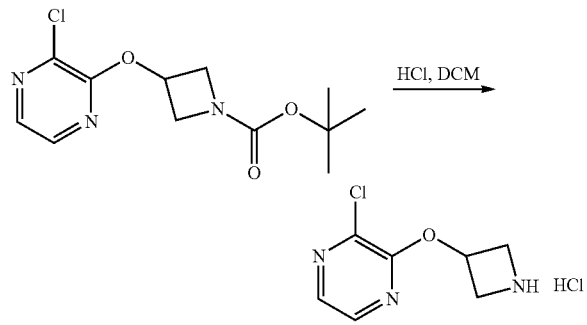

To a solution of tert-butyl 3-(3-chloropyrazin-2-yloxy)azetidine-1-carboxylate (see PREPARATION P20.2; 4.3 g, 15.05 mmol) and DCM (50 mL) was added 4M HCl in dioxane (3.76 mL, 15.05 mmol). After 72 hours, a precipitate coated the walls of the flask. The liquid was carefully decanted off and the rinsed with DCM (20 mL) and again carefully decanted off. The precipitate coated round bottomed flask was treated with DCM:saturated NaHCO₃ (1:1, 150 mL). The aqueous layer was extracted with 10% MeOH in DCM (4×25 mL). The combined organic layers were concentrated in vacuo to give crude product. The aqueous layer still contained the majority of the product. The aqueous layer was concentrated in vacuo and the solids stirred with 10% MeOH in DCM (200 mL) for 2 hours, then filtered. The filtrate was concentrated in vacuo to give more crude product. The separate lots of crude product were combined to give crude 2-(azetidin-3-yloxy)-3-chloropyrazine (1.75 g, 62.6% yield), as a tan solid. The product was carried forward in the next step without further purification. MS (ESI) m/z 186.1 (MH+).

TABLE P22.1

EXAMPLES P22.1-P22.2 PREPARED ANALOGOUS TO PREPARATION P22.1

| Example | Structure | Chemical Name | M + 1 |
|---|---|---|---|
| P22.1 | 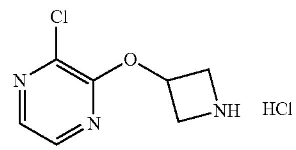 [SMILES: Clc1nccnc1OC1CNC1 ; Cl] | 2-(azetidin-3-yloxy)-3-chloropyrazine hydrochloride | 186 |
| P22.2 | 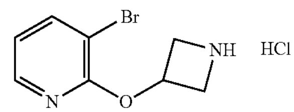 [SMILES: Brc1cccnc1OC1CNC1 ; Cl] | 2-(azetidin-3-yloxy)-3-bromopyridine hydrochloride | 229, 231 |

Preparation P23.1: (1H-benzo[d]imidazol-2-yl)(3-(3-chloropyrazin-2-yloxy)azetidin-1-yl)methanone

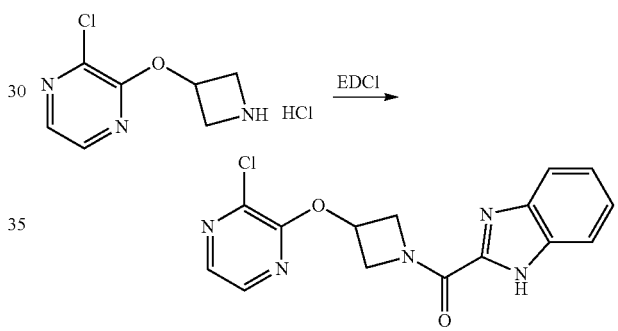

To a solution of 2-(azetidin-3-yloxy)-3-chloropyrazine (see PREPARATION P22.1; 0.38 g, 2.047 mmol), 1H-benzo[d]imidazole-2-carboxylic acid (0.37 g, 2.282 mmol), EDCI (0.392 g, 2.047 mmol), butanol (0.121 g, 0.790 mmol) and DCM (25 mL) was added DIPEA (0.62 mL, 3.56 mmol). After 2 hours, the crude reaction was adsorbed onto a plug of silica gel and chromatographed through a Redi-Sep® pre-packed silica gel column (12 g), eluting with 0% to 50% EtOAc in hexane, to provide (1H-benzo[d]imidazol-2-yl)(3-(3-chloropyrazin-2-yloxy)azetidin-1-yl)methanone (270 mg, 0.819 mmol, 40.0% yield), as a white solid. MS (ESI) m/z 330.0 (MH⁺). IC$_{50}$ (uM) 1.375.

TABLE P23

EXAMPLES P23.1-P23.2 PREPARED ANALOGOUS TO PREPARATION P23.1

| Example | Structure | Chemical Name | M + 1 |
|---|---|---|---|
| P23.1 | 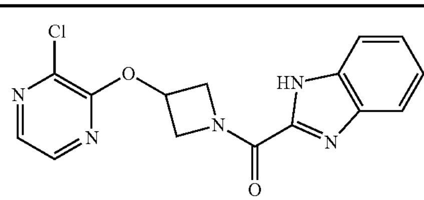 | (1H-benzo[d]imidazol-2-yl)(3-(3-chloropyrazin-2-yloxy)azetidin-1-yl)methanone | 330 |

TABLE P23-continued

EXAMPLES P23.1-P23.2 PREPARED ANALOGOUS TO PREPARATION P23.1

| Example | Structure | Chemical Name | M + 1 |
|---|---|---|---|
| P23.2 | 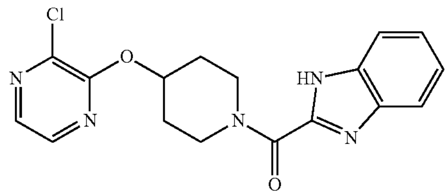 [SMILES: O=C(c1nc2ccccc2[nH]1)N1CCC(Oc2nccnc2Cl)CC1] | (1H-benzo[d]imidazol-2-yl)(4-((3-chloropyrazin-2-yl)oxy)piperidin-1-yl)methanone | |

Preparation P24.1: (1H-Benzo[D]Imidazol-2-Yl)(3-Hydroxyazetidin-1-yl)Methanone

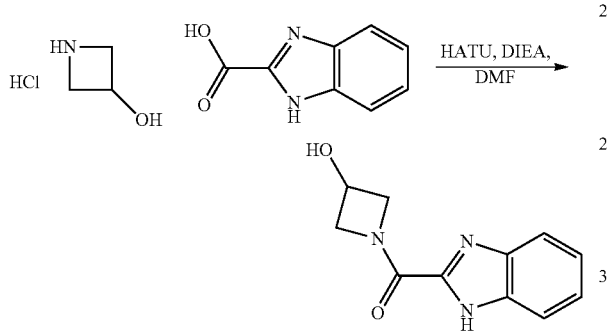

1H-benzo[d]imidazole-2-carboxylic acid (1.788 g, 11.03 mmol) was dissolved in 50 ml DMF and HATU (4.19 g, 11.03 mmol) was added. This mixture (A) was stirred for 30 min. 3-hydroxyazetidine hydrochloride (1.2083 g, 11.03 mmol) was added to 50 ml DMF, diisopropylethyl amine (5.76 mL, 33.1 mmol) was added and the mixture (B) was stirred for 5 min. Mixture (B) was added to mixture (A) and the resulting reaction mixture was stirred for 6 hours. The reaction was hydrolyzed with 30 ml water and 30 ml 1M HCl and the resulting mixture was extracted with EtOAc (3×200 ml). The combined organic layers were dried with magnesium sulfate and evaporated. Silica gel chromatography (0-10% MeOH in DCM) provided (1H-benzo[d]imidazol-2-yl)(3-hydroxyazetidin-1-yl)methanone (0.570 g, 2.62 mmol, 23.79% yield) as a yellow oil.

TABLE P24

EXAMPLES P24.1-P24.3 PREPARED ANALOGOUS TO PREPARATION P24.1

| Example | Structure | Chemical Name | M + 1 |
|---|---|---|---|
| P24.1 | | (1H-benzo[d]imidazol-2-yl)(3-hydroxy-azetidin-1-yl)methanone | |
| P24.2 | 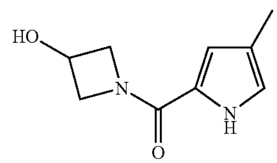 | (3-hydroxy-azetidin-1-yl)(4-methyl-1H-pyrrol-2-yl)methanone | |
| P24.3 | 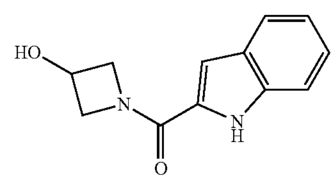 [SMILES: O=C(c1cc2ccccc2[nH]1)N1CC(O)C1] | (3-hydroxy-azetidin-1-yl)(1H-indol-2-yl)methanone | |

Preparation P25.1: Tert-Butyl 3-((3-(3,6-Dihydro-2H-Pyran-4-yl)Pyridin-2-yl)Oxy)Azetidine-1-Carboxylate

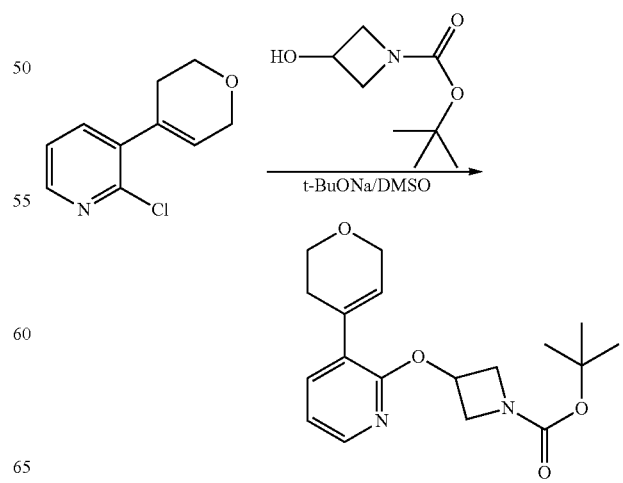

2-chloro-3-(3,6-dihydro-2H-pyran-4-yl)-pyridine (see PREPARATION P13.1; 3.5 g, 17.9 mmol) and tert-butyl 3-hydroxyazetidine-1-carboxylate (2.8 g, 17.9 mmol) were dissolved in DMSO (20 mL) and sodium tert-butoxide (t-BuONa) (3.4 g, 35.8 mmol) was added to the above solution. The reaction mixture was stirred at room temperature for overnight. The reaction mixture was diluted with water and extracted with ethyl acetate (2×10 mL). The combined organic layers were dried over $Na_2SO_4$ and concentrated to give the crude product. The crud product was purified by silica gel column chromatography to give the title compound (2.3 g, 7.8 mmol, yield 75%). $^1$H NMR (DMSO-$D_6$, 300 MHz) δ (ppm) 1.38 (s, 9H), 2.41-2.47 (m, 2H), 3.75-3.86 (m, 4H), 4.19-4.30 (m, 4H), 5.26-5.35 (m, 1H), 6.15-6.20 (m, 1H), 7.01 (dd, 1H, J=7.31 Hz, 4.97 Hz), 7.62 (d, 1H, J=7.45 Hz), 8.02 (d, 1H, J=4.82 Hz)

TABLE P25.1

EXAMPLES P25.1-P25.2 PREPARED ANALOGOUS TO PREPARATION P25.1

| Example | Structure | Chemical Name | M + 1 |
|---|---|---|---|
| P25.1 | 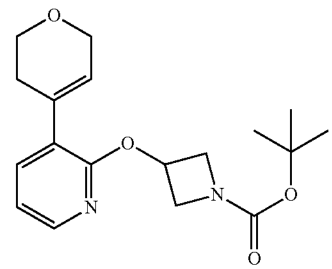 [SMILES: CC(C)(C)OC(=O)N1CC(Oc2ncccc2C2=CCOCC2)C1] | tert-butyl 3-((3-(3,6-dihydro-2H-pyran-4-yl)pyridin-2-yl)oxy)azetidine-1-carboxylate | |
| P25.2 | 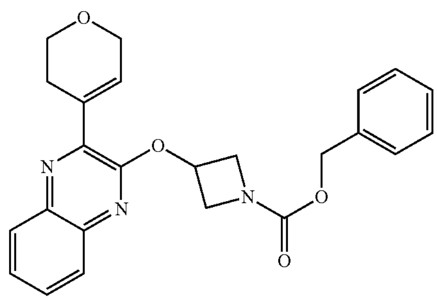 [SMILES: O=C(OCc1ccccc1)N1CC(Oc2nc3ccccc3nc2C2=CCOCC2)C1] | benzyl 3-((3-(3,6-dihydro-2H-pyran-4-yl)quinoxalin-2-yl)oxy)azetidine-1-carboxylate | 418 |

Preparation P26.1. 2-(Azetidin-3-yloxy)-3-(3,6-Dihydro-2H-Pyran-4-yl)Pyridine Hydrochloride

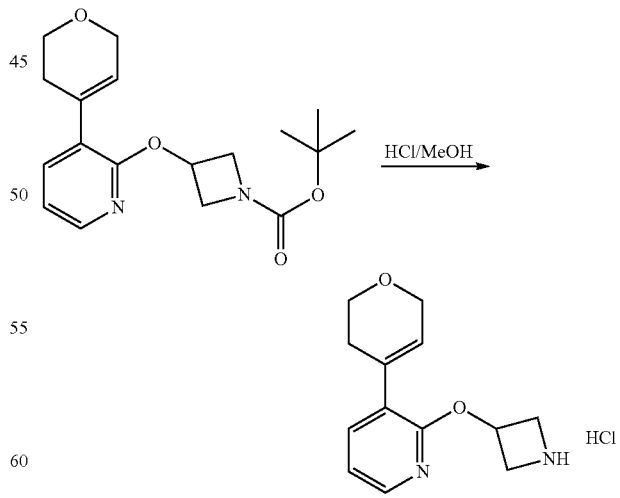

To tert-butyl 3-((3-(3,6-dihydro-2H-pyran-4-yl)pyridin-2-yl)oxy)azetidine-1-carboxylate (see PREPARATION P25.1; 2.3 g, 6.9 mmol) was added 4 M HCl in MeOH (100 mL). The reaction mixture was stirred at room temperature for 2 hours. The solvent was removed to give the title compound (1.5 g, 6.5 mmol, yield 95%).

TABLE P26.1

EXAMPLES P26.1-26.8 PREPARED ANALOGOUS TO PREPARATION P26.1

| Example | Structure | Chemical Name | M + 1 |
|---|---|---|---|
| P26.1 | 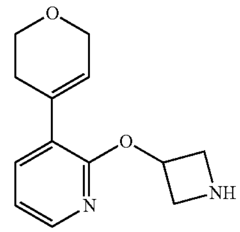 | 2-(azetidin-3-yloxy)-3-(3,6-dihydro-2H-pyran-4-yl)pyridine hydrochloride | 233 |
| P26.2 | 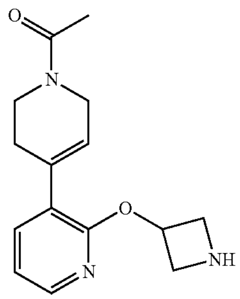 | 1-(2-(azetidin-3-yloxy)-5',6'-dihydro-[3,4'-bipyridin]-1'(2'H)-yl)ethanone hydrochloride | |
| P26.3 | 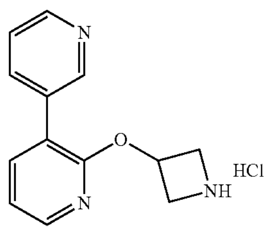 [SMILES: c1cncc(-c2cccnc2OC2CNC2)c1 ; Cl] | 2-(azetidin-3-yloxy)-3,3'-bipyridine hydrochloride | |
| P26.4 | 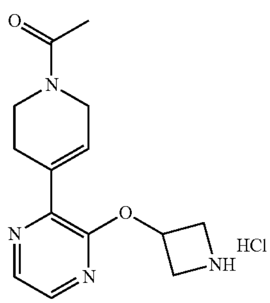 [SMILES: CC(=O)N1CC=C(c2nccnc2OC2CNC2)CC1 ; Cl] | 1-(4-(3-(azetidin-3-yloxy)pyrazin-2-yl)-5,6-dihydropyridin-1(2H)-yl)ethanone hydrochloride | |
| P26.5 | 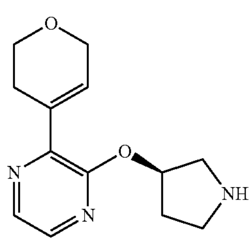 | (R)-2-(3,6-dihydro-2H-pyran-4-yl)-3-(pyrrolidin-3-yloxy)pyrazine hydrochloride | 248 |
| P26.6 | 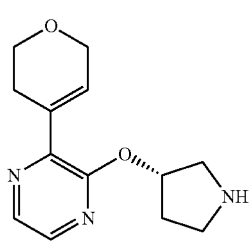 | (S)-2-(3,6-dihydro-2H-pyran-4-yl)-3-(pyrrolidin-3-yloxy)pyrazine hydrochloride | 248 |

TABLE P26.1-continued

EXAMPLES P26.1-26.8 PREPARED ANALOGOUS TO PREPARATION P26.1

| Example | Structure | Chemical Name | M + 1 |
|---|---|---|---|
| P26.7 | 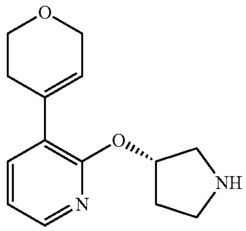 | (S)-3-(3,6-dihydro-2H-pyran-4-yl)-2-(pyrrolidin-3-yloxy)pyridine hydrochloride | 247 |
| P26.8 | 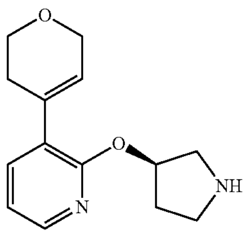 | (R)-3-(3,6-dihydro-2H-pyran-4-yl)-2-(pyrrolidin-3-yloxy)pyridine hydrochloride | 247 |

Preparation P27.1: 2-(Azetidin-3-yloxy)-3-(Tetrahydro-2H-Pyran-4-yl)Pyridine

A mixture of 2-(azetidin-3-yloxy)-3-(3,6-dihydro-2H-pyran-4-yl)pyridine hydrochloride (see PREPARATION P26.1; 3.5 g, 15 mmol) and wet Pd—C (50%, 1.0 g) in MeOH (100 ml) was stirred under $H_2$ (40 psi) at 30° C. for 3 hours then the reaction mixture was filtered through CELITE® and the filtrate was concentrated in vacuo to give the title compound (3.2 g, 14.6 mmol, yield 91%).

TABLE P27

EXAMPLES P27.1-P27.8 PREPARED ANALOGOUS TO PREPARATION P27.1

| Example | Structure | Chemical Name | M + 1 |
|---|---|---|---|
| P27.1 | 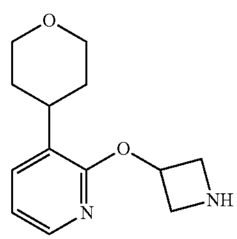 [SMILES: c1cnc(OC2CNC2)c(C2CCOCC2)c1] | 2-(azetidin-3-yloxy)-3-(tetrahydro-2H-pyran-4-yl)pyridine | 235 |
| P27.2 | 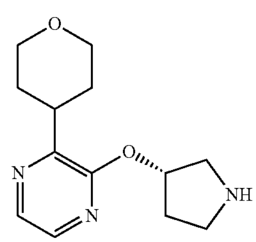 | (S)-2-(pyrrolidin-3-yloxy)-3-(tetrahydro-2H-pyran-4-yl)pyrazine hydrochloride | |
| P27.3 | 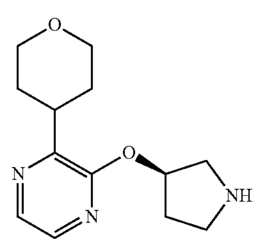 | (R)-2-(pyrrolidin-3-yloxy)-3-(tetrahydro-2H-pyran-4-yl)pyrazine hydrochloride | |

TABLE P27-continued

EXAMPLES P27.1-P27.8 PREPARED ANALOGOUS TO PREPARATION P27.1

| Example | Structure | Chemical Name | M + 1 |
|---|---|---|---|
| P27.4 | 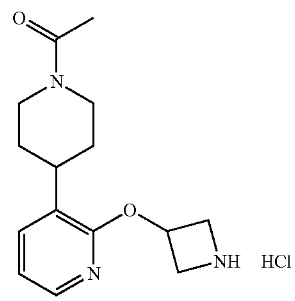 [SMILES: CC(=O)N1CCC(c2cccnc2OC2CNC2)CC1 ; Cl] | 1-(4-(2-(azetidin-3-yloxy)pyridin-3-yl)piperidin-1-yl)ethanone hydrochloride | |
| P27.5 | 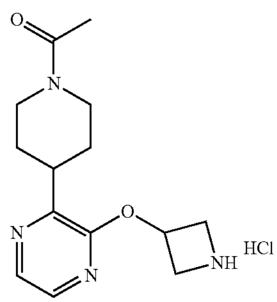 [SMILES: CC(=O)N1CCC(c2nccnc2OC2CNC2)CC1 ; Cl] | 1-(4-(3-(azetidin-3-yloxy)pyrazin-2-yl)piperidin-1-yl)ethanone hydrochloride | |
| P27.6 | 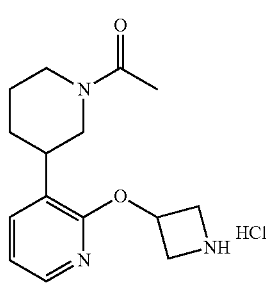 [SMILES: CC(=O)N1CCCC(c2cccnc2OC2CNC2)C1 ; Cl] | 1-(3-(2-(azetidin-3-yloxy)pyridin-3-yl)piperidin-1-yl)ethanone hydrochloride | |
| P27.7 | 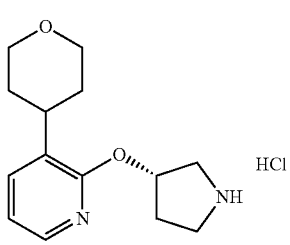 [SMILES: c1cnc(O[C@H]2CCNC2)c(C2CCOCC2)c1 ; Cl] | (S)-2-(pyrrolidin-3-yloxy)-3-(tetrahydro-2H-pyran-4-yl)pyridine hydrochloride | |
| P27.8 | 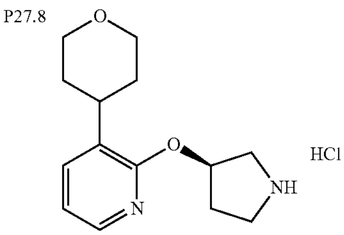 | (R)-2-(pyrrolidin-3-yloxy)-3-(tetrahydro-2H-pyran-4-yl)pyridine hydrochloride | |

Preparation P28.1: Tert-Butyl 4-((3-(3,6-Dihydro-2H-Pyran-4-yl)Pyridin-2-yl)Oxy)Piperidine-1-Carboxylate To a solution tert-butyl 4-((3-bromopyridin-2-yl)oxy)piperidine-1-carboxylate (see PREPARATION P20.4; 4 g, 11.2 mmol), 2-(3,6-dihydro-2H-pyran-4-yl)-4,4,5,5-tetramethyl-1,3,2-dioxaborolane (2.58 g, 12.4 mmol) and $Na_2CO_3$ (2.38 g, 22.4 mmol) in 1,4-dioxane (60 mL) and $H_2O$ (6 mL) was added Pd(dppf)Cl$_2$ (410 mg, 0.56 mmol) then the reaction mixture was stirred at 110° C. under $N_2$ for overnight. The reaction mixture was filtered through CELITE® and washed with $CH_2Cl_2$. The organic layer was concentrated and the crude product was purified by silica gel column to give the desired compound (3.5 g, 8.7 mmol, yield 70%).

TABLE P28

EXAMPLES P28.1-P28.4 PREPARED ANALOGOUS TO PREPARATION P28.1

| Example | Structure | Chemical Name | M + 1 |
| --- | --- | --- | --- |
| P28.1 | 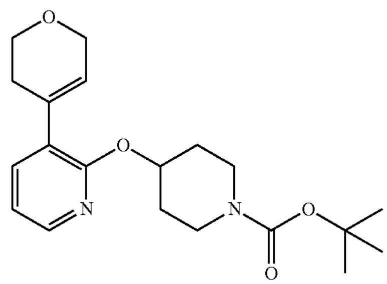 [SMILES: CC(C)(C)OC(=O)N1CCC(Oc2ncccc2C2=CCOCC2)CC1] | tert-butyl 4-((3-(3,6-dihydro-2H-pyran-4-yl)pyridin-2-yl)oxy)piperidine-1-carboxylate | |
| P28.2 | 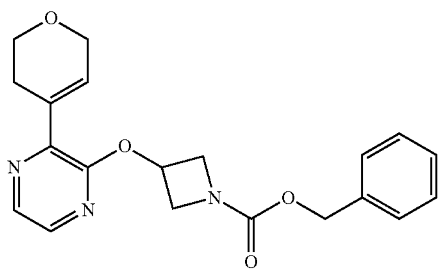 [SMILES: O=C(OCc1ccccc1)N1CC(Oc2nccnc2C2=CCOCC2)C1] | benzyl 3-(3-(3,6-dihydro-2H-pyran-4-yl)pyrazin-2-yloxy)azetidine-1-carboxylate | 368 |
| P28.3 | 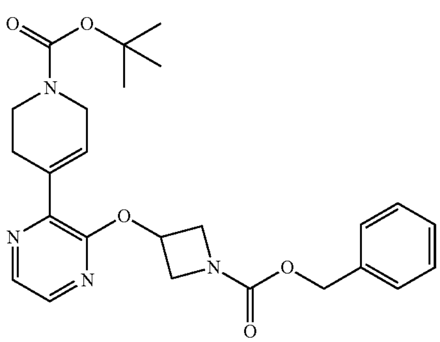 [SMILES: CC(C)(C)OC(=O)N1CC=C(c2nccnc2OC2CN(C(=O)OCc3ccccc3)C2)CC1] | tert-butyl 4-(3-((1-((benzyloxy)carbonyl)azetidin-3-yl)oxy)pyrazin-2-yl)-5,6-dihydropyridine-1(2H)-carboxylate | |
| P28.4 | 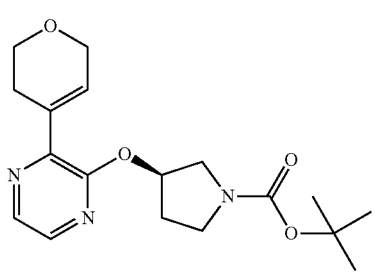 [SMILES: CC(C)(C)OC(=O)N1CC[C@@H](Oc2nccnc2C2=CCOCC2)C1] | (R)-tert-butyl 3-((3-(3,6-dihydro-2H-pyran-4-yl)pyrazin-2-yl)oxy)pyrrolidine-1-carboxylate | 348 |

Preparation P29.1: 2-(Piperidin-4-yloxy)-3-(Tetrahydro-2H-Pyran-4-yl)Pyridine Hydrochloride

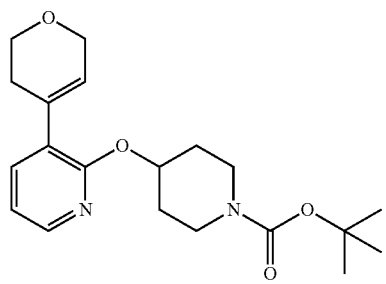

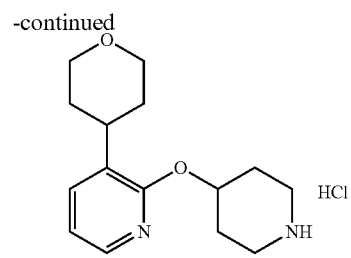

Step 1. Tert-Butyl 4-((3-(Tetrahydro-2H-Pyran-4-yl)Pyridin-2-yl)Oxy)Piperidine-1-Carboxylate A mixture of tert-butyl 4-((3-(3,6-dihydro-2H-pyran-4-yl)pyridin-2-yl)oxy)piperidine-1-carboxylate (see PREPARATION P28.1; 3.5 g, 9.6 mmol) and wet Pd—C (50%, 1.0 g) in MeOH (100 mL) was stirred under $H_2$ (40 psi) at 30° C. overnight then the reaction mixture was filtered through CELITE® and washed with MeOH. The filtrate was concentrated to give of the desired compound (3.2 g, 8.1 mmol, yield 91%).

Step 2. 2-(Piperidin-4-yloxy)-3-(Tetrahydro-2H-Pyran-4-yl)Pyridine Hydrochloride To tert-butyl 4-((3-(tetrahydro-2H-pyran-4-yl)pyridin-2-yl)oxy)piperidine-1-carboxylate (3.2 g, 8.8 mmol) was added 4 M HCl in MeOH (100 mL). The solution was stirred at room temperature for 2 hours. The solvent was removed under reduced pressure to give the title compound (2 g, 9.8 mmol, yield 95%). ESI-MS (M+1): 263 calc. for $C_{15}H_{22}N_2O_2$ 262.

TABLE P29

| EXAMPLES P29.1-P29.7 PREPARED ANALOGOUS TO PREPARATION P29.1 | | | |
|---|---|---|---|
| Example | Structure | Chemical Name | M + 1 |
| P29.1 | | 2-(piperidin-4-yloxy)-3-(tetrahydro-2H-pyran-4-yl)pyridine hydrochloride | 263 |
| P29.2 | | 2-(azetidin-3-yloxy)-3-(tetrahydro-2H-pyran-4-yl)pyrazine hydrochloride | 236 |
| P29.3 | | 2-(piperidin-4-yloxy)-3-(tetrahydro-2H-pyran-4-yl)pyrazine hydrochloride | 264 |

TABLE P29-continued

EXAMPLES P29.1-P29.7 PREPARED ANALOGOUS TO PREPARATION P29.1

| Example | Structure | Chemical Name | M + 1 |
|---|---|---|---|
| P29.4 | 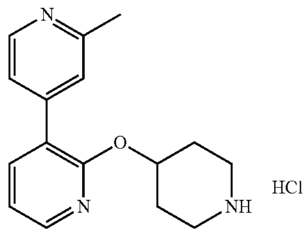 [SMILES: Cc1cc(-c2cccnc2OC2CCNCC2)ccn1 ; Cl] | 2'-methyl-2-(piperidin-4-yloxy)-3,4'-bipyridine hydrochloride | 270 |
| P29.5 | 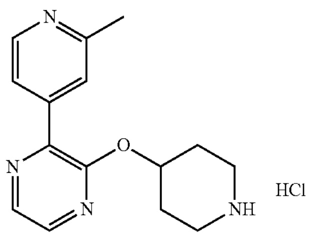 [SMILES: Cc1cc(-c2nccnc2OC2CCNCC2)ccn1 ; Cl] | 2-(2-methylpyridin-4-yl)-3-(piperidin-4-yloxy)pyrazine hydrochloride | 271 |
| P29.6 | 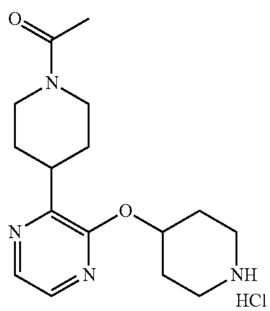 [SMILES: CC(=O)N1CCC(c2nccnc2OC2CCNCC2)CC1 ; Cl] | 1-(4-(3-(piperidin-4-yloxy)pyrazin-2-yl)piperidin-1-yl)ethanone hydrochloride | 305 |
| P29.7 | 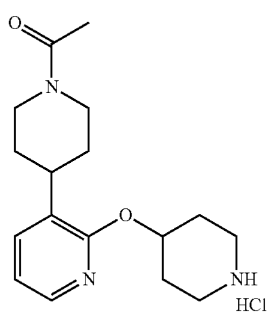 [SMILES: CC(=O)N1CCC(c2cccnc2OC2CCNCC2)CC1 ; Cl] | 1-(4-(2-(piperidin-4-yloxy)pyridin-3-yl)piperidin-1-yl)ethanone hydrochloride | 304 |

Preparation P30.1. 2-(Azetidin-3-yloxy)-3-(Tetrahydro-2H-Pyran-4-yl)Pyrazine

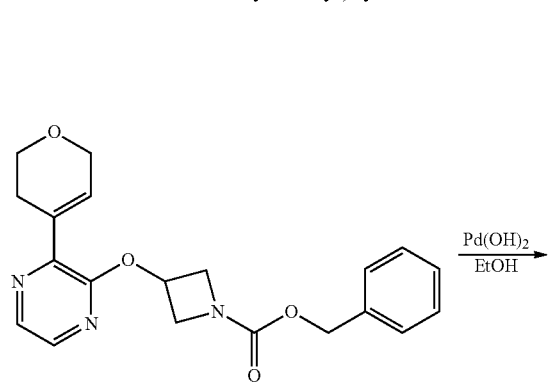

-continued

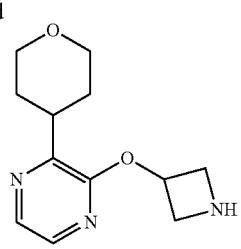

To a $N_2$ purged round bottom flask was added benzyl 3-(3-(3,6-dihydro-2H-pyran-4-yl)pyrazin-2-yloxy)azetidine-1-carboxylate (see PREPARATION P28.2; 490 mg, 1.334 mmol), pearlman's catalyst (37.5 mg, 0.267 mmol) and EtOH (10 mL). A balloon of $H_2$ was placed atop the round bottom flask. After 20 hours, the reaction was filtered through CELITE® and the cake was washed with EtOAc. The filtrate was concentrated in vacuo to give 2-(azetidin-3-yloxy)-3-(tetrahydro-2H-pyran-4-yl)pyrazine (240 mg, 1.020 mmol, 76% yield), as a tan residue. MS (ESI) m/z 236.1 (MH+).

TABLE P30.1

EXAMPLES P30.1-P30.2 PREPARED ANALOGOUS TO PREPARATION P30.1

| Example | Structure | Chemical Name | M + 1 |
|---|---|---|---|
| P30.1 | 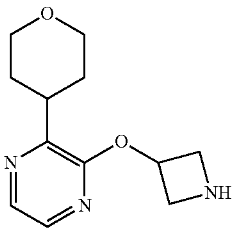 [SMILES: c1cnc(C2CCOCC2)c(OC2CNC2)n1] | 2-(azetidin-3-yloxy)-3-(tetrahydro-2H-pyran-4-yl)pyrazine | 236 |
| P30.2 | 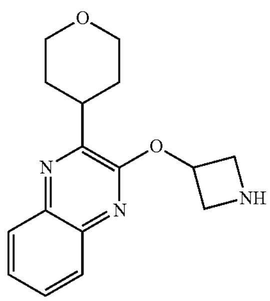 [SMILES: c1ccc2nc(C3CCOCC3)c(OC3CNC3)nc2c1] | 2-(azetidin-3-yloxy)-3-(tetrahydro-2H-pyran-4-yl)quinoxaline | 286 |

Preparation P31.1:
4-(2-(Piperidin-4-yloxy)Pyridin-3-yl)Morpholine Hydrochloride

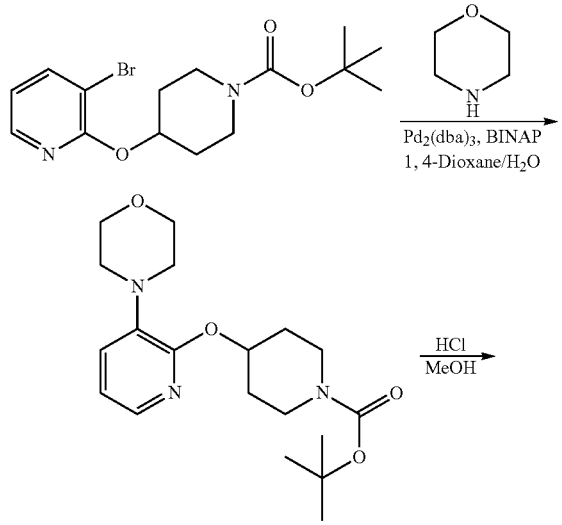

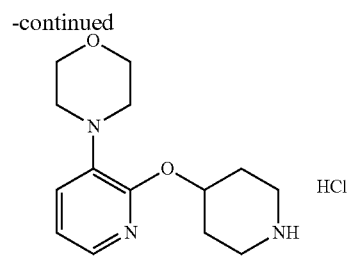

Step 1. Tert-Butyl 4-((3-Morpholinopyridin-2-yl)Oxy)Piperidine-1-Carboxylate

To a solution of tert-butyl 4-((3-bromopyridin-2-yl)oxy)piperidine-1-carboxylate (see PREPARATION P20.4; 4 g, 11.2 mmol), morpholine (1.46 g, 16.8 mmol), Pd$_2$(dba)$_3$ (513 mg, 0.56 mmol), 2,2'-bis(diphenylphosphino)-1,1'-binaphthyl (BINAP) (349 mg, 0.56 mmol), sodium tert-butoxide (t-BuONa) (2.15 g, 22.4 mmol) then the reaction mixture was stirred at 90° C. for overnight. The mixture was left to reach room temperature, then the reaction mixture was filtered through a pad of CELITE® and the filter cake was washed with CH$_2$Cl$_2$ (3×20 mL). The combined filtrates were evaporated in vacuo and the residue was purified by column chromatography to give the product (3.1 g, 8.7 mmol, yield 70%). ESI-MS (M+1): 364 calc. for C$_{19}$H$_{29}$N$_3$O$_4$ 363.

Step 2. 4-(2-(Piperidin-4-yloxy)Pyridin-3-yl)Morpholine Hydrochloride

To tert-butyl 4-((3-morpholinopyridin-2-yl)oxy)piperidine-1-carboxylate (3.2 g, 8.8 mmol) was added 4 M HCl in MeOH (100 mL). The solution was stirred at room temperature for 2 hours. The solvent was removed under reduced pressure to give the title compound (2.2 g, 8.36 mmol, yield 95%). ESI-MS (M+1): 264 calc. for C$_{14}$H$_{21}$N$_3$O$_2$ 263

TABLE P31

EXAMPLES P31.1-P31.2 PREPARED ANALOGOUS TO PREPARATION P31.1

| Example | Structure | Chemical Name | M + 1 |
|---|---|---|---|
| P31.1 | 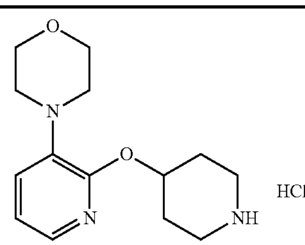 | 4-(2-(piperidin-4-yloxy)pyridin-3-yl)morpholine hydrochloride | 264 |
| P31.2 | 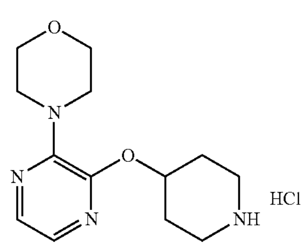 [SMILES: c1cnc(N2CCOCC2)c(OC2CCNCC2)n1 ; Cl] | 4-(3-(piperidin-4-yloxy)pyrazin-2-yl)morpholine hydrochloride | 265 |

SCHEME 1

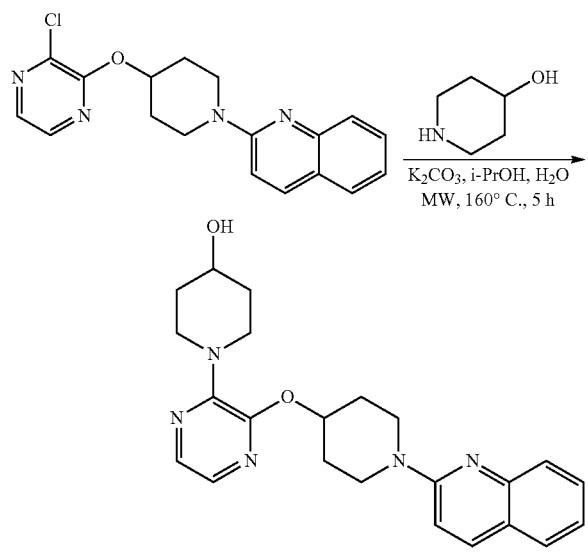

Example 1.1

1-(3-((1-(Quinolin-2-yl)Piperidin-4-yl)Oxy)Pyrazin-2-yl)Piperidin-4-Ol

To a mixture of 2-(4-((3-chloropyrazin-2-yl)oxy)piperidin-1-yl)quinoline (see PREPARATION P1.1; 0.1 g, 0.29 mmol) and piperidin-4-ol (0.029 g, 0.29 mmol) and $K_2CO_3$ (0.08 g, 0.58 mmol) was added isopropyl alcohol (i-PrOH) (2 mL) and water (0.5 ml). The solution was heated to 160° C. under microwave for 5 hours. Then the mixture was concentrated and extracted with EtOAc (2×20 mL). The combined organic extracts were washed with water (10 mL) and brine (10 mL), dried over $Na_2SO_4$, and filtered. The filtrate was evaporated in vacuo and the residue was purified by flash column chromatography on silica gel (20% to 60% EtOAc in petroleum ether) to give the title product (0.02 g, 0.04 mmol, 17% yield) as white solid. ESI-MS (M+1): 406 calc. for $C_{23}H_{27}N_5O_2$ 405.

TABLE 1A

EXAMPLES 1.1-1.65 PREPARED ANALOGOUS TO SCHEME 1

| Ex. # | Structure | Chemical Name | ESI-MS (M + 1) | $IC_{50}$ (uM) |
|---|---|---|---|---|
| 1.1 | 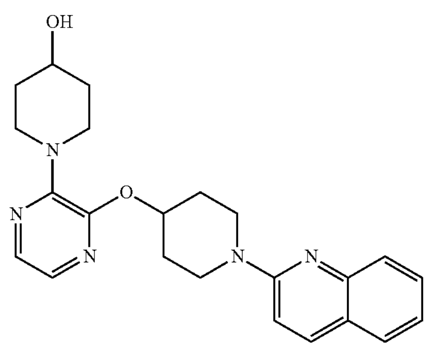 [SMILES: OC1CCN(c2nccnc2OC2CCN(c3ccc4ccccc4n3)CC2)CC1] | 1-(3-((1-(quinolin-2-yl)piperidin-4-yl)oxy)pyrazin-2-yl)piperidin-4-ol | 406 | 0.198 |
| 1.2 | 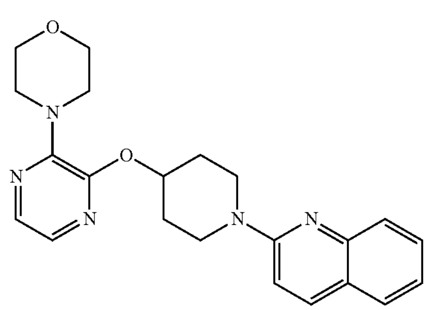 [SMILES: c1ccc2nc(N3CCC(Oc4nccnc4N4CCOCC4)CC3)ccc2c1] | 4-(3-((1-(quinolin-2-yl)piperidin-4-yl)oxy)pyrazin-2-yl)morpholine | 392 | 0.254 |

TABLE 1A-continued

EXAMPLES 1.1-1.65 PREPARED ANALOGOUS TO SCHEME 1

| Ex. # | Structure | Chemical Name | ESI-MS (M + 1) | IC$_{50}$ (uM) |
|---|---|---|---|---|
| 1.3 | 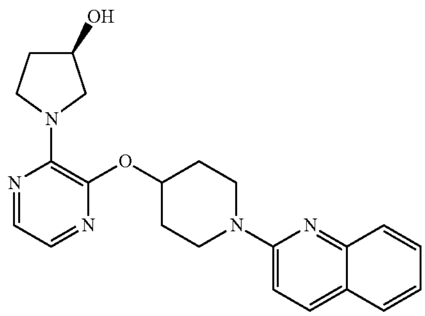 [SMILES: O[C@@H]1CCN(c2nccnc2OC2CCN(c3ccc4ccccc4n3)CC2)C1] | (R)-1-(3-((1-(quinolin-2-yl)piperidin-4-yl)oxy)pyrazin-2-yl)pyrrolidin-3-ol | 392 | 0.356 |
| 1.4 | 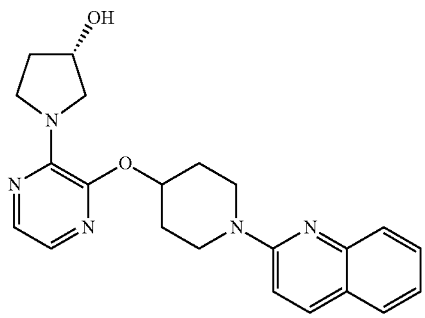 [SMILES: O[C@H]1CCN(c2nccnc2OC2CCN(c3ccc4ccccc4n3)CC2)C1] | (S)-1-(3-((1-(quinolin-2-yl)piperidin-4-yl)oxy)pyrazin-2-yl)pyrrolidin-3-ol | 392 | 0.198 |
| 1.5 | 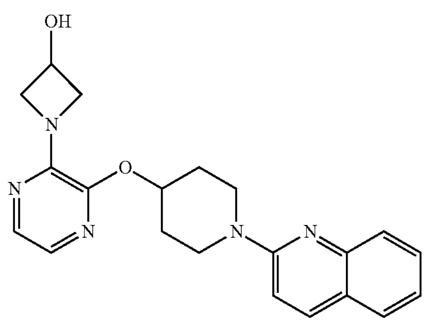 [SMILES: OC1CN(c2nccnc2OC2CCN(c3ccc4ccccc4n3)CC2)C1] | 1-(3-((1-(quinolin-2-yl)piperidin-4-yl)oxy)pyrazin-2-yl)azetidin-3-ol | 378 | 1.22 |
| 1.6 | 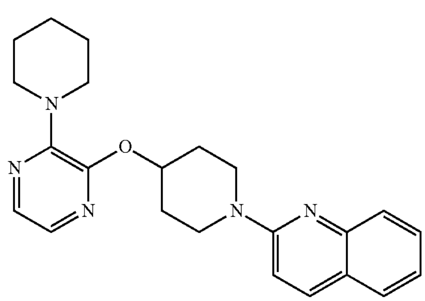 [SMILES: c1ccc2nc(N3CCC(Oc4nccnc4N4CCCCC4)CC3)ccc2c1] | 2-(4-((3-(piperidin-1-yl)pyrazin-2-yl)oxy)piperidin-1-yl)quinoline | 390 | 0.403 |
| 1.7 | 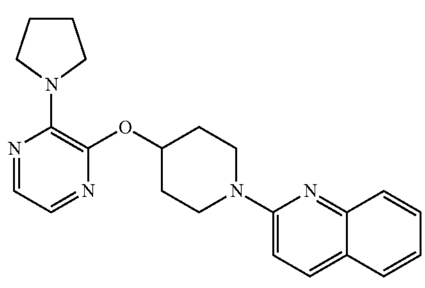 [SMILES: c1ccc2nc(N3CCC(Oc4nccnc4N4CCCC4)CC3)ccc2c1] | 2-(4-((3-(pyrrolidin-1-yl)pyrazin-2-yl)oxy)piperidin-1-yl)quinoline | 376 | 0.286 |

TABLE 1A-continued

EXAMPLES 1.1-1.65 PREPARED ANALOGOUS TO SCHEME 1

| Ex. # | Structure | Chemical Name | ESI-MS (M + 1) | IC$_{50}$ (uM) |
|---|---|---|---|---|
| 1.8 | 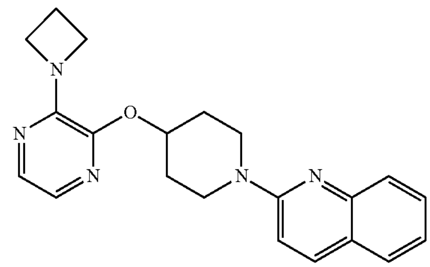 [SMILES: c1ccc2nc(N3CCC(Oc4nccnc4N4CCC4)CC3)ccc2c1] | 2-(4-((3-(azetidin-1-yl)pyrazin-2-yl)oxy)piperidin-1-yl)quinoline | 362 | 0.273 |
| 1.9 | 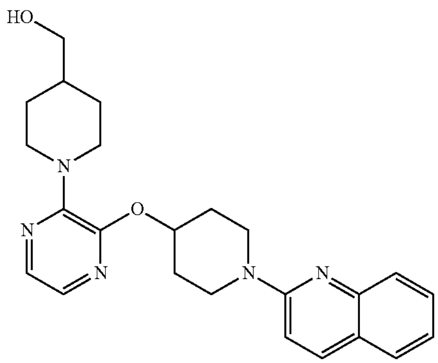 [SMILES: OCC1CCN(c2nccnc2OC2CCN(c3ccc4ccccc4n3)CC2)CC1] | (1-(3-((1-(quinolin-2-yl)piperidin-4-yl)oxy)pyrazin-2-yl)piperidin-4-yl)methanol | 420 | 0.00435 |
| 1.10 | 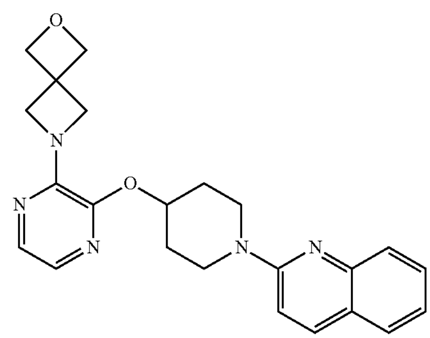 [SMILES: c1ccc2nc(N3CCC(Oc4nccnc4N4CC5(COC5)C4)CC3)ccc2c1] | 6-(3-((1-(quinolin-2-yl)piperidin-4-yl)oxy)pyrazin-2-yl)-2-oxa-6-azaspiro[3.3]heptane | 404 | 0.345 |
| 1.11 | 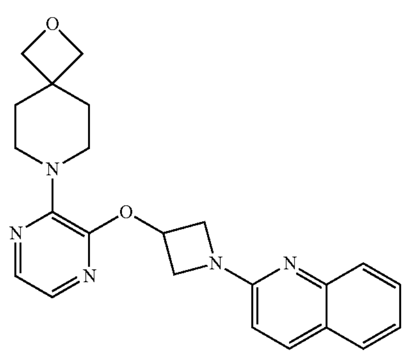 [SMILES: c1ccc2nc(N3CC(Oc4nccnc4N4CCC5(CC4)COC5)C3)ccc2c1] | 7-(3-((1-(quinolin-2-yl)azetidin-3-yl)oxy)pyrazin-2-yl)-2-oxa-7-azaspiro[3.5]nonane | 404 | 0.0436 |

TABLE 1A-continued

EXAMPLES 1.1-1.65 PREPARED ANALOGOUS TO SCHEME 1

| Ex. # | Structure | Chemical Name | ESI-MS (M + 1) | IC$_{50}$ (uM) |
|---|---|---|---|---|
| 1.12 | 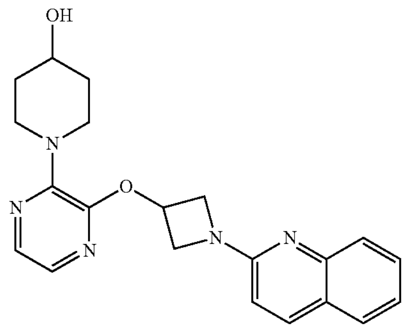 [SMILES: OC1CCN(c2nccnc2OC2CN(c3ccc4ccccc4n3)C2)CC1] | 1-(3-((1-(quinolin-2-yl)azetidin-3-yl)oxy)pyrazin-2-yl)piperidin-4-ol | 378 | 0.0261 |
| 1.13 | 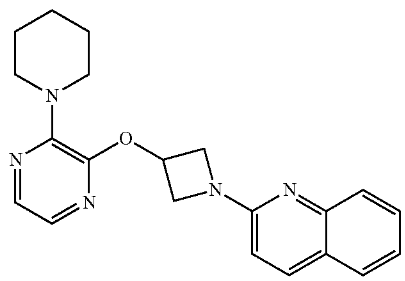 [SMILES: c1ccc2nc(N3CC(Oc4nccnc4N4CCCCC4)C3)ccc2c1] | 2-(3-((3-(piperidin-1-yl)pyrazin-2-yl)oxy)azetidin-1-yl)quinoline | 362 | 0.0397 |
| 1.14 | 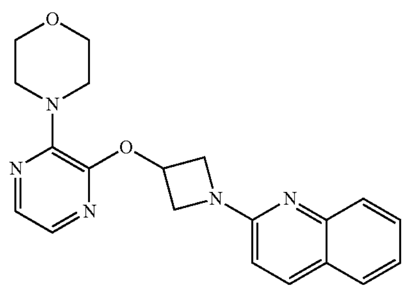 [SMILES: c1ccc2nc(N3CC(Oc4nccnc4N4CCOCC4)C3)ccc2c1] | 4-(3-((1-(quinolin-2-yl)azetidin-3-yl)oxy)pyrazin-2-yl)morpholine | 364 | 0.0483 |
| 1.15 | 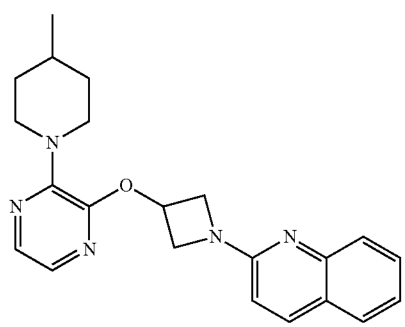 | 2-(3-((3-(4-methylpiperidin-1-yl)pyrazin-2-yl)oxy)azetidin-1-yl)quinoline | 376 | 0.124 |
| 1.16 | 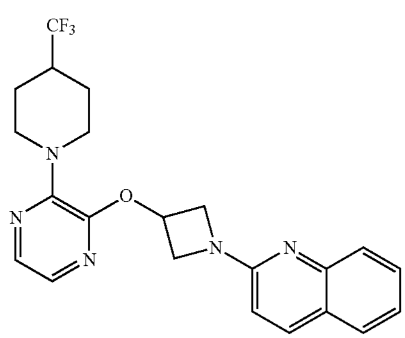 [SMILES: FC(F)(F)C1CCN(c2nccnc2OC2CN(c3ccc4ccccc4n3)C2)CC1] | 2-(3-((3-(4-(trifluoromethyl)piperidin-1-yl)pyrazin-2-yl)oxy)azetidin-1-yl)quinoline | 430 | 0.0614 |

TABLE 1A-continued

EXAMPLES 1.1-1.65 PREPARED ANALOGOUS TO SCHEME 1

| Ex. # | Structure | Chemical Name | ESI-MS (M + 1) | IC$_{50}$ (uM) |
|---|---|---|---|---|
| 1.17 | 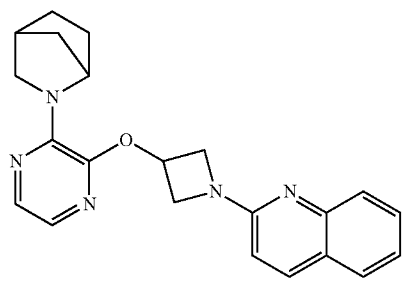 [SMILES: c1ccc2nc(N3CC(Oc4nccnc4N4CC5CCC4C5)C3)ccc2c1] | 2-(3-((3-(2-azabicyclo[2.2.1]heptan-2-yl)pyrazin-2-yl)oxy)azetidin-1-yl)quinoline | 374 | 0.109 |
| 1.18 | 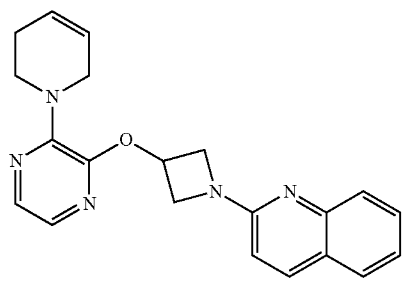 [SMILES: C1=CCN(c2nccnc2OC2CN(c3ccc4ccccc4n3)C2)CC1] | 2-(3-((3-(5,6-dihydropyridin-1(2H)-yl)pyrazin-2-yl)oxy)azetidin-1-yl)quinoline | 360 | 0.314 |
| 1.19 | 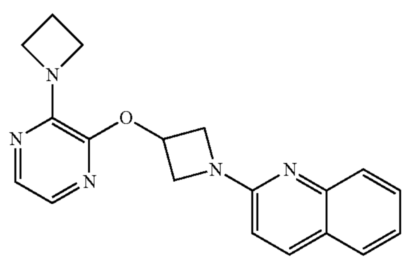 [SMILES: c1ccc2nc(N3CC(Oc4nccnc4N4CCC4)C3)ccc2c1] | 2-(3-((3-(azetidin-1-yl)pyrazin-2-yl)oxy)azetidin-1-yl)quinoline | 334 | 0.0861 |
| 1.20 | 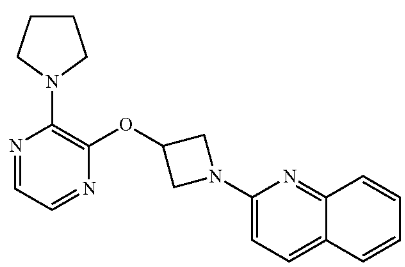 [SMILES: c1ccc2nc(N3CC(Oc4nccnc4N4CCCC4)C3)ccc2c1] | 2-(3-((3-(pyrrolidin-1-yl)pyrazin-2-yl)oxy)azetidin-1-yl)quinoline | 348 | 10 |
| 1.21 | 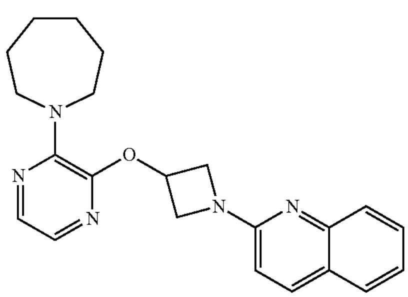 [SMILES: c1ccc2nc(N3CC(Oc4nccnc4N4CCCCCC4)C3)ccc2c1] | 2-(3-((3-(azepan-1-yl)pyrazin-2-yl)oxy)azetidin-1-yl)quinoline | 376 | 0.334 |

TABLE 1A-continued

EXAMPLES 1.1-1.65 PREPARED ANALOGOUS TO SCHEME 1

| Ex. # | Structure | Chemical Name | ESI-MS (M + 1) | IC$_{50}$ (uM) |
|---|---|---|---|---|
| 1.22 | 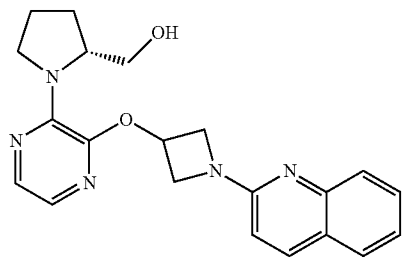 [SMILES: OC[C@H]1CCCN1c1nccnc1OC1CN(c2ccc3ccccc3n2)C1] | (R)-(1-(3-((1-(quinolin-2-yl)azetidin-3-yl)oxy)pyrazin-2-yl)pyrrolidin-2-yl)methanol | 378 | 0.150 |
| 1.23 | 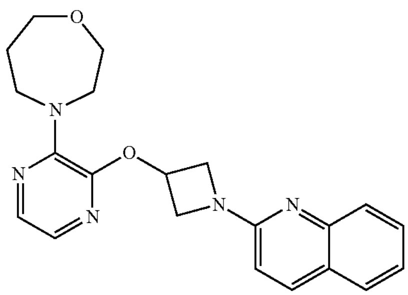 [SMILES: c1ccc2nc(N3CC(Oc4nccnc4N4CCCOCC4)C3)ccc2c1] | 4-(3-((1-(quinolin-2-yl)azetidin-3-yl)oxy)pyrazin-2-yl)-1,4-oxazepane | 378 | 0.0446 |
| 1.24 | (racemic mixture) | 1-(3-((1-(quinolin-2-yl)azetidin-3-yl)oxy)pyrazin-2-yl)azepan-4-ol | 392 | 0.0295 |
| 1.25 | (racemic mixture) | (1-(3-((1-(quinolin-2-yl)azetidin-3-yl)oxy)pyrazin-2-yl)pyrrolidin-3-yl)methanol | 378 | 0.0434 |

TABLE 1A-continued

EXAMPLES 1.1-1.65 PREPARED ANALOGOUS TO SCHEME 1

| Ex. # | Structure | Chemical Name | ESI-MS (M + 1) | IC$_{50}$ (uM) |
|---|---|---|---|---|
| 1.26 | 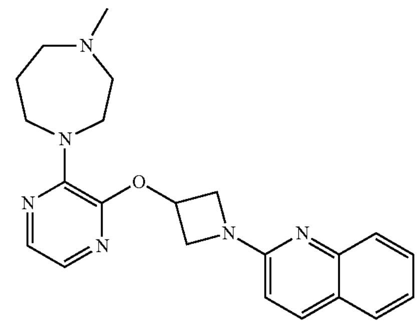 [SMILES: CN1CCCN(c2nccnc2OC2CN(c3ccc4ccccc4n3)C2)CC1] | 2-(3-((3-(4-methyl-1,4-diazepan-1-yl)pyrazin-2-yl)oxy)azetidin-1-yl)quinoline | 391 | 2.99 |
| 1.27 | 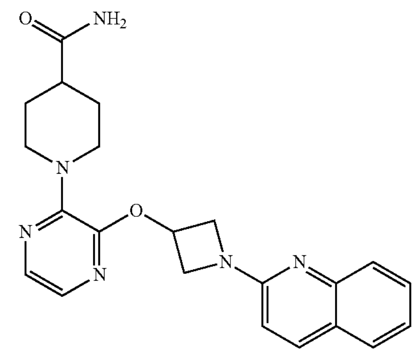 [SMILES: NC(=O)C1CCN(c2nccnc2OC2CN(c3ccc4ccccc4n3)C2)CC1] | 1-(3-((1-(quinolin-2-yl)azetidin-3-yl)oxy)pyrazin-2-yl)piperidine-4-carboxamide | 405 | 0.00968 |
| 1.28 | 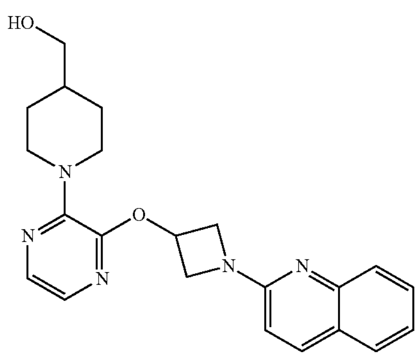 [SMILES: OCC1CCN(c2nccnc2OC2CN(c3ccc4ccccc4n3)C2)CC1] | (1-(3-((1-(quinolin-2-yl)azetidin-3-yl)oxy)pyrazin-2-yl)piperidin-4-yl)methanol | 392 | 0.0023 |
| 1.29 | 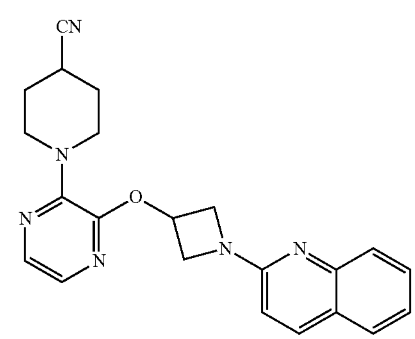 [SMILES: N#CC1CCN(c2nccnc2OC2CN(c3ccc4ccccc4n3)C2)CC1] | 1-(3-((1-(quinolin-2-yl)azetidin-3-yl)oxy)pyrazin-2-yl)piperidine-4-carbonitrile | 387 | 0.00608 |

TABLE 1A-continued

EXAMPLES 1.1-1.65 PREPARED ANALOGOUS TO SCHEME 1

| Ex. # | Structure | Chemical Name | ESI-MS (M + 1) | IC$_{50}$ (uM) |
|---|---|---|---|---|
| 1.30 | 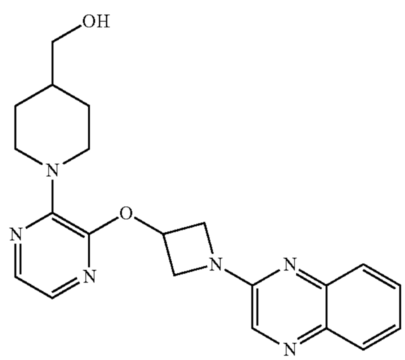 [SMILES: OCC1CCN(c2nccnc2OC2CN(c3cnc4ccccc4n3)C2)CC1] | (1-(3-((1-(quinoxalin-2-yl)azetidin-3-yl)oxy)pyrazin-2-yl)piperidin-4-yl)methanol | 393 | 0.0378 |
| 1.31 | 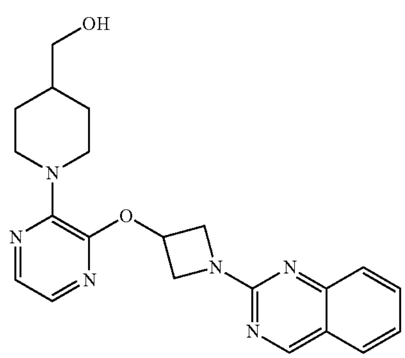 [SMILES: OCC1CCN(c2nccnc2OC2CN(c3ncc4ccccc4n3)C2)CC1] | (1-(3-((1-(quinazolin-2-yl)azetidin-3-yl)oxy)pyrazin-2-yl)piperidin-4-yl)methanol | 393 | 0.014 |
| 1.32 | 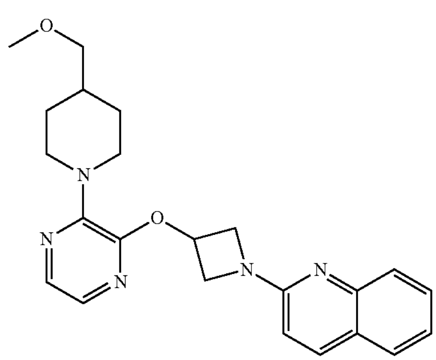 [SMILES: COCC1CCN(c2nccnc2OC2CN(c3ccc4ccccc4n3)C2)CC1] | 2-(3-((3-(4-(methoxymethyl)piperidin-1-yl)pyrazin-2-yl)oxy)azetidin-1-yl)quinoline | 406 | 0.0276 |
| 1.33 | 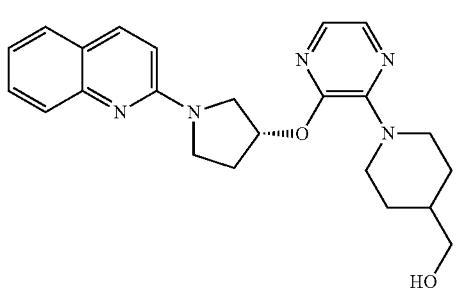 [SMILES: OCC1CCN(c2nccnc2O[C@@H]2CCN(c3ccc4ccccc4n3)C2)CC1] | (R)-(1-(3-((1-(quinolin-2-yl)pyrrolidin-3-yl)oxy)pyrazin-2-yl)piperidin-4-yl)methanol | 406 | 0.167 |

TABLE 1A-continued

EXAMPLES 1.1-1.65 PREPARED ANALOGOUS TO SCHEME 1

| Ex. # | Structure | Chemical Name | ESI-MS (M + 1) | IC$_{50}$ (uM) |
|---|---|---|---|---|
| 1.34 | 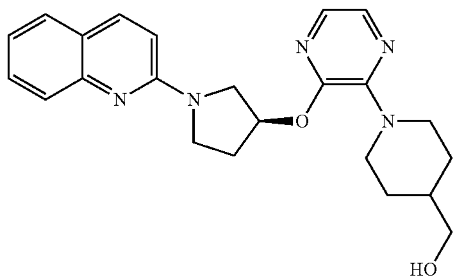 [SMILES: OCC1CCN(c2nccnc2O[C@H]2CCN(c3ccc4ccccc4n3)C2)CC1] | (S)-(1-(3-((1-(quinolin-2-yl)pyrrolidin-3-yl)oxy)pyrazin-2-yl)piperidin-4-yl)methanol | 406 | 0.078 |
| 1.35 | 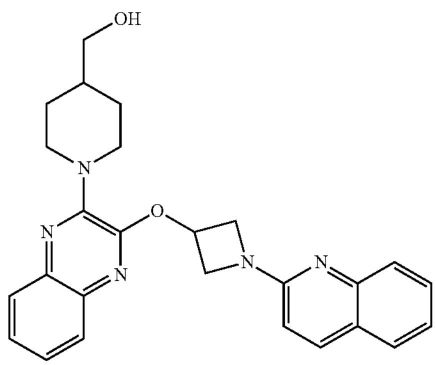 [SMILES: OCC1CCN(c2nc3ccccc3nc2OC2CN(c3ccc4ccccc4n3)C2)CC1] | (1-(3-((1-(quinolin-2-yl)azetidin-3-yl)oxy)quinoxalin-2-yl)piperidin-4-yl)methanol | 442 | 0.00975 |
| 1.36 | 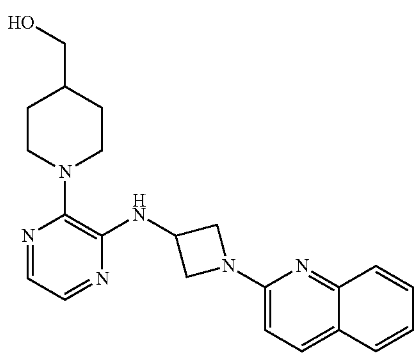 [SMILES: OCC1CCN(c2nccnc2NC2CN(c3ccc4ccccc4n3)C2)CC1] | (1-(3-((1-(quinolin-2-yl)azetidin-3-yl)amino)pyrazin-2-yl)piperidin-4-yl)methanol | 391 | 0.02 |
| 1.37 | 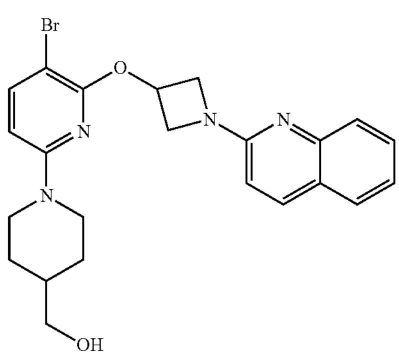 [SMILES: OCC1CCN(c2ccc(Br)c(OC3CN(c4ccc5ccccc5n4)C3)n2)CC1] | (1-(5-bromo-6-((1-(quinolin-2-yl)azetidin-3-yl)oxy)pyridin-2-yl)piperidin-4-yl)methanol | 469, 471 | 0.000229 |

TABLE 1A-continued

EXAMPLES 1.1-1.65 PREPARED ANALOGOUS TO SCHEME 1

| Ex. # | Structure | Chemical Name | ESI-MS (M + 1) | IC$_{50}$ (uM) |
|---|---|---|---|---|
| 1.38 | 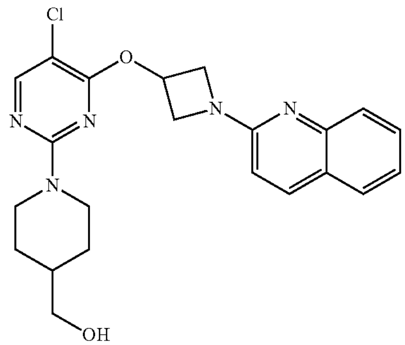 [SMILES: OCC1CCN(c2ncc(Cl)c(OC3CN(c4ccc5ccccc5n4)C3)n2)CC1] | (1-(5-chloro-4-((1-(quinolin-2-yl)azetidin-3-yl)oxy)pyrimidin-2-yl)piperidin-4-yl)methanol | 426 | 0.01 |
| 1.39 | 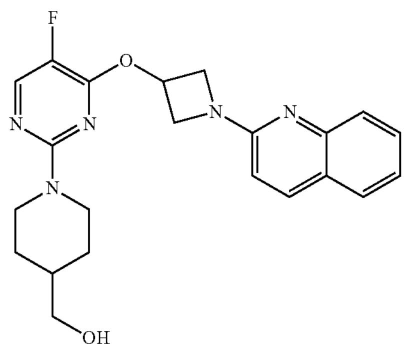 [SMILES: OCC1CCN(c2ncc(F)c(OC3CN(c4ccc5ccccc5n4)C3)n2)CC1] | (1-(5-fluoro-4-((1-(quinolin-2-yl)azetidin-3-yl)oxy)pyrimidin-2-yl)piperidin-4-yl)methanol | 410 | 0.02 |
| 1.40 | 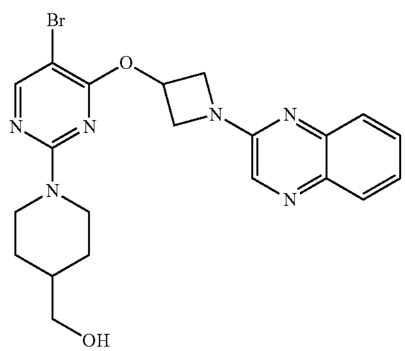 [SMILES: OCC1CCN(c2ncc(Br)c(OC3CN(c4cnc5ccccc5n4)C3)n2)CC1] | (1-(5-bromo-4-((1-(quinoxalin-2-yl)azetidin-3-yl)oxy)pyrimidin-2-yl)piperidin-4-yl)methanol | 471, 473 | 0.0242 |
| 1.41 | 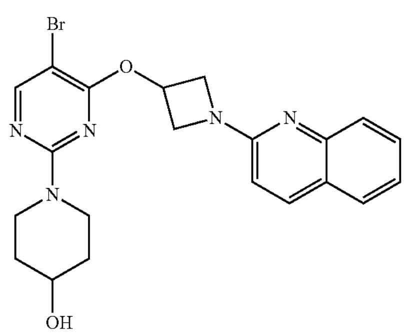 [SMILES: OC1CCN(c2ncc(Br)c(OC3CN(c4ccc5ccccc5n4)C3)n2)CC1] | (1-(5-bromo-4-((1-(quinolin-2-yl)azetidin-3-yl)oxy)pyrimidin-2-yl)piperidin-4-ol | 456, 458 | 0.0737 |

TABLE 1A-continued

EXAMPLES 1.1-1.65 PREPARED ANALOGOUS TO SCHEME 1

| Ex. # | Structure | Chemical Name | ESI-MS (M + 1) | IC$_{50}$ (uM) |
|---|---|---|---|---|
| 1.42 | 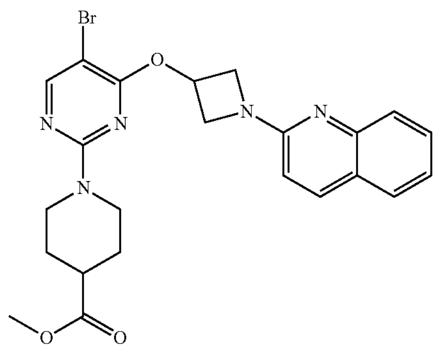 [SMILES: COC(=O)C1CCN(c2ncc(Br)c(OC3CN(c4ccc5ccccc5n4)C3)n2)CC1] | methyl 1-(5-bromo-4-((1-(quinolin-2-yl)azetidin-3-yl)oxy)pyrimidin-2-yl)piperidine-4-carboxylate | 498, 500 | 1.34 |
| 1.43 | 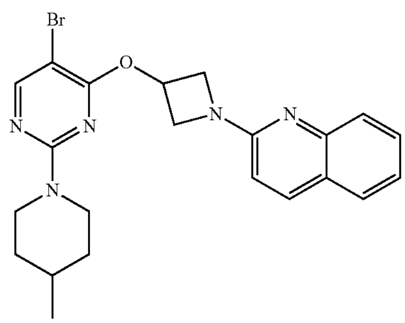 [SMILES: CC1CCN(c2ncc(Br)c(OC3CN(c4ccc5ccccc5n4)C3)n2)CC1] | 2-(3-((5-bromo-2-(4-methylpiperidin-1-yl)pyrimidin-4-yl)oxy)azetidin-1-yl)quinoline | 454, 456 | 0.358 |
| 1.44 | (racemic mixture) | (1-(5-bromo-4-((1-(quinolin-2-yl)azetidin-3-yl)oxy)pyrimidin-2-yl)pyrrolidin-3-yl)methanol | 456, 458 | 0.0206 |
| 1.45 | 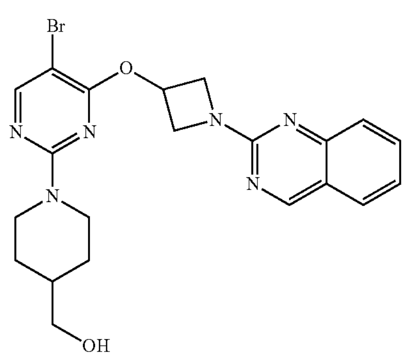 | (1-(5-bromo-4-((1-(quinazolin-2-yl)azetidin-3-yl)oxy)pyrimidin-2-yl)piperidin-4-yl)methanol | 472 | 0.0146 |

TABLE 1A-continued

EXAMPLES 1.1-1.65 PREPARED ANALOGOUS TO SCHEME 1

| Ex. # | Structure | Chemical Name | ESI-MS (M + 1) | IC$_{50}$ (uM) |
|---|---|---|---|---|
| 1.46 | 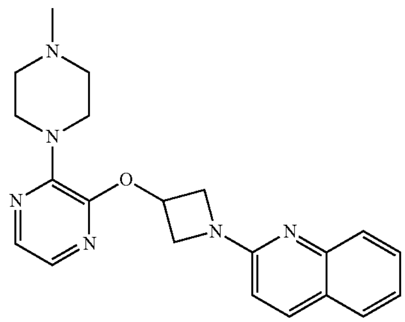 [SMILES: CN1CCN(c2nccnc2OC2CN(c3ccc4ccccc4n3)C2)CC1] | 2-(3-((3-(4-methylpiperazin-1-yl)pyrazin-2-yl)oxy)azetidin-1-yl)quinoline | 377 | 0.6830 |
| 1.47 | 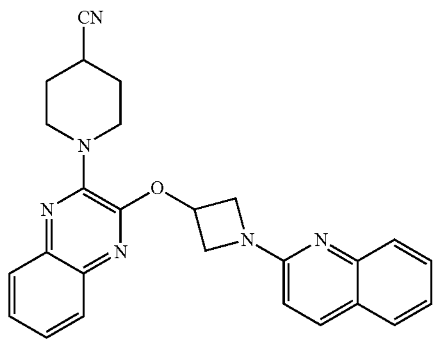 [SMILES: N#CC1CCN(c2nc3ccccc3nc2OC2CN(c3ccc4ccccc4n3)C2)CC1] | 1-(3-((1-(quinolin-2-yl)azetidin-3-yl)oxy)quinoxalin-2-yl)piperidine-4-carbonitrile | 437 | 0.0192 |
| 1.48 | 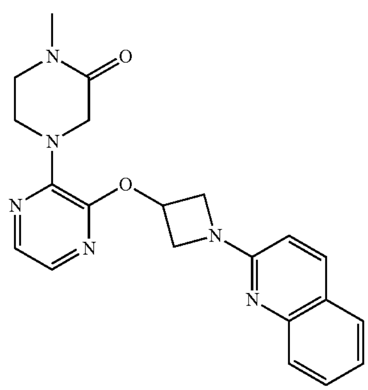 [SMILES: CN1CCN(c2nccnc2OC2CN(c3ccc4ccccc4n3)C2)CC1=O] | 1-methyl-4-(3-((1-(quinolin-2-yl)azetidin-3-yl)oxy)pyrazin-2-yl)piperazin-2-one | 391 | 0.0339 |
| 1.49 | (racemic mixture) | (1-(3-((1-(quinolin-2-yl)azetidin-3-yl)oxy)pyrazin-2-yl)piperidin-3-yl)methanol | 392 | 0.0406 |

TABLE 1A-continued

EXAMPLES 1.1-1.65 PREPARED ANALOGOUS TO SCHEME 1

| Ex. # | Structure | Chemical Name | ESI-MS (M + 1) | IC$_{50}$ (uM) |
|---|---|---|---|---|
| 1.50 | 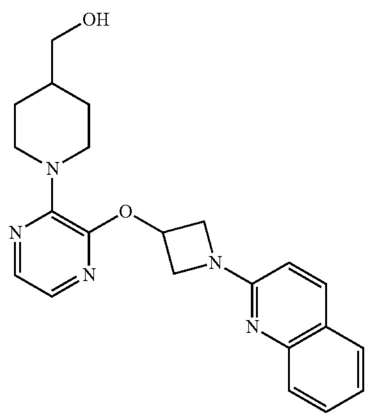 [SMILES: OCC1CCN(c2nccnc2OC2CN(c3ccc4ccccc4n3)C2)CC1] | (1-(3-((1-(2-quinolinyl)-3-azetidinyl)oxy)-2-pyrazinyl)-4-piperidinyl)methanol | 392 | 0.0233 |
| 1.51 | 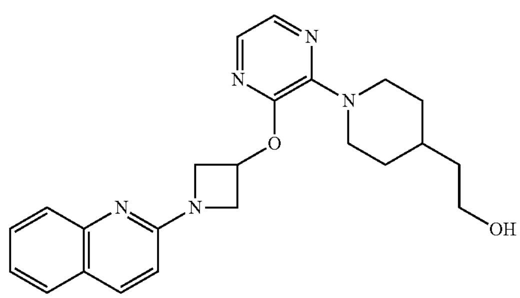 [SMILES: OCCC1CCN(c2nccnc2OC2CN(c3ccc4ccccc4n3)C2)CC1] | 2-(1-(3-((1-(2-quinolinyl)-3-azetidinyl)oxy)-2-pyrazinyl)-4-piperidinyl)ethanol | 406 | 0.0124 |
| 1.52 | 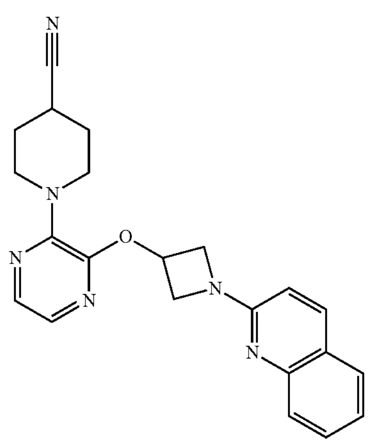 [SMILES: N#CC1CCN(c2nccnc2OC2CN(c3ccc4ccccc4n3)C2)CC1] | 1-(3-((1-(2-quinolinyl)-3-azetidinyl)oxy)-2-pyrazinyl)-4-piperidinecarbonitrile | 387 | 0.0608 |
| 1.53 | 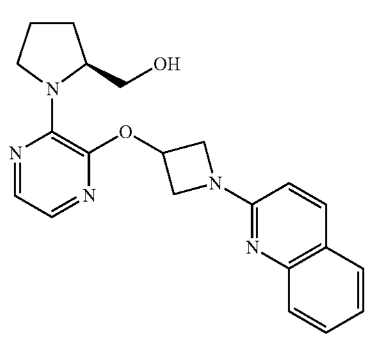 [SMILES: OC[C@@H]1CCCN1c1nccnc1OC1CN(c2ccc3ccccc3n2)C1] | ((2S)-1-(3-((1-(2-quinolinyl)-3-azetidinyl)oxy)-2-pyrazinyl)-2-pyrrolidinyl)methanol | 378 | 0.0226 |

TABLE 1A-continued

EXAMPLES 1.1-1.65 PREPARED ANALOGOUS TO SCHEME 1

| Ex. # | Structure | Chemical Name | ESI-MS (M + 1) | IC$_{50}$ (uM) |
|---|---|---|---|---|
| 1.54 | (racemic mixture) | 1-(3-((1-(quinolin-2-yl)azetidin-3-yl)oxy)pyrazin-2-yl)pyrrolidin-3-ol | 364 | 0.067 |
| 1.55* | 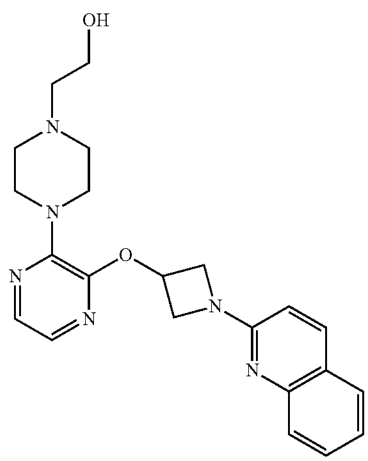 [SMILES: OCCN1CCN(c2nccnc2OC2CN(c3ccc4ccccc4n3)C2)CC1] | 2-(4-(3-((1-(2-quinolinyl)-3-azetidinyl)oxy)-2-pyrazinyl)-1-piperazinyl)ethanol | 407 | Not available |
| 1.56 | 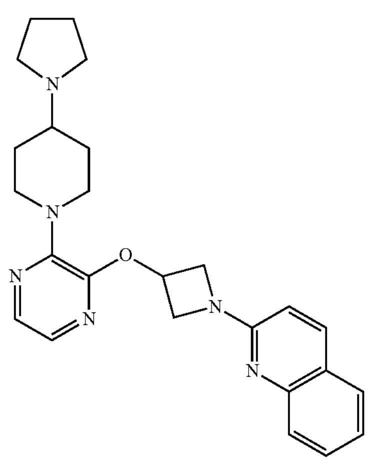 [SMILES: c1ccc2nc(N3CC(Oc4nccnc4N4CCC(N5CCCC5)CC4)C3)ccc2c1] | 2-(3-((3-(4-(1-pyrrolidinyl)-1-piperidinyl)-2-pyrazinyl)oxy)-1-azetidinyl)quinoline | 431 | 0.571 |

TABLE 1A-continued

EXAMPLES 1.1-1.65 PREPARED ANALOGOUS TO SCHEME 1

| Ex. # | Structure | Chemical Name | ESI-MS (M + 1) | IC$_{50}$ (uM) |
|---|---|---|---|---|
| 1.57 | 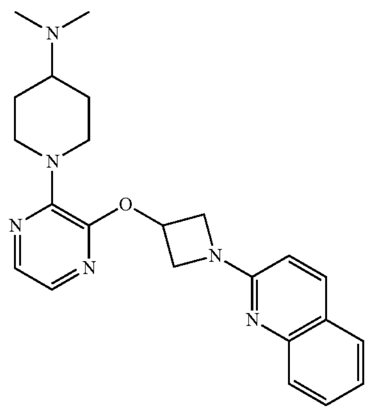 [SMILES: CN(C)C1CCN(c2nccnc2OC2CN(c3ccc4ccccc4n3)C2)CC1] | N,N-dimethyl-1-(3-((1-(2-quinolinyl)-3-azetidinyl)oxy)-2-pyrazinyl)-4-piperidinamine | 405 | 0.520 |
| 1.58 | (racemic mixture) | 2-methyl-4-(3-((1-(quinolin-2-yl)azetidin-3-yl)oxy)pyrazin-2-yl)morpholine | 378 | 0.0628 |
| 1.59 | (racemic mixture) | (4-(3-((1-(quinolin-2-yl)azetidin-3-yl)oxy)pyrazin-2-yl)morpholin-2-yl)methanol | 394 | 0.0886 |

TABLE 1A-continued

EXAMPLES 1.1-1.65 PREPARED ANALOGOUS TO SCHEME 1

| Ex. # | Structure | Chemical Name | ESI-MS (M + 1) | IC$_{50}$ (uM) |
|---|---|---|---|---|
| 1.60 | 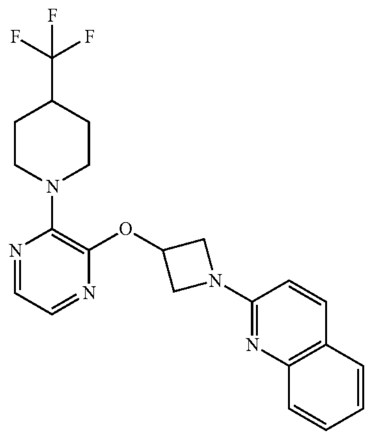 [SMILES: FC(F)(F)C1CCN(c2nccnc2OC2CN(c3ccc4ccccc4n3)C2)CC1] | 2-(3-((3-(4-(trifluoromethyl)-1-piperidinyl)-2-pyrazinyl)oxy)-1-azetidinyl)quinoline | 430 | 0.0614 |
| 1.61 | 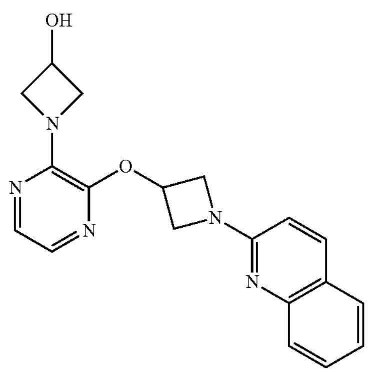 [SMILES: OC1CN(c2nccnc2OC2CN(c3ccc4ccccc4n3)C2)C1] | 1-(3-((1-(2-quinolinyl)-3-azetidinyl)oxy)-2-pyrazinyl)-3-azetidinol | 350 | 0.0947 |
| 1.62 | 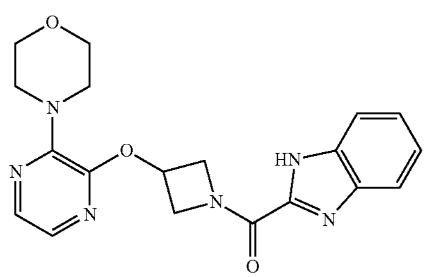 [SMILES: O=C(c1nc2ccccc2[nH]1)N1CC(Oc2nccnc2N2CCOCC2)C1] | (1H-benzo[d]imidazol-2-yl)(3-((3-morpholinopyrazin-2-yl)oxy)azetidin-1-yl)methanone | 381 | 0.3768 |
| 1.63 | 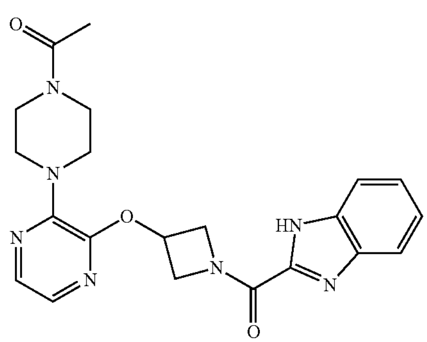 [SMILES: CC(=O)N1CCN(c2nccnc2OC2CN(C(=O)c3nc4ccccc4[nH]3)C2)CC1] | 1-(4-(3-(1-(1H-benzo[d]imidazole-2-carbonyl)azetidin-3-yloxy)pyrazin-2-yl)piperazin-1-yl)ethanone | 422 | 0.6371 |

TABLE 1A-continued

EXAMPLES 1.1-1.65 PREPARED ANALOGOUS TO SCHEME 1

| Ex. # | Structure | Chemical Name | ESI-MS (M + 1) | $IC_{50}$ (uM) |
|---|---|---|---|---|
| 1.64 | 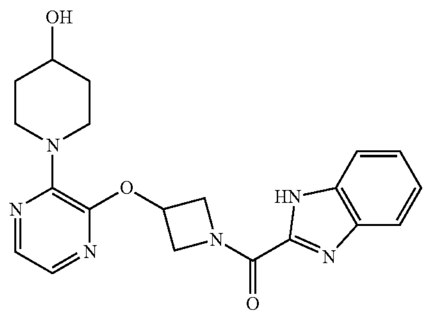 [SMILES: O=C(c1nc2ccccc2[nH]1)N1CC(Oc2nccnc2N2CCC(O)CC2)C1] | (1H-benzo[d]imidazol-2-yl)(3-((3-(4-hydroxypiperidin-1-yl)pyrazin-2-yl)oxy)azetidin-1-yl)methanone | 395 | 0.186 |
| 1.65 | 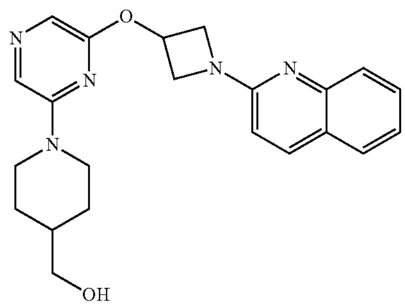 [SMILES: OCC1CCN(c2cncc(OC3CN(c4ccc5ccccc5n4)C3)n2)CC1] | (1-(6-((1-(quinolin-2-yl)azetidin-3-yl)oxy)pyrazin-2-yl)piperidin-4-yl)methanol | 392 | 0.000639 |

*Note:
Example 1.55 can be prepared according to Scheme 1. However, pure product NMR data is not available.

TABLE 1B

PREPARATION AND NMR DATA OF EXAMPLES 1.1-1.65

| Ex. # | Starting Material (1) | Starting Material (2) | Reaction Condition | $^1$H NMR (CD$_3$OD, 400 MHz) δ (ppm) |
|---|---|---|---|---|
| 1.1 | (see Preparation P2.1)-hereinafter in this column, compound A | OH, piperidine (NH) | K$_2$CO$_3$, i-PrOH, H$_2$O, MW 160° C., 5 h | 7.98 (d, J = 9.2 Hz, 1H); 7.66-7.65 (m, 3H); 7.53-7.52 (m, 2H); 7.23-7.19 (m, 2H); 5.45-5.41 (m, 1H); 4.02-3.98 (m, 4H); 3.81-3.75 (m, 3H); 3.09-3.02 (m, 2H); 2.19-2.12 (m, 2H); 1.95-1.63 (m, 4H); 1.63-1.59 (m, 2H). |
| 1.2 | compound A | morpholine | K$_2$CO$_3$, i-PrOH, H$_2$O, MW 160° C., 5 h | 8.03-8.00 (m, 1H); 7.71-7.62 (m, 3H); 7.58-7.57 (m, 2H); 7.23-7.20 (m, 2H); 5.43 (S, 1H); 4.04-4.02 (m, 2H); 3.78-3.76 (m, 6H); 3.49-3.47 (m, 4H); 2.20-2.14 (m, 2H); 1.93-1.89 (m, 2H). |
| 1.3 | compound A | 3-hydroxypyrrolidine (single enantiomer, R) | K$_2$CO$_3$, i-PrOH, H$_2$O, MW 160° C., 5 h | 8.41 (d, J = 10.0 Hz, 1H); 7.94-7.89 (m, 2H); 7.83-7.81 (m, 1H); 7.56-7.53 (m, 2H); 7.41 (m, 2H); 5.58-5.54 (m, 1H); 4.55-4.53 (m, 1H); 4.11-4.06 m, 4H); 4.02-3.87 (m, 4H); 2.36-2.30 (m, 2H); 2.22-2.09 (m, 4H). |

TABLE 1B-continued

PREPARATION AND NMR DATA OF EXAMPLES 1.1-1.65

| Ex. # | Starting Material (1) | Starting Material (2) | Reaction Condition | $^1$H NMR (CD$_3$OD, 400 MHz) δ (ppm) |
|---|---|---|---|---|
| 1.4 | compound A | (S)-3-hydroxypyrrolidine (single enantiomer, S) | K$_2$CO$_3$, i-PrOH, H$_2$O, MW 160° C., 5 h | 8.18-8.15 (m, 2H); 7.72-7.69 (m, 2H); 7.55 (d, J = 3.2 Hz, 1H); 7.48-7.44 (m, 1H); 7.27-7.26 (m, 2H); 7.17 (d, J = 10.0 Hz, 1H); 5.50-5.48 (m, 1H); 4.51-4.50 (m, 1H);; 4.06-3.83 (m, 8H); 2.16-2.03 (m, 4H); 2.03-2.01 (m, 2H). |
| 1.5 | compound A | 3-hydroxyazetidine | K$_2$CO$_3$, i-PrOH, H$_2$O, MW 160° C., 5 h | (CDCl$_3$) 7.77 (d, J = 9.2 Hz, 1H); 7.62 (d, J = 8.8 Hz, 1H); 7.50-7.42 (m, 3H); 7.24 (d, J = 3.2 Hz, 1H); 7.14-7.10 (m, 1H); 6.90 (d, J = 9.2 Hz, 1H); 5.23-5.21 (m, 1H); 4.57-4.51 (m, 1H); 4.30-4.26 (m, 2H); 3.91-3.87 (m, 4H); 3.66-3.60 (m, 2H); 2.03-1.98 (m, 2H); 1.83-1.77 (m, 2H). |
| 1.6 | compound A | piperidine | K$_2$CO$_3$, i-PrOH, H$_2$O, MW 160° C., 5 h | 8.40 (d, J = 9.6 Hz, 1H); 7.92-7.89 (m, 2H); 7.83-7.81 (m, 1H); 7.67 (d, J = 3.2 Hz, 1H); 7.56-7.53 (m, 3H); 5.54-5.52 (m, 1H); 4.09-4.06 (m, 4H); 3.49-3.47 (m, 4H); 2.35-2.27 (m, 2H); 2.18-2.12 (m, 2H); 1.90-1.68 (m, 6H). |
| 1.7 | compound A | pyrrolidine | K$_2$CO$_3$, i-PrOH, H$_2$O, MW 160° C., 5 h | 7.90 (d, J = 8.8 Hz, 1H); 7.61-7.60 (m, 2H); 7.49-7.47 (m, 2H); 7.24-7.13 (m, 3H); 5.33-5.31 (m, 1H); 4.03-3.98 (m, 2H); 3.80-3.65 (m, 6H); 2.14-2.09 (m, 2H); 2.00-1.88 (m, 6H). |
| 1.8 | compound A | azetidine | K$_2$CO$_3$, i-PrOH, H$_2$O, MW 160° C., 5 h | 7.96 (d, J = 9.2 Hz, 1H); 7.63-7.61 (m, 2H); 7.49-7.47 (m, 2H); 7.29 (d, J = 3.2 Hz, 1H); 7.21-7.161 (m, 2H); 5.32-5.30 (m, 1H); 4.22-4.18 (m, 4H); 4.05-3.99 (m, 2H); 3.73-3.69 (m, 2H); 2.33-2.29 (m, 2H); 2.14-2.09 (m, 2H); 1.89-1.84 (m, 2H). |
| 1.9 | compound A | 4-(hydroxymethyl)piperidine | K$_2$CO$_3$, i-PrOH, H$_2$O, MW 160° C., 5 h | 8.40 (d, J = 9.6 Hz, 1H); 7.91 (s, 2H); 7.67-7.66 (m, 1H); 7.57-7.53 (m, 4H); 5.56-5.54 (m, 1H); 4.23-4.20 (m, 2H); 4.09-4.06 (m, 5H); 3.47-3.40 (m, 2H); 2.94-2.87 (m, 2H); 2.35-2.69 (m, 2H); 2.17-2.12 (m, 2H); 2.00 (s, 2H); 1.85-1.81 (m, 1H); 1.37-1.35 (m, 2H). |

TABLE 1B-continued

PREPARATION AND NMR DATA OF EXAMPLES 1.1-1.65

| Ex. # | Starting Material (1) | Starting Material (2) | Reaction Condition | $^1$H NMR (CD$_3$OD, 400 MHz) δ (ppm) |
|---|---|---|---|---|
| 1.10 | compound A | 2-oxa-6-azaspiro[3.3]heptane | TEA, DMSO, 100° C. | 7.98 (d, J - 9.2 Hz, 1H); 7.64-7.62 (m, 2H); 7.52-7.51 (m, 2H); 7.34-7.33 (m, 1H); 7.22-7.18 (m, 2H); 5.33-5.31 (m, 1H); 5.01-4.79 (m, 4H); 4.33 (s, 4H); 4.11-4.05 (m, 2H); 3.72-3.67 (m, 2H); 2.17-2.12 (m, 2H); 1.94-1.89 (m, 2H). |
| 1.11 | 3-chloro-2-((1-(quinolin-2-yl)azetidin-3-yl)oxy)pyrazine (see Preparation P2.6)- hereinafter in this column, compound B | 2-oxa-7-azaspiro[3.5]nonane | K$_2$CO$_3$, i-PrOH, H$_2$O, MW 160° C., 5 h | (CDCl$_3$) 7.83 (d, J = 8.8 Hz, 1H); 7.69-7.68 (m, 2H); 7.56-7.45 (m, 3H); 7.19-7.18 (m, 1H); 6.54 (d, J = 8.8 Hz, 1H); 5.48 (s, 1H); 4.62-4.60 (m, 2H); 4.40 (s, 4H); 4.19-4.18 (m, 2H); 3.36-3.33 (m, 4H); 1.92-1.89 (m, 4H). |
| 1.12 | compound B | piperidin-4-ol | K$_2$CO$_3$, i-PrOH, H$_2$O, MW 160° C., 5 h | 7.86-7.72 (m, 3H); 7.58-7.47 (m, 3H); 7.30-7.20 (m, 1H); 6.56 (d, J = 8.8 Hz, 1H); 5.51 (s, 1H); 4.63-4.59 (m, 2H); 4.23-4.19 (m, 1H); 3.97-3.94 (m, 2H); 3.86-3.84 (m, 1H); 3.12-3.09 (m, 2H); 2.20-1.93 (m, 3H); 1.66-1.60 (m, 2H). |
| 1.13 | compound B | piperidine | K$_2$CO$_3$, i-PrOH, H$_2$O, MW 160° C., 5 h | (CDCl$_3$) 7.88 (d, J = 8.8 Hz, 1H); 7.76-7.75 (m, 2H); 7.61 (d, J = 8.4 Hz, 1H); 7.60-7.55 (m, 1H); 7.48 (d, J = 2.8 Hz, 1H); 7.25-7.21 (m, 1H); 6.61 (d, J = 8.8 Hz, 1H); 5.56-5.52 (m, 1H); 4.66-4.62 (m, 2H); 4.26-4.23 (m, 2H); 3.48-3.45 (m, 4H); 1.68-1.658 (m, 6H). |
| 1.14 | compound B | morpholine | K$_2$CO$_3$, i-PrOH, H$_2$O, MW 160° C., 5 h | (CDCl$_3$) 8.35 (d, J - 9.2 Hz, 1H); 7.90 (d, J = 8.0 Hz, 1H); 7.81-7.78 (m, 3H); 7.59 (d, J = 3.2 Hz, 1H); 7.54-7.52 (m, 1H); 6.98 (d, J = 9.2 Hz, 1H); 5.67-5.64 (m 1H); 4.98-4.93 (m, 2H); 4.61-4.55 (m, 2H); 3.81-3.79 (m, 4H); 3.56-3.53 (m, 4H). |
| 1.15 | compound B | 4-methylpiperidine | K$_2$CO$_3$, i-PrOH, H$_2$O, MW 160° C., 5 h | 8.32 (d, J = 9.6 Hz, 1H); 7.87 (d, J = 8.0 Hz, 1H); 7.78-7.76 (m, 3H); 7.52-7.50 (m, 2H); 6.96 (d, J = 9.6 Hz, 1H); 5.66-5.61 (m, 1H); 4.97 (s, 2H); 4.55-4.59 (m, 2H); 4.22-4.19 (m, 2H); 2.94-2.87 (m, 2H); 1.98-1.72 (m, 2H); 1.65-1.60 (m, 1H); 1.35-1.26 (m, 2H); 1.27-1.26 (s, 3H). |

TABLE 1B-continued

PREPARATION AND NMR DATA OF EXAMPLES 1.1-1.65

| Ex. # | Starting Material (1) | Starting Material (2) | Reaction Condition | $^1$H NMR (CD$_3$OD, 400 MHz) δ (ppm) |
|---|---|---|---|---|
| 1.16 | compound B | 4-CF$_3$-piperidine | K$_2$CO$_3$, i-PrOH, H$_2$O, MW 160° C., 5 h | 8.33 (d, J = 9.6 Hz, 1H); 7.88 (d, J = 7.6 Hz, 1H); 7.79-7.76 (m, 3H); 7.56-7.50 (m, 2H); 6.97 (d, J = 9.6 Hz, 1H); 5.66-5.62 (m, 1H); 4.97-4.92 (m, 2H); 4.59-4.55 (m, 2H); 4.34-4.30 (m, 2H); 2.90-2.83 (m, 2H); 2.46-2.38 (m, 1H); 1.94-1.91 (m, 2H); 1.71-1.60 (m, 2H). |
| 1.17 | compound B | 2-azabicyclo[2.1.1] | K$_2$CO$_3$, i-PrOH, H$_2$O, MW 160° C., 5 h | 7.92 (d, J = 9.2 Hz, 1H); 7.59-7.57 (m, 2H); 7.48-7.43 (m, 2H); 7.18-7.13 (m, 2H); 6.64 (d, J = 9.2 Hz, 1H); 5.42-5.40 (m, 1H); 4.55-4.50 (m, 2H); 4.16-4.08 (m, 2H); 3.63-3.61 (m, 1H); 3.24-3.20 (m, 2H); 2.48-2.46 (m, 1H); 1.42-1.39 (m, 4H); 1.29-1.28 (m, 2H). |
| 1.18 | compound B | 1,2,3,6-tetrahydropyridine | K$_2$CO$_3$, i-PrOH, H$_2$O, MW 160° C., 5 h | 8.40-8.31 (m, 1H); 7.87-7.78 (m, 1H); 7.78-7.72 (m, 3H); 7.52-7.48 (m, 2H); 6.96 (d, J = 2.4 Hz, 1H); 5.88-5.85 (m, 1H); 5.79-5.75 (m, 1H); 5.66-5.63 (m, 1H); 4.97-4.94 (m, 2H); 4.60-4.55 (m, 2H); 4.02-4.01 (m, 2H); 3.73-3.70 (m, 2H); 2.31-2.29 (m, 2H). |
| 1.19 | compound B | azetidine | K$_2$CO$_3$, i-PrOH, H$_2$O, MW 160° C., 5 h | (CDCl$_3$) 7.77-7.69 (m, 1H); 7.67-7.66 (m, 1H); 7.66-7.64 (m, 1H); 7.55-7.43 (m, 2H); 7.22-7.12 (m, 2H); 6.50-6.40 (m, 1H); 5.49-5.42 (m, 1H); 4.539-4.49 (m, 2H); 4.15-4.11 (m, 6H); 2.35-2.26 (m, 2H). |
| 1.20 | compound B | pyrrolidine | K$_2$CO$_3$, i-PrOH, H$_2$O, MW 160° C., 5 h | (CDCl$_3$) 7.79 (s, 1H); 7.47-7.45 (m, 1H); 7.41-7.39 (m, 1H); 7.33-7.31 (m, 2H); 6.99 (s, 1H); 6.56-6.55 (m, 1H); 6.51-6.48 (m, 1H); 5.15-5.11 (m, 1H); 4.46-4.41 (m, 1H); 3.88-3.79 (m, 2H); 3.61-3.56 (m, 5H); 1.81-1.78 (m, 4H). |
| 1.21 | compound B | azepane | K$_2$CO$_3$, i-PrOH, H$_2$O, MW 160° C., 5 h | 8.01-7.99 (m, 1H); 7.68-7.66 (m, 3H); 7.57-7.55 (m, 1H); 7.31-7.25 (m, 2H); 6.73-6.71 (m, 1H); 5.54-5.51 (m, 1H); 4.64-4.60 (m, 2H); 4.22-4.18 (m, 2H); 3.72-3.69 (m, 4H); 1.83-1.81 (m, 4H); 1.56-1.54 (m, 4H). |

TABLE 1B-continued

PREPARATION AND NMR DATA OF EXAMPLES 1.1-1.65

| Ex. # | Starting Material (1) | Starting Material (2) | Reaction Condition | $^1$H NMR (CD$_3$OD, 400 MHz) δ (ppm) |
|---|---|---|---|---|
| 1.22 | compound B | pyrrolidine-2-methanol (single enantiomer, R) | K$_2$CO$_3$, i-PrOH, H$_2$O, MW 160° C., 5 h | 8.34 (s, 1H); 7.91-7.78 (m, 3H); 7.57-7.50 (m, 2H); 7.40-7.39 (m, 1H); 6.69-6.97 (m, 1H); 5.67-5.66 (m, 1H); 4.95 (s, 2H); 4.72-4.62 (m, 3H); 3.92-3.88 (m, 1H); 3.78-3.63 (m, 2H); 3.61-3.58 (m, 1H); 2.08-2.05 (m, 4H). |
| 1.23 | compound B | 1,4-oxazepane | K$_2$CO$_3$, i-PrOH, H$_2$O, MW 160° C., 5 h | 7.94-7.96 (m, 1H); 7.62-7.67 (m, 3H); 7.52-7.54 (m, 1H); 7.38-7.52 (m, 1H); 7.20-7.24 (m, 1H); 6.67-6.69 (m, 1H); 5.52 (s, 1H); 4.59-4.60 (m, 2H); 4.14-4.17 (m, 2H); 3.82-3.85 (m, 6H); 3.69-3.81 (m, 2H); 1.95-1.98 (m, 2H). |
| 1.24 | compound B | azepan-4-ol (racemic mixture) | K$_2$CO$_3$, i-PrOH, H$_2$O, MW 160° C., 5 h | 8.37-8.35 (m, 1H); 7.91-7.89 (m, 1H); 7.80-7.79 (m, 2H); 7.63 (s, 1H); 7.54-7.50 (m, 1H); 7.43-7.42 (m, 1H); 7.00-6.98 (m, 1H); 5.66 (s, 1H); 4.99-4.96 (m, 2H); 4.62-4.59 (m, 2H); 3.91-3.88 (m, 2H); 3.74-3.70 (m, 3H); 2.16-1.83 (m, 5H); 1.74 (s, 1H). |
| 1.25 | compound B | pyrrolidin-3-ylmethanol (racemic mixture) | K$_2$CO$_3$, i-PrOH, H$_2$O, MW 160° C., 5 h | 8.35 (d, J = 9.6 Hz, 1H); 7.95 (d, J = 8.0 Hz, 1H); 7.80-7.78 (m, 2H); 7.53-7.51 (m, 2H); 6.99-6.98 (m, 1H); 6.97 (d, J = 9.2 Hz, 1H); 5.69 (s, 1H); 4.97-4.95 (m, 2H); 4.70-4.66 (m, 2H); 4.12-4.04 (m, 2H); 3.95-3.92 (m, 1H); 3.78-3.73 (m, 2H); 3.66-3.57 (m, 1H); 2.61-2.57 (m, 2H); 2.17-1.93 (m, 1H); 1.91-1.88 (m, 1H). |
| 1.26 | compound B | 1-methyl-1,4-diazepane | K$_2$CO$_3$, i-PrOH, H$_2$O, MW 160° C., 5 h | 8.33 (d, J = 9.2 Hz, 1H); 7.88 (d, J = 7.6 Hz, 1H); 7.76-7.78 (m, 3H); 7.52-7.50 (m, 2H); 6.97 (d, J = 9.2 Hz, 1H); 5.64-5.62 (m, 1H); 4.96 (s, 2H); 4.61 (s, 2H); 4.14 (s, 1H); 3.87-3.75 (m, 4H); 3.54-3.50 (m, 2H); 3.41-3.39 (m, 1H); 2.96 (s, 3H); 2.31-2.30 (m, 2H). |
| 1.27 | compound B | piperidine-4-carboxamide | K$_2$CO$_3$, i-PrOH, H$_2$O, MW 160° C., 5 h | 7.97-7.96 (m, 1H); 7.89 (d, J = 9.2 Hz, 1H); 7.70-7.69 (m, 2H); 7.57-7.52 (m, 1H); 7.44-7.43 (m, 1H); 6.53 (d, J = 9.2 Hz, 1H); 5.54-5.47 (m, 2H); 5.39 (s, 1H); 4.73 (s, 1H); 4.32 (s, 1H); 4.19-4.18 (m, 2H); 2.84-2.77 (m, 2H); 2.54-2.51 (m, 1H); 2.37-2.29 (m, 1H); 1.96-1.73 (m, 4H). |

TABLE 1B-continued

PREPARATION AND NMR DATA OF EXAMPLES 1.1-1.65

| Ex. # | Starting Material (1) | Starting Material (2) | Reaction Condition | $^1$H NMR (CD$_3$OD, 400 MHz) δ (ppm) |
|---|---|---|---|---|
| 1.28 | compound B | HO-CH$_2$-(4-piperidine) | K$_2$CO$_3$, i-PrOH, H$_2$O, MW 160° C., 5 h | 7.96 (d, J = 9.2 Hz, 1H); 7.70-7.31 (m, 3H); 7.54-7.49 (m, 2H); 7.25-7.23 (m, 1H); 6.66 (d, J = 9.2 Hz, 1H); 5.52 (s, 2H); 4.62-4.58 (s, 2H); 4.22-4.17 (m 4H); 3.41-3.39 (m, 2H); 2.79-2.78 (m, 2H); 1.79-1.75 (m, 3H); 1.34-1.30 (m, 2H). |
| 1.29 | compound B | 4-cyanopiperidine | K$_2$CO$_3$, i-PrOH, H$_2$O, MW 160° C., 5 h | 7.94-7.92 (m, 1H); 7.73 (d, J = 2.8 Hz, 1H); 7.65-7.64 (m, 2H); 7.55-7.51 (m, 2H); 7.20-7.18 (m, 1H); 6.65 (d, J = 9.2 Hz, 1H); 5.51 (s, 1H); 4.60-4.55 (m, 2H); 4.18-4.14 (s, 2H); 3.79-3.73 (m, 2H); 3.35-3.29 (m, 2H); 2.95-2.93 (m, 1H); 2.01-1.96 (m, 2H); 1.94-1.89 (m, 2H). |
| 1.30 | 3-chloro-2-(azetidin-3-yloxy)pyrazine with quinoxaline (see Preparation P3.7) | HO-CH$_2$-(4-piperidine) | K$_2$CO$_3$, i-PrOH, H$_2$O, MW 160° C., 5 h | 8.23 (s, 1H); 7.82-7.79 (m, 1H); 7.69 (d, J = 2.8 Hz, 1H); 7.64-7.62 (m, 2H); 7.59 (d, J = 1.2 Hz, 1H); 7.40-7.36 (m, 1H); 5.56-5.55 (m, 1H); 4.72-4.68 (m, 2H); 4.31-4.20 (m, 4H); 3.40-3.39 (m, 2H); 2.84-2.77 (m, 2H); 1.79-1.76 (m, 3H); 1.34-1.30 (m, 2H). |
| 1.31 | 3-chloro-2-(azetidin-3-yloxy)pyrazine with quinazoline (see Preparation P2.13) | HO-CH$_2$-(4-piperidine) | K$_2$CO$_3$, i-PrOH, H$_2$O, MW 160° C., 5 h | 9.02 (s, 1H); 7.74-7.67 (m, 3H); 7.53 (d, J = 8.4 Hz, 1H); 7.47 (d, J = 2.8 Hz, 1H); 7.27-7.23 (m, 1H); 5.51-5.54 (m, 1H); 4.64-4.59 (m, 2H); 4.22-4.18 (m, 4H); 3.49-3.40 (m, 2H); 2.81-2.75 (m, 2H); 1.78-1.75 (m, 2H); 1.66-1.64 (m, 2H); 1.37-1.27 (m, 2H). |
| 1.32 | compound B | MeO-CH$_2$-(4-piperidine) | K$_2$CO$_3$, i-PrOH, H$_2$O, MW 160° C., 5 h | 7.87-7.73 (m, 3H); 7.59-7.47 (m, 3H); 7.22-7.21 (m, 1H); 6.58-6.56 (m, 1H); 5.51 (s, 1H); 4.62-4.61 (m, 2H); 4.20-4.16 (m, 4H); 3.31-3.22 (m, 5H); 2.81-2.75 (m, 2H); 1.80-1.77 (m, 3H); 1.36-1.27 (m, 2H). |
| 1.33 | 3-chloro-2-(pyrrolidin-3-yloxy)pyrazine with quinoline (see Preparation P2.4) | HO-CH$_2$-(4-piperidine) | K$_2$CO$_3$, i-PrOH, H$_2$O, MW 160° C., 5 h | (CDCl$_3$) 8.16 (s, 1H); 8.03-7.98 (m, 1H); 7.72-7.67 (m, 2H); 7.54-7.52 (m, 1H); 7.46-7.41 (m, 2H); 6.88-6.86 (m, 1H); 5.83 (s, 1H); 4.27-3.98 (m, 7H); 3.59-3.40 (m, 1H); 2.99-2.83 (m, 2H); 2.54-2.53 (m, 2H); 2.01-1.72 (m, 3H); 1.41-1.32 (m, 2H). |

TABLE 1B-continued

PREPARATION AND NMR DATA OF EXAMPLES 1.1-1.65

| Ex. # | Starting Material (1) | Starting Material (2) | Reaction Condition | $^1$H NMR (CD$_3$OD, 400 MHz) δ (ppm) |
|---|---|---|---|---|
| 1.34 | (see Preparation P2.5) | | K$_2$CO$_3$, i-PrOH, H$_2$O, MW 160° C., 5 h | 8.37 (s, 1H); 7.91-7.88 (m, 2H); 7.68-7.67 (m, 1H); 7.60-7.59 (m, 1H); 7.54-7.50 (m, 1H); 7.30-7.20 (m, 2H); 5.90-5.89 (m, 1H); 4.23-4.09 (m, 7H); 4.01-3.99 (m, 1H); 2.93-2.86 (m, 2H); 2.61-2.59 (m, 2H); 1.78-1.75 (m, 3H); 1.33-1.27 (m, 2H). |
| 1.35 | (see Preparation P2.8) | | K$_2$CO$_3$, i-PrOH, water MW 160° C. | 8.35 (d, J = 9.2 Hz, 1H); 7.90 (d, J = 8.0 Hz, 1H); 7.82-7.78 (m, 2H); 7.71-7.66 (m, 2H); 7.54-7.40 (m, 3H); 7.00 (d, J = 9.2 Hz, 1H); 5.79-5.83 (m, 1H); 5.07-5.03 (m, 2H); 4.68-4.65 (m, 2H); 4.52-4.49 (m, 2H); 3.47-3.45 (m, 2H); 3.07-3.01 (m, 2H); 1.92-1.76 (m, 3H); 1.49-1.39 (m, 2H). |
| 1.36 | (see Preparation P9.1) | | K$_2$CO$_3$, i-PrOH, water MW 160° C. | 8.05 (d, J = 9.2 Hz, 1H); 7.67-7.64 (m, 3H); 7.55 (m, 1H); 7.54-7.50 (m, 1H); 7.25-7.246 (m, 1H); 6.72 (d, J = 9.2 Hz, 1H); 4.81-4.79 (m, 1H); 4.60-4.56 (m, 2H); 4.14-4.11 (m, 2H); 3.53-3.43 (m, 4H); 2.73-2.66 (m, 2H); 1.83-1.79 (m, 2H); 1.62-1.56 (m, 2H); 1.51-1.44 (m, 3H). |
| 1.37 | (see Preparation P3.3) | | TEA, DMSO, 150° C. | 7.93 (d, J = 9.2 Hz, 1H); 7.86-7.61 (m, 2H); 7.53-7.49 (m, 2H); 7.22-7.18 (m, 1H); 6.65 (d, J = 8.8 Hz, 1H); 6.24 (d, J = 8.8 Hz, 1H); 5.44-5.41 (m, 1H); 4.58-4.54 (m, 2H); 4.27-4.24 (m, 2H); 4.16-4.12 (m, 2H); 3.41-3.40 (m, 2H); 2.84-2.77 (m, 2H); 1.79-1.76 (m, 2H); 1.71-1.67 (m, 1H); 1.26-1.15 (m, 2H). |
| 1.38 | (see Preparation P3.4) | | TEA, DMSO, 150° C. | 8.32 (d, J = 9.6 Hz, 1H); 8.14 (d, J = 2.4 Hz, 1H); 7.88 (d, J = 8.0 Hz, 1H); 7.76-7.81 (m, 2H); 7.53-7.49 (m, 1H); 6.95 (d, J = 9.6 Hz, 1H); 5.70-5.66 (m, 1H); 5.06-4.97 (m, 2H); 4.66-4.60 (m, 4H); 4.30-4.28 (m, 1H); 3.45-3.44 (m, 1H); 3.02-2.96 (m, 2H); 2.14-1.76 (m, 3H); 1.36-1.18 (m, 2H). |

TABLE 1B-continued

PREPARATION AND NMR DATA OF EXAMPLES 1.1-1.65

| Ex. # | Starting Material (1) | Starting Material (2) | Reaction Condition | $^1$H NMR (CD$_3$OD, 400 MHz) δ (ppm) |
|---|---|---|---|---|
| 1.39 | 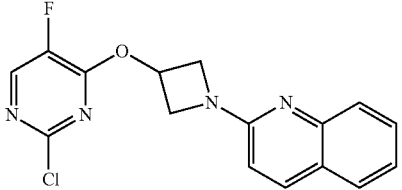 (see Preparation P3.5) | 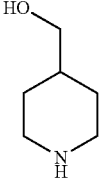 | TEA, DMSO, 150° C. | 7.90 (d, J = 2.8 Hz, 1H); 7.80 (d, J = 8.8 Hz, 1H); 7.67 (d, J = 8.4 Hz, 1H); 7.53-7.45 (m, 2H); 7.18-7.14 (m, 1H); 6.51 (d, J = 9.2 Hz, 1H); 5.49-5.44 (m, 1H); 4.54-4.50 (m, 4H); 4.22-4.19 (m, 2H); 3.44-3.43 (m, 2H); 2.80-2.74 (m, 2H); 1.74-1.67 (m, 2H); 1.17-1.09 (m, 3H). |
| 1.40 | 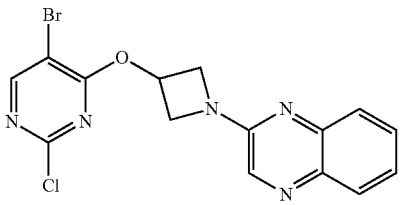 (see Preparation P3.7) | 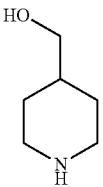 | TEA, DMSO, 150° C. | 8.52 (s, 1H); 8.21-20 (m, 1H); 7.97-7.95 (m, 1H); 7.70-7.67 (m, 2H); 7.57-7.53 (m, 1H); 5.68-5.66 (m, 1H); 5.00-4.90 (m, 2H); 4.70-4.59 (m, 4H); 4.29-4.28 (m, 1H); 3.44-3.42 (m, 1H); 2.97-2.94 (m, 2H); 1.91-1.80 (m, 3H); 1.32-1.15 (m, 2H). |
| 1.41 | 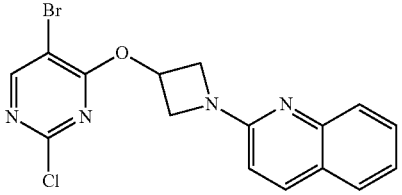 (see Preparation P2-11)- herinafter in this column, compound C | 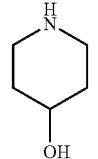 | TEA, DMSO, 150° C. | 8.34 (d, J = 9.2 Hz, 1H); 8.24-8.22 (m, 1H); 7.89 (d, J = 8.0 Hz, 1H); 7.80-7.78 (m, 2H); 7.54-7.50 (m, 1H); 6.97 (d, J = 9.2 Hz, 1H); 5.70-5.66 (m, 1H); 4.97-4.90 (m, 2H); 4.63-4.59 (m, 2H); 4.29-4.25 (m, 2H); 3.91-3.90 (m, 1H); 3.40-3.31 (m, 2H); 1.95-1.91 (m, 2H); 1.54-1.49 (m, 2H). |
| 1.42 | compound C | 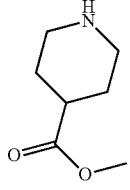 | Et$_3$N, DMSO, MW 150° C. | 8.38-8.40 (m, 1H); 8.22-8.21 (m, 1H); 7.90 (d, J = 8.0 Hz, 1H); 7.82-7.76 (m, 2H); 7.54-7.50 (m, 1H); 6.99 (d, J = 9.6 Hz, 1H); 5.69-5.65 (m, 1H); 4.99-4.95 (m, 2H); 4.63-4.50 (m, 4H); 3.69 (s, 3H); 3.16-3.09 (m, 2H); 2.72-2.66 (m, 1H); 2.00-1.96 (m, 2H); 1.70-1.60 (m, 2H). |
| 1.43 | compound C | 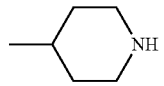 | Et$_3$N, DMSO, MW 150° C. | (CD$_3$Cl$_3$) 8.13 (s, 1H); 7.85 (d, J = 8.8 Hz, 1H); 7.73 (d, J = 8.4 Hz, 1H); 7.60-7.51 (m, 2H); 7.25-7.19 (m, 1H); 6.57 (d, J = 8.8 Hz, 1H); 5.53-5.49 (m, 1H); 4.60-4.55 (m, 4H); 4.28-4.24 (m, 2H); 2.88-2.81 (m, 2H); 1.71-1.60 (m, 3H); 1.25-1.10 (m, 2H); 0.97-0.95 (m, 3H). |

TABLE 1B-continued

PREPARATION AND NMR DATA OF EXAMPLES 1.1-1.65

| Ex. # | Starting Material (1) | Starting Material (2) | Reaction Condition | $^1$H NMR (CD$_3$OD, 400 MHz) δ (ppm) |
|---|---|---|---|---|
| 1.44 | compound C | [HOCH$_2$-pyrrolidine-NH structure] | Et$_3$N, DMSO, MW 150° C. | (CD$_3$Cl$_3$) 8.13 (s, 1H); 7.85 (d, J = 8.8 Hz, 1H); 7.72 (d, J = 8.4 Hz, 1H); 7.59-7.57 (m, 1H); 7.54-7.50 (m, 1H); 7.25-7.19 (m, 1H); 6.56 (d, J = 8.8 Hz, 1H); 5.51-5.47 (m, 1H); 4.59-4.55 (m, 2H); 4.27-4.24 (m, 2H); 3.70-3.61 (m, 4H); 3.51-3.46 (m, 1H); 3.32-3.27 (m, 1H); 2.54-2.50 (m, 1H); 2.09-2.08 (m, 1H); 1.81-1.76 (m, 1H). |
| 1.45 | [Br-pyrimidine-O-azetidine-N-quinazoline with Cl structure] (see Preparation P3.6) | [HOCH$_2$-piperidine-NH structure] | TEA, DMSO, 150° C. | (CDCl$_3$) 9.04 (s, 1H); 8.15 (s, 1H); 7.71-7.71 (m, 3H); 7.28-7.27 (m, 1H); 5.53 (s, 1H); 4.72-4.67 (m, 4H); 4.40-4.37 (m, 2H); 3.55-3.54 (m, 2H); 2.92-2.85 (m, 2H); 1.85-1.82 (m, 2H); 1.26-1.22 (m, 3H). |
| 1.46 | compound B | [N-methylpiperazine structure] | NEAT, MW 150° C. | (CDCl$_3$) 7.84 (d, J = 9.2 Hz, 1H); 7.76-7.72 (m, 2H); 7.59-7.51 (m, 3H); 7.21 (d, s, 1H); 6.56 (d, J = 9.2 Hz, 1H); 5.52-5.51 (m, 1H); 4.63-4.59 (m, 2H); 4.23-4.20 (m, 2H); 3.57 (s, 4H); 2.55-2.51 (m, 4H); 2.31 (s, 3H). |
| 1.47 | [Cl-quinoxaline-O-azetidine-N-quinoline structure] (see Preparation P2.8) | [CN-piperidine-NH structure] | TEA, DMSO, 150° C. | (CDCl$_3$) 7.91 (d, J = 9.2 Hz, 1H); 7.77-7.69 (m, 3H); 7.64-7.62 (m, 1H); 7.58-7.55 (m, 1H); 7.50-7.45 (m, 2H); 7.27-7.23 (m, 1H); 6.64 (d, J = 8.8 Hz, 1H); 5.76-5.73 (m, 1H); 4.76-4.72 (m, 2H); 4.31-4.28 (m, 2H); 4.02-3.96 (m, 2H); 3.59-3.54 (m, 2H); 2.90-2.89 (m, 1H); 2.10-2.01 (m, 4H) |
| 1.48 | compound B | [N-methylpiperazinone structure] | DMSO 120° C. | (DMSO-d$_6$) 2.86 (s, 4H) 3.82 (t, J = 5.50 Hz, 2H) 4.08 (s, 3H) 4.31 (d, J = 13.20 Hz, 2H) 4.61-4.76 (m, 2H) 5.48-5.61 (m, 1H) 6.91 (d, J = 9.68 Hz, 1H) 7.35 (t, J = 7.92 Hz, 1H) 7.60-7.72 (m, 3H) 7.78-7.89 (m, 2H) 8.21 (d, J = 10.12 Hz, 1H). |

TABLE 1B-continued

PREPARATION AND NMR DATA OF EXAMPLES 1.1-1.65

| Ex. # | Starting Material (1) | Starting Material (2) | Reaction Condition | $^1$H NMR (CD$_3$OD, 400 MHz) δ (ppm) |
|---|---|---|---|---|
| 1.49 | compound B | 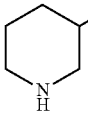<br>(racemic mixture) | DMSO 120° C. | (DMSO-d$_6$) 1.16 (d, J = 10.12 Hz, 1H) 1.46-1.61 (m, 1H) 1.64-1.81 (m, 3H) 2.61 (dd, J = 12.76, 10.56 Hz, 1H) 2.74-2.90 (m, 1H) 3.17-3.34 (m, 2H) 4.03 (d, J = 13.64 Hz, 1H) 4.11-4.26 (m, 3H) 4.58 (dd, J = 10.34, 7.26 Hz, 2H) 5.44-5.61 (m, 1H) 6.81 (d, J = 9.68 Hz, 1H) 7.20-7.33 (m, 1H) 7.49-7.67 (m, 3H) 7.70-7.82 (m, 2H) 8.08 (d, J = 9.68 Hz, 1H). |
| 1.50 | compound B | 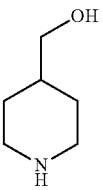 | DMSO 120° C. | (DMSO-d$_6$) 1.10-1.32 (m, 2H) 1.71 (d, J = 14.08 Hz, 3H) 2.68-2.85 (m, 2H) 3.27 (d, J = 6.16 Hz, 1H) 4.08-4.25 (m, 5H) 4.64 (dd, J = 10.78, 7.26 Hz, 2H) 5.43-5.58 (m, 1H) 6.86 (d, J = 9.24 Hz, 1H) 7.30 (t, J = 8.14 Hz, 1H) 7.51-7.69 (m, 3H) 7.72-7.84 (m, 2H) 8.14 (d, J = 9.68 Hz, 1H). |
| 1.51 | compound B | 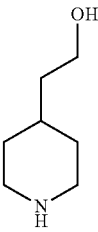 | DMSO 120° C. | (DMSO-d$_6$) 1.09-1.44 (m, 4H) 1.71 (d, J = 14.96 Hz, 3H) 2.76 (t, J = 13.86 Hz, 2H) 4.05-4.25 (m, 6H) 4.62 (dd, J = 10.56, 7.04 Hz, 2H) 5.43-5.57 (m, 1H) 6.85 (d, J = 9.24 Hz, 1H) 7.29 (t, J = 8.36 Hz, 1H) 7.50-7.68 (m, 3H) 7.71-7.84 (m, 2H) 8.12 (d, J = 9.68 Hz, 1H). |
| 1.52 | compound B | 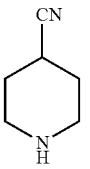 | DMSO 120° C. | (DMSO-d$_6$) 1.82 (td, J = 8.80, 3.52 Hz, 2H) 1.96 (br. s., 3H) 3.08-3.31 (m, 4H) 4.27 (d, J = 14.96 Hz, 2H) 4.59-4.74 (m, 2H) 5.47-5.58 (m, 1H) 6.89 (d, J = 9.68 Hz, 1H) 7.34 (d, J = 7.92 Hz, 1H) 7.58-7.70 (m, 3H) 7.76-7.86 (m, 2H) 8.18 (d, J = 10.12 Hz, 1H). |
| 1.53 | compound B | 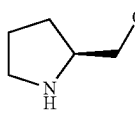<br>(single enantiomer, S) | DMSO 120° C. | (DMSO-d$_6$) 1.74-2.02 (m, 8H) 4.13-4.28 (m, 2H) 4.37-4.48 (m, 1H) 4.52-4.65 (m, 2H) 5.41-5.56 (m, 1H) 6.83 (d, J = 9.24 Hz, 1H) 7.21-7.37 (m, 2H) 7.52-7.70 (m, 3H) 7.76 (d, J = 8.80 Hz, 1H) 8.11 (d, J = 9.68 Hz, 1H) |
| 1.54 | compound B | 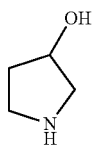<br>(racemic mixture) | DMSO 120° C. | 1.76-1.99 (m, 4H) 4.14-4.27 (m, 4H) 4.32 (br. s., 2H) 4.55-4.68 (m, 2H) 5.41-5.56 (m, 1H) 6.86 (d, J = 9.68 Hz, 1H) 7.23-7.36 (m, 2H) 7.54-7.70 (m, 3H) 7.77 (d, J = 8.80 Hz, 1H) 8.14 (d, J = 9.68 Hz, 1H) |

TABLE 1B-continued

PREPARATION AND NMR DATA OF EXAMPLES 1.1-1.65

| Ex. # | Starting Material (1) | Starting Material (2) | Reaction Condition | $^1$H NMR (CD$_3$OD, 400 MHz) δ (ppm) |
|---|---|---|---|---|
| 1.55* | compound B | 2-(piperazin-1-yl)ethanol | DMSO 120° C. | Not Available |
| 1.56 | compound B | 4-(pyrrolidin-1-yl)piperidine | DMSO 120° C. | (DMSO-d$_6$) 1.37-1.54 (m, 2H) 1.65 (br. s., 4H) 1.89 (d, J = 16.28 Hz, 2H) 2.18 (t, J = 10.78 Hz, 1H) 2.48 (br. s., 3H) 2.87 (t, J = 13.86 Hz, 3H) 4.03-4.16 (m, 4H) 4.55 (dd, J = 10.56, 6.60 Hz, 2H) 5.45-5.57 (m, 1H) 6.79 (d, J = 8.80 Hz, 1H) 7.16-7.29 (m, 1H) 7.52-7.62 (m, 3H) 7.68-7.82 (m, 2H) 8.04 (d, J = 9.24 Hz, 1H). |
| 1.57 | compound B | N,N-dimethylpiperidin-4-amine | DMSO 120° C. | (DMSO-d$_6$) 1.33-1.51 (m, 2H) 1.74-1.88 (m, 2H) 2.15 (s, 6H) 2.78 (t, J = 14.08 Hz, 2H) 4.04-4.24 (m, 5H) 4.55 (dd, J = 10.12, 7.04 Hz, 2H) 5.45-5.57 (m, 1H) 6.79 (d, J = 8.80 Hz, 1H) 7.18-7.29 (m, 1H) 7.48-7.62 (m, 3H) 7.67-7.83 (m, 2H) 8.04 (d, J = 9.68 Hz, 1H). |
| 1.58 | compound B | 2-methylmorpholine (racemic mixture) | DMSO 120° C. | (DMSO-d$_6$) 1.11 (d, J = 6.16 Hz, 3H) 2.58 (dd, J = 12.98, 10.34 Hz, 2H) 2.80-2.95 (m, 3H) 3.94-4.19 (m, 4H) 4.55 (dd, J = 10.12, 7.04 Hz, 2H) 5.45-5.59 (m, 1H) 6.79 (d, J = 9.24 Hz, 1H) 7.19-7.28 (m, 1H) 7.49-7.66 (m, 3H) 7.71 (d, J = 9.24 Hz, 1H) 7.82 (d, J = 3.08 Hz, 1H) 8.04 (d, J = 9.68 Hz, 1H). |
| 1.59 | compound B | morpholin-2-ylmethanol (racemic mixture) | DMSO 120° C. | (DMSO-d$_6$) 2.60-2.72 (m, 1H) 2.84-2.96 (m, 1H) 3.97-4.21 (m, 7H) 4.55 (dd, J = 10.12, 7.04 Hz, 2H) 4.82 (t, J = 5.94 Hz, 2H) 5.47-5.60 (m, 1H) 6.79 (d, J = 9.24 Hz, 1H) 7.18-7.29 (m, 1H) 7.49-7.65 (m, 3H) 7.71 (d, J = 9.24 Hz, 1H) 7.82 (d, J = 3.08 Hz, 1H) 8.04 (d, J = 9.24 Hz, 1H). |

TABLE 1B-continued

PREPARATION AND NMR DATA OF EXAMPLES 1.1-1.65

| Ex. # | Starting Material (1) | Starting Material (2) | Reaction Condition | $^1$H NMR (CD$_3$OD, 400 MHz) δ (ppm) |
|---|---|---|---|---|
| 1.60 | compound B | 4-(trifluoromethyl)piperidine | DMSO 120° C. | (DMSO-d$_6$) 1.48-1.62 (m, 2H) 1.80-1.92 (m, 2H) 2.85 (t, J = 14.52 Hz, 2H) 4.07-4.18 (m, 2H) 4.26 (d, J = 14.08 Hz, 2H) 4.55 (dd, J = 10.56, 7.04 Hz, 2H) 5.52 (t, J = 3.96 Hz, 1H) 6.79 (d, J = 9.24 Hz, 2H) 7.18-7.28 (m, 1H) 7.49-7.64 (m, 3H) 7.72 (d, J = 9.24 Hz, 1H) 7.81 (d, J = 3.08 Hz, 1H) 8.05 (d, J = 9.24 Hz, 1H). |
| 1.61 | compound B | 3-hydroxyazetidine | DMSO 120° C. | (DMSO-d$_6$) 3.84-3.88 (m, 1H) 4.02-4.14 (m, 2H) 4.27-4.38 (m, 2H) 4.52 (dd, J = 10.56, 6.60 Hz, 3H) 5.44-5.53 (m, 1H) 5.66 (d, J = 6.16 Hz, 1H) 6.79 (d, J = 9.24 Hz, 1H) 7.19-7.28 (m, 1H) 7.38 (d, J - 3.08 Hz, 1H) 7.49-7.75 (m, 4H) 8.04 (d, J = 9.24 Hz, 1H). |
| 1.62 | (see Preparation P19.1) chloropyrazinyl-oxy-azetidinyl-benzimidazole carbonyl | morpholine | Cs$_2$CO$_3$, DMSO, 90° C. | 3.57 (t, 4H, J = 4.68 Hz), 3.84 (t, 4H, J = 4.38 Hz), 4.24-4.32 (m, 1H), 4.53-4.61 (m, 1H), 4.68 (dd, 1H, J = 11.25 Hz, 5.41 Hz), 5.23 (dd, 1H, J = 11.84 Hz, 6.28 Hz), 5.53-5.60 (m, 1H), 7.31-7.38 (m, 2H), 7.61 (d, 1H, J = 2.78 Hz), 7.64-7.74 (m, 2H), 7.80 (d, 1H, J = 2.92 Hz) |
| 1.63 | (see Preparation P23.1) chloropyrazinyl-oxy-azetidinyl-benzimidazole carbonyl | 1-acetylpiperazine | Cs$_2$CO$_3$, DMSO | (DMSO-D$_6$) 2.02 (s, 3H), 3.44-3.49 (m, 2H), 3.52-3.60 (m, 6H), 4.19 (dd, 1H, J = 11.54 Hz, 3.52 Hz), 4.57 (dd, 1H, J = 11.15 Hz, 6.65 Hz), 4.71 (dd, 1H, J = 11.54 Hz, 3.52 Hz), 5.15 (dd, 1H, J = 11.54 Hz, 6.65 Hz), 5.44-5.50 (m, 1H), 7.26 (t, 1H, J = 7.43 Hz), 7.32 (t, 1H, J = 7.24 Hz), 7.52 (d, 1H, J = 8.02 Hz), 7.64 (d, 1H, J = 2.93 Hz), 7.73 (d, 1H, J = 8.02 Hz), 7.84 (d, 1H, J = 2.93 Hz), 13.25 (s, 1H) |
| 1.64 | (see Preparation P23.1) chloropyrazinyl-oxy-azetidinyl-benzimidazole carbonyl | 4-hydroxypiperidine | Cs$_2$CO$_3$, DMSO | (CDCl$_3$) 1.67-1.75 (m, 1H), 1.96-2.08 (m, 4H), 3.11-3.22 (m, 2H), 3.86-4.07 (m, 3H), 4.34 (dd, 1H, J - 11.84 Hz, 3.80 Hz), 4.74 (dd, 1H, J = 11.55 Hz, 6.43 Hz), 4.90 (dd, 1H, J = 12.13 Hz, 2.78 Hz), 5.27-5.39 (m, 1H), 5.49-5.58 (m, 1H), 7.28-7.41 (m, 2H), 7.52 (d, 1H, J = 2.92 Hz), 7.54 (d, 1H, J = 7.60 Hz), 7.78 (d, 1H, J = 2.78 Hz), 7.81 (d, 1H, J = 7.89 Hz), 11.07 (s, 1H) |

TABLE 1B-continued

PREPARATION AND NMR DATA OF EXAMPLES 1.1-1.65

| Ex. # | Starting Material (1) | Starting Material (2) | Reaction Condition | $^1$H NMR (CD$_3$OD, 400 MHz) δ (ppm) |
|---|---|---|---|---|
| 1.65 | (see Preparation P2.15) | | K$_2$CO$_3$, i-PrOH, H$_2$O, MW 160° C. | 8.35 (d, J = 9.6 Hz, 1H); 7.89 (d, J = 7.6 Hz, 1H); 7.82-7.78 (m, 3H); 7.53-7.49 (m, 2H); 6.98 (d, J = 9.6 Hz, 1H); 5.62 (s, 1H); 5.01-5.00 (m, 2H); 4.60-4.55 (m, 2H); 4.40-4.37 (m, 2H); 3.46-3.45 (m, 2H); 3.31-3.30 (m, 2H); 1.89-1.86 (m, 3H); 1.29-1.28 (m, 2H). |

*Note:
Example 1.55 can be prepared according to Scheme 1. However, pure product NMR data is not available.

SCHEME 2

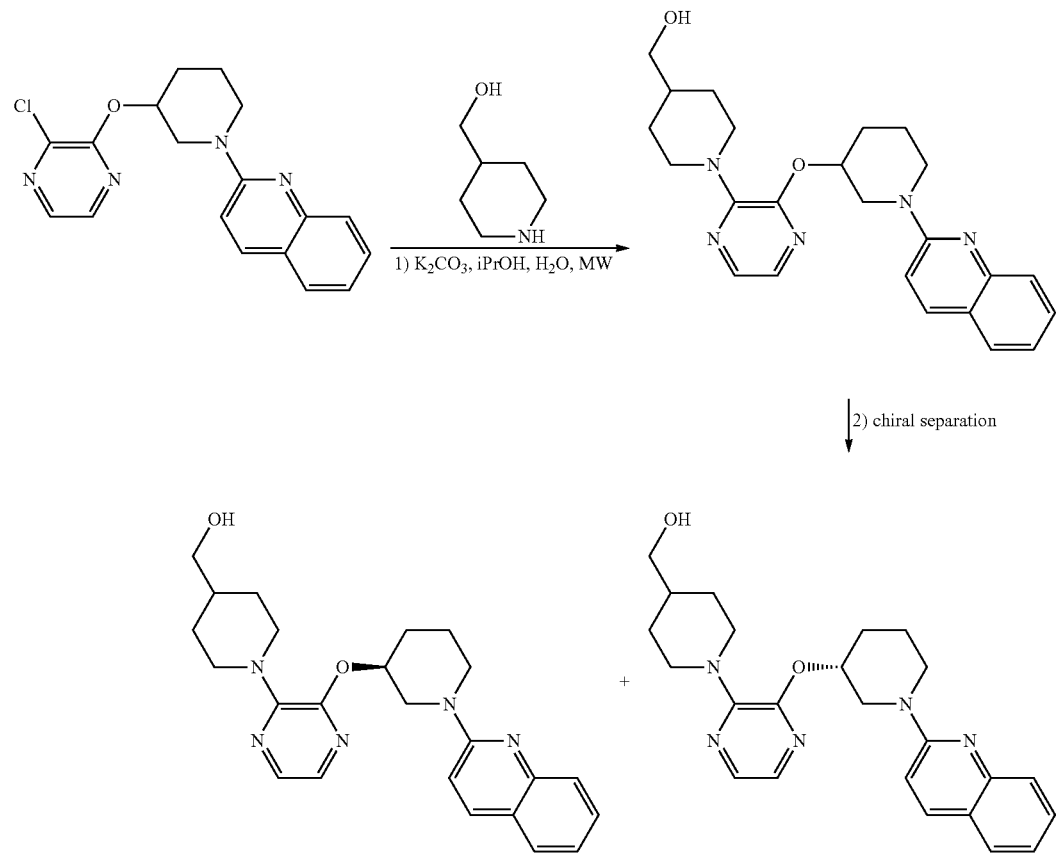

Examples 2.1 and 2.2

(S)-(1-(3-((1-(Quinolin-2-yl)Piperidin-3-yl)Oxy) Pyrazin-2-yl)Piperidin-4-yl)Methanol and (R)-(1-(3-((1-(Quinolin-2-yl)Piperidin-3-yl)Oxy)Pyrazin-2-yl) Piperidin-4-yl)Methanol as Separated Isomers Step 1: (1-(3-((1-(Quinolin-2-yl)Piperidin-3-yl)Oxy) Pyrazin-2-yl)Piperidin-4-yl)Methanol To a mixture of 2-(3-((3-chloropyrazin-2-yl)oxy)piperidin-1-yl)quinoline (racemix mixture) (see PREPARATION P2.3; 0.1 g, 0.29 mmol) and piperidin-4-ylmethanol (0.033 g, 0.29 mmol) and K$_2$CO$_3$ (0.08, 0.58 mmol) was added i-PrOH (2 mL) and water (0.5 ml). The solution was heated to 160° C. under microwave for 5 hours. Then the mixture was concentrated and extracted with EtOAc (2×20 mL). The combined organic extracts were washed with water (10 mL) and brine (10 mL), dried over Na$_2$SO$_4$, and filtered. The filtrate was evaporated in vacuo and the residue was purified by flash column chromatography on silica gel (20% to 60% EtOAc in petroleum ether) to give the title product (0.020 g, 0.04 mmol, 17% yield) as white solid. ESI-MS (M+1): 420 calc. for C$_{24}$H$_{29}$N$_5$O$_2$ 419.

Step 2. (S)-(1-(3-((1-(Quinolin-2-yl)Piperidin-3-yl)Oxy)Pyrazin-2-yl)Piperidin-4-yl)Methanol and (R)-(1-(3-((1-(Quinolin-2-yl)Piperidin-3-yl)Oxy)Pyrazin-2-yl)Piperidin-4-yl)Methanol (1-(3-((1-(quinolin-2-yl)piperidin-3-yl)oxy)pyrazin-2-yl)piperidin-4-yl)methanol (0.020 g, 0.04 mmol) was separated by chiral prep. HPLC (Column: Chiralcel OD-H 250*30 mm, 5u; Mobile phase: 85% hexane in EtOH (0.05% diethyl amine); Flow rate: 30 mL/minute) to give examples 2.1 and 2.2. as separated enantiomers, and the absolute configuration of each compound was not further determined ¹H NMR (CD₃OD, 400 MHz): δ (ppm) of the two separated isomers:

7.95 (d, J=9.2 Hz, 1H); 7.60-7.50 (m, 1H); 7.40-7.37 (m, 2H); 7.29-7.27 (m, 1H); 7.14-7.12 (m, 1H); 6.99 (d, J=9.2 Hz, 1H); 5.26-5.25 (m, 1H); 4.71-4.68 (m, 1H); 4.39-4.34 (m, 1H); 3.93-3.90 (m, 1H); 3.57-3.48 (m, 2H); 3.46-3.30 (m, 1H); 3.11 (m, 2H); 2.437-2.37 (m, 1H); 2.22-2.16 (m, 1H); 2.06-2.04 (m, 3H); 1.44-1.404 (m, 1H); 1.35-1.32 (m, 3H); 0.93-0.70 (m, 2H).

7.77 (d, J=9.2 Hz, 1H); 7.60 (d, J=2.8 Hz, 1H); 7.52 (s, 2H); 7.41-7.39 (m, 1H); 7.30-7.28 (m, 1H); 7.16-7.14 (m, 1H); 6.91 (d, J=9.2 Hz, 1H); 5.27 (s, 1H); 4.72-4.37 (m, 1H); 4.35-4.32 (m, 1H); 3.93-3.90 (m, 1H); 3.55-3.50 (m, 2H); 3.40-3.37 (m, 1H); 3.12-3.00 (m, 2H); 2.42-2.36 (m, 1H); 2.22-2.16 (m, 1H); 2.05 (s, 2H); 1.68-1.66 (m, 1H); 1.29-1.25 (m, 1H); 1.16-1.15 (m, 5H); 0.82-0.79 (m, 2H).

SCHEME 3

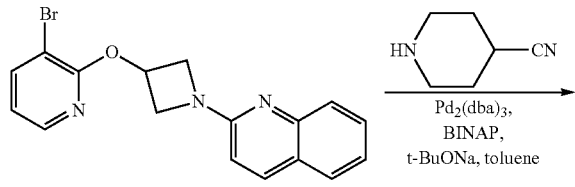

Example 3.1

1-(2-((1-(Quinolin-2-yl)Azetidin-3-yl)Oxy)Pyridin-3-yl)Piperidine-4-Carbonitrile

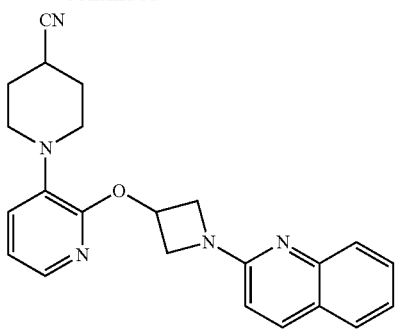

A mixture of 2-(3-((3-bromopyridin-2-yl)oxy)azetidin-1-yl)quinoline (see PREPARATION P2.9; 177 mg, 0.50 mmol), piperidine-4-carbonitrile (55 mg, 0.50 mmol), Pd₂(dba)₃ (22 mg, 0.025 mmol), 2,2'-Bis(diphenylphosphino)-1,1'-binaphthyl (BINAP) (16 mg, 0.025 mmol) and t-BuONa (106 mg, 1.0 mmol) in toluene (10 mL) was stirred at 100° C. for 10 hours. The mixture was left to reach RT and filtered through a pad of CELITE® and the filter cake was washed with CH₂Cl₂ (30 mL). The combined filtrate was evaporated in vacuo and the residue was purified by flash column chromatography (30% to 50% EtOAc in petroleum ether) and followed by purification by reverse phase HPLC (10% to 80% water/MeCN) to afford 1-(2-((1-(quinolin-2-yl)azetidin-3-yl)oxy)pyridin-3-yl)piperidine-4-carbonitrile (80 mg, 0.20 mmol, yield 40%). ESI-MS (M+1): 386 calc. for $C_{23}H_{23}N_5O$ 385.

TABLE 2A

EXAMPLES 3.1-3.9 PREPARED ANALOGOUS TO SCHEME 3

| Ex. # | Structure | Chemical Name | M + 1 | IC₅₀ (uM) |
|---|---|---|---|---|
| 3.1 | (structure) | 1-(5-fluoro-2-((1-(quinolin-2-yl)azetidin-3-yl)oxy)pyrridin-3-yl)piperidine-4-carbonitrile | 404 | 0.0151 |

TABLE 2A-continued

EXAMPLES 3.1-3.9 PREPARED ANALOGOUS TO SCHEME 3

| Ex. # | Structure | Chemical Name | M + 1 | IC$_{50}$ (uM) |
|---|---|---|---|---|
| 3.2 | 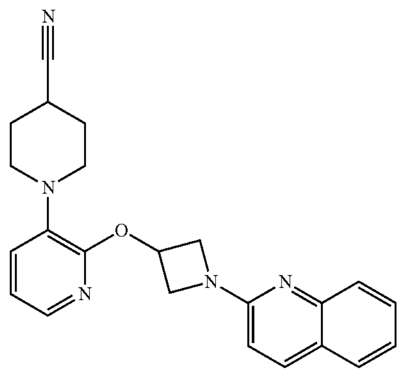 [SMILES: N#CC1CCN(c2cccnc2OC2CN(c3ccc4ccccc4n3)C2)CC1] | 1-(2-((1-(quinolin-2-yl)azetidin-3-yl)oxy)puridin-3-yl)piperidine-4-carbonitrile | 386 | 0.0689 |
| 3.3 | 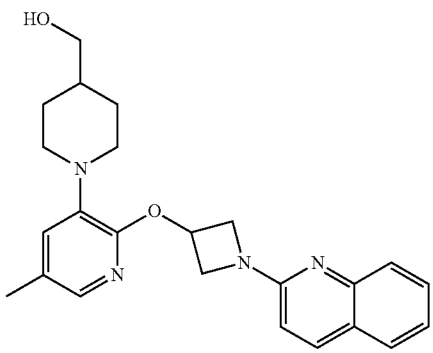 [SMILES: Cc1cnc(OC2CN(c3ccc4ccccc4n3)C2)c(N2CCC(CO)CC2)c1] | (1-(5-methyl-2-((1-(quinolin-2-yl)azetidin-3-yl)oxy)pyridin-3-yl)piperidin-4-yl)methanol | 405 | 0.00152 |
| 3.4 | 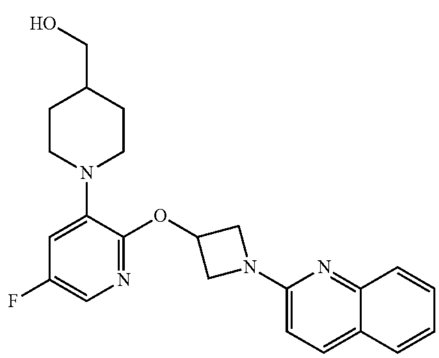 [SMILES: OCC1CCN(c2cc(F)cnc2OC2CN(c3ccc4ccccc4n3)C2)CC1] | (1-(5-fluoro-2-((1-(quinolin-2-yl)azetidin-3-yl)oxy)pyridin-3-yl)piperidin-4-yl)methanol | 409 | 0.00168 |
| 3.5 | 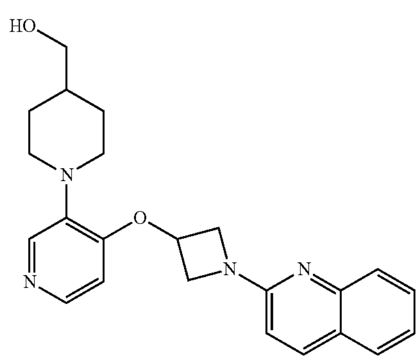 [SMILES: OCC1CCN(c2cnccc2OC2CN(c3ccc4ccccc4n3)C2)CC1] | (1-(4-((1-(quinolin-2-yl)azetidin-3-yl)oxy)pyridin-3-yl)piperidin-4-yl)methanol | 391 | 0.00708 |

TABLE 2A-continued

EXAMPLES 3.1-3.9 PREPARED ANALOGOUS TO SCHEME 3

| Ex. # | Structure | Chemical Name | M + 1 | IC$_{50}$ (uM) |
|---|---|---|---|---|
| 3.6 | 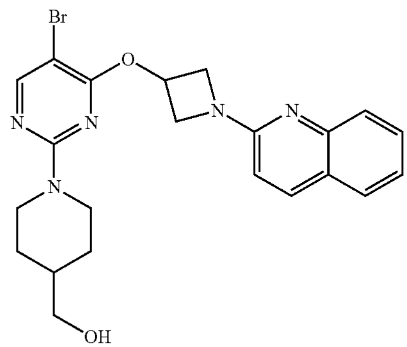 [SMILES: OCC1CCN(c2ncc(Br)c(OC3CN(c4ccc5ccccc5n4)C3)n2)CC1] | (1-(5-bromo-4-((1-(quinolin-2-yl)azetidin-3-yl)oxy)pyrimidin-2-yl)piperidin-4-yl)methanol | 471 | 0.007 |
| 3.7 | (racemic mixture) | (1-(5-bromo-4-((1-(quinolin-2-yl)azetidin-3-yl)oxy)pyrimidin-2-yl)piperidin-3-yl)methanol | 470, 472 | 0.06 |
| 3.8 | (racemic mixture) | (1-(5-bromo-4-((1-(quinolin-2-yl)azetidin-3-yl)oxy)pyrimidin-2-yl)piperidin-2-yl)methanol | 470, 472 | 0.26 |
| 3.9 | 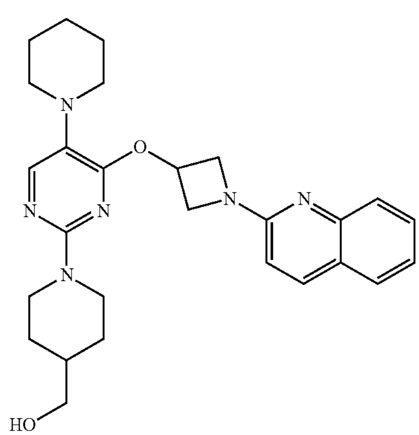 [SMILES: OCC1CCN(c2ncc(N3CCCCC3)c(OC3CN(c4ccc5ccccc5n4)C3)n2)CC1] | (1-(5-(piperidin-1-yl)-4-((1-(quinolin-2-yl)azetidin-3-yl)oxy)pyrimidin-2-yl)piperidin-4-yl)methanol | 475 | 0.0184 |

TABLE 2B

PREPARATION AND NMR DATA OF EXAMPLES 3.1-3.9

| Ex. # | Starting Materials (1) and (2) | Reaction condition | $^1$H NMR (CD$_3$OD, 400 MHz) δ (ppm) |
|---|---|---|---|
| 3.1 | 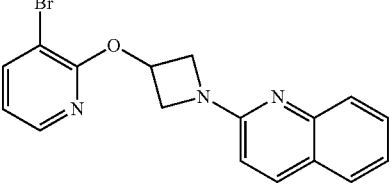<br>(see Preparation P2.9)<br>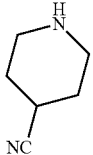 | Pd$_2$(dba)$_3$, BINAP, t-BuONa, toluene | 8.31 (d, J = 9.2 Hz, 1H); 7.87 (d, J = 7.6 Hz, 1H); 7.77 (d, J = 1.2 Hz, 1H); 7.77-7.76 (m, 1H); 7.61-7.47 (m, 2H); 7.16-7.13 (m, 1H); 6.95 (d, J = 21.6 Hz, 1H); 5.59-5.48 (m, 1H); 4.95-4.89 (m, 2H); 4.54-4.50 (m, 2H) 3.34-3.27 (m, 2H); 3.03-2.93 (m, 3H); 2.10-2.05 (m, 2H); 1.96-1.93 (m, 2H). |
| 3.2 | 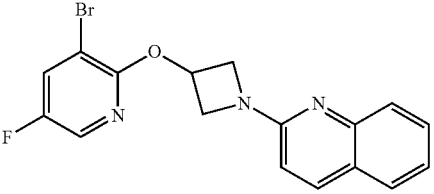<br>(see Preparation P2.10)<br> | Pd$_2$(dba)$_3$, BINAP, t-BuONa, toluene | 8.32 (d, J = 9.6 Hz, 1H); 7.87 (d, J = 7.6 Hz, 1H); 7.84-7.76 (m, 3H); 7.51-7.42 (m, 1H); 7.34-7.31 (m, 1H); 6.99-6.95 (m, 2H); 5.65-5.62 (m, 1H); 4.96-4.92 (m, 2H); 4.56-4.52 (m, 2H) 3.33-3.30 (m, 2H); 3.02-2.94 (m, 3H); 2.11-2.07 (m, 2H); 1.99-1.94 (m, 2H). |
| 3.3 | 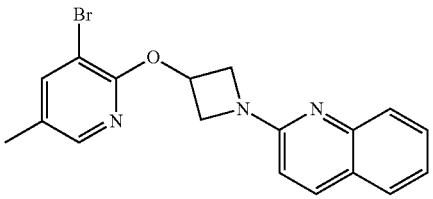 [SMILES: Cc1cnc(OC2CN(c3ccc4ccccc4n3)C2)c(Br)c1]<br>(see Preparation P2.7)<br>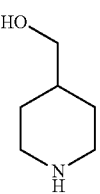 | Pd$_2$(dba)$_3$, t-Butylxphos K$_3$PO$_4$, toluene | 8.30 (s, 1H); 7.71-7.67 (m, 2H); 7.60-7.55 (m, 2H); 7.30-7.26 (m, 1H); 7.12 (d, J = 2.8 Hz, 1H); 6.77 (d, J = 9.2 Hz, 1H); 5.55-5.54 (m, 1H); 4.71-4.60 (m, 2H); 4.26-4.22 (m, 2H); 3.44-3.43 (m, 2H); 3.31-3.29 (m, 2H); 2.59-2.58 (m, 2H); 2.20 (s, 3H); 1.84-1.80 (m, 2H); 1.61-1.30 (m, 3H). |

TABLE 2B-continued

PREPARATION AND NMR DATA OF EXAMPLES 3.1-3.9

| Ex. # | Starting Materials (1) and (2) | Reaction condition | $^1$H NMR (CD$_3$OD, 400 MHz) δ (ppm) |
|---|---|---|---|
| 3.4 | 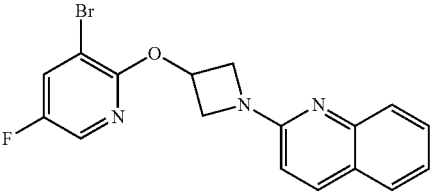 [SMILES: Fc1cnc(OC2CN(c3ccc4ccccc4n3)C2)c(Br)c1]<br>(see Preparation P2.10)<br>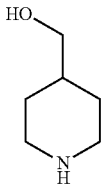 | Pd$_2$(dba)$_3$, t-Butylxphos K$_3$PO$_4$, toluene | 8.01-7.99 (m, 1H); 7.68-7.47 (m, 4H); 7.21-7.12 (m, 2H); 6.75 (d, J = 9.2 Hz, 1H); 5.43-5.40 (m, 1H); 4.52-4.45 (m, 3H); 4.03-4.00 (m, 2H); 3.25-3.23 (m, 2H); 3.50-3.11 (m, 3H); 2.51 (s, 2H); 1.70-1.67 (m, 2H); 1.29-1.19 (m, 1H). |
| 3.5 | 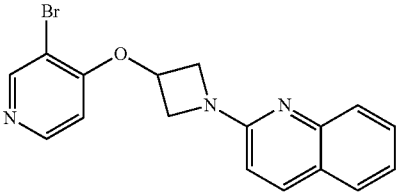 [SMILES: Brc1cnccc1OC1CN(c2ccc3ccccc3n2)C1]<br>(see Preparation P3.1)<br>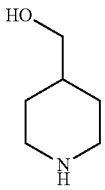 | Pd$_2$(dba)$_3$, BINAP, NaOtBu, toluene | 8.16-8.14 (m, 2H); 7.89 (d, J = 8.8 Hz, 1H); 7.73 (d, J = 8.2 Hz, 1H); 7.61-7.59 (m, 2H); 7.25-7.23 (m, 1H); 6.59 (d, J = 9.2 Hz, 1H); 6.46 (d, J = 4.2 Hz, 1H); 5.14-5.12 (m, 1H); 4.62-4.58 (m, 2H); 4.26-4.23 (m, 2H) 3.52-3.50 (m, 4H); 2.83-2.62 (m, 3H); 1.83-1.80 (m, 2H); 1.63-1.62 (m, 1H); 1.48-1.41 (m, 2H). |
| 3.6 | 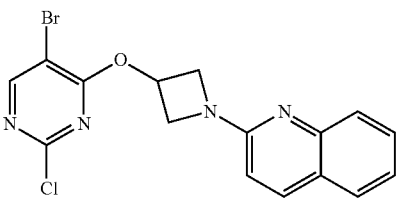 [SMILES: Clc1ncc(Br)c(OC2CN(c3ccc4ccccc4n3)C2)n1]<br>(see Preparation P2.11)<br>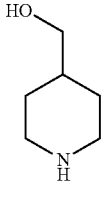 | Pd$_2$(dba)$_3$, BINAP, NaOtBu, dioxane | (CDCl$_3$) 8.07(s, 1H), 7.81 (d, J = 8.8 Hz, 1H), 7.67 (d, J = 8.4 Hz, 1H), 7.54 (d, J = 8.0 Hz, 1H), 7.50-7.45 (m, 1H), 7.19-7.14 (m, 1H), 6.53 (d, J = 8.8 Hz, 1H), 5.49-5.43 (m, 1H), 4.61-4.51 (m, 4H), 4.23-4.19 (m, 2H), 3.46-3.39 (m, 2H), 2.83-2.76 (m, 2H), 1.76-1.68 (m, 3H), 1.20-1.10 (m, 2H). |

TABLE 2B-continued

PREPARATION AND NMR DATA OF EXAMPLES 3.1-3.9

| Ex. # | Starting Materials (1) and (2) | Reaction condition | $^1$H NMR (CD$_3$OD, 400 MHz) δ (ppm) |
|---|---|---|---|
| 3.7 | 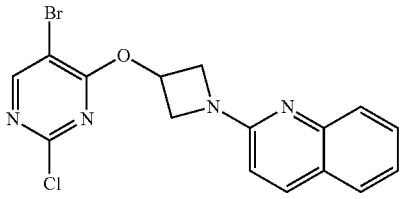 [SMILES: Clc1ncc(Br)c(OC2CN(c3ccc4ccccc4n3)C2)n1] (see Preparation P2.11) <br><br> (racemic mixture) | Pd$_2$(dba)$_3$, BINAP, NaOtBu, dioxane | 8.35 (d, J = 9.2 Hz, 1H); 8.21-8.19 (m, 1H); 7.99 (d, J = 8.0 Hz, 1H); 7.80-7.55 (m, 2H); 7.54-7.50 (m, 1H); 6.98 (d, J = 9.2 Hz, 1H); 5.67-5.646 (m, 1H); 5.01-4.94 (m, 2H); 4.64-4.58 (m, 4H); 3.56-3.52 (m, 1H); 3.46-3.41 (m, 1H); 3.30-3.03 (m, 2H); 1.86-1.74 (m, 3H); 1.54-1.32 (m, 2H). |
| 3.8 |  (see Preparation P2.11) <br><br> (racemic mixture) | Pd$_2$(dba)$_3$, BINAP, NaOtBu, dioxane | 8.14 (s, 1H); 8.04 (d, J = 8.8 Hz, 1H); 7.70-7.68 (m, 2H); 7.66-7.55 (m, 1H); 7.29-7.25 (m, 1H); 6.77 (d, J = 8.8 Hz, 1H); 5.59-5.56 (m, 1H); 4.71-4.65 (m, 2H); 4.29-4.25 (m, 1H); 3.77-3.66 (m, 2H); 3.29-3.27 (m, 2H); 2.97-2.99 (m, 1H); 2.95-2.94 (m, 1H); 1.91-1.97 (m, 1H); 1.71-1.64 (m, 5H). |
| 3.9 | 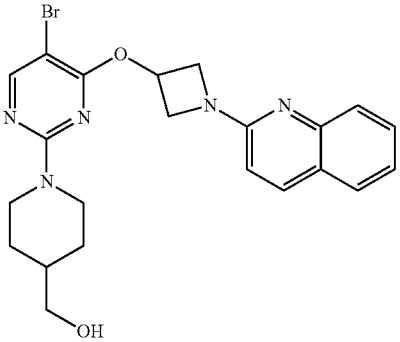 (see Preparation P6.1) | Pd2(dba)3, BINAP, t-BuONa, toluene | 8.39 (d, J = 9.6 Hz, 1H); 7.93-7.90 (m, 2H); 7.82-7.80 (m, 2H); 7.56-7.52 (m, 1H); 7.01 (d, J = 9.2 Hz, 1H); 5.79 (s, 1H); 5.01-4.99 (m, 2H); 4.71-4.67 (m, 4H); 3.47-3.46 (m, 1H); 3.35-3.25 (m, 4H); 3.16-3.11 (m, 2H); 1.93-1.83 (m, 8H); 1.67-1.66 (m, 2H); 1.29 (s, 2H). |

SCHEME 4

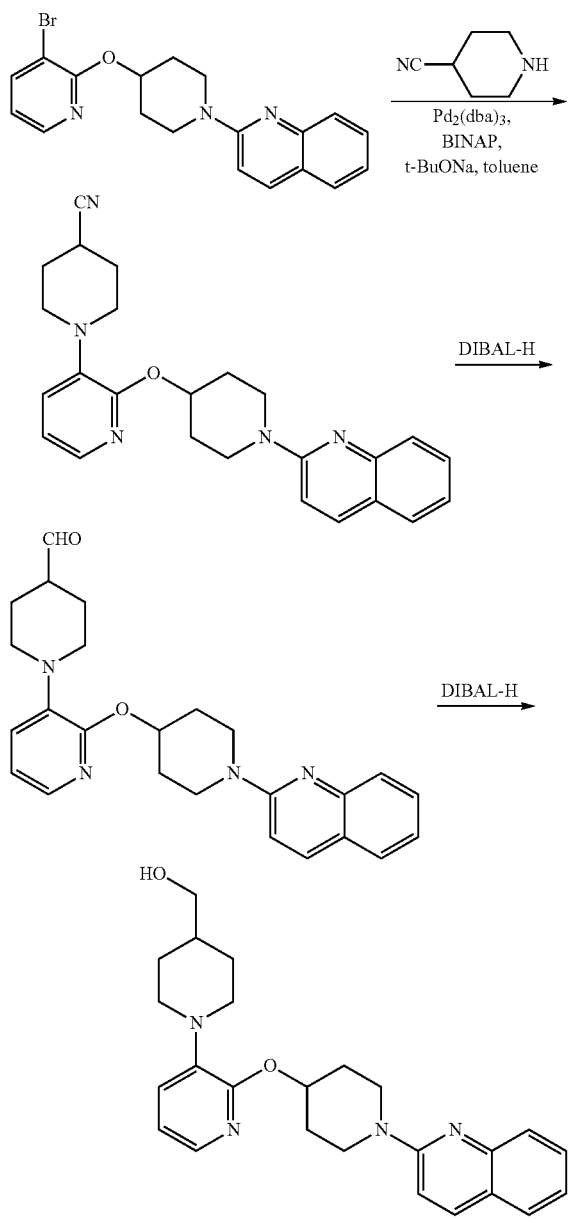

Example 4.1

(1-(2-((1-(Quinolin-2-yl)Piperidin-4-yl)Oxy)Pyridin-3-yl)Piperidin-4-yl)Methanol Step 1: 1-(2-((1-(Quinolin-2-yl)Piperidin-4-yl)Oxy)Pyridin-3-yl)Piperidine-4-Carbonitrile To a solution of 2-(4-((3-bromopyridin-2-yl)oxy)piperidin-1-yl)quinoline (see PREPARATION P2.2; 383 mg, 1.0 mmol) in toluene (10 mL) were added piperidine-4-carbonitrile (110 mg, 1.0 mmol), $Pd_2(dba)_3$ (92 mg, 0.1 mmol), 2,2'-bis(diphenylphosphino)-1,1'-binaphthyl (BINAP) (62 mg, 0.1 mmol) and sodium tert-butoxide (t-BuONa) (180 mg, 2.0 mmol). The mixture was stirred and heated at reflux overnight under $N_2$ atmosphere. Then the reaction mixture was filtered, diluted with water (50 mL), and extracted with EtOAc (3×20 mL). The combined organic extracts were washed with water (60 mL) and brine (60 mL), dried over $Na_2SO_4$, and filtered. The filtrate was evaporated in vacuo and the residue was purified by flash column chromatography on silica gel (20% to 50% EtOAc in hexanes) to give the title product (290 mg, 0.7 mmol, 70% yield) as white solid. ESI-MS (M+1): 414 calc. for $C_{25}H_{27}BrN_5O$ 413.

Step 2: 1-(2-((1-(Quinolin-2-yl)Piperidin-4-yl)Oxy)Pyridin-3-yl)Piperidine-4-Carbaldehyde To a solution of 1-(2-((1-(quinolin-2-yl)piperidin-4-yl)oxy)pyridin-3-yl)piperidine-4-carbonitrile (290 mg, 0.70 mol) in 20 mL of THF was added DIBAL-H (1.4 mol, 1 M in toluene) dropwise at −65° C. The mixture was stirred for 1 hour at RT and then quenched with saturated aqueous $NH_4Cl$. The resulting mixture was extracted with EtOAc (2×20 mL) and the combined organic layers were dried over anhydrous $Na_2SO_4$, filtered and concentrated to give the product (0.232 g, 0.56 mmol, 80% yield). ESI-MS (M+1): 417 calc. for $C_{25}H_{28}N_4O_2$ 416.

Step 3: (1-(2-((1-(Quinolin-2-yl)Piperidin-4-yl)Oxy)Pyridin-3-yl)Piperidin-4-yl)Methanol To a solution of 1-(2-((1-(quinolin-2-yl)piperidin-4-yl)oxy)pyridin-3-yl)piperidine-4-carbaldehyde (232 mg, 0.56 mol) in 20 mL of THF was added DIBAL-H (1.4 mol, 1 M in toluene) dropwise at RT. The mixture was stirred for 1 hour at RT and then quenched with saturated aqueous $NH_4Cl$. The resulting mixture was extracted with EtOAc (2×20 mL) and the combined organic layers were dried over anhydrous $Na_2SO_4$, filtered and concentrated to give the product (0.150 g, 0.36 mmol, 60% yield). ESI-MS (M+1): 419 calc. for $C_{25}H_{30}N_4O_2$ 418. $^1$H NMR ($CD_3OD$, 400 MHz) δ (ppm): 7.96 (d, J=9.2 Hz, 1H); 7.72-7.70 (m, 1H); 7.64-7.60 (m, 2H); 7.52-7.48 (m, 1H); 7.23-7.16 (m, 3H); 6.87-6.84 (m, 1H); 5.38 (s, 1H); 4.81-4.79 (m, 2H); 4.01-3.98 (m, 2H); 3.79-3.74 (m, 2H); 3.40-3.39 (m, 2H); 2.58-2.51 (m, 2H); 2.11-2.08 (m, 2H); 1.93-1.77 (m, 4H); 1.40-1.36 (m, 3H). PDE10 $IC_{50}$ (uM): 0.01.

SCHEME 5

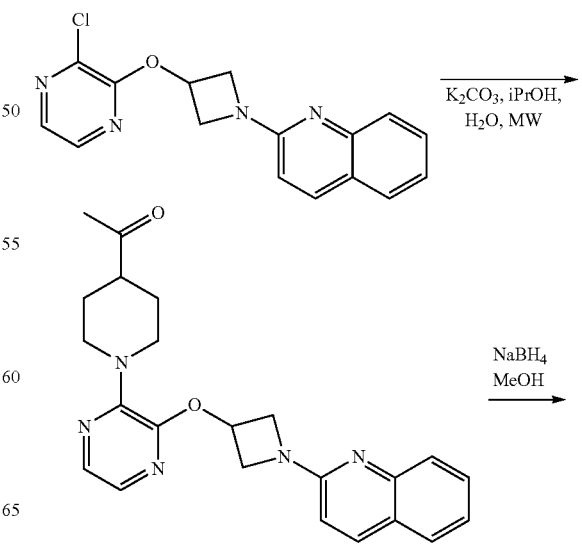

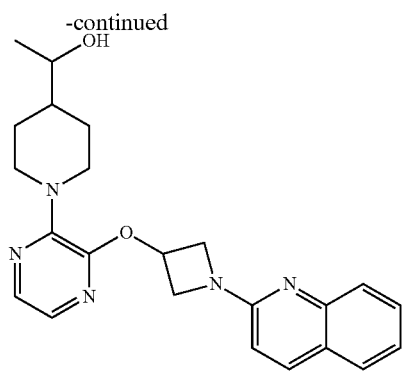

Example 5.1

(Racemic Mixture) 1-(1-(3-((1-(Quinolin-2-yl)Azetidin-3-yl)Oxy)Pyrazin-2-yl)Piperidin-4-yl)Ethanol Step 1. 1-(1-(3-((1-(Quinolin-2-yl)Azetidin-3-yl)Oxy)Pyrazin-2-yl)Piperidin-4-yl)Ethanone To a mixture of 2-(3-((3-chloropyrazin-2-yl)oxy)azetidin-1-yl)quinoline (see PREPARATION P2.6; 312 mg, 1.0 mmol) and 1-(piperidin-4-yl)ethanone (127 mg, 1.0 mmol) and $K_2CO_3$ (276 mg, 2.0 mmol) was added i-PrOH (3 mL) and water (1.0 ml). The solution was heated to 160° C. under microwave for 5 hours. Then the mixture was concentrated and extracted with EtOAc (2×30 mL). The combined organic extracts were washed with water (10 mL) and brine (10 mL), dried over $Na_2SO_4$, and filtered. The filtrate was evaporated in vacuo and the residue was purified by flash column chromatography on silica gel (20% to 60% EtOAc in petroleum ether) to give the title product (72 mg, 0.18 mmol, 18% yield) as white solid. ESI-MS (M+1): 404 calc. for $C_{23}H_{25}N_5O_2$ 403.

Step 2: (Racemic Mixture) 1-(1-(3-((1-(Quinolin-2-yl)Azetidin-3-yl)Oxy)Pyrazin-2-yl)Piperidin-4-yl)Ethanol 1-(1-(3-((1-(quinolin-2-yl)azetidin-3-yl)oxy)pyrazin-2-yl)piperidin-4-yl)ethanone (100 mg, 0.25 mmol) was dissolved in 10 ml of methanol. This solution was cooled down to 0° C. using an ice bath and sodium tetraborohydride (19 mg, 0.50 mmol) was added in portions. The reaction mixture was stirred for 4 hours at ambient temperature, and then saturated aqueous solution of ammonium chloride (5 mL) was added. The methanol was evaporated off under reduced pressure then the reaction mixture was taken up in ethyl acetate. The organic layer was separated from the aqueous layer. This extraction was repeated one more time and then the organic layers were combined and dried over magnesium sulphate, followed by concentrating under reduced pressure. The residue was purified by column chromatography on silica gel to give (racemic mixture) 1-(1-(3-((1-(quinolin-2-yl)azetidin-3-yl)oxy)pyrazin-2-yl)piperidin-4-yl)ethanol (75 mg, 0.19 mmol, 75% yield). ESI-MS (M+1): 406 calc. for $C_{23}H_{27}N_5O_2$ 405.

TABLE 3A

EXAMPLES 5.1-5.2 PREPARED ANALOGOUS TO SCHEME 5

| Ex. # | Structure | Chemical Name | M + 1 | IC$_{50}$ (uM) |
|---|---|---|---|---|
| 5.1 | (as racemic mixture) | 1-(1-(3-((1-quinolin-2-yl)azetidin-3-yl)oxy)pyrazin-2-yl)piperidin-4-yl)ethanol | 406 | 0.0469 |
| 5.2 | (as racemic mixture) | 1-(1-(5-bromo-4-((1-(quinolin-2-yl)azetidin-3-yl)oxy)pyrimidin-2-yl)piperidin-4-yl)ethanol | 484, 486 | 0.242 |

TABLE 3B

PREPARATION AND NMR DATA OF EXAMPLES 5.1-5.2

| Ex. # | Starting material (1) | Reaction condition | $^1$H NMR (CDCl$_3$, 400 MHz) δ (ppm) |
|---|---|---|---|
| 5.1 | | NaBH$_4$, MeOH | 8.35 (d, J = 9.2 Hz, 1H); 7.90 (d, J = 7.6 Hz, 1H); 7.82-7.13 (m, 4H); 6.94 (d, J = 5.6 Hz, 1H); 5.68-5.63 (m, 1H); 4.61-4.57 (m, 2H); 4.64-4.60 (m, 2H); 4.20-4.15 (m, 2H); 3.54-3.51 (m, 1H); 2.94-2.6 (m, 2H); 1.98-1.95 (m, 1H); 1.93-1.76 (m, 1H); 1.76-1.73 (m, 4H); 1.17-1.16 (d, 3H). |
| 5.2 | | NaBH$_4$, MeOH | 8.09 (s, 1H); 7.90 (d, J = 9.2 Hz, 1H); 7.64-7.59 (m, 2H); 7.52-7.50 (m, 1H); 7.20-7.19 (m, 1H); 6.61(d, J = 9.2 Hz, 1H); 5.45 (s, 1H); 4.67-4.63 (m, 2H); 4.55-4.51 (m, 2H); 4.16-4.12 (m, 2H); 3.50-47 (m, 1H); 3.32-3.27 (m, 2H); 1.98-1.88 (m, 1H); 1.68-1.65 (m, 1H); 1.52-1.51 (m, 1H); 1.50-1.48 (m, 2H); 1.15-1.13 (m, 3H). |

SCHEME 6

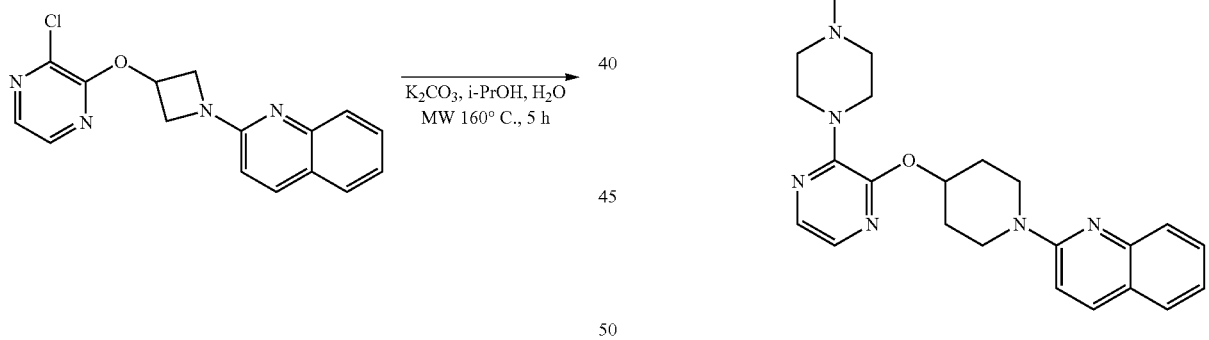

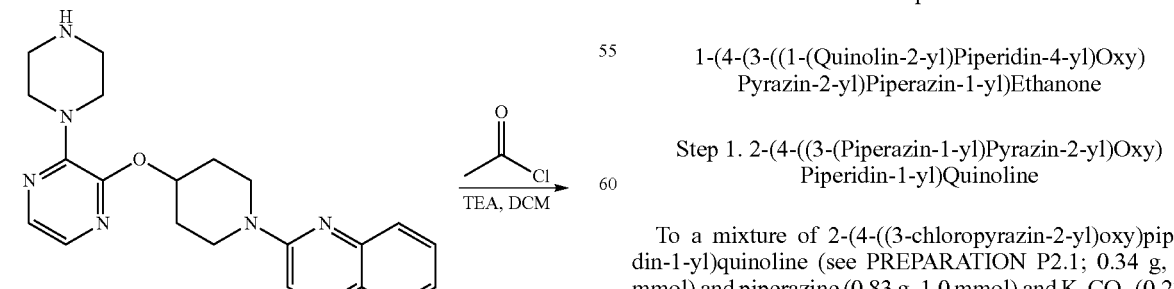

Example 6.1

1-(4-(3-((1-(Quinolin-2-yl)Piperidin-4-yl)Oxy)Pyrazin-2-yl)Piperazin-1-yl)Ethanone Step 1. 2-(4-((3-(Piperazin-1-yl)Pyrazin-2-yl)Oxy)Piperidin-1-yl)Quinoline To a mixture of 2-(4-((3-chloropyrazin-2-yl)oxy)piperidin-1-yl)quinoline (see PREPARATION P2.1; 0.34 g, 1.0 mmol) and piperazine (0.83 g, 1.0 mmol) and K$_2$CO$_3$ (0.27 g, 2.0 mmol) was added i-PrOH (2 mL) and water (0.5 ml). The solution was heated to 160° C. under microwave for 5 hours. Then the mixture was concentrated and extracted with EtOAc (2×20 mL). The combined organic extracts were washed with water (10 mL) and brine (10 mL), dried over $Na_2SO_4$, and filtered. The filtrate was evaporated in vacuo and the residue was purified by flash column chromatography on silica gel (20% to 60% EtOAc in petroleum ether) to give the title product (0.11 g, 0.30 mmol, 30% yield) as white solid. ESI-MS (M+1): 391 calc. for $C_{22}H_{26}N_6O$ 390.

Step 2. 1-(4-(3-((1-(Quinolin-2-yl)Piperidin-4-yl)Oxy)Pyrazin-2-yl)Piperazin-1-yl)Ethanone To a solution of 2-(4-((3-(piperazin-1-yl)pyrazin-2-yl)oxy)piperidin-1-yl)quinoline (130 mg, 0.33 mmol) in dry DCM (10 mL) was added $Et_3N$ (1 mL). The reaction mixture was cooled to 0° C. with an ice bath, and acetyl chloride (80 mg, 0.66 mmol) was added dropped to the reaction mixture. 1 hour later, the reaction mixture was warmed to RT, and stirred overnight. Then the reaction mixture was washed with brine, dried over $Na_2SO_4$, filtered, and concentrated under vacuum to give the crude product. The crude product was purified via flash chromatography on silica gel (20% to 45% EtOAc in petroleum ether) to give 1-(4-(3-((1-(quinolin-2-yl)piperidin-4-yl)oxy)pyrazin-2-yl)piperazin-1-yl)ethanone (108 mg, 0.25 mmol, 78% yield) as a white solid. ESI-MS (M+1): 433 calc. for $C_{24}H_{28}N_6O_2$ 432.

TABLE 4A

EXAMPLES 6.1-6.4 PREPARED ANALOGOUS TO SCHEME 6

| Ex. # | Structure | Chemical Name | M + 1 | $IC_{50}$ (uM) |
|---|---|---|---|---|
| 6.1 | 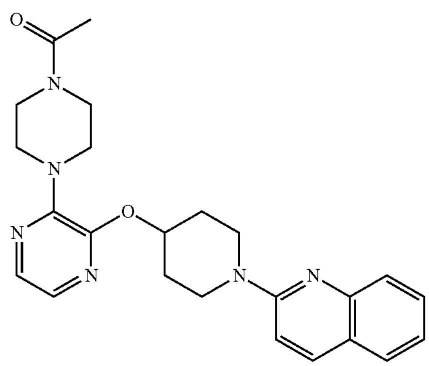 [SMILES: CC(=O)N1CCN(c2nccnc2OC2CCN(c3ccc4ccccc4n3)CC2)CC1] | 1-(4-(3-((1-(quinolin-2-yl)piperidin-4-yl)oxy)pyrazin-2-yl)piperazin-1-yl)ethanone | 433 | 0.0306 |
| 6.2 | 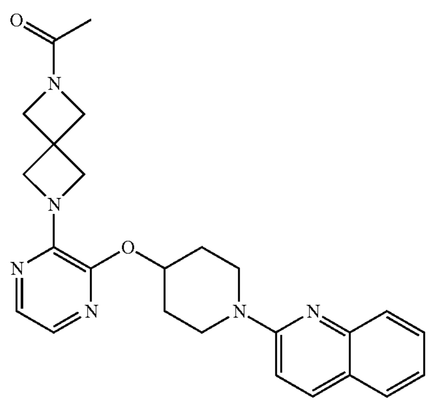 [SMILES: CC(=O)N1CC2(C1)CN(c1nccnc1OC1CCN(c3ccc4ccccc4n3)CC1)C2] | 1-(6-(3-((1-(quinolin-2-yl)piperidin-4-yl)oxy)pyrazin-2-yl)-2,6-diazaspiro[3.3]heptan-2-yl)ethanone | 445 | 1.27 |
| 6.3 | 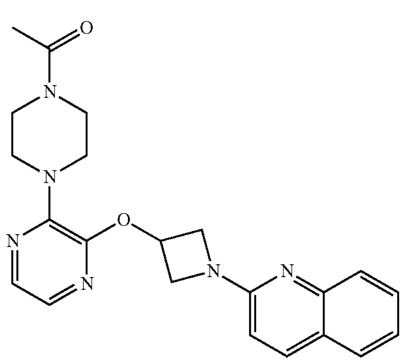 [SMILES: CC(=O)N1CCN(c2nccnc2OC2CN(c3ccc4ccccc4n3)C2)CC1] | (1-(4-(3-((1-(quinolin-2-yl)azetidin-3-yl)oxy)pyrazin-2-yl)piperazin-1-yl)ethanone | 405 | 0.0775 |

TABLE 4A-continued

EXAMPLES 6.1-6.4 PREPARED ANALOGOUS TO SCHEME 6

| Ex. # | Structure | Chemical Name | M + 1 | IC$_{50}$ (uM) |
|---|---|---|---|---|
| 6.4 | 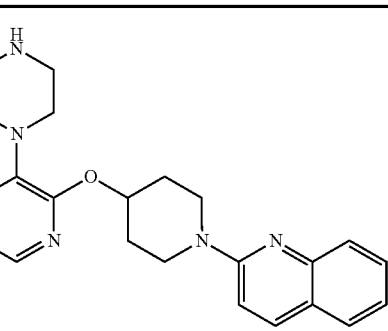 | 1-(4-(3-((1-(quinolin-2-yl)azetidin-3-yl)oxy)pyrazin-2-yl)-1,4-diazepan-1-yl)ethanone | 419 | 0.0903 |

TABLE 4B

PREPARATION AND NMR DATA OF EXAMPLES 6.1-6.4

| Ex. # | Starting Material (1) | Starting Material (2) | Reaction Condition | $^1$H NMR (CD$_3$OD, 400 MHz) δ (ppm) |
|---|---|---|---|---|
| 6.1 | <br>Prepared from compound of preparation P2.1 and piperazine according to Scheme 3 | 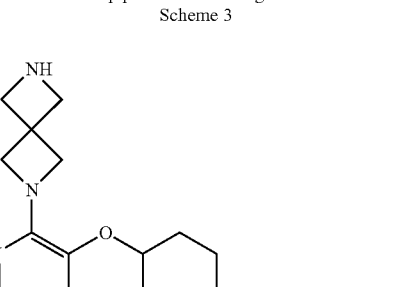 | Et$_3$N, DCM | 7.95-7.88 (m, 1H); 7.70-7.57 (m, 4H); 7.50-7.46 (m, 1H); 7.21-7.12 (m, 2H); 5.41-5.39 (m, 1H); 4.05-3.99 (m, 2H); 3.71-3.63 (m, 4H); 3.59-3.57 (m, 2H); 3.51-3.43 (m, 4H); 2.14-2.10 (m, 2H); 2.14 (s, 3H); 1.92-1.84 (m, 2H). |
| 6.2 | <br>Prepared from compound of preparation P2.1 and 2,6-diazaspiro[3.3]heptane according to Scheme 3 | 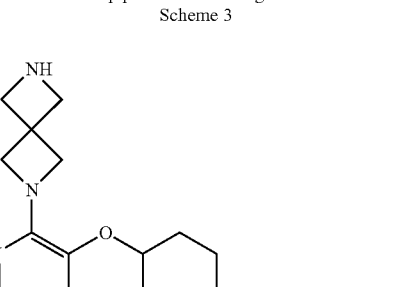 | Et$_3$N, DCM | 7.88 (d, J = 9.2 Hz, 1H); 7.71 (d, J = 8.0 Hz, 1H); 7.59-7.53 (m, 2H); 7.52-7.49 (m, 1H); 7.37-7.36 (m, 1H); 7.24-7.19 (m, 1H); 7.01 (d, J = 9.2 Hz, 1H); 5.35-5.31 (m, 1H); 4.29-4.23 (m, 6H); 4.09-4.02 (m, 4H); 3.71-3.65 (m, 2H); 2.129-2.09 (m, 2H); 1.92-1.89 (m, 2H); 1.82 (s, 3H). |

TABLE 4B-continued

PREPARATION AND NMR DATA OF EXAMPLES 6.1-6.4

| Ex. # | Starting Material (1) | Starting Material (2) | Reaction Condition | $^1$H NMR (CD$_3$OD, 400 MHz) δ (ppm) |
|---|---|---|---|---|
| 6.3 | (Prepared from compound of preparation P2.6 and piperazine according to Scheme 3) | acetyl chloride | TEA, DCM | 7.97 (d, J = 8.8 Hz, 1H); 7.70 (d, J = 7.6 Hz, 1H); 7.67-7.63 (m, 2H); 7.59 (d, J = 3.2 Hz, 1H); 7.55-7.51 (m, 1H); 7.24-7.20 (m, 1H); 6.70 (d, J = 8.8 Hz, 1H); 5.59-5.56 (m, 1H); 4.64-4.60 (m, 2H); 4.22-4.13 (m, 2H); 3.69-3.50 (m, 8H); 2.10 (s, 3H). |
| 6.4 | (Prepared from compound of preparation P2.6 and 1,4-diazepane according to Scheme 3) | acetyl chloride | TEA, DCM | 8.31 (d, J = 9.6 Hz, 1H); 7.87 (d, J = 8.0 Hz, 1H); 7.76-7.78 (m, 3H); 7.51-7.49 (m, 1H); 7.43-7.42 (m, 1H); 6.95 (d, J = 9.6 Hz, 1H); 5.63 (s, 1H); 4.94-4.93 (m, 2H); 4.61-4.58 (m, 2H); 3.95-3.84 (m, 4H); 3.79-3.76 (m, 2H); 3.60-3.53 (m, 2H); 2.06-1.95 (m, 5H). |

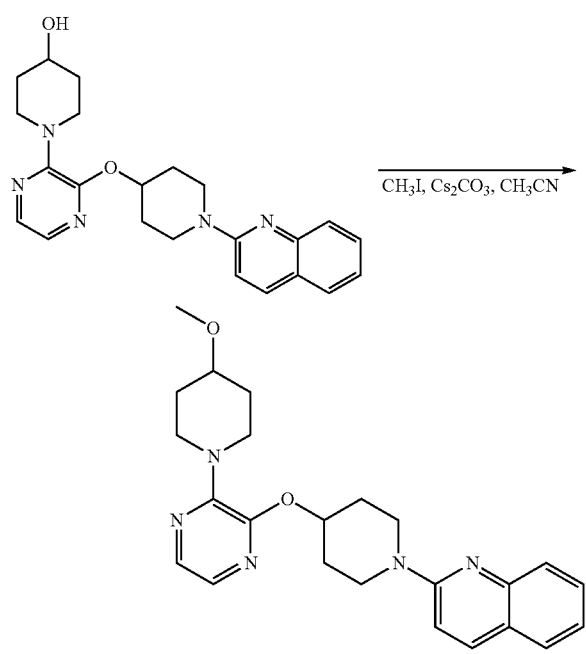

SCHEME 7

Example 7.1

2-(4-((3-(4-Methoxypiperidin-1-yl)Pyrazin-2-yl)Oxy)Piperidin-1-yl)Quinoline

To a solution of 1-(3-((1-(quinolin-2-yl)piperidin-4-yl)oxy)pyrazin-2-yl)piperidin-4-ol (see EXAMPLE 1.1; 100 mg, 0.25 mmol) in dry acetonitrile (CH$_3$CN) (10 mL) was added Cs$_2$CO$_3$ (162 mg, 0.5 mmol). The reaction mixture was cooled to 0° C. with an ice bath, and iodomethane (70 mg, 0.50 mmol) was added dropwise to the reaction mixture. 1 hour later, the reaction mixture was warmed to RT, and stirred overnight. Then the reaction mixture was washed with brine, dried over Na$_2$SO$_4$, filtered, and concentrated under vacuum to give the crude product. The crude product was purified via flash chromatography on silica gel (20% to 45% EtOAc in petroleum ether) to give 2-(4-((3-(4-methoxypiperidin-1-yl)pyrazin-2-yl)oxy)piperidin-1-yl)quinoline (81 mg, 0.19 mmol, 78% yield) as a white solid. ESI-MS (M+1): 420 calc. for C$_{24}$H$_{29}$N$_5$O$_2$ 419.

TABLE 5A

EXAMPLES 7.1-7.2 PREPARED ANALOGOUS TO SCHEME 7

| Ex. # | Structure | Chemical Name | M + 1 | IC$_{50}$ (uM) |
|---|---|---|---|---|
| 7.1 | 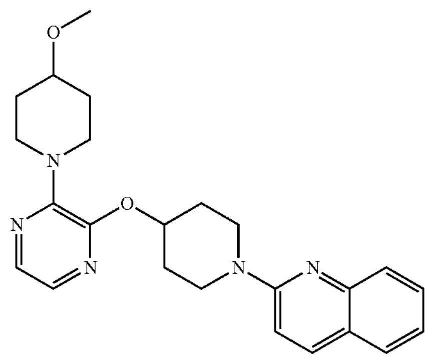 [SMILES: COC1CCN(c2nccnc2OC2CCN(c3ccc4ccccc4n3)CC2)CC1] | 2-(4-((3-(4-methoxypiperidin-1-yl)pyrazin-2-yl)oxy)piperidin-1-yl)quinoline | 420 | 0.0596 |
| 7.2 | 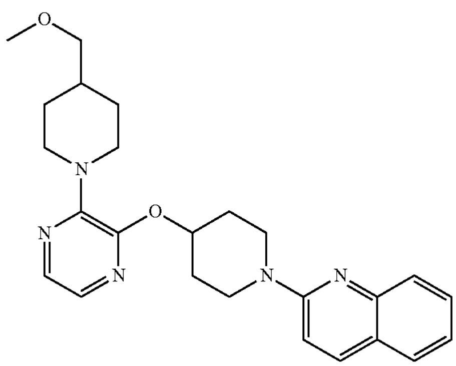 [SMILES: COCC1CCN(c2nccnc2OC2CCN(c3ccc4ccccc4n3)CC2)CC1] | 2-(4-((3-(4-(methoxymethyl)piperidin-1-yl)pyrazin-2-yl)oxy)piperidin-1-yl)quinoline | 434 | 1.12 |

TABLE 5B

PREPARATION AND NMR DATA OF EXAMPLES 7.1-7.2

| Ex. # | Starting Material (1) | Starting Material (2) | Reaction Condition | $^1$H NMR (CD$_3$OD, 400 MHz) δ (ppm) |
|---|---|---|---|---|
| 7.1 | (see Example 1.1) | CH$_3$I | Cs$_2$CO$_3$, CH$_3$CN | 7.95 (d, J = 9.2 Hz, 1H); 7.65-7.51 (m, 5H); 7.22-7.15 (m, 2H); 5.42-5.39 (m, 1H); 4.41-4.01 (m, 1H); 3.99-3.41 (m, 6H); 3.15 (s, 3H); 3.12-3.08 (m, 2H); 2.15-2.10 (m, 2H); 1.99-1.87 (m, 4H); 1.60-1.56 (m, 2H). |

TABLE 5B-continued

PREPARATION AND NMR DATA OF EXAMPLES 7.1-7.2

| Ex. # | Starting Material (1) | Starting Material (2) | Reaction Condition | $^1$H NMR (CD$_3$OD, 400 MHz) δ (ppm) |
|---|---|---|---|---|
| 7.2 | (see Example 1.9) | CH$_3$I | Cs$_2$CO$_3$, CH$_3$CN | 7.95 (d, J = 9.2 Hz, 1H); 7.63-7.60 (m, 3H); 7.50-7.49 (m, 2H); 7.19-7.15 (m, 2H); 5.46-5.38 (m, 1H); 4.17-4.14 (m, 2H); 3.99-3.94 (m, 2H); 3.78-3.72 (m, 2H); 3.32-3.20 (m, 7H); 2.79-2.72 (m, 2H); 2.13-2.09 (m, 2H); 1.77-1.72 (m, 3H); 1.33-1.30 (m, 2H). |

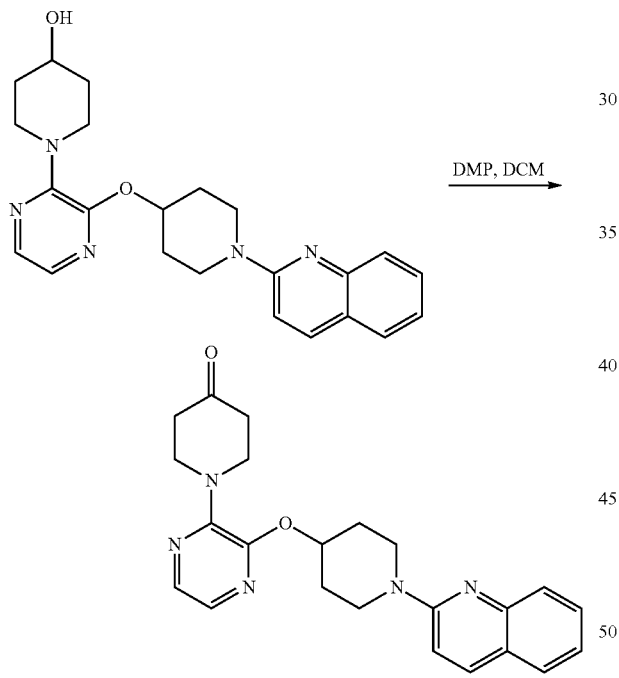

SCHEME 8

Example 8.1
1-(3-((1-(Quinolin-2-yl)Piperidin-4-yl)Oxy)Pyrazin-2-yl)Piperidin-4-One 1-(3-((1-(quinolin-2-yl)piperidin-4-yl)oxy)pyrazin-2-yl)piperidin-4-ol (see Example 1.1; 0.10 g, 0.25 mmol) was dissolved in anhydrous CH$_2$Cl$_2$ (10 mL), treated with Dess-Martin periodinane (DMP) (200 mg, 0.50 mmol, 2.0 equiv) and stirred at RT until complete conversion. The organic layer was washed with an aqueous solution of NaHCO$_3$/Na$_2$S$_2$O$_3$ (3×10 mL)), dried over Na$_2$SO$_4$, filtered and evaporated. The resulting residue was purified by flash chromatography on silica gel (20% to 40% EtOAc in petroleum ether) to give 1-(3-((1-(quinolin-2-yl)piperidin-4-yl)oxy)pyrazin-2-yl)piperidin-4-one (0.084 g, 0.20 mmol, 83% yield) as a white solid. ESI-MS (M+1): 404 calc. for C$_{23}$H$_{25}$N$_5$O$_2$ 403.

TABLE 6A

EXAMPLES 8.1-8.2 PREPARED ANALOGOUS TO SCHEME 8

| Ex. # | Structure | Chemical Name | M + 1 | IC$_{50}$ (uM) |
|---|---|---|---|---|
| 8.1 | 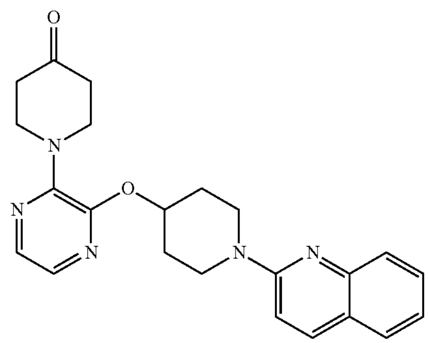 [SMILES: O=C1CCN(c2nccnc2OC2CCN(c3ccc4ccccc4n3)CC2)CC1] | 1-(3-((1-(quinolin-2-yl)piperidin-4-yl)oxy)pyrazin-2-yl)piperidin-4-one | 404 | 0.195 |
| 8.2 | 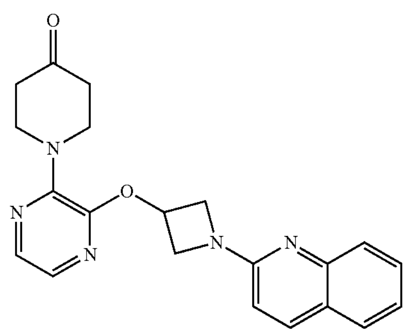 [SMILES: O=C1CCN(c2nccnc2OC2CN(c3ccc4ccccc4n3)C2)CC1] | 1-(3-((1-(quinolin-2-yl)azetidin-3-yl)oxy)pyrazin-2-yl)piperidin-4-one | 376 | 0.11 |

TABLE 6B

PREPARATION AND NMR DATA OF EXAMPLES 8.1-8.2

| Ex. # | Starting Material (1) | Reaction Condition | $^1$H NMR (CDCl$_3$, 400 MHz) δ (ppm) |
|---|---|---|---|
| 8.1 | (see Example 1.1) | DMP, DCM | 7.86 (d, J = 9.6 Hz, 1H); 7.72-7.68 (m, 2H); 7.58-7.49 (m, 3H); 7.21-7.191 (m, 1H); 7.10 (d, J = 9.2 Hz, 1H); 5.42-5.40 (m, 1H); 4.13-4.07 (m, 2H); 3.86-3.83 (m, 4H); 3.67-3.61 (m, 2H); 2.53-2.50 (m, 4H); 2.20-2.15 (m, 2H); 1.94-1.89 (m, 2H). |

TABLE 6B-continued

PREPARATION AND NMR DATA OF EXAMPLES 8.1-8.2

| Ex. # | Starting Material (1) | Reaction Condition | $^1$H NMR (CDCl$_3$, 400 MHz) δ (ppm) |
|---|---|---|---|
| 8.2 | 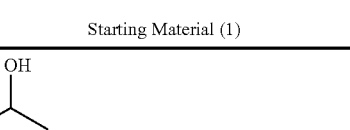<br>(see Example 1.12) | DMP, DCM | 7.83 (d, J = 8.8 Hz, 1H); 7.74-7.73 (m, 2H); 7.56-7.48 (m, 3H); 7.19-7.17 (m, 1H); 6.54 (d, J = 9.2 Hz, 1H); 5.52 (s, 1H); 4.62-4.58 (m, 2H); 4.20-4.17 (m, 2H); 3.84-3.81 (m, 4H); 2.50-2.47 (m, 4H). |

SCHEME 9

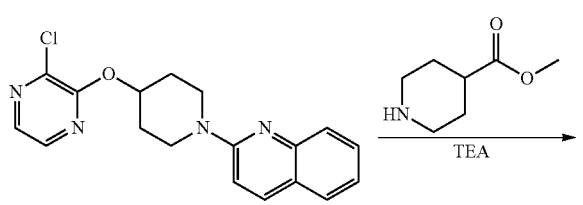

TEA

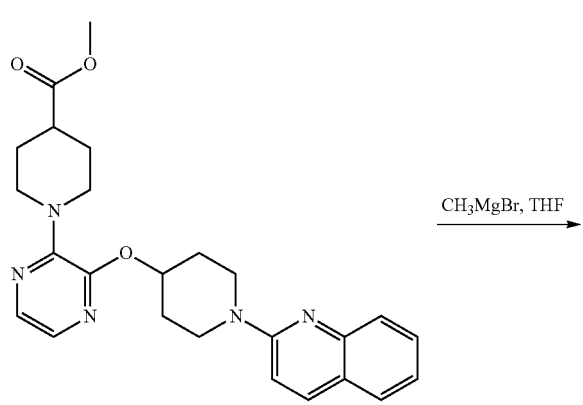

CH$_3$MgBr, THF

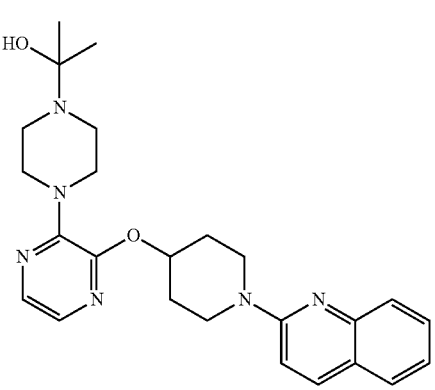

Example 9.1

2-(1-(3-((1-(Quinolin-2-yl)Piperidin-4-yl)Oxy)Pyrazin-2-yl)Piperidin-4-yl)Propan-2-Ol Step 1. Methyl 1-(3-((1-(Quinolin-2-yl)Piperidin-4-yl)Oxy)Pyrazin-2-yl)Piperidine-4-Carboxylate To a mixture of 2-[4-(3-chloro-pyrazin-2-yloxy)-piperidin-1-yl]-quinoline (see PREPARATION P2.1; 0.34 g, 1.0 mmol) and methyl piperidine-4-carboxylate (0.14 g, 1.0 mmol) and K$_2$CO$_3$ (0.27 g, 2.0 mmol) was added i-PrOH (2 mL) and water (0.5 ml). The solution was heated to 160° C. under microwave for 5 hours. Then the mixture was concentrated and extracted with EtOAc (2×20 mL). The combined organic extracts were washed with water (10 mL) and brine (10 mL), dried over Na$_2$SO$_4$, and filtered. The filtrate was evaporated in vacuo and the residue was purified by flash column chromatography on silica gel (20% to 60% EtOAc in petroleum ether) to give the title product (0.12 g, 0.27 mmol, 27% yield) as white solid. ESI-MS (M+1): 448 calc. for C$_{25}$H$_{29}$N$_5$O$_3$ 447.

Step 2. 2-(1-(3-((1-(Quinolin-2-yl)Piperidin-4-yl)Oxy)Pyrazin-2-yl)Piperidin-4-yl)Propan-2-ol To a methyl 1-(3-((1-(quinolin-2-yl)piperidin-4-yl)oxy)pyrazin-2-yl)piperidine-4-carboxylater (130 mg, 0.30 mol) in 20 mL of THF was added CH$_3$MgBr (0.50 mol, 3 M in ether) dropwise at RT. The mixture was stirred for 1 hour at RT and then quenched with saturated aqueous NH$_4$Cl. The resulting mixture was extracted with EtOAc (2×20 mL) and the combined organic layers were dried over anhydrous Na$_2$SO$_4$, filtered and concentrated to give crude product which was purified by silica gel chromatography (EtOAc: Petrol ether=1:1) to give 2-(1-(3-((1-(quinolin-2-yl)piperidin-4-yl)oxy)pyrazin-2-yl)piperidin-4-yl)propan-2-ol (0.125 g, 0.28 mmol, 66% yield) as a white solid. ESI-MS (M+1): 448 calc. for C$_{26}$H$_{33}$N$_5$O$_2$ 447.

TABLE 7A

EXAMPLES 9.1-9.2 PREPARED ANALOGOUS TO SCHEME 9

| Ex. # | Structure | Chemical Name | M + 1 | IC$_{50}$ (uM) |
|---|---|---|---|---|
| 9.1 | 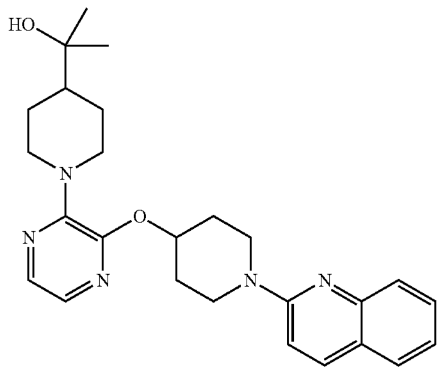 [SMILES: CC(C)(O)C1CCN(c2nccnc2OC2CCN(c3ccc4ccccc4n3)CC2)CC1] | 2-(1-(3-((1-(quinolin-2-yl)piperidin-4-yl)oxy)pyrazin-2-yl)piperidin-4-yl)propan-2-ol | 448 | 0.0858 |
| 9.2 | 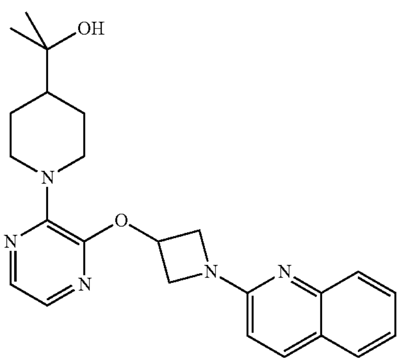 [SMILES: CC(C)(O)C1CCN(c2nccnc2OC2CN(c3ccc4ccccc4n3)C2)CC1] | 2-(1-(3-((1-(quinolin-2-yl)azetidin-3-yl)oxy)pyrazin-2-yl)piperidin-4-yl)propan-2-ol | 420 | 0.0836 |

TABLE 7B

PREPARATION AND NMR DATA OF EXAMPLES 9.1-9.2

| Ex. # | Starting Material (1) | Starting Material (2) | Reaction Condition | $^1$H NMR (CDCl$_3$, 400 MHz) δ (ppm) |
|---|---|---|---|---|
| 9.1 | | CH$_3$MgBr | THF | 7.89-7.86 (m, 1H); 7.69-7.67 (m, 2H); 7.57 (d, J = 8.0 Hz, 1H); 7.53-7.48 (m, 2H); 7.24-7.18 (m, 1H); 7.01 (d, J = 9.2 Hz, 1H); 5.36-5.41 (m, 1H); 4.30-4.27 (m, 2H); 4.07-4.01 (m, 2H); 3.89-3.73 (m, 2H); 2.73-2.67 (m, 2H); 2.17-2.12 (m, 2H); 1.97-1.90 (m, 2H); 1.81-1.78 (m, 2H); 1.48-1.40 (m, 3H); 1.16 (s, 6H). |

TABLE 7B-continued

PREPARATION AND NMR DATA OF EXAMPLES 9.1-9.2

| Ex. # | Starting Material (1) | Starting Material (2) | Reaction Condition | $^1$H NMR (CDCl$_3$, 400 MHz) δ (ppm) |
|---|---|---|---|---|
| 9.2 | (structure shown) | CH$_3$MgBr | THF | (CDCl$_3$) 7.85 (d, J = 8.8 Hz, 1H); 7.75-7.73 (m, 2H); 7.58 (d, J = 8.0 Hz, 1H); 7.57-7.52 (m, 2H); 7.24-7.20 (m, 1H); 6.57 (d, J = 8.8 Hz, 1H); 5.54-5.50 (m, 1H); 4.64-4.60 (m, 2H); 4.28-4.21 (m, 4H); 2.74-2.39 (m, 2H); 1.82-1.79 (m, 3H); 1.29-1.20 (m, 2H); 1.16 (s, 6H). |

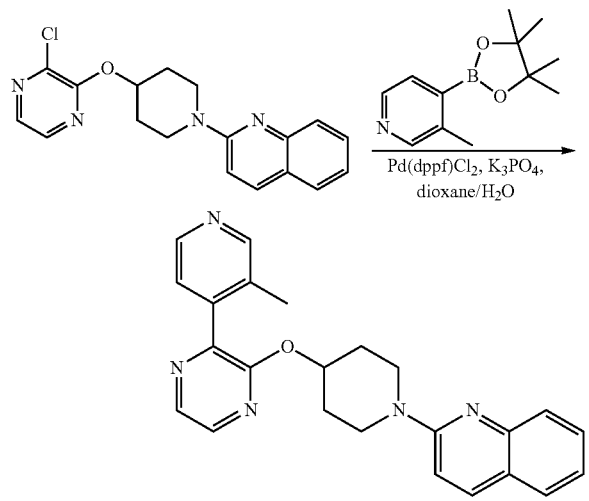

SCHEME 10

Example 10.1

2-(4-((3-(2-Methylpyridin-4-yl)Pyrazin-2-yl)Oxy)Piperidin-1-yl)Quinoline

To a solution of 2-(4-((3-chloropyrazin-2-yl)oxy)piperidin-1-yl)quinoline (see PREPARATION P2.1; 340 mg, 1.0 mmol), 3-methyl-4-(4,4,5,5-tetramethyl-[1,3,2]dioxaborolan-2-yl)-pyridine (see PREPARATION P12.1; 219 mg, 1.0 mmol) and K$_3$PO$_4$ (424 mg, 2.0 mmol) in 1,4-dioxane (10 mL) and H$_2$O (2 mL) was added Pd(dppf)Cl$_2$ (73 mg, 0.1 mmol) then the reaction mixture was stirred at 110° C. under N$_2$ atmosphere overnight. The reaction mixture was filtered through CELITE® and washed with CH$_2$Cl$_2$ (30 mL). The filtrate was concentrated and the crude product was purified by silica gel column to give 2-(4-((3-(2-methylpyridin-4-yl)pyrazin-2-yl)oxy)piperidin-1-yl)quinoline (200 mg, 0.50 mmol, yield 60%). ESI-MS (M+1): 398 calc. for C$_{24}$H$_{23}$N$_5$O 397.

TABLE 8A

EXAMPLES 10.1-10.78 PREPARED ANALOGOUS TO SCHEME 10

| Ex. # | Structure | Chemical Name | ESI-MS (M + 1) | IC$_{50}$ (uM) |
|---|---|---|---|---|
| 10.1 | (structure shown) | 2-(4-((3-(3-methylpyridin-4-yl)pyrazin-2-yl)oxy)piperidin-1-yl)quinoline | 398 | 0.0347 |

TABLE 8A-continued

EXAMPLES 10.1-10.78 PREPARED ANALOGOUS TO SCHEME 10

| Ex. # | Structure | Chemical Name | ESI-MS (M + 1) | IC$_{50}$ (uM) |
|---|---|---|---|---|
| 10.2 | 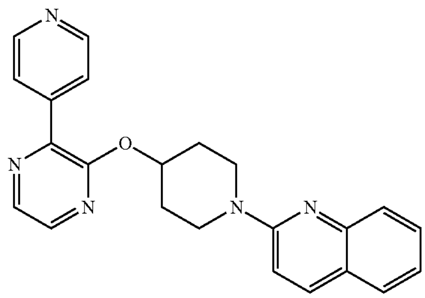 [SMILES: c1ccc2nc(N3CCC(Oc4nccnc4-c4ccncc4)CC3)ccc2c1] | 2-(4-((3-(pyridin-4-yl)pyrazin-2-yl)oxy)piperidin-1-yl)quinoline | 384 | 0.0357 |
| 10.3* | 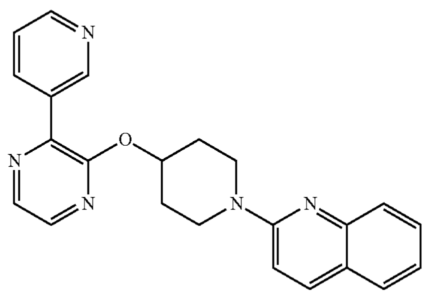 [SMILES: c1cncc(-c2nccnc2OC2CCN(c3ccc4ccccc4n3)CC2)c1] | 2-(4-((3-(pyridin-3-yl)pyrazin-2-yl)oxy)piperidin-1-yl)quinoline | 384 | Not available |
| 10.4 | 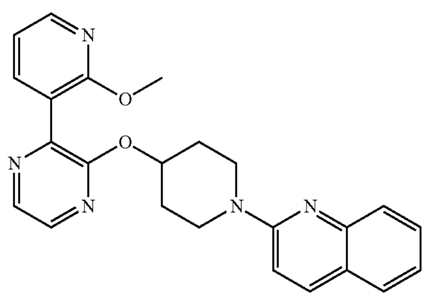 [SMILES: COc1ncccc1-c1nccnc1OC1CCN(c2ccc3ccccc3n2)CC1] | 2-(4-((3-(2-methoxypyridin-3-yl)pyrazin-2-yl)oxy)piperidin-1-yl)quinoline | 414 | 0.118 |
| 10.5 | 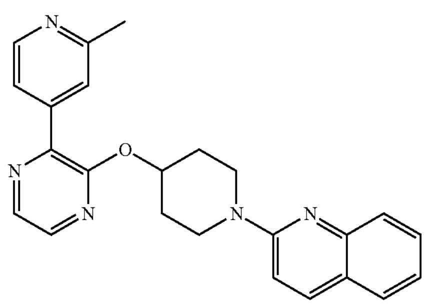 [SMILES: Cc1cc(-c2nccnc2OC2CCN(c3ccc4ccccc4n3)CC2)ccn1] | 2-{4-[3-(2-Methyl-pyridin-4-yl)-pyrazin-2-yloxy]-piperidin-1-yl}-quinoline | 398 | 0.0816 |
| 10.6 | 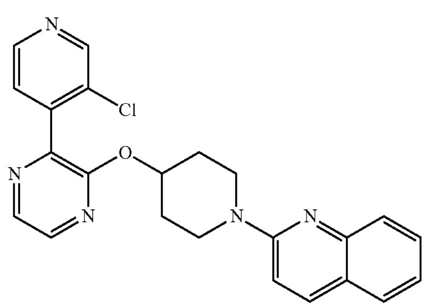 [SMILES: Clc1cnccc1-c1nccnc1OC1CCN(c2ccc3ccccc3n2)CC1] | 2-(4-((3-(3-chloropyridin-4-yl)pyrazin-2-yl)oxy)piperidin-1-yl)quinoline | 418 | 0.0839 |

TABLE 8A-continued

EXAMPLES 10.1-10.78 PREPARED ANALOGOUS TO SCHEME 10

| Ex. # | Structure | Chemical Name | ESI-MS (M + 1) | IC$_{50}$ (uM) |
|---|---|---|---|---|
| 10.7 | 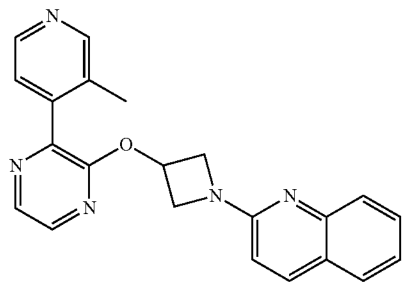 [SMILES: Cc1cnccc1-c1nccnc1OC1CN(c2ccc3ccccc3n2)C1] | 2-(3-((3-(3-methylpyridin-4-yl)pyrazin-2-yl)oxy)azetidin-1-yl)quinoline | 370 | 0.298 |
| 10.8 | 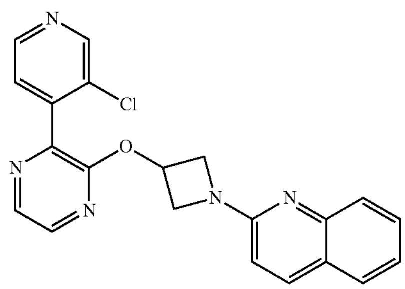 [SMILES: Clc1cnccc1-c1nccnc1OC1CN(c2ccc3ccccc3n2)C1] | 2-(3-((3-(3-chloropyridin-4-yl)pyrazin-2-yl)oxy)azetidin-1-yl)quinoline | 390 | 0.155 |
| 10.9 | 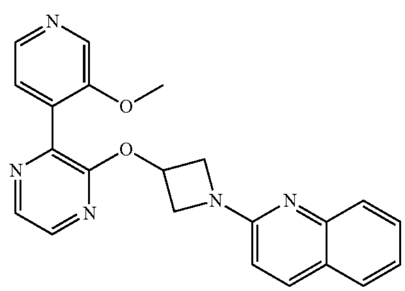 [SMILES: COc1cnccc1-c1nccnc1OC1CN(c2ccc3ccccc3n2)C1] | 2-(3-((3-(2-methoxypyridin-3-yl)pyrazin-2-yl)oxy)azetidin-1-yl)quinoline | 386 | 0.0837 |
| 10.10 | 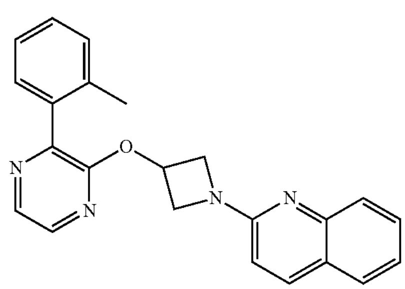 [SMILES: Cc1ccccc1-c1nccnc1OC1CN(c2ccc3ccccc3n2)C1] | 2-(3-((3-(o-tolyl)pyrazin-2-yl)oxy)azetidin-1-yl)quinoline | 369 | 0.128 |
| 10.11 | 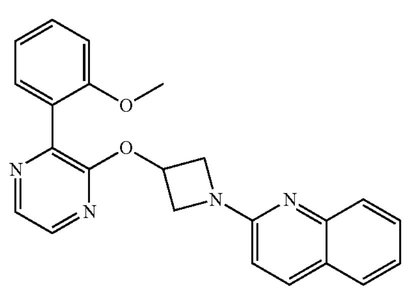 [SMILES: COc1ccccc1-c1nccnc1OC1CN(c2ccc3ccccc3n2)C1] | 2-(3-((3-(2-methoxyphenyl)pyrazin-2-yl)oxy)azetidin-1-yl)quinoline | 385 | 0.15 |

TABLE 8A-continued

EXAMPLES 10.1-10.78 PREPARED ANALOGOUS TO SCHEME 10

| Ex. # | Structure | Chemical Name | ESI-MS (M + 1) | IC$_{50}$ (uM) |
|---|---|---|---|---|
| 10.12 | 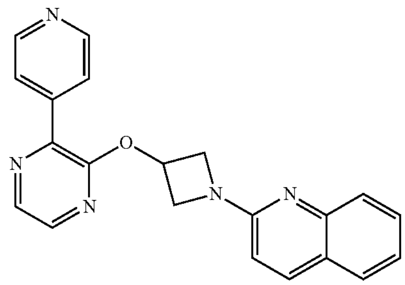 [SMILES: c1ccc2nc(N3CC(Oc4nccnc4-c4ccncc4)C3)ccc2c1] | 2-(3-((3-(pyridin-4-yl)pyrazin-2-yl)oxy)azetidin-1-yl)quinoline | 356 | 0.0245 |
| 10.13 | 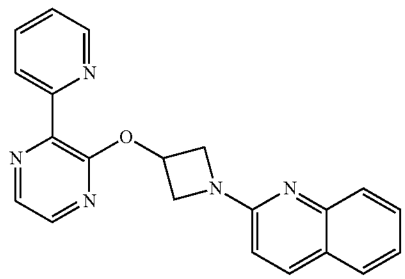 [SMILES: c1ccc(-c2nccnc2OC2CN(c3ccc4ccccc4n3)C2)nc1] | 2-(3-((3-(pyridin-2-yl)pyrazin-2-yl)oxy)azetidin-1-yl)quinoline | 356 | 1.22 |
| 10.14 | 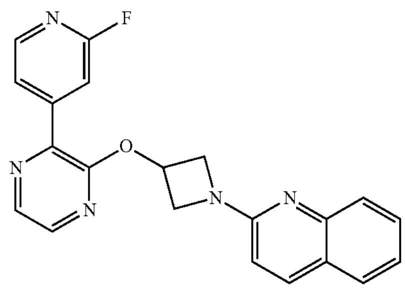 [SMILES: Fc1cc(-c2nccnc2OC2CN(c3ccc4ccccc4n3)C2)ccn1] | 2-(3-((3-(2-fluoropyridin-4-yl)pyrazin-2-yl)oxy)azetidin-1-yl)quinoline | 374 | 0.0395 |
| 10.15 | 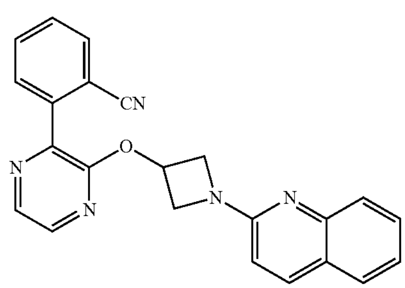 [SMILES: N#Cc1ccccc1-c1nccnc1OC1CN(c2ccc3ccccc3n2)C1] | 2-(3-((1-(quinolin-2-yl)azetidin-3-yl)oxy)pyrazin-2-yl)benzonitrile | 380 | 0.377 |
| 10.16* | 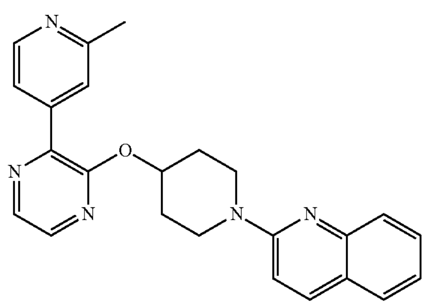 [SMILES: Cc1cc(-c2nccnc2OC2CCN(c3ccc4ccccc4n3)CC2)ccn1] | 2-(3-((3-(2-methylpyridin-4-yl)pyrazin-2-yl)oxy)azetidin-1-yl)quinoline | 369 | Not available |

TABLE 8A-continued

EXAMPLES 10.1-10.78 PREPARED ANALOGOUS TO SCHEME 10

| Ex. # | Structure | Chemical Name | ESI-MS (M + 1) | IC$_{50}$ (uM) |
|---|---|---|---|---|
| 10.17 | 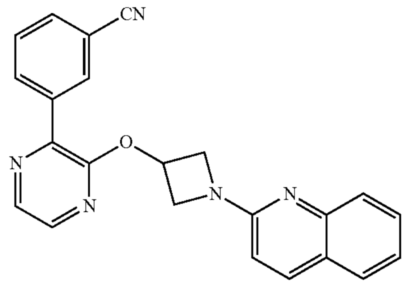 [SMILES: N#Cc1cccc(-c2nccnc2OC2CN(c3ccc4ccccc4n3)C2)c1] | 3-(3-((1-(quinolin-2-yl)azetidin-3-yl)oxy)pyrazin-2-yl)benzonitrile | 380 | 0.0413 |
| 10.18 | 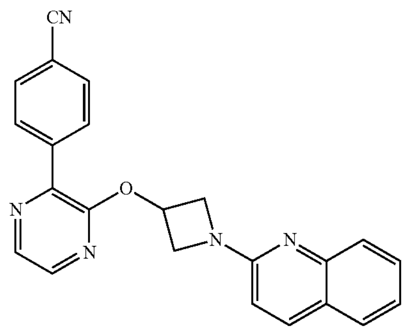 [SMILES: N#Cc1ccc(-c2nccnc2OC2CN(c3ccc4ccccc4n3)C2)cc1] | 4-(3-((1-(quinolin-2-yl)azetidin-3-yl)oxy)pyrazin-2-yl)benzonitrile | 380 | 0.0394 |
| 10.19 | 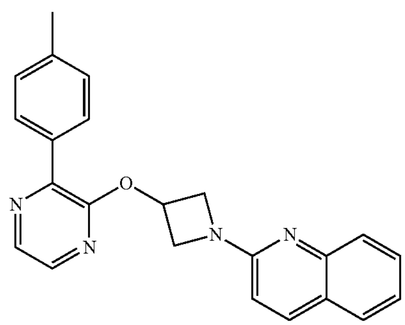 [SMILES: Cc1ccc(-c2nccnc2OC2CN(c3ccc4ccccc4n3)C2)cc1] | 2-(3-((3-(p-tolyl)pyrazin-2-yl)oxy)azetidin-1-yl)quinoline | 369 | 0.0987 |
| 10.20 | 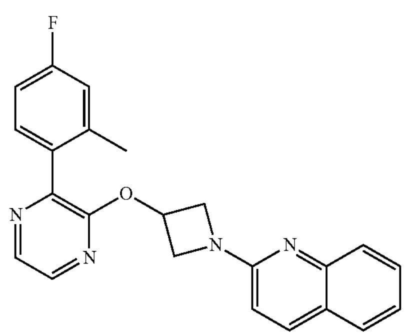 [SMILES: Cc1cc(F)ccc1-c1nccnc1OC1CN(c2ccc3ccccc3n2)C1] | 2-(3-((3-(4-fluoro-2-methylphenyl)pyrazin-2-yl)oxy)azetidin-1-yl)quinoline | 387 | 0.918 |
| 10.21 | 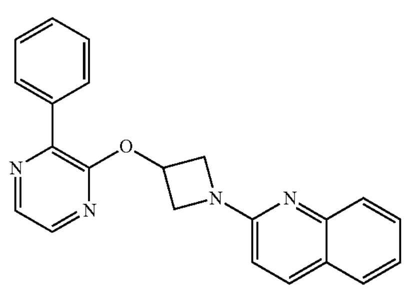 [SMILES: c1ccc(-c2nccnc2OC2CN(c3ccc4ccccc4n3)C2)cc1] | 2-(3-((3-phenylpyrazin-2-yl)oxy)azetidin-1-yl)quinoline | 355 | 0.0961 |

TABLE 8A-continued

EXAMPLES 10.1-10.78 PREPARED ANALOGOUS TO SCHEME 10

| Ex. # | Structure | Chemical Name | ESI-MS (M + 1) | IC$_{50}$ (uM) |
|---|---|---|---|---|
| 10.22 | 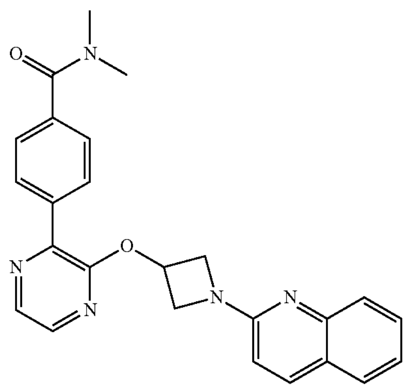 [SMILES: CN(C)C(=O)c1ccc(-c2nccnc2OC2CN(c3ccc4ccccc4n3)C2)cc1] | N,N-dimethyl-4-(3-((1-(quinolin-2-yl)azetidin-3-yl)oxy)pyrazin-2-yl)benzamide | 426 | 0.015 |
| 10.23 | 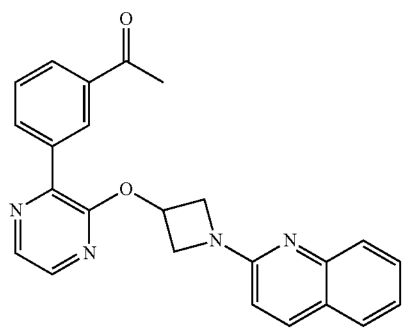 [SMILES: CC(=O)c1cccc(-c2nccnc2OC2CN(c3ccc4ccccc4n3)C2)c1] | 1-(3-(3-((1-(quinolin-2-yl)azetidin-3-yl)oxy)pyrazin-2-yl)phenyl)ethanone | 397 | 0.0112 |
| 10.24 | 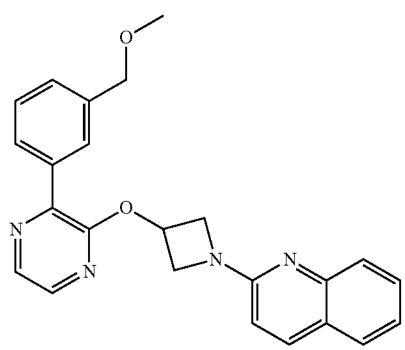 [SMILES: COCc1cccc(-c2nccnc2OC2CN(c3ccc4ccccc4n3)C2)c1] | 2-(3-((3-(3-(methoxymethyl)phenyl)pyrazin-2-yl)oxy)azetidin-1-yl)quinoline | 399 | 0.0452 |
| 10.25 | 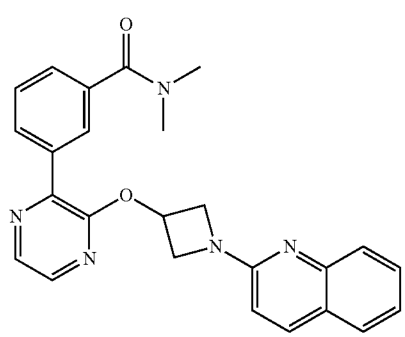 [SMILES: CN(C)C(=O)c1cccc(-c2nccnc2OC2CN(c3ccc4ccccc4n3)C2)c1] | N,N-dimethyl-3-(3-((1-(quinolin-2-yl)azetidin-3-yl)oxy)pyrazin-2-yl)benzamide | 426 | 0.0228 |

TABLE 8A-continued

EXAMPLES 10.1-10.78 PREPARED ANALOGOUS TO SCHEME 10

| Ex. # | Structure | Chemical Name | ESI-MS (M + 1) | IC$_{50}$ (uM) |
|---|---|---|---|---|
| 10.26 | 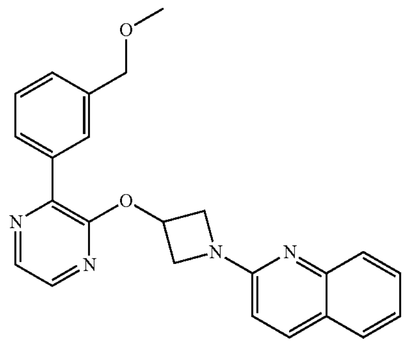 [SMILES: COCc1cccc(-c2nccnc2OC2CN(c3ccc4ccccc4n3)C2)c1] | 1-(4-(3-((1-(quinolin-2-yl)azetidin-3-yl)oxy)pyrazin-2-yl)phenyl)ethanone | 397 | 0.0244 |
| 10.27 | 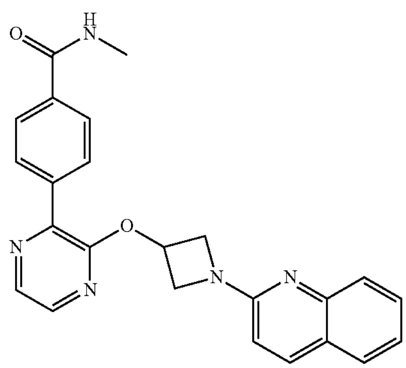 [SMILES: CNC(=O)c1ccc(-c2nccnc2OC2CN(c3ccc4ccccc4n3)C2)cc1] | N-methyl-4-(3-((1-(quinolin-2-yl)azetidin-3-yl)oxy)pyrazin-2-yl)benzamide | 412 | 0.015 |
| 10.28 | 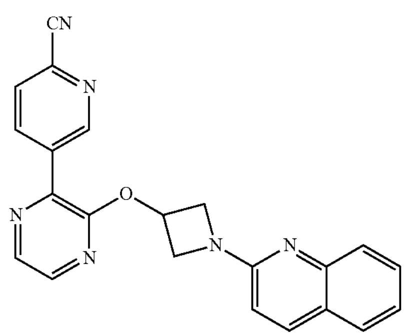 [SMILES: N#Cc1ccc(-c2nccnc2OC2CN(c3ccc4ccccc4n3)C2)cn1] | 5-(3-((1-(quinolin-2-yl)azetidin-3-yl)oxy)pyrazin-2-yl)picolinonitrile | 381 | 0.0506 |
| 10.29 | 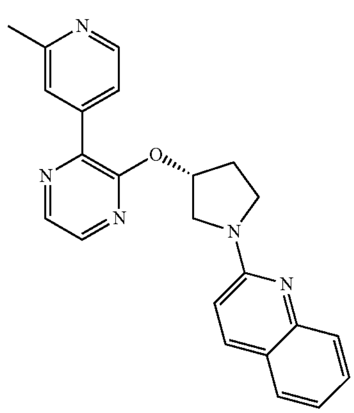 [SMILES: Cc1cc(-c2nccnc2O[C@@H]2CCN(c3ccc4ccccc4n3)C2)ccn1] | (R)-2-(3-((3-(2-methylpyridin-4-yl)pyrazin-2-yl)oxy)pyrrolidin-1-yl)quinoline | 398 | 0.255 |

TABLE 8A-continued

EXAMPLES 10.1-10.78 PREPARED ANALOGOUS TO SCHEME 10

| Ex. # | Structure | Chemical Name | ESI-MS (M + 1) | IC$_{50}$ (uM) |
|---|---|---|---|---|
| 10.30 | 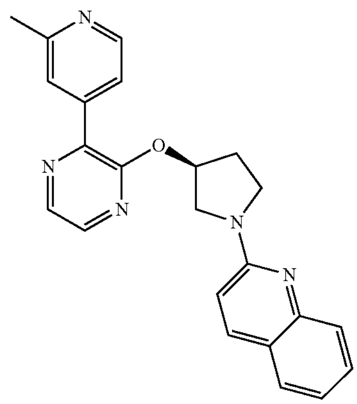 [SMILES: Cc1cc(-c2nccnc2O[C@H]2CCN(c3ccc4ccccc4n3)C2)ccn1] | (S)-2-(3-((3-(2-methylpyridin-4-yl)pyrazin-2-yl)oxy)pyrrolidin-1-yl)quinoline | 398 | 0.639 |
| 10.31 | 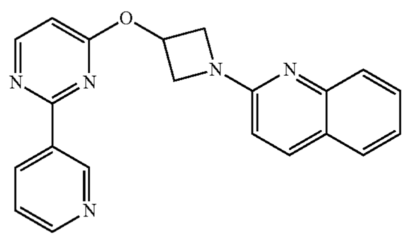 [SMILES: c1cncc(-c2nccc(OC3CN(c4ccc5ccccc5n4)C3)n2)c1] | 2-(3-((2-(pyridin-3-yl)pyrimidin-4-yl)oxy)azetidin-1-yl)quinoline | 356 | 0.0356 |
| 10.32 | 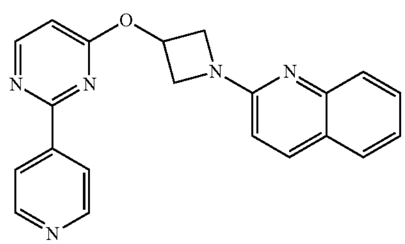 [SMILES: c1ccc2nc(N3CC(Oc4ccnc(-c5ccncc5)n4)C3)ccc2c1] | 2-(3-((2-(pyridin-4-yl)pyrimidin-4-yl)oxy)azetidin-1-yl)quinoline | 356 | 0.0323 |
| 10.33 | 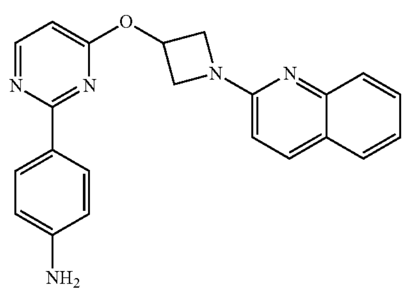 [SMILES: Nc1ccc(-c2nccc(OC3CN(c4ccc5ccccc5n4)C3)n2)cc1] | 4-(4-((1-(quinolin-2-yl)azetidin-3-yl)oxy)pyrimidin-2-yl)aniline | 370 | 0.110 |
| 10.34 | 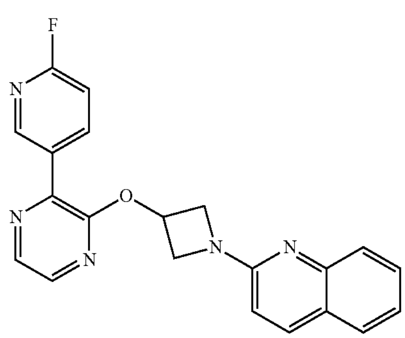 [SMILES: Fc1ccc(-c2nccnc2OC2CN(c3ccc4ccccc4n3)C2)cn1] | 2-(3-((3-(6-fluoropyridin-3-yl)pyrazin-2-yl)oxy)azetidin-1-yl)quinoline | 374 | 0.0457 |

TABLE 8A-continued

EXAMPLES 10.1-10.78 PREPARED ANALOGOUS TO SCHEME 10

| Ex. # | Structure | Chemical Name | ESI-MS (M + 1) | IC$_{50}$ (uM) |
|---|---|---|---|---|
| 10.35 | 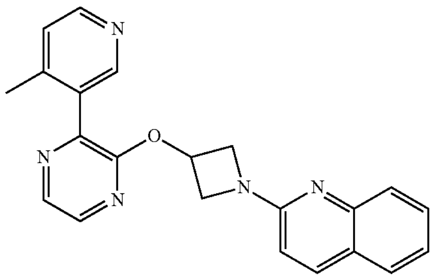 [SMILES: Cc1ccncc1-c1nccnc1OC1CN(c2ccc3ccccc3n2)C1] | 2-(3-((3-(4-methylpyridin-3-yl)pyrazin-2-yl)oxy)azetidin-1-yl)quinoline | 370 | 0.251 |
| 10.36 | 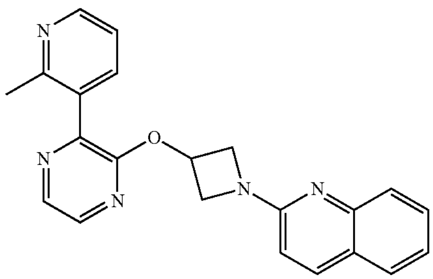 [SMILES: Cc1ncccc1-c1nccnc1OC1CN(c2ccc3ccccc3n2)C1] | 2-(3-((3-(2-methylpyridin-3-yl)pyrazin-2-yl)oxy)azetidin-1-yl)quinoline | 370 | 0.135 |
| 10.37 | 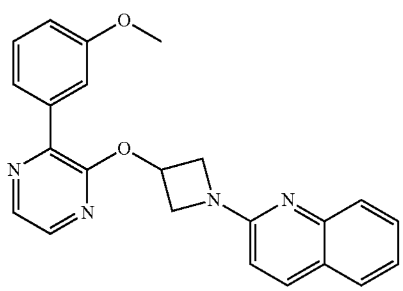 [SMILES: COc1cccc(-c2nccnc2OC2CN(c3ccc4ccccc4n3)C2)c1] | 2-(3-((3-(3-methoxyphenyl)pyrazin-2-yl)oxy)azetidin-1-yl)quinoline | 385 | 0.019 |
| 10.38 | 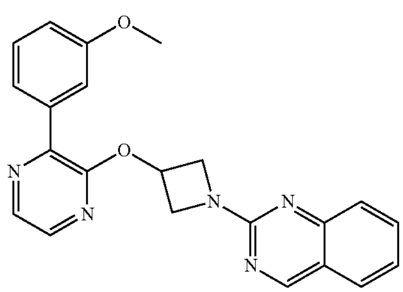 [SMILES: COc1cccc(-c2nccnc2OC2CN(c3ncc4ccccc4n3)C2)c1] | 2-(3-((3-(3-methoxyphenyl)pyrazin-2-yl)oxy)azetidin-1-yl)quinazoline | 386 | 0.148 |
| 10.39 | 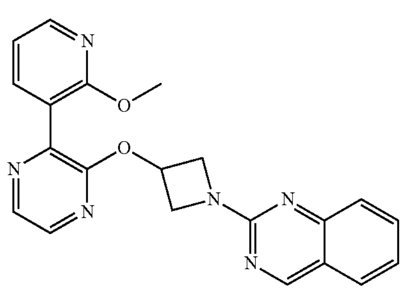 [SMILES: COc1ncccc1-c1nccnc1OC1CN(c2ncc3ccccc3n2)C1] | 2-(3-((3-(2-methoxypyridin-3-yl)pyrazin-2-yl)oxy)azetidin-1-yl)quinazoline | 387 | 0.1780 |

TABLE 8A-continued

EXAMPLES 10.1-10.78 PREPARED ANALOGOUS TO SCHEME 10

| Ex. # | Structure | Chemical Name | ESI-MS (M + 1) | IC$_{50}$ (uM) |
|---|---|---|---|---|
| 10.40 | 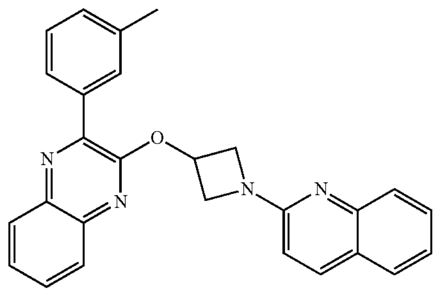 [SMILES: Cc1cccc(-c2nc3ccccc3nc2OC2CN(c3ccc4ccccc4n3)C2)c1] | 2-((1-(quinolin-2-yl)azetidin-3-yl)oxy)-3-(m-tolyl)quinoxaline | 419 | 0.0535 |
| 10.41 | 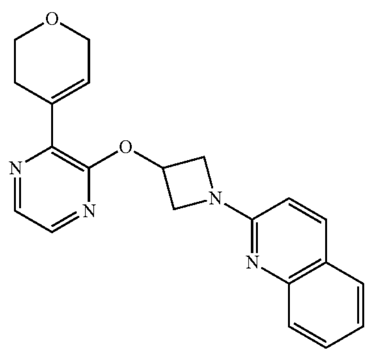 [SMILES: C1=C(c2nccnc2OC2CN(c3ccc4ccccc4n3)C2)CCOC1] | 2-(3-((3-(3,6-dihydro-2H-pyran-4-yl)pyrazin-2-yl)oxy)azetidin-1-yl)quinoline | 361 | 0.0149 |
| 10.42 | 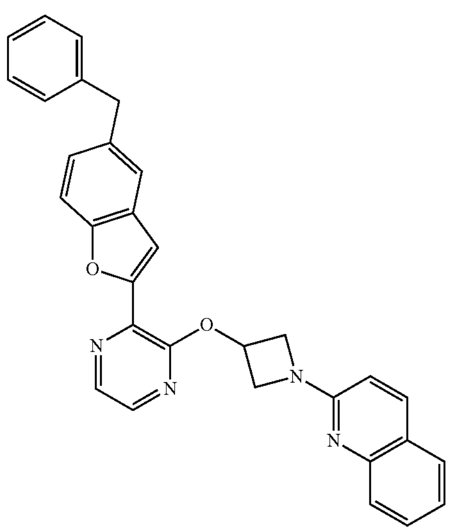 [SMILES: c1ccc(Cc2ccc3oc(-c4nccnc4OC4CN(c5ccc6ccccc6n5)C4)cc3c2)cc1] | 2-(3-((3-(5-benzyl-1-benzofuran-2-yl)-2-pyrazinyl)oxy)-1-azetidinyl)quinoline | 485 | 0.363 |

TABLE 8A-continued

EXAMPLES 10.1-10.78 PREPARED ANALOGOUS TO SCHEME 10

| Ex. # | Structure | Chemical Name | ESI-MS (M + 1) | IC$_{50}$ (uM) |
|---|---|---|---|---|
| 10.43 | 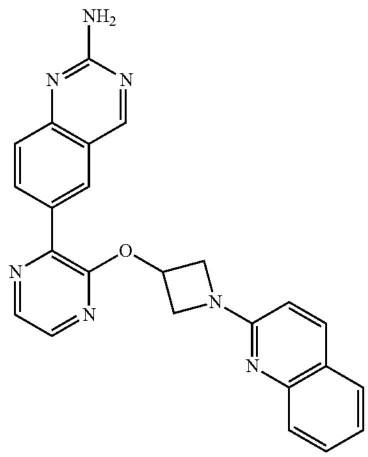 [SMILES: Nc1ncc2cc(-c3nccnc3OC3CN(c4ccc5ccccc5n4)C3)ccc2n1] | 6-(3-((1-(2-quinolinyl)-3-azetidinyl)oxy)-2-pyrazinyl)-2-quinazolinamine | 422 | 0.0033 |
| 10.44 | 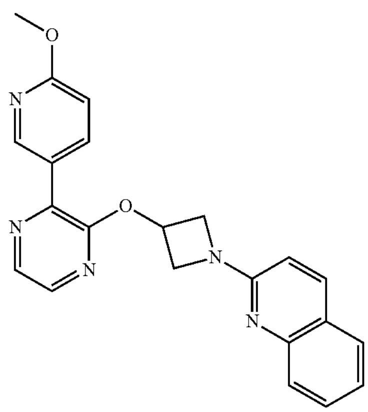 [SMILES: COc1ccc(-c2nccnc2OC2CN(c3ccc4ccccc4n3)C2)cn1] | 2-(3-((3-(6-methoxy-3-pyridinyl)-2-pyrazinyl)oxy)-1-azetidinyl)quinoline | 386 | 0.0254 |
| 10.45 | 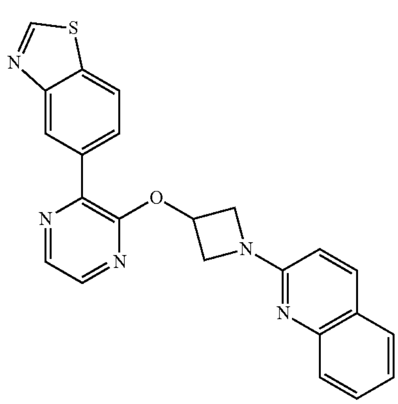 [SMILES: c1ccc2nc(N3CC(Oc4nccnc4-c4ccc5scnc5c4)C3)ccc2c1] | 2-(3-((3-(1,3-benzothiazol-5-yl)-2-pyrazinyl)oxy)-1-azetidinyl)quinoline | 412 | 0.0307 |

TABLE 8A-continued

EXAMPLES 10.1-10.78 PREPARED ANALOGOUS TO SCHEME 10

| Ex. # | Structure | Chemical Name | ESI-MS (M + 1) | IC$_{50}$ (uM) |
|---|---|---|---|---|
| 10.46 | 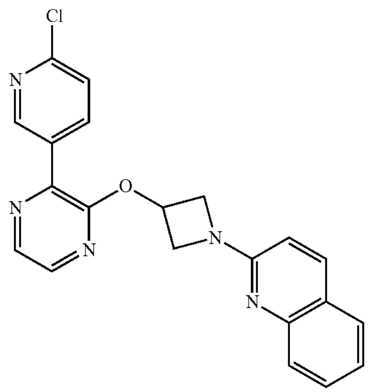 [SMILES: Clc1ccc(-c2nccnc2OC2CN(c3ccc4ccccc4n3)C2)cn1] | 2-(3-((3-(6-chloro-3-pyridinyl)-2-pyrazinyl)oxy)-1-azetidinyl)quinoline | 390 | 0.0097 |
| 10.47 | 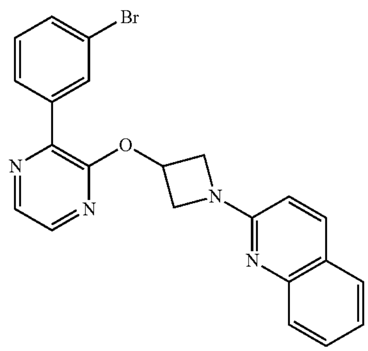 [SMILES: Brc1cccc(-c2nccnc2OC2CN(c3ccc4ccccc4n3)C2)c1] | 2-(3-((3-(3-bromophenyl)-2-pyrazinyl)oxy)-1-azetidinyl)quinoline | 433 | 0.0459 |
| 10.48 | 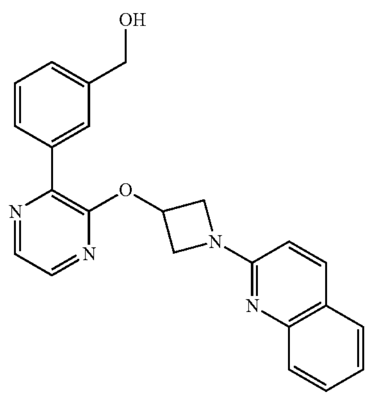 [SMILES: OCc1cccc(-c2nccnc2OC2CN(c3ccc4ccccc4n3)C2)c1] | (3-(3-((1-(2-quinolinyl)-3-azetidinyl)oxy)-2-pyrazinyl)phenyl)methanol | 385 | 0.0233 |
| 10.49 | 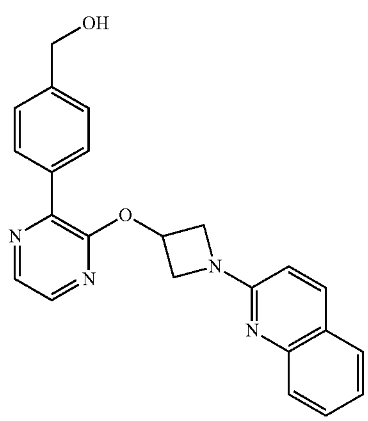 [SMILES: OCc1ccc(-c2nccnc2OC2CN(c3ccc4ccccc4n3)C2)cc1] | (4-(3-((1-(2-quinolinyl)-3-azetidinyl)oxy)-2-pyrazinyl(phenyl)methanol | 385 | 0.0105 |

TABLE 8A-continued
EXAMPLES 10.1-10.78 PREPARED ANALOGOUS TO SCHEME 10
| Ex. # | Structure | Chemical Name | ESI-MS (M + 1) | IC$_{50}$ (uM) |
|---|---|---|---|---|
| 10.50 | 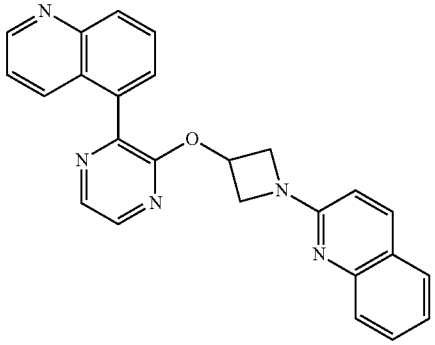 [SMILES: c1ccc2nc(N3CC(Oc4nccnc4-c4cccc5ncccc45)C3)ccc2c1] | 2-(3-((3-(5-quinolinyl)-2-pyrazinyl)oxy)-1-azetidinyl)quinoline | 406 | 0.087 |
| 10.51 | 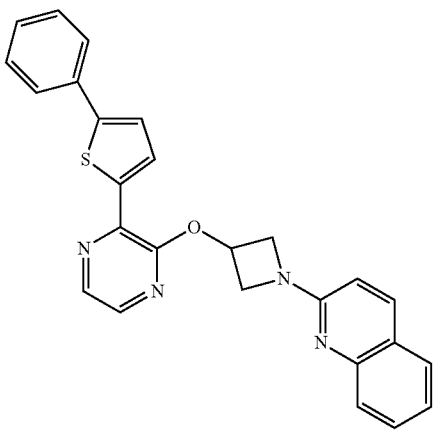 [SMILES: c1ccc(-c2ccc(-c3nccnc3OC3CN(c4ccc5ccccc5n4)C3)s2)cc1] | 2-(3-((3-(5-phenyl-2-thiophenyl)-2-pyrazinyl)oxy)-1-azetidinyl)quinoline | 437 | 0.254 |
| 10.52 | 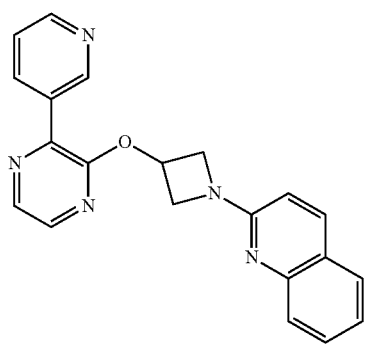 [SMILES: c1cncc(-c2nccnc2OC2CN(c3ccc4ccccc4n3)C2)c1] | 2-(3-((3-(3-pyridinyl)-2-pyrazinyl)oxy)-1-azetidinyl)quinoline | 356 | 0.0137 |
| 10.53 | 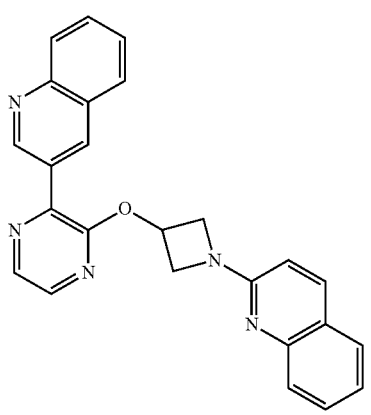 [SMILES: c1ccc2ncc(-c3nccnc3OC3CN(c4ccc5ccccc5n4)C3)cc2c1] | 2-(3-((3-(3-quinolinyl)-2-pyrazinyl)oxy)-1-azetidinyl)quinoline | 406 | 0.0193 |

TABLE 8A-continued

EXAMPLES 10.1-10.78 PREPARED ANALOGOUS TO SCHEME 10

| Ex. # | Structure | Chemical Name | ESI-MS (M + 1) | IC$_{50}$ (uM) |
|---|---|---|---|---|
| 10.54 | 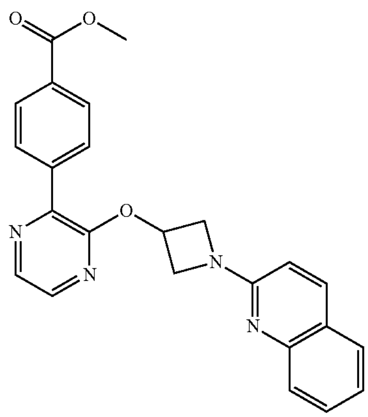 [SMILES: COC(=O)c1ccc(-c2nccnc2OC2CN(c3ccc4ccccc4n3)C2)cc1] | methyl 4-(3-((1-(2-quinolinyl)-3-azetidinyl)oxy)-2-pyrazinyl)benzoate | 413 | 0.0432 |
| 10.55 | 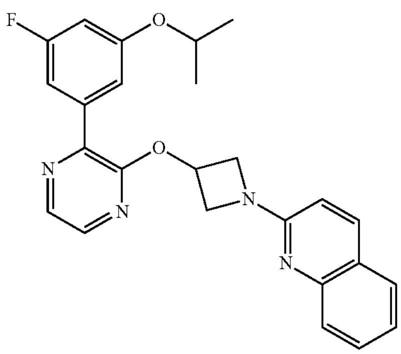 [SMILES: CC(C)Oc1cc(F)cc(-c2nccnc2OC2CN(c3ccc4ccccc4n3)C2)c1] | 2-(3-((3-(3-fluoro-5-(1-methyl-ethoxy)phenyl)-2-pyrazinyl)oxy)-1-azetidinyl)quinoline | 431 | 0.174 |
| 10.56 | 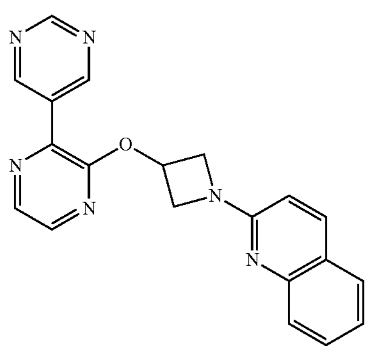 | 2-(3-((3-(5-pyrimidinyl)-2-pyrazinyl)oxy)-1-azetidinyl)quinoline | 357 | 0.0821 |
| 10.57 | 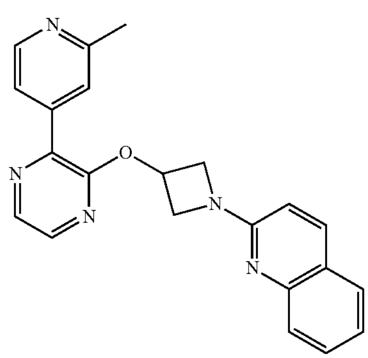 [SMILES: Cc1cc(-c2nccnc2OC2CN(c3ccc4ccccc4n3)C2)ccn1] | 2-(3-((3-(2-methyl-4-pyridinyl)-2-pyrazinyl)oxy)-1-azetidinyl)quinoline | 370 | 0.0127 |

TABLE 8A-continued

EXAMPLES 10.1-10.78 PREPARED ANALOGOUS TO SCHEME 10

| Ex. # | Structure | Chemical Name | ESI-MS (M + 1) | IC$_{50}$ (uM) |
|---|---|---|---|---|
| 10.58 | 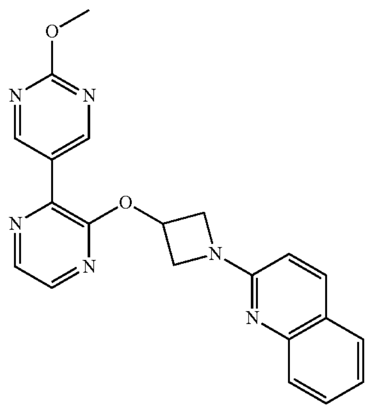 [SMILES: COc1ncc(-c2nccnc2OC2CN(c3ccc4ccccc4n3)C2)cn1] | 2-(3-((3-(2-methoxy-5-pyrimidinyl)-2-pyrazinyl)oxy)-1-azetidinyl)quinoline | 387 | 0.0428 |
| 10.59 | 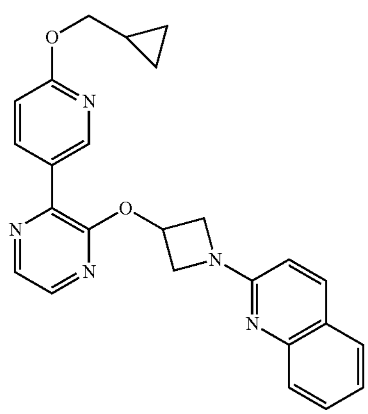 [SMILES: c1ccc2nc(N3CC(Oc4nccnc4-c4ccc(OCC5CC5)nc4)C3)ccc2c1] | 2-(3-((3-(6-(cyclopropylmethoxy)-3-pyridinyl)-2-pyrazinyl)oxy)-1-azetidinyl)quinoline | 426 | 0.0502 |
| 10.60 | 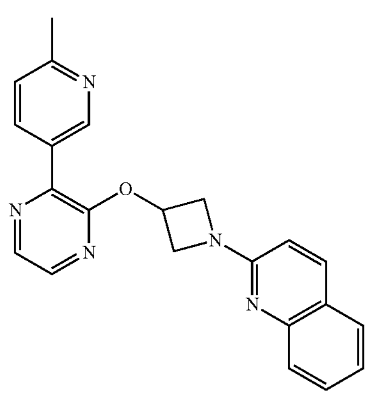 [SMILES: Cc1ccc(-c2nccnc2OC2CN(c3ccc4ccccc4n3)C2)cn1] | 2-(3-((3-(6-methyl-3-pyridinyl)-2-pyrazinyl)oxy)-1-azetidinyl)quinoline | 370 | 0.0078 |

TABLE 8A-continued

EXAMPLES 10.1-10.78 PREPARED ANALOGOUS TO SCHEME 10

| Ex. # | Structure | Chemical Name | ESI-MS (M + 1) | IC$_{50}$ (uM) |
|---|---|---|---|---|
| 10.61 | 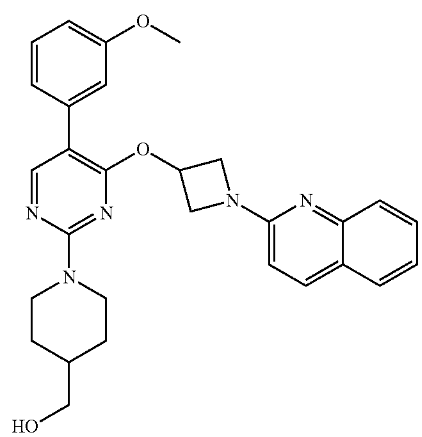 [SMILES: COc1cccc(-c2cnc(N3CCC(CO)CC3)nc2OC2CN(c3ccc4ccccc4n3)C2)c1] | (1-(5-(3-methoxyphenyl)-4-((1-(quinolin-2-yl)azetidin-3-yl)oxy)pyrimidin-2-yl)piperidin-4-yl)methanol | 498 | 0.0033 |
| 10.62 | 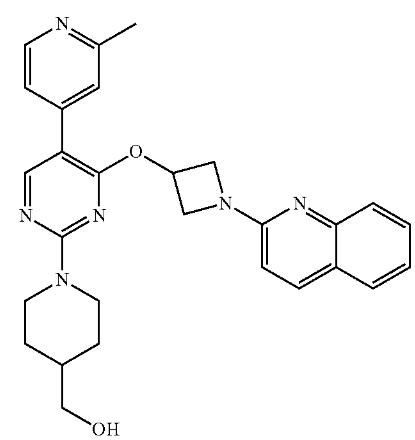 [SMILES: Cc1cc(-c2cnc(N3CCC(CO)CC3)nc2OC2CN(c3ccc4ccccc4n3)C2)ccn1] | (1-(5-(2-methylpyridin-4-yl)-4-((1-(quinolin-2-yl)azetidin-3-yl)oxy)pyrimidin-2-yl)piperidin-4-yl)methanol | 483 | 0.0003 |
| 10.63 | 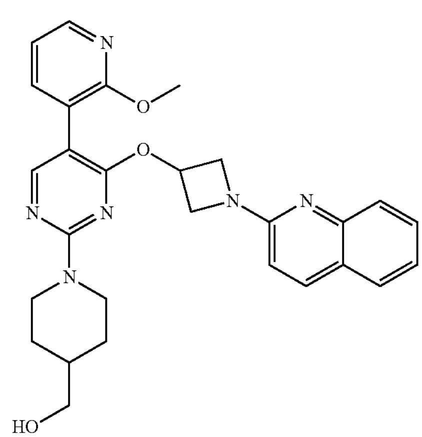 [SMILES: COc1ncccc1-c1cnc(N2CCC(CO)CC2)nc1OC1CN(c2ccc3ccccc3n2)C1] | (1-(5-(2-methoxypyridin-3-yl)-4-((1-(quinolin-2-yl)azetidin-3-yl)oxy)pyrimidin-2-yl)piperidin-4-yl)methanol | 499 | 0.0006 |

TABLE 8A-continued

EXAMPLES 10.1-10.78 PREPARED ANALOGOUS TO SCHEME 10

| Ex. # | Structure | Chemical Name | ESI-MS (M + 1) | IC$_{50}$ (uM) |
|---|---|---|---|---|
| 10.64 | 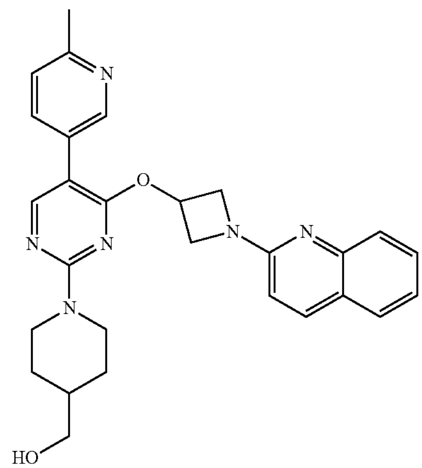 | (1-(5-(6-methylpyridin-3-yl)-4-((1-(quinolin-2-yl)azetidin-3-yl)oxy)pyrimidin-2-yl)piperidin-4-yl)methanol | 483 | 0.0002 |
| 10.65 | 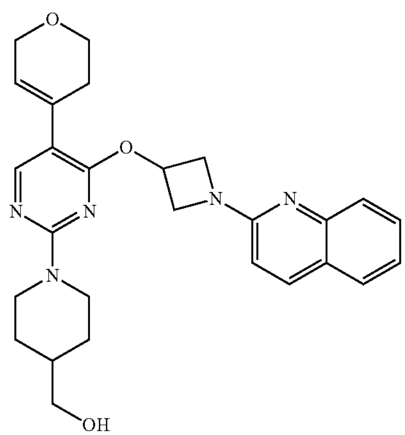 [SMILES: OCC1CCN(c2ncc(C3=CCOCC3)c(OC3CN(c4ccc5ccccc5n4)C3)n2)CC1] | (1-(5-(3,6-dihydro-2H-pyran-4-yl)-4-((1-(quinolin-2-yl)azetidin-3-yl)oxy)pyrimidin-2-yl)piperidin-4-yl(methanol | 474 | 0.0011 |
| 10.66 | 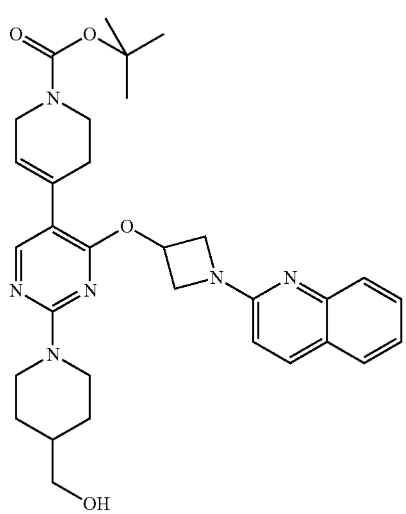 [SMILES: CC(C)(C)OC(=O)N1CC=C(c2cnc(N3CCC(CO)CC3)nc2OC2CN(c3ccc4ccccc4n3)C2)CC1] | tert-butyl 4-(2-(4-(hydroxy-methyl)piperidin-1-yl)-4-((1-(quinolin-2-yl)azetidin-3-yl)oxy)pyrimidin-5-yl)-5,6-dihydro-pyridine-1(2H)-carboxylate | 573 | 0.0003 |

TABLE 8A-continued

EXAMPLES 10.1-10.78 PREPARED ANALOGOUS TO SCHEME 10

| Ex. # | Structure | Chemical Name | ESI-MS (M + 1) | IC$_{50}$ (uM) |
|---|---|---|---|---|
| 10.67 | 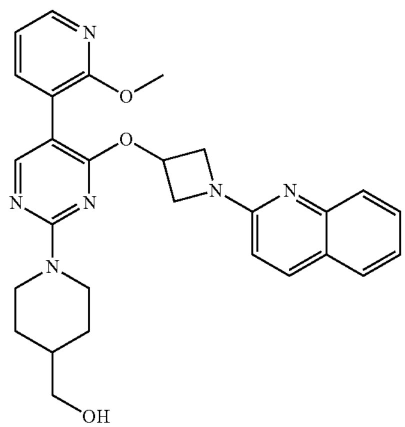 [SMILES: COc1ncccc1-c1cnc(N2CCC(CO)CC2)nc1OC1CN(c2ccc3ccccc3n2)C1] | (1-(5-(2-methoxy-pyridin-3-yl)-4-((1-(quinazolin-2-yl)azetidin-3-yl)oxy)pyrimidin-2-yl)piperidin-4-yl)methanol | 500 | 0.0031 |
| 10.68 | 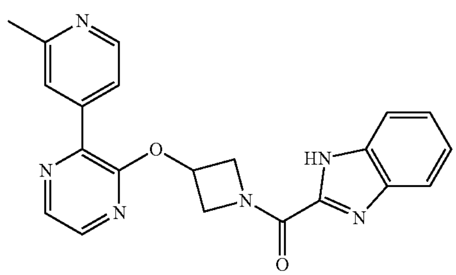 [SMILES: Cc1cc(-c2nccnc2OC2CN(C(=O)c3nc4ccccc4[nH]3)C2)ccn1] | (1H-benzo[d]imidazol-2-yl)(3-(3-(2-methylpyridin-4-yl)pyrazin-2-yloxy)azetidin-1-yl)methanone | 387 | 0.156 |
| 10.69 | 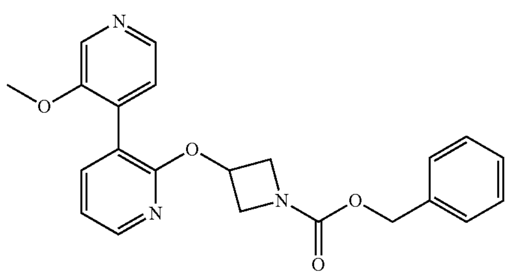 [SMILES: COc1cnccc1-c1cccnc1OC1CN(C(=O)OCc2ccccc2)C1] | benzyl 3-(3'-methoxy-3,4'-bipyridin-2-yloxy)azetidine-1-carboxylate | 393.2 | 7.641 |
| 10.70 | 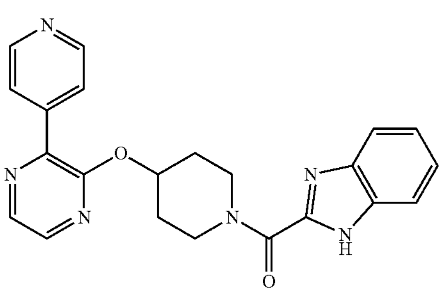 [SMILES: O=C(c1nc2ccccc2[nH]1)N1CCC(Oc2nccnc2-c2ccncc2)CC1] | (1H-Benzo[d]imidazol-2-yl)(4-(3-(pyridine-4-yl)pyrazin-2-yloxy)piperidin-1-yl)methanone. | 401 | 0.2295 |
| 10.71 | 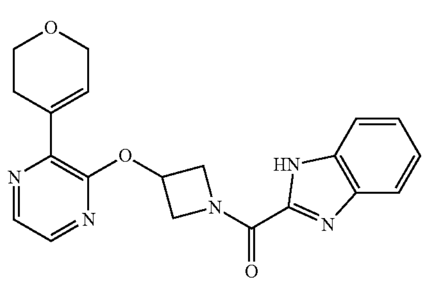 [SMILES: O=C(c1nc2ccccc2[nH]1)N1CC(Oc2nccnc2C2=CCOCC2)C1] | (1H-benzo[d]imidazol-2-yl)(3-((3-(3,6-dihydro-2H-pyran-4-yl)pyrazin-2-yl)oxy)azetidin-1-yl)methanone | 378 | 0.222 |

TABLE 8A-continued

EXAMPLES 10.1-10.78 PREPARED ANALOGOUS TO SCHEME 10

| Ex. # | Structure | Chemical Name | ESI-MS (M + 1) | IC$_{50}$ (uM) |
|---|---|---|---|---|
| 10.72 | 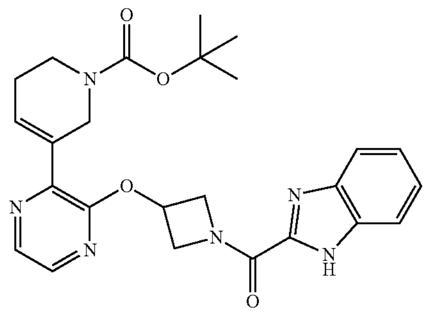 [SMILES: CC(C)(C)OC(=O)N1CCC=C(c2nccnc2OC2CN(C(=O)c3nc4ccccc4[nH]3)C2)C1] | tert-butyl 3-(3-(1-(1H-benzo[d]imidazole-2-carbonyl)azetidin-3-yloxy)pyrazin-2-yl)-3,4-dihydropyridine-1(2H)-carboxylate | 477.2 | 0.227 |
| 10.73 | 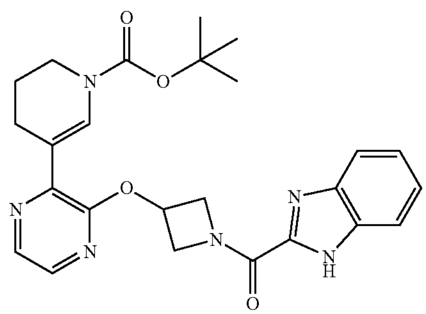 [SMILES: CC(C)(C)OC(=O)N1C=C(c2nccnc2OC2CN(C(=O)c3nc4ccccc4[nH]3)C2)CCC1] | tert-butyl 5-(3-(1-(1H-benzo[d]imidazole-2-carbonyl)azetidin-3-yloxy)pyrazin-2-yl)-3,4-dihydropyridine-1(2H)-carboxylate | 477.2 | 0.0365 |
| 10.74 | 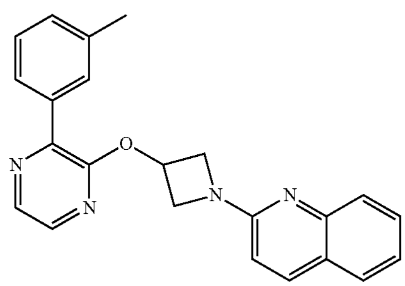 [SMILES: Cc1cccc(-c2nccnc2OC2CN(c3ccc4ccccc4n3)C2)c1] | 2-(3-((3-(m-tolyl)pyrazin-2-yl)oxy)azetidin-1-yl)quinoline | 369 | 0.0573 |
| 10.75 | 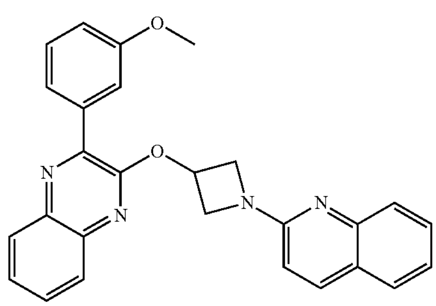 [SMILES: COc1cccc(-c2nc3ccccc3nc2OC2CN(c3ccc4ccccc4n3)C2)c1] | 2-(3-methoxyphenyl)-3-((1-(quinolin-2-yl)azetidin-3-yl)oxy)quinoxaline | 435 | 0.00668 |
| 10.76 | 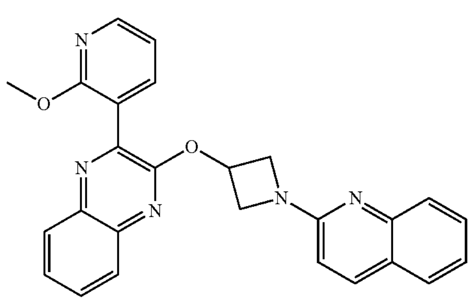 [SMILES: COc1ncccc1-c1nc2ccccc2nc1OC1CN(c2ccc3ccccc3n2)C1] | 2-(2-methoxypyridin-3-yl)-3-((1-(quinolin-2-yl)azetidin-3-yl)oxy)quinoxaline | 436 | 0.0055 |

TABLE 8A-continued

EXAMPLES 10.1-10.78 PREPARED ANALOGOUS TO SCHEME 10

| Ex. # | Structure | Chemical Name | ESI-MS (M + 1) | IC$_{50}$ (uM) |
|---|---|---|---|---|
| 10.77 | 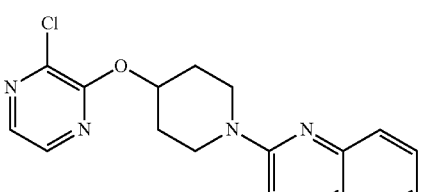 | 2-(3-((2-(pyridin-2-yl)pyrimidin-4-yl)oxy)azetidin-1-yl)quinoline | 355 | 0.109 |
| 10.78 | 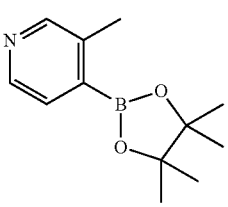 | (4-(4-((1-(quinolin-2-yl)azetidin-3-yl)oxy)pyrimidin-2-yl)phenyl)methanol | 384 | 0.00845 |

*Note:
Examples 10.3 and 10.15 can be prepared according to Scheme 10. However, NMR data of pure products are not available.

TABLE 8B

PREPARATION AND NMR DATA OF EXAMPLES 10.1-10.78

| Ex. # | Starting Material (1) | Starting Material (2) | Reaction Condition | $^1$H NMR (CD$_3$OD, 400 MHz) δ (ppm) |
|---|---|---|---|---|
| 10.1 | 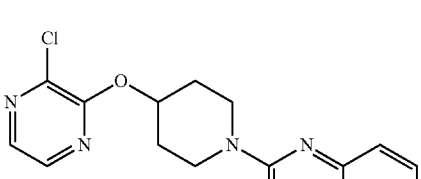<br>(see Preparation P2.1) | (see Preparation P10.1) | Pd(dppf)Cl$_2$, K$_3$PO$_4$, dioxane/water | 8.83-8.74 (m, 2H); 8.42-8.40 (m, 3H); 8.20-8.10 (m, 1H); 7.90-7.88 (m, 3H); 7.54-7.48 (m, 2H); 5.65-5.61 (m, 1H); 4.01-3.93 (m, 4H); 2.45 (s, 3H); 2.35-2.30 (m, 2H); 2.07-2.02 (m, 2H). |
| 10.2 | 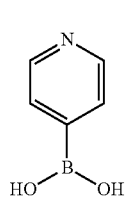<br>(see Preparation P2.1) | | Pd(dppf)Cl$_2$, K$_3$PO$_4$, dioxane/water | 8.59 (dd, J = 1.6, 0.4 Hz, 2H); 8.30 (d, J =2.4 Hz, 1H); 8.23 (d, J = 2.8 Hz, 1H); 8.09 (dd, J = 1.6, 2.0 Hz, 2H); 7.94 (d, J = 4.8 Hz, 1H); 7.95-7.93 (m, 2H); 7.62-7.51 (m, 1H); 7.47-7.14 (m, 2H); 5.54-5.52 (m, 1H); 4.08-4.03 (m, 2H); 3.64-3.62 (m, 2H); 2.17-2.15 (m, 2H); 1.94-1.90 (m, 2H) |

TABLE 8B-continued

PREPARATION AND NMR DATA OF EXAMPLES 10.1-10.78

| Ex. # | Starting Material (1) | Starting Material (2) | Reaction Condition | $^1$H NMR (CD$_3$OD, 400 MHz) δ (ppm) |
|---|---|---|---|---|
| 10.3* | (see Preparation P2.1) | | Pd(dppf)Cl$_2$, K$_3$PO$_4$, dioxane/water | See * note. |
| 10.4 | (see Preparation P2.1) | | Pd(dppf)Cl$_2$, K$_3$PO$_4$, dioxane/water | 8.20-8.17 (m, 3H); 7.94 (d, J = 9.2 Hz, 1H); 7.74 (d, J = 5.2 Hz, 1H); 7.62-7.59 (m, 2H); 7.51-7.47 (m, 1H); 7.20-7.07 (m, 2H); 7.06-7.04 (m, 1H); 5.43-5.39 (m, 1H); 3.86 (s, 5H); 3.70-3.63 (m, 2H); 2.10-2.04 (m, 2H); 1.85-1.77 (m, 2H). |
| 10.5 | (see Preparation P2.1) | | Pd(dppf)Cl$_2$, K$_3$PO$_4$, dioxane/water | 8.29 (d, J = 2.8 Hz, 1H); 8.23-8.10 (m, 2H); 7.96-7.89 (m, 3H); 7.63-7.61 (m, 3H); 7.22-7.15 (m, 2H); 5.56-5.53 (m, 1H); 4.06-4.00 (m, 2H); 3.74-3.68 (m, 2H); 2.56 (s, 3H); 2.21-2.16 (m, 2H); 1.97-1.91 (m, 2H). |
| 10.6 | (see Preparation P2.1) | (see Preparation P10.2) | Pd(dppf)Cl$_2$, K$_3$PO$_4$, dioxane/water | 8.69-8.60 (m, 2H); 8.35-8.34 (m, 3H); 7.95-7.90 (m, 3H); 7.53-7.46 (m, 3H); 5.61-5.58 (m, 1H); 3.97-3.93 (m, 4H); 2.67-2.32 (m, 2H); 2.09-2.02 (m, 2H). |
| 10.7 | (see Preparation P2.6) | | Pd(dppf)Cl$_2$, K$_3$PO$_4$, dioxane/water | (CDCl$_3$) 8.70-8.60 (m, 2H); 8.41 (d, J = 2.0 Hz, 1H); 8.07 (d, J = 8.8 Hz, 1H); 7.94 (s, 1H); 7.85-7.83 (m, 1H); 7.64-7.58 (m, 2H); 7.37-7.34 (m, 2H); 6.63 (d, J = 8.8 Hz, 1H); 5.65 (s, 1H); 4.94-4.50 (m, 4H); 2.4 (s, 3H). |

TABLE 8B-continued

PREPARATION AND NMR DATA OF EXAMPLES 10.1-10.78

| Ex. # | Starting Material (1) | Starting Material (2) | Reaction Condition | $^1$H NMR (CD$_3$OD, 400 MHz) δ (ppm) |
|---|---|---|---|---|
| 10.8 | (see Preparation P2.6) | | Pd(dppf)Cl$_2$, K$_3$PO$_4$, dioxane/water | (CDCl$_3$) 8.75-8.60 (m, 2H); 8.45-8.31 (m, 3H); 7.78-7.72 (m, 3H); 7.32 (d, J = 5.2 Hz, 1H); 7.52-7.48 (m, 1H); 6.95-6.93 (m, 1H); 5.76-5.73 (m, 1H); 4.96-4.91 (m, 2H); 4.52-4.48 (m, 2H). |
| 10.9 | (see Preparation P2.6) | | Pd(dppf)Cl$_2$, K$_3$PO$_4$, dioxane/water | (CDCl$_3$) 8.28-8.27 (m, 2H); 8.26-8.07 (m, 2H); 7.91 (d, J = 8.0 Hz, 1H); 7.75-7.73 (m, 1H); 7.70-7.66 (m, 2H); 7.44-7.40 (m, 1H); 7.03-7.00 (m, 1H); 6.56 (d, J = 9.6 Hz, 1H); 5.64-5.62 (m, 1H); 5.10-4.46 (m, 4H); 3.89 (s, 3H). |
| 10.10 | (see Preparation P2.6) | | Pd(dppf)Cl$_2$, K$_3$PO$_4$, dioxane/water | (CDCl$_3$) 8.29 (d, J = 2.4 Hz, 1H); 8.08 (d, J = 5.6 Hz, 1H); 7.83 (d, J = 8.8 Hz, 1H); 7.72 (d, J = 8.4 Hz, 1H); 7.59-7.52 (m, 2H); 7.36-7.21 (m, 5H); 6.53 (d, J = 8.8 Hz, 1H); 5.55 (s, 1H); 4.60-4.56 (m, 2H); 4.16-4.13 (m, 2H); 2.22 (s, 3H). |
| 10.11 | (see Preparation P2.6) | | Pd(dppf)Cl$_2$, K$_3$PO$_4$, dioxane/water | (CDCl$_3$) 8.30-8.25 (m, 1H); 8.09-8.03 (m, 1H); 7.83-7.81 (m, 1H); 7.74-7.72 (m, 1H); 7.57-7.50 (m, 3H); 7.40-7.35 (m, 2H); 7.24-7.19 (m, 1H); 7.05-7.01 (m, 1H); 6.56 (d, J = 8.8 Hz, 1H); 5.58-5.55 (m, 1H); 4.60-4.58 (m, 2H); 4.56-4.12 (m, 2H); 2.22 (s, 3H). |
| 10.12 | (see Preparation P2.6) | | Pd(dppf)Cl$_2$, K$_3$PO$_4$, dioxane/water | (CDCl$_3$) 8.71-8.60 (m, 2H); 8.30-8.29 (s, 1H); 8.07 (d, J = 2.8 Hz, 1H); 7.95-7.97 (m, 2H); 7.81 (d, J = 8.4 Hz, 1H); 7.54-7.52 (m, 1H); 7.49-7.45 (m, 2H); 7.18-7.15 (m, 1H); 6.53 (d, J = 8.8 Hz, 1H); 5.60-5.57 (m, 1H); 4.62-4.58 (m, 2H); 4.23-4.20 (m, 2H). |

TABLE 8B-continued

PREPARATION AND NMR DATA OF EXAMPLES 10.1-10.78

| Ex. # | Starting Material (1) | Starting Material (2) | Reaction Condition | $^1$H NMR (CD$_3$OD, 400 MHz) δ (ppm) |
|---|---|---|---|---|
| 10.13 | 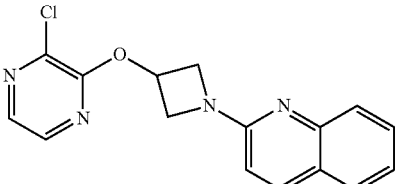<br>(see Preparation P2.6) | 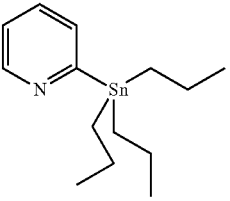 [SMILES: CC[CH2][Sn]([CH2]CC)([CH2]CC)[c]1ccccn1] | Pd(PPh$_3$)$_4$, toluene | 9.09-8.97 (m, 2H); 8.74-8.70 (m, 2H); 8.70-8.60 (m, 1H); 8.51 (d, J = 2.4 Hz, 1H); 8.33 (d, J = 9.6 Hz, 1H); 8.12-8.09 (m, 1H); 7.86 (d, J = 8.4 Hz, 1H); 7.78-7.76 (m, 2H); 7.47-7.50 (m, 1H); 6.98 (d, J = 9.2 Hz, 1H); 5.91-5.88 (m, 1H); 5.153-5.03 (m, 4H). |
| 10.14 | 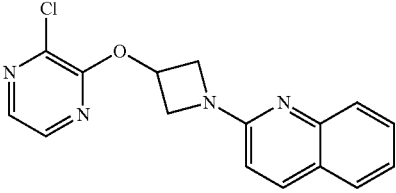<br>(see Preparation P2.6) | 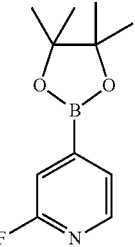 | Pd(dppf)Cl$_2$, K$_3$PO$_4$, dioxane/water | 8.39-8.34 (m, 2H); 8.29-8.16 (m, 1H); 8.11-8.09 (m, 2H); 7.96-7.89 (m, 4H); 7.52-7.24 (m, 1H); 6.64-6.62 (m, 1H); 5.69 (s, 1H); 5.25-5.01 (m, 2H); 4.91-4.63 (m, 2H). |
| 10.15* | 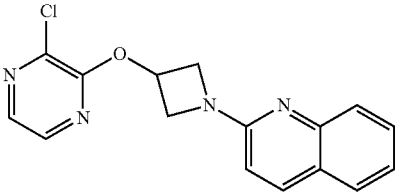<br>(see Preparation P2.6) | 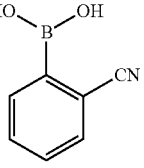 | Pd(dppf)Cl$_2$, K$_3$PO$_4$, dioxane/water | See * note. |
| 10.16 | 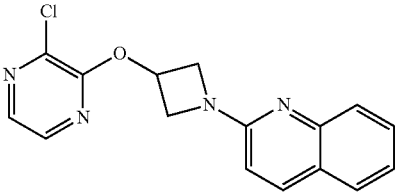<br>(see Preparation P2.1) | 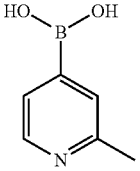 | Pd(dppf)Cl$_2$, K$_3$PO$_4$, dioxane/water | (CDCl$_3$) 7.74 (s, 1H); 7.65 (d, J = 8.4 Hz, 1H); 7.50-7.42 (m, 6H); 7.26-7.22 (m, 1H); 7.14-7.10 (m, 2H); 6.47 (d, J = 8.8 Hz, 1H); 5.52-5.49 (m, 1H); 4.56-4.52 (m, 2H); 4.51-4.15 (m, 2H); 2.31 (s, 3H). |
| 10.17 | 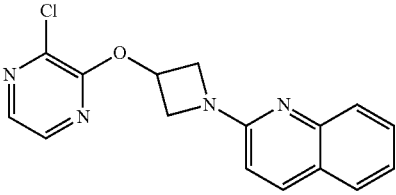<br>(see Preparation P2.6) | 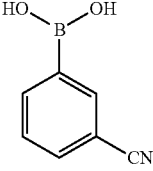 | Pd(dppf)Cl$_2$, K$_3$PO$_4$, dioxane/water | (CDCl$_3$) 8.35 (s, 1H); 8.34-8.30 (m, 1H); 8.1 (d, J = 0.28 Hz, 1H); 7.75 (d, J = 3.6 Hz, 1H); 7.65 (d, J = 7.6 Hz, 2H); 7.59-7.459 (m, 3H); 7.24-7.19 (m, 1H); 5.61-5.57 (m, 1H); 6.58 (d, J = 8.8 Hz, 1H); 5.64-5.61 (m, 1H); 4.66-4.62 (m, 2H); 4.26-4.23 (m, 2H). |

TABLE 8B-continued

PREPARATION AND NMR DATA OF EXAMPLES 10.1-10.78

| Ex. # | Starting Material (1) | Starting Material (2) | Reaction Condition | $^1$H NMR (CD$_3$OD, 400 MHz) δ (ppm) |
|---|---|---|---|---|
| 10.18 | 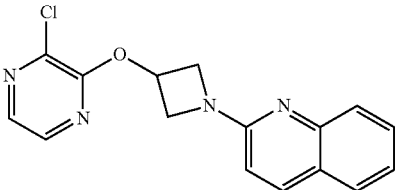<br>(see Preparation P2.6) | 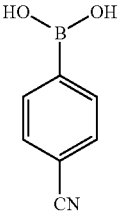 | Pd(dppf) Cl$_2$, K$_3$PO$_4$, dioxane/ water | (CDCl$_3$) 8.25 (d, J = 1.6 Hz, 1H); 8.21 (d, J = 2.8 Hz, 1H); 7.87-7.82 (m, 3H); 7.80-7.55 (m, 5H); 7.50-7.46 (m, 1H); 6.95 (d, J = 9.6 Hz, 1H); 5.77-5.73 (m, 1H); 5.00-4.91 (m, 2H); 4.64-4.60 (m, 2H). |
| 10.19 | 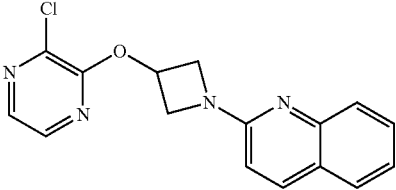<br>(see Preparation P2.6) | 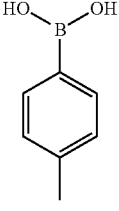 | Pd(dppf) Cl$_2$, K$_3$PO$_4$, dioxane/ water | (CDCl$_3$) 8.27 (d, J = 2.8 Hz, 1H); 8.00-7.97 (m, 3H); 7.86 (d, J = 9.2 Hz, 1H); 7.74 (d, J = 8.4 Hz, 1H); 7.60-7.51 (m, 2H); 7.26-7.20 (m, 3H); 6.58 (d, J = 9.2 Hz, 1H); 5.63-5.59 (m, 1H); 4.06-4.62 (m, 2H); 4.29-4.25 (m, 2H); 2.38 (s, 3H). |
| 10.20 | 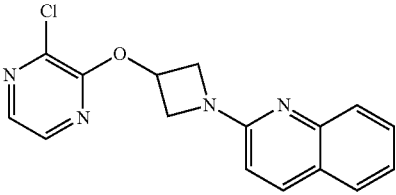<br>(see Preparation P2.6) |  | Pd(dppf) Cl$_2$, K$_3$PO$_4$, dioxane/ water | 8.33-8.22 (m, 3H); 7.84 (d, J = 8.0 Hz, 1H); 7.74-7.73 (m, 2H); 7.47 (s, 1H); 7.36-7.34 (m, 1H); 7.03-6.97 (m, 2H); 6.89-6.87 (m, 1H); 5.70-5.67 (m, 1H); 4.939-4.89 (m, 2H); 4.47-4.43 (m, 2H); 2.18 (s, 3H). |
| 10.21 | 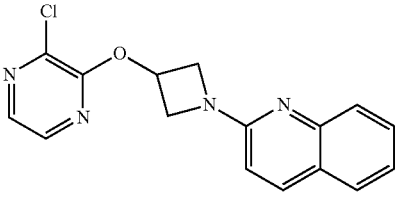<br>(see Preparation P2.6) | 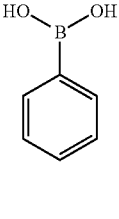 | Pd(dppf) Cl$_2$, K$_3$PO$_4$, dioxane/ water | 8.28-8.25 (m, 1H); 8.10-8.08 (m, 1H); 7.98-7.95 (m, 2H); 7.84 (d, J = 8.8 Hz, 1H); 7.61-7.55 (m, 2H); 7.47-7.30 (m, 4H); 7.19-7.16 (m, 1H); 6.55 (d, J = 8.8 Hz, 1H); 5.52-5.49 (m, 1H); 4.54-4.49 (m, 2H); 4.13-4.09 (m, 2H). |
| 10.22 | 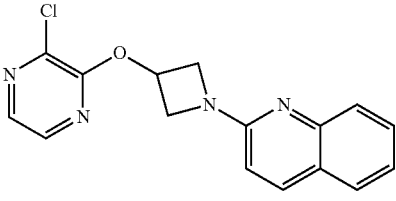<br>(see Preparation P2.6) | 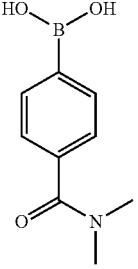 | Pd(dppf) Cl$_2$, K$_3$PO$_4$, dioxane/ water | 8.23 (s, 1H); 8.10-8.06 (m, 1H); 7.85 (s, 3H); 7.61-7.54 (m, 2H); 7.45-7.43 (m, 3H); 7.16-7.15 (m, 1H); 6.55 (d, J = 8.8 Hz, 1H); 5.52 (s, 1H); 4.54-4.50 (m, 2H); 4.151-4.11 (m, 2H); 3.03 (s, 3H); 2.91 (s, 3H). |

TABLE 8B-continued

PREPARATION AND NMR DATA OF EXAMPLES 10.1-10.78

| Ex. # | Starting Material (1) | Starting Material (2) | Reaction Condition | $^1$H NMR (CD$_3$OD, 400 MHz) δ (ppm) |
|---|---|---|---|---|
| 10.23 | (see Preparation P2.6) | | Pd(dppf)Cl$_2$, K$_3$PO$_4$, dioxane/water | (CDCl$_3$) 8.63 (s, 1H); 8.35 (d, J = 1.6 Hz, 1H); 8.25 (d, J = 7.6 Hz, 1H); 8.08-8.06 (m, 2H); 7.99-7.97 (m, 2H); 7.65-7.63 (m, 2H); 7.39-7.35 (m, 1H); 7.25 (s, 1H); 6.61-6.59 (m, 1H); 5.64 (s, 1H); 5.01-4.58 (m, 4H); 2.62 (s, 3H). |
| 10.24 | (see Preparation P2.6) | | Pd(dppf)Cl$_2$, K$_3$PO$_4$, dioxane/water | 8.33 (d, J = 2.4 Hz, 1H); 8.90-7.09 (m, 5H); 7.66-7.62 (m, 2H); 7.47-7.36 (m, 3H); 6.57 (d, J = 9.2 Hz, 1H); 5.60 (s, 1H); 5.07-4.70 (m, 5H); 4.43-4.33 (m, 1H); 3.39 (s, 3H). |
| 10.25 | (see Preparation P2.6) | | Pd(dppf)Cl$_2$, K$_3$PO$_4$, dioxane/water | (CDCl$_3$) 8.30 (s, 1H); 8.08-8.03 (m, 4H); 7.83-7.82 (m, 1H); 7.64-7.59 (m, 2H); 7.49-7.34 (m, 2H); 7.32-7.25 (m, 1H); 6.61 (d, J = 7.6 Hz, 1H); 5.59 (s, 1H); 5.03-4.44 (m, 4H); 3.09 (s, 3H); 3.00 (s, 3H). |
| 10.26 | (see Preparation P2.6) | | Pd(dppf)Cl$_2$, K$_3$PO$_4$, dioxane/water | (CDCl$_3$) 8.36 (d, J = 2.4 Hz, 1H); 8.17-7.98 (m, 7H); 7.68-7.64 (m, 2H); 7.40-7.37 (m, 1H); 6.59 (d, J = 9.2 Hz, 1H); 5.65 (s, 1H); 5.02-4.62 (m, 4H); 3.61 (s, 3H). |
| 10.27 | (see Preparation P2.6) | | Pd(dppf)Cl$_2$, K$_3$PO$_4$, dioxane/water | 8.31-8.25 (m, 2H); 8.09-8.08 (m, 2H); 8.07-7.79 (m, 3H); 7.70-7.69 (m, 2H); 7.43-7.39 (m, 1H); 6.90-6.87 (m, 1H); 5.69-5.65 (m, 1H); 4.92-4.88 (m, 4H); 4.55-4.51 (m, 2H); 2.84 (s, 3H). |

TABLE 8B-continued

PREPARATION AND NMR DATA OF EXAMPLES 10.1-10.78

| Ex. # | Starting Material (1) | Starting Material (2) | Reaction Condition | $^1$H NMR (CD$_3$OD, 400 MHz) δ (ppm) |
|---|---|---|---|---|
| 10.28 | (see Preparation P2.6) | | Pd(dppf)Cl$_2$, K$_3$PO$_4$, dioxane/ water | (CDCl$_3$) 9.42 (s, 1H); 8.52 (d, J = 6.0 Hz, 1H); 8.31 (d, J = 5.2 Hz, 1H); 8.11 (d, J = 5.6 Hz, 1H); 7.83 (d, J = 9.2 Hz, 1H); 7.69 (d, J = 8.4 Hz, 1H); 7.79-7.15 (m, 1H); 7.55-7.46 (m, 2H); 7.29-7.15 (m, 1H); 6.54 (d, J = 8.8 Hz, 1H); 5.63-5.61 (m, 1H); 4.65-4.61 (m, 2H); 4.24-4.21 (m, 2H). |
| 10.29 | (see Preparation P2.4) | | Pd(dppf)Cl$_2$, K$_3$PO$_4$, dioxane/ water | 8.51 (d, J = 4.4 Hz, 1H); 8.59-8.50 (m, 2H); 8.45-8.46 (m, 2H); 8.37-8.40 (m, 1H); 7.89-7.96 (m, 2H); 7.77-7.81 (m, 1H); 7.50-7.54 (m, 1H); 7.23-7.28 (m, 1H); 6.08-6.11 (m, 1H); 4.24-4.33 (m, 2H); 4.05-4.18 (m, 2H); 2.80 (s, 3H); 2.65-2.70 (m, 2H). |
| 10.30 | (see Preparation P2.5) | | Pd(dppf)Cl$_2$, K$_3$PO$_4$, dioxane/ water | 8.71 (d, 7 = 4.4 Hz, 1H); 8.57-8.51 (m, 3H); 8.46-8.45 (m, 1H); 8.44-8.40 (m, 1H); 7.96-7.92 (m, 2H); 7.91-7.80 (m, 1H); 7.78-7.54 (m, 1H); 7.53-7.25 (m, 1H); 6.11-6.08 (m, 1H); 4.33-4.04 (m, 4H); 2.80 (s, 3H); 2.70-2.65 (m, 2H). |
| 10.31 | (see Preparation P3.2) | | Pd(dppf)Cl$_2$, K$_3$PO$_4$, dioxane/ water | (CDCl$_3$) 10.00 (s, 1H); 9.29 (d, J = 8 Hz, 1H); 8.86 (d, J = 4.8 Hz, 1H); 8.70 (d, J = 1.6 Hz, 1H); 8.13 (d, J = 9.2 Hz, 1H); 8.00-7.93 (m, 2H); 7.75-7.71 (m, 2H); 7.48-7.44 (m, 1H); 6.97-6.94 (m, 2H); 5.69 (s, 1H); 5.27-5.23 (m, 2H); 4.85-4.65 (m, 2H). |
| 10.32 | (see Preparation P3.2) | | Pd(dppf)Cl$_2$, K$_3$PO$_4$, dioxane/ water | (CDCl$_3$) 8.95 (s, 2H); 8.76-8.75 (m, 3H); 8.15 (d, J = 9.2 Hz, 1H); 7.96-7.94 (m, 1H); 7.73-7.71 (m, 2H); 7.47-7.45 (m, 1H); 7.00 (d, J = 5.6 Hz, 1H); 6.70 (d, J = 9.2 Hz, 1H); 5.80 (s, 1H); 5.32-5.04 (m, 2H); 4.70-4.69 (m, 2H). |

TABLE 8B-continued

PREPARATION AND NMR DATA OF EXAMPLES 10.1-10.78

| Ex. # | Starting Material (1) | Starting Material (2) | Reaction Condition | $^1$H NMR (CD$_3$OD, 400 MHz) δ (ppm) |
|---|---|---|---|---|
| 10.33 | (see Preparation P3.2) | | Pd(dppf)Cl$_2$, K$_3$PO$_4$, dioxane/water | (CDCl$_3$) 8.50 (d, J = 1.6 Hz, 1H); 8.27 (d, J = 8 Hz, 2H); 7.92 (d, J = 8.8 Hz, 1H); 7.78-7.76 (m, 1H); 7.66-7.64 (m, 1H); 7.60-7.55 (m, 1H); 7.27-7.25 (m, 1H); 6.77 (d, J = 8 Hz, 2H); 6.68-6.66 (m, 1H); 6.60 (d, J = 5.6 Hz, 1H); 5.77-5.75 (m, 1H); 4.77-4.73 (m, 2H); 4.34-4.30 (m, 2H); 3.99 (s, 2H). |
| 10.34 | (see Preparation P2.6) | | Pd(dppf)Cl$_2$, K$_3$PO$_4$, dioxane/water | (CDCl$_3$) 9.06-9.01 (m, 1H); 858-8.50 (m, 1H); 8.31-8.29 (m, 1H); 8.19-8.16 (m, 1H); 7.82-7.70 (m, 1H); 7.58-7.49 (m, 3H); 7.21-7.17 (m, 1H); 6.99-6.96 (m, 1H); 6.56 (d, J = 8.8 Hz, 1H); 5.62-5.59 (m, 1H); 4.64-4.60 (m, 2H); 4.25-4.22 (m, 2H). |
| 10.35 | (see Preparation P2.6) | | Pd(dppf)Cl$_2$, K$_3$PO$_4$, dioxane/water | (CDCl$_3$) 8.60 (s, 1H); 8.51-8.50 (m, 1H); 8.35-8.34 (m, 1H); 8.17-8.15 (m, 1H); 7.88-7.86 (m, 1H); 7.72-7.70 (m, 1H); 7.61-7.52 (m, 2H); 7.26-7.21 (m, 2H); 6.59-6.56 (m, 1H); 5.62-5.57 (m, 1H); 4.62-4.59 (m, 2H); 4.16-4.13 (m, 2H); 2.27 (s, 3H). |
| 10.36 | (see Preparation P2.6) | | Pd(dppf)Cl$_2$, K$_3$PO$_4$, dioxane/water | (CDCl$_3$) 8.78 (s, 1H); 851-8.38 (m, 2H); 8.27 (s, 1H); 8.13-8.10 (m, 1H); 7.86-7.84 (m, 2H); 7.69-7.62 (m, 2H); 7.42-7.38 (m, 1H); 6.68 (d, J = 8.4 Hz, 1H); 5.68 (s, 1H); 5.01-4.90 (m, 2H); 4.57-4.52 (m, 2H); 2.75 (s, 3H). |
| 10.37 | (see Preparation P2.6) | | Pd(dppf)Cl$_2$, K$_3$PO$_4$, dioxane/water | (CDCl$_3$) 833-8.32 (m, 1H); 8.07-8.06 (m, 1H); 8.13-8.10 (m, 1H); 7.89 (d, J = 9.2 Hz, 1H); 7.79-7.70 (m, 3H); 7.64-7.56 (m, 2H); 7.42-7.38 (m, 1H); 7.02-7.00 (m, 1H); 6.68 (d, J = 8.8 Hz, 1H); 5.65-5.63 (m, 1H); 4.70-4.66 (m, 2H); 4.32-4.29 (m, 2H); 3.87 (s, 3H). |

TABLE 8B-continued

PREPARATION AND NMR DATA OF EXAMPLES 10.1-10.78

| Ex. # | Starting Material (1) | Starting Material (2) | Reaction Condition | $^1$H NMR (CD$_3$OD, 400 MHz) δ (ppm) |
|---|---|---|---|---|
| 10.38 | (see Preparation P2.13) | | Pd(dppf)Cl$_2$, K$_3$PO$_4$, dioxane/water | (CDCl$_3$) 9.02 (s, 1H); 8.30-8.29 (m, 1H); 8.13-8.12 (m, 1H); 7.72-7.63 (m, 5H); 7.39-7.35 (m, 1H); 7.27-7.23 (m, 1H); 7.00-6.97 (m, 1H); 5.64-5.61 (m, 1H); 4.76-4.71 (m, 2H); 4.38-4.35 (m, 2H); 3.85 (s, 3H). |
| 10.39 | (see Preparation P2.13) | | Pd(dppf)Cl$_2$, K$_3$PO$_4$, dioxane/water | (CDCl$_3$) 9.01 (s, 1H); 8.26-8.23 (m, 2H); 8.11-8.09 (m, 1H); 7.76-7.74 (m, 1H); 7.68-7.66 (m, 2H); 7.62-7.61 (m, 1H); 7.26-7.22 (m, 1H); 7.01-6.98 (m, 1H); 5.62-5.59 (m, 1H); 4.69-4.65 (m, 2H); 4.25-4.22 (m, 2H); 3.83 (s, 3H). |
| 10.40 | (see Preparation P2.8) | | Pd(dppf)Cl$_2$, K$_3$PO$_4$, Dioxane/water | (CDCl$_3$) 8.15-8.13 (m, 1H); 7.73-7.71 (m, 2H); 7.70-7.63 (m, 2H); 7.60-7.56 (m, 5H); 7.44-7.40 (m, 1H); 7.34-7.32 (m, 1H); 7.28-7.25 (m, 1H); 6.65 (d, J = 8.8 Hz, 1H); 5.85-5.79 (m, 1H); 4.79-4.76 (m, 2H); 4.38-4.35 (m, 2H); 2.48 (s, 3H). |
| 10.41 | (see Preparation P2.6) | | Pd(PPh$_3$)$_4$, Na$_2$CO$_3$, Dioxane/water | (d$_6$-DMSO) 2.57 (br. s., 2H) 4.11-4.22 (m, 4H) 4.29 (d, J = 2.20 Hz, 2H) 4.51-4.63 (m, 2H) 5.58 (d, J = 6.60 Hz, 1H) 6.79 (d, J = 9.68 Hz, 1H) 7.09 (s, 1H), 7.19-7.29 (m, 1H) 7.46-7.63 (m, 2H) 7.72 (d, J = 8.80 Hz, 1H) 8.00-8.12 (m, 2H) 8.27 (d, J = 2.64 Hz, 1H). |
| 10.42 | (see Preparation P2.6) | (from Amgen ASDI) | Pd(PPh$_3$)$_4$, Na$_2$CO$_3$, Dioxane/water | (d$_6$-DMSO) 4.03 (s, 2H) 4.28-4.40 (m, 2H) 4.57-4.69 (m, 2H) 5.67-5.78 (m, 1H) 6.82 (d, J = 9.24 Hz, 1H) 7.12-7.32 (m, 7H) 7.49-7.64 (m, 4H) 7.72 (d, J = 9.24 Hz, 1H) 7.83 (s, 1H) 8.06 (d, J = 9.24 Hz, 1H) 8.24 (d, J = 2.64 Hz, 1H) 8.41 (d, J = 2.64 Hz, 1H). |

TABLE 8B-continued

PREPARATION AND NMR DATA OF EXAMPLES 10.1-10.78

| Ex. # | Starting Material (1) | Starting Material (2) | Reaction Condition | $^1$H NMR (CD$_3$OD, 400 MHz) δ (ppm) |
|---|---|---|---|---|
| 10.43 | (see Preparation P2.6) | (from Amgen ASDI) | Pd(PPh$_3$)$_4$, Na$_2$CO$_3$, Dioxane/ water | (d$_6$-DMSO) 4.35 (d, J = 5.67 Hz, 2H) 4.73 (t, J = 7.82 Hz, 2H) 5.35 (br s, 2H) 5.64-5.75 (m, 1H) 6.64 (d, J = 8.80 Hz, 1H) 7.52-7.70 (m, 4H) 7.77 (d, J = 7.63 Hz, 1H) 7.92 (d, J = 9.00 Hz, 1H) 8.09 (d, J = 2.54 Hz, 1H) 8.35 (d, J = 2.54 Hz, 1H) 8.49-8.60 (m, 2H) 9.11 (s, 1H). |
| 10.44 | (see Preparation P2.6) | (from Amgen ASDI) | Pd(PPh$_3$)$_4$, Na$_2$CO$_3$, Dioxane/ water | (d$_6$-DMSO) 3.90 (s, 3H) 4.13-4.26 (m, 2H) 4.60 (dd, J = 10.34, 7.26 Hz, 2H) 5.57-5.72 (m, 1H) 6.81 (d, J = 9.24 Hz, 1H) 6.95 (d, J = 9.68 Hz, 1H) 7.24 (t, J = 8.14 Hz, 1H) 7.48-7.64 (m, 2H) 7.72 (d, J = 9.24 Hz, 1H) 8.06 (d, J = 9.24 Hz, 1H) 8.21 (d, J = 2.64 Hz, 1H) 8.34-8.43 (m, 2H) 8.91 (d, J = 2.64 Hz, 1H). |
| 10.45 | (see Preparation P2.6) | (from Amgen ASDI) | Pd(PPh$_3$)$_4$, Na$_2$CO$_3$, Dioxane/ water | (d$_6$-DMSO) 4.24 (d, J = 14.96 Hz, 2H) 4.59-4.68 (m, 2H) 5.68 (s, 1H) 6.83 (d, J = 9.24 Hz, 1H) 7.21-7.31 (m, 1H) 7.51-7.66 (m, 3H) 7.73 (d, J = 8.36 Hz, 1H) 8.08 (d, J = 9.68 Hz, 1H) 8.17-8.32 (m, 3H) 8.45 (d, J = 2.64 Hz, 1H) 8.80 (s, 1H). |
| 10.46 | (see Preparation P2.6) | (from Amgen ASDI) | Pd(PPh$_3$)$_4$, Na$_2$CO$_3$, Dioxane/ water | (d$_6$-DMSO) 4.18-4.27 (m, 2H) 4.54-4.66 (m, 2H) 5.59-5.69 (m, 1H) 6.81 (d, J = 9.24 Hz, 1H) 7.20-7.29 (m, 1H) 7.49-7.76 (m, 4H) 8.07 (d, J = 9.68 Hz, 1H) 8.31 (d, J = 2.20 Hz, 1H) 8.41-8.56 (m, 2H) 9.07 (d, J = 2.64 Hz, 1H). |
| 10.47 | (see Preparation P2.6) | (from Amgen ASDI) | Pd(PPh$_3$)$_4$, Na$_2$CO$_3$, Dioxane/ water | (d$_6$-DMSO) 4.19 (d, J = 9.68 Hz, 2H) 4.56-4.65 (m, 2H) 5.64 (d, J = 6.60 Hz, 1H) 6.82 (d, J = 9.24 Hz, 1H) 7.18-7.29 (m, 1H) 7.41-7.77 (m, 6H) 8.02-8.17 (m, 2H) 8.21-8.29 (m, 1H) 8.42 (d, J = 2.64 Hz, 1H) |

TABLE 8B-continued

PREPARATION AND NMR DATA OF EXAMPLES 10.1-10.78

| Ex. # | Starting Material (1) | Starting Material (2) | Reaction Condition | $^1$H NMR (CD$_3$OD, 400 MHz) δ (ppm) |
|---|---|---|---|---|
| 10.48 | (see Preparation P2.6) | (from Amgen ASDI) | Pd(PPh$_3$)$_4$, Na$_2$CO$_3$, Dioxane/ water | (d$_6$-DMSO) 4.16 (dd, J = 10.56, 4.40 Hz, 2H) 4.51-4.63 (m, 4H) 5.34 (d, J = 5.72 Hz, 1H) 5.58-5.68 (m, 1H) 6.79 (d, J = 9.24 Hz, 1H) 7.23 (t, J = 8.14 Hz, 1H) 7.35-7.63 (m, 4H) 7.71 (d, J = 8.80 Hz, 1H) 7.91-8.08 (m, 3H) 8.22 (d, J = 2.64 Hz, 1H) 8.39 (d, J = 2.64 Hz, 1H). |
| 10.49 | (see Preparation P2.6) | (from Amgen ASDI) | Pd(PPh$_3$)$_4$, Na$_2$CO$_3$, Dioxane/ water | (d$_6$-DMSO) 3.92-4.01 (m, 2H) 4.29-4.43 (m, 4H) 5.36-5.46 (m, 1H) 6.59 (d, J = 9.24 Hz, 1H) 7.03 (t, J = 7.70 Hz, 1H) 7.22 (d, J = 8.36 Hz, 2H) 7.28-7.43 (m, 2H) 7.51 (d, J = 8.80 Hz, 1H) 7.82 (d, J = 8.36 Hz, 3H) 7.99 (d, J = 2.64 Hz, 1H) 8.16 (d, J = 2.64 Hz, 1H). |
| 10.50 | (see Preparation P2.6) | (from Amgen ASDI) | Pd(PPh$_3$)$_4$, Na$_2$CO$_3$, Dioxane/ water | (d$_6$-DMSO) 3.92 (dd, J = 10.56, 4.40 Hz, 2H) 4.49 (dd, J = 9.90, 7.26 Hz, 2H) 5.51-5.65 (m, 1H) 6.71 (d, J = 9.24 Hz, 1H) 7.17-7.27 (m, 1H) 7.36-7.75 (m, 4H) 7.77-7.92 (m, 2H) 8.01 (d, J = 9.68 Hz, 1H) 8.13 (d, J = 8.80 Hz, 2H) 8.38 (d, J = 2.64 Hz, 1H) 8.49 (d, J = 3.08 Hz, 1H) 8.88 (dd, J = 4.18, 1.54 Hz, 1H) |
| 10.51 | (see Preparation P2.6) | (from Amgen ASDI) | Pd(PPh$_3$)$_4$, Na$_2$CO$_3$, Dioxane/ water | (d$_6$-DMSO) 4.31 (dd, J = 9.68, 3.96 Hz, 2H) 4.57-4.70 (m, 2H) 5.72 (br. s., 1H) 6.83 (d, J = 9.24 Hz, 1H) 7.24 (t, J = 7.70 Hz, 1H) 7.33-7.65 (m, 6H) 7.73 (d, J = 7.92 Hz, 3H) 8.03-8.11 (m, 2H) 8.15 (d, J = 2.64 Hz, 1H) 8.30 (d, J = 2.64 Hz, 1H) |
| 10.52 | (see Preparation P2.6) | (from Amgen ASDI) | Pd(PPh$_3$)$_4$, Na$_2$CO$_3$, Dioxane/ water | (d$_6$-DMSO) 4.19 (dd, J = 10.56, 3.96 Hz, 2H) 4.59 (dd, J = 10.56, 7.04 Hz, 2H) 5.57-5.73 (m, 1H) 6.80 (d, J = 9.24 Hz, 1H) 7.19-7.30 (m, 1H) 7.48-7.64 (m, 3H) 7.72 (d, J = 9.24 Hz, 1H) 8.05 (d, J = 9.24 Hz, 1H) 8.29 (d, J = 2.64 Hz, 1H) 8.39-8.49 (m, 2H) 8.63 (d, J = 5.28 Hz, 1H) 9.22 (s, 1H) |

TABLE 8B-continued

PREPARATION AND NMR DATA OF EXAMPLES 10.1-10.78

| Ex. # | Starting Material (1) | Starting Material (2) | Reaction Condition | ¹H NMR (CD$_3$OD, 400 MHz) δ (ppm) |
|---|---|---|---|---|
| 10.53 | (see Preparation P2.6) | (from Amgen ASDI) | Pd(PPh$_3$)$_4$, Na$_2$CO$_3$, Dioxane/ water | (d$_6$-DMSO) 4.23-4.36 (m, 2H) 4.60-4.70 (m, 2H) 5.64-5.75 (m, 1H) 6.84 (d, J = 9.24 Hz, 1H) 7.27 (d, J = 7.92 Hz, 1H) 7.50-7.90 (m, 5H) 8.03-8.20 (m, 3H) 8.33 (d, J = 2.64 Hz, 1H) 8.51 (d, J = 2.64 Hz, 1H) 9.07 (s, 1H) 9.55 (d, J = 2.20 Hz, 1H). |
| 10.54 | (see Preparation P2.6) | (from Amgen ASDI) | Pd(PPh$_3$)$_4$, Na$_2$CO$_3$, Dioxane/ water | (d$_6$-DMSO) 3.87 (s, 3H) 4.20 (dd, J = 10.34, 4.18 Hz, 2H) 4.59 (dd, J = 10.34, 6.82 Hz, 2H) 5.59-5.70 (m, 1H) 6.80 (d, J = 9.24 Hz, 1H) 7.18-7.29 (m, 1H) 7.49-7.64 (m, 2H) 7.72 (d, J = 9.24 Hz, 1H) 8.00-8.11 (m, 3H) 8.17-8.31 (m, 3H) 8.44 (d, J = 2.64 Hz, 1H) |
| 10.55 | (see Preparation P2.6) | (from Amgen ASDI) | Pd(PPh$_3$)$_4$, Na$_2$CO$_3$, Dioxane/ water | (d$_6$-DMSO) 1.24 (d, J = 6.16 Hz, 6H) 4.09-4.24 (m, 2H) 4.54-4.67 (m, 3H) 5.57-5.71 (m, 1H) 6.75-6.93 (m, 2H) 7.18-7.29 (m, 1H) 7.36-7.63 (m, 4H) 7.72 (d, J = 9.24 Hz, 1H) 8.05 (d, J = 9.24 Hz, 1H) 8.26 (d, J = 2.64 Hz, 1H) 8.40 (d, J = 2.64 Hz, 1H). |
| 10.56 | (see Preparation P2.6) | (from Amgen ASDI) | Pd(PPh$_3$)$_4$, Na$_2$CO$_3$, Dioxane/ water | (d$_6$-DMSO) 4.22 (dd, J = 10.34, 4.18 Hz, 2H) 4.59 (dd, J = 10.34, 7.26 Hz, 2H) 5.62-5.71 (m, 1H) 6.81 (d, J = 9.24 Hz, 1H) 7.18-7.29 (m, 1H) 7.49-7.76 (m, 5H) 8.05 (d, J = 9.68 Hz, 1H) 8.35 (d, J = 2.64 Hz, 1H) 8.48 (d, J = 2.64 Hz, 1H) 9.42 (s, 1H) |
| 10.57 | (see Preparation P2.6) | (from Amgen ASDI) | Pd(PPh$_3$)$_4$, Na$_2$CO$_3$, Dioxane/ water | (d$_6$-DMSO) 2.54 (s, 3H) 4.21 (dd, J = 10.56, 4.40 Hz, 2H) 4.60 (dd, J = 10.34, 7.26 Hz, 2H) 5.60-5.69 (m, 1H) 6.80 (d, J = 9.24 Hz, 1H) 7.19-7.29 (m, 1H) 7.49-7.63 (m, 2H) 7.72 (d, J = 9.24 Hz, 1H) 7.83-7.92 (m, 2H) 8.05 (d, J = 9.24 Hz, 1H) 8.33 (d, J = 2.64 Hz, 1H) 8.45 (d, J = 2.64 Hz, 1H) 8.56 (d, J = 5.28 Hz, 1H) |

TABLE 8B-continued

PREPARATION AND NMR DATA OF EXAMPLES 10.1-10.78

| Ex. # | Starting Material (1) | Starting Material (2) | Reaction Condition | $^1$H NMR (CD$_3$OD, 400 MHz) δ (ppm) |
|---|---|---|---|---|
| 10.58 | (see Preparation P2.6) | (from Amgen ASDI) | Pd(PPh$_3$)$_4$, Na$_2$CO$_3$, Dioxane/ water | (d$_6$-DMSO) 3.98 (s, 3H) 4.17-4.26 (m, 2H) 4.59 (dd, J = 10.56, 7.04 Hz, 2H) 5.60-5.72 (m, 1H) 6.81 (d, J = 9.68 Hz, 1H) 7.24 (t, J = 8.14 Hz, 1H) 7.49-7.64 (m, 3H) 7.72 (d, J = 8.36 Hz, 1H) 8.05 (d, J = 9.24 Hz, 1H) 8.27 (d, J = 2.64 Hz, 1H) 8.41 (s, 1H) 9.25 (s, 1H). |
| 10.59 | (see Preparation P2.6) | (from Amgen ASDI) | Pd(PPh$_3$)$_4$, Na$_2$CO$_3$, Dioxane/ water | (d$_6$-DMSO) 0.31 (d, J = 5.28 Hz, 2H) 0.54 (d, J = 8.36 Hz, 2H) 4.08-4.27 (m, 5H) 4.51-4.67 (m, 2H) 5.64 (br. s., 1H) 6.73-7.01 (m, 2H) 7.24 (d, J = 8.36 Hz, 1H) 7.46-7.79 (m, 4H) 8.04 (d, J = 9.68 Hz, 1H) 8.20 (br. s., 1H) 8.32-8.46 (m, 1H) 8.87 (br. S., 1H) |
| 10.60 | (see Preparation P2.6) | (from Amgen ASDI) | Pd(PPh$_3$)$_4$, Na$_2$CO$_3$, Dioxane/ water | (d$_6$-DMSO) 2.52 (s, 3H) 4.19 (dd, J = 10.12, 3.96 Hz, 2H) 4.60 (dd, J = 10.34, 7.26 Hz, 2H) 5.65 (d, J = 6.60 Hz, 1H) 6.80 (d, J = 9.24 Hz, 1H) 7.19-7.30 (m, 1H) 7.39 (d, J = 9.24 Hz, 1H) 7.49-7.64 (m, 2H) 7.72 (d, J = 8.36 Hz, 1H) 8.06 (d, J = 9.24 Hz, 1H) 8.22-8.46 (m, 3H) 9.10 (s, 1H) |
| 10.61 | (see Preparation P7.1) | | Pd(dppf)Cl$_2$, K$_3$PO$_4$, dioxane/ water | 8.35 (d, J = 9.6 Hz, 1H); 8.19 (s, 1H); 7.89 (d, J = 8.0 Hz, 1H); 7.80-7.76 (m, 2H); 7.54-7.50 (m, 1H); 7.34-7.30 (m, 1H); 7.11-7.10 (m, 2H); 6.98-6.96 (m, 2H); 5.83-5.81 (m, 1H); 5.02 (s, 2H); 4.65-4.61 (m, 4H); 3.81 (s, 3H); 3.49 (d, J = 6 Hz; 2H); 3.31-3.29 (m, 2H); 1.92-1.89 (m, 3H); 1.42-1.38 (m, 2H). |

TABLE 8B-continued

PREPARATION AND NMR DATA OF EXAMPLES 10.1-10.78

| Ex. # | Starting Material (1) | Starting Material (2) | Reaction Condition | ¹H NMR (CD₃OD, 400 MHz) δ (ppm) |
|---|---|---|---|---|
| 10.62 | (see Preparation P7.1) | | Pd(dppf)Cl₂, K₃PO₄, dioxane/ water | (CDCl₃) 8.56-8.51 (m, 2H); 8.16 (d, J = 9.6 Hz, 1H); 7.90 (d, J = 6.4 Hz, 1H); 7.89-7.80 (m, 1H); 7.78-7.72 (m, 3H); 7.47 (m, 1H); 6.72-6.69 (m, 1H); 5.75-5.72 (m, 1H); 4.80-4.68 (m, 3H); 4.30-4.29 (m, 2H); 3.61 (s, 2H); 3.08-3.02 (m, 2H); 2.78 (s, 3H); 1.93-1.85 (m, 3H); 1.40-1.25 (m, 3H). |
| 10.63 | (see Preparation P7.1) | | Pd(dppf)Cl₂, K₃PO₄, dioxane/ water | 8.37-8.35 (m, 1H); 8.33-8.19 (m, 2H); 7.89-7.87 (m, 1H); 7.80-7.77 (m, 3H); 7.52-7.49 (m, 1H); 7.07-7.04 (m, 1H); 6.98 (d, J = 9.2 Hz, 1H); 5.83-5.80 (m, 1H); 4.97 (br, 3H); 4.57-4.53 (m, 4H); 4.35-4.34 (m, 1H); 3.91 (s, 3H); 3.50-3.49 (m, 1H); 3.30-3.29 (m, 2H); 2.02-1.95 (m, 2H); 1.41-1.37 (m, 2H). |
| 10.64 | (see Preparation P7.1) | | Pd(dppf)Cl₂, K₃PO₄, dioxane/ water | (CDCl₃) 8.59 (s, 1H); 8.18 (s, 1H); 7.86 (d, J = 8.4 Hz, 1H); 7.75-7.69 (m, 2H); 7.59-7.51 (m, 2H); 7.26-7.13 (m, 2H); 6.57 (d, J = 8.8 Hz, 1H); 5.59 (s, 1H); 4.78-4.75 (m, 2H); 4.61-4.58 (m, 2H); 4.23-4.21 (m, 2H); 3.73-3.68 (m, 3H); 2.94-2.88 (m, 2H); 2.54 (s, 3H); 1.86-1.83 (m, 2H); 1.26-1.24 (m, 2H). |

TABLE 8B-continued

PREPARATION AND NMR DATA OF EXAMPLES 10.1-10.78

| Ex. # | Starting Material (1) | Starting Material (2) | Reaction Condition | $^1$H NMR (CD$_3$OD, 400 MHz) δ (ppm) |
|---|---|---|---|---|
| 10.65 | (see Preparation P7.1) | | Pd(dppf)Cl$_2$, K$_3$PO$_4$, dioxane/ water | (CDCl$_3$) 8.40 (d, J = 9.2, 1H); 8.06 (d, J = 10.8 Hz, 1H); 7.95 (d, J = 8.0 Hz, 1H); 7.84-7.80 (m, 2H); 7.58-7.55 (m, 1H); 7.03 (d, J = 9.6 Hz, 1H); 6.24-6.22 (m, 1H); 5.82-5.81 (m, 1H); 5.03-5.01 (m, 2H); 4.72-7.69 (m, 2H); 4.62-4.55 (m, 2H); 4.37-4.35 (m, 1H); 4.29 (s, 2H); 3.91-3.89 (m, 2H); 3.51 (d, J =6.0 Hz, 1H); 3.25 (t, J = 12.8 Hz, 2H); 2.50 (s, 2H); 2.26-1.89 (m, 3H); 1.52-1.34 (m, 2H). |
| 10.66 | (see Preparation P7.1) | | Pd(dppf)Cl$_2$, K$_3$PO$_4$, dioxane/ water | (CDCl$_3$) 7.95 (s, 1H); 7.83 (d, J = 9.2 Hz, 1H); 7.76-7.74 (m, 1H); 7.54 (d, J = 8.0 Hz, 1H); 7.51-7.47 (m, 1H); 7.17 (d, J = 11.2 Hz, 1H); 6.55-6.53 (m, 1H); 5.77 (s, 1H); 5.52-5.46 (m, 1H); 4.65 (d, J = 13.4 Hz, 2H); 4.57 (t, J = 9.2 Hz, 2H); 4.20-4.17 (m, 2H); 3.94 (s, 2H); 3.50-3.46 (m, 4H); 2.85-2.79 (m, 2H); 2.36 (s, 2H); 1.76-1.73 (m, 3H); 1.42 (s, 9H); 1.22-1.13 (m, 2H). |
| 10.67 | (see Preparation P7.2) | | Pd(dppf)Cl$_2$, K$_3$PO$_4$, dioxane/ water | (CDCl$_3$) 9.24 (s, 1H); 8.27-8.26 (m, 2H); 7.99-7.87 (m, 3H); 7.64-7.52 (m, 2H); 7.03-6.99 (m, 1H); 5.71-5.70 (m, 1H); 5.06-5.05 (m, 2H); 4.71-4.58 (m, 4H); 3.94 (s, 3H); 3.60-3.58 (m, 2H); 3.21-3.20 (m, 2H); 2.07-1.93 (m, 3H); 1.47-1.41 (m, 2H). |
| 10.68 | (see Preparation P23.1) | | Pd(PPh$_3$)$_4$, Na$_2$CO$_3$, dioxane/ water | (CDCl$_3$, 300 MHz) 2.65 (s, 3H), 4.34-4.43 (m, 1H), 4.74 (dd, 1H, J = 11.11 Hz, 6.58 Hz), 4.90-4.99 (m, 1H), 5.35 (dd, 1H, J = 11.69 Hz, 6.58 Hz), 5.59-5.68 (m, 1H), 7.29-7.42 (m, 2H), 7.52 (d, 1H, J = 7.75 Hz), 7.78-7.89 (m, 3H), 8.16 (br s, 1H), 8.39 (br s, 1H), 8.62 (d, 1H, J = 4.97 Hz), 10.37 (br s, 1H) |

TABLE 8B-continued

PREPARATION AND NMR DATA OF EXAMPLES 10.1-10.78

| Ex. # | Starting Material (1) | Starting Material (2) | Reaction Condition | $^1$H NMR (CD$_3$OD, 400 MHz) δ (ppm) |
|---|---|---|---|---|
| 10.69 | (see Preparation P20.1) | | Pd(PPh$_3$)$_4$, Na$_2$CO$_3$, dioxane, water | (CDCl$_3$:CD$_3$OD) 3.86 (s, 3H), 3.96 (dd, 2H, J = 10.17 Hz, 3.91 Hz), 4.40 (dd, 2H, J = 9.98 Hz, 6.65 Hz), 5.10 (s, 2H), 5.40-5.45 (m, 1H), 7.30-7.37 (m, 5H), 7.39-7.40 (m, 1H), 8.15 (d, 1H, J = 2.74 Hz), 8.30 (d, 1H, J = 2.74 Hz), 8.33 (d, 1H, J = 4.69 Hz), 8.36 (s, 1H) |
| 10.70 | (see Preparation P23.2) | | Pd(t-Bu$_3$P)$_2$ K$_2$CO$_3$ dioxane/ H$_2$O | (CDCl$_3$) 10.54 (1H, br. s.), 8.73 (2H, d, J = 5.1 Hz), 8.27-8.37 (1H, m), 8.11-8.20 (1H, m), 8.01 (2H, d, J = 5.6 Hz), 7.82 (1H, d, J = 7.9 Hz), 7.53 (1H, d, J = 8.0 Hz), 7.28-7.44 (2H, m), 5.59 (1H, d, J = 3.4 Hz), 5.00 (1H, d, J = 8.0 Hz), 4.63-4.84 (1H, m), 4.07 (1H, d, J = 7.9 Hz), 3.75-3.96 (1H, m), 2.24 (2H, m), 2.06 (2H, m). |
| 10.71 | (see Preparation P23.1) | | Pd(PPh$_3$)$_4$, Na$_2$CO$_3$, dioxane, water | (DMSO-D$_6$) 2.55-2.62 (m, 2H), 3.82 (t, 1H, J = 5.26 Hz), 4.20-4.34 (m, 3H), 4.58 (dd, 1H, J = 11.11 Hz, 6.58 Hz), 4.73 (dd, 1H, J = 11.40 Hz, 2.92 Hz), 5.16 (dd, 1H, J = 11.55 Hz, 6.14 Hz), 5.48-5.58 (m, 1H), 7.12 (br s, 1H), 7.22-7.35 (m, 2H), 7.52 (d, 1H, J = 7.45 Hz), 7.73 (d, 1H, J = 7.45 Hz), 8.10 (d, 1H, J = 2.19 Hz), 8.28 (d, 1H, J = 2.48 Hz), 13.25 (s, 1H). |

TABLE 8B-continued

PREPARATION AND NMR DATA OF EXAMPLES 10.1-10.78

| Ex. # | Starting Material (1) | Starting Material (2) | Reaction Condition | $^1$H NMR (CD$_3$OD, 400 MHz) δ (ppm) |
|---|---|---|---|---|
| 10.72 | 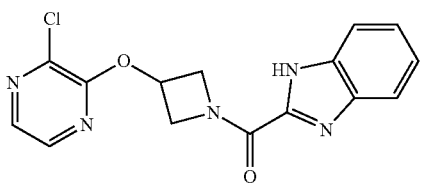 (see Preparation P23.1) | 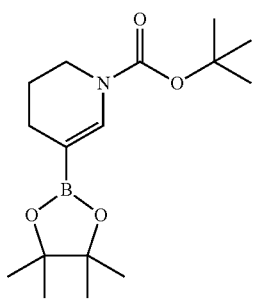 and 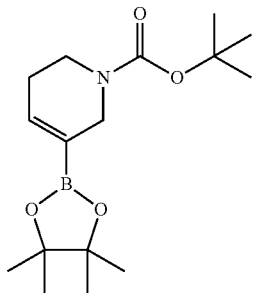 (see Preparation P11.1) | (dppf)PdCl$_2$, KOAc, dioxane, 80° C. | 8.27 (1H, d, J = 2.5 Hz), 8.05 (1H, d, J = 2.0 Hz), 7.60-7.72 (2H, m), 7.33-7.40 (2H, m), 7.20 (1H, br. s.), 5.63 (1H, br. s.), 5.23-5.40 (1H, m), 4.63-4.80 (2H, m), 4.46 (2H, br. s.), 4.35 (1H, d, J = 12.0 Hz), 3.56-3.70 (4H, m), 2.45 (2H, br. s.), 1.47 (10 H, s) |
| 10.73 | 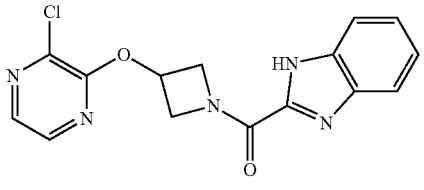 (see Preparation P23.1) | 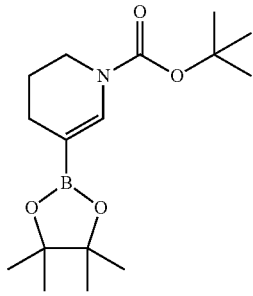 (see Preparation P11.1) | (dppf)PdCl$_2$, KOAc, dioxane, 80° C. | 8.21 (1H, d, J = 2.5 Hz), 8.03 (1H, d, J = 2.0 Hz), 7.59-7.77 (2H, m), 7.29-7.47 (2H, m), 7.19 (1H, br. s.), 5.61 (1H, br. s.), 5.15-5.35 (1H, m), 4.62-4.78 (2H, m), 4.44 (2H, br. s.), 4.31 (1H, d, J = 12.4 Hz), 3.47-3.69 (4H, m), 2.42 (2H, br. s.), 1.47 (10H, s) |

TABLE 8B-continued

PREPARATION AND NMR DATA OF EXAMPLES 10.1-10.78

| Ex. # | Starting Material (1) | Starting Material (2) | Reaction Condition | ¹H NMR (CD₃OD, 400 MHz) δ (ppm) |
|---|---|---|---|---|
| 10.74 | 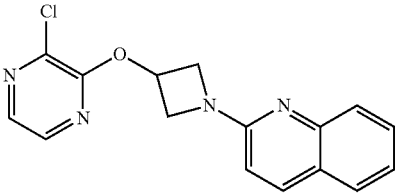<br>(see Preparation P2.6) | 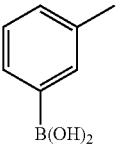 | Pd(PPh₃)₄, Na₂CO₃, Dioxane/ water | (CDCl₃) 7.74 (s, 1H); 7.65 (d, J= 8.4 Hz, 1H); 7.50-7.42 (m, 6H); 7.26-7.22 (m, 1H); 7.14-7.10 (m, 2H); 6.47 (d, J= 8.8 Hz, 1H); 5.52-5.49 (m, 1H); 4.56-4.52 (m, 2H); 4.51-4.15 (m, 2H); 2.31 (s, 3H). |
| 10.75 | 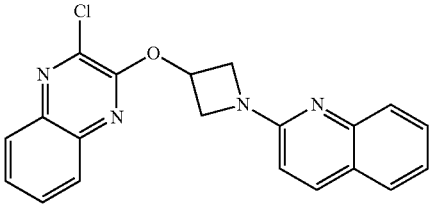<br>(see Preparation P2.8) | 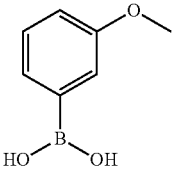 | Pd(dppf) Cl₂, K₃PO₄, Dioxane/ water | (CDCl₃) 8.07-8.02 (m, 3H); 7.83-7.81 (m, 1H); 7.72-7.60 (m, 6H); 7.45-7.35 (m, 2H); 7.05-7.02 (m, 1H); 6.59-6.56 (m, 1H); 5.74-5.72 (m, 1H); 5.17-4.55 (m, 4H); 3.88 (s, 3H). |
| 10.76 | 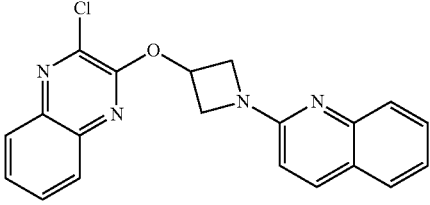<br>(see Preparation P2.8) | 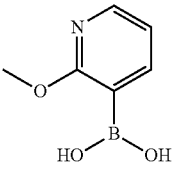 | Pd(dppf) Cl₂, K₃PO₄, Dioxane/ water | (CDCl₃) 8.33-8.32 (m, 1H); 8.14-8.10 (m, 2H); 7.91-7.85 (m, 3H); 7.77-7.65 (m, 4H); 7.46-7.44 (m, 1H); 7.10-7.08 (m, 1H); 6.63-6.60 (m, 1H); 5.86-5.81 (m, 1H); 5.20-4.40 (m, 4H); 3.92 (s, 3H). |
| 10.77 | 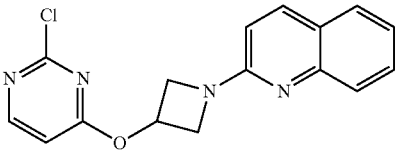<br>(see Preparation P3.2) | 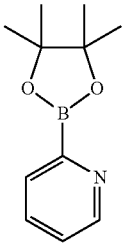 | Pd(dppf) Cl₂, K₃PO₄, Dioxane/ water | (CDCl₃) 8.79-8.77 (m, 1H); 8.71-8.70 (m, 1H); 8.50-8.49 (m, 1H); 8.11-8.10 (m, 1H); 7.94-7.88 (m, 2H); 7.79-7.76 (m, 1H); 7.66-7.56 (m, 2H); 7.47-7.44 (m, 1H); 7.27-7.24 (m, 1H); 6.68-6.66 (m, 1H); 5.73-7.50 (m, 1H); 4.77-7.73 (m, 2H); 4.42-4.39 (m, 2H). |
| 10.78 | 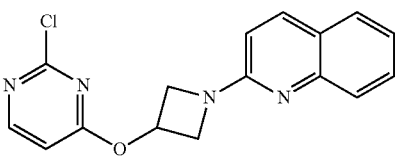<br>(see Preparation P3.2) | 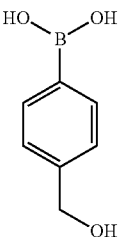 | Pd(dppf) Cl₂, K₃PO₄, Dioxane/ water | (CDCl₃) 8.60-8.59 (m, 1H); 8.45-8.43 (m, 2H); 7.96-7.94 (m, 1H); 7.86-7.84 (m, 1H); 7.67-7.51 (m, 4H); 7.30-7.29 (m, 1H); 6.74-6.72 (m, 1H); 6.68-6.66 (m, 1H); 5.82-5.76 (m, 1H); 4.83 (s, 2H); 4.82-4.80 (m, 2H); 4.39-4.36 (m, 2H). |

*Note:
Examples 10.3 and 10.15 can be prepared according to Scheme 10. However, NMR data of pure products are not available.

SCHEME 11

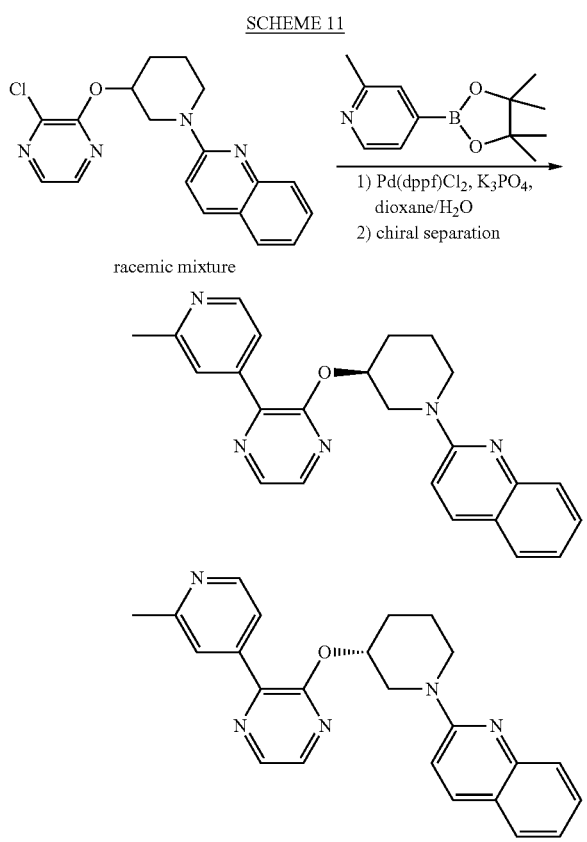

racemic mixture

1) Pd(dppf)Cl$_2$, K$_3$PO$_4$, dioxane/H$_2$O
2) chiral separation

Example 11.1

(S)-2-(3-((3-(2-Methylpyridin-4-yl)Pyrazin-2-yl)Oxy)Piperidin-1-yl)Quinoline or (R)-2-(3-((3-(2-Methylpyridin-4-yl)Pyrazin-2-yl)Oxy)Piperidin-1-yl)Quinoline as Racemic Mixture Step 1: (Racemic Mixture) 2-(3-((3-(2-Methylpyridin-4-yl)Pyrazin-2-yl)Oxy)Piperidin-1-yl)Quinoline To a solution of (racemic mixture) 2-(3-((3-chloropyrazin-2-yl)oxy)piperidin-1-yl)quinoline (see PREPARATION P2.3; 340 mg, 1.0 mmol), 2-methyl-4-(4,4,5,5-tetramethyl-1,3,2-dioxaborolan-2-yl)pyridine (219 mg, 1.0 mmol) and K$_3$PO$_4$ (424 mg, 2.0 mmol) in 1,4-dioxane (10 mL) and water (2 mL) was added Pd(dppf)Cl$_2$ (73 mg, 0.1 mmol) then the reaction mixture was stirred at 110° C. under N$_2$ atmosphere overnight. The reaction mixture was filtered through CELITE® and washed with CH$_2$Cl$_2$ (30 mL). The filtrate was concentrated and the crude product was purified by silica gel column to give (racemic mixture) 2-(3-((3-(2-methylpyridin-4-yl)pyrazin-2-yl)oxy)piperidin-1-yl)quinoline (200 mg, 0.50 mmol, yield 60%). ESI-MS (M+1): 384 calc. for C$_{23}$H$_{21}$N$_5$O 383.

Step 2. (S)-2-(3-((3-(2-Methylpyridin-4-yl)Pyrazin-2-yl)Oxy)Piperidin-1-yl)Quinoline and (R)-2-(3-((3-(2-Methylpyridin-4-yl)Pyrazin-2-yl)Oxy)Piperidin-1-yl)Quinoline as Separated Single Isomer 2-(3-((3-(2-methylpyridin-4-yl)pyrazin-2-yl)oxy)piperidin-1-yl)quinoline (0.020 g, 0.04 mmol) was separated by chiral prep. HPLC (Column: Chiralcel OD-H 250*30 mm, 5u; Mobile phase: 85% hexane in EtOH (0.05% diethyl amine); Flow rate: 30 mL/minute) to give Examples 11.1 and 11.2; wherein each of the absolute configuration was not further determined.

TABLE 9A

EXAMPLES 11.1-11.8 PREPARATION ANALOGOUS TO SCHEME 11

| Ex. # | Structure | Chemical Name | ESI-MS (M + 1) | IC$_{50}$ (uM) |
|---|---|---|---|---|
| 11.1 and 11.2* | | (S)-2-(3-((3-(2-methylpyridin-4-yl)pyrazin-2-yl)oxy)piperidin-1-yl)quinoline and (R)-2-(3-((3-(2-methylpyridin-4-yl)pyrazin-2-yl)oxy)piperidin-1-yl)quinoline | 398 | 5.1 and 3.95 |

(as separated)

TABLE 9A-continued

EXAMPLES 11.1-11.8 PREPARATION ANALOGOUS TO SCHEME 11

| Ex. # | Structure | Chemical Name | ESI-MS (M + 1) | IC$_{50}$ (uM) |
|---|---|---|---|---|
| 11.3 and 11.4* | 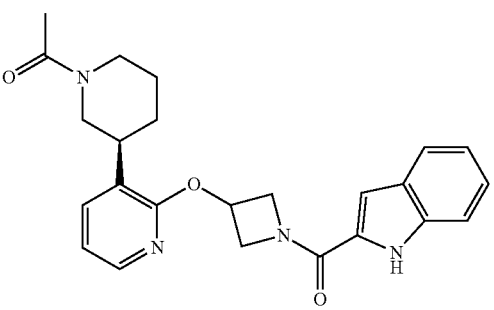<br>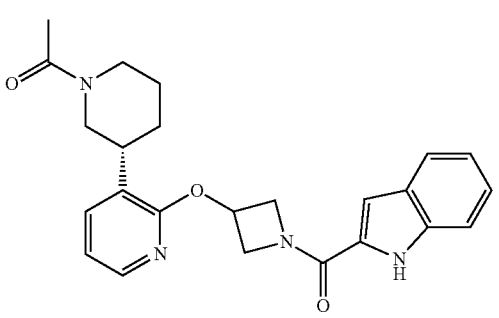<br>(single enantiomer; absolute stereospecificity not determined) | (S)-1-(3-(2-((1-(1H-indole-2-carbonyl)azetidin-3-yl)oxy)pyridin-3-yl)piperidin-1-yl)ethanone and (R)-1-(3-(2-((1-(1H-indole-2-carbonyl)azetidin-3-yl)oxy)pyridin-3-yl)piperidin-1-yl)ethanone | 419 | 0.2992 and 1.983 |
| 11.5 and 11.6* | 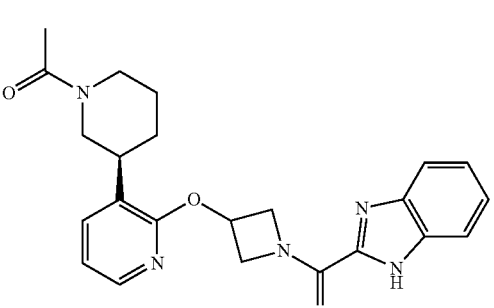<br>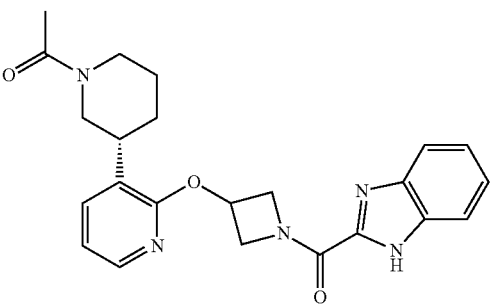<br>(single enantiomer; absolute stereospecificity not determined) | (S)-1-(3-(2-((1-(1H-benzo[d]imidazole-2-carbonyl)azetidin-3-yl)oxy)pyridin-3-yl)piperidin-1-yl)ethanone and (R)-1-(3-(2-((1-(1H-benzo[d]imidazole-2-carbonyl)azetidin-3-yl)oxy)pyridin-3-yl)piperidin-1-yl)ethanone | 420 | 0.04487 and 0.002515 |

TABLE 9A-continued

EXAMPLES 11.1-11.8 PREPARATION ANALOGOUS TO SCHEME 11

| Ex. # | Structure | Chemical Name | ESI-MS (M + 1) | IC$_{50}$ (uM) |
|---|---|---|---|---|
| 11.7 and 11.8* | | (S)-1-(3-(2-((1-(1H-benzo[d]imidazole-2-carbonyl)azetidin-3-yl)oxy)pyridin-3-yl)piperidin-1-yl)-2-methylpropan-1-one and (R)-1-(3-(2-((1-(1H-benzo[d]imidazole-2-carbonyl)azetidin-3-yl)oxy)pyridin-3-yl)piperidin-1-yl)-2-methylpropan-1-one | 448 | 1.337 and 0.0271 | and (single enantiomer; absolute stereospecificity not determined)

*The examples are separated enantiomers, wherein each absolute configuration was not further determined. Their M + 1 mass is the same. Therefore the reported NMR and PDE10 data herein can be for either isomer.

TABLE 9B

PREPARATION AND NMR DATA OF EXAMPLES 11.1-11.8

| Ex. # | Starting Material (1) and (2) | Reaction Condition | $^1$H NMR (CD$_3$OD, 400 MHz): δ (ppm) |
|---|---|---|---|
| 11.1 and 11.2* | 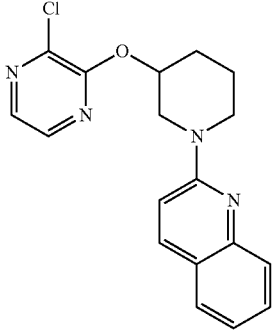 (see Preparation P2.3), and 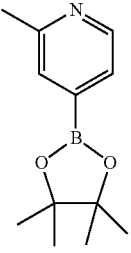 | Pd(dppf)Cl$_2$, K$_3$PO$_4$ dioxane/ water | 8.25-8.24 (m, 2H); 7.98-7.96 (m, 1H); 7.61 (d, J = 9.2 Hz, 1H); 7.45-7.43 (m, 1H); 7.38-7.34 (m, 2H); 7.30-7.21 (m, 2H); 7.21-7.09 (m, 1H); 7.13-6.85 (m, 1H); 5.46-5.45 (m, 1H); 4.90-4.85 (m, 1H); 3.44-3.43 (m, 1H); 3.43-3.29 (m, 2H); 2.26 (s, 3H); 2.12-2.08 (m, 3H); 1.60-1.55 (m, 1H). and 8.25-8.235 (m, 2 H); 7.97-7.96 (m, 1H); 7.61 (d, J = 8.8 Hz, 1H); 7.45-7.42 (m, 1H); 7.38-7.34 (m, 2H); 7.30-6.82 (m, 3H); 5.46-5.44 (m, 1H); 4.88-4.87 (m, 1H); 3.44-3.43 (m, 1H); 3.40-3.29 (m, 2H); 3.26 (s, 3H); 2.11-2.08 (m, 3H); 1.70-1.61 (m, 1H). |
| 11.3 and 11.4* | 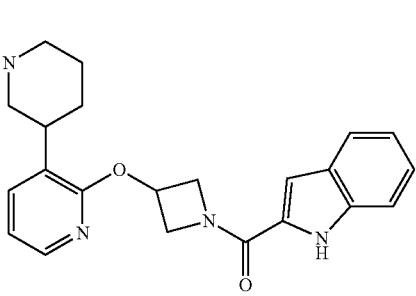 (see Example 18.10) | (see Example 18.10) | 7.96-8.12 (1H, m), 7.55-7.75 (2H, m), 7.45 (1H, d, J = 8.3 Hz), 7.23 (1H, t, J = 7.6 Hz), 6.95-7.15 (2H, m), 6.90 (1H, d, J = 4.4 Hz), 5.59 (1H, m), 5.02 (1H, m.), 4.56-4.77 (3H, m), 4.15-4.22 (1H, m), 3.95-4.07 (1H, dd, J = 9.6 Hz, J = 13.2 Hz), 2.88-3.24 (2H, m), 2.65 (1H, t, J = 12.9 Hz), 2.13 (3H, s), 1.95-2.06 (1H, m), 1.77-1.95 (2H, m), 1.48-1.77 (1H, m) and 7.96-8.12 (1H, m), 7.55-7.75 (2H, m), 7.45 (1H, d, J = 8.3 Hz), 7.23 (1H, t, J = 7.6 Hz), 6.95-7.15 (2H, m), 6.90 (1H, d, J = 4.4 Hz), 5.59 (1H, m), 5.02 (1H, m.), 4.56-4.77 (3H, m), 4.15-4.22 (1H, m), 3.95-4.07 (1H, dd, J = 9.6 Hz, J = 13.2 Hz), 2.88-3.24 (2H, m), 2.65 (1H, t, J = 12.9 Hz), 2.13 (3H, s), 1.95-2.06 (1H, m), 1.77-1.95 (2H, m), 1.48-1.77 (1H, m) |

TABLE 9B-continued

PREPARATION AND NMR DATA OF EXAMPLES 11.1-11.8

| Ex. # | Starting Material (1) and (2) | Reaction Condition | $^1$H NMR (CD$_3$OD, 400 MHz): δ (ppm) |
|---|---|---|---|
| 11.5 and 11.6* | (see Example 15.14) | (see Example 15.14) | 8.04 (1H, t, J = 5.1 Hz), 7.59-7.72 (3H, m), 7.33 (2H, d, J = 2.8 Hz), 6.95-7.07 (1H, m), 5.46-5.66 (1H, m), 5.17-5.34 (1H, m), 4.63-4.75 (2H, m), 4.58 (1H, d, J = 12.0 Hz), 4.26 (1H, d, J = 12.0 Hz), 3.95-4.08 (1H, dd, J = 9.4 Hz, J = 13.7 Hz), 2.92-3.26 (3H, m), 2.50-2.76 (1H, m), 2.07-2.19 (3H, m), 1.97-2.07 (1H, m), 1.76-1.96 (2H, m), 1.45-1.76 (1H, m) and 8.04 (1H, t, J = 5.1 Hz), 7.59-7.72 (3H, m), 7.33 (2H, d, J = 2.8 Hz), 6.95-7.07 (1H, m), 5.46-5.66 (1H, m), 5.17-5.34 (1H, m), 4.63-4.75 (2H, m), 4.58 (1H, d, J = 12.0 Hz), 4.26 (1H, d, J = 12.0 Hz), 3.95-4.08 (1H, dd, J = 9.4 Hz, J = 13.7 Hz), 2.92-3.26 (3H, m), 2.50-2.76 (1H, m), 2.07-2.19 (3H, m), 1.97-2.07 (1H, m), 1.76-1.96 (2H, m), 1.45-1.76 (1H, m) |
| 11.7 and 11.8* | (see Example 15.15) | (see Example 15.15) | (CDCl$_3$) 10.57 (1H, br. s.), 8.04 (1H, d, J = 13.3 Hz), 7.82 (1H, d, J = 8.0 Hz), 7.49-7.62 (2H, m), 7.28-7.41 (2H, m), 6.82-7.02 (1H, m), 5.45-5.65 (1H, m), 5.25-5.35 (1H, m), 4.80-4.98 (1H, m), 4.72 (2H, m), 4.30-4.38 (1H, m), 3.85-4.15 (1H, dd, J = 9.5 Hz, J = 14.9 Hz), 2.97-3.20 (2H, m), 2.68-2.97 (2H, m), 1.95-2.16 (1H, m), 1.72-1.85 (2H, m), 1.51-1.67 (1H, m), 1.15 (6H, m) and (CDCl$_3$) 10.57 (1H, br. s.), 8.04 (1H, d, J = 13.3 Hz), 7.82 (1H, d, J = 8.0 Hz), 7.49-7.62 (2H, m), 7.28-7.41 (2H, m), 6.82-7.02 (1H, m), 5.45-5.65 (1H, m), 5.25-5.35 (1H, m), 4.80-4.98 (1H, m), 4.72 (2H, m), 4.30-4.38 (1H, m), 3.85-4.15 (1H, dd, J = 9.5 Hz, J = 14.9 Hz), 2.97-3.20 (2H, m), 2.68-2.97 (2H, m), 1.95-2.16 (1H, m), 1.72-1.85 (2H, m), 1.51-1.67 (1H, m), 1.15 (6H, m). |

*The starting materials and reaction condition used in Preparation and NMR data of examples 11.1-11.8 are the same for each pair of examples.

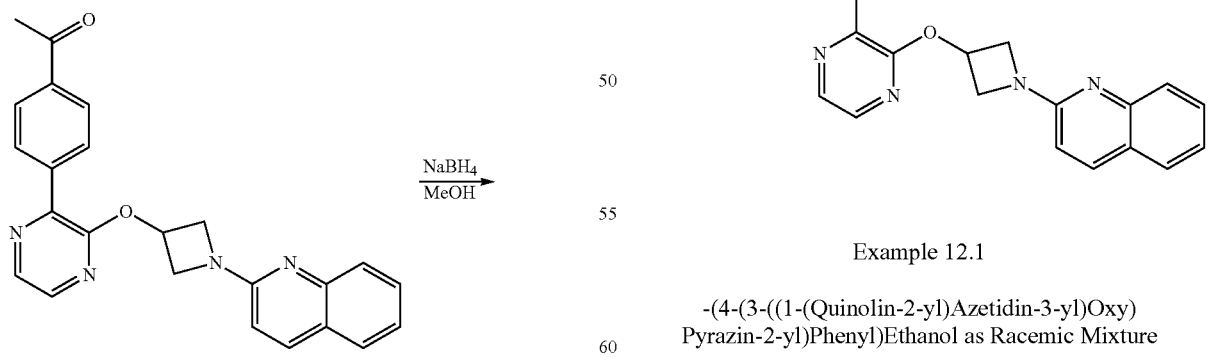

SCHEME 12

Example 12.1

-(4-(3-((1-(Quinolin-2-yl)Azetidin-3-yl)Oxy) Pyrazin-2-yl)Phenyl)Ethanol as Racemic Mixture 1-(4-(3-((1-(quinolin-2-yl)azetidin-3-yl)oxy)pyrazin-2-yl)phenyl)ethanone (see EXAMPLE 10.26; 99 mg, 0.25 mmol) was dissolved in 10 ml of methanol. This solution was cooled down to 0° C. using an ice bath and sodium tetraborohydride (19 mg, 0.50 mmol) was added in portions. The reaction mixture was stirred for 4 hours at ambient temperature, and then saturated aqueous solution of ammonium chloride (5 mL) was added. The methanol was evaporated off under reduced pressure then the reaction mixture was taken up in ethyl acetate. The organic layer was separated from the aqueous layer. This extraction was repeated one more time and then the organic layers were combined and dried over magnesium sulphate, followed by concentrating under reduced pressure. The residue was purified by column chromatography on silica gel to give (racemic mixture) 1-(4-(3-((1-(quinolin-2-yl)azetidin-3-yl)oxy)pyrazin-2-yl)phenyl)ethanol (75 mg, 0.19 mmol, 75% yield). ESI-MS (M+1): 399 calc. for $C_{24}H_{22}N_4O_2$ 398.

TABLE 10A

EXAMPLES 12.1-12.2 PREPARED ANALOGOUS TO SCHEME 12

| Ex. # | Structure | Chemical Name | M + 1 | IC$_{50}$ (uM) |
|---|---|---|---|---|
| 12.1 | (as racemic mixture) | 1-(4-(3-((1-(quinolin-2-yl)azetidin-3-yl)oxy)pyrazin-2-yl)phenyl)ethanol | 399 | 0.0553 |
| 12.2 | (as racemic mixture) | 1-(3-(3-((1-(quinolin-2-yl)azetidin-3-yl)oxy)pyrazin-2-yl)phenyl)ethanol | 399 | 0.045 |

TABLE 10B

PREPARATION AND NMR DATA OF EXAMPLES 12.1-12.2

| Ex. # | Starting material (1) | Reaction Condition | $^1$H NMR (CD$_3$OD, 400 MHz) δ (ppm) |
|---|---|---|---|
| 12.1 | (see Example 10.26) | NaBH$_4$, MeOH | 8.14-8.05 (m, 2H); 8.04-8.02 (m, 3H); 7.90-7.88 (m, 1H); 7.79-7.75 (m, 2H); 7.53-7.47 (m, 3H); 6.98-6.95 (m, 1H); 5.76-5.73 (m, 1H); 5.00-4.96 (m, 2H); 4.91-4.89 (m, 1H); 4.63-4.59 (m, 2H); 1.46-1.45 (d, 3H). |

TABLE 10B-continued

PREPARATION AND NMR DATA OF EXAMPLES 12.1-12.2

| Ex. # | Starting material (1) | Reaction Condition | $^1$H NMR (CD$_3$OD, 400 MHz) δ (ppm) |
|---|---|---|---|
| 12.2 | (see Example 10.23) | NaBH$_4$, MeOH | 8.14-8.05 (m, 2H); 8.04-8.02 (m, 3H); 7.90-7.88 (m, 1H); 7.79-7.75 (m, 2H); 7.53-7.47 (m, 3H); 6.98-6.95 (m, 1H); 5.76-5.73 (m, 1H); 5.00-4.96 (m, 2H); 4.91-4.89 (m, 1H); 4.63-4.59 (m, 2H); 1.46-1.45 (d, 3H). |

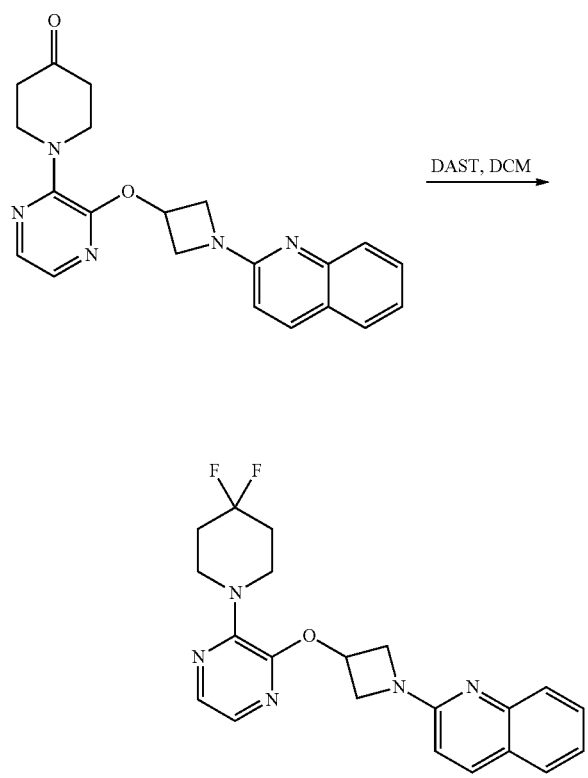

SCHEME 13

Example 13.1

2-(3-((3-(4,4-Difluoropiperidin-1-yl)Pyrazin-2-yl)Oxy)Azetidin-1-yl)Quinoline

In a 50 mL flask, 1-(3-((1-(quinolin-2-yl)azetidin-3-yl)oxy)pyrazin-2-yl)piperidin-4-one (see PREPARATION P8.1 and Example 8.2; 0.187 g, 0.50 mmol) was dissolved in anhydrous CH$_2$Cl$_2$ (15 mL). The solution was cooled to −10° C. under nitrogen atmosphere and diethylaminosulfur trifluoride (DAST) (0.26 g, 0.10 mmol) was added dropwise. The reaction mixture was allowed to warm to RT and stirred for 2 hours. The mixture was poured into cold water (10 mL). The separated aqueous layer was back extracted twice with CH$_2$Cl$_2$ (20 mL). The combined organic layers were dried over magnesium sulfate (MgSO$_4$). After filtration, the solvent was evaporated in vacuo, and the concentrate was purified via flash chromatography on silica gel (20% to 45% EtOAc in petroleum ether) to give 2-(3-((3-(4,4-difluoropiperidin-1-yl)pyrazin-2-yl)oxy)azetidin-1-yl)quinoline (0.148 g, 0.37 mmol, 75% yield) as a white solid. ESI-MS (M+1): 398 calc. for C$_{21}$H$_{21}$F$_2$N$_5$O 397.

TABLE 13A

EXAMPLES 13.1-13.5 PREPARATION ANALOGOUS TO SCHEME 13

| Ex. # | Structure | Chemical Name | ESI-MS (M + 1) | IC$_{50}$ (uM) |
|---|---|---|---|---|
| 13.1 | 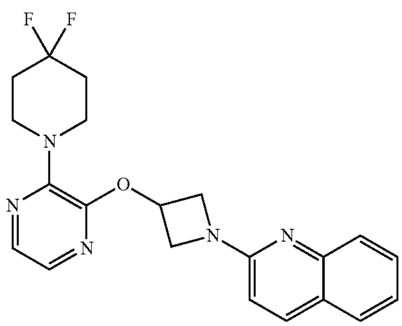 [SMILES: FC1(F)CCN(c2nccnc2OC2CN(c3ccc4ccccc4n3)C2)CC1] | 2-(3-((3-(4,4-difluoropiperidin-1-yl)pyrazin-2-yl)oxy)azetidin-1-yl)quinoline | 398 | 0.00423 |
| 13.2 | 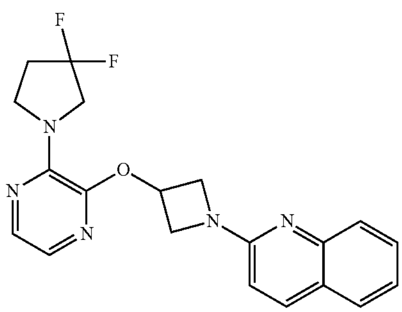 [SMILES: FC1(F)CCN(c2nccnc2OC2CN(c3ccc4ccccc4n3)C2)C1] | 2-(3-((3-(3,3-difluoropyrrolidin-1-yl)pyrazin-2-yl)oxy)azetidin-l-yl)quinoline | 384 | 0.0953 |
| 13.3 | 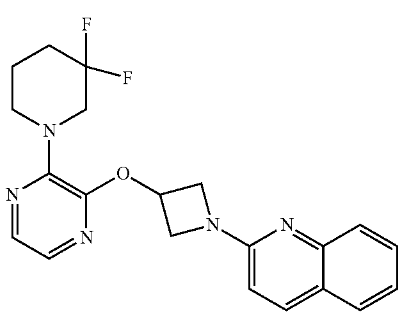 [SMILES: FC1(F)CCCN(c2nccnc2OC2CN(c3ccc4ccccc4n3)C2)C1] | 2-(3-((3-(3,3-difluoropiperidin-1-yl)pyrazin-2-yl)oxy)azetidin-1-yl)quinoline | 398 | 0.0921 |
| 13.4 | 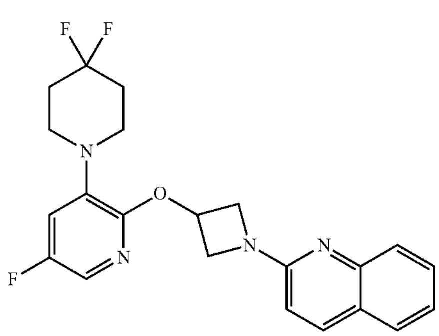 [SMILES: Fc1cnc(OC2CN(c3ccc4ccccc4n3)C2)c(N2CCC(F)(F)CC2)c1] | 2-(3-((3-(4,4-difluoropiperidin-1-yl)-5-fluoropyridin-2-yl)oxy)azetidin-1-yl)quinoline | 415 | 0.144 |

TABLE 13A-continued

EXAMPLES 13.1-13.5 PREPARATION ANALOGOUS TO SCHEME 13

| Ex. # | Structure | Chemical Name | ESI-MS (M + 1) | IC$_{50}$ (uM) |
|---|---|---|---|---|
| 13.5 | 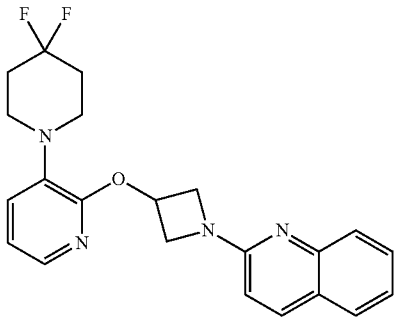 [SMILES: FC1(F)CCN(c2cccnc2OC2CN(c3ccc4ccccc4n3)C2)CC1] | 2-(3-((3-(4,4-difluoropiperidin-1-yl)pyridin-2-yl)oxy)azetidin-1-yl)quinoline | 397 | 0.0359 |

TABLE 13B

PREPARATION AND NMR DATA OF EXAMPLES 13.1-13.5

| Ex. # | Starting Material (1) | Reaction Condition | $^1$H NMR (CDCl$_3$, 400 MHz) δ (ppm) |
|---|---|---|---|
| 13.1 | (see Preparation P8.1) | DAST, DCM | (CD$_3$OD) 7.91 (s, 1H); 7.68-7.59 (m, 1H); 7.59-7.50 (m, 2H); 7.49-7.44 (m, 2H); 7.18-7.14 (m, 1H); 6.66 (d, J = 9.2 Hz, 1H); 5.52-5.48 (m, 1H); 4.59-4.54 (m, 2H); 4.18-4.12 (m, 2H); 3.60-3.58 (m, 4H); 2.02-1.92 (m, 4H). |
| 13.2 | (see Preparation P8.2) | DAST, DCM | 8.08 (d, J = 2.8 Hz, 1H); 7.94 (d, J = 8.4 Hz, 1H); 7.73-7.67 (m, 3H); 7.43-7.34 (m, 2H); 6.61-6.58 (m, 1H); 5.54-5.53 (m, 1H); 5.11-4.40 (m, 6H); 3.98-3.90 (m, 2H); 2.41-2.37 (m, 2H). |
| 13.3 | (see Preparation P8.3) | DAST, DCM | 8.40-8.37 (m, 1H); 7.83-7.76 (m, 4H); 7.55 (d, J = 2.8 Hz, 1H); 7.54-7.50 (m, 1H); 6.95 (d, J = 9.6 Hz, 1H); 5.69-5.65 (m, 1H); 4.99-4.94 (m, 2H); 4.61-4.54 (m, 2H); 3.86-3.80 (m, 2H); 3.59-3.57 (m, 2H); ; 2.11-2.02 (m, 2H); 1.94-1.90 (m, 2H). |

TABLE 13B-continued
PREPARATION AND NMR DATA OF EXAMPLES 13.1-13.5
| Ex. # | Starting Material (1) | Reaction Condition | $^1$H NMR (CDCl$_3$, 400 MHz) δ (ppm) |
|---|---|---|---|
| 13.4 | (see Preparation P8.4) | DAST, DCM | 8.09-8.01 (m, 1H); 7.68-7.66 (m, 2H); 7.61-7.55 (m, 2H); 7.29-7.25 (m, 1H); 7.15 (dd, J - 1.6, 4.8 Hz, 1H); 6.76 (d, J = 8.8 Hz, 1H); 5.56-5.53 (m, 1H); 4.70-4.65 (m, 2H); 4.26-4.22 (m, 2H); 3.29-3.21 (m, 4H); 2.14-2.07 (m, 4H). |
| 13.5 | (see Preparation P8.5) | DAST, DCM | 7.66 (d, J = 3.6 Hz, 1H); 7.66-7.55 (m, 3H); 7.47-7.43 (m, 1H); 7.20-7.13 (m, 2H); 6.86-6.83 (m, 1H); 6.63 (d, J = 8.8 Hz, 1H); 5.50-5.46 (m, 1H); 4.57-4.53 (m, 2H); 4.139-4.09 (m, 2H); 3.09 (s, 4H); 2.05-1.98 (m, 4H). |
SCHEME 14
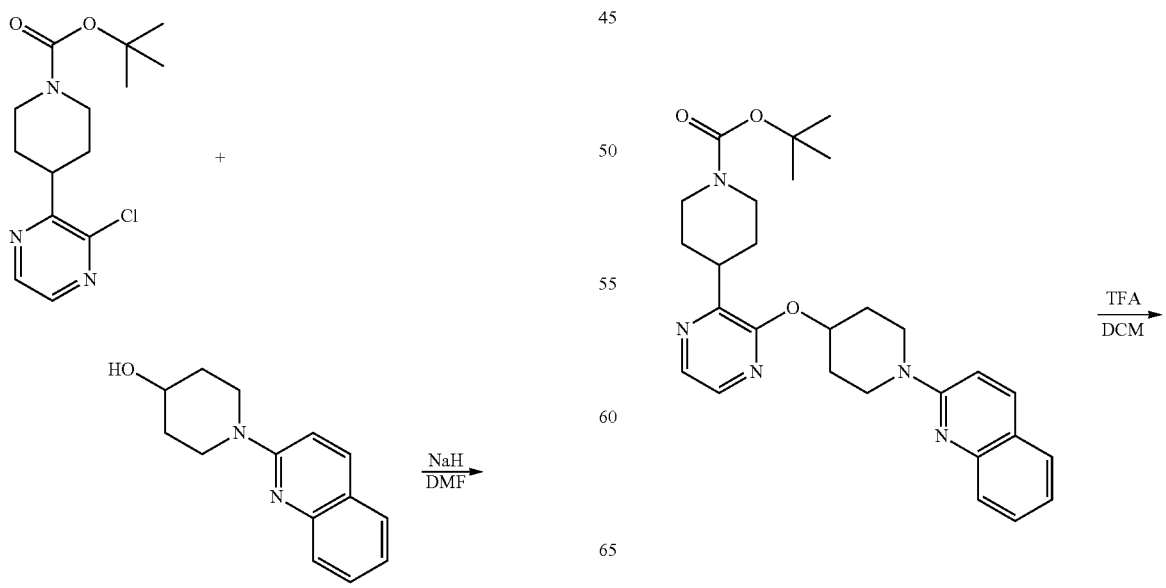

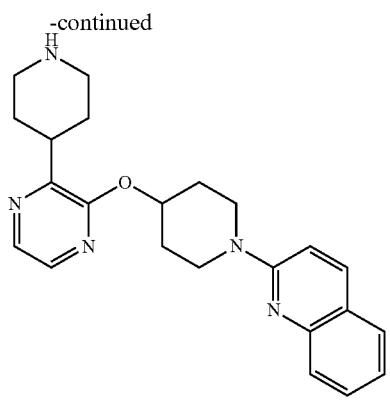

Example 14.1

2-(4-(3-(Piperidin-4-yl)Pyridin-2-yloxy)Piperidin-1-yl)Quinoline

Step 1. Tert-Butyl 4-(2-(1-(Quinolin-2-yl)Piperidin-4-yloxy)Pyridin-3-yl)Piperidine-1-Carboxylate Sodium hydride (60% dispersion in mineral oil, 254 mg, 10.58 mmol) was added to a solution of 1-(quinolin-2-yl)piperidin-4-ol (see PREPARATION P1.1; 805 mg, 3.53 mmol) in DMF (16.8 ml) under an atmosphere of nitrogen and the mixture was stirred for 15 mins at RT. Tert-butyl 4-(3-chloropyrazin-2-yl)piperidine-1-carboxylate (see PREPARATION P16.1; 1050 mg, 3.53 mmol) was next added, and the mixture was heated at 100° C. After the reaction was complete, the mixture was cooled to RT and diluted with EtOAc and water. The layers were separated and the aqueous was extracted with EtOAc (2×). The combined organic layers were dried over sodium sulfate, filtered and concentrated and used in the next step without further purification.

Step 3. 2-(4-(3-(Piperidin-4-yl)Pyridin-2-yloxy)Piperidin-1-yl)Quinoline

Trifluoroacetic acid (0.272 mL, 3.53 mmol) was added to a solution of tert-butyl 4-(3-(1-(quinolin-2-yl)piperidin-4-yloxy)pyrazin-2-yl)piperidine-1-carboxylate (1726 mg, 3.53 mmol) in DCM (2 mL) and stirred at RT until the starting material was completely consumed. The mixture was then diluted with ethyl acetate and neutralized with saturated aqueous sodium bicarbonate. The layers were separated and the aqueous layer was extracted with ethyl acetate. The combined organics were washed with saturated aqueous sodium chloride, dried over sodium sulfate, filtered and concentrated. The brown solid was triturated with acetone and dried to give the title compound as a white solid (370 mg, 27% yield). [M+1] 390.2. $IC_{50}$ (uM) 0.05444. $^1$H NMR (CDCl$_3$, 400 MHz) δ (ppm): 1.53-1.69 (m, 1H) 1.86-2.00 (m, 2H) 2.12-2.34 (m, 6H) 3.03-3.14 (m, 2H) 3.23-3.32 (m, 1H) 3.53-3.71 (m, 4H) 4.13-4.22 (m, 2H) 5.35-5.43 (m, 1H) 7.06 (d, J=9.19 Hz, 1H) 7.20-7.26 (m, 1H) 7.52-7.59 (m, 1H) 7.62 (d, J=7.82 Hz, 1H) 7.67-7.82 (m, 1H) 7.89-7.95 (m, 1H) 7.97 (d, J=2.74 Hz, 1H) 8.06 (d, J=2.74 Hz, 1H)

SCHEME 15

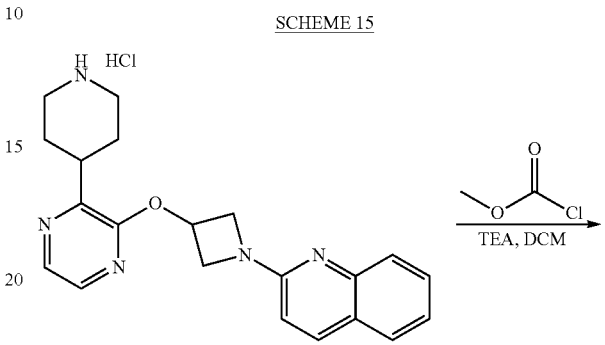

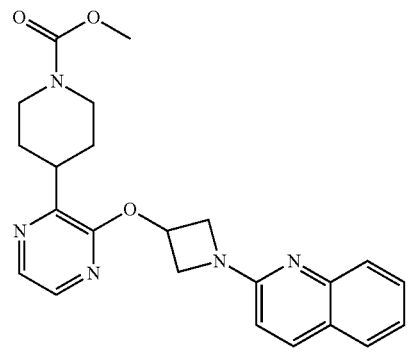

Example 15.1

Methyl 4-(3-((1-(Quinolin-2-yl)Azetidin-3-yl)Oxy)Pyrazin-2-yl)Piperidine-1-Carboxylate To a solution of 2-(3-((3-(piperidin-4-yl)pyrazin-2-yl)oxy)azetidin-1-yl)quinoline hydrochloride (see PREPARATION P4.1; 100 mg, 0.29 mmol) in dry DCM (10 mL) was added Et$_3$N (1 mL). The reaction mixture was cooled to 0° C. with an ice bath, and methyl carbonochloridate (54 mg, 0.58 mmol) was added dropped to the reaction mixture. After 1 hour, the reaction mixture was warmed to RT, and stirred overnight. Then the reaction mixture was washed with brine, dried over Na$_2$SO$_4$, filtered, and concentrated under vacuum to give the crude product. The crude product was purified via flash chromatography on silica gel (20% to 45% EtOAc in petroleum ether) to give methyl 4-(3-((1-(quinolin-2-yl)azetidin-3-yl)oxy)pyrazin-2-yl)piperidine-1-carboxylate (93 mg, 0.23 mmol, 79% yield) as a white solid. ESI-MS (M+1): 404 calc. for C$_{23}$H$_{25}$N$_5$O$_2$ 403.

TABLE 12A

EXAMPLES 15.1-15.18 PREPARED ANALOGOUS TO SCHEME 15

| Ex. # | Structure | Chemical Name | ESI-MS (M + 1) | IC$_{50}$ (uM) |
|---|---|---|---|---|
| 15.1 | 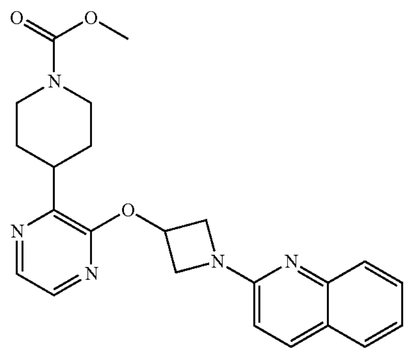 [SMILES: COC(=O)N1CCC(c2nccnc2OC2CN(c3ccc4ccccc4n3)C2)CC1] | methyl 4-(3-((1-(quinolin-2-yl)azetidin-3-yl)oxy)pyrazin-2-yl)piperidine-1-carboxylate | 420 | 0.158 |
| 15.2 | 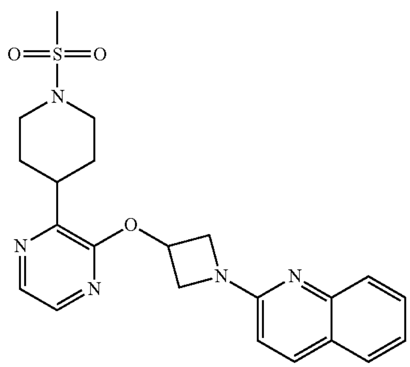 [SMILES: CS(=O)(=O)N1CCC(c2nccnc2OC2CN(c3ccc4ccccc4n3)C2)CC1] | 2-(3-((3-(1-(methylsulfonyl)piperidin-4-yl)pyrazin-2-yl)oxy)azetidin-1-yl)quinoline | 440 | 0.208 |
| 15.3 | 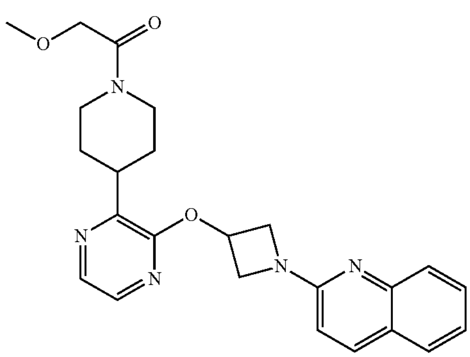 [SMILES: COCC(=O)N1CCC(c2nccnc2OC2CN(c3ccc4ccccc4n3)C2)CC1] | 2-methoxy-1-(4-(3-((1-(quinolin-2-yl)azetidin-3-yl)oxy)pyrazin-2-yl)piperidin-1-yl)ethanone | 434 | 0.165 |
| 15.4 | 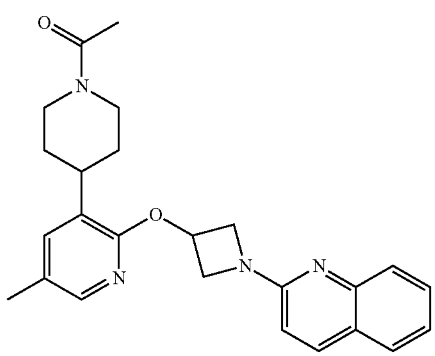 [SMILES: CC(=O)N1CCC(c2cc(C)cnc2OC2CN(c3ccc4ccccc4n3)C2)CC1] | 1-(4-(5-methyl-2-((1-(quinolin-2-yl)azetidin-3-yl)oxy)pyridin-3-yl)piperidin-1-yl)ethanone | 417 | 0.0678 |

TABLE 12A-continued

EXAMPLES 15.1-15.18 PREPARED ANALOGOUS TO SCHEME 15

| Ex. # | Structure | Chemical Name | ESI-MS (M + 1) | IC$_{50}$ (uM) |
|---|---|---|---|---|
| 15.5 | 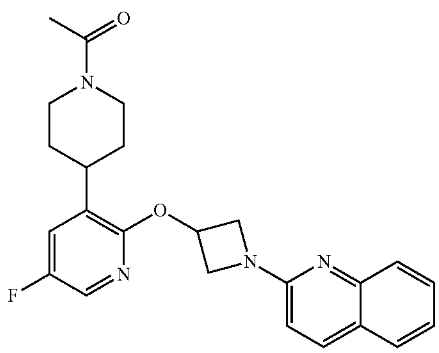 [SMILES: CC(=O)N1CCC(c2cc(F)cnc2OC2CN(c3ccc4ccccc4n3)C2)CC1] | 1-(4-(5-fluoro-2-((1-(quinolin-2-yl)azetidin-3-yl)oxy)pyridin-3-yl)piperidin-1-yl)ethanone | 421 | 0.0648 |
| 15.6 | 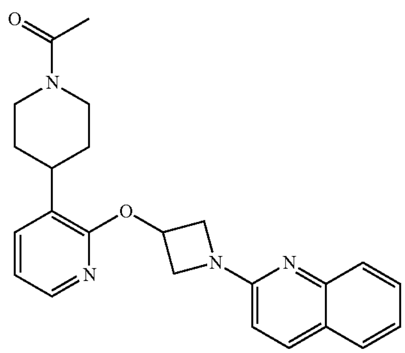 | 1-(4-(2-((1-(quinolin-2-yl)azetidin-3-yl)oxy)pyridin-3-yl)piperidin-1-yl)ethanone | 403 | 0.0688 |
| 15.7 | 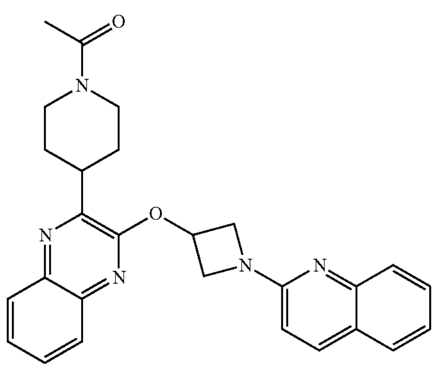 [SMILES: CC(=O)N1CCC(c2nc3ccccc3nc2OC2CN(c3ccc4ccccc4n3)C2)CC1] | 1-(4-(3-((1-(quinolin-2-yl)azetidin-3-yl)oxy)quinoxalin-2-yl)piperidin-1-yl)ethanone | 454 | 0.0029 |
| 15.8 | 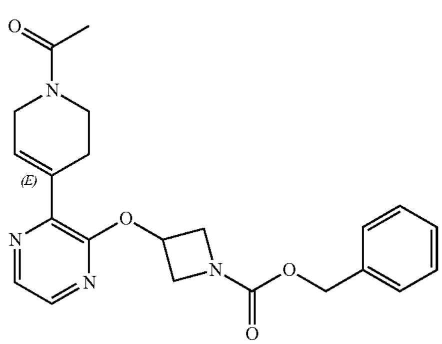 [SMILES: CC(=O)N1CC=C(c2nccnc2OC2CN(C(=O)OCc3ccccc3)C2)CC1] | Benzyl 3-(3-(1-acetyl-1,2,3,6-tetrahydropyridin-4-yl)pyrazin-2-yloxy)azetidine-1-carboxylate | 409 | 0.5825 |

TABLE 12A-continued

EXAMPLES 15.1-15.18 PREPARED ANALOGOUS TO SCHEME 15

| Ex. # | Structure | Chemical Name | ESI-MS (M + 1) | IC$_{50}$ (uM) |
|---|---|---|---|---|
| 15.9 | 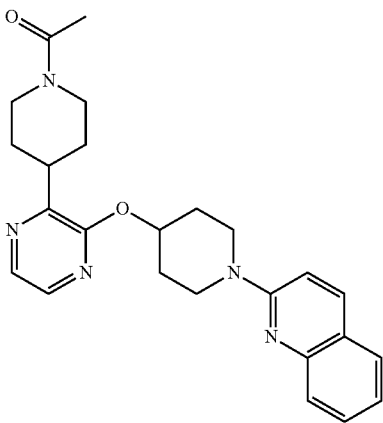 [SMILES: CC(=O)N1CCC(c2nccnc2OC2CCN(c3ccc4ccccc4n3)CC2)CC1] | 1-(4-(2-(1-(quinolin-2-yl)piperidin-4-yloxy)pyridin-3-yl)piperidin-1-yl)ethanone | 432 | 1.64 |
| 15.10 | 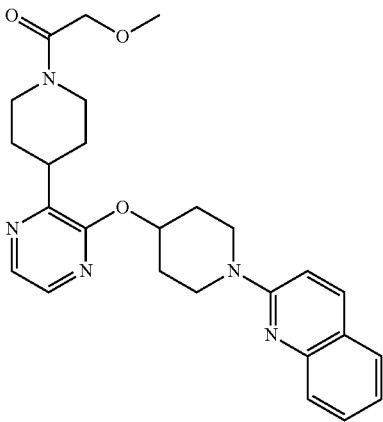 [SMILES: COCC(=O)N1CCC(c2nccnc2OC2CCN(c3ccc4ccccc4n3)CC2)CC1] | 2-methoxy-1-(4-(3-(1-(quinolin-2-yl)piperidin-4-yloxy)pyrazin-2-yl)piperidin-1-yl)ethanone | 462.2 | 0.04166 |
| 15.11 | 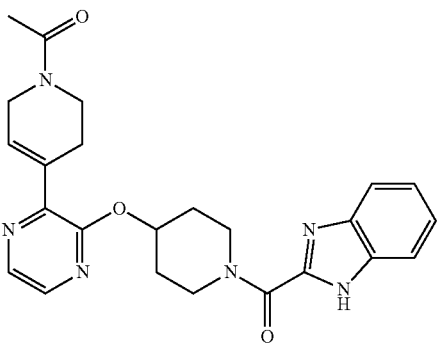 [SMILES: CC(=O)N1CC=C(c2nccnc2OC2CCN(C(=O)c3nc4ccccc4[nH]3)CC2)CC1] | 1-(4-(3-(1-(1H-Benzo[d]imidazol-2-carbonyl)piperidin-4-yloxy)pyrazin-2-yl)-5,6-dihydropyridin-1(2H)-yl)ethanone | 447 | 0.07184 |
| 15.12 | 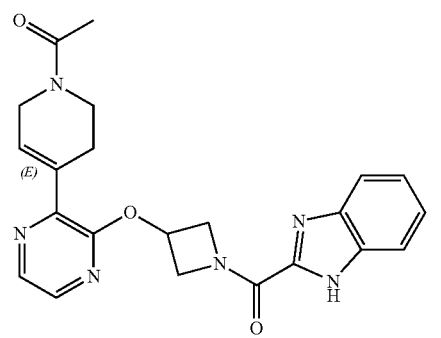 [SMILES: CC(=O)N1CC=C(c2nccnc2OC2CN(C(=O)c3nc4ccccc4[nH]3)C2)CC1] | 1-(4-(3-(1-(1H-benzo[d]imidazole-2-carbonyl)azetidin-3-yloxy)pyrazin-2-yl)-5,6-dihydropyridin-1(2H)-yl)ethanone | 419 | 0.010379 |

TABLE 12A-continued

EXAMPLES 15.1-15.18 PREPARED ANALOGOUS TO SCHEME 15

| Ex. # | Structure | Chemical Name | ESI-MS (M + 1) | IC$_{50}$ (uM) |
|---|---|---|---|---|
| 15.13 | 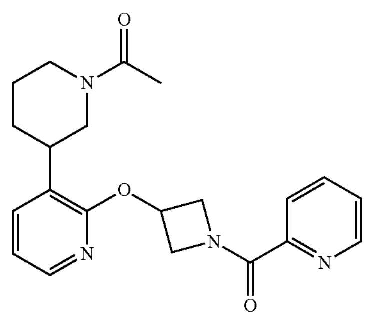 [SMILES: CC(=O)N1CCCC(c2cccnc2OC2CN(C(=O)c3ccccn3)C2)C1] | 1-(3-(2-(1-picolinoylazetidin-3-yloxy)pyridin-3-yl)piperidin-1-yl)ethanone | 381 | 0.04099 |
| 15.14 | 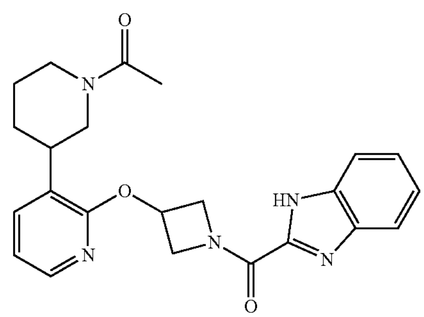 [SMILES: CC(=O)N1CCCC(c2cccnc2OC2CN(C(=O)c3nc4ccccc4[nH]3)C2)C1] | (R) and (S)-1-(3-(2-(1-(1H-benzo[d]imidazole-2-carbonyl)azetidin-3-yloxy)pyridin-3-yl)piperidin-1-yl)ethanone | 420 | 0.006468 |
| 15.15 | 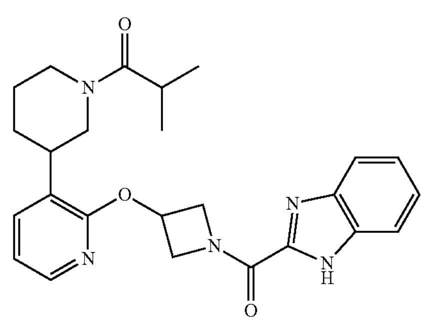 [SMILES: CC(C)C(=O)N1CCCC(c2cccnc2OC2CN(C(=O)c3nc4ccccc4[nH]3)C2)C1] | (R) and (S)-1-(3-(2-(1-(1H-benzo[d]imidazole-2-carbonyl)azetidin-3-yloxy)pyridin-3-yl)piperidin-1-yl)-2-methylpropan-1-one | 448 | 0.0414 |
| 15.16 | 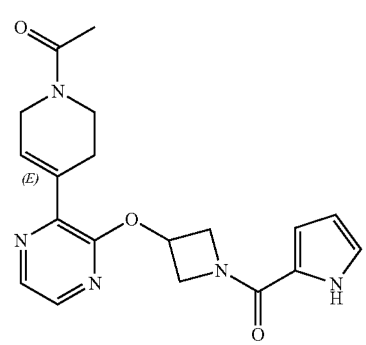 [SMILES: CC(=O)N1CC=C(c2nccnc2OC2CN(C(=O)c3ccc[nH]3)C2)CC1] | 1-(4-(3-(1-(1H-pyrrole-2-carbonyl)azetidin-3-yloxy)pyrazin-2-yl)-5,6-dihydropyridin-1(2H)-yl)ethanone | 368 | 0.2099 |

TABLE 12A-continued

EXAMPLES 15.1-15.18 PREPARED ANALOGOUS TO SCHEME 15

| Ex. # | Structure | Chemical Name | ESI-MS (M + 1) | IC$_{50}$ (uM) |
|---|---|---|---|---|
| 15.17 | 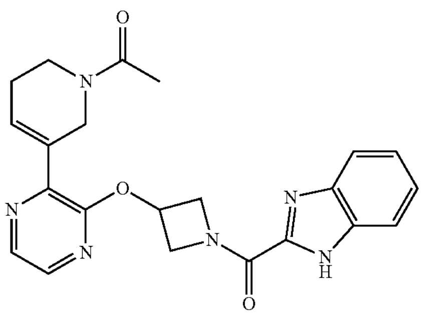 | 1-(3-(3-(1-(1H-benzo[d]imidazole-2-carbonyl)azetidin-3-yloxy)pyrazin-2-yl)-5,6-dihydropyridin-1(2H)-yl)ethanone 2TFA | 419.1 | 0.121 |
| 15.18 | 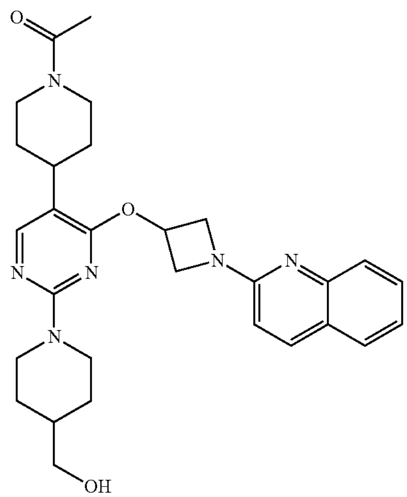 [SMILES: CC(=O)N1CCC(c2cnc(N3CCC(CO)CC3)nc2OC2CN(c3ccc4ccccc4n3)C2)CC1] | 1-(4-(2-(4-(hydroxymethyl)piperidin-1-yl)-4-((1-(quinolin-2-yl)azetidin-3-yl)oxy)pyrimidin-5-yl)piperidin-1-yl)ethanone | 517 | 0.00039 |

TABLE 12B

PREPARATION AND NMR DATA OF EXAMPLES 15.1-15.18

| Ex. # | Starting Material (1) and (2) | Reaction Condition | $^1$H NMR (CD$_3$OD, 400 MHz) δ (ppm) |
|---|---|---|---|
| 15.1 | (see Preparation P4.1) and | TEA, DCM | 8.38-8.35 (m, 1H); 8.18-8.17 (m, 1H); 8.17-8.02 (m, 1H); 7.92-7.90 (m, 1H); 7.83-7.76 (m, 2H); 7.55-7.51 (m, 1H); 7.01-6.99 (m, 1H); 5.70-5.67 (m, 1H); 5.00-4.95 (m, 1H); 4.63-4.59 (m, 2H); 4.58-4.24 (m, 2H); 4.21-3.69 (m, 2H); 3.35 (s, 3H); 3.35-3.34 (m, 2H); 3.02-3.01 (m, 2H); 1.81-1.75 (m, 2H). |

TABLE 12B-continued

PREPARATION AND NMR DATA OF EXAMPLES 15.1-15.18

| Ex. # | Starting Material (1) and (2) | Reaction Condition | $^1$H NMR (CD$_3$OD, 400 MHz) δ (ppm) |
|---|---|---|---|
| 15.2 | 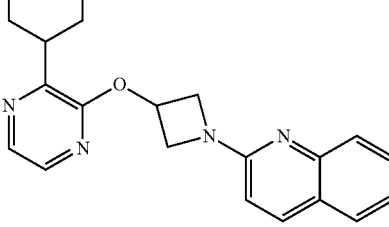<br>(see Preparation P4.1)<br>and<br> | TEA, DCM | (CDCl$_3$) 8.19 (d, J = 2.8 Hz, 1H); 8.13 (d, J = 9.2 Hz, 1H); 7.99-7.93 (m, 2H); 7.76-7.70 (m, 2H); 7.48-7.44 (m, 1H); 6.62 (d, J = 9.2 Hz, 1H); 5.58 (s, 1H); 5.14-4.39 (m, 4H); 3.23-3.10 (m, 1H); 3.92-3.93 (m, 2H); 2.90-2.81 (m, 2H); 2.81 (s, 3H); 1.97-1.96 (m, 4H). |
| 15.3 | 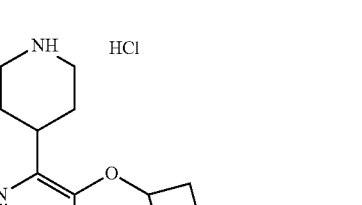<br>(see Preparation P4.1)<br>and<br>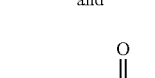 | TEA, DCM | 8.11 (d, J = 2.8 Hz, 1H); 8.03-8.01 (m, 2H); 7.66-7.55 (m, 3H); 7.30-7.25 (m, 1H); 6.75 (d, J = 8.8 Hz, 1H); 5.63-5.59 (m, 1H); 4.69-4.64 (m, 2H); 4.58-4.55 (m, 1H); 4.12-3.92 (m, 2H); 3.43-3.36 (m, 4H); 3.23-3.14 (m, 1H); 2.07 (s, 3H); 2.82-2.79 (m, 1H); 1.98-1.71 (m, 4H). |
| 15.4 | 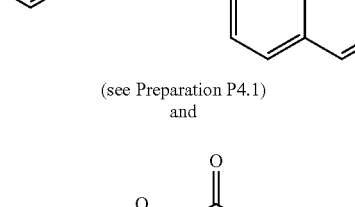<br>(see Preparation P4.2)<br>and<br> | TEA, DCM | 8.33 (d, J = 9.6 Hz, 1H); 7.89-7.87 (m, 1H); 7.89-7.77 (m, 3H); 7.51-7.45 (m, 2H); 6.98-6.96 (m, 1H); 5.61-5.60 (m, 1H); 4.68-4.65 (m, 2H); 4.67-4.52 (m, 3H); 4.02-4.05 (m, 1H); 3.27-3.11 (m, 2H); 2.72-2.71 (m, 1H); 2.25 (s, 3H); 2.12 (s, 3H); 1.73-1.68 (m, 2H); 1.61-1.58 (m, 2H). |

TABLE 12B-continued

PREPARATION AND NMR DATA OF EXAMPLES 15.1-15.18

| Ex. # | Starting Material (1) and (2) | Reaction Condition | ¹H NMR (CD₃OD, 400 MHz) δ (ppm) |
|---|---|---|---|
| 15.5 | 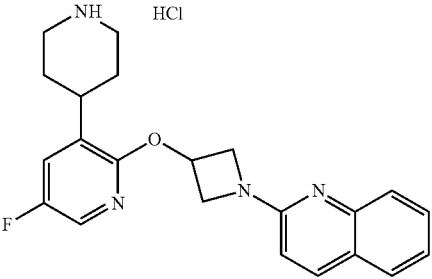<br>(see Preparation P4.3)<br>and<br> | TEA, DCM | (CDCl₃) 7.83 (d, J = 8.2 Hz, 1H); 7.77-7.69 (m, 2H); 7.56-7.47 (m, 2H); 7.19-7.10 (m, 2H); 6.54 (d, J = 8.8 Hz, 1H); 5.49-5.46 (m, 1H); 4.74-4.70 (m, 1H); 4.60-4.56 (m, 2H); 4.15-4.13 (m, 2H); 3.86-3.82 (m, 1H); 3.13-2.96 (m, 2H); 2.58-2.51 (m, 1H); 2.04 (s, 3H); 1.90-1.79 (m, 2H); 1.49-1.40 (m, 2H). |
| 15.6 | 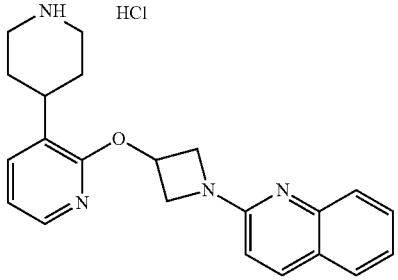<br>(see Preparation P4.4)<br>and<br> | TEA, DCM | 7.99-7.96 (m, 2H); 7.64-7.52 (m, 4H); 7.22 (s, 1H); 6.96-6.93 (m, 1H); 6.70 (d, J = 8.8 Hz, 1H); 5.56 (s, 1H); 4.63-4.59 (m, 3H); 4.19-4.15 (m, 2H); 3.99-3.94 (m, 1H); 3.22-3.12 (m, 2H); 2.68-2.67 (m, 1H); 2.07 (s, 3H); 1.88-1.83 (m, 2H); 1.64-1.53 (m, 2H). |
| 15.7 | 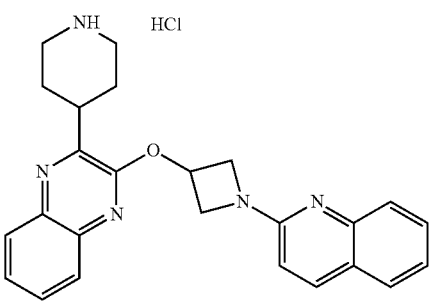<br>(see Preparation P4.5)<br>and<br> | TEA, DCM | (CDCl₃) 8.12 (d, J = 9.2 Hz, 1H); 8.03-7.95 (m, 2H); 7.79-7.58 (m, 5H); 7.56-7.41 (m, 1H); 6.64 (d, J = 9.6 Hz, 1H); 5.76-5.75 (m, 1H); 5.20-4.71 (m, 4H); 3.99-3.96 (m, 1H); 3.48-3.43 (m, 2H); 2.82-2.71 (m, 1H); 2.145 (s, 3H); 2.03-2.00 (m, 3H); 1.97-1.84 (m, 1H). |

TABLE 12B-continued

PREPARATION AND NMR DATA OF EXAMPLES 15.1-15.18

| Ex. # | Starting Material (1) and (2) | Reaction Condition | $^1$H NMR (CD$_3$OD, 400 MHz) δ (ppm) |
|---|---|---|---|
| 15.8 | (see Preparation P28.3) and [1-acetylimidazole] | TFA; DIEA, DCM | 8.11-8.20 (1H, m), 7.97 (1H, s), 7.24-7.42 (5H, m), 6.92 (1H, br. s.), 5.35-5.52 (1H, m), 5.09 (2H, s), 4.36-4.56 (2H, m), 4.19-4.36 (2H, m), 4.07 (2H, d, J = 6.6 Hz), 3.74 (2H, dt, J = 15.3, 5.7 Hz), 2.77 (1H, br. s.), 2.57-2.73 (1H, m), 2.16 (3H, s) |
| 15.9 | (see Preparation P14.1) and [acetyl chloride] | DIPEA, DMF | (CDCl$_3$) 1.65-1.79 (m, 1H) 1.85-1.96 (m, 5H) 2.10 (s, 3H) 2.13-2.21 (m, 2H) 2.65-2.75 (m, 1H) 3.13-3.28 (m, 2H) 3.68 (td, J = 8.71, 4.30 Hz, 2H) 3.92 (d, J = 12.52 Hz, 1H) 4.08-4.18 (m, 2H) 4.70 (d, J = 13.50 Hz, 1H) 5.40 (dt, J = 7.78, 4.03 Hz, 1H) 7.05 (d, J = 9.19 Hz, 1H) 7.20-7.26 (m, 1H) 7.50-7.57 (m, 1H) 7.61 (d, J = 7.63 Hz, 1H) 7.71 (d, J = 8.41 Hz, 1H) 7.91 (d, J = 9.19 Hz, 1H) 7.94 (d, J = 2.74 Hz, 1H) 8.05 (d, J = 2.74 Hz, 1H) |

TABLE 12B-continued

PREPARATION AND NMR DATA OF EXAMPLES 15.1-15.18

| Ex. # | Starting Material (1) and (2) | Reaction Condition | $^1$H NMR (CD$_3$OD, 400 MHz) δ (ppm) |
|---|---|---|---|
| 15.10 | 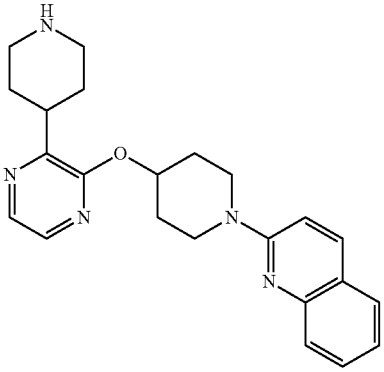<br>(see Example 14.1)<br>and<br>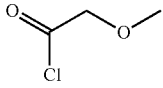 | DIPEA, DMF | (CDCl3) 1.69-1.81 (m, 1H) 1.84-1.98 (m, 5H) 2.16 (dd, J = 7.63, 2.93 Hz, 2H) 2.75 (t, J = 11.64 Hz, 1H) 3.09-3.19 (m, 1H) 3.20-3.29 (m, 1H) 3.42 (s, 3H) 3.68 (t, J = 9.10 Hz, 2H) 3.99 (d, J = 12.72 Hz, 1H) 4.09-4.18 (m, 4H) 4.67 (d, J = 12.52 Hz, 1H) 5.40 (dt, J = 7.53, 3.86 Hz, 1H) 7.05 (d, J = 9.00 Hz, 1H) 7.21-7.24 (m, 1H) 7.55 (t, J = 7.53 Hz, 1H) 7.61 (d, J = 7.63 Hz, 1H) 7.71 (d, J = 8.61 Hz, 1H) 7.91 (d, J = 9.19 Hz, 1H) 7.94 (d, J = 2.74 Hz, 1H) 8.05 (d, J = 2.74 Hz, 1H) |
| 15.11 | 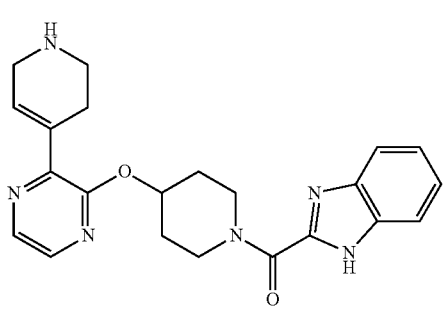<br>(see Preparation P28.3)<br>and<br>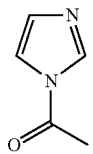 | THF | (CDCl$_3$) 10.47 (1H, br. s.), 8.13 (1H, d, J = 2.6 Hz), 7.96 (1H, br. s.), 7.83 (1H, d, J = 7.7 Hz), 7.54 (1H, d, J = 7.7 Hz), 7.29-7.45 (2H, m), 6.91 (1H, br. s.), 5.52 (1H, d, J = 3.7 Hz), 5.06 (1H, d, J = 5.4 Hz), 4.58-4.74 (1H, m), 4.31 (1H, br. s.), 4.20 (1H, br. s.), 4.11 (1H, d, J = 5.7 Hz), 3.80 (2H, t, J = 5.6 Hz), 3.64 (1H, t, J = 5.6 Hz), 2.74 (2H, d, J = 15.5 Hz), 2.19-2.32 (2H, m), 2.15 (3H, d, J = 7.3 Hz), 1.90-2.10 (2H, m) |

TABLE 12B-continued

PREPARATION AND NMR DATA OF EXAMPLES 15.1-15.18

| Ex. # | Starting Material (1) and (2) | Reaction Condition | $^1$H NMR (CD$_3$OD, 400 MHz) δ (ppm) |
|---|---|---|---|
| 15.12 | 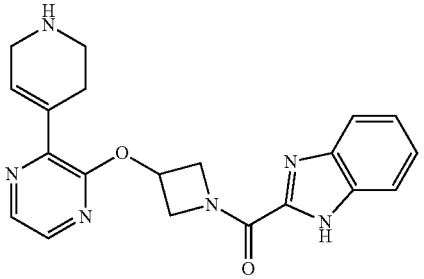<br>(see Preparation P28.2)<br>and<br>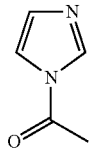 | THF | (CDCl$_3$) 10.79 (1H, br. s.), 8.22 (1H, dd, J = 6.8, 2.5 Hz), 7.93-8.04 (1H, m), 7.69 (2H, br. s.), 7.31-7.44 (2H, m), 6.95 (1H, br. s.), 5.48-5.67 (1H, m), 5.36 (1H, dd, J = 12.0, 6.4 Hz), 4.85-5.05 (1H, m), 4.75 (1H, dd, J = 11.7, 6.5 Hz), 4.30-4.43 (2H, m), 4.23 (1H, d, J = 2.7 Hz), 3.82 (1H, t, J = 5.7 Hz), 3.66 (1H, t, J = 5.8 Hz), 2.76 (2H, d, J = 19.0 Hz), 2.16 (3H, d, J = 8.8 Hz) |
| 15.13 | 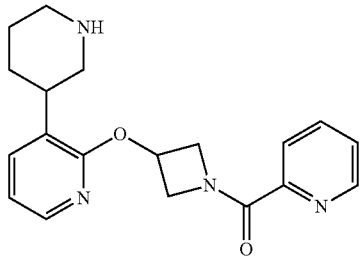<br>(see Preparation P4.9)<br>and<br>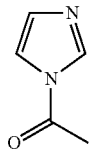 | DCM | (CDCl$_3$) 8.58 (1H, t, J = 5.6 Hz), 8.13 (1H, d, J = 7.8 Hz), 8.03 (1H, br. s.), 7.82 (1H, t, J = 7.5 Hz), 7.42-7.55 (1H, m), 7.37 (1H, br. s.), 6.92 (1H, br. s.), 5.51 (1H, br. s.), 5.15 (1H, dd, J = 11.2, 6.4 Hz), 4.53-4.82 (3H, m), 4.25 (1H, br. s.), 3.81-4.05 (1H, m), 2.83-3.04 (2H, m), 2.51-2.75 (1H, m), 2.13 (3H, s), 1.95-2.12 (1H, m), 1.74-1.94 (3H, m) |
| 15.14 | 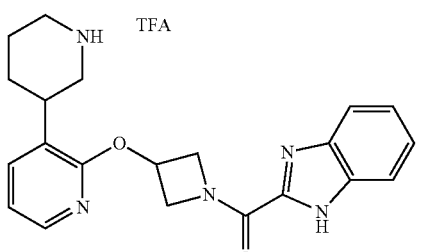 TFA<br>(see Preparation P4.8)<br>and<br>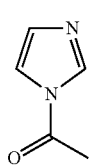 | DCM | ppm 8.04 (1H, ddd, J = 9.1, 5.0, 1.8 Hz), 7.52-7.81 (3H, m), 7.33 (2H, br. s.), 7.01 (1H, ddd, J = 10.4, 7.4, 4.9 Hz), 5.48-5.66 (1H, m), 5.25 (1H, dd, J = 11.6, 6.4 Hz), 4.76-4.85 (1H, m), 4.58-4.76 (2H, m), 4.22-4.33 (1H, m), 3.95-4.15 (1H, m), 2.95-3.21 (2H, m), 2.56-2.70 (1H, m), 2.21 (3H, s), 1.98-2.07 (1H, m), 1.78-1.99 (2H, m), 1.51-1.76 (1H, m) |

TABLE 12B-continued

PREPARATION AND NMR DATA OF EXAMPLES 15.1-15.18

| Ex. # | Starting Material (1) and (2) | Reaction Condition | $^1$H NMR (CD$_3$OD, 400 MHz) δ (ppm) |
|---|---|---|---|
| 15.15 | 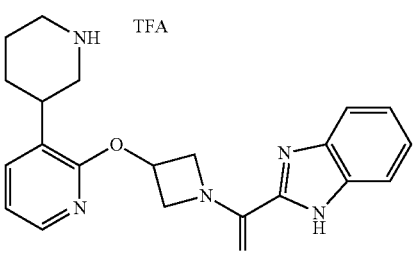 (see Preparation P4.8) and isobutyryl chloride | [(CH$_3$)$_2$CH]$_2$NC$_2$H$_5$ DCM TFA | (CDCl$_3$) 10.57 (1H, br. s.), 8.04 (1H, d, J = 13.3 Hz), 7.82 (1H, d, J = 8.0 Hz), 7.49-7.62 (2H, m), 7.28-7.41 (2H, m), 6.82-7.02 (1H, m), 5.45-5.65 (1H, m), 5.25-5.35 (1H, m), 4.80-4.98 (1H, m), 4.72 (2H, m), 4.30-4.38 (1H, m), 3.85-4.15 (1H, dd, J = 9.5 Hz, J = 14.9 Hz), 2.97-3.20 (2H, m), 2.68-2.97 (2H, m), 1.95-2.16 (1H, m), 1.72-1.85 (2H, m), 1.51-1.67 (1H, m), 1.15 (6H, m). |
| 15.16 | 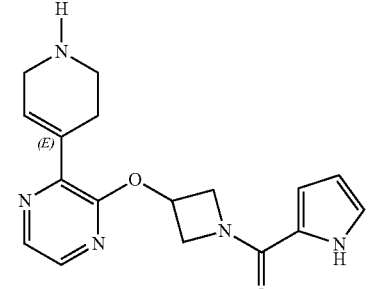 (see Preparation P28.9) and 1-acetylimidazole | DCM | (CDCl$_3$) 9.36 (1H, br. s.), 8.10-8.29 (1H, d, J = 2.5 Hz), 7.94 (1H, d, J = 2.5 Hz), 6.95 (1H, br. s.), 6.47 (1H, br. s.), 6.27 (1H, d, J = 2.8 Hz), 5.52 (1H, m), 4.52-4.79 (2H, m), 4.22-4.32 (4H, m), 3.81 (1H, t, J = 5.6 Hz), 3.66 (1H, t, J = 5.6 Hz), 2.65-2.74 (2H, m), 2.17 (3H, s) |
| 15.17 | 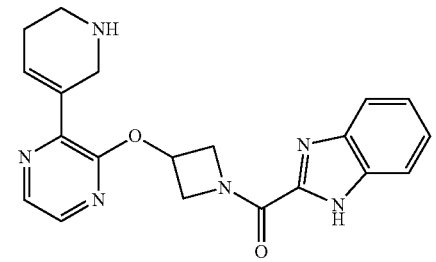 (see Preparation P28.1) and acetic acid | EDI, DIPEA, DMF | (DMSO-d$_6$) δ ppm 8.30 (1H, br. s.), 8.12 (1H, br. s.), 7.63 (2H, br. s.), 7.15-7.38 (3H, m), 5.53 (1H, br. s.), 5.19 (1H, dd, J = 11.3, 6.0 Hz), 4.75 (1H, d, J = 11.1 Hz), 4.52-4.67 (1H, m), 4.45 (2H, br. s.), 4.24 (1H, d, J = 10.8 Hz), 3.57 (peak obscured by solvent), 3.17 (2H, s), 2.48 (peak obscured by solvent), 2.35 (1H, br. s.), 2.06 (3H, s). |

TABLE 12B-continued

PREPARATION AND NMR DATA OF EXAMPLES 15.1-15.18

| Ex. # | Starting Material (1) and (2) | Reaction Condition | $^1$H NMR (CD$_3$OD, 400 MHz) δ (ppm) |
|---|---|---|---|
| 15.18 | 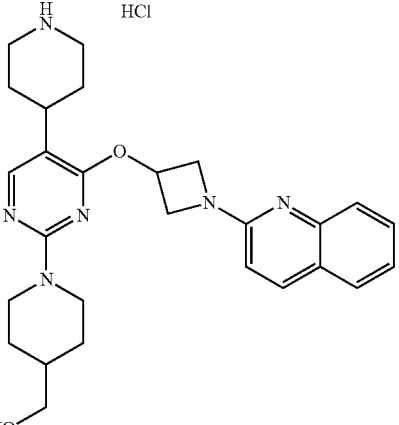<br>(see Preparation P4.7)<br>and<br>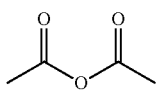 | TEA, DCM;<br>4M NaOH, MeOH | 8.06-8.04 (m, 1H); 7.96 (s, 1H); 7.72-7.70 (m, 2H); 7.59-7.56 (m, 1H); 7.28-7.26 (m, 1H); 6.80-6.78 (m, 1H); 5.63-5.60 (m, 1H); 4.72-4.64 (m, 4H); 4.25-4.23 (m, 2H); 4.04-4.01 (m, 1H); 3.47-3.45 (m, 2H). 3.25-3.20 (m, 2H); 2.96-2.90 (m, 2H); 2.73-2.67 (m, 1H); 2.13 (s, 3H); 1.93-1.61 (m, 7H); 1.33-1.17 (m, 3H). |

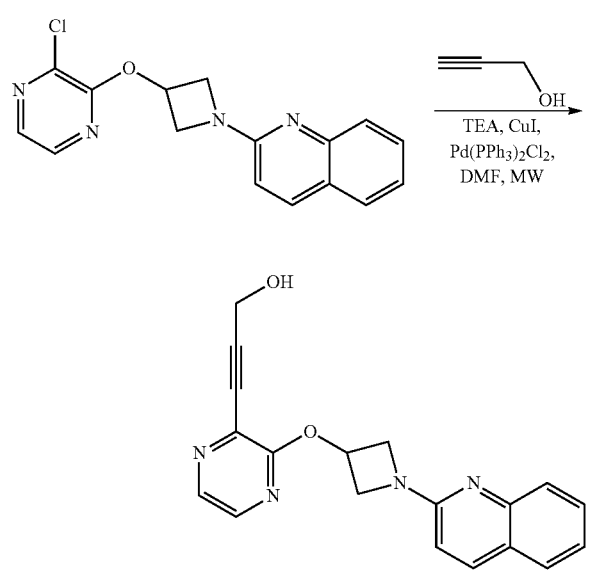

SCHEME 16

Example 16.1

3-(3-((1-(Quinolin-2-yl)Azetidin-3-yl)Oxy)Pyrazin-2-yl)Prop-2-yn-1-ol

A microwave tube was charged with 2-(3-((3-chloropyrazin-2-yl)oxy)azetidin-1-yl)quinoline (see PREPARATION P2.6; 150 mg, 0.5 mmol), triethylamine (100 mg, 1.0 mmol), CuI (10 mg, 0.05 mmol), Pd (PPh$_3$)$_2$Cl$_2$ (35 mg, 0.05 mmol), prop-2-yn-1-ol (28 mg, 0.05 mmol). After several cycles of vacuum/purge with argon, 2 mL of DMF are added. The reaction mixture is then stirred at 110° C. under microwave for 2 hours. The reaction mixture is poured onto a solution of NaHCO$_3$ and diluted with EtOAc and the layers are separated. The organic extracts were washed with water (10 mL) and brine (10 mL), dried over Na$_2$SO$_4$, and filtered. The filtrate was evaporated in vacuo and the residue was purified by flash column chromatography on silica gel (5% to 30% EtOAc in petroleum ether) to give the title product (99 mg, 0.3 mmol, 61% yield) as white solid. ESI-MS (M+1): 333 calc. for C$_{19}$H$_{16}$N$_4$O$_2$ 332.

TABLE 13A

EXAMPLES 16.1-16.3 PREPARATION ANALOGOUS TO SCHEME 16

| Ex. # | Structure | Chemical Name | ESI-MS (M + 1) | IC$_{50}$ (uM) |
|---|---|---|---|---|
| 16.1 | 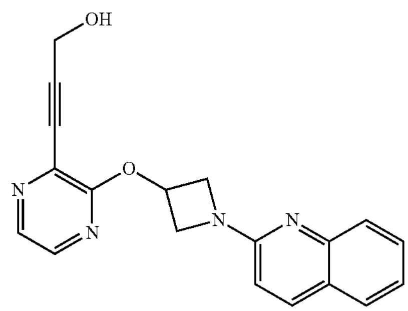 [SMILES: OCC#Cc1nccnc1OC1CN(c2ccc3ccccc3n2)C1] | 3-(3-((1-(quinolin-2-yl)azetidin-3-yl)oxy)pyrazin-2-yl)prop-2-yn-1-ol | 333 | 0.342 |
| 16.2 | (as racemic mixture) | 4-(3-((1-(quinolin-2-yl)azetidin-3-yl)oxy)pyrazin-2-yl)but-3-yn-2-ol | 347 | 0.212 |
| 16.3 | 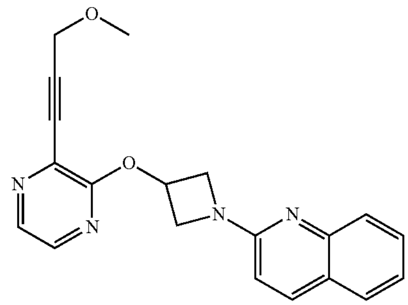 [SMILES: COCC#Cc1nccnc1OC1CN(c2ccc3ccccc3n2)C1] | 2-(3-((3-(3-methoxyprop-1-yn-1-yl)pyrazin-2-yl)oxy)azetidin-1-yl)quinoline | 347 | 0.282 |

TABLE 13B

PREPARATION AND NMR DATA OF EXAMPLES 16.1-16.3

| Ex. # | Strarting Material (1) and (2) | Reaction Condition | $^1$H NMR(CD$_3$OD, 400 MHz): δ (ppm) |
|---|---|---|---|
| 16.1 | (see Preparation P2.6); propargyl alcohol (HC≡C-CH$_2$-OH) | TEA, CuI, Pd(PPh$_3$)$_2$Cl$_2$, DMF, MW | 8.15-8.11 (m, 2H); 7.98 (d, J = 8.8 Hz, 1H); 7.65 (d, J = 8.2 Hz, 1H); 7.55-7.54 (m, 2H); 7.24 (s, 1H); 6.66 (d, J = 9.6 Hz, 1H); 5.58 (s, 1H); 4.64-4.60 (m, 2H); 4.49 (s, 2H); 4.40-4.24 (m, 2H). |
| 16.2 | (see Preparation P2.6); but-3-yn-2-ol | TEA, CuI, Pd(PPh$_3$)$_2$Cl$_2$, DMF, MW | 7.90 (d, J = 8.0 Hz, 1H); 7.82-7.76 (m, 3H); 7.54-7.50 (m, 2H); 6.99-6.97 (m, 1H); 5.71-5.67 (m, 1H); 5.00-4.75 (m, 2H); 4.77-4.72 (m, 1H); 4.64-4.60 (m, 2H); 1.53-1.51 (d, 3H). |
| 16.3 | (see Preparation P2.6); methyl propargyl ether | TEA, CuI, Pd(PPh$_3$)$_2$Cl$_2$, DMF, MW | 7.98 (d, J = 9.6 Hz, 1H); 7.92-7.90 (m, 1H); 7.81-7.78 (m, 3H); 7.55-7.51 (m, 1H); 6.98 (d, J = 9.6 Hz, 1H); 5.73-5.69 (m, 1H); 5.00-4.96 (m, 3H); 4.96-4.60 (m, 2H); 4.40 (s, 2H); 3.46 (s, 3H). |

SCHEME 17

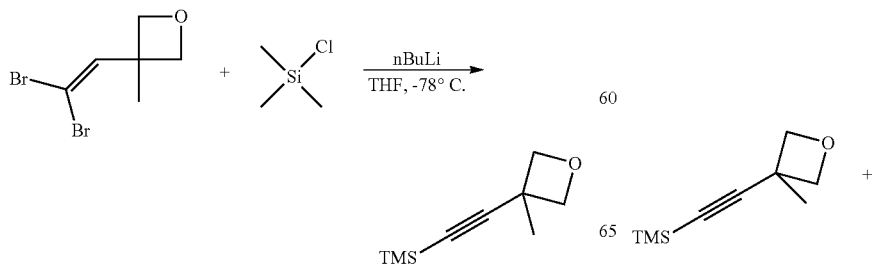

-continued

-continued

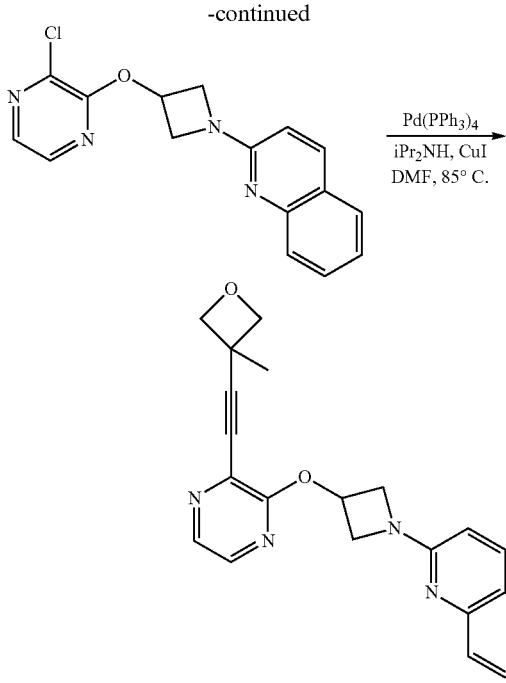

Example 17.1

2-(3-((3-((3-Methyloxetan-3-yl)Ethynyl)Pyrazin-2-yl)Oxy)Azetidin-1-yl)Quinoline

Step. 1. Trimethyl((3-Methyloxetan-3-yl)Ethynyl)Silane

A 250-mL round-bottom flask was charged with 3-(2,2-dibromovinyl)-3-methyloxetane (2.177 g, 8.51 mmol) in THF (85 mL) to give a clear solution. The flask was cooled in a dry ice/acetone bath for 15 min, then n-butyllithium (7.83 mL, 19.56 mmol) (as a 2.5 M solution in hexane) was added dropwise over five min. After stirring at −78° C. for 45 min, trimethylchlorosilane (3.81 mL, 29.8 mmol) was added over 2 min. The cooling bath was removed after 30 min and the reaction was allowed to warm to RT for 30 min. The mixture was diluted with water (50 mL) and ether (50 mL). The layers were separated, and the aqueous layer was extracted with ether (25 mL). The combined organic extracts were dried over magnesium sulfate, filtered, and evaporated. The residue was dissolved in a small amount of ether and filtered through a small pad of silica gel. The filtrate was evaporated to give trimethyl((3-methyloxetan-3-yl)ethynyl)silane (1.344 g, 7.99 mmol, 94% yield) as a pale-yellow oil.

Step. 2. 2-(3-((3-((3-Methyloxetan-3-yl)Ethynyl)Pyrazin-2-yl)Oxy)Azetidin-1-yl)Quinoline Tetrakis(triphenylphosphine)palladium (288 mg, 0.249 mmol), copper(i) iodide (190 mg, 0.998 mmol) and 2-(3-(3-chloropyrazin-2-yloxy)azetidin-1-yl)quinoline (see PREPARATION P2.6; 312 mg, 0.998 mmol) were combined in a microwave vial which was degassed and backfilled with nitrogen (procedure was repeated three times). DMF (1663 μL) was added followed by diisopropylamine (2097 μL, 14.96 mmol) and trimethyl((3-methyloxetan-3-yl)ethynyl)silane (840 mg, 4.99 mmol). The tube was sealed and heated to 85° C. for 16 hours. The solvent was removed under reduced pressure. The residue was dissolved in EtOAc and washed with brine and water. The aqueous layer was back extracted with EtOAc (3×) and the combined organic phase was dried over $Na_2SO_4$. The solvent was removed under reduced pressure. The crude material was purified by chromatography through a Redi-Sep pre-packed silica gel column (40 g), eluting with a gradient of 0% to 50% EtOAc in hexane, to provide 2-(3-(3-((3-methyloxetan-3-yl)ethynyl)pyrazin-2-yloxy)azetidin-1-yl)quinoline (45 mg, 0.121 mmol, 12.11% yield) as orange powder. $^1$H NMR (400 MHz, chloroform-d) δ ppm 1.76 (s, 3H) 4.28 (dd, J=9.88, 4.21 Hz, 2H) 4.47 (d, J=5.48 Hz, 2H) 4.67 (dd, J=9.59, 6.65 Hz, 2H) 4.97 (d, J=5.48 Hz, 2H) 5.52-5.62 (m, 1H) 6.63 (d, J=8.80 Hz, 1H) 7.21-7.41 (m, 2H) 7.45-7.65 (m, 1H) 7.76 (d, J=8.22 Hz, 1H) 7.90 (d, J=8.80 Hz, 1H) 8.03 (d, J=2.74 Hz, 1H) 8.17 (d, J=2.54 Hz, 1H). ESI (M+1) 373.1; calc for $C_{22}H_{20}N_4O_2$ 372. (PDE10 $IC_{50}$=0.0446 nM).

SCHEME 18

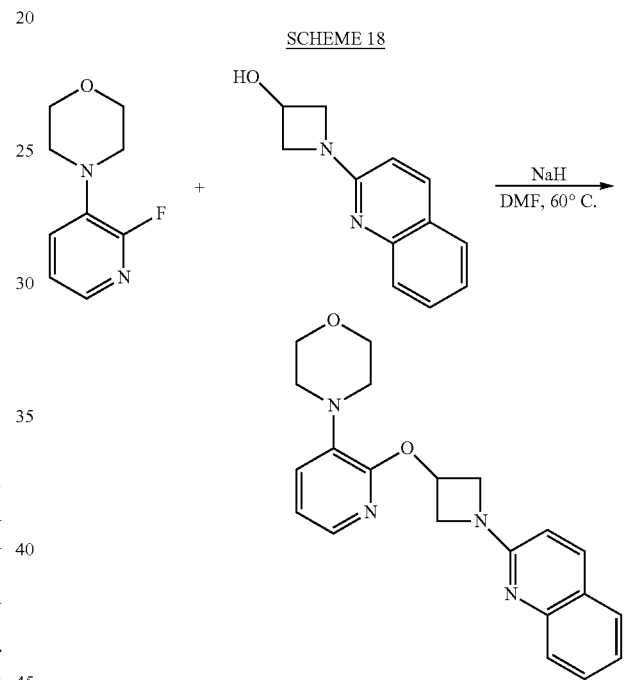

Example 18.1

4-(2-((1-(Quinolin-2-yl)Azetidin-3-yl)Oxy)Pyridin-3-yl)Morpholine

To a solution of 1-(quinolin-2-yl)azetidin-3-ol (see PREPARATION P1.2; 237 mg, 1.186 mmol) in DMF (1.6 mL) was added sodium hydride, 60% in oil (49.4 mg, 1.235 mmol). The reaction mixture was stirred at RT for 15 min and 4-(2-fluoropyridin-3-yl)morpholine (see PREPARATION P17.1; 150 mg, 0.823 mmol) was added. The reaction mixture was heated at 60° C. for 3 hours. The reaction mixture was partitioned between EtOAc and brine. The aqueous layer was back extracted with EtOAc (3×) and the combined organic layers were dried ($Na_2SO_4$) and concentrated. The crude material was purified by chromatography through a Redi-Sep pre-packed silica gel column (40 g), eluting with a gradient of 0% to 80% EtOAc in hexane, to provide 4-(2-(1-(quinolin-2-yl)azetidin-3-yloxy)pyridin-3-yl)morpholine (273 mg, 0.753 mmol, 91% yield) as off-white solid.

TABLE 14A

EXAMPLES 18.1-18.10 PREPARED ANALOGOUS TO SCHEME 18

| Ex. # | Structure | Chemical Name | M + 1 | IC$_{50}$ (uM) |
|---|---|---|---|---|
| 18.1 | 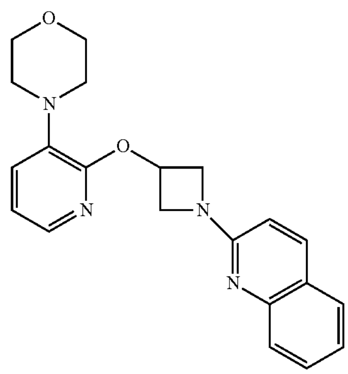 [SMILES: c1cnc(OC2CN(c3ccc4ccccc4n3)C2)c(N2CCOCC2)c1] | 4-(2-((1-(quinolin-2-yl)azetidin-3-yl)oxy)pyridin-3-yl)morpholine | 363 | 0.012 |
| 18.2 | 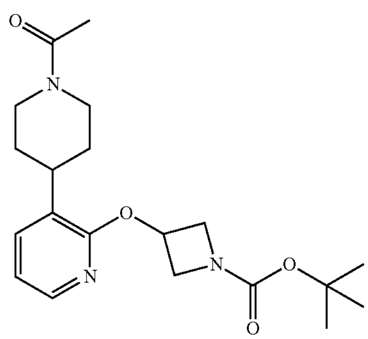 [SMILES: CC(=O)N1CCC(c2cccnc2OC2CN(C(=O)OC(C)(C)C)C2)CC1] | tert-butyl 3-(3-(1-acetylpiperidin-4-yl)pyridin-2-yloxy)azetidine-1-carboxylate | 376.3 | 10.2 |
| 18.3 | 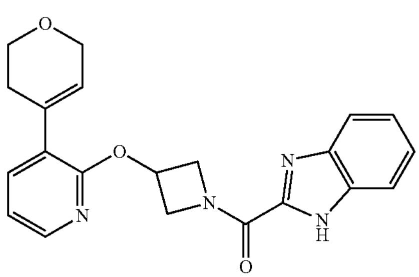 [SMILES: O=C(c1nc2ccccc2[nH]1)N1CC(Oc2ncccc2C2=CCOCC2)C1] | (1H-benzo[d]imidazol-2-yl)(3-((3-(3,6-dihydro-2H-pyran-4-yl)pyridin-2-yl)oxy)azetidin-1-yl)methanone | 377 | 0.000864 |
| 18.4 | 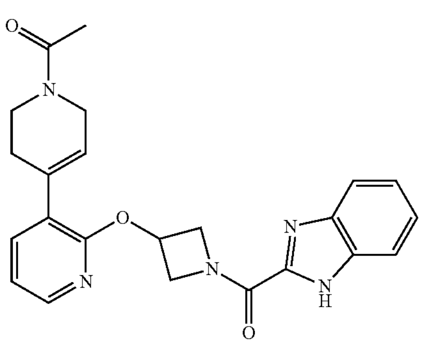 [SMILES: CC(=O)N1CC=C(c2cccnc2OC2CN(C(=O)c3nc4ccccc4[nH]3)C2)CC1] | 1-(4-(2-(1-(1H-benzo[d]imidazole-2-carbonyl)azetidin-3-yloxy)pyridin-3-yl)-5,6-dihydropyridin-1(2H-yl)ethanone | 418.0 | 0.07689 |

TABLE 14A-continued

EXAMPLES 18.1-18.10 PREPARED ANALOGOUS TO SCHEME 18

| Ex. # | Structure | Chemical Name | M + 1 | IC$_{50}$ (uM) |
|---|---|---|---|---|
| 18.5 | 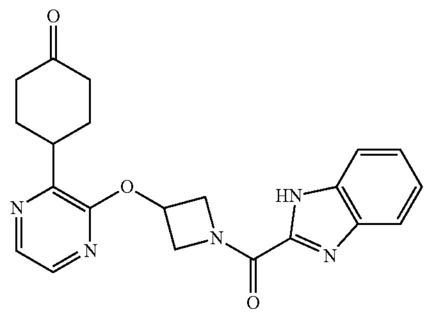 [SMILES: O=C1CCC(c2nccnc2OC2CN(C(=O)c3nc4ccccc4[nH]3)C2)CC1] | 4-(3-(1-(1H-benzo[d]imidazole-2-carbonyl)azetidin-3-yloxy)pyrazin-2-yl)cyclohexanone | 392.1 | 0.1142 |
| 18.6 | 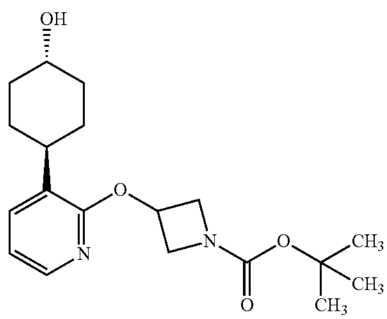 [SMILES: CC(C)(C)OC(=O)N1CC(Oc2ncccc2[C@H]2CC[C@H](O)CC2)C1] | tert-butyl 3-((3-((1r,4r)-4-hydroxycyclohexyl)pyridin-2-yl)oxy)azetidine-1-carboxylate | 349.1 | 0.01575 |
| 18.7 | 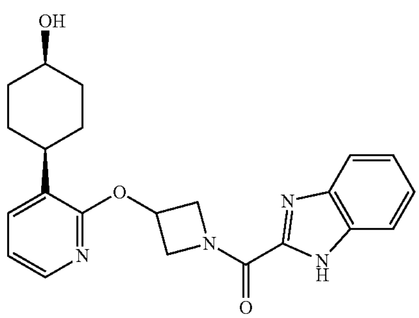 [SMILES: O=C(c1nc2ccccc2[nH]1)N1CC(Oc2ncccc2[C@H]2CC[C@@H](O)CC2)C1] | (1H-benzo[d]imidazol-2-yl)(3-((3-((1s,4s)-4-hydroxycyclohexyl)pyridin-2-yl)oxy)azetidin-1-yl)methanone | 393.2 | 0.02111 |
| 18.8 | 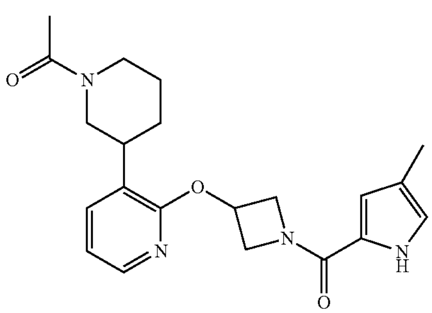 [SMILES: CC(=O)N1CCCC(c2cccnc2OC2CN(C(=O)c3cc(C)c[nH]3)C2)C1] | 1-(3-(2-((1-(4-methyl-1H-pyrrole-2-carbonyl)azetidin-3-yl)oxy)pyridin-3-yl)piperidin-1-yl)ethanone | 383 | 7.942 |

TABLE 14A-continued

EXAMPLES 18.1-18.10 PREPARED ANALOGOUS TO SCHEME 18

| Ex. # | Structure | Chemical Name | M + 1 | IC$_{50}$ (uM) |
|---|---|---|---|---|
| 18.9 | (E) | 1-(4-(3-(1-(4-methyl-1H-pyrrole-2-carbonyl)azetidin-3-yloxy)pyrazin-2-yl)-5,6-dihydropyridin-1(2H)-yl)ethanone | 382 | 0.2495 |
| 18.10 | (as racemic mixture) | 1-(3-(2-((1-(1H-indole-2-carbonyl)azetidin-3-yl)oxy)pyridin-3-yl)piperidin-1-yl)ethanone | 419 | 0.8864 |

TABLE 14B

PREPARATION AND NMR DATA OF EXAMPLES 18.1-18.10

| Ex. # | Starting Material (1) and (2) | Reaction Condition | $^1$H NMR (CD$_3$OD, 400 MHz) δ (ppm) |
|---|---|---|---|
| 18.1 | (see Preparation P17.1) and 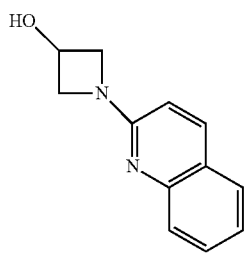 (see Preparation P1.2) | NaH, DMF, 60° C. | (CDCl$_3$) 3.07-3.15 (m, 4H) 3.82-3.92 (m, 4H) 4.24 (dd, J = 9.39, 4.30 Hz, 2H) 4.65 (dd, J = 9.39, 6.65 Hz, 2H) 5.55-5.64 (m, 1H) 6.61 (d, J = 8.80 Hz, 1H) 6.90 (dd, J = 7.73, 4.99 Hz, 1H) 7.12 (d, J = 7.63 Hz, 1H) 7.23 (t, J = 7.43 Hz, 1H) 7.50-7.64 (m, 2H) 7.71-7.91 (m, 3H). |

TABLE 14B-continued
PREPARATION AND NMR DATA OF EXAMPLES 18.1-18.10
| Ex. # | Starting Material (1) and (2) | Reaction Condition | $^1$H NMR (CD$_3$OD, 400 MHz) δ (ppm) |
|---|---|---|---|
| 18.2 | 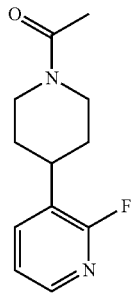<br>(see Preparation P15.1)<br>and<br>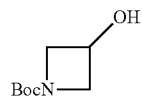 | NaOtBu, DMSO | (DMSO-D$_6$) 1.39 (s, 9H), 1.41-1.48 (m, 1H), 1.53-1.63 (m, 1H), 1.73-1.83 (m, 2H), 2.02 (s, 3H), 2.61 (t, 1H, J = 10.76 Hz), 2.98-3.07 (m, 1H), 3.15 (t, 1H, J = 10.95 Hz), 3.78-3.86 (m, 2H), 3.90 (d, 1H, J = 11.93 Hz), 4.21-4.31 (m, 2H), 4.51 (d, 1H, J = 11.54 Hz), 5.27-5.33 (m, 1H), 6.97 (dd, 1H, J = 7.24 Hz, 4.89 Hz), 7.59 (dd, 1H, J = 7.24 Hz, 1.56 Hz), 7.97 (dd, 1H, J = 4.89 Hz, 1.76 Hz) |
| 18.3 | 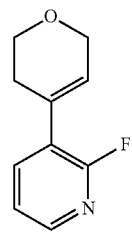<br>(see Preparation P13.2)<br>and<br>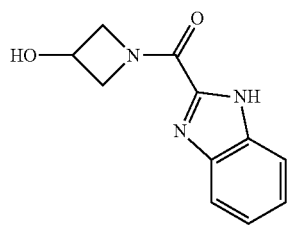<br>(see Preparation P24.1) | KOtBu, DMSO | (CDCl$_3$) 8.11-7.95 (m, 1H); 7.70-7.21 (m, 5H); 6.91-6.85 (m, 1H); 6.00 (s, 1H); 5.52-5.45 (m, 1H); 5.30-5.28 (m, 1H); 4.85-4.60 (m, 2H); 4.30-4.20 (m, 3H); 3.85-3.78 (m, 2H); 2.51-2.40 (m, 2H). |

TABLE 14B-continued

PREPARATION AND NMR DATA OF EXAMPLES 18.1-18.10

| Ex. # | Starting Material (1) and (2) | Reaction Condition | $^1$H NMR (CD$_3$OD, 400 MHz) δ (ppm) |
|---|---|---|---|
| 18.4 | 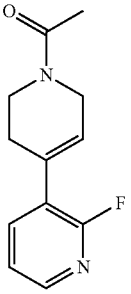<br>(see Preparation P14.1)<br>and<br>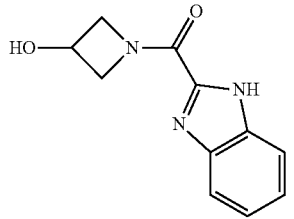<br>(see Preparation P24.1) | KOtBu, DMSO | (DMSO-d$_6$) ppm 13.23 (1H, br. s.), 8.07 (1H, d, J = 4.8 Hz), 7.44-7.80 (3H, m), 7.28 (2H, br. s.), 6.91-7.09 (2H, m), 5.75 (2H, s), 5.51 (1H, br. s.), 5.16 (1H, br. s.), 4.93 (1H, br. s.), 4.51-4.77 (2H, m), 4.14 (1H, d, J = 13.3 Hz), 3.80 (1H, br. s.), 3.61 (1H, d, J = 4.4 Hz), 3.46 (1H, br. s.), 2.01-2.20 (4H, m), 1.78 (1H, br. s.) |
| 18.5 | 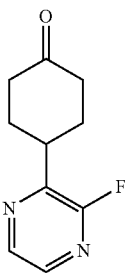<br>(see Preparation P18.1)<br>and<br>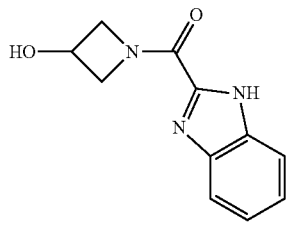<br>(see Preparation P24.1) | NaOtBu, DMSO | (CDCl$_3$) 2.06-2.30 (m, 4H), 2.43-2.63 (m, 4H), 3.47-3.60 (m, 1H), 4.37 (dd, 1H, J = 11.84 Hz, 3.80 Hz), 4.74 (dd, 1H, J = 11.11 Hz, 6.43 Hz), 4.91 (dd, 1H, J = 11.98 Hz, 3.07 Hz), 5.28-5.39 (m, 1H), 5.52-5.62 (m, 1H), 7.29-7.42 (m, 2H), 7.53 (d, 1H, J = 7.75 Hz), 7.81 (d, 1H, J = 8.04 Hz), 7.97 (d, 1H, J = 2.78 Hz), 8.15 (d, 1H, J = 2.63 Hz), 10.35 (s, 1H) |

TABLE 14B-continued

PREPARATION AND NMR DATA OF EXAMPLES 18.1-18.10

| Ex. # | Starting Material (1) and (2) | Reaction Condition | $^1$H NMR (CD$_3$OD, 400 MHz) δ (ppm) |
|---|---|---|---|
| 18.6 | 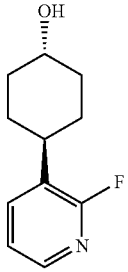<br>(see Preparation P19.1)<br>and<br>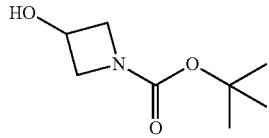 | KOtBu DMSO | (CDCl$_3$) 7.95 (d, J = 4.1 Hz, 1H), 7.60 (d, J = 7.2 Hz, 1H), 6.96 (dd, J = 5.3, 6.9 Hz, 1H), 5.47-5.27 (m, 1H), 4.50-4.27 (m, 2H), 3.94 (dd, J = 3.7, 9.8 Hz, 2H), 3.75-3.53 (m, 1H), 2.86 (t, J = 11.5 Hz, 1H), 2.10 (d, J = 11.5 Hz, 2H), 1.94 (d, J = 12.6 Hz, 2H), 1.77-1.16 (m, 13H) |
| 18.7 | 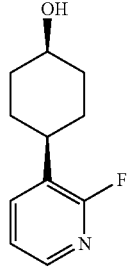<br>(see Preparation P19.1)<br>and<br>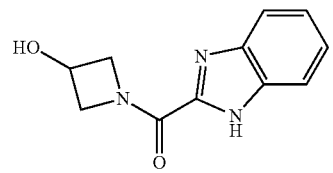<br>(see Preparation P24.1) | KOtBu DMSO | (CDCl$_3$) 8.02-7.91 (m, 1H), 7.69 (br. s., 2H), 7.56-7.46 (m, 2H), 7.34 (dd, J = 2.9, 6.1 Hz, 2H), 7.02-6.87 (m, 1H), 5.54 (br. s., 1H), 5.29 (dd, J = 6.4, 11.6 Hz, 1H), 4.99-4.79 (m, 1H), 4.71 (dd, J = 6.8, 11.5 Hz, 1H), 4.35-4.21 (m, 1H), 3.72-3.55 (m, 1H), 2.85 (t, J = 10.2 Hz, 1H), 2.09 (d, J = 10.6 Hz, 2H), 1.95 (d, J = 11.9 Hz, 2H), 1.60-1.38 (m, 4H) |

TABLE 14B-continued

PREPARATION AND NMR DATA OF EXAMPLES 18.1-18.10

| Ex. # | Starting Material (1) and (2) | Reaction Condition | ¹H NMR (CD₃OD, 400 MHz) δ (ppm) |
|---|---|---|---|
| 18.8 | 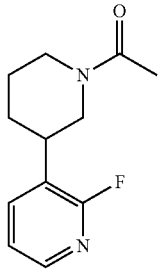<br>(see Preparation P14.2)<br>and<br>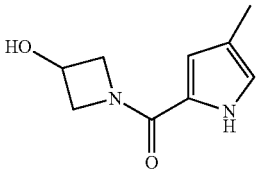<br>(see Preparation P24.2) | NaOtBu DMSO | 8.02 (1H, ddd, J = 6.9, 5.1, 1.7 Hz), 7.65 (1H, td, J = 9.2, 1.4 Hz), 7.00 (1H, td, J = 7.5, 5.1 Hz), 6.73 (1H, s), 6.41 (1H, d, J = 3.2 Hz), 5.40-5.62 (1H, m), 4.47-4.75 (3H, m), 4.43 (3H, m), 4.01-4.27 (1H, m), 2.90-3.24 (2H, m), 2.13 (3H, s), 2.09 (3H, s), 1.95-2.06 (1H, m), 1.80-1.95 (2H, m), 1.53-1.80 (1H, m) |
| 18.9 | 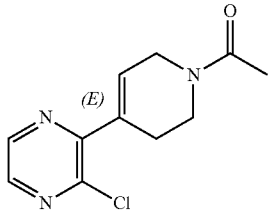<br>(see Preparation P13.5)<br>and<br>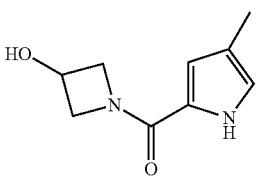<br>(see Preparation P24.2) | NaOtBu DMSO | (CDCl₃) 9.09 (1H, br. s.), 8.16 (1H, d, J = 2.6 Hz), 7.96 (1H, d, J = 2.6 Hz), 6.83 (1H, d, J = 8.2 Hz), 6.72 (1H, br. s.), 6.29 (1H, s), 5.51 (1H, m), 5.08 (1H, m), 4.75 (2H, m), 4.32 (2H, m), 4.01 (2H, m), 3.57-3.74 (1H, m), 2.28 (3H, s), 2.15 (1H, m), 2.11 (3H, s), 2.01 (1H, m) |

TABLE 14B-continued

PREPARATION AND NMR DATA OF EXAMPLES 18.1-18.10

| Ex. # | Starting Material (1) and (2) | Reaction Condition | $^1$H NMR (CD$_3$OD, 400 MHz) δ (ppm) |
|---|---|---|---|
| 18.10 | 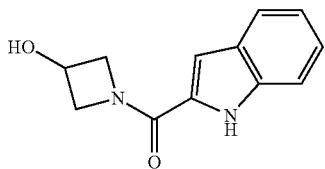<br>(see Preparation P14.2)<br>and<br>(see Preparation P24.3) | NaOtBu DMSO | 8.04 (1H, t, J = 5.3 Hz), 7.58-7.72 (2H, m), 7.45 (1H, d, J = 8.2 Hz), 7.23 (1H, t, J = 7.7 Hz), 6.95-7.12 (2H, m), 6.90 (1H, d, J = 4.5 Hz), 5.61 (1H, m), 5.02 (1H, m), 4.55-4.68 (2H, m), 4.22 (1H, m), 4.08-3.96 (1H, dd, J = 9.5 Hz, J = 14.9 Hz), 3.00-3.26 (3H, m), 2.49-2.80 (1H, m), 2.13 (3H, s), 2.03 (1H, m), 1.86 (2H, m), 1.45-1.77 (1H, m) |

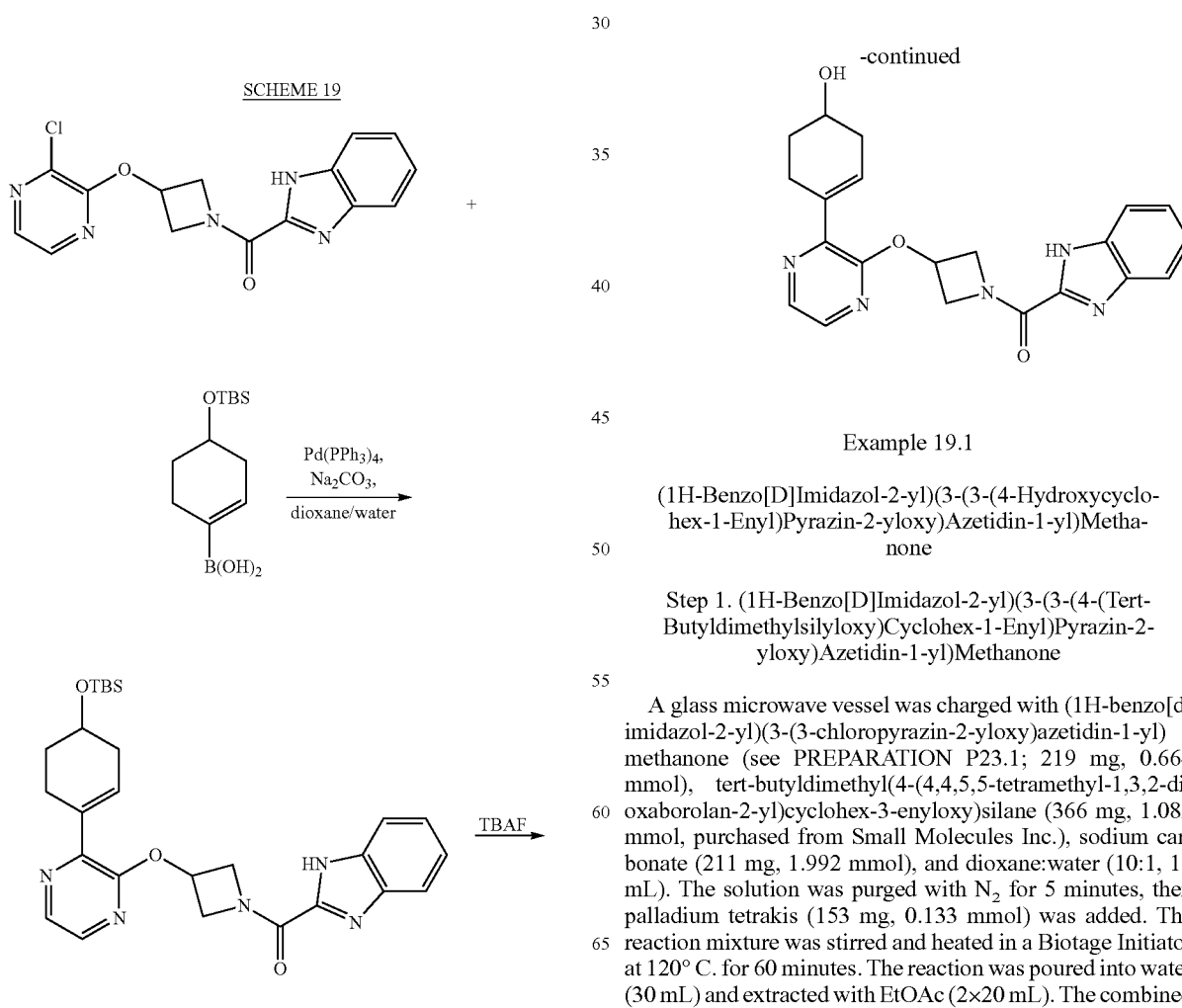

Example 19.1

(1H-Benzo[D]Imidazol-2-yl)(3-(3-(4-Hydroxycyclohex-1-Enyl)Pyrazin-2-yloxy)Azetidin-1-yl)Methanone Step 1. (1H-Benzo[D]Imidazol-2-yl)(3-(3-(4-(Tert-Butyldimethylsilyloxy)Cyclohex-1-Enyl)Pyrazin-2-yloxy)Azetidin-1-yl)Methanone A glass microwave vessel was charged with (1H-benzo[d]imidazol-2-yl)(3-(3-chloropyrazin-2-yloxy)azetidin-1-yl) methanone (see PREPARATION P23.1; 219 mg, 0.664 mmol), tert-butyldimethyl(4-(4,4,5,5-tetramethyl-1,3,2-dioxaborolan-2-yl)cyclohex-3-enyloxy)silane (366 mg, 1.082 mmol, purchased from Small Molecules Inc.), sodium carbonate (211 mg, 1.992 mmol), and dioxane:water (10:1, 15 mL). The solution was purged with N$_2$ for 5 minutes, then palladium tetrakis (153 mg, 0.133 mmol) was added. The reaction mixture was stirred and heated in a Biotage Initiator at 120° C. for 60 minutes. The reaction was poured into water (30 mL) and extracted with EtOAc (2×20 mL). The combined EtOAc layers were eluted through a plug of silica gel. The filtrate was concentrated in vacuo to give crude (1H-benzo[d]imidazol-2-yl)(3-(3-(4-(tert-butyldimethylsilyloxy)cyclohex-1-enyl)pyrazin-2-yloxy)azetidin-1-yl)methanone (550 mg, 164% yield), as a yellow solid. The product was carried forward in the next step without further purification. MS (ESI) m/z 506.3 (MH+).

Step 2. (1H-Benzo[D]Imidazol-2-yl)(3-(3-(4-(Tert-Butyldimethylsilyloxy)Cyclohex-1-Enyl)Pyrazin-2-yloxy)Azetidin-1-yl)Methanone To a solution of (1H-benzo[d]imidazol-2-yl)(3-(3-(4-(tert-butyldimethylsilyloxy)cyclohex-1-enyl)pyrazin-2-yloxy)azetidin-1-yl)methanone (336 mg, 0.664 mmol) and THF (6 mL) was added 1M TBAF in THF (1.6 mL, 1.600 mmol). After 24 hours, the reaction solution was eluted through a short plug of silica gel. The filtrate was concentrated in vacuo and adsorbed onto a plug of silica gel and chromatographed through a Redi-Sep® pre-packed silica gel column (12 g), eluting with 0% to 4% MeOH in DCM, to provide (1H-benzo[d]imidazol-2-yl)(3-(3-(4-hydroxycyclohex-1-enyl)pyrazin-2-yloxy)azetidin-1-yl)methanone (75 mg, 28.8% yield), as a light yellow solid. MS (ESI) m/z 392.1 (MH+). IC$_{50}$ (uM) 0.07168. $^1$H NMR (CDCl$_3$, 400 MHz) δ (ppm): 1.63-1.67 (m, 1H), 1.77-1.87 (m, 1H), 2.00-2.07 (m, 1H), 2.26-2.35 (m, 1H), 2.60-2.71 (m, 2H), 2.74-2.84 (m, 1H), 4.07-4.13 (m, 1H), 4.33 (dd, 1H, J=11.74 Hz, 4.11 Hz), 4.71 (dd, 1H, J=11.74 Hz, 6.65 Hz), 4.90 (dd, 1H, J=11.93 Hz, 4.11 Hz), 5.31 (dd, 1H, J=11.93 Hz, 6.65 Hz), 5.52-5.58 (m, 1H), 6.76 (br s, 1H), 7.29-7.41 (m, 2H), 7.54 (d, 1H, J=7.82 Hz), 7.82 (d, 1H, J=8.02 Hz), 7.93 (d, 1H, J=2.54 Hz), 8.19 (d, 1H, J=2.54 Hz), 10.59 (s, 1H).

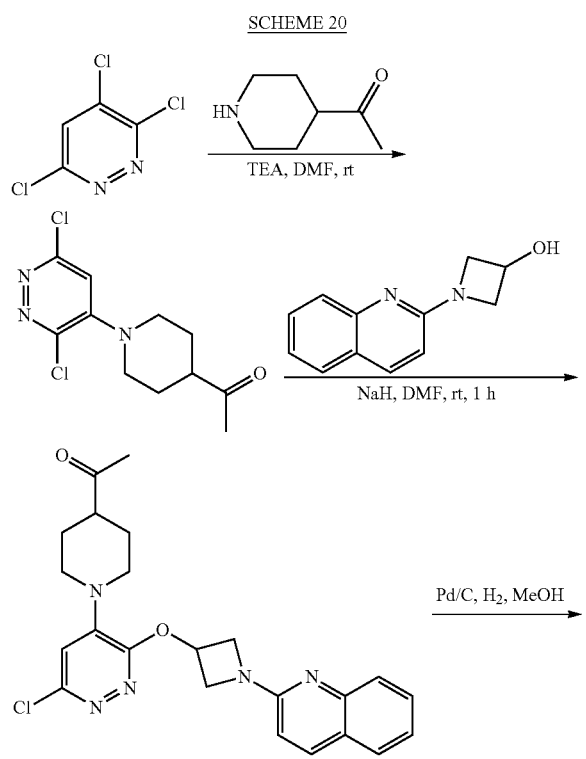

SCHEME 20

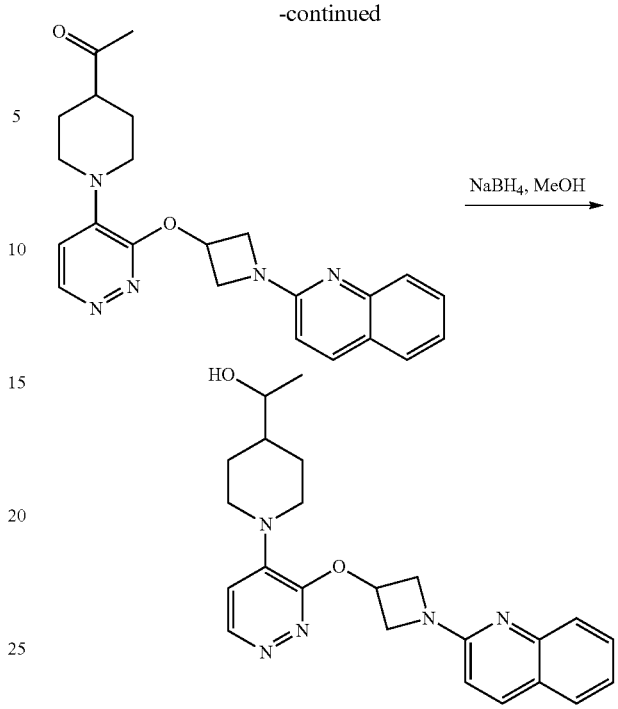

Example 20.1

(Racemic Mixture) 1-(1-(3-((1-(Quinolin-2-yl)Azetidin-3-yl)Oxy)Pyridazin-4-yl)Piperidin-4-yl)Ethanol

Step 1: 1-(1-(3,6-Dichloropyridazin-4-yl)Piperidin-4-yl)Ethanone

Triethylamine (2.2 g, 20.0 mmol), 3,4,6-trichloro-pyridazine (1.8 g, 10.0 mmol) and 1-(piperidin-4-yl)ethanone (1.3 g, 10.0 mmol) was dissolved in DMF (20 mL) and the resulting mixture was stirred at room temperature overnight. The mixture was then diluted with water (50 mL) and extracted with EtOAc (2×50 mL). The combined organic extracts were combined and washed with water (20 mL) and brine (20 mL), dried over Na$_2$SO$_4$, and filtered. The filtrate was evaporated in vacuo and the residue was purified by flash column chromatography on silica gel (20% to 50% EtOAc in hexanes) to give 1-(1-(3,6-dichloropyridazin-4-yl)piperidin-4-yl)ethanone (1.0 g, 3.8 mmol, 39% yield) as white solid. ESI-MS (M+1): 274 calc. for C$_{11}$H$_{13}$ClN$_3$O 273.

Step 2: 1-(1-(6-Chloro-3-(1-(Quinolin-2-yl)Azetidin-3-yl)Oxy)Pyridazin-4-yl)Piperidin-4-yl)Ethanone To a solution of 1-(quinolin-2-yl)azetidin-3-ol (see PREPARATION P1.2, step 1; 0.78 g, 3.8 mmol) in DMF (20 mL) at room temperature was added sodium hydride (60% wt in mineral oil) (0.18 g, 7.6 mmol). The mixture was stirred at room temperature for 10 min and then 1-(1-(3,6-dichloropyridazin-4-yl)piperidin-4-yl)ethanone (1.0 g, 3.8 mmol) was added. The reaction mixture was stirred at room temperature for 1 hour and then diluted with water (20 mL) and extracted with EtOAc (2×30 mL). The combined organic extracts were washed with water (10 mL) and brine (10 mL), dried over Na$_2$SO$_4$, and filtered. The filtrate was evaporated in vacuo and the residue was purified by flash column chromatography on silica gel (5% to 30% EtOAc in hexanes) to give the title product (1.1 g, 2.6 mmol, 70% yield) as white solid. ESI-MS (M+1): 438 calc. for $C_{24}H_{25}ClN_4O_2$ 437.

Step 3: 1-(1-(3-((1-(Quinolin-2-yl)Azetidin-3-yl)Oxy)Pyridazin-4-yl)Piperidin-4-yl)Ethanone A mixture of 1-(1-(6-chloro-3-((1-(quinolin-2-yl)azetidin-3-yl)oxy)pyridazin-4-yl)piperidin-4-yl)ethanone (1.1 g, 2.6 mmol) and wet Pd—C (50%, 1.0 g) in MeOH (30 mL) was stirred under $H_2$ (40 psi) at room temperature for 1.5 hours then the reaction mixture was filtered through CELITE® and washed with MeOH. The filtrate was concentrated in vacuo to give 1-(1-(3-((1-(quinolin-2-yl)azetidin-3-yl)oxy)pyridazin-4-yl)piperidin-4-yl)ethanone (0.98 g, 2.5 mmol, yield 96%). ESI-MS (M+1): 404 calc. for $C_{24}H_{26}N_4O_2$ 403.

Step 4: (Racemic Mixture) 1-(1-(3-((1-(Quinolin-2-yl)Azetidin-3-yl)Oxy)Pyridazin-4-yl)Piperidin-4-yl)Ethanol 1-(1-(3-((1-(quinolin-2-yl)azetidin-3-yl)oxy)pyridazin-4-yl)piperidin-4-yl)ethanone (100 mg, 0.25 mmol) was dissolved in 10 ml of methanol. This solution was cooled down to 0° C. using an ice bath and sodium tetraborohydride (19 mg, 0.50 mmol) was added by portions. The reaction mixture was stirred for 4 hours at ambient temperature, and then saturated aqueous solution of ammonium chloride (5 mL) was added. The methanol was evaporated off under reduced pressure then the reaction mixture was taken up in ethyl acetate. The organic layer was separated from the aqueous layer. The aqueous layer was back extracted one more time with ethyl acetate. The organic layers were combined and dried over magnesium sulfate, followed by concentration under reduced pressure. The residue was purified by column chromatography on silica gel to give (racemic mixture) 1-(1-(3-((1-(quinolin-2-yl)azetidin-3-yl)oxy)pyridazin-4-yl)piperidin-4-yl)ethanol (76 mg, 0.19 mmol, 75% yield). ESI-MS (M+1): 406 calc. for $C_{23}H_{22}N_5O_2$ 405. PDE10 $IC_{50}$ (uM): 0.0767. $^1$HNMR ($CD_3OD$, 400 MHz) δ (ppm): δ (ppm) 8.40 (m, 1H); 8.14-8.10 (d, J=8.8 Hz, 1H); 7.97 (d, J=8.8 Hz, 1H); 7.64-7.58 (m, 2H); 7.51-7.46 (m, 1H); 7.20-7.16 (m, 1H); 6.80-6.79 (m, 1H); 6.62 (d, J=9.2 Hz, 1H); 5.62-5.59 (m, 1H); 4.61-4.57 (m, 2H); 4.18-4.15 (m, 2H); 3.96-3.93 (m, 2H); 3.48-3.43 (m, 1H); 2.73-2.67 (m, 2H); 1.91-1.88 (m, 1H); 1.66-1.64 (m, 1H); 1.42-1.34 (m, 3H); 1.11-1.10 (d, 3H).

TABLE 15A

EXAMPLE 20.1 PREPARED ANALOGOUS TO SCHEME 20

| Ex. # | Structure | Chemical Name | M + 1 | $IC_{50}$ (uM) |
|---|---|---|---|---|
| 20.1 | (as racemic mixture) | 1-(1-(3-((1-(quinolin-2-yl)azetidin-3-yl)oxy)pyridazin-4-yl)piperidin-4-yl)ethanol | 406 | 0.0767 |

SCHEME 21

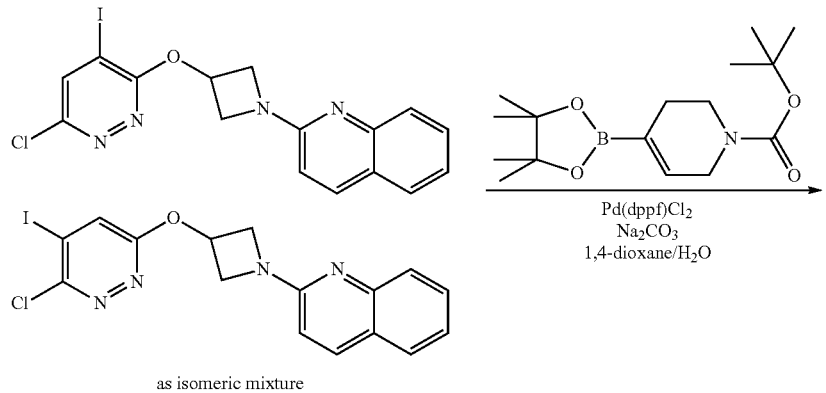

as isomeric mixture

359                                    360
-continued
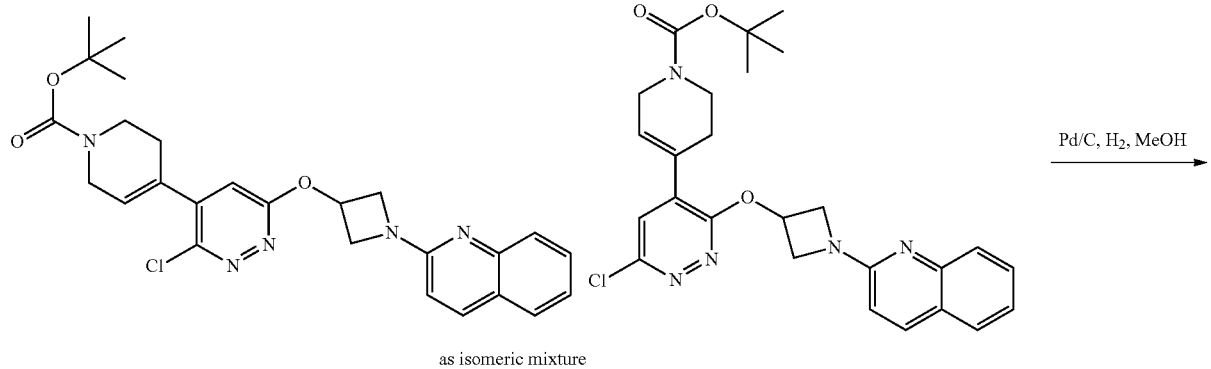
as isomeric mixture
Pd/C, H₂, MeOH
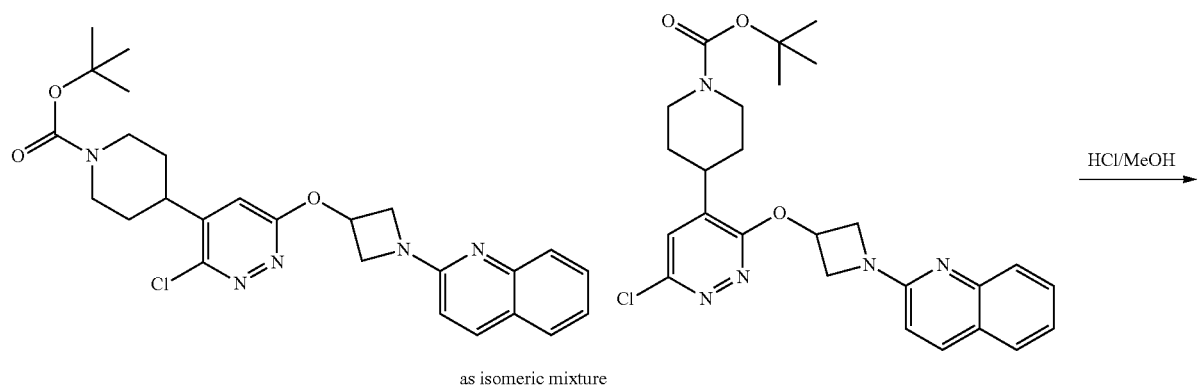
as isomeric mixture
HCl/MeOH
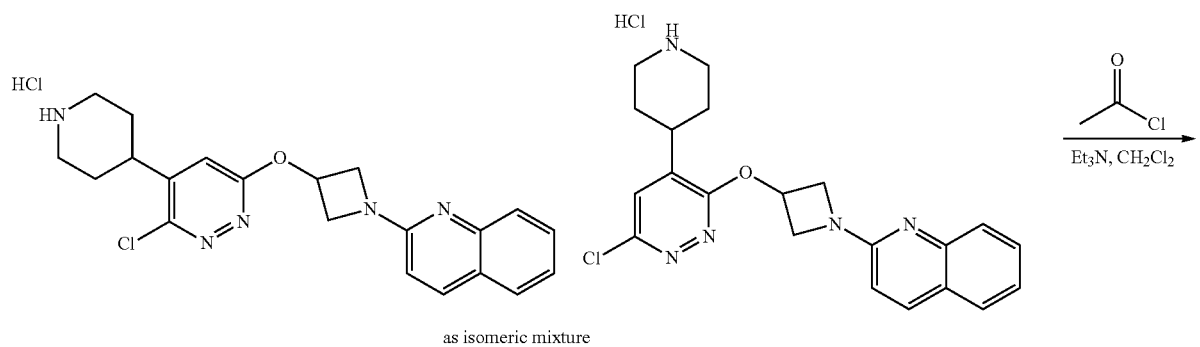
as isomeric mixture
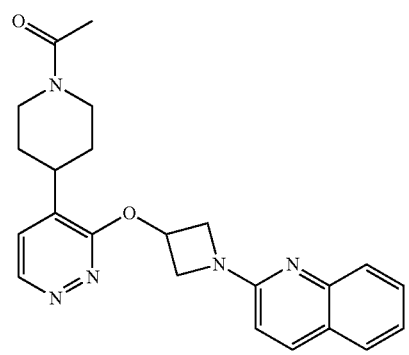
major product

Example 21.1

1-(4-(3-((1-(Quinolin-2-yl)Azetidin-3-yl)Oxy)Pyridazin-4-yl)Piperidin-1-yl)Ethanone

Step 1. Tert-Butyl 4-(3-Chloro-6-((1-(Quinolin-2-yl)Azetidin-3-yl)Oxy)Pyridazin-4-yl)-5,6-Dihydropyridine-1(2H)-Carboxylate and Tert-Butyl 4-(6-Chloro-3-((1-(Quinolin-2-yl)Azetidin-3-yl)Oxy)Pyridazin-4-yl)-5,6-Dihydropyridine-1(2H)-Carboxylate, as Isomeric Mixture To a solution of 2-(3-((6-chloro-5-iodopyridazin-3-yl)oxy)azetidin-1-yl)quinoline and 2-(3-((6-chloro-4-iodopyridazin-3-yl)oxy)azetidin-1-yl)quinoline as isomeric mixture, (see PREPARATION P6.1; 521 mg, 1.2 mmol) in 1,4-dioxane (15 mL) was treated with $Na_2CO_3$ (255 mg, 2.4 mmol) in 2 mL of water as a solution, followed by additional of tert-butyl 4-(4,4,5,5-tetramethyl-1,3,2-dioxaborolan-2-yl)-5,6-dihydropyridine-1(2H)-carboxylate (557 mg, 1.8 mmol) and Pd(dppf)Cl$_2$ (88 mg, 0.12 mmol). The resulting mixture was heated at refluxing overnight under $N_2$ atmosphere. The solution was filtered, and the filtrate was concentrated. The residue was purified by flash column chromatography on silica gel (20% to 70% EtOAc in petroleum ether) to give the title product (509 mg, 1.0 mmol, yield: 83%). ESI-MS (M+1): 494 calc. for $C_{26}H_{28}ClN_5O_3$ 493.

Step 2. Tert-Butyl 4-(3-Chloro-6-((1-(Quinolin-2-yl)Azetidin-3-yl)Oxy)Pyridazin-4-yl)Piperidine-1-Carboxylate and Tert-Butyl 4-(6-Chloro-3-((1-(Quinolin-2-yl)Azetidin-3-yl)Oxy)Pyridazin-4-yl)Piperidine-1-Carboxylate as Isomeric Mixture To a solution of tert-butyl 4-(3-chloro-6-((1-(quinolin-2-yl)azetidin-3-yl)oxy)pyridazin-4-yl)-5,6-dihydropyridine-1(2H)-carboxylate and tert-butyl 4-(6-chloro-3-((1-(quinolin-2-yl)azetidin-3-yl)oxy)pyridazin-4-yl)-5,6-dihydropyridine-1(2H)-carboxylate (509 mg, 1.0 mmol) as isomeric mixture obtained in Step 1 in MeOH (10 mL) was added Pd/C (50%, 300 mg). The reaction solution was stirred at room temperature overnight under $H_2$ atmosphere. The mixture was filtered through CELITE® and concentrated to give the product (334 mg, 0.73 mmol, yield: 73%). ESI-MS (M+1): 462 calc. for $C_{26}H_{31}N_5O_3$ 461.

Step 3. 1-(4-(3-((1-(Quinolin-2-yl)Azetidin-3-yl)Oxy)Pyridazin-4-yl) Piperidin-1-yl)Ethanone A mixture of product obtained in Step 2 (334 mg, 0.73 mmol) in HCl/MeOH (10 mL, saturated with HCl gas) was stirred at room temperature for 1 hour. Then it was concentrated to give 2-(3-((6-chloro-5-(piperidin-4-yl)pyridazin-3-yl)oxy)azetidin-1-yl)quinoline hydrochloride and 2-(3-((6-chloro-4-(piperidin-4-yl)pyridazin-3-yl)oxy)azetidin-1-yl)quinoline hydrochloride as isomeric mixture, which was used in the next step without further purification.

Step 4. 1-(4-(3-((1-(Quinolin-2-yl)Azetidin-3-yl)Oxy)Pyridazin-4-yl)Piperidin-1-yl)Ethanone To a solution of mixture of product obtained in Step 3 in $CH_2Cl_2$ (10 mL) was added $Et_3N$ (148 mg, 1.46 mmol) and acetyl chloride (69 mg, 0.88 mmol). The reaction mixture was stirred at room temperature for 1 hour, then diluted with $CH_2Cl_2$ (20 mL), washed with water (20 mL). The organic layer was washed with brine (20 mL), dried over $Na_2SO_4$, and filtered, evaporated to give the crude product. Purified by column chromatography, and followed by prep. HPLC (10% to 80% water/MeCN) to give the title compound as the major product, whereas the other isomer was not generated in sufficient quantity to be characterized (30 mg, 0.07 mmol, yield: 10%). PDE10 IC$_{50}$ (uM): 0.851. $^1$HNMR (CD$_3$OD, 400 MHz) δ (ppm): 8.83-8.81 (m, 1H), 8.36 (d, J=9.2 Hz, 1H), 7.90 (d, J=8.0 Hz, 1H), 7.80-7.77 (m, 2H), 7.57-7.49 (m, 2H), 7.00 (d, J=9.2 Hz, 1H), 5.81-5.79 (m, 1H), 5.03-4.98 (m, 2H), 4.73-4.68 (m, 3H), 4.04 (d, J=10 Hz, 1H), 3.30-3.14 (m, 2H), 2.74-2.69 (m, 1H), 2.12 (s, 3H), 2.00-1.95 (m, 2H), 1.72-1.55 (m, 2H).

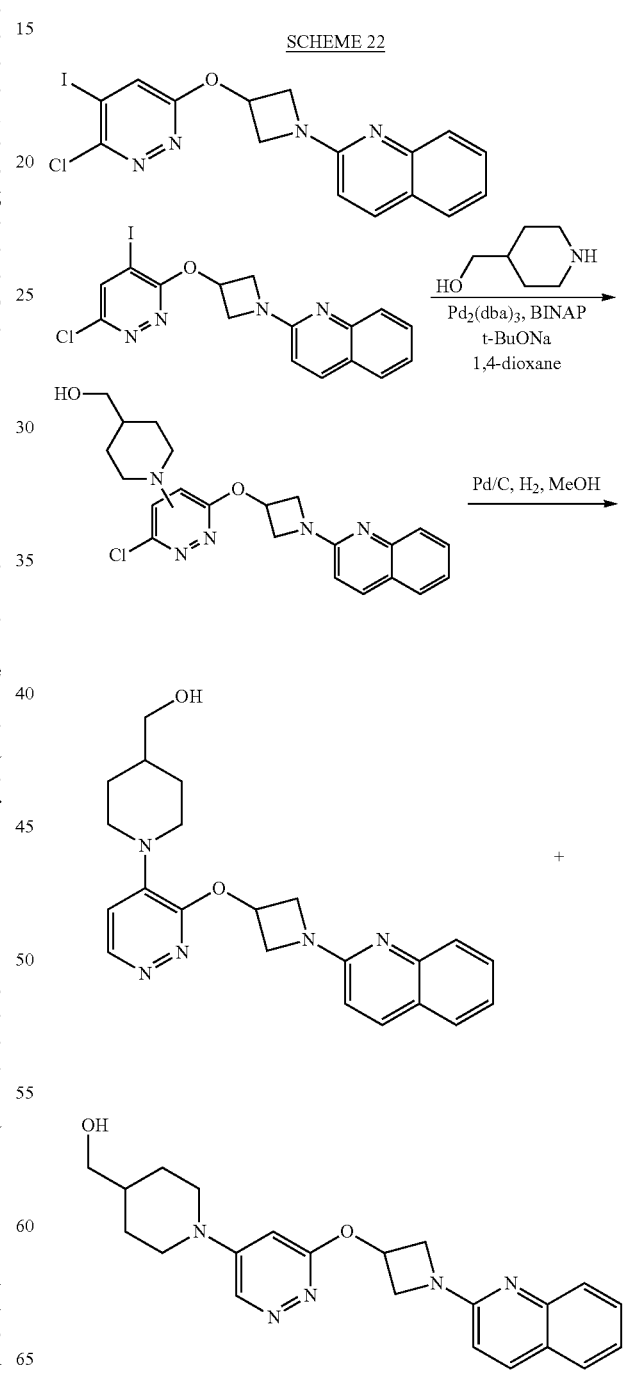

SCHEME 22

Example 22.1 and 22.2

(1-(3-((1-(Quinolin-2-yl)Azetidin-3-yl)Oxy)Pyridazin-4-yl)Piperidin-4-yl)Methanol and (1-(6-((1-(Quinolin-2-yl)Azetidin-3-yl)Oxy)Pyridazin-4-yl)Piperidin-4-yl)Methanol as Isomeric Mixture Step 1. (1-(3-Chloro-6-((1-(Quinolin-2-yl)Azetidin-3-yl)Oxy)Pyridazin-4-yl)Piperidin-4-yl)Methanol and (1-(6-Chloro-3-((1-(Quinolin-2-yl)Azetidin-3-yl)Oxy)Pyridazin-4-yl)Piperidin-4-yl)Methanol as Isomeric Mixture To a solution of 2-(3-((6-chloro-5-iodopyridazin-3-yl)oxy)azetidin-1-yl)quinoline and 2-(3-((6-chloro-4-iodopyridazin-3-yl)oxy)azetidin-1-yl)quinoline as isomeric mixture, (see PREPARATION P6.1; 655 mg, 1.5 mmol) in 1,4-dioxane (15 mL) was added $Pd_2(dba)_3$ (83 mg, 0.09 mmol), 2,2'-bis(diphenylphosphino)-1,1'-binaphthyl (BINAP) (56 mg, 0.09 mmol), sodium tertbutoxide (t-BuONa) (177 mg, 1.84 mmol) and piperidin-4-ylmethanol (212 mg, 1.84 mmol). The resulting mixture was heated at refluxing overnight under $N_2$ atmosphere. The solution was filtered through CELITE®, and the filter was concentrated. The residue was purified by flash column chromatography on silica gel (20% to 70% EtOAc in petroleum ether) to give the title product (423 mg, 0.99 mmol, yield: 60%). ESI-MS (M+1): 426 calc. for $C_{22}H_{24}ClN_5O_2$ 425.

Step 2. (1-(3-((1-(Quinolin-2-yl)Azetidin-3-yl)Oxy)Pyridazin-4-yl)Piperidin-4-yl)Methanol and (1-(6-((1-(Quinolin-2-yl)Azetidin-3-yl)Oxy)Pyridazin-4-yl)Piperidin-4-yl)Methanol as Isomeric Mixture To a solution of (mixture) (1-(3-chloro-6-((1-(quinolin-2-yl)azetidin-3-yl)oxy)pyridazin-4-yl)piperidin-4-yl)methanol and (1-(6-chloro-3-((1-(quinolin-2-yl)azetidin-3-yl)oxy)pyridazin-4-yl)piperidin-4-yl)methanol (423 mg, 0.99 mmol) in MeOH (15 mL) was added Pd/C (50%, 200 mg). The reaction solution was stirred at room temperature overnight under $H_2$ atmosphere. The mixture was filtered through CELITE® and the filtrate was concentrated, the residue was purified by reverse phase prep. HPLC (10% to 80% water/MeCN) to give the products examples 22.1 and 22.2 as isomeric mixture without further separation. ESI-MS (M+1): 392 calc. for $C_{22}H_{25}N_5O_2$ 391. M+1:392 PDE10 $IC_{50}$ (uM): 0.001 and 0.04 NMR; $^1$H NMR ($CD_3OD$, 400 MHz) δ (ppm) 8.58 (d, J=6.8 Hz, 1H), 8.38 (d, J=9.6 Hz, 1H), 7.93-7.90 (m, 1H), 7.82-7.80 (m, 2H), 7.56-7.51 (m, 1H), 7.28 (d, J=6.8 Hz, 1H), 7.01 (d, J=9.2 Hz, 1H), 5.72-5.68 (m, 1H), 5.02-4.97 (m, 2H), 4.74-4.69 (m, 2H), 4.58-4.55 (m, 2H), 3.46 (d, J=6.0 Hz, 2H), 3.41-3.34 (m, 2H), 1.98-1.93 (m, 3H), 1.49-1.45 (m, 2H). and 8.80 (d, J=2.4 Hz, 1H), 8.39 (dd, J=9.6 Hz, 1.6 Hz, 1H), 7.92 (d, J=7.6 Hz, 1H), 7.93-7.80 (m, 2H), 7.56-7.52 (m, 1H), 7.00 (d, J=9.2 Hz, 1H), 6.88-6.67 (m, 1H), 5.72-5.70 (m, 1H), 5.04-4.98 (m, 2H), 4.67-4.63 (m, 2H), 4.33-4.23 (m, 2H), 3.47-3.45 (m, 2H), 3.30-3.18 (m, 2H), 1.96-1.92 (m, 3H), 1.50-1.38 (m, 2H).

SCHEME 23

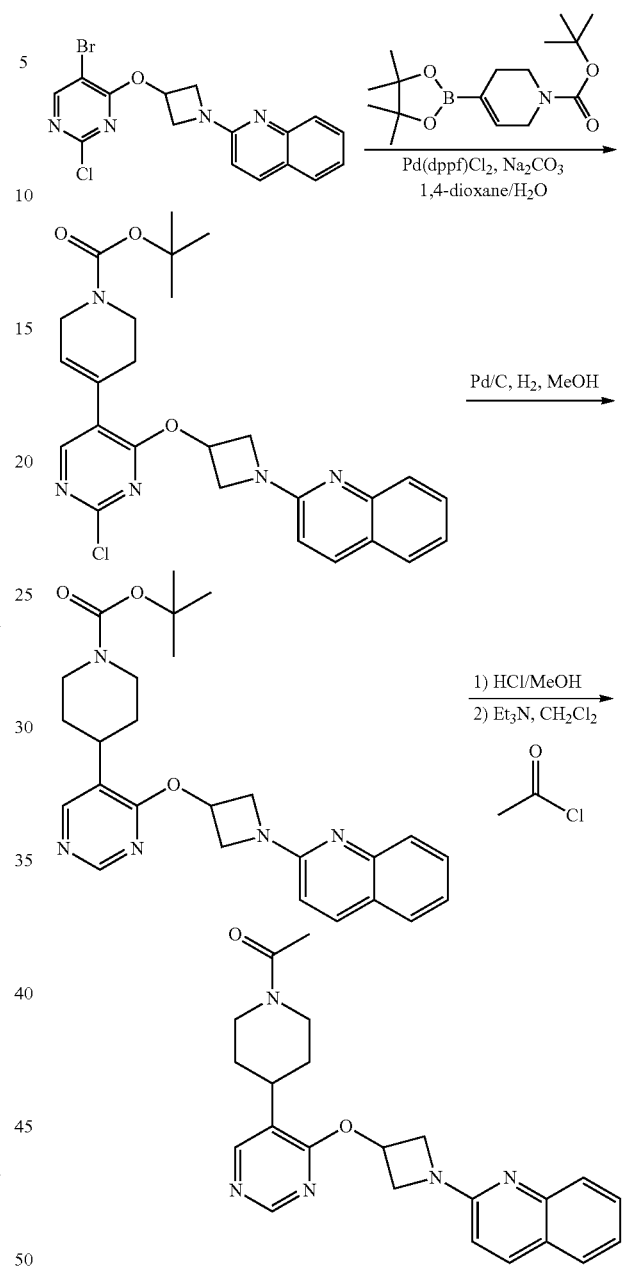

Example 23.1

1-(4-(4-((1-(Quinolin-2-yl)Azetidin-3-yl)Oxy)Pyrimidin-5-yl)Piperidin-1-yl)Ethanone Step 1. Tert-Butyl 4-(2-Chloro-4-((1-(Quinolin-2-yl)Azetidin-3-yl)Oxy)Pyrimidin-5-yl)-5,6-Dihydropyridine-1(2H)-Carboxylate To a solution of 2-(3-((5-bromo-2-chloropyrimidin-4-yl)oxy)azetidin-1-yl)quinoline (see PREPARATION P2.11; 600 mg, 1.5 mmol) in 1,4-dioxane (15 mL) was treated with $Na_2CO_3$ (318 mg, 3 mmol) in 3 mL of water as a solution, followed by additional of tert-butyl 4-(4,4,5,5-tetramethyl-1, 3,2-dioxaborolan-2-yl)-5,6-dihydropyridine-1(2H)-carboxylate (556 mg 1.8 mmol) and Pd(dppf)Cl$_2$ (110 mg, 0.15 mmol). The resulting mixture was heated at refluxing overnight under N$_2$ atmosphere. The solution was filtered through CELITE®, and the filter was concentrated. The residue was purified by flash column chromatography on silica gel (20% to 70% EtOAc in petroleum ether) to give the title product (472 mg, 0.95 mmol, yield: 63%). ESI-MS (M+1): 494 calc. for C$_{26}$H$_{28}$ClN$_5$O$_3$ 493.

Step 2. Tert-Butyl 4-(4-((1-(Quinolin-2-yl)Azetidin-3-yl)Oxy)Pyrimidin-5-yl)Piperidine-1-Carboxylate To a solution of tert-butyl 4-(2-chloro-4-((1-(quinolin-2-yl)azetidin-3-yl)oxy)pyrimidin-5-yl)-5,6-dihydropyridine-1(2H)-carboxylate (472 mg, 0.95 mmol) in MeOH (10 mL) was added Pd/C (10%, 200 mg). The reaction solution was stirred at room temperature overnight under H$_2$ atmosphere. The mixture was filtered through CELITE® and concentrated to give the product (307 mg, 0.66 mmol, yield: 78%). ESI-MS (M+1): 462 calc. for C$_{26}$H$_{31}$N$_5$O$_3$ 461.

Step 3. 1-(4-(4-((1-(Quinolin-2-yl)Azetidin-3-yl)Oxy)Pyrimidin-5-yl)Piperidin-1-yl)Ethanone The mixture of tert-butyl 4-(4-((1-(quinolin-2-yl)azetidin-3-yl)oxy)pyrimidin-5-yl)piperidine-1-carboxylate (307 mg, 0.66 mmol) in HCl/MeOH (10 mL, saturated with HCl gas) was stirred at room temperature for 1 hour. Then it was concentrated to give 2-(3-((5-(piperidin-4-yl)pyrimidin-4-yl)oxy)azetidin-1-yl)quinoline hydrochloride which was used in the next step below without further purification.

To a solution of 2-(3-((5-(piperidin-4-yl)pyrimidin-4-yl)oxy)azetidin-1-yl)quinoline hydrochloride in CH$_2$Cl$_2$ (10 mL) were added Et$_3$N (100 mg, 0.99 mmol) and acetyl chloride (62 mg, 0.79 mmol). The reaction mixture was stirred at room temperature for 1 hour, then diluted with CH$_2$Cl$_2$ (20 mL), washed with water (20 mL). The organic layer was washed with brine (20 mL), dried over Na$_2$SO$_4$, and filtered, evaporated to give the crude product. Purified by column chromatography, and followed by prep. HPLC (10% to 80% water/MeCN) to give 1-(4-(4-((1-(quinolin-2-yl)azetidin-3-yl)oxy)pyrimidin-5-yl)piperidin-1-yl)ethanone (34 mg, 0.08 mmol, yield 13%). M+1 IC$_{50}$ (uM) 404 0.765 $^1$H NMR (CDCl$_3$, 400 MHz) δ (ppm) 8.73 (s, 1H), 8.44 (s, 1H), 8.14 (d, J=9.2 Hz, 1H), 7.91 (d, J=8.4 Hz, 1H), 7.75-7.65 (m, 2H), 7.47-7.40 (m, 1H), 6.64 (d, J=9.2 Hz, 1H), 5.71 (s, 1H), 5.04-4.98 (m, 2H), 4.79-4.71 (m, 2H), 4.68-4.63 (m, 1H), 3.97-3.93 (m, 1H), 3.26-3.19 (m, 1H), 3.11-3.04 (m, 1H), 2.71-2.64 (m, 1H), 2.14 (s, 3H), 2.03-1.89 (m, 2H), 1.69-1.63 (m, 2H).

SCHEME 24

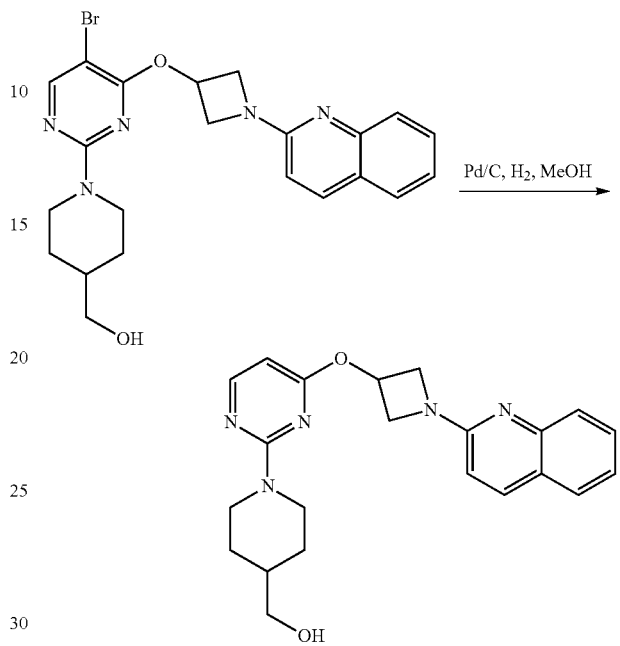

Example 24.1

(1-(4-((1-(Quinolin-2-yl)Azetidin-3-yl)Oxy)Pyrimidin-2-yl)Piperidin-4-yl)Methanol A mixture of (1-(5-bromo-4-((1-(quinolin-2-yl)azetidin-3-yl)oxy)pyrimidin-2-yl)piperidin-4-yl)methanol (see PREPARATION P7.1; 115 mg, 0.25 mmol) and wet Pd—C (50%, 50 mg) in MeOH (10 mL) was stirred under H$_2$ (15 psi) at room temperature for 1.5 hours then the reaction mixture was filtered through CELITE® and washed with MeOH. The filtrate was concentrated in vacuo to give (1-(4-((1-(quinolin-2-yl)azetidin-3-yl)oxy)pyrimidin-2-yl)piperidin-4-yl)methanol (93 mg, 0.24 mmol, yield 96%). ESI-MS (M+1): 392 calc. for C$_{22}$H$_{25}$N$_5$O$_2$ 391.

TABLE 16A

EXAMPLES 24.1-24.3 PREPARED ANALOGOUS TO SCHEME 24

| Ex. # | Structure | Chemical Name | M + 1 | IC$_{50}$ (uM) |
|---|---|---|---|---|
| 24.1 | 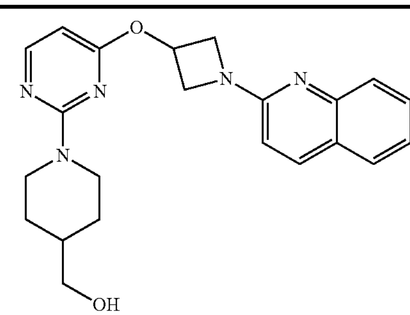 | (1-(4-((1-(quinolin-2-yl)azetidin-3-yl)oxy)pyrimidin-2-yl)piperidin-4-yl)methanol | 392 | 0.0142 |

TABLE 16A-continued

EXAMPLES 24.1-24.3 PREPARED ANALOGOUS TO SCHEME 24

| Ex. # | Structure | Chemical Name | M + 1 | IC$_{50}$ (uM) |
|---|---|---|---|---|
| 24.2 | 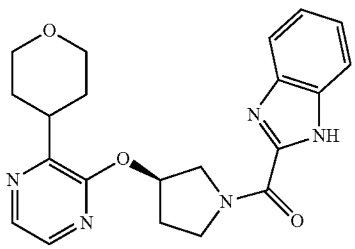 [SMILES: O=C(c1nc2ccccc2[nH]1)N1CC[C@@H](Oc2nccnc2C2CCOCC2)C1] | (R)-(1H-benzo[d]imidazol-2-yl)(3-(3-(tetrahydro-2H-pyran-4-yl)pyrazin-2-yloxy)pyrrolidin-1-yl)methanone | 394 | 2.782 |
| 24.3 | 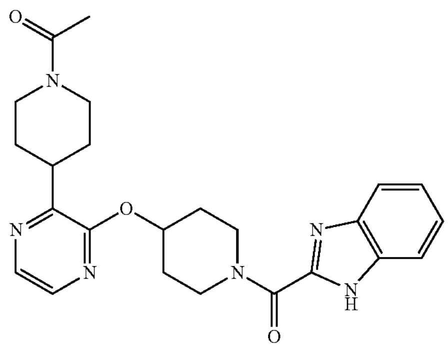 [SMILES: CC(=O)N1CCC(c2nccnc2OC2CCN(C(=O)c3nc4ccccc4[nH]3)CC2)CC1] | 1-(4-(3-(1-(1H-benzo[d]imidazole-2-carbonyl)piperidin-4-yloxy)pyrazin-2-yl)piperidin-1-yl)ethanone | 449 | 0.2591 |

TABLE 16B

PREPARATION AND NMR DATA OF EXAMPLES 24.1-24.3

| Ex. # | Starting material (1) | Reaction Condition | $^1$H NMR (CD$_3$OD, 400 MHz) δ (ppm) |
|---|---|---|---|
| 24.1 | (see Preparation P7.1) | H$_2$, Pd/C, MeOH | 8.35 (d, J = 9.2 Hz, 1H); 8.14-8.10 (m, 1H); 7.89 (d, J = 8.0 Hz, 1H); 7.79-7.78 (m, 2H); 7.53-7.49 (m, 1H); 6.97 (d, J = 9.2 Hz, 1H); 6.55 (d, J = 6.8 Hz, 1H); 5.78-5.74 (m, 1H); 5.00-4.96 (m, 1H); 4.67-4.63 (m, 3H); 4.33-4.31 (m, 2H); 3.47-3.46 (m, 2H); 3.29-3.21 (m, 2H); 1.97-1.86 (m, 3H); 1.41-1.34 (m, 2H). |
| 24.2 | (see Example 26.16) | Pd/C, H$_2$, MeOH | (CDCl$_3$) 8.12-8.09 (m, 1H); 7.95-7.94 (m, 1H); 7.72-7.70 (m, 2H); 7.36-7.35 (m, 2H); 5.79-5.71 (m, 1H); 4.78-4.37 (m, 2H); 4.10-3.95 (m, 4H); 3.53-3.49 (m, 2H); 3.21-3.16 (m, 1H); 2.44-2.34 (m, 2H); 1.95-1.92 (m, 2H); 1.73-1.69 (m, 2H). |

TABLE 16B-continued

PREPARATION AND NMR DATA OF EXAMPLES 24.1-24.3

| Ex. # | Starting material (1) | Reaction Condition | $^1$H NMR (CD$_3$OD, 400 MHz) δ (ppm) |
|---|---|---|---|
| 24.3 | (see Example 15.11) | Pd/C, H$_2$, MeOH | (CDCl$_3$) 10.47 (1H, br. s.), 8.07 (1H, d, J = 2.5 Hz), 7.94 (1H, d, J = 2.6 Hz), 7.83 (1H, d, J = 7.6 Hz), 7.54 (1H, d, J = 7.6 Hz), 7.29-7.43 (2H, m), 5.38-5.53 (1H, m), 5.06 (1H, br. s.), 4.56-4.81 (2H, m), 4.12 (1H, d, J = 4.7 Hz), 3.95 (1H, d, J = 13.2 Hz), 3.82 (1H, br. s.), 3.09-3.33 (2H, m), 2.71 (1H, t, J = 12.0 Hz), 2.19 (2H, br. s.), 2.12 (3H, s), 2.01 (2H, br. s.), 1.84-1.97 (3H, m), 1.63-1.84 (1H, m) |

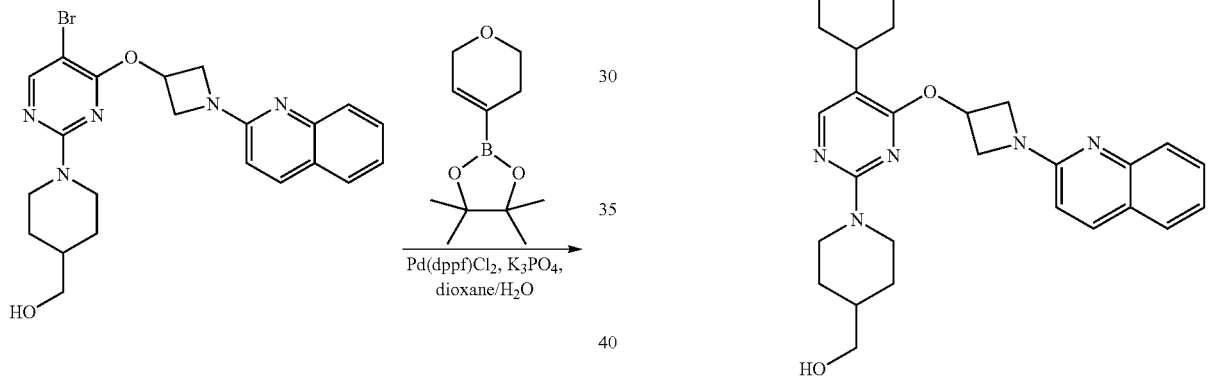

SCHEME 25

Example 25.1

(1-(4-((1-(Quinolin-2-yl)Azetidin-3-yl)Oxy)-5-(Tetrahydro-2H-Pyran-4-yl)Pyrimidin-2-yl)Piperidin-4-yl)Methanol Step 1. (1-(5-(3,6-Dihydro-2H-Pyran-4-yl)-4-((1-(Quinolin-2-yl)Azetidin-3-yl)Oxy)Pyrimidin-2-yl)Piperidin-4-yl)Methanol To a solution of (1-(5-bromo-4-((1-(quinolin-2-yl)azetidin-3-yl)oxy)pyrimidin-2-yl)piperidin-4-yl)methanol (see PREPARATION P7.1; 115 mg, 0.25 mmol), 2-(3,6-dihydro-2H-pyran-4-yl)-4,4,5,5-tetramethyl-1,3,2-dioxaborolane (52.5 mg, 0.25 mmol) and K$_3$PO$_4$ (100 mg, 0.5 mmol) in 1,4-dioxane (10 mL) and H$_2$O (2 mL) was added Pd(dppf)Cl$_2$ (15 mg, 0.02 mmol) then the reaction mixture was stirred at 110° C. under N$_2$ atmosphere overnight. The reaction mixture was filtered through CELITE® and washed with CH$_2$Cl$_2$ (30 mL). The filtrate was concentrated and the crude product was purified by silica gel column to give (1-(5-(3,6-dihydro-2H-pyran-4-yl)-4-(1-(quinolin-2-yl)azetidin-3-yl)oxy)pyrimidin-2-yl)piperidin-4-yl)methanol (100 mg, 0.21 mmol, yield 84%). ESI-MS (M+1): 474 calc. for C$_{27}$H$_{31}$N$_5$O$_3$ 473.

Step 2. (1-(4-((1-(Quinolin-2-yl)Azetidin-3-yl)Oxy)-5-(Tetrahydro-2H-Pyran-4-yl)Pyrimidin-2-yl)Piperidin-4-yl)Methanol A mixture of (1-(5-(3,6-dihydro-2H-pyran-4-yl)-4-(1-(quinolin-2-yl)azetidin-3-yl)oxy)pyrimidin-2-yl)piperidin-4-yl)methanol (100 mg, 0.21 mmol) and wet Pd—C (50%, 50 mg) in MeOH (10 mL) was stirred under $H_2$ (30 psi) at room temperature for 6 hours then the reaction mixture was filtered through CELITE® and washed with MeOH. The filtrate was concentrated in vacuo to give (1-(4-((1-(quinolin-2-yl)azetidin-3-yl)oxy)-5-(tetrahydro-2H-pyran-4-yl)pyrimidin-2-yl)piperidin-4-yl)methanol (90 mg, 0.19 mmol, yield 90%). ESI-MS (M+1): 476 calc. for $C_{27}H_{33}N_5O_3$ 475. PDE10 $IC_{50}$ (uM): 0.0029 $^1$H NMR (CDCl$_3$, 400 MHz) δ (ppm): 8.23 (d, J=9.2 Hz, 1H); 8.08-8.06 (m, 1H); 7.95-7.93 (m, 1H); 7.80-7.78 (m, 2H); 7.55-7.51 (m, 1H); 6.74-6.70 (m, 1H); 5.73-5.72 (m, 1H); 5.19-5.10 (m, 2H); 4.70-4.51 (m, 4H); 4.27 (d, J=6.4 Hz, 1H); 4.08-4.06 (m, 2H); 3.57-3.48 (m, 3H); 3.20-3.14 (m, 2H); 2.89-2.88 (m, 1H); 2.02-1.93 (m, 3H); 1.78-1.76 (m, 4H); 1.42-4.37 (m, 2H).

SCHEME 26

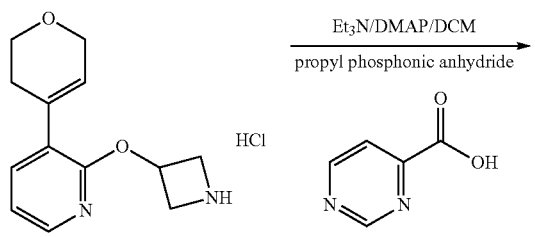

Example 26.1

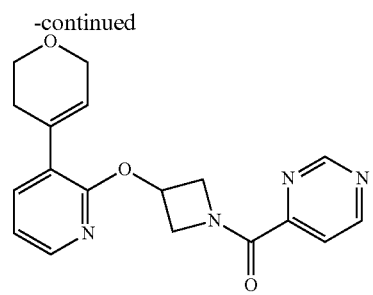

(3-((3-(3,6-Dihydro-2H-Pyran-4-yl)Pyridin-2-yl)Oxy)Azetidin-1-yl)(Pyrimidin-4-yl)Methanone To a solution of 2-(azetidin-3-yloxy)-3-(3,6-dihydro-2H-pyran-4-yl)pyridine hydrochloride (see PREPARATION P26.1; 100 mg, 0.45 mmol), pyrimidine-4-carboxylic acid (55 mg, 0.45 mmol) and triethylamine (96.13 mg, 0.95 mmol) in $CH_2Cl_2$ (10 mL) was added 4-Dimethylaminopyridine (DMAP) (55 mg, 0.47 mmol) and propyl phosphonic anhydride (500 mg, 0.9 mmol). The reaction mixture was stirred at room temperature for overnight. Then the reaction mixture was concentrated and the crude product was purified by silica gel column chromatography to give the desired compound (48 mg, 0.16 mmol, yield 66%). [M+1]: 339. $IC_{50}$ (uM): 0.99.

TABLE 17A

EXAMPLES 26.1-26.42 PREPARED ANALOGOUS TO SCHEME 26

| Ex. # | Structure | Chemical Name | M + 1 | $IC_{50}$ (uM) |
|---|---|---|---|---|
| 26.1 | 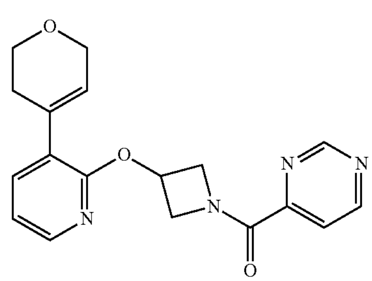 [SMILES: O=C(c1ccncn1)N1CC(Oc2ncccc2C2=CCOCC2)C1] | (3-((3-(3,6-dihydro-2H-pyran-4-yl)pyridin-2-yl)oxy)azetidin-1-yl)(pyrimidin-4-yl)methanone | 339 | 0.99 |
| 26.2 | 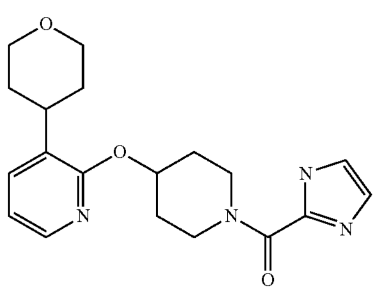 [SMILES: O=C(c1ncc[nH]1)N1CCC(Oc2ncccc2C2CCOCC2)CC1] | (1H-imidazol-2-yl)(4-(3-(tetrahydro-2H-pyran-4-yl)pyridin-2-yloxy)piperidin-1-yl)methanone | 357 | 3.673 |

TABLE 17A-continued

EXAMPLES 26.1-26.42 PREPARED ANALOGOUS TO SCHEME 26

| Ex. # | Structure | Chemical Name | M + 1 | IC$_{50}$ (uM) |
|---|---|---|---|---|
| 26.3 | 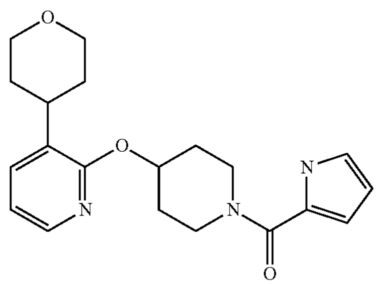 [SMILES: O=C(c1ccc[nH]1)N1CCC(Oc2ncccc2C2CCOCC2)CC1] | (1H-pyrrol-2-yl)(4-(3-(tetrahydro-2H-pyran-4-yl)pyridin-2-yloxy)piperidin-1-yl)methanone | 356 | 4.261 |
| 26.4 | 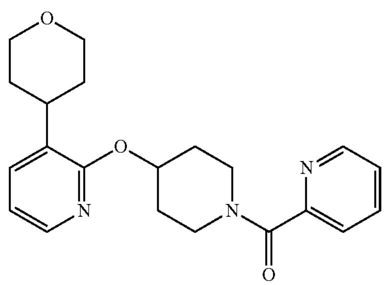 [SMILES: O=C(c1ccccn1)N1CCC(Oc2ncccc2C2CCOCC2)CC1] | pyridin-2-yl(4-(3-(tetrahydro-2H-pyran-4-yl)pyridin-2-yloxy)piperidin-1-yl)methanone | 368 | 1.26 |
| 26.5 | 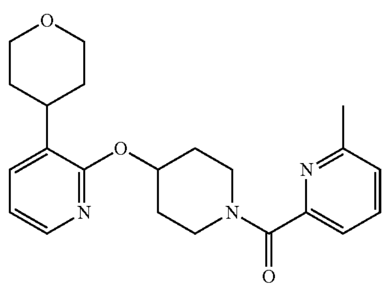 [SMILES: Cc1cccc(C(=O)N2CCC(Oc3ncccc3C3CCOCC3)CC2)n1] | (6-methylpyridin-2-yl)(4-(3-(tetrahydro-2H-pyran-4-yl)pyridin-2-yloxy)piperidin-1-yl)methanone | 382 | 1.177 |
| 26.6 | 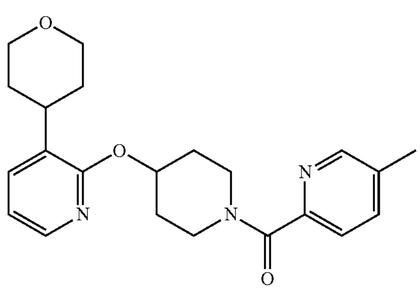 [SMILES: Cc1ccc(C(=O)N2CCC(Oc3ncccc3C3CCOCC3)CC2)nc1] | (5-methylpyridin-2-yl)(4-(3-(tetrahydro-2H-pyran-4-yl)pyridin-2-yloxy)piperidin-1-yl)methanone | 382 | 1.648 |
| 26.7 | 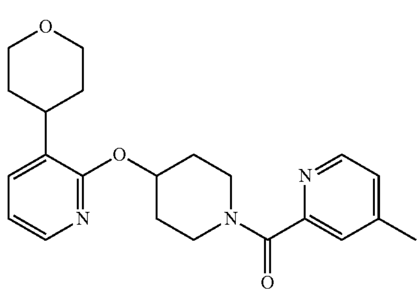 [SMILES: Cc1ccnc(C(=O)N2CCC(Oc3ncccc3C3CCOCC3)CC2)c1] | (4-methylpyridin-2-yl)(4-(3-(tetrahydro-2H-pyran-4-yl)pyridin-2-yloxy)piperidin-1-yl)methanone | 382 | 0.118 |

TABLE 17A-continued

EXAMPLES 26.1-26.42 PREPARED ANALOGOUS TO SCHEME 26

| Ex. # | Structure | Chemical Name | M + 1 | IC$_{50}$ (uM) |
|---|---|---|---|---|
| 26.8 | 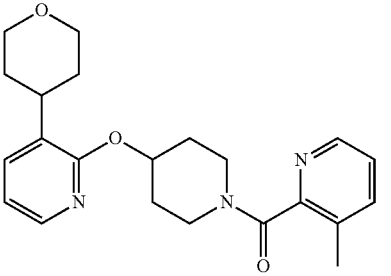 [SMILES: Cc1cccnc1C(=O)N1CCC(Oc2ncccc2C2CCOCC2)CC1] | (3-methylpyridin-2-yl)(4-(3-(tetrahydro-2H-pyran-4-yl)pyridin-2-yloxy)piperidin-1-yl)methanone | 382 | 1.002 |
| 26.9 | 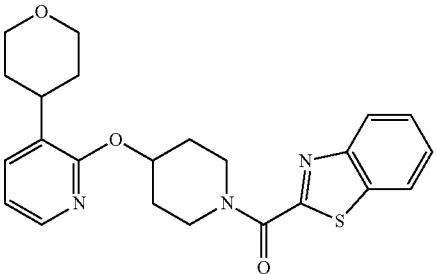 [SMILES: O=C(c1nc2ccccc2s1)N1CCC(Oc2ncccc2C2CCOCC2)CC1] | benzo[d]thiazol-2-yl(4-(3-(tetrahydro-2H-pyran-4-yl)pyridin-2-yloxy)piperidin-1-yl)methanone | 424 | 0.324 |
| 26.10 | 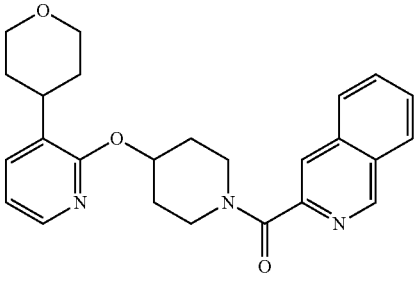 [SMILES: O=C(c1cc2ccccc2cn1)N1CCC(Oc2ncccc2C2CCOCC2)CC1] | isoquinolin-3-yl(4-(3-(tetrahydro-2H-pyran-4-yl)pyridin-2-yloxy)piperidin-1-yl)methanone | 418 | 0.126 |
| 26.11 | 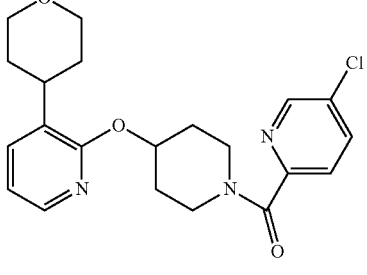 | (5-chloropyridin-2-yl)(4-(3-(tetrahydro-2H-pyran-4-yl)pyridin-2-yloxy)piperidin-1-yl)methanone | 402 | >10 |
| 26.12 | 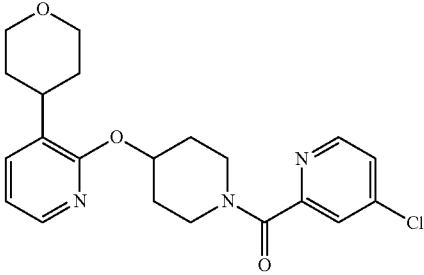 [SMILES: O=C(c1cc(Cl)ccn1)N1CCC(Oc2ncccc2C2CCOCC2)CC1] | (4-chloropyridin-2-yl)(4-(3-(tetrahydro-2H-pyran-4-yl)pyridin-2-yloxy)piperidin-1-yl)methanone | 402 | 8.89 |

TABLE 17A-continued

EXAMPLES 26.1-26.42 PREPARED ANALOGOUS TO SCHEME 26

| Ex. # | Structure | Chemical Name | M + 1 | IC$_{50}$ (uM) |
|---|---|---|---|---|
| 26.13 | 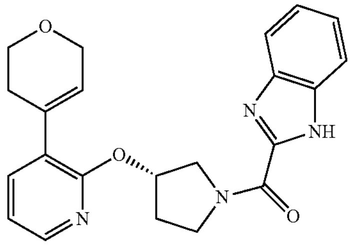 [SMILES: O=C(c1nc2ccccc2[nH]1)N1CC[C@H](Oc2ncccc2C2=CCOCC2)C1] | (S)-(1H-benzo[d]imidazol-2-yl)(3-(3-(3,6-dihydro-2H-pyran-4-yl)pyridin-2-yloxy)pyrrolidin-1-yl)methanone | 391 | 0.715 |
| 26.14 | 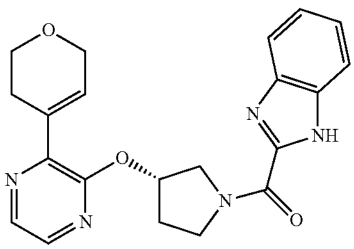 [SMILES: O=C(c1nc2ccccc2[nH]1)N1CC[C@H](Oc2nccnc2C2=CCOCC2)C1] | (S)-(1H-benzo[d]imidazol-2-yl)(3-(3-(3,6-dihydro-2H-pyran-4-yl)pyrazin-2-yloxy)pyrrolidin-1-yl)methanone | 392 | 0.201 |
| 26.15 | 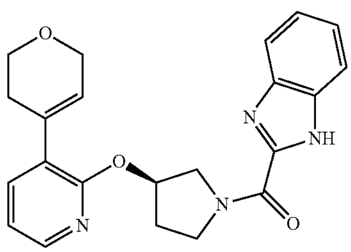 [SMILES: O=C(c1nc2ccccc2[nH]1)N1CC[C@@H](Oc2ncccc2C2=CCOCC2)C1] | (R)-(1H-benzo[d]imidazol-2-yl)(3-(3-(3,6-dihydro-2H-pyran-4-yl)pyridin-2-yloxy)pyrrolidin-1-yl)methanone | 391 | 0.767 |
| 26.16 | 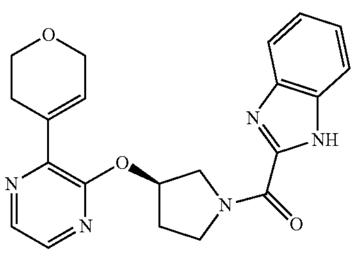 [SMILES: O=C(c1nc2ccccc2[nH]1)N1CC[C@@H](Oc2nccnc2C2=CCOCC2)C1] | (R)-(1H-benzo[d]imidazol-2-yl)(3-(3-(3,6-dihydro-2H-pyran-4-yl)pyrazin-2-yloxy)pyrrolidin-1-yl)methanone | 392 | 1.464 |
| 26.17 | 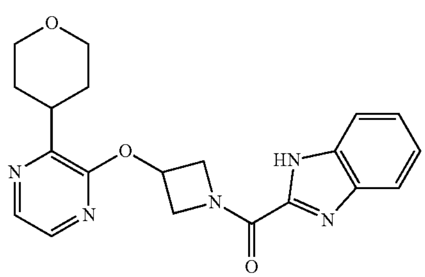 [SMILES: O=C(c1nc2ccccc2[nH]1)N1CC(Oc2nccnc2C2CCOCC2)C1] | (1H-benzo[d]imidazol-2-yl)(3-(3-(tetrahydro-2H-pyran-4-yl)pyrazin-2-yloxy)azetidin-1-yl)methanone | 380 | 0.8837 |
| 26.18 | 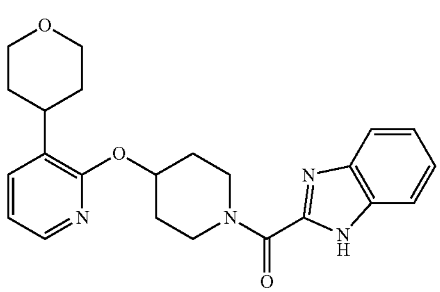 [SMILES: O=C(c1nc2ccccc2[nH]1)N1CCC(Oc2ncccc2C2CCOCC2)CC1] | (1H-benzo[d]imidazol-2-yl)(4-((3-(tetrahydro-2H-pyran-4-yl)pyridin-2-yl)oxy)piperidin-1-yl)methanone | 407 | 0.116 |

TABLE 17A-continued

EXAMPLES 26.1-26.42 PREPARED ANALOGOUS TO SCHEME 26

| Ex. # | Structure | Chemical Name | M + 1 | IC$_{50}$ (uM) |
|---|---|---|---|---|
| 26.19 | 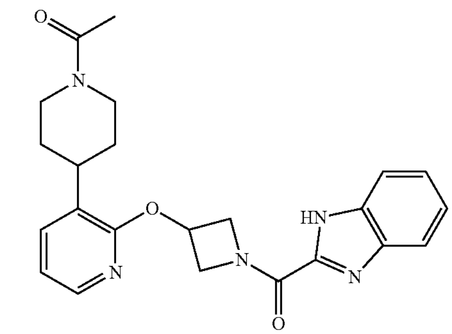 [SMILES: CC(=O)N1CCC(c2cccnc2OC2CN(C(=O)c3nc4ccccc4[nH]3)C2)CC1] | 1-(4-(2-(1-(1H-benzo[d]imidazole-2-carbonyl)azetidin-3-yloxy)pyridin-3-yl)piperidin-1-yl)ethanone | 420.2 | 0.1016 |
| 26.20 | 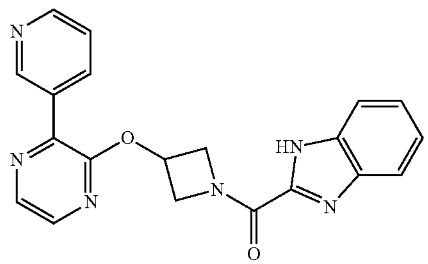 [SMILES: O=C(c1nc2ccccc2[nH]1)N1CC(Oc2nccnc2-c2cccnc2)C1] | (1H-benzo[d]imidazol-2-yl)(3-(3-(pyridin-3-yl)pyrazin-2-yloxy)azetidin-1-yl)methanone | 373.1 | 0.1786 |
| 26.21 | 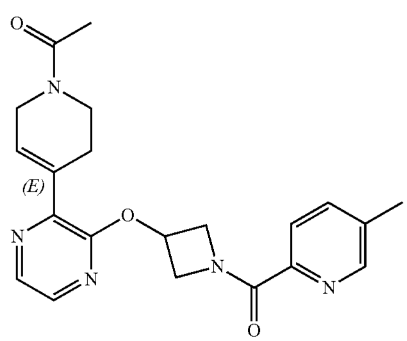 [SMILES: CC(=O)N1CC=C(c2nccnc2OC2CN(C(=O)c3ccc(C)cn3)C2)CC1] | 1-(4-(3-(1-(5-methylpicolinyl)azetidin-3-yloxy)pyrazin-2-yl)-5,6-dihydropyridin-1(2H)-yl)ethanone | 394 | 1.03 |
| 26.22 | 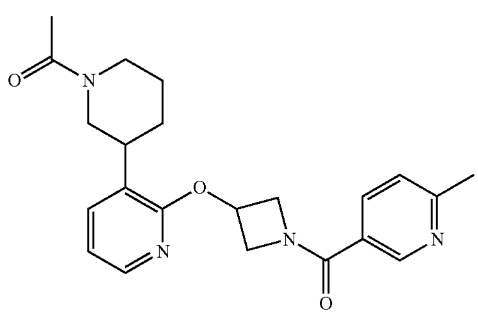 [SMILES: CC(=O)N1CCCC(c2cccnc2OC2CN(C(=O)c3ccc(C)nc3)C2)C1] | (R) and (S)-1-(3-(2-(1-(6-methylnicotinoyl)azetidin-3-yloxy)pyridin-3-yl)piperidin-1-yl)ethanone | 395 | 8.34 |
| 26.23 | 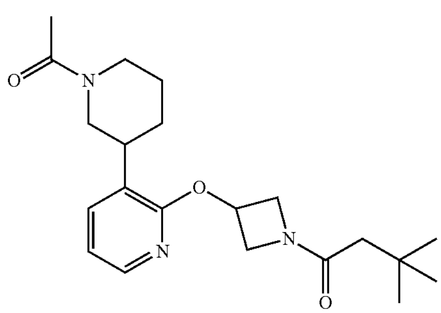 [SMILES: CC(=O)N1CCCC(c2cccnc2OC2CN(C(=O)CC(C)(C)C)C2)C1] | (R) and (S)-1-(3-(3-(1-acetylpiperidin-3-yl)pyridin-2-yloxy)azetidin-1-yl)-3,3-dimethylbutan-1-one | 374 | 41.85 |

TABLE 17A-continued

EXAMPLES 26.1-26.42 PREPARED ANALOGOUS TO SCHEME 26

| Ex. # | Structure | Chemical Name | M + 1 | IC$_{50}$ (uM) |
|---|---|---|---|---|
| 26.24 | 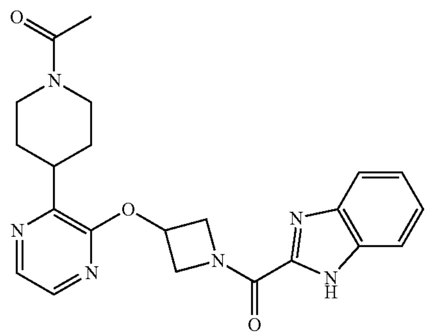 [SMILES: CC(=O)N1CCC(c2nccnc2OC2CN(C(=O)c3nc4ccccc4[nH]3)C2)CC1] | 1-(4-(3-(1-(1H-benzo[d]imidazole-2-carbonyl)azetidin-3-yloxy)pyrazin-2-yl)piperidin-1-yl)ethanone | 421 | 0.1614 |
| 26.25 | 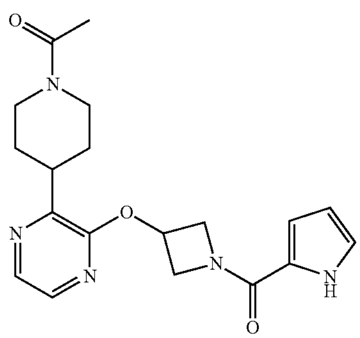 [SMILES: CC(=O)N1CCC(c2nccnc2OC2CN(C(=O)c3ccc[nH]3)C2)CC1] | 1-(4-(3-(1-(1H-pyrrole-2-carbonyl)azetidin-3-yloxy)pyrazin-2-yl)piperidin-1-yl)ethanone | 370 | 0.1386 |
| 26.26 | 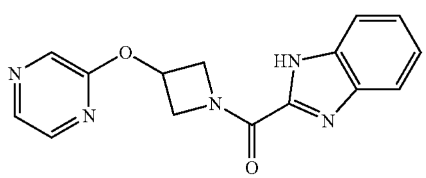 [SMILES: O=C(c1nc2ccccc2[nH]1)N1CC(Oc2cnccn2)C1] | (1H-benzo[d]imidazol-2-yl)(3-(pyrazin-2-yloxy)azetidin-1-yl)methanone | 296 | 12.31 |
| 26.27 | 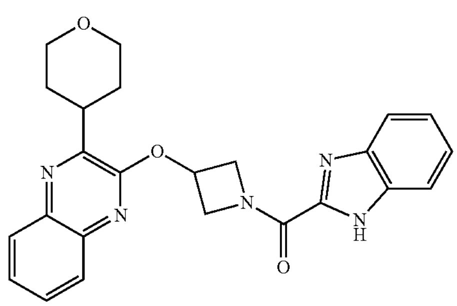 [SMILES: O=C(c1nc2ccccc2[nH]1)N1CC(Oc2nc3ccccc3nc2C2CCOCC2)C1] | (1H-Benzo[d]imidazol-2-yl)(3-(3-(tetrahydro-2H-pyran-4-yl)quinoxalin-2-yloxy)azetidin-1-yl)methanone | 430.1 | 0.786 |
| 26.28 | 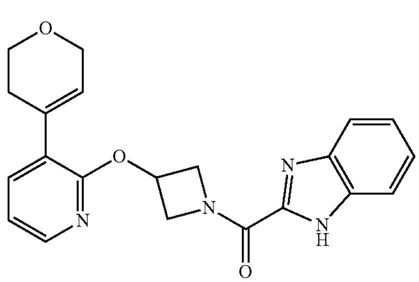 [SMILES: O=C(c1nc2ccccc2[nH]1)N1CC(Oc2ncccc2C2=CCOCC2)C1] | (1H-benzo[d]imidazol-2-yl)(3-((3-(3,6-dihydro-2H-pyran-4-yl)pyridin-2-yl)oxy)azetidin-1-yl)methanone | 377 | 0.000864 |

TABLE 17A-continued

EXAMPLES 26.1-26.42 PREPARED ANALOGOUS TO SCHEME 26

| Ex. # | Structure | Chemical Name | M + 1 | IC$_{50}$ (uM) |
|---|---|---|---|---|
| 26.29 | 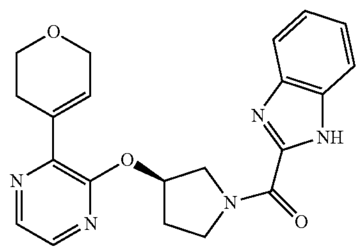 [SMILES: O=C(c1nc2ccccc2[nH]1)N1CC[C@@H](Oc2nccnc2C2=CCOCC2)C1] | isoquinolin-1-yl(4-((3-(tetrahydro-2H-pyran-4-yl)pyridin-2-yl)oxy)piperidin-1-yl)methanone | 418 | 0.640 |
| 26.30 | 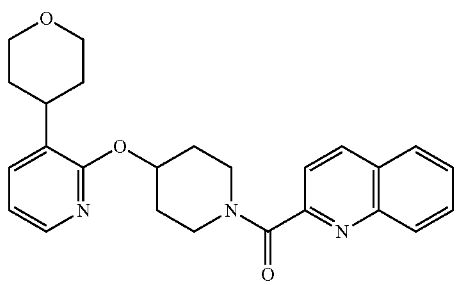 [SMILES: O=C(c1ccc2ccccc2n1)N1CCC(Oc2ncccc2C2CCOCC2)CC1] | quinolin-2-yl(4-((3-(tetrahydro-2H-pyran-4-yl)pyrazin-2-yl)oxy)piperidin-1-yl)methanone | 418 | 0.809 |
| 26.31 | 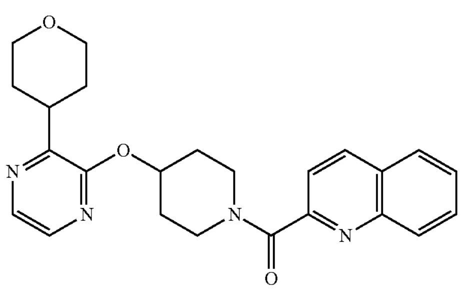 [SMILES: O=C(c1ccc2ccccc2n1)N1CCC(Oc2nccnc2C2CCOCC2)CC1] | quinolin-2-yl(4-((3-(tetrahydro-2H-pyran-4-yl)pyrazin-2-yl)oxy)piperidin-1-yl)methanone | 419 | 0.994 |
| 26.32 | 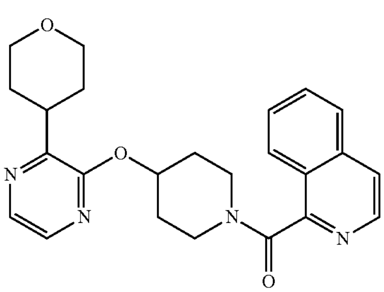 [SMILES: O=C(c1nccc2ccccc12)N1CCC(Oc2nccnc2C2CCOCC2)CC1] | isoquinolin-1-yl(4-((3-(tetrahydro-2H-pyran-4-yl)pyrazin-2-yl)oxy)piperidin-1-yl)methanone | 419 | 7.32 |
| 26.33 | 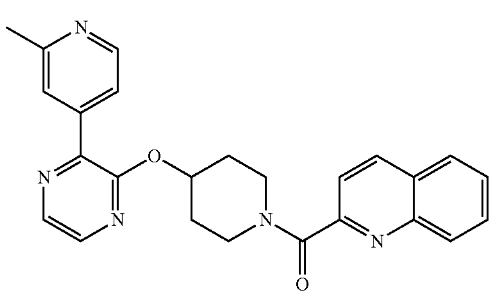 [SMILES: Cc1cc(-c2nccnc2OC2CCN(C(=O)c3ccc4ccccc4n3)CC2)ccn1] | (4-((3-(2-methylpyridin-4-yl)pyrazin-2-yl)oxy)piperidin-1-yl)(quinolin-2-yl)methanone | 426 | 2.66 |

TABLE 17A-continued

EXAMPLES 26.1-26.42 PREPARED ANALOGOUS TO SCHEME 26

| Ex. # | Structure | Chemical Name | M + 1 | IC$_{50}$ (uM) |
|---|---|---|---|---|
| 26.34 | 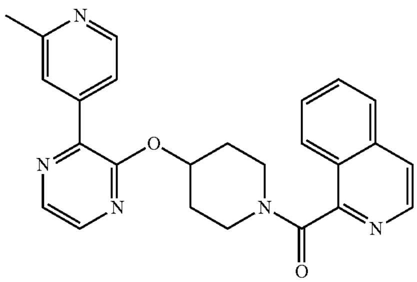 [SMILES: Cc1cc(-c2nccnc2OC2CCN(C(=O)c3nccc4ccccc34)CC2)ccn1] | isoquinolin-1-yl(4-((3-(2-methylpyridin-4-yl)pyrazin-2-yl)oxy)piperidin-1-yl)methanone | 426 | 3.59 |
| 26.35 | 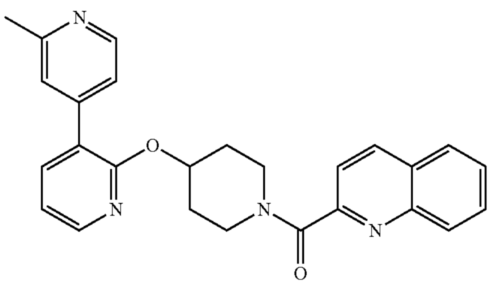 [SMILES: Cc1cc(-c2cccnc2OC2CCN(C(=O)c3ccc4ccccc4n3)CC2)ccn1] | (4-((2'-methyl-[3,4'-bipyridin]-2-yl)oxy)piperidin-1-yl)(quinolin-2-yl)methanone | 425 | 1.23 |
| 26.36 | 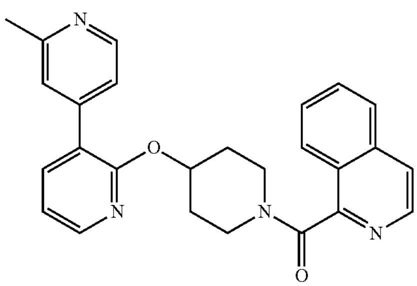 [SMILES: Cc1cc(-c2cccnc2OC2CCN(C(=O)c3nccc4ccccc34)CC2)ccn1] | isoquinolin-1-yl(4-((2'-methyl-[3,4'-bipyridin]-2-yl)oxy)piperidin-1-yl)methanone | 425 | 2.13 |
| 26.37 | 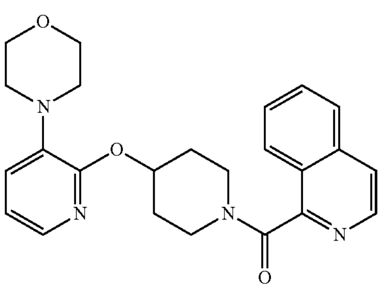 [SMILES: O=C(c1nccc2ccccc12)N1CCC(Oc2ncccc2N2CCOCC2)CC1] | isoquinolin-1-yl(4-((3-morpholinopyridin-2-yl)oxy)piperidin-1-yl)methanone | 419 | 11.1 |
| 26.38 | 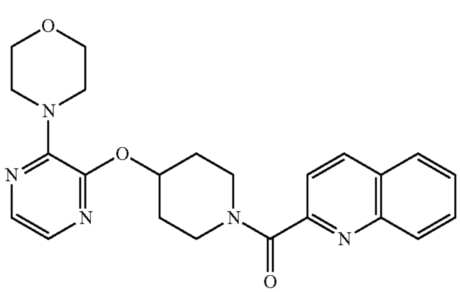 [SMILES: O=C(c1ccc2ccccc2n1)N1CCC(Oc2nccnc2N2CCOCC2)CC1] | (4-((3-morpholinopyridin-2-yl)oxy)piperidin-1-yl)(quinolin-2-yl)methanone | 420 | 1.08 |

TABLE 17A-continued

EXAMPLES 26.1-26.42 PREPARED ANALOGOUS TO SCHEME 26

| Ex. # | Structure | Chemical Name | M + 1 | IC$_{50}$ (uM) |
|---|---|---|---|---|
| 26.39 | 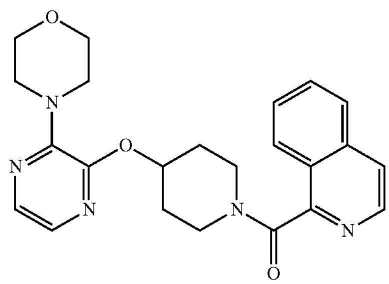 [SMILES: O=C(c1nccc2ccccc12)N1CCC(Oc2nccnc2N2CCOCC2)CC1] | isoquinolin-1-yl(4-((3-morpholinopyrazin-2-yl)oxy)piperidin-1-yl)methanone | 420 | 5.4 |
| 26.40 | 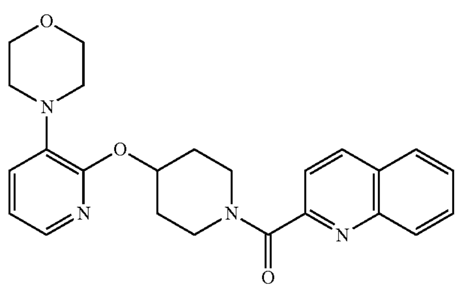 [SMILES: O=C(c1ccc2ccccc2n1)N1CCC(Oc2ncccc2N2CCOCC2)CC1] | (4-((3-morpholinopyridin-2-yl)oxy)piperidin-1-yl)(quinolin-2-yl)methanone | 419 | 16.1 |
| 26.41 | 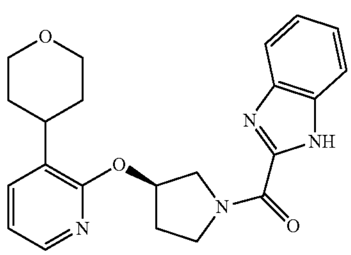 [SMILES: O=C(c1nc2ccccc2[nH]1)N1CC[C@@H](Oc2ncccc2C2CCOCC2)C1] | (R)-(1H-benzo[d]imidazol-2-yl)(3-((3-(tetrahydro-2H-pyran-4-yl)pyridin-2-yl)oxy)pyrrolidin-1-yl)methanone | 3933 | 1.82 |
| 26.42 | 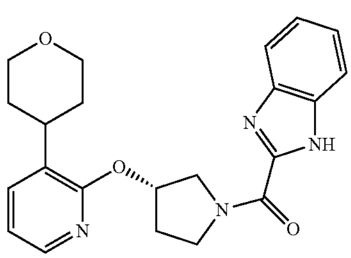 [SMILES: O=C(c1nc2ccccc2[nH]1)N1CC[C@H](Oc2ncccc2C2CCOCC2)C1] | (S)-(1H-benzo[d]imidazol-2-yl)(3-(3-(tetrahydro-2H-pyran-4-yl)pyridin-2-yloxy)pyrrolidin-1-yl)methanone | 393 | 0.409 |

TABLE 17B
PREPARATION AND NMR DATA OF EXAMPLES 26.1-26.42
| Ex. # | Starting Material (1) and (2) | Reaction Condition | $^1$H NMR (CD$_3$OD, 400 MHz) δ (ppm) |
|---|---|---|---|
| 26.1 | 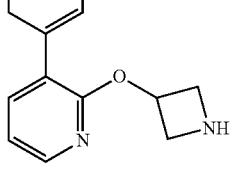 (see Preparation P26.1) and  | TEA, DCM, DMAP, PPA | 9.24-9.23 (m, 1H); 9.02-9.00 (m, 1H); 8.40-8.27 (m, 1H); 8.06-8.04 (m, 1H); 7.50-7.46 (m, 1H); 6.67-6.66 (m, 1H); 5.71-5.60 (m, 1H); 5.20-5.05 (m, 1H); 4.91-4.85 (m, 1H); 4.31-4.28 (m, 2H); 4.05-4.00 (m, 2H); 3.90-3.87 (m, 2H); 2.51-2.45 (m, 1H); 1.31-1.27 (m, 2H). |
| 26.2 | 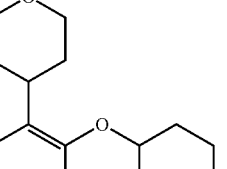 (see Preparation P29.1) and 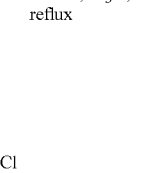 | HATU, Et$_3$N, THF, reflux | 7.88-7.86 (m, 1H); 7.47-7.44 (m, 1H); 7.08 (s, 2H); 6.83-6.80 (m, 1H); 5.33-5.30 (m, 1H); 4.37-3.92 (m, 4H); 3.86-3.64 (m, 2H); 3.51-3.42 (m, 2H); 3.02-2.98 (m, 1H); 2.03-1.98 (m, 2H); 1.81-1.67 (m, 6H). |
| 26.3 | 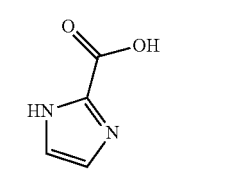 (see Preparation P29.1) and  | HATU, Et$_3$N, THF, reflux | 7.96-7.94 (m, 1H); 7.56-7.54 (m, 1H); 6.92-6.89 (m, 2H); 6.58-6.57 (m, 1H); 6.18-6.16 (m, 1H); 5.40-5.37 (m, 1H); 4.04-3.99 (m, 4H); 3.78-3.76 (m, 2H); 3.58-3.51 (m, 2H); 3.07-3.01 (m, 1H); 2.10-2.05 (m, 2H); 1.88-1.75 (m, 6H). |

TABLE 17B-continued
PREPARATION AND NMR DATA OF EXAMPLES 26.1-26.42
| Ex. # | Starting Material (1) and (2) | Reaction Condition | $^1$H NMR (CD$_3$OD, 400 MHz) δ (ppm) |
|---|---|---|---|
| 26.4 | 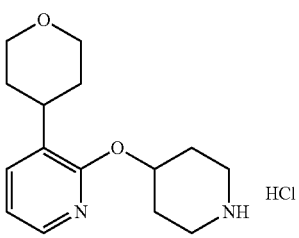 (see Preparation P29.1) and 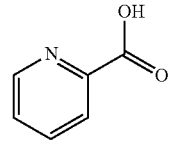 | HATU, Et$_3$N, THF, reflux | 8.61-8.58 (m, 1H); 8.01-7.90 (m, 2H); 7.64-7.60 (m, 1H); 7.55-7.50 (m, 2H); 6.92-6.88 (m, 1H); 5.41-5.37 (m, 1H); 4.06-3.78 (m, 4H); 3.62-3.40 (m, 4H); 3.12-3.06 (m, 1H); 2.18-1.72 (m, 8H). |
| 26.5 | 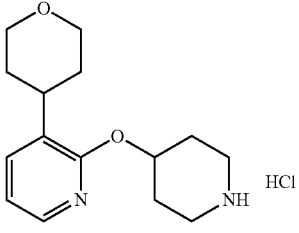 (see Preparation P29.1) and 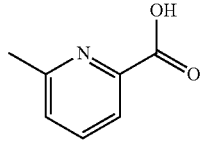 | HATU, Et$_3$N, THF, reflux | 7.86-7.85 (m, 1H); 7.75-7.71 (m, 1H); 7.46-7.44 (m, 1H); 7.295-7.26 (m, 2H); 6.83-6.80 (m, 1H); 5.33-5.30 (m, 1H); 3.97-3.73 (m, 4H); 3.52-3.45 (m, 3H); 3.34-3.29 (m, 1H); 3.00-3.98 (m, 1H); 2.47 (s, 3H); 2.08-1.65 (m, 8H). |
| 26.6 | 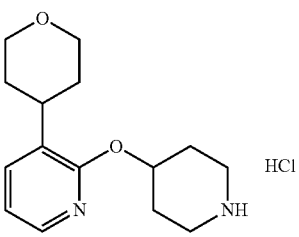 (see Preparation P29.1) and 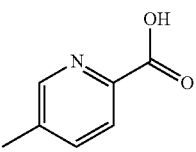 | HATU, Et$_3$N, THF, reflux | 8.34-8.33 (m, 1H); 7.88-7.82 (m, 1H); 7.71-7.68 (m, 1H); 7.45-7.40 (m, 2H); 6.82-6.78 (m, 1H); 5.35-5.25 (m, 1H); 3.95-3.32 (m, 8H); 3.05-2.95 (m, 1H); 2.99 (s, 3H); 2.08-1.44 (m, 8H). |

TABLE 17B-continued
PREPARATION AND NMR DATA OF EXAMPLES 26.1-26.42
| Ex. # | Starting Material (1) and (2) | Reaction Condition | $^1$H NMR (CD$_3$OD, 400 MHz) δ (ppm) |
|---|---|---|---|
| 26.7 | 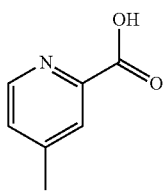 (see Preparation P29.1) and 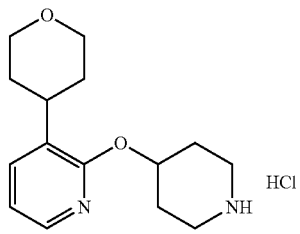 | HATU, Et$_3$N, THF, reflux | 8.50-8.47 (m, 1H); 7.95-7.93 (m, 1H); 7.59-7.43 (m, 3H); 6.91-6.88 (m, 1H); 5.46-5.38 (m, 1H); 4.05-3.35 (m, 8H); 3.10-3.02 (m, 1H); 2.48 (s, 3H); 2.21-1.76 (m, 8H). |
| 26.8 | 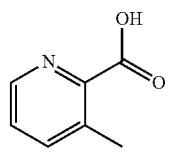 (see Preparation P29.1) and 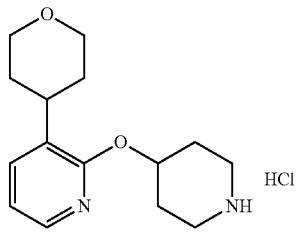 | HATU, Et$_3$N, THF, reflux | 8.42-8.41 (m, 1H); 7.94-7.92 (m, 1H); 7.85-7.83 (m, 1H); 7.54-7.42 (m, 2H); 6.91-6.88 (m, 1H); 5.39-5.37 (m, 1H); 4.04-3.84 (m, 4H); 3.58-3.67 (m, 5H); 2.35 (s, 3H); 2.18-1.70 (m, 8H). |
| 26.9 | (see Preparation P29.1) and 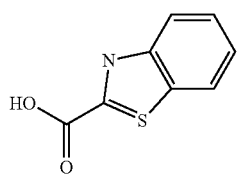 | HATU, Et$_3$N, THF, reflux | 8.18-7.97 (m, 3H); 7.58-7.53 (m, 3H); 6.93-6.90 (m, 1H); 5.45-5.38 (m, 1H); 4.42-4.22 (m, 2H); 3.92-3.70 (m, 4H); 3.44-3.35 (m, 2H); 3.05-2.95 (m, 1H); 2.11-2.04 (m, 2H); 1.85-1.61 (m, 6H). |

TABLE 17B-continued
PREPARATION AND NMR DATA OF EXAMPLES 26.1-26.42
| Ex. # | Starting Material (1) and (2) | Reaction Condition | $^1$H NMR (CD$_3$OD, 400 MHz) δ (ppm) |
|---|---|---|---|
| 26.10 | 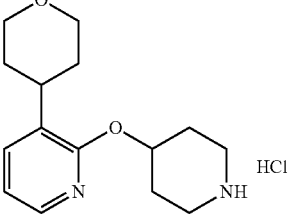<br>(see Preparation P29.1)<br>and<br>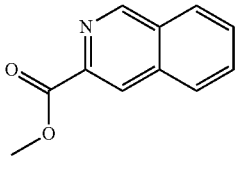 | HATU, Et$_3$N, THF, reflux | 9.29 (s, 1H); 8.16-7.71 (m, 6H); 7.54-7.48 (m, 1H); 6.90-6.87 (m, 1H); 5.42-5.38 (m, 1H); 4.10-3.45 (m, 8H); 3.11-3.05 (m, 1H); 2.21-1.70 (m, 8H). |
| 26.11 | 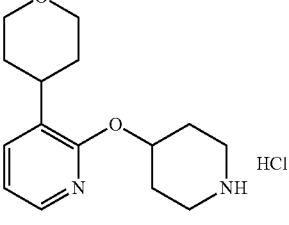<br>(see Preparation P29.1)<br>and<br>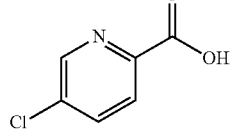 | HATU, Et$_3$N, THF, reflux | (CDCl$_3$) 8.48-8.47 (m, 1H); 7.93-7.91 (m, 1H); 7.71-7.70 (m, 1H); 7.60-7.58 (m, 1H); 7.38-7.36 (m, 1H); 6.81-6.78 (m, 1H); 5.39-5.36 (m, 1H); 4.23-3.90 (m ,3H); 3.78-3.69 (m, 2H); 3.54-3.45 (m, 3H); 2.97-2.96 (m, 1H); 2.06-1.82 (m, 4H); 1.71-1.69 (m, 4H). |

TABLE 17B-continued
PREPARATION AND NMR DATA OF EXAMPLES 26.1-26.42
| Ex. # | Starting Material (1) and (2) | Reaction Condition | $^1$H NMR (CD$_3$OD, 400 MHz) δ (ppm) |
|---|---|---|---|
| 26.12 | (see Preparation P29.1) and 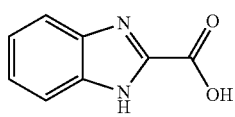 | HATU, Et$_3$N, THF, reflux | (CDCl$_3$) 8.50-8.48 (m, 1H); 8.00-7.98 (m, 1H); 7.67-7.66 (m, 1H); 7.46-7.44 (m, 1H); 7.37-7.35 (m, 1H); 6.88-6.85 (m, 1H); 5.44-5.40 (m, 1H); 4.09-3.96 (m, 3H); 3.82-3.71 (m, 2H); 3.57-3.50 (m, 3H); 3.04-3.00 (m, 1H); 2.13-1.96 (m, 4H); 1.76-1.74 (m, 4H). |
| 26.13 | (see Preparation P26.7) and | HATU, Et$_3$N, THF, reflux | (CDCl$_3$) 8.05-8.04 (m, 1H); 7.66 (s, 2H); 7.44-7.43 (m, 1H); 7.37-7.29 (m, 2H); 6.88-6.84 (m, 1H); 5.92-5.77 (m, 2H); 4.83-4.32 (m, 2H); 4.21-4.02 (m, 3H); 3.90-3.75 (m, 3H); 2.38-2.26 (m, 4H). |
| 26.14 | (see Preparation P26.6) and | HATU, Et$_3$N, THF, reflux | 8.11-8.07 (m, 1H); 8.00-7.96 (m, 1H); 7.67-7.62 (m, 2H); 7.35-7.29 (m, 2H); 6.76 (s, 1H); 5.38-5.26 (m, 1H); 4.62-4.31 (m, 3H); 4.26-4.22 (m, 2H); 3.99-3.98 (m, 1H); 3.83-3.78 (m, 3H); 2.58-2.32 (m, 4H). |

TABLE 17B-continued

PREPARATION AND NMR DATA OF EXAMPLES 26.1-26.42

| Ex. # | Starting Material (1) and (2) | Reaction Condition | $^1$H NMR (CD$_3$OD, 400 MHz) δ (ppm) |
|---|---|---|---|
| 26.15 | 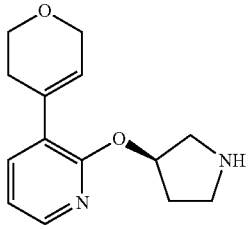<br>(see Preparation P26.8)<br>and<br>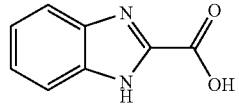 | HATU, Et$_3$N, THF, reflux | (CDCl$_3$) 8.08-8.07 (m, 1H); 7.93-7.92 (m, 1H); 7.69-7.68 (m, 2H); 7.37-7.35 (m, 2H); 5.71-5.67 (m, 1H); 4.64-4.62 (m, 1H); 4.43-4.40 (m, 1H); 4.06-3.95 (m, 4H); 3.50-3.48 (m, 2H); 3.13-3.11 (m, 1H); 2.37-2.29 (m, 2H); 1.95-1.88 (m, 2H); 1.68-1.64 (m, 2H). |
| 26.16 | 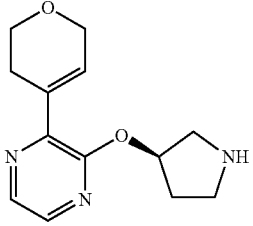<br>(see Preparation P26.5)<br>and<br>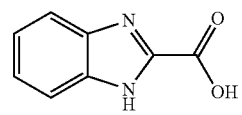 | HATU, Et$_3$N, THF, reflux | (CDCl$_3$) 8.06-8.05 (m, 1H); 7.68 (br, 2H); 7.44-7.42 (m, 1H); 7.34-7.30 (m, 2H); 6.89-6.87 (m, 1H); 5.95-5.90 (m, 1H); 5.85-5.75 (m, 1H); 4.72-4.68 (m, 1H); 4.58-4.57 (m, 1H); 4.39-4.38 (m, 1H); 4.23-4.13 (m, 3H); 3.79-3.77 (m, 2H); 2.43-2.41 (m, 4H). |
| 26.17 | 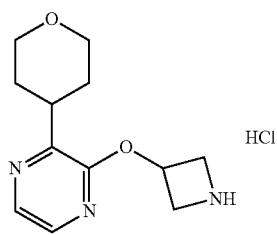<br>(see Preparation P29.2)<br>and<br>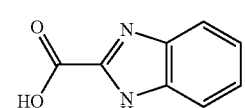 | EDCI, HOBt, DIPEA, DCM | (DMSO-D$_6$) 1.73-1.83 (m, 4H), 3.28 (peak obscured by residual water), 3.43-3.55 (m, 2H), 3.90 (d, 2H, J = 10.67 Hz), 4.16 (dd, 1H, J = 12.13 Hz, 3.22 Hz), 4.57 (dd, 1H, J = 11.55 Hz, 6.43 Hz), 4.69 (dd, 1H, J = 10.82 Hz, 3.51 Hz), 5.14 (dd, 1H, J = 12.28 Hz, 7.45 Hz), 5.46-5.55 (m, 1H), 7.22-7.36 (m, 2H), 7.52 (d, 1H, J = 7.75 Hz), 7.72 (d, 1H, J = 7.60 Hz), 8.09 7.52 (d, 1H, J = 2.34 Hz), 8.22 7.52 (d, 1H, J = 2.48 Hz), 13.24 (s, 1H) |

TABLE 17B-continued

PREPARATION AND NMR DATA OF EXAMPLES 26.1-26.42

| Ex. # | Starting Material (1) and (2) | Reaction Condition | $^1$H NMR (CD$_3$OD, 400 MHz) δ (ppm) |
|---|---|---|---|
| 26.18 | 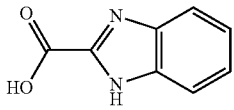<br><br>(see Preparation P29.1)<br>and<br>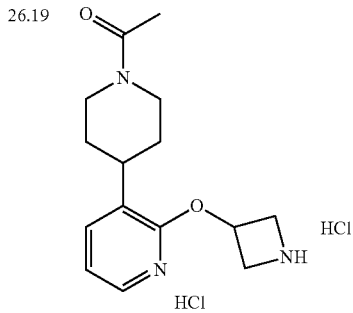 | HATU, TEA, THF | 7.95-7.90 (m, 1H); 7.71-7.22 (m, 5H); 6.92-6.88 (m, 1H); 5.43-5.41 (m, 1H); 4.28-3.80 (m, 6H); 3.60-3.51 (m, 2H); 3.10-3.01 (m, 1H); 2.20-1.70 (m, 8H). |
| 26.19 | 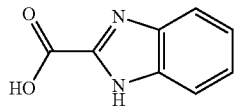<br><br>(see Preparation P27.4)<br>and<br>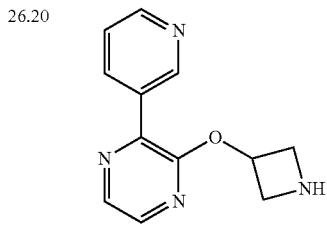 | EDCI, HOBt, DIPEA, DCM | (DMSO-D$_6$) 1.34-1.68 (m, 2H), 1.75-1.88 (m, 1H), 1.99 (d, 3H, J = 6.72 Hz), 2.55-2.67 (m, 1H), 3.02-3.22 (m, 2H), 3.89 (d, 1H, J = 12.86 Hz), 4.11 (d, 1H, J = 9.94 Hz), 4.47-4.70 (m, 3H), 5.11-5.20 (m, 1H), 5.43-5.52 (m, 1H), 7.01 (dd, 1H, J = 7.02 Hz, 4.97 Hz), 7.21-7.35 (m, 2H), 7.51 (d, 1H, J = 8.48 Hz), 7.62 (d, 1H, J = 8.48 Hz), 7.72 (d, 1H, J = 8.18 Hz), 8.03 (d, 1H, J = 4.97 Hz), 13.23 (s, 1H) |
| 26.20 | 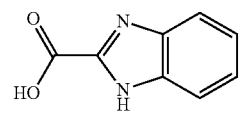<br><br>(see Preparation P26.3)<br>and<br>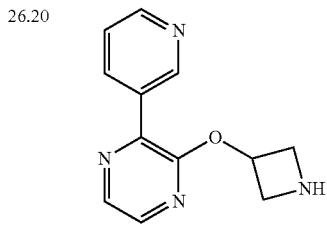 | EDCI, HOBt, DIPEA, DCM | (DMSO-D) 4.23 (dd, 1H, J = 10.96 Hz, 3.23 Hz), 4.59 (dd, 1H, J = 11.11 Hz, 7.02 Hz), 4.77 (dd, 1H, J = 11.40 Hz, 3.36 Hz), 5.17 (dd, 1H, J = 11.55 Hz, 6.43 Hz), 5.54-5.64 (m, 1H), 7.21-7.36 (m, 2H), 7.49-7.59 (m, 2H), 7.73 (d, 1H, J = 7.89 Hz), 8.30 (d, 1H, J = 2.48 Hz), 8.43-8.51 (m, 2H), 8.65 (d, 1H, J = 4.68 Hz), 9.25 (d, 1H, J = 1.90 Hz), 13.24 (s, 1H) |

TABLE 17B-continued

PREPARATION AND NMR DATA OF EXAMPLES 26.1-26.42

| Ex. # | Starting Material (1) and (2) | Reaction Condition | $^1$H NMR (CD$_3$OD, 400 MHz) δ (ppm) |
|---|---|---|---|
| 26.21 | 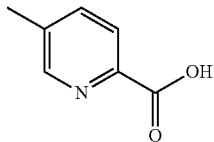<br>(see Preparation P26.4)<br>and<br>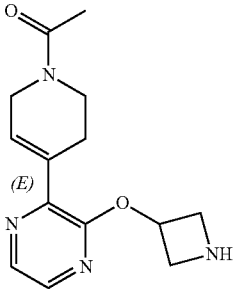 | EDC<br>HOBT<br>DIEA<br>DCM | 8.46 (1H, s), 8.15-8.24 (1H, m), 7.97-8.06 (1H, m), 7.92 (1H, d, J = 8.0 Hz), 7.74 (1H, d, J = 7.9 Hz), 6.88-7.01 (1H, m), 5.50-5.59 (1H, m), 5.14 (1H, dd, J = 11.3, 6.9 Hz), 4.70-5.80 (1H, m), 4.64 (1H, dd, J = 11.5, 6.9 Hz), 4.16-4.35 (3H, m), 3.75 (2H, dt, J = 14.0, 5.8 Hz), 2.80 (1H, br. s.), 2.70 (1H, br. s.), 2.40 (3H, s), 2.22 (3H, s) |
| 26.22 | 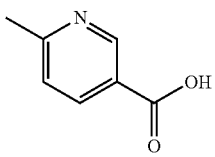<br>(see Preparation P27.6)<br>and<br>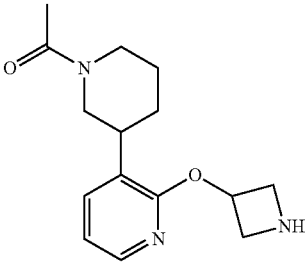 | EDC<br>HOBT<br>DIEA<br>DCM | 8.73 (1H, br. s.), 7.94-8.09 (2H, m), 7.57-7.71 (1H, m), 7.40 (1H, d, J = 7.9 Hz), 6.99 (1H, td, J = 7.1, 5.0 Hz), 5.50 (1H, br. s.), 4.74 (4H, m), 4.23 (1H, m), 3.87-4.13 (1H, m), 2.87-3.24 (2H, m), 2.63-2.74 (1H, m), 2.58 (3H, s), 2.09-2.21 (3H, m), 1.96-2.09 (1H, m), 1.76-1.96 (2H, m), 1.47-1.76 (1H, m) |

TABLE 17B-continued

PREPARATION AND NMR DATA OF EXAMPLES 26.1-26.42

| Ex. # | Starting Material (1) and (2) | Reaction Condition | $^1$H NMR (CD$_3$OD, 400 MHz) δ (ppm) |
|---|---|---|---|
| 26.23 | (see Preparation P27.6) and | DIEA DCM | 7.94-8.06 (1H, m), 7.64 (1H, dd, J = 10.9, 7.4 Hz), 6.99 (1H, td, J = 7.6, 5.0 Hz), 5.30-5.53 (1H, m), 4.50-4.76 (2H, m), 4.33-4.48 (1H, m), 4.16-4.33 (1H, m), 3.88-4.12 (2H, m), 2.86-3.25 (2H, m), 2.53-2.77 (1H, m), 2.10-2.20 (3H, m), 2.07 (2H, s), 1.95-2.03 (1H, m), 1.74-1.94 (2H, m), 1.46-1.74 (1H, m), 1.04 (9H, s) |
| 26.24 | (see Preparation P27.5) and | HATU DIEA DMF | (CDCl$_3$) 10.67 (1H, br. s.), 8.15 (1H, d, J = 2.3 Hz), 7.96 (1H, d, J = 2.3 Hz), 7.82 (1H, d, J = 7.7 Hz), 7.55 (1H, d, J = 7.7 Hz), 7.28-7.44 (2H, m), 5.45-5.64 (1H, m), 5.34 (1H, dd, J = 12.0, 6.6 Hz), 4.92 (1H, t, J = 8.3 Hz), 4.74 (2H, dd, J = 11.9, 5.0 Hz), 4.34 (1H, t, J = 8.7 Hz), 3.95 (1H, d, J = 13.9 Hz), 3.08-3.40 (2H, m), 2.73 (1H, t, J = 11.7 Hz), 2.12 (3H, s), 1.85-2.04 (3H, m), 1.76 (1H, m) |
| 26.25 | (see Preparation P27.5) and | HATU DIEA DMF | (CDCl$_3$) 9.42 (1H, br. s.), 8.14 (1H, d, J = 2.5 Hz), 7.93 (1H, d, J = 2.5 Hz), 6.96 (1H, br. s.), 6.48 (1H, br. s.), 6.28 (1H, d, J = 2.6 Hz), 5.36-5.63 (1H, m), 4.68-5.02 (2H, m), 4.64 (1H, br. s.), 4.36 (2H, br. s.), 3.96 (1H, d, J = 13.3 Hz), 3.06-3.41 (2H, m), 2.72 (1H, t, J = 12.0 Hz), 2.13 (3H, s), 1.90 (3H, d, J = 3.7 Hz), 1.68-1.81 (1H, m) |

TABLE 17B-continued

PREPARATION AND NMR DATA OF EXAMPLES 26.1-26.42

| Ex. # | Starting Material (1) and (2) | Reaction Condition | $^1$H NMR (CD$_3$OD, 400 MHz) δ (ppm) |
|---|---|---|---|
| 26.26 | 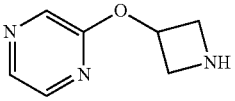<br>(see Preparation P21.1)<br>and<br>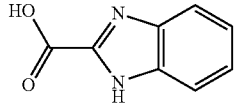 | HATU<br>DIEA<br>DMF | (DMSO-D$_6$) 4.16 (dd, 1H, J = 11.40, 2.92 Hz), 4.54-4.71 (m, 2H), 5.15 (dd, 1H, J = 11.40, 6.28 Hz), 5.45-5.53 (m, 1H), 7.21-7.37 (m, 2H), 7.52 (d, 1H, J = 7.75 Hz), 7.73 (d, 1H, J = 7.89 Hz), 8.26 (dd, 2H, J = 11.98, 2.48 Hz), 8.43 (s, 1H), 13.25 (s, 1H). |
| 26.27 | 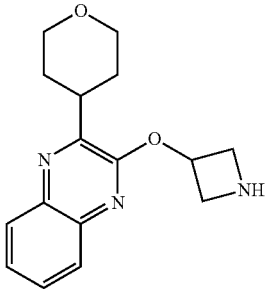<br>(see Preparation P25.2)<br>and<br>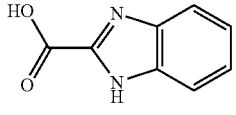 | EDC, HOBt, DIEA | (CDCl$_3$) 11.22 (br. s., 1H), 8.02 (d, J = 7.9 Hz, 1H), 7.83 (d, J = 7.9 Hz, 1H), 7.52-7.80 (m, 4H), 7.36 (dd, J = 5.8, 2.9 Hz, 2H), 5.71-5.84 (m, 1H), 5.46 (dd, J = 11.7, 6.4 Hz, 1H), 5.01 (dd, J = 11.8, 2.9 Hz, 1H), 4.87 (dd, J = 11.3, 6.9 Hz, 1H), 4.45 (dd, J = 11.5, 2.3 Hz, 1H), 4.15 (d, J = 10.1 Hz, 2H), 3.64 (t, J = 11.3 Hz, 2H), 3.39-3.56 (m, 1H), 2.04-2.24 (m, 2H), 1.92 (d, J = 12.6 Hz, 2H) |
| 26.28 | 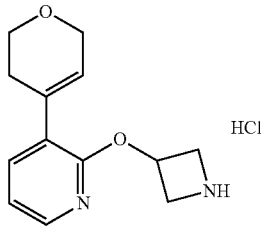<br>(see Preparation P26.1)<br>and<br>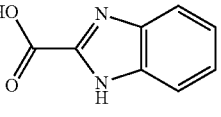 | Et$_3$N, DMAP, DCM, propyl phosphonic anhydride | (CDCl$_3$) 8.11-7.95 (m, 1H); 7.70-7.21 (m, 5H); 6.91-6.85 (m, 1H); 6.00 (s, 1H); 5.52-5.45 (m, 1H); 5.30-5.28 (m, 1H); 4.85-4.60 (m, 2H); 4.30-4.20 (m, 3H); 3.85-3.78 (m, 2H); 2.51-2.40 (m, 2H). |

TABLE 17B-continued

PREPARATION AND NMR DATA OF EXAMPLES 26.1-26.42

| Ex. # | Starting Material (1) and (2) | Reaction Condition | $^1$H NMR (CD$_3$OD, 400 MHz) δ (ppm) |
|---|---|---|---|
| 26.29 | 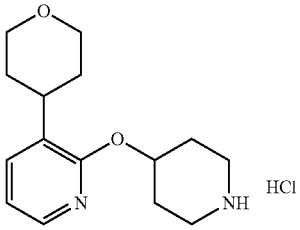 (see Preparation P29.1) and 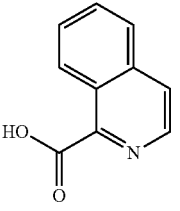 | HATU, Et$_3$N, THF, reflux | (CDCl$_3$) 8.57-5.56 (m, 1H); 8.11-8.09 (m, 1H); 78.00-7.96 (m, 2H); 7.92-7.86 (m, 2H); 7.78-7.75 (m, 1H); 7.51-7.49 (m, 1H); 6.92-6.89 (m, 1H); 5.41-5.39 (m, 1H); 4.20-4.18 (m, 1H); 4.09-4.04 (m, 2H); 3.92-3.90 (m, 1H); 3.59-3.52 (m, 2H); 3.37-3.35 (m, 1H); 3.19-3.17 (m, 1H); 3.05-3.03 (m, 1H); 2.22-2.20 (m, 1H); 2.08-2.07 (m, 1H); 1.94-1.93 (m, 1H); 1.84-1.77 (m, 1H); 1.76-1.69 (m, 4H). |
| 26.30 | 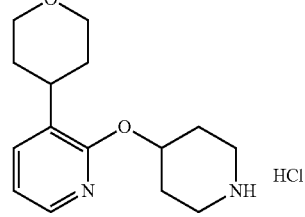 (see Preparation P29.1) and 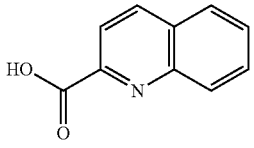 | HATU, Et$_3$N, THF, reflux | 8.50-8.47 (m, 1H); 8.09-8.06 (m, 1H); 8.01-7.99 (m, 1H); 7.96-7.95 (m, 1H); 7.86-7.81 (m, 1H); 7.70-7.66 (m, 2H); 7.57-7.54 (m, 1H); 6.93-6.90 (m, 1H); 5.45-5.44 (m, 1H); 4.07-4.03 (m, 3H); 3.92-3.85 (m, 1H); 3.61-3.52 (m, 4H); 3.17-3.12 (m, 1H); 2.25-1.77 (m, 8H). |
| 26.31 | 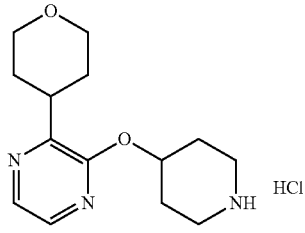 (see Preparation P29.3) and 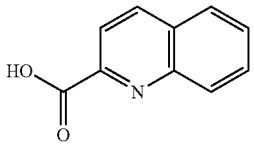 | HATU, Et$_3$N, THF, reflux | (CDCl$_3$) 11.2 (s, 1H); 8.36 (d, J = 8.4 Hz, 1H); 8.18 (d, J = 8.4 Hz, 1H); 8.05 (d, J = 2.8 Hz, 1H); 7.91 (d, J = 2.8 Hz, 1H); 7.88 (d, J = 8 Hz, 1H); 7.80 (d, J = 7.2 Hz, 1H); 7.74 (d, J = 24.4 Hz, 1H); 7.65 (dd, J = 16.4 Hz, J = 24 Hz, 1H); 5.40 (t, J = 3.6 Hz, 1H); 4.10-4.05 (m, 3H); 3.88-3.76 (m, 1H); 3.60-3.58 (m, 1H); 3.57-3.53 (m, 3H); 3.24 (t, J = 3.6 Hz, 1H); 2.17-2.03 (m, 1H); 2.01-1.91 (m, 5H); 1.77 (t, J = 10.4 Hz, 1H). |

TABLE 17B-continued
PREPARATION AND NMR DATA OF EXAMPLES 26.1-26.42
| Ex. # | Starting Material (1) and (2) | Reaction Condition | ¹H NMR (CD₃OD, 400 MHz) δ (ppm) |
|---|---|---|---|
| 26.32 | 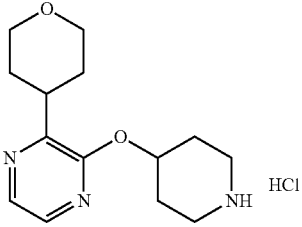 (see Preparation P29.3) and 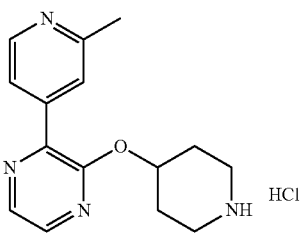 | HATU, TEA, THF | (CDCl₃) 8.61 (s, 1H); 8.19-7.90 (m, 7H); 5.41 (s, 1H); 4.14-3.98 (m, 4H); 3.63-3.55 (m, 2H); 3.40-3.20 (m, 3H); 2.25-2.24 (m, 1H); 2.11-1.86 (m, 4H); 1.81-1.73 (m, 3H). |
| 26.33 | 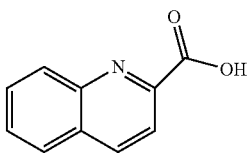 (see Preparation P29.5) and 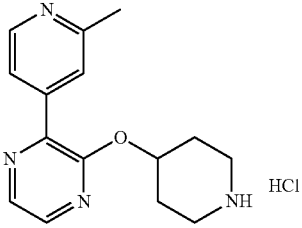 | HATU, TEA, THF | (CDCl₃) 8.48-8.47 (m, 1H); 8.44-8.40 (m, 3H); 8.33-8.30 (m, 2H); 8.14-8.11 (m, 1H); 7.89-7.87 (m, 1H); 7.81-7.74 (m, 2H); 7.65-7.61 (m, 1H); 5.63-5.59 (m, 1H); 4.30-4.28 (m, 1H); 3.99-3.96 (m, 1H); 3.73-3.66 (m, 1H); 3.63-3.57 (m, 1H); 2.91 (s, 3H); 2.33-2.32 (m, 1H); 2.23-2.21 9m, 1H); 2.10-1.98 (m, 2H). |
| 26.34 | 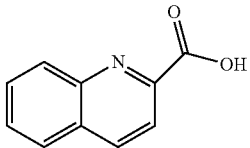 (see Preparation P29.5) and  | HATU, TEA, THF | (CDCl₃) 8.81-8.79 (m, 1H); 8.55-8.51 (m, 2H); 8.43-8.38 (m, 2H); 8.28-8.27 (m, 1H); 8.15-8.13 (m, 1H); 7.98-7.92 (m, 2H); 7.90-7.88 (m, 1H); 7.82-7.78 (m, 1H); 5.56-5.55 (m, 1H); 4.24-4.22 (m, 1H); 3.89-3.87 (m, 1H); 3.44-3.40 (m, 1H); 3.24-3.20 (m, 1H); 2.88 (s, 3H); 2.34-3.21 (m, 1H); 2.16-2.03 (m, 2H); 1.94-1.91 (m, 1H). |

TABLE 17B-continued

PREPARATION AND NMR DATA OF EXAMPLES 26.1-26.42

| Ex. # | Starting Material (1) and (2) | Reaction Condition | $^1$H NMR (CD$_3$OD, 400 MHz) δ (ppm) |
|---|---|---|---|
| 26.35 | (see Preparation P29.4) and [structure: 2-methylpyridinyl-pyridinyl-O-piperidine·HCl] and [quinoline-2-carboxylic acid] | HATU, TEA, THF | (CDCl$_3$) 8.76-8.75 (m, 1H); 8.36-8.29 (m, 2H); 8.14-8.13 (m, 1H); 7.94-7.71 (m, 5H); 6.69-6.65 (m, 1H); 7.63-7.61 (m, 1H); 7.11-7.08 (m, 1H); 5.55-5.51 (m, 1H); 4.12-4.09 (m, 1H); 3.78-3.69 (m, 2H); 3.52-3.48 (m, 1H); 2.86 (s, 3H); 2.25-2.22 (m, 1H); 2.15-2.09 (m, 1H); 1.97-1.86 (m, 2H). |
| 26.36 | (see Preparation P29.4) and [structure: 2-methylpyridinyl-pyridinyl-O-piperidine·HCl] and [isoquinoline-1-carboxylic acid] | HATU, TEA, THF | (CDCl$_3$) 8.70-8.69 (m, 1H); 8.55 (br, 1H); 8.29-8.28 (m, 1H); 8.12-8.09 (m, 1H); 8.04-7.94 (m, 4H); 7.84-7.80 (m, 3H); 7.11-7.08 (m, 1H); 5.51-5.50 (m, 1H); 4.13-4.11 (m, 1H); 3.89-3.85 (m, 1H); 3.30-3.27 (m, 1H); 3.18-3.13 (m, 1H); 2.85 (s, 3H); 2.27-2.24 (m, 1H); 2.06-1.98 (m, 2H); 1.81-1.79 (m, 1H). |
| 26.37 | (see Preparation P31.1) and [structure: morpholino-pyridinyl-O-piperidine·HCl] and [isoquinoline-1-carboxylic acid] | HATU, TEA, THF | (CDCl$_3$) 8.55 (d, J = 6.0 Hz, 1H); 8.10 (d, J = 8.4 Hz, 1H); 8.01-7.81 (m, 4H); 7.79-7.74 (m, 1H); 7.35-7.33 (m, 1H); 6.94-6.91 (m, 1H); 5.43-5.42 (m, 1H); 4.22-4.16 (m, 1H); 3.91-3.89 (m, 5H); 3.41-3.37 (m, 1H); 3.22-3.14 (m, 5H); 2.26-2.07 (m, 2H); 2.00-1.96 (m, 1H); 1.87-1.83 (m, 1H). |

TABLE 17B-continued

PREPARATION AND NMR DATA OF EXAMPLES 26.1-26.42

| Ex. # | Starting Material (1) and (2) | Reaction Condition | $^1$H NMR (CD$_3$OD, 400 MHz) δ (ppm) |
|---|---|---|---|
| 26.38 | (see Preparation P31.2) and | HATU, TEA, THF | (CDCl$_3$) 8.40 (d, J = 8.4 Hz, 1H); 8.18 (d, J = 8.8 Hz, 1H); 7.90-7.79 (m, 1H); 7.71-7.69 (m, 1H); 7.67-7.63 (m, 3H); 7.53-7.52 (m, 1H); 5.44-5.40 (m, 1H); 4.08-4.04 (m, 1H); 3.82-3.69 (m, 6H); 3.59-3.48 (m, 5H); 2.22-2.18 (m, 1H); 2.12-2.09 (m, 1H); 1.98-1.97 (m, 1H); 1.93-1.91 (m, 1H). |
| 26.39 | (see Preparation P31.2) and | HATU, TEA, THF | (CDCl$_3$) 8.57-8.56 (m, 1H); 8.12-7.94 (m, 4H); 7.84-7.80 (m, 1H); 7.65-7.64 (m, 1H); 7.52-7.51 (m, 1H); 5.39-5.38 (m, 1H); 4.16-4.15 (m, 1H); 3.88-3.80 (m, 5H); 3.60-3.59 (m, 4H); 3.32-3.31 (m, 1H); 3.17-3.16 (m, 1H); 2.25-2.24 (m, 1H); 2.07-1.97 (m, 2H); 1.84-1.83 (m, 1H). |
| 26.40 | (see Preparation P31.1) and | HATU, TEA, THF | (CDCl$_3$) 8.35 (d, J = 8.4 Hz, 1H); 8.15 (d, J = 8.4 Hz, 1H); 7.88-7.80 (m, 2H); 7.78-7.60 (m, 3H); 7.31-7.29 (m, 1H); 6.92-6.89 (m, 1H); 5.46-5.45 (m, 1H); 4.13-4.11 (m, 1H); 3.90-3.89 (m, 4H); 3.79-3.77 (m, 2H); 3.52-3.51 (m, 1H); 3.21-3.20 (m, 4H); 2.21-2.20 (m, 1H); 2.11-2.10 (m, 1H); 2.03-2.02 (m, 1H); 1.96-1.95 (m, 1H).. |

TABLE 17B-continued

PREPARATION AND NMR DATA OF EXAMPLES 26.1-26.42

| Ex. # | Starting Material (1) and (2) | Reaction Condition | $^1$H NMR (CD$_3$OD, 400 MHz) δ (ppm) |
|---|---|---|---|
| 26.41 | (see Preparation P27.8) and [benzimidazole-2-carboxylic acid] | HATU, Et$_3$N, THF, | (CDCl$_3$) 8.05-7.99 (m, 1H); 7.73-7.71 (m, 2H); 7.51-7.41 (m, 3H); 6.97-6.89 (m, 1H); 5.73-5.72 (m, 1H); 4.47-4.40 (m, 1H); 4.26-4.23 (m, 1H); 4.05-3.92 (m, 4H); 3.54-3.51 (m, 2H); 3.04-2.93 (m, 1H); 2.39-2.33 (m, 2H); 1.76-1.73 (m, 4H). |
| 26.42 | (see Preparation P27.7) and [benzimidazole-2-carboxylic acid] | HATU, Et$_3$N, THF, | (CDCl$_3$) 7.98-7.96 (m, 1H); 7.65-7.64 (m, 2H); 7.37-7.29 (m, 3H); 6.86-6.81 (m, 1H); 5.77-5.69 (m, 1H); 4.75-4.73 (m, 1H); 4.56-4.50 (m, 1H); 4.35-4.29 (m, 1H); 3.97-3.80 (m, 3H); 3.44-3.39 (m, 2H); 2.96-2.86 (m, 1H); 2.37-2.26 (m, 2H); 1.68-1.62 (m, 4H). |

SCHEME 27

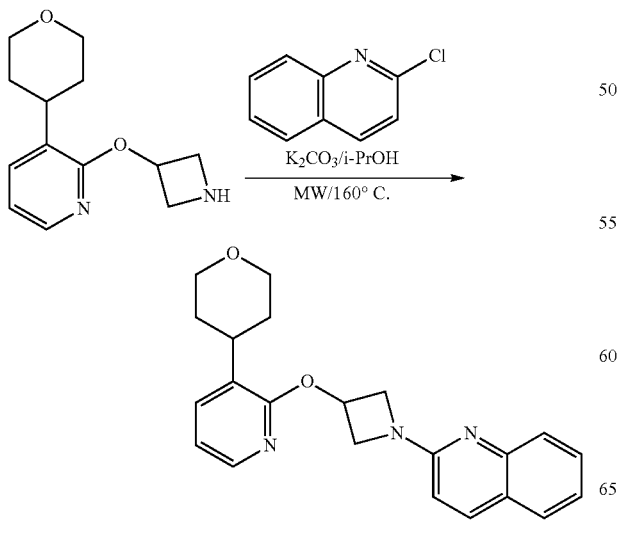

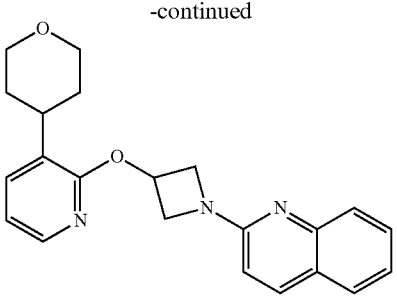

Example 27.1

2-(3-((3-(Tetrahydro-2H-Pyran-4-yl)Pyridin-2-yl)Oxy)Azetidin-1-yl)Quinoline

A mixture of 2-(azetidin-3-yloxy)-3-(tetrahydro-2H-pyran-4-yl)pyridine (see PREPARATION P27.1; 100 mg, 0.45 mmol), 2-chloroquinoline (73 mg, 0.45 mmol), Pd$_2$(dba)$_3$ (56 mg, 0.062 mmol), 2,2'-bis(diphenylphosphino)-1,1'-binaphthyl (BINAP) (40 mg, 0.06 mmol), KI (40 mg, 0.13 mmol)

and sodium tert-butoxide (t-BuONa) (110 mg, 1.2 mmol) was dissolved in toluene (5 mL). The reaction mixture was heated in a microwave at 130° C. for 4 hours. The solvent was evaporated and the crude product was purified by silica gel column chromatography to give the product (6.7 mg, 0.018 mmol, yield 10%). [M+1] 363. IC50 (uM) 0.331.

TABLE 18A

EXAMPLES 27.1-27.84 PREPARED ANALOGOUS TO SCHEME 27

| Ex. # | Structure | Chemical Name | M + 1 | IC$_{50}$ (uM) |
|---|---|---|---|---|
| 27.1 | 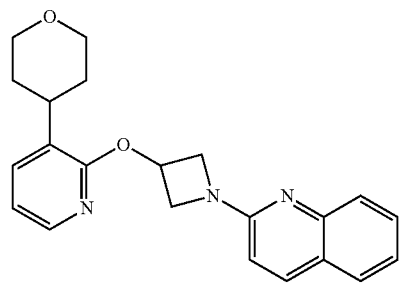 [SMILES: c1cnc(OC2CN(c3ccc4ccccc4n3)C2)c(C2CCOCC2)c1] | 2-(3-(3-(tetrahydro-2H-pyran-4-yl)pyridin-2-yloxy)azetidin-1-yl)quinoline | 362 | 1.8 |
| 27.2 | 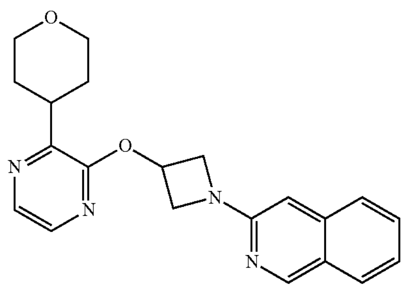 [SMILES: c1ccc2cc(N3CC(Oc4nccnc4C4CCOCC4)C3)ncc2c1] | 3-(3-(3-(tetrahydro-2H-pyran-4-yl)pyrazin-2-yloxy)azetidin-1-yl)isoquinoline | 363 | 4.965 |
| 27.3 | 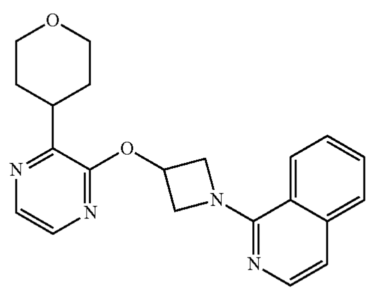 [SMILES: c1ccc2c(N3CC(Oc4nccnc4C4CCOCC4)C3)nccc2c1] | 1-(3-(3-(tetrahydro-2H-pyran-4-yl)pyrazin-2-yloxy)azetidin-1-yl)isoquinoline | 363 | 4.413 |
| 27.4 | 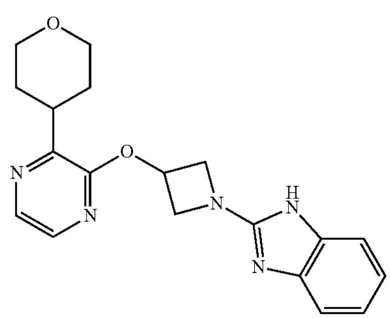 [SMILES: c1ccc2[nH]c(N3CC(Oc4nccnc4C4CCOCC4)C3)nc2c1] | 2-(3-(3-(tetrahydro-2H-pyran-4-yl)pyrazin-2-yloxy)azetidin-1-yl)-1H-benzo[d]imidazole | 352 | 1.009 |
| 27.5 | 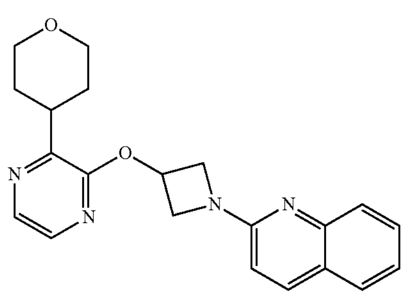 [SMILES: c1ccc2nc(N3CC(Oc4nccnc4C4CCOCC4)C3)ccc2c1] | 2-(3-((3-(tetrahydro-2H-pyran-4-yl)pyrazin-2-yl)oxy)azetidin-1-yl)quinoline | 363 | 0.331 |

TABLE 18A-continued

EXAMPLES 27.1-27.84 PREPARED ANALOGOUS TO SCHEME 27

| Ex. # | Structure | Chemical Name | M + 1 | IC$_{50}$ (uM) |
|---|---|---|---|---|
| 27.6 | 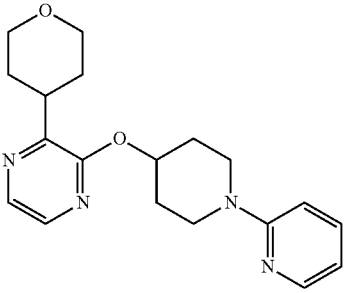 [SMILES: c1ccc(N2CCC(Oc3nccnc3C3CCOCC3)CC2)nc1] | 2-(1-(pyridin-2-yl)piperidin-4-yloxy)-3-(tetrahydro-2H-pyran-4-yl)pyrazine | 341 | 2.389 |
| 27.7 | 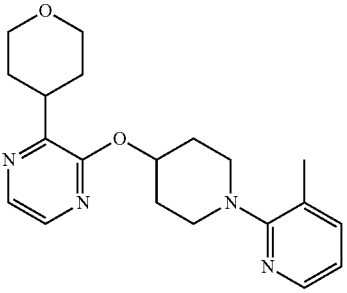 [SMILES: Cc1cccnc1N1CCC(Oc2nccnc2C2CCOCC2)CC1] | 2-(1-(3-methylpyridin-2-yl)piperidin-4-yloxy)-3-(tetrahydro-2H-pyran-4-yl)pyrazine | 355 | 1.723 |
| 27.8 | 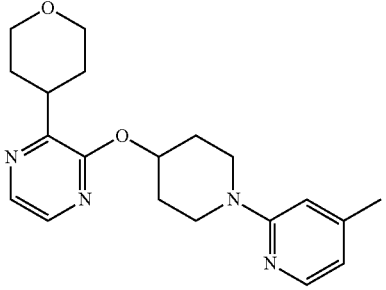 [SMILES: Cc1ccnc(N2CCC(Oc3nccnc3C3CCOCC3)CC2)c1] | 2-(1-(4-methylpyridin-2-yl)piperidin-4-yloxy)-3-(tetrahydro-2H-pyran-4-yl)pyrazine | 355 | 1.334 |
| 27.9 | 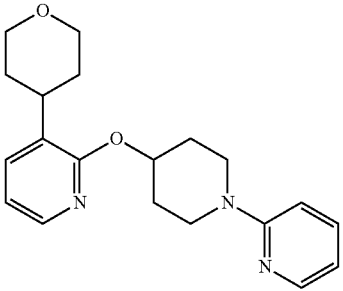 [SMILES: c1ccc(N2CCC(Oc3ncccc3C3CCOCC3)CC2)nc1] | 2-(1-(pyridin-2-yl)piperidin-4-yloxy)-3-(tetrahydro-2H-pyran-4-yl)pyridine | 340 | 1.015 |
| 27.10 | 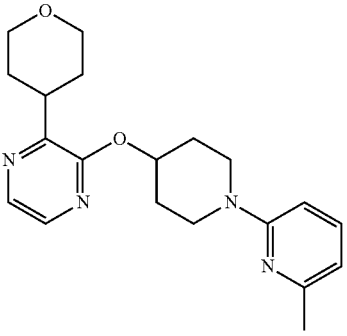 [SMILES: Cc1cccc(N2CCC(Oc3nccnc3C3CCOCC3)CC2)n1] | 2-(1-(6-methylpyridin-2-yl)piperidin-4-yloxy)-3-(tetrahydro-2H-pyrazin-4-yl)pyrazine | 355 | 1.441 |

TABLE 18A-continued

EXAMPLES 27.1-27.84 PREPARED ANALOGOUS TO SCHEME 27

| Ex. # | Structure | Chemical Name | M + 1 | IC$_{50}$ (uM) |
|---|---|---|---|---|
| 27.11 | 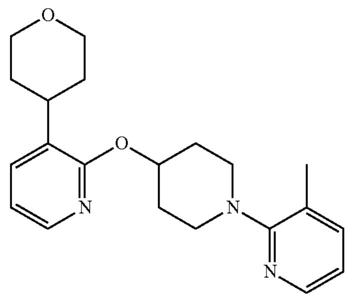 [SMILES: Cc1cccnc1N1CCC(Oc2ncccc2C2CCOCC2)CC1] | 3-methyl-2-(4-(3-(tetrahydro-2H-pyran-4-yl)pyridin-2-yloxy)piperidin-1-yl)pyridine | 354 | 0.568 |
| 27.12 | 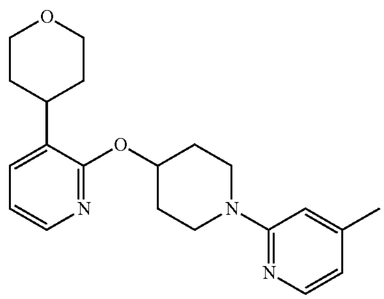 [SMILES: Cc1ccnc(N2CCC(Oc3ncccc3C3CCOCC3)CC2)c1] | 2-(1-(4-methylpyridin-2-yl)piperidin-4-yloxy)-3-(tetrahydro-2H-pyran-4-yl)pyridine | 354 | 0.236 |
| 27.13 | 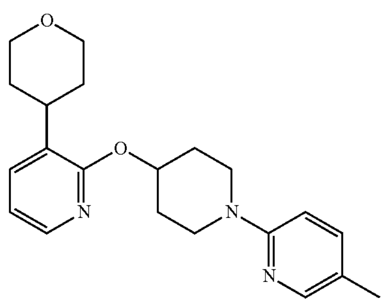 [SMILES: Cc1ccc(N2CCC(Oc3ncccc3C3CCOCC3)CC2)nc1] | 2-(1-(5-methylpyridin-2-yl)piperidin-4-yloxy)-3-(tetrahydro-2H-pyran-4-yl)pyridine | 354 | 0.262 |
| 27.14 | 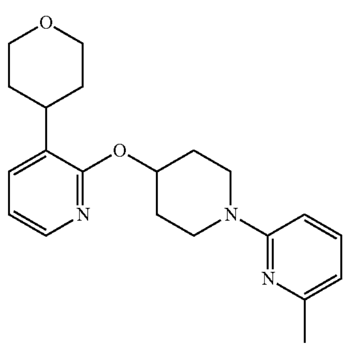 [SMILES: Cc1cccc(N2CCC(Oc3ncccc3C3CCOCC3)CC2)n1] | 2-(1-(6-methylpyridin-2-yl)piperidin-4-yloxy)-3-(tetrahydro-2H-pyran-4-yl)pyridine | 354 | 1.668 |
| 27.15 | 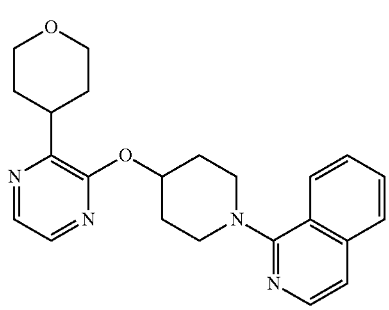 [SMILES: c1ccc2c(N3CCC(Oc4nccnc4C4CCOCC4)CC3)nccc2c1] | 1-(4-(3-(tetrahydro-2H-pyran-4-yl)pyrazin-2-yloxy)piperidin-1-yl)isoquinoline | 391 | 2.808 |

TABLE 18A-continued

EXAMPLES 27.1-27.84 PREPARED ANALOGOUS TO SCHEME 27

| Ex. # | Structure | Chemical Name | M + 1 | IC$_{50}$ (uM) |
|---|---|---|---|---|
| 27.16 | 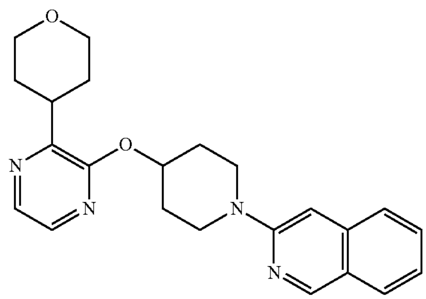 [SMILES: c1ccc2cc(N3CCC(Oc4nccnc4C4CCOCC4)CC3)ncc2c1] | 3-(4-(3-(tetrahydro-2H-pyran-4-yl)pyrazin-2-yloxy)piperidin-1-yl)isoquinoline | 391 | 0.235 |
| 27.17 | 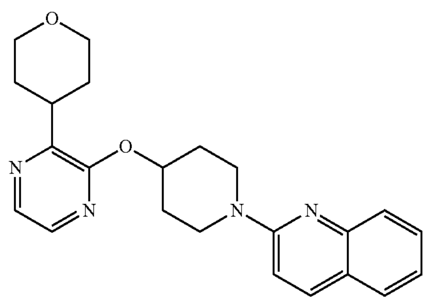 | 2-(4-(3-(tetrahydro-2H-pyran-4-yl)pyrazin-2-yloxy)piperidin-1-yl)quinoline | 391 | 0.0693 |
| 27.18 | 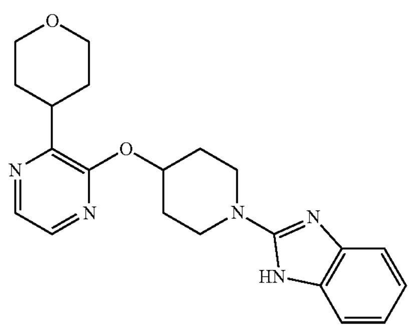 [SMILES: c1ccc2[nH]c(N3CCC(Oc4nccnc4C4CCOCC4)CC3)nc2c1] | 2-(4-(3-(tetrahydro-2H-pyran-4-yl)pyrazin-2-yloxy)piperidin-1-yl)-1H-indole | 380 | 0.229 |
| 27.19 | 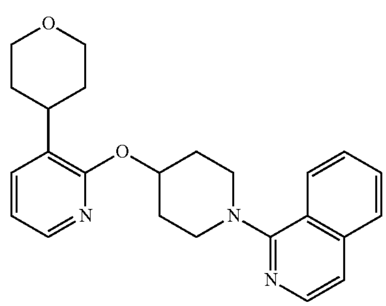 [SMILES: c1cnc(OC2CCN(c3nccc4ccccc34)CC2)c(C2CCOCC2)c1] | 1-(4-(3-(tetrahydro-2H-pyran-4-yl)pyridin-2-yloxy)piperidin-1-yl)isoquinoline | 390 | 1.813 |
| 27.20 | 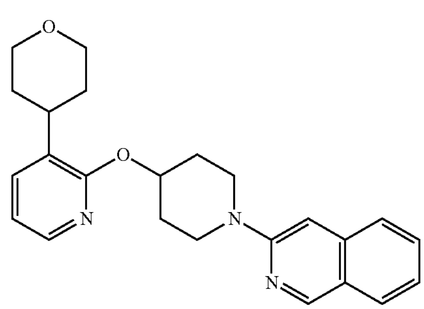 [SMILES: c1cnc(OC2CCN(c3cc4ccccc4cn3)CC2)c(C2CCOCC2)c1] | 3-(4-(3-(tetrahydro-2H-pyran-4-yl)pyridin-2-yloxy)piperidin-1-yl)isoquinoline | 390 | 0.353 |

TABLE 18A-continued

EXAMPLES 27.1-27.84 PREPARED ANALOGOUS TO SCHEME 27

| Ex. # | Structure | Chemical Name | M + 1 | IC$_{50}$ (uM) |
|---|---|---|---|---|
| 27.21 | 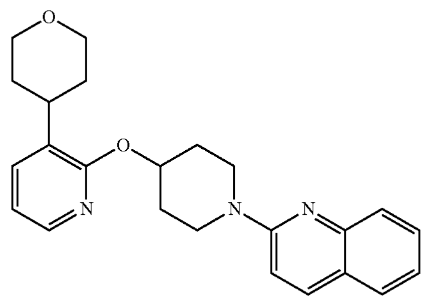 [SMILES: c1cnc(OC2CCN(c3ccc4ccccc4n3)CC2)c(C2CCOCC2)c1] | 2-(4-(3-(tetrahydro-2H-pyran-4-yl)pyridin-2-yloxy)piperidin-1-yl)quinoline | 390 | 0.0098 |
| 27.22 | 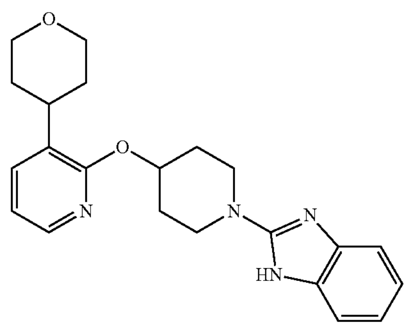 [SMILES: c1cnc(OC2CCN(c3nc4ccccc4[nH]3)CC2)c(C2CCOCC2)c1] | 2-(4-(3-(tetrahydro-2H-pyran-4-yl)pyridin-2-yloxy)piperidin-1-yl)-1H-benzo[d]imidazole | 379 | 0.199 |
| 27.23 | 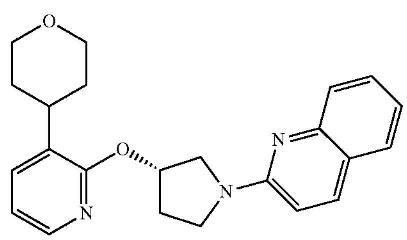 [SMILES: c1cnc(O[C@H]2CCN(c3ccc4ccccc4n3)C2)c(C2CCOCC2)c1] | (S)-2-(3-(3-(tetrahydro-2H-pyran-4-yl)pyridin-2-yloxy)pyrrolidin-1-yl)quinoline | 376 | 0.340 |
| 27.24 | 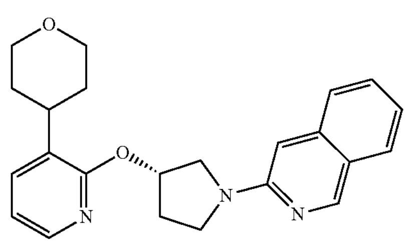 [SMILES: c1cnc(O[C@H]2CCN(c3cc4ccccc4cn3)C2)c(C2CCOCC2)c1] | (S)-3-(3-(3-(tetrahydro-2H-pyran-4-yl)pyridin-2-yloxy)pyrrolidin-1-yl)isoquinoline | 376 | 2.971 |
| 27.25 | 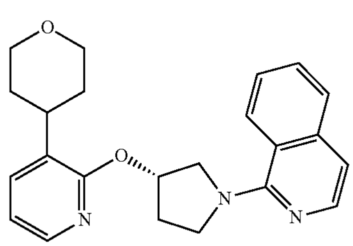 [SMILES: c1cnc(O[C@H]2CCN(c3nccc4ccccc34)C2)c(C2CCOCC2)c1] | (S)-1-(3-(3-(tetrahydro-2H-pyran-4-yl)pyridin-2-yloxy)pyrrolidin-1-yl)isoquinoline | 376 | 0.730 |

TABLE 18A-continued

EXAMPLES 27.1-27.84 PREPARED ANALOGOUS TO SCHEME 27

| Ex. # | Structure | Chemical Name | M + 1 | IC₅₀ (uM) |
|---|---|---|---|---|
| 27.26 | 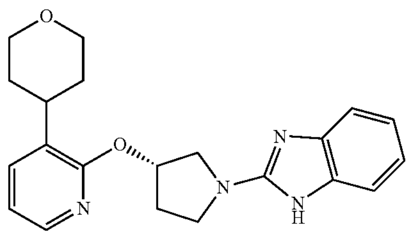 [SMILES: c1cnc(O[C@H]2CCN(c3nc4ccccc4[nH]3)C2)c(C2CCOCC2)c1] | (S)-2-(2-(3-(tetrahydro-2H-pyran-4-yl)pyridin-2-yloxy)pyrrolidin-1-yl)-1H-benzo[d]imidazole | 418 | 2.472 |
| 27.27 | 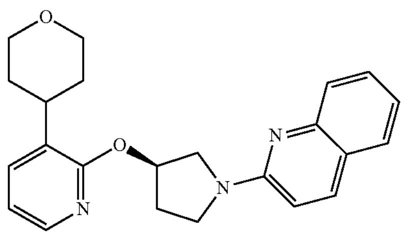 [SMILES: c1cnc(O[C@@H]2CCN(c3ccc4ccccc4n3)C2)c(C2CCOCC2)c1] | (R)-2-(3-(3-(tetrahydro-2H-pyran-4-yl)pyridin-2-yloxy)pyrrolidin-1-yl)quinoline | 376 | 0.384 |
| 27.28 | 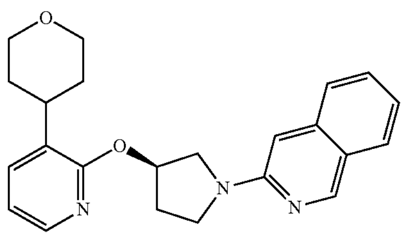 | (R)-3-(3-(3-(tetrahydro-2H-pyran-4-yl)pyridin-2-yloxy)pyrrolidin-1-yl)isoquinoline | 376 | 1.829 |
| 27.29 | 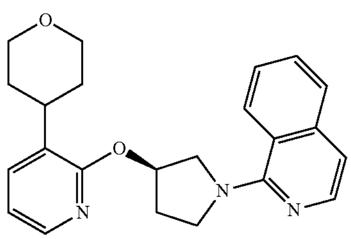 [SMILES: c1cnc(O[C@@H]2CCN(c3nccc4ccccc34)C2)c(C2CCOCC2)c1] | (R)-1-(3-(3-(tetrahydro-2H-pyran-4-yl)pyridin-2-yloxy)pyrrolidin-1-yl)isoquinoline | 376 | 0.981 |
| 27.30 | 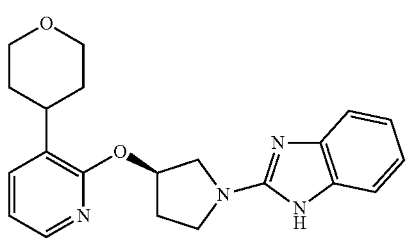 [SMILES: c1cnc(O[C@@H]2CCN(c3nc4ccccc4[nH]3)C2)c(C2CCOCC2)c1] | (R)-2-(3-(3-(tetrahydro-2H-pyran-4-yl)pyridin-2-yloxy)pyrrolidin-1-yl)-1H-benzo[d]imidazole | 365 | 3.587 |
| 27.31 | 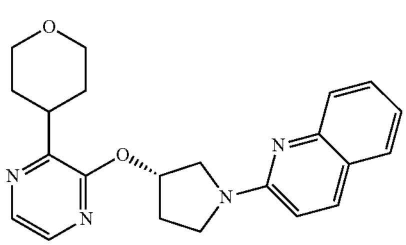 [SMILES: c1ccc2nc(N3CC[C@H](Oc4nccnc4C4CCOCC4)C3)ccc2c1] | (S)-2-(3-(3-(tetrahydro-2H-pyran-4-yl)pyrazin-2-yloxy)pyrrolidin-1-yl)quinoline | 377 | 0.447 |

TABLE 18A-continued

EXAMPLES 27.1-27.84 PREPARED ANALOGOUS TO SCHEME 27

| Ex. # | Structure | Chemical Name | M + 1 | IC$_{50}$ (uM) |
|---|---|---|---|---|
| 27.32 | 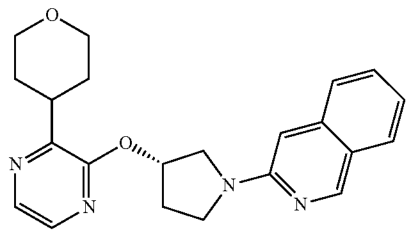 [SMILES: c1ccc2cc(N3CC[C@H](Oc4nccnc4C4CCOCC4)C3)ncc2c1] | (S)-3-(3-(3-(tetrahydro-2H-pyran-4-yl)pyrazin-2-yloxy)pyrrolidin-1-yl)isoquinoline | 377 | 1.362 |
| 27.33 | 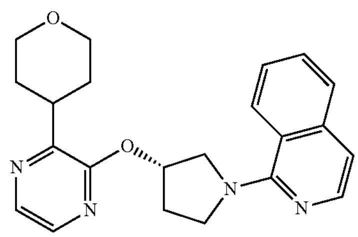 [SMILES: c1ccc2c(N3CC[C@H](Oc4nccnc4C4CCOCC4)C3)nccc2c1] | (S)-1-(3-(3-(tetrahydro-2H-pyran-4-yl)pyrazin-2-yloxy)pyrrolidin-1-yl)isoquinoline | 377 | 0.819 |
| 27.34 | 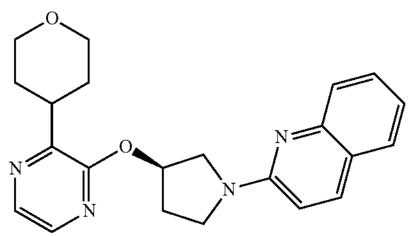 [SMILES: c1ccc2nc(N3CC[C@@H](Oc4nccnc4C4CCOCC4)C3)ccc2c1] | (R)-2-(3-(3-(tetrahydro-2H-pyran-4-yl)pyrazin-2-yloxy)pyrrolidin-1-yl)quinoline | 377 | 0.109 |
| 27.35 | 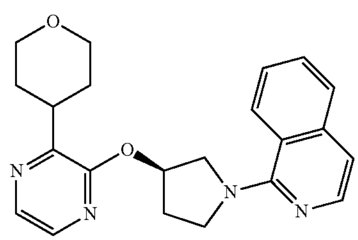 [SMILES: c1ccc2c(N3CC[C@@H](Oc4nccnc4C4CCOCC4)C3)nccc2c1] | (R)-1-(3-(3-(tetrahydro-2H-pyran-4-yl)pyrazin-2-yloxy)pyrrolidin-1-yl)isoquinoline | 377 | 4.43 |
| 27.36 | 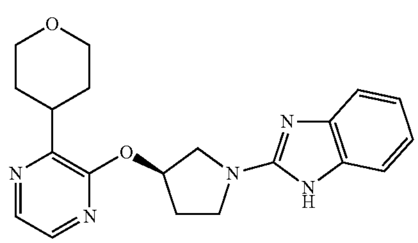 [SMILES: c1ccc2[nH]c(N3CC[C@@H](Oc4nccnc4C4CCOCC4)C3)nc2c1] | (R)-2-(3-(3-(tetrahydro-2H-pyran-4-yl)pyrazin-2-yloxy)pyrrolidin-1-yl)-1H-benzo[d]imidazole | 366 | 0.306 |
| 27.37 | 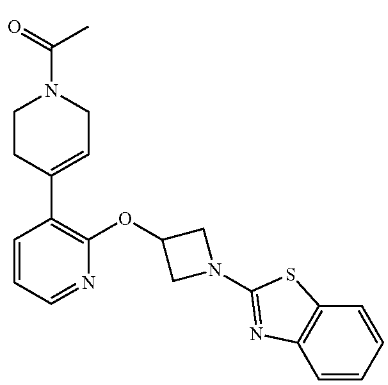 [SMILES: CC(=O)N1CC=C(c2cccnc2OC2CN(c3nc4ccccc4s3)C2)CC1] | 1-(4-(2-(1-(benzo[d]thiazol-2-yl)azetidin-3-yloxy)pyridin-3-yl)-5,6-dihydropyridin-1(2H)-yl)ethanone | 407.0 | 0.3457 |

TABLE 18A-continued

EXAMPLES 27.1-27.84 PREPARED ANALOGOUS TO SCHEME 27

| Ex. # | Structure | Chemical Name | M + 1 | IC$_{50}$ (uM) |
|---|---|---|---|---|
| 27.38 | 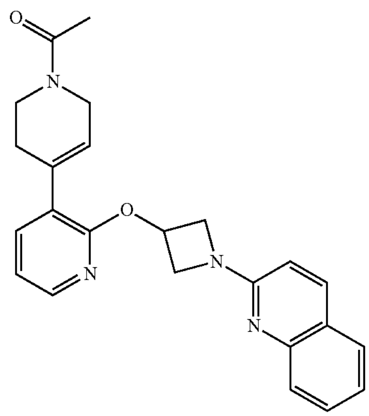 [SMILES: CC(=O)N1CC=C(c2cccnc2OC2CN(c3ccc4ccccc4n3)C2)CC1] | 1-(4-(2-(1-(quinolin-2-yl)azetidin-3-yloxy)pyridin-3-yl)-5,6-dihydropyridin-1(2H)-yl)ethanone | 401.0 | 0.04343 |
| 27.39 | 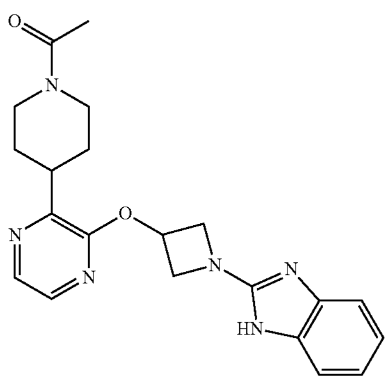 [SMILES: CC(=O)N1CCC(c2nccnc2OC2CN(c3nc4ccccc4[nH]3)C2)CC1] | 1-(4-(3-(1-(1H-benzo[d]imidazol-2-yl)azetidin-3-yloxy)pyrazin-2-yl)piperidin-1-yl)ethanone | 393 | 0.6896 |
| 27.40 | 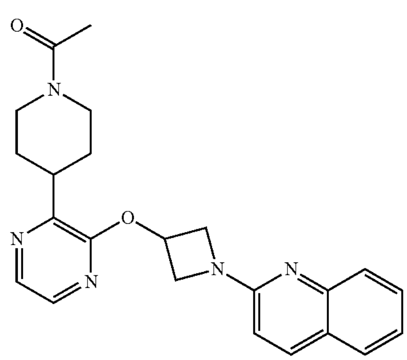 [SMILES: CC(=O)N1CCC(c2nccnc2OC2CN(c3ccc4ccccc4n3)C2)CC1] | 1-(4-(3-(1-(quinolin-2-yl)azetidin-3-yloxy)pyrazin-2-yl)piperidin-1-yl)ethanone | 404 | 0.00839 |
| 27.41 | 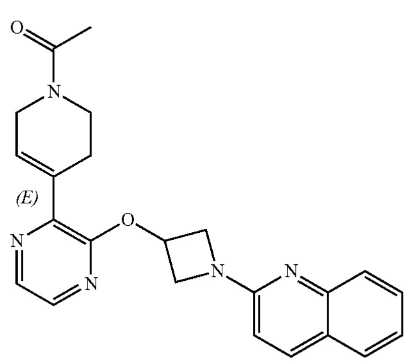 [SMILES: CC(=O)N1CC=C(c2nccnc2OC2CN(c3ccc4ccccc4n3)C2)CC1] | 1-(4-(3-(1-(quinolin-2-yl)azetidin-3-yloxy)pyrazin-2-yl)-5,6-dihydropyridin-1(2H)-yl)ethanone | 402 | 0.004109 |

TABLE 18A-continued

EXAMPLES 27.1-27.84 PREPARED ANALOGOUS TO SCHEME 27

| Ex. # | Structure | Chemical Name | M + 1 | IC$_{50}$ (uM) |
|---|---|---|---|---|
| 27.42 | (E) | 1-(4-(3-(1-(benzo[d]thiazol-2-yl)azetidin-3-yloxy)pyrazin-2-yl)-5,6-dihydropyridin-1(2H)-yl)ethanone | 408 | 0.06307 |
| 27.43 | 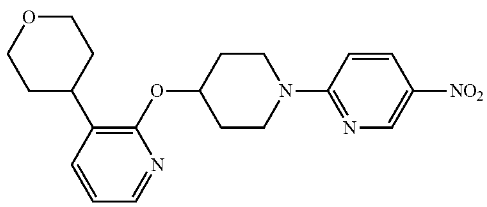 | 2-((1-(5-nitropyridin-2-yl)piperidin-4-yl)oxy)-3-(tetrahydro-2H-pyran-4-yl)pyridine | 385 | 1.4 |
| 27.44 | 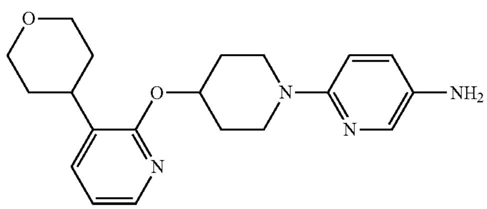 | 6-(4-((3-(tetrahydro-2H-pyran-4-yl)pyridin-2-yl)oxy)piperidin-1-yl)pyridin-3-amine | 355 | 1.7 |
| 27.45 | 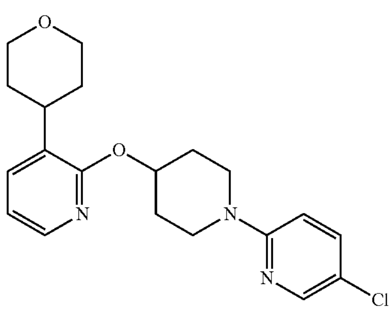 | 2-((1-(5-chloropyridin-2-yl)piperidin-4-yl)oxy)-3-(tetrahydro-2H-pyran-4-yl)pyridine | 374 | 1.41 |
| 27.46 | 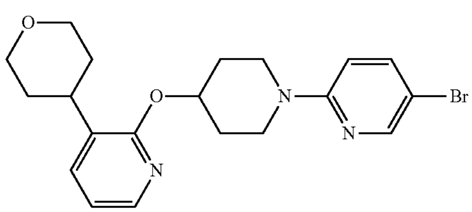 | 2-((1-(5-chloropyridin-2-yl)piperidin-4-yl)oxy)-3-(tetrahydro-2H-pyran-4-yl)pyridine | 418 | 0.138 |
| 27.47 | 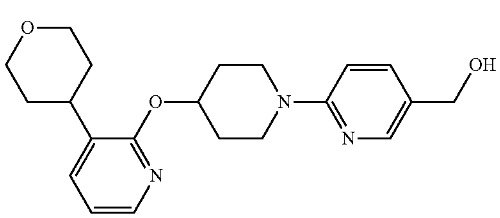 | (6-(4-((3-(tetrahydro-2H-pyran-4-yl)pyridin-2-yl)oxy)piperidin-1-yl)pyridin-3-yl)methanol | 370 | 1.17 |

TABLE 18A-continued

EXAMPLES 27.1-27.84 PREPARED ANALOGOUS TO SCHEME 27

| Ex. # | Structure | Chemical Name | M + 1 | IC$_{50}$ (uM) |
|---|---|---|---|---|
| 27.48 | 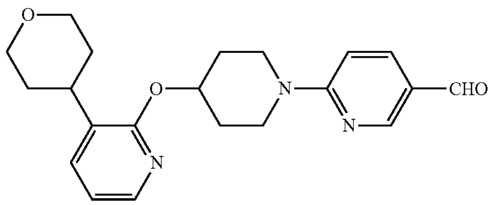 [SMILES: O=Cc1ccc(N2CCC(Oc3ncccc3C3CCOCC3)CC2)nc1] | 6-(4-((3-(tetrahydro-2H-pyran-4-yl)pyridin-2-yl)oxy)piperidin-1-yl)nicotinaldehyde | 368 | 1.48 |
| 27.49 | 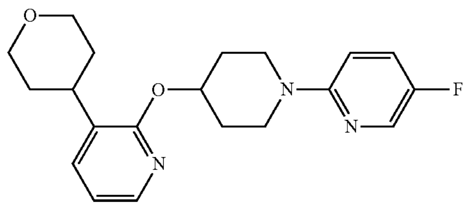 [SMILES: Fc1ccc(N2CCC(Oc3ncccc3C3CCOCC3)CC2)nc1] | 2-((1-(5-fluoropyridin-2-yl)piperidin-4-yl)oxy)-3-(tetrahydro-2H-pyran-4-yl)pyridine | 358 | 2.96 |
| 27.50 | 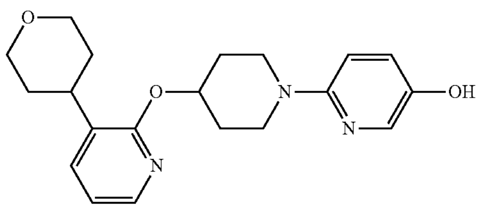 | 2-((1-(5-chloropyridin-2-yl)piperidin-4-yl)oxy)-3-(tetrahydro-2H-pyran-4-yl)pyridine | 356 | 1.1 |
| 27.51 | 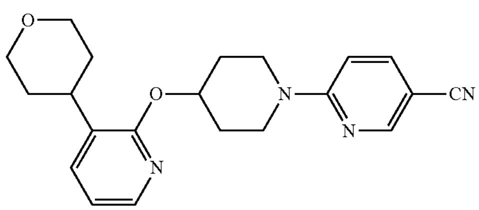 [SMILES: N#Cc1ccc(N2CCC(Oc3ncccc3C3CCOCC3)CC2)nc1] | 6-(4-((3-(tetrahydro-2H-pyran-4-yl)pyridin-2-yl)oxy)piperidin-1-yl)nicotinonitrile | 365 | 0.828 |
| 27.52 | 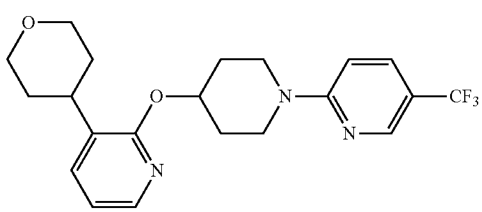 [SMILES: FC(F)(F)c1ccc(N2CCC(Oc3ncccc3C3CCOCC3)CC2)nc1] | 3-(tetrahydro-2H-pyran-4-yl)-2-((1-(5-(trifluoromethyl)pyridin-2-yl)piperidin-4-yl)oxy)pyridine | 408 | 2.20 |
| 27.53 | 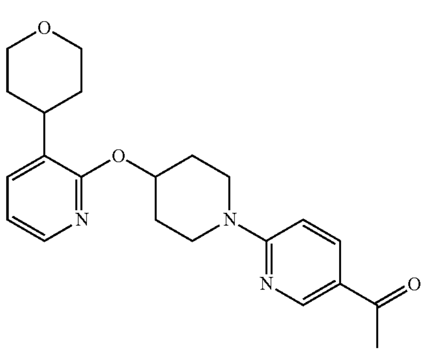 [SMILES: CC(=O)c1ccc(N2CCC(Oc3ncccc3C3CCOCC3)CC2)nc1] | 1-(6-(4-((3-(tetrahydro-2H-pyran-4-yl)pyridin-2-yl)oxy)piperidin-1-yl)pyridin-3-yl)ethanone | 382 | 0.384 |

TABLE 18A-continued

EXAMPLES 27.1-27.84 PREPARED ANALOGOUS TO SCHEME 27

| Ex. # | Structure | Chemical Name | M + 1 | IC$_{50}$ (uM) |
|---|---|---|---|---|
| 27.54 | 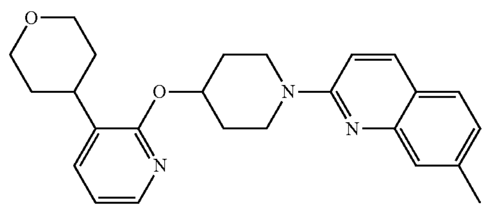 [SMILES: Cc1ccc2ccc(N3CCC(Oc4ncccc4C4CCOCC4)CC3)nc2c1] | 7-methyl-2-(4-((3-(tetrahydro-2H-pyran-4-yl)pyridin-2-yl)oxy)piperidin-1-yl)quinoline | 404 | 0.266 |
| 27.55 | 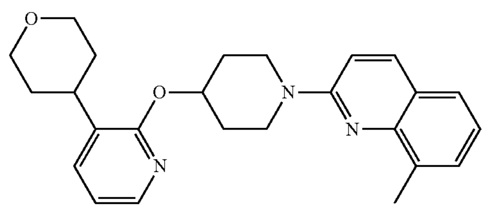 [SMILES: Cc1cccc2ccc(N3CCC(Oc4ncccc4C4CCOCC4)CC3)nc12] | 8-methyl-2-(4-((3-(tetrahydro-2H-pyran-4-yl)pyridin-2-yl)oxy)piperidin-1-yl)quinoline | 404 | >10 |
| 27.56 | 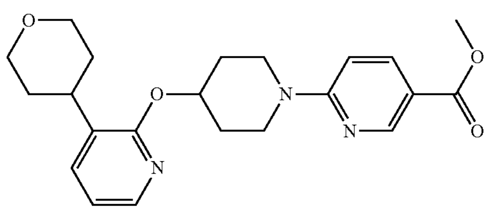 [SMILES: COC(=O)c1ccc(N2CCC(Oc3ncccc3C3CCOCC3)CC2)nc1] | methyl 6-(4-((3-(tetrahydro-2H-pyran-4-yl)pyridin-2-yl)oxy)piperidin-1-yl)nicotinate | 398 | 0.1980 |
| 27.57 | 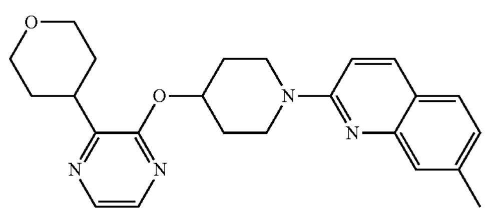 [SMILES: Cc1ccc2ccc(N3CCC(Oc4nccnc4C4CCOCC4)CC3)nc2c1] | 7-methyl-2-(4-((3-(tetrahydro-2H-pyran-4-yl)pyrazin-2-yl)oxy)piperidin-1-yl)quinoline | 405 | 0.5150 |
| 27.58 | 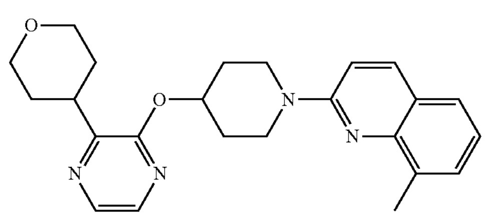 [SMILES: Cc1cccc2ccc(N3CCC(Oc4nccnc4C4CCOCC4)CC3)nc12] | 8-methyl-2-(4-((3-(tetrahydro-2H-pyran-4-yl)pyrazin-2-yl)oxy)piperidin-1-yl)quinoline | 405 | 7.84 |
| 27.59 | 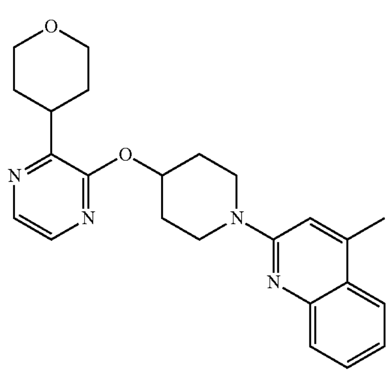 [SMILES: Cc1cc(N2CCC(Oc3nccnc3C3CCOCC3)CC2)nc2ccccc12] | 4-methyl-2-(4-((3-(tetrahydro-2H-pyran-4-yl)pyrazin-2-yl)oxy)piperidin-1-yl)quinoline | 405 | 0.125 |

TABLE 18A-continued

EXAMPLES 27.1-27.84 PREPARED ANALOGOUS TO SCHEME 27

| Ex. # | Structure | Chemical Name | M + 1 | IC$_{50}$ (uM) |
|---|---|---|---|---|
| 27.60 | 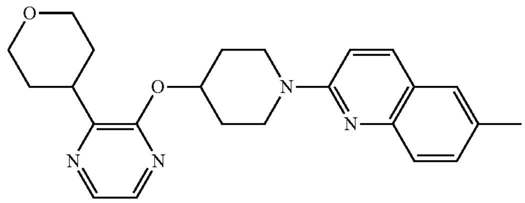 [SMILES: Cc1ccc2nc(N3CCC(Oc4nccnc4C4CCOCC4)CC3)ccc2c1] | 6-methyl-2-(4-((3-(tetrahydro-2H-pyran-4-yl)pyrazin-2-yl)oxy)piperidin-1-yl)quinoline | 405 | 0.276 |
| 27.61 | 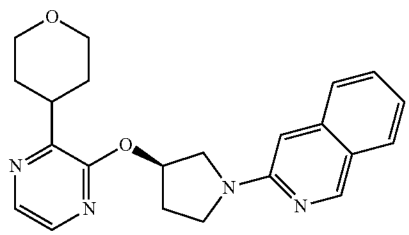 [SMILES: c1ccc2cc(N3CC[C@@H](Oc4nccnc4C4CCOCC4)C3)ncc2c1] | (R)-2-(3-((3-(tetrahydro-2H-pyran-4-yl)pyridin-2-yl)oxy)pyrrolidin-1-yl)quinoline | 377 | 1.43 |
| 27.62 | 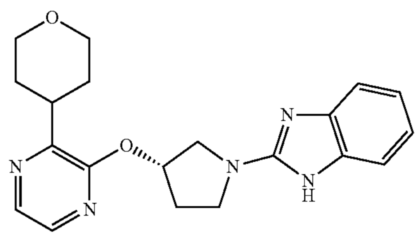 [SMILES: c1ccc2[nH]c(N3CC[C@H](Oc4nccnc4C4CCOCC4)C3)nc2c1] | (S)-2-(3-((3-(tetrahydro-2H-pyran-4-yl)pyrazin-2-yl)oxy)pyrrolidin-1-yl)-1H-benzo[d]imidazole | 366 | 3.93 |
| 27.63 | 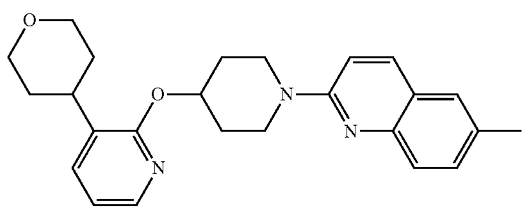 [SMILES: Cc1ccc2nc(N3CCC(Oc4ncccc4C4CCOCC4)CC3)ccc2c1] | 6-methyl-2-(4-((3-(tetrahydro-2H-pyran-4-yl)pyridin-2-yl)oxy)piperidin-1-yl)quinoline | 404 | 0.472 |
| 27.64 | 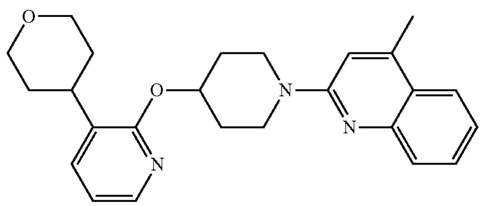 [SMILES: Cc1cc(N2CCC(Oc3ncccc3C3CCOCC3)CC2)nc2ccccc12] | 4-methyl-2-(4-((3-(tetrahydro-2H-pyran-4-yl)pyridin-2-yl)oxy)piperidin-1-yl)quinoline | 404 | 0.101 |
| 27.65 | 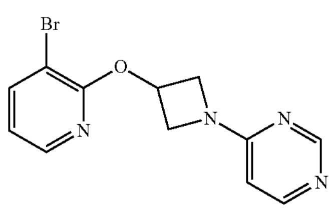 [SMILES: Brc1cccnc1OC1CN(c2ccncn2)C1] | 4-(3-((3-bromopyridin-2-yl)oxy)azetidin-1-yl)pyrimidine | 307 | 57.7 |
| 27.66 | 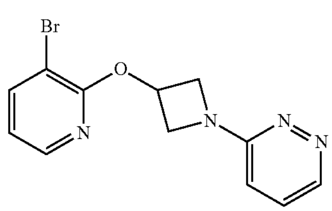 [SMILES: Brc1cccnc1OC1CN(c2cccnn2)C1] | 3-(3-((3-bromopyridin-2-yl)oxy)azetidin-1-yl)pyridazine | 307 | 0.0253 |

TABLE 18A-continued

EXAMPLES 27.1-27.84 PREPARED ANALOGOUS TO SCHEME 27

| Ex. # | Structure | Chemical Name | M + 1 | IC$_{50}$ (uM) |
|---|---|---|---|---|
| 27.67 | 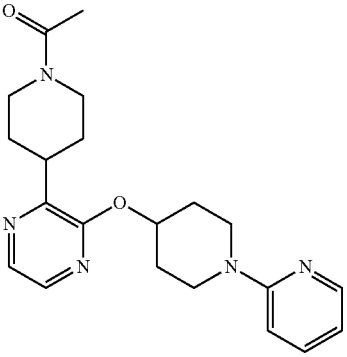 [SMILES: CC(=O)N1CCC(c2nccnc2OC2CCN(c3ccccn3)CC2)CC1] | 1-(4-(3-((1-(pyridin-2-yl)piperidin-4-yl)oxy)pyrazin-2-yl)piperidin-1-yl)ethanone | 381 | 2.85 |
| 27.68 | 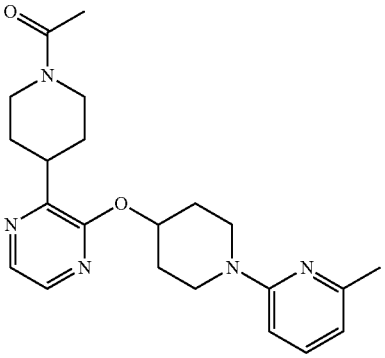 [SMILES: CC(=O)N1CCC(c2nccnc2OC2CCN(c3cccc(C)n3)CC2)CC1] | 1-(4-(3-((1-(6-methylpyridin-2-yl)piperidin-4-yl)oxy)pyrazin-2-yl)piperidin-1-yl)ethanone | 395 | 1.05 |
| 27.69 | 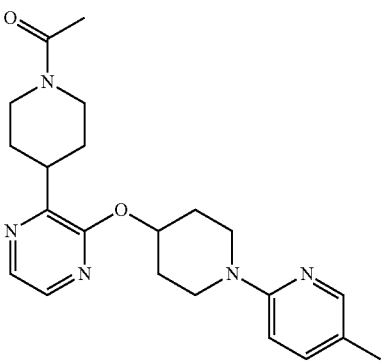 [SMILES: CC(=O)N1CCC(c2nccnc2OC2CCN(c3ccc(C)cn3)CC2)CC1] | 1-(4-(3-((1-(5-methylpyridin-2-yl)piperidin-4-yl)oxy)pyrazin-2-yl)piperidin-1-yl)ethanone | 395 | 1.62 |
| 27.70 | 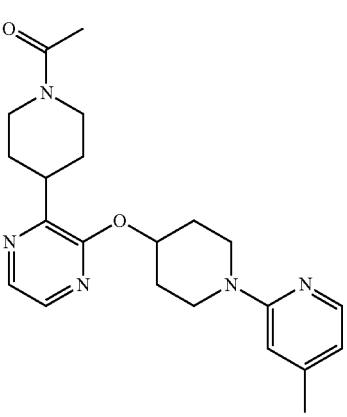 [SMILES: CC(=O)N1CCC(c2nccnc2OC2CCN(c3cc(C)ccn3)CC2)CC1] | 1-(4-(3-((1-(4-methylpyridin-2-yl)piperidin-4-yl)oxy)pyrazin-2-yl)piperidin-1-yl)ethanone | 395 | 0.997 |

TABLE 18A-continued

EXAMPLES 27.1-27.84 PREPARED ANALOGOUS TO SCHEME 27

| Ex. # | Structure | Chemical Name | M + 1 | IC$_{50}$ (uM) |
|---|---|---|---|---|
| 27.71 | 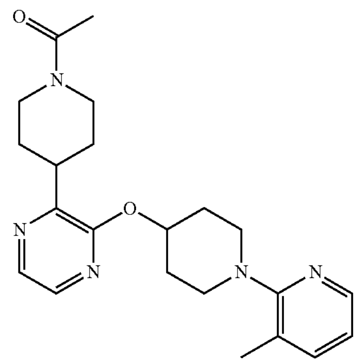 [SMILES: CC(=O)N1CCC(c2nccnc2OC2CCN(c3ncccc3C)CC2)CC1] | 1-(4-(3-((1-(3-methylpyridin-2-yl)piperidin-4-yl)oxy)pyrazin-2-yl)piperidin-1-yl)ethanone | 395 | 3.01 |
| 27.72 | 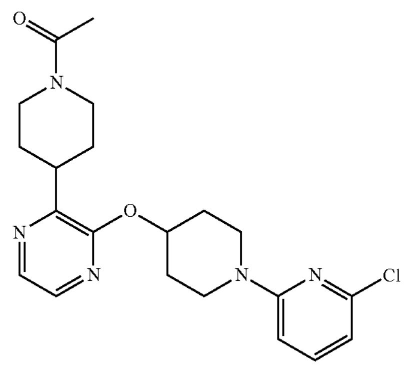 [SMILES: CC(=O)N1CCC(c2nccnc2OC2CCN(c3cccc(Cl)n3)CC2)CC1] | 1-(4-(3-((1-(6-chloropyridin-2-yl)piperidin-4-yl)oxy)pyrazin-2-yl)piperidin-1-yl)ethanone | 415 | 0.235 |
| 27.73 | 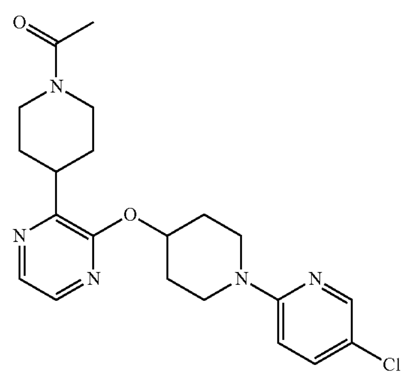 [SMILES: CC(=O)N1CCC(c2nccnc2OC2CCN(c3ccc(Cl)cn3)CC2)CC1] | 1-(4-(3-((1-(5-chloropyridin-2-yl)piperidin-4-yl)oxy)pyrazin-2-yl)piperidin-1-yl)ethanone | 415 | 0.821 |
| 27.74 | 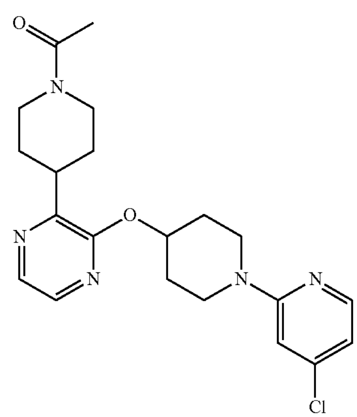 [SMILES: CC(=O)N1CCC(c2nccnc2OC2CCN(c3cc(Cl)ccn3)CC2)CC1] | 1-(4-(3-((1-(4-chloropyridin-2-yl)piperidin-4-yl)oxy)pyrazin-2-yl)piperidin-1-yl)ethanone | 415 | 0.096 |

TABLE 18A-continued

EXAMPLES 27.1-27.84 PREPARED ANALOGOUS TO SCHEME 27

| Ex. # | Structure | Chemical Name | M + 1 | IC$_{50}$ (uM) |
|---|---|---|---|---|
| 27.75 | 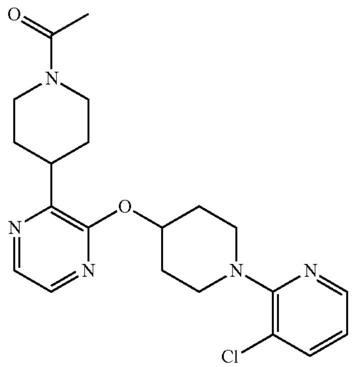 [SMILES: CC(=O)N1CCC(c2nccnc2OC2CCN(c3ncccc3Cl)CC2)CC1] | 1-(4-(3-((1-(3-chloropyridin-2-yl)piperidin-4-yl)oxy)pyrazin-2-yl)piperidin-1-yl)ethanone | 415 | 1.44 |
| 27.76 | 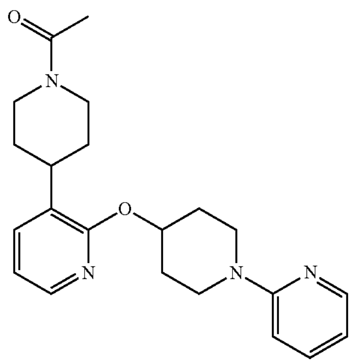 [SMILES: CC(=O)N1CCC(c2cccnc2OC2CCN(c3ccccn3)CC2)CC1] | 1-(4-(2-((1-(pyridin-2-yl)piperidin-4-yl)oxy)pyridin-3-yl)piperidin-1-yl)ethanone | 380 | 1.08 |
| 27.77 | 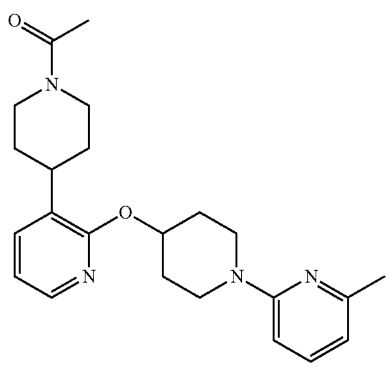 [SMILES: CC(=O)N1CCC(c2cccnc2OC2CCN(c3cccc(C)n3)CC2)CC1] | 1-(4-(2-((1-(5-methylpyridin-2-yl)piperidin-4-yl)oxy)pyridin-3-yl)piperidin-1-yl)ethanone | 394 | 1.18 |
| 27.78 | 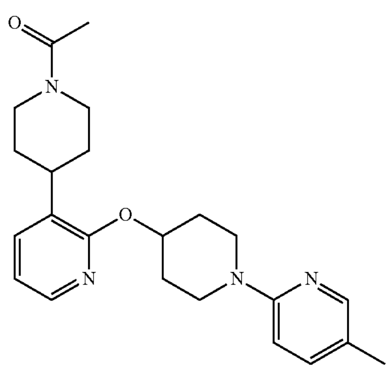 [SMILES: CC(=O)N1CCC(c2cccnc2OC2CCN(c3ccc(C)cn3)CC2)CC1] | 1-(4-(2-((1-(6-methylpyridin-2-yl)piperidin-4-yl)oxy)pyridin-3-yl)piperidin-1-yl)ethanone | 394 | 1.17 |

TABLE 18A-continued

EXAMPLES 27.1-27.84 PREPARED ANALOGOUS TO SCHEME 27

| Ex. # | Structure | Chemical Name | M + 1 | IC$_{50}$ (uM) |
|---|---|---|---|---|
| 27.79 | 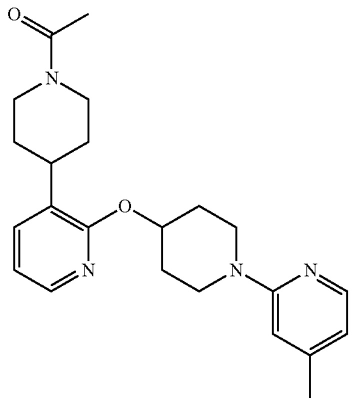 [SMILES: CC(=O)N1CCC(c2cccnc2OC2CCN(c3cc(C)ccn3)CC2)CC1] | 1-(4-(2-((1-(4-methylpyridin-2-yl)piperidin-4-yl)oxy)pyridin-3-yl)piperidin-1-yl)ethanone | 394 | 1.77 |
| 27.80 | 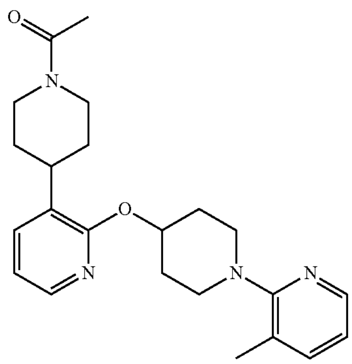 [SMILES: CC(=O)N1CCC(c2cccnc2OC2CCN(c3ncccc3C)CC2)CC1] | 1-(4-(2-((1-(3-methylpyridin-2-yl)piperidin-4-yl)oxy)pyridin-3-yl)piperidin-1-yl)ethanone | 394 | 1.49 |
| 27.81 | 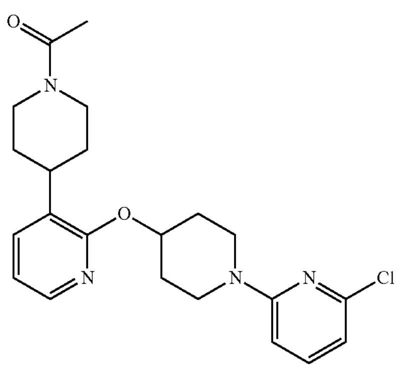 [SMILES: CC(=O)N1CCC(c2cccnc2OC2CCN(c3cccc(Cl)n3)CC2)CC1] | 1-(4-(2-((1-(6-chloropyridin-2-yl)piperidin-4-yl)oxy)pyridin-3-yl)piperidin-1-yl)ethanone | 414 | 0.558 |
| 27.82 | 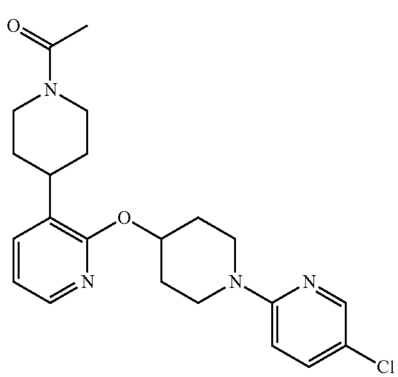 [SMILES: CC(=O)N1CCC(c2cccnc2OC2CCN(c3ccc(Cl)cn3)CC2)CC1] | 1-(4-(2-((1-(5-chloropyridin-2-yl)piperidin-4-yl)oxy)pyridin-3-yl)piperidin-1-yl)ethanone | 414 | 1.2 |

TABLE 18A-continued

EXAMPLES 27.1-27.84 PREPARED ANALOGOUS TO SCHEME 27

| Ex. # | Structure | Chemical Name | M + 1 | IC$_{50}$ (uM) |
|---|---|---|---|---|
| 27.83 | 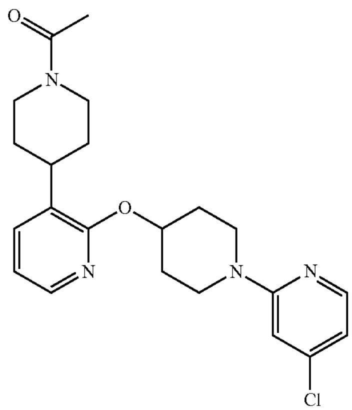 [SMILES: CC(=O)N1CCC(c2cccnc2OC2CCN(c3cc(Cl)ccn3)CC2)CC1] | 1-(4-(2-((1-(4-chloropyridin-2-yl)piperidin-4-yl)oxy)pyridin-3-yl)piperidin-1-yl)ethanone | 414 | >10 |
| 27.84 | 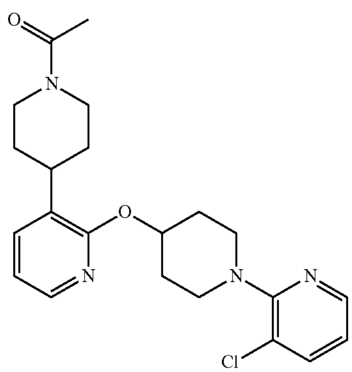 [SMILES: CC(=O)N1CCC(c2cccnc2OC2CCN(c3ncccc3Cl)CC2)CC1] | 1-(4-(2-((1-(3-chloropyridin-2-yl)piperidin-4-yl)oxy)pyridin-3-yl)piperidin-1-yl)ethanone | 414 | 3.58 |

TABLE 18B

PREPARATION AND NMR DATA OF EXAMPLES 27.1-27.84

| Ex. # | Starting material (1) and (2) | Reaction condition | $^1$H NMR (CD$_3$OD, 400 MHz) δ (ppm) |
|---|---|---|---|
| 27.1 | (see Preparation P27.1) and | Pd$_2$(dba)$_3$, BINAP, KI, t-BuONa, toluene | 8.41-8.39 (m, 1H); 7.95-7.91 (m, 2H); 7.80-7.78 (m, 1H); 7.53-7.44 (m, 2H); 7.33-7.28 (m, 1H); 7.14-7.12 (m, 1H); 6.32-6.27 (m, 1H); 5.92-5.84 (m, 1H); 4.82-4.77 (m, 1H); 4.24-4.12 (m, 3H); 4.02-3.94 (m, 2H); 3.56-3.48 (m, 2H); 2.92-2.84 (m, 1H); 1.73-1.48 (m, 4H). |

TABLE 18B-continued

PREPARATION AND NMR DATA OF EXAMPLES 27.1-27.84

| Ex. # | Starting material (1) and (2) | Reaction condition | $^1$H NMR (CD$_3$OD, 400 MHz) δ (ppm) |
|---|---|---|---|
| 27.2 | 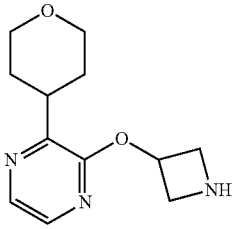<br>(see Preparation P27.1)<br>and<br>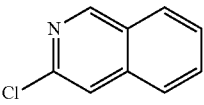 | Pd$_2$(dba)$_3$, BINAP, NaOtBu, Toluene | (CDCl$_3$) 8.92 (s, 1H); 8.13-8.12 (m, 1H); 7.94-7.93 (m, 1H); 7.28-7.26 (m, 1H); 7.55-7.48 (m, 2H); 7.27-7.21 (m, 1H); 6.51-6.45 (m, 1H); 5.61-5.59 (m, 1H); 4.60-4.56 (m, 2H); 4.14-4.05 (m, 2H); 3.58-3.52 (m, 2H); 3.34-3.25 (m, 1H); 1.99-1.95 (m, 2H); 1.80-1.76 (m, 2H). |
| 27.3 | 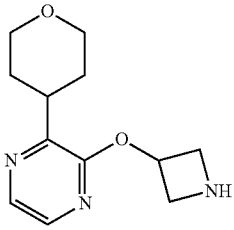<br>(see Preparation P29.2)<br>and<br>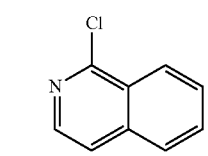 | Pd$_2$(dba)$_3$, BINAP, NaOtBu, Toluene | (d$_6$-DMSO) 8.18-8.17 (m, 1H); 8.05-8.04 (m, 1H); 7.95-7.93 (m, 2H); 7.28-7.25 (m, 1H); 7.17-7.09 (m, 1H); 7.48-7.42 (m, 1H); 7.09-7.08 (m, 1H); 5.55-5.51 (m, 1H); 4.80-7.76 (m, 2H); 4.36-4.33 (m, 2H); 3.91-3.89 (m, 2H); 3.44-3.43 (m, 2H); 3.33-3.32 (m, 1H); 1.76-1.71 (m, 4H). |
| 27.4 | 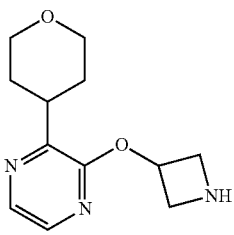<br>(see Preparation P29.2)<br>and<br>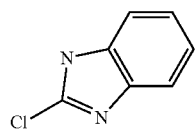 | Pyridine, MW | 8.18-8.17 (m, 1H); 8.01-8.00 (m, 1H); 7.40-7.29 (m, 4H); 5.70-5.67 (m, 1H); 4.52-4.48 (m, 2H); 4.07-4.03 (m, 2H); 3.62-3.56 (m, 2H); 3.40-3.30 (m, 1H); 2.00-1.94 (m, 2H); 1.83-1.78 (m, 2H); 1.48-1.20 (m, 3H). |

TABLE 18B-continued

PREPARATION AND NMR DATA OF EXAMPLES 27.1-27.84

| Ex. # | Starting material (1) and (2) | Reaction condition | $^1$H NMR (CD$_3$OD, 400 MHz) δ (ppm) |
|---|---|---|---|
| 27.5 | (see Preparation P29.2) and 2-chloroquinoline | i-PrOH, K$_2$CO$_3$, MW | 8.10-8.09 (m, 1H); 7.97-7.90 (m, 2H); 7.67-7.48 (m, 3H); 7.21-7.29 (m, 1H); 6.70-6.65 (m, 1H); 5.59-5.51 (m, 1H); 4.62-4.58 (m, 2H); 4.19-4.15 (m, 2H); 4.00-3.97 (m, 2H); 3.56-3.53 (m, 2H); 3.43-3.41 (m, 1H); 1.92-1.72 (m, 4H). |
| 27.6 | (see Preparation P29.1) and 2-chloropyridine | K$_2$CO$_3$, i-PrOH, MW, 160° C. | 8.08-7.96 (m, 3H); 7.55-7.50 (m, 1H); 6.86-6.82 (m, 1H); 6.64-6.60 (m, 1H); 5.40-5.32 (m, 1H); 4.04-3.81 (m, 4H); 3.58-3.42 (m, 4H); 3.32-3.21 (m, 1H); 2.15-2.05 (m, 2H); 1.92-1.71 (m, 6H). |
| 27.7 | (see Preparation P29.1) and 2-chloro-3-methylpyridine | K$_2$CO$_3$, i-PrOH, MW, 160° C. | 8.19-7.96 (m, 3H); 7.52-7.50 (m, 1H); 6.94-6.91 (m, 1H); 5.36-5.29 (m, 1H); 4.08-4.01 (m, 2H); 3.62-3.54 (m, 2H); 3.36-3.31 (m, 3H); 3.11-3.08 (m, 2H); 2.30 (s, 3H); 2.17-2.15 (m, 2H); 1.99-1.77 (m, 6H). |

TABLE 18B-continued
PREPARATION AND NMR DATA OF EXAMPLES 27.1-27.84
| Ex. # | Starting material (1) and (2) | Reaction condition | ¹H NMR (CD₃OD, 400 MHz) δ (ppm) |
|---|---|---|---|
| 27.8 | 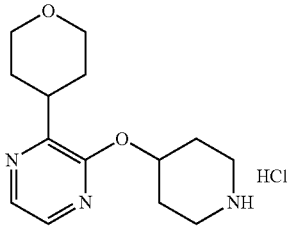<br>(see Preparation P29.1)<br>and<br>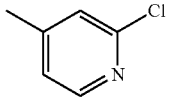 | K₂CO₃, i-PrOH, MW, 160° C. | 8.02-7.91 (m, 3H); 6.69 (s, 1H); 6.52-6.50 (m, 1H); 5.35-5.33 (m, 1H); 4.02-3.98 (m, 2H); 3.86-3.82 (m, 2H); 3.57-3.40 (m, 4H); 3.28-3.27 (m, 1H); 2.26 (s, 3H); 2.08-2.06 (m, 2H); 1.92-1.73 (m, 6H) |
| 27.9 | 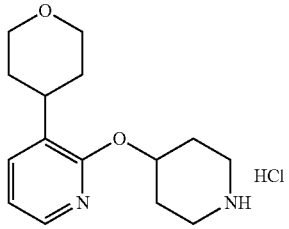<br>(see Preparation P29.1)<br>and<br>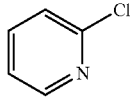 | K₂CO₃, i-PrOH, MW, 160° C. | 8.07-8.05 (m, 1H); 7.95-7.94 (m, 1H); 7.53-7.51 (m, 2H); 6.90-6.84 (m, 2H); 6.64-6.61 (m, 1H); 5.33-5.32 (m, 1H); 4.02-3.98 (m, 2H); 3.87-3.82 (m, 2H); 3.55-3.44 (m, 4H); 3.12-3.08 (m, 1H); 2.08-2.04 (m, 2H); 1.84-1.72 (m, 6H) |
| 27.10 | 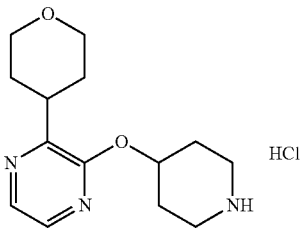<br>(see Preparation P29.1)<br>and<br>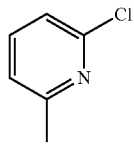 | K₂CO₃, i-PrOH, MW, 160° C. | 8.02-7.95 (m, 2H); 7.47-7.38 (m, 1H); 6.61-6.49 (m, 2H); 5.35-5.33 (m, 1H); 4.03-3.99 (m, 2H); 3.89-3.84 (m, 2H); 3.58-3.51 (m, 2H); 3.46-3.40 (m, 2H); 3.28-3.27 (m, 1H); 2.33 (s, 3H); 2.11-2.06 (m, 2H); 1.92-1.74 (m, 6H) |

TABLE 18B-continued
PREPARATION AND NMR DATA OF EXAMPLES 27.1-27.84
| Ex. # | Starting material (1) and (2) | Reaction condition | $^1$H NMR (CD$_3$OD, 400 MHz) δ (ppm) |
|---|---|---|---|
| 27.11 | 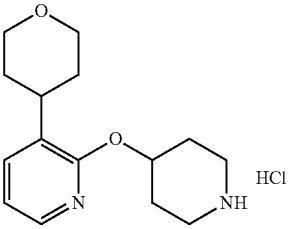 (see Preparation P29.1) and 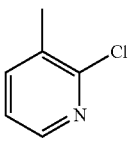 | K$_2$CO$_3$, i-PrOH, MW, 160° C. | 8.05 (m, 1H); 8.03-7.94 (m, 1H); 7.54-7.51 (m, 2H); 6.93-6.87 (m, 2H); 5.30-5.29 (m, 1H); 4.04-4.01 (m, 2H); 3.60-3.54 (m, 2H); 3.36-3.32 (m, 2H); 3.11-3.05 (m, 3H); 2.30 (s, 3H); 2.18-2.13 (m, 2H); 1.97-1.93 (m, 2H); 1.80-1.77 (m, 4H) |
| 27.12 | 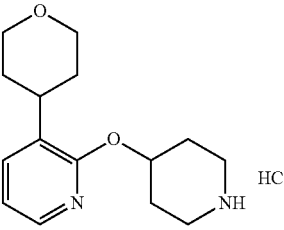 (see Preparation P29.1) and 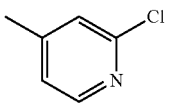 | K$_2$CO$_3$, i-PrOH, MW, 160° C. | 7.95-7.90 (m, 2H); 7.50-7.48 (m, 1H); 6.89-6.85 (m, 1H); 6.67 (s, 1H); 6.49-6.47 (m, 1H); 5.30-5.29 (m, 1H); 4.00-3.96 (m, 2H); 3.85-3.79 (m, 2H); 3.53-3.29 (m, 4H), 3.12-3.03 (m, 1H); 2.24 (s, 3H); 2.07-2.02 (m, 2H); 1.81-1.70 (m, 6H) |
| 27.13 | 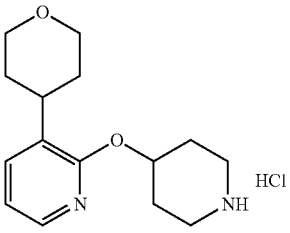 (see Preparation P29.1) and  | K$_2$CO$_3$, i-PrOH, MW, 160° C. | 7.98-7.96 (m, 1H); 7.92-7.91 (m, 1H); 7.53-7.51 (m, 1H); 7.35-7.32 (m, 1H); 6.92-6.89 (m, 1H); 6.77 (d, J = 8.8 Hz, 1H); 5.30-5.26 (m, 1H); 3.91-3.88 (m, 2H); 3.79-3.73 (m, 2H); 3.41-3.36 (m, 4H); 2.95-2.91 (m, 1H); 2.11 (s, 3H); 1.97-1.92 (m, 2H); 1.66-1.63 (m, 6H) |

TABLE 18B-continued

PREPARATION AND NMR DATA OF EXAMPLES 27.1-27.84

| Ex. # | Starting material (1) and (2) | Reaction condition | $^1$H NMR (CD$_3$OD, 400 MHz) δ (ppm) |
|---|---|---|---|
| 27.14 | (see Preparation P29.1) and [2-chloro-6-methylpyridine] | K$_2$CO$_3$, i-PrOH, MW, 160° C. | 7.95-7.94 (m, 1H); 7.53-7.51 (m, 1H); 7.42-7.38 (m, 1H); 6.90-6.87 (m, 1H); 6.60 (d, J = 8.8 Hz, 1H); 6.50 (d, J = 7.2 Hz, 1H); 5.31-5.29 (m, 1H); 4.02-3.98 (m, 2H); 3.87-3.82 (m, 2H); 3.56-3.41 (m, 4H); 3.12-3.08 (m, 1H); 2.33 (s, 3H); 2.07-2.03 (m, 2H); 1.83-1.72 (m, 6H) |
| 27.15 | (see Preparation P29.3) and [1-chloroisoquinoline] | K$_2$CO$_3$, i-PrOH, MW, 160° C. | (CDCl$_3$) 8.11 (d, J = 8.4 Hz, 1H); 8.06-8.05 (m, 1H); 7.95-7.94 (m, 1H); 7.89-7.85 (m, 3H); 7.70-7.66 (m, 1H); 7.32-7.31 (m, 1H); 5.47-5.45 (m, 1H); 4.08-4.03 (m, 4H); 3.88-3.87 (m, 2H); 3.56-3.50 (m, 2H); 3.25-3.19 (m, 1H); 2.37-2.33 (m, 2H); 2.17-2.16 (m, 2H); 1.99-1.89 (m, 2H); 1.75-1.72 (m, 2H) |
| 27.16 | (see Preparation P29.3) and [3-chloroisoquinoline] | K$_2$CO$_3$, i-PrOH, MW, 160° C. | 8.91 (s, 1H); 8.05-8.04 (m, 1H); 7.99-7.98 (m, 1H); 7.83 (d, J = 8.4 Hz, 1H); 7.67-7.64 (m, 1H); 7.55-7.51 (m, 1H); 7.31-7.27 (m, 1H); 7.01 (s, 1H); 5.39-5.38 (m, 1H); 4.03-3.94 (m, 2H); 3.93-3.90 (m, 2H); 3.58-3.49 (m, 4H); 3.42-3.37 (m, 1H); 2.18-2.16 (m, 2H); 1.97-1.90 (m, 4H); 1.80-1.76 (m, 2H) |

TABLE 18B-continued

PREPARATION AND NMR DATA OF EXAMPLES 27.1-27.84

| Ex. # | Starting material (1) and (2) | Reaction condition | $^1$H NMR (CD$_3$OD, 400 MHz) δ (ppm) |
|---|---|---|---|
| 27.17 | 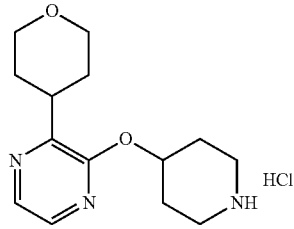<br>(see Preparation P29.3)<br>and<br>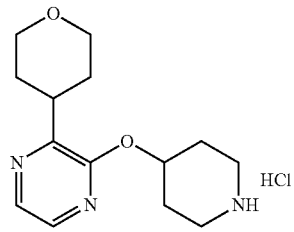 | K$_2$CO$_3$, i-PrOH, MW, 160° C. | 8.03-7.95 (m, 3H); 7.63-7.61 (m, 2H); 7.52-7.48 (m, 1H); 7.22-7.17 (m, 2H); 5.41-5.40 (m, 1H); 4.08-3.98 (m, 4H); 3.71-3.65 (m, 2H); 3.57-3.51 (m, 2H); 3.28-3.27 (m, 1H); 2.14-2.13 (m, 2H); 1.93-1.87 (m, 4H); 1.79-1.75 (m, 2H) |
| 27.18 | 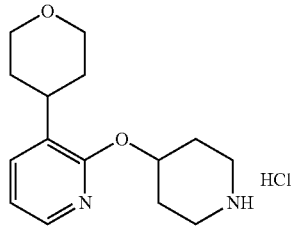<br>(see Preparation P29.3)<br>and | K$_2$CO$_3$, i-PrOH, MW, 160° C. | 8.09-8.00 (m, 2H); 7.42-7.31 (m, 4H); 5.50-5.48 (m, 1H); 4.06-4.02 (m, 2H); 3.94-3.88 (m, 2H) 3.80-3.74 (m, 2H); 3.61-3.54 (m, 2H); 3.36-3.35 (m, 1H); 2.31-2.26 (m, 2H); 2.15-2.09 (m, 2H) 1.97-1.93 (m, 2H); 1.81-1.77 (m, 2H) |
| 27.19 | 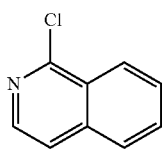<br>(see Preparation P29.1)<br>and | K$_2$CO$_3$, i-PrOH, MW, 160° C. | (CDCl$_3$) 8.09-8.04 (m, 2H); 7.96-7.94 (m, 1H); 7.71-7.69 (m, 1H); 7.59-7.55 (m, 1H); 7.49-7.45 (m, 1H); 7.38-7.36 (m, 1H); 7.20-7.18 (m, 1H); 6.81-6.78 (m, 1H); 5.38-5.37 (m, 1H); 4.03-4.01 (m, 2H); 3.67-3.66 (m, 2H); 3.54-3.49 (m, 2H); 3.42-3.39 (m, 2H); 3.07-3.01 (m, 1H); 2.25-2.04 (m, 4H); 1.77-1.68 (m, 4H) |

TABLE 18B-continued

PREPARATION AND NMR DATA OF EXAMPLES 27.1-27.84

| Ex. # | Starting material (1) and (2) | Reaction condition | $^1$H NMR (CD$_3$OD, 400 MHz) δ (ppm) |
|---|---|---|---|
| 27.20 | 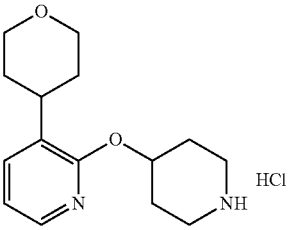<br>(see Preparation P29.1)<br>and<br>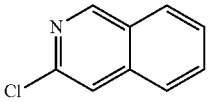 | K$_2$CO$_3$, i-PrOH, MW, 160° C. | (CDCl$_3$) 8.96 (s, 1H); 8.03-8.01 (m, 1H); 7.79-7.77 (m, 1H); 7.57-7.42 (m, 3H); 7.26-7.25 (m, 1H); 6.87-6.84 (m, 2H); 5.43-5.41 (m, 1H); 4.08-3.92 (m, 4H); 3.62-3.50 (m, 4H); 3.13-3.06 (m, 1H); 2.17-2.16 (m, 2H); 1.98-1.95 (m, 2H); 1.79-1.73 (m, 4H) |
| 27.21 | 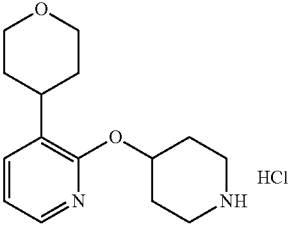<br>(see Preparation P29.1)<br>and<br>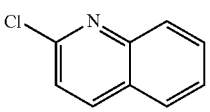 | K$_2$CO$_3$, i-PrOH, MW, 160° C. | 7.98-7.95 (m, 2H); 7.63-7.61 (m, 2H); 7.54-7.50 (m, 2H); 7.22-7.17 (m, 2H); 6.92-6.88 (m, 1H); 5.38-5.37 (m, 1H); 4.09-3.98 (m, 4H); 3.73-3.67 (m, 2H); 3.56-3.50 (m, 2H); 3.12-3.07 (m, 1H); 2.13-2.10 (m, 2H); 1.89-1.85 (m, 2H); 1.78-1.75 (m, 4H) |
| 27.22 | 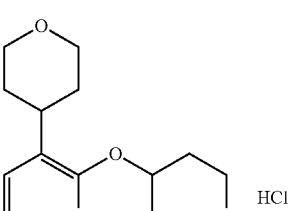<br>(see Preparation P29.1)<br>and<br>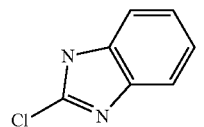 | K$_2$CO$_3$, i-PrOH, MW, 160° C. | 7.97-7.95 (m, 1H); 7.55-7.53 (m, 1H); 7.24-7.21 (m, 2H); 7.00-6.97 (m, 2H); 6.92-6.89 (m, 1H); 5.37-5.35 (m, 1H); 4.02-3.98 (m, 2H); 3.84-3.78 (m, 2H); 3.58-3.52 (m, 4H); 2.14-2.12 (m, 3H); 1.94-1.89 (m, 2H); 1.78-1.74 (m, 4H) |

TABLE 18B-continued

PREPARATION AND NMR DATA OF EXAMPLES 27.1-27.84

| Ex. # | Starting material (1) and (2) | Reaction condition | $^1$H NMR (CD$_3$OD, 400 MHz) δ (ppm) |
|---|---|---|---|
| 27.23 | (see Preparation P27.7) and 2-chloroquinoline | HATU, Et$_3$N, THF, reflux | (CDCl$_3$) 8.03-8.02 (m, 1H); 7.86-7.83 (m, 1H); 7.73-7.71 (m, 1H); 7.57-7.51 (m, 2H); 7.42-7.40 (m, 1H); 7.19-7.15 (m, 1H); 6.88-6.85 (m, 1H); 6.74-6.71 (m, 1H); 5.80-5.79 (m, 1H); 4.02-3.82 (m, 6H); 3.46-3.41 (m, 2H); 2.98-2.95 (m, 1H); 2.38-2.34 (m, 2H); 1.72-1.61 (m, 4H). |
| 27.24 | (see Preparation P27.7) and 3-chloroisoquinoline | HATU, Et$_3$N, THF, reflux | (CDCl$_3$) 8.90 (s, 1H); 8.05-8.03 (m, 1H); 7.75-7.73 (m, 1H); 7.54-7.52 (m, 1H); 7.47-7.40 (m, 2H); 7.18-7.15 (m, 1H); 6.89-6.86 (m, 1H); 6.50-6.49 (m, 1H); 5.81-5.79 (m, 1H); 3.99-3.91 (m, 3H); 3.78-3.70 (m, 3H); 3.49-3.43 (m, 2H); 2.98-2.96 (m, 1H); 2.41-2.39 (m, 2H); 1.74-1.62 (m, 4H). |
| 27.25 | (see Preparation P27.7) and 1-chloroisoquinoline | HATU, Et$_3$N, THF, reflux | (CDCl$_3$) 8.21-8.19 (m, 1H); 8.03-7.98 (m, 2H); 7.70-7.59 (m, 1H); 7.58-7.46 (m, 1H); 7.40-7.38 (m, 2H); 7.03-7.01 (m, 1H); 6.86-6.83 (m, 1H); 5.78-5.77 (m, 1H); 4.25-4.05 (m, 2H); 4.02-3.94 (m, 4H); 3.53-3.43 (m, 2H); 3.12-2.96 (m, 1H); 2.39-2.36 (m, 2H); 1.74-1.57 (m, 4H). |

TABLE 18B-continued

PREPARATION AND NMR DATA OF EXAMPLES 27.1-27.84

| Ex. # | Starting material (1) and (2) | Reaction condition | $^1$H NMR (CD$_3$OD, 400 MHz) δ (ppm) |
|---|---|---|---|
| 27.26 | (see Preparation P27.7) and 2-chloro-1H-benzimidazole | Pyridine, MW | (CDCl$_3$) 7.99-7.98 (m, 1H); 7.42-7.39 (m, 3H); 7.27-7.25 (m, 2H); 6.92-6.88 (m, 1H); 5.38-5.37 (m, 1H); 3.97-3.90 (m, 2H); 3.53-3.21 (m, 6H); 2.80-2.78 (m, 1H); 2.07-2.03 (m, 1H); 1.68-1.50 (m, 5H). |
| 27.27 | (see Preparation P27.8) and 2-chloroquinoline | Pd$_2$(dba)$_3$, BINAP, NaOtBu, Toluene | (CDCl$_3$) 8.44-8.42 (m, 1H); 8.00-7.99 (m, 1H); 7.98-7.78 (m, 3H); 7.68-7.64 (m, 1H); 7.45-7.43 (m, 1H); 7.08-7.06 (m, 1H); 6.92-6.90 (m, 1H); 5.85-5.83 (m, 1H); 4.64-4.60 (m, 1H); 4.39-4.30 (m, 1H); 4.28-4.27 (m, 2H); 4.02-3.96 (m, 2H); 3.54-3.46 (m, 2H); 3.00-2.95 (m, 1H); 2.66-2.52 (m, 1H); 2.50-2.42 (m, 1H); 1.72-1.62 (m, 4H). |
| 27.28 | (see Preparation P27.8) and 3-chloroisoquinoline | Pd$_2$(dba)$_3$, BINAP, NaOtBu, Toluene | (CDCl$_3$) 9.22 (s, 1H); 8.03-8.02 (m, 1H); 8.02-7.85 (m, 1H); 7.67-7.58 (m, 2H); 7.45-7.43 (m, 1H); 7.34-7.30 (m, 1H); 6.93-6.89 (m, 1H); 6.85-6.80 (m, 1H); 5.84-5.83 (m, 1H); 4.07-3.81 (m, 6H); 3.52-3.44 (m, 2H); 3.00-2.93 (m, 1H); 2.50-2.44 (m, 2H); 1.73-1.67 (m, 4H). |

TABLE 18B-continued

PREPARATION AND NMR DATA OF EXAMPLES 27.1-27.84

| Ex. # | Starting material (1) and (2) | Reaction condition | $^1$H NMR (CD$_3$OD, 400 MHz) δ (ppm) |
|---|---|---|---|
| 27.29 | (see Preparation P27.8) and [1-chloroisoquinoline] | Pd$_2$(dba)$_3$, BINAP, NaOtBu, Toluene | (CDCl$_3$) 8.19-8.10 (m, 2H); 8.01-7.99 (m, 1H); 7.71-7.67 (m, 2H); 7.45-7.25 (m, 2H); 6.93-6.90 (m, 2H); 5.83-5.80 (m, 1H); 4.37-4.09 (m 2H); 4.01-3.91 (m, 4H); 3.60-3.38 (m, 2H); 3.00-2.87 (m, 1H); 2.51-2.42 (m, 2H); 1.74-1.62 (m, 4H). |
| 27.30 | (see Preparation P27.8) and [2-chlorobenzimidazole] | Pyridine, MW | (CDCl$_3$) 8.00-7.99 (m, 1H); 7.43-7.21 (m, 5H); 6.92-6.89 (m, 1H); 5.44 (s, 1H); 3.98-3.92 (m, 2H); 3.59-3.32 (m, 6H); 2.83-2.78 (m, 1H); 2.137-2.11 (m, 1H); 2.00-1.99 (m, 1H); 1.77-1.45 (m, 5H). |
| 27.31 | (see Preparation P27.2) and [2-chloroquinoline] | i-PrOH, H$_2$O, K$_2$CO$_3$, MW | 8.41-8.38 (m, 1H); 8.14-8.06 (m, 2H); 8.05-7.81 (m, 3H); 7.51-7.45 (m, 1H); 7.35-7.25 (m, 1H); 5.91-5.92 (m, 1H); 4.26-3.94 (m, 7H); 3.56-3.48 (m, 2H); 2.68-2.48 (m, 2H); 1.96-1.85 (m, 2H); 1.78-1.66 (m, 2H). |

TABLE 18B-continued

PREPARATION AND NMR DATA OF EXAMPLES 27.1-27.84

| Ex. # | Starting material (1) and (2) | Reaction condition | $^1$H NMR (CD$_3$OD, 400 MHz) δ (ppm) |
|---|---|---|---|
| 27.32 | 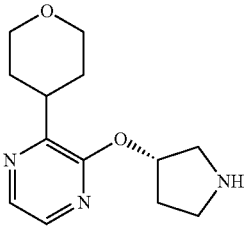<br>(see Preparation P27.2)<br>and | i-PrOH, H$_2$O, K$_2$CO$_3$, MW | 8.95 (s, 1H); 8.12-8.10 (m, 1H); 8.05-8.04 (m, 1H); 7.96-7.93 (m, 1H); 7.77-7.71 (m, 1H); 7.69-7.67 (m, 1H); 7.38-7.36 (m, 1H); 7.18-7.17 (m, 1H); 5.95-5.77 (m, 1H); 4.05-3.80 (m, 7H); 3.53-3.43 (m, 2H); 2.60-2.51 (m, 2H); 1.94-1.82 (m, 2H); 1.76-1.71 (m, 1H); 1.66-1.65 (m, 1H). |
| 27.33 | 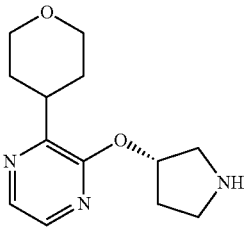<br>(see Preparation P27.2)<br>and | Pd$_2$(dba)$_3$, BINAP, NaOtBu, Toluene | 8.15-8.13 (m, 1H); 7.93-7.87 (m, 2H); 7.78-7.76 (m, 1H); 7.63-7.61 (m, 1H); 7.53-7.48 (m, 1H); 7.40-7.35 (m, 1H); 6398-6.97 (m, 1H); 5.66-5.65 (m, 1H); 4.24-4.12 (m, 2H); 3.95-3.87 (m, 1H); 3.78-3.71 (m, 3H); 3.41-3.33 (m, 2H); 3.12-3.00 (m, 1H); 2.30-2.25 (m, 2H); 1.77-1.69 (m, 1H); 1.67-1.59 (m, 2H); 1.48-1.41 (m, 1H). |
| 27.34 | 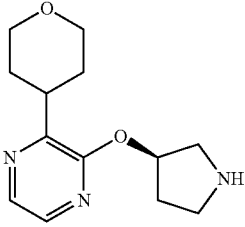<br>(see Preparation P27.3)<br>and 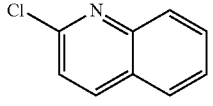 | Pd$_2$(dba)$_3$, BINAP, NaOtBu, Toluene | (CDCl$_3$) 8.25-8.15 (m, 3H); 7.96-7.95 (m, 1H); 7.75-7.70 (m, 2H); 7.48-7.45 (m, 1H); 6.91-6.90 (m, 1H); 5.81-5.80 (m, 1H); 4.47-4.25 (m, 2H); 4.05-4.01 (m, 4H); 3.54-3.50 (m, 2H); 3.27-3.07 (m, 1H); 2.65-2.45 (m, 2H); 1.97-1.90 (m, 2H); 1.74-1.65 (m, 2H). |

TABLE 18B-continued

PREPARATION AND NMR DATA OF EXAMPLES 27.1-27.84

| Ex. # | Starting material (1) and (2) | Reaction condition | ¹H NMR (CD₃OD, 400 MHz) δ (ppm) |
|---|---|---|---|
| 27.35 | (see Preparation P27.3) and [structure: 3-(tetrahydropyran-4-yl)-2-(pyrrolidin-3-yloxy)pyrazine HCl]; [structure: 1-chloroisoquinoline] | Pd₂(dba)₃, BINAP, NaOtBu, Toluene | (CDCl₃) 8.06-8.05 (m, 1H); 8.03-8.01 (m, 2H); 7.91-7.90 (m, 1H); 7.70-7.68 (m, 1H); 7.56-7.55 (m, 1H); 7.43-7.42 (m, 1H); 7.05-7.03 (m, 1H); 5.73-5.72 (m, 1H); 4.33-4.29 (m, 1H); 4.23-4.21 (m, 1H); 4.07-3.97 (m, 2H); 3.91-3.88 (m, 2H); 3.55-3.49 (m, 2H); 3.16-3.14 (m, 1H); 2.37-2.34 (m, 2H); 1.96-1.78 (m, 3H); 1.65-1.64 (m, 1H). |
| 27.36 | (see Preparation P27.3) and [structure: 3-(tetrahydropyran-4-yl)-2-(pyrrolidin-3-yloxy)pyrazine HCl]; [structure: 2-chlorobenzimidazole] | i-PrOH H₂O K₂CO₃ MW | 8.14-8.13 (m, 1H0; 8.05-8.04 (m, 1H); 7.40-7.38 (m, 2H); 7.31-7.28 (m, 2H); 5.85-5.84 (m, 1H); 4.13-4.10 (m, 1H); 3.98-3.87 (m, 6H); 3.53-3.50 (m, 2H); 3.28-3.24 (m, 1H); 2.57-2.54 (m, 2H); 1.92-1.86 (m, 2H); 1.77-1.66 (m, 2H). |
| 27.37 | (see Preparation P26.2) and [structure: 1-acetyl-4-[3-(azetidin-3-yloxy)pyridin-2-yl]-1,2,3,6-tetrahydropyridine HCl]; [structure: 2-chlorobenzothiazole] | Pd₂dba₃, DavePhos | 8.04 (1H, dd, J = 5.0, 1.8 Hz), 7.69 (1H, d, J = 7.9 Hz), 7.54-7.63 (1H, m), 7.51 (1H, d, J = 8.0 Hz), 7.25-7.45 (2H, m), 7.06-7.21 (1H, m), 7.01 (2H, td, J = 4.3, 2.4 Hz), 5.58-5.74 (1H, m), 4.98-5.22 (1H, m), 4.56-4.74 (2H, m), 4.15-4.33 (2H, m), 3.90 (1H, br. s.), 3.51-3.80 (2H, m), 2.10-2.29 (4H, m), 1.71-2.00 (1H, m) |

TABLE 18B-continued

PREPARATION AND NMR DATA OF EXAMPLES 27.1-27.84

| Ex. # | Starting material (1) and (2) | Reaction condition | $^1$H NMR (CD$_3$OD, 400 MHz) δ (ppm) |
|---|---|---|---|
| 27.38 | 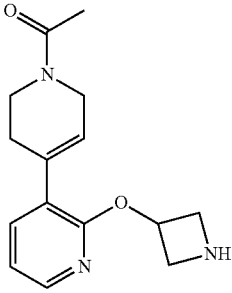<br>(see Preparation P26.2)<br>and<br>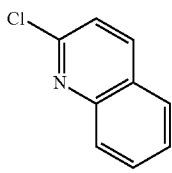 | Pd$_2$dba$_3$, DavePhos | 7.93-8.13 (2H, m), 7.69 (2H, d, J = 8.0 Hz), 7.49-7.63 (2H, m), 7.19-7.32 (1H, m), 6.94-7.07 (2H, m), 6.77 (1H, d, J = 8.9 Hz), 5.64 (1H, br. s.), 5.01-5.22 (1H, m), 4.60-4.72 (2H, m), 4.09-4.29 (2H, m), 3.90 (1H, br. s.), 3.49-3.82 (2H, m), 2.08-2.29 (4H, m), 1.87 (1H, br. s.) |
| 27.39 | 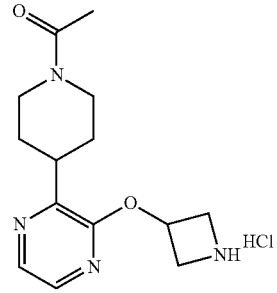<br>(see Preparation P27.5)<br>and<br>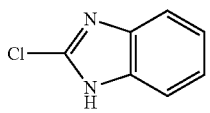 | 1,10-phenanthroline<br>CuI<br>Cs$_2$CO$_3$<br>DMF/H$_2$O | 8.13 (1H, d, J = 2.6 Hz), 8.00 (1H, d, J = 2.8 Hz), 7.17-7.32 (2H, m), 6.95-7.07 (2H, m), 5.50-5.74 (1H, m), 4.62 (3H, dd, J = 8.8, 6.7 Hz), 4.13-4.32 (2H, m), 4.02 (1H, d, J = 13.7 Hz), 3.34-3.55 (2H, m), 2.69-2.91 (1H, m), 2.11 (3H, s), 1.63-2.03 (4H, m) |

TABLE 18B-continued

PREPARATION AND NMR DATA OF EXAMPLES 27.1-27.84

| Ex. # | Starting material (1) and (2) | Reaction condition | $^1$H NMR (CD$_3$OD, 400 MHz) δ (ppm) |
|---|---|---|---|
| 27.40 | (see Preparation P27.5) and 2-chloroquinoline | 1,10-phenanthroline CuI Cs$_2$CO$_3$ DMF/H$_2$O | 8.13 (1H, d, J = 2.8 Hz), 7.96-8.07 (2H, m), 7.68 (2H, d, J = 8.3 Hz), 7.55 (1H, td, J = 7.7, 1.3 Hz), 7.25 (1H, t, J = 7.5 Hz), 6.76 (1H, d, J = 8.9 Hz), 5.55-5.70 (1H, m), 4.53-4.74 (3H, m), 4.16-4.33 (2H, m), 4.03 (1H, d, J = 13.9 Hz), 3.36-3.45 (2H, m), 2.70-2.89 (1H, m), 2.11 (3H, s), 1.65-2.04 (4H, m) |
| 27.41 | (see Preparation P26.4) and 2-chloroquinoline | 1,10-phenanthroline CuI Cs$_2$CO$_3$ DMF/H$_2$O | 8.15-8.23 (1H, m), 7.96-8.07 (2H, m), 7.68 (2H, d, J = 8.3 Hz), 7.55 (1H, t, J = 7.7 Hz), 7.25 (1H, t, J = 7.3 Hz), 6.96 (1H, d, J = 3.8 Hz), 6.75 (1H, d, J = 8.9 Hz), 5.65 (1H, dt, J = 6.4, 3.2 Hz), 4.59-4.75 (2H, m), 4.16-4.36 (4H, m), 3.74 (2H, dt, J = 14.9, 5.8 Hz), 2.80 (1H, br. s.), 2.70 (1H, br. s.), 2.09-2.22 (3H, s) |
| 27.42 | (see Preparation P26.4) and 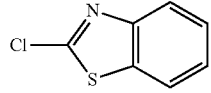 | 1,10-phenanthroline CuI Cs$_2$CO$_3$ DMF/H$_2$O | 8.22 (1H, t, J = 2.2 Hz), 7.99-8.06 (1H, m), 7.69 (1H, d, J = 8.0 Hz), 7.51 (1H, d, J = 8.0 Hz), 7.33 (1H, t, J = 7.7 Hz), 7.09-7.17 (1H, m), 6.97 (1H, d, J = 3.7 Hz), 5.70 (1H, td, J = 6.7, 3.0 Hz), 4.63-4.73 (2H, m), 4.31 (4H, dd, J = 10.2, 3.1 Hz), 3.77 (2H, dt, J = 19.8, 5.8 Hz), 2.81 (1H, m), 2.72 (1H, m), 2.13-2.22 (3H, m) |

TABLE 18B-continued
PREPARATION AND NMR DATA OF EXAMPLES 27.1-27.84
| Ex. # | Starting material (1) and (2) | Reaction condition | $^1$H NMR (CD$_3$OD, 400 MHz) δ (ppm) |
|---|---|---|---|
| 27.43 | 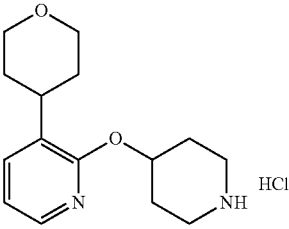 (see Preparation P29.1) and | K$_2$CO$_3$, i-PrOH, MW, 160° C. | (CDCl$_3$) 9.04 (d, J = 2.8 Hz, 1H); 8.20 (d, J = 2.8 Hz, 1H); 8.19-8.00 (m, 1H); 7.45 (d, J = 7.2 Hz, 1H); 6.90-6.86 (m, 1H); 5.47-5.45 (m, 1H); 6.62 (dd, J = 2 Hz, J = 9.2 Hz, 1H); 4.08-4.00 (m, 4H); 3.83-3.78 (m, 2H); 3.56-3.50 (m, 2H); 3.06-2.99 (m, 1H); 2.14-2.09 (m, 2H); 1.96-1.81 (m, 2H); 1.78-1.75 (m, 4H). |
| 27.44 | 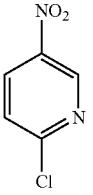 (see Preparation P29.1) and | K$_2$CO$_3$, i-PrOH, MW, 160° C. | (CDCl$_3$) 10.72 (s, 2H); 8.03-7.50 (m, 3H); 7.12-7.93 (m, 3H); 5.43-5.42 (m, 1H); 4.07-4.04 (m, 2H); 3.83-3.50 (m, 6H); 3.05-3.01 (m, 1H); 2.19-2.14 (m, 2H); 2.05-1.99 (m, 2H); 1.77-1.72 (m, 4H). |

TABLE 18B-continued
PREPARATION AND NMR DATA OF EXAMPLES 27.1-27.84
| Ex. # | Starting material (1) and (2) | Reaction condition | $^1$H NMR (CD$_3$OD, 400 MHz) δ (ppm) |
|---|---|---|---|
| 27.45 | 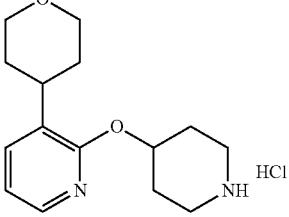<br>(see Preparation P29.1)<br>and<br>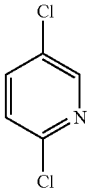 | K$_2$CO$_3$, i-PrOH, MW, 160° C. | (CDCl$_3$) 8.05-8.04 (m, 1H); 7.95-7.92 (m, 1H); 7.37-7.33 (m, 2H); 6.81-6.77 (m, 1H); 6.57 (d, J = 9.2 Hz, 1H); 5.32 (s, 1H); 4.00 (dd, J = 2 Hz, J = 3.2 Hz, 2H); 3.80-3.75 (m, 2H); 3.49-3.43 (m, 4H); 3.05-2.94 (m, 1H); 2.04-2.00 (m, 2H); 1.82-1.79 (m, 2H); 1.72-1.51 (m, 4H). |
| 27.46 | 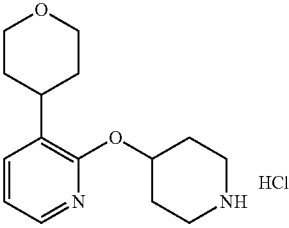<br>(see Preparation P29.1)<br>and<br>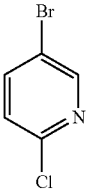 | K$_2$CO$_3$, i-PrOH, MW, 160° C. | 8.10 (d, J = 2.4 Hz, 1H); 7.97 (dd, J = 1.6 Hz, J = 4.8 Hz, 1H); 7.75 (dd, J = 2.4 Hz, J = 9.2 Hz, 1H); 7.56-7.54 (m, 1H); 6.99 (d, J = 9.2 Hz, 1H); 6.92 (dd, J = 4.8 Hz, J = 7.2 Hz, 1H); 5.39-5.37 (m, 1H); 4.04-4.03 (m, 2H); 4.01-3.85 (m, 2H); 3.62-3.51 (m, 4H); 3.15-3.02 (m, 1H); 2.15-2.09 (m, 2H); 1.92-1.80 (m, 2H); 1.78-1.75 (m, 4H). |

TABLE 18B-continued

PREPARATION AND NMR DATA OF EXAMPLES 27.1-27.84

| Ex. # | Starting material (1) and (2) | Reaction condition | $^1$H NMR (CD$_3$OD, 400 MHz) δ (ppm) |
|---|---|---|---|
| 27.47 | (see Preparation P29.1) and [structure with HO-CH2-pyridine-Cl] | K$_2$CO$_3$, i-PrOH, MW, 160° C. | 8.03-7.98 (m, 2H); 7.88-7.87 (m, 1H); 7.58-7.56 (m, 1H); 7.45 (d, J = 9.6 Hz, 1H); 6.94 (dd, J = 5.2 Hz, J = 7.6 Hz, 1H); 5.46 (m, 1H); 4.57 (s, 5H); 4.05-4.00 (m, 2H); 3.95-3.90 (m, 2H); 3.82-3.77 (m, 2H); 3.58-3.52 (m, 2H); 3.14-3.03 (m, 1H); 2.25-2.20 (m, 2H); 2.05-2.02 (m, 2H); 1.82-1.76 (m, 4H). |
| 27.48 | (see Preparation P29.1) and [structure with CHO-pyridine-Cl] | K$_2$CO$_3$, i-PrOH, MW, 160° C. | (CDCl$_3$) 9.77 (s, 1H); 8.63 (s, 1H); 8.02 (dd, J = 9.2 Hz, J = 15.2 Hz, 2H); 7.47 (d, J = 7.2 Hz, 1H); 6.91-6.85 (m, 2H); 5.45 (s, 1H); 4.06-4.00 (m, 4H); 3.99-3.80 (m, 2H); 3.53-3.47 (m, 2H); 3.02-2.99 (m, 1H); 2.17-2.12 (m, 2H); 2.00-1.97 (m, 2H); 1.77-1.72 (m, 4H). |

TABLE 18B-continued
PREPARATION AND NMR DATA OF EXAMPLES 27.1-27.84
| Ex. # | Starting material (1) and (2) | Reaction condition | $^1$H NMR (CD$_3$OD, 400 MHz) δ (ppm) |
|---|---|---|---|
| 27.49 | 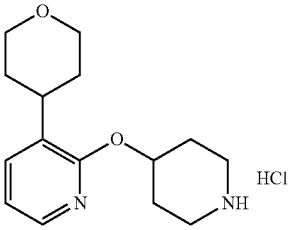<br>(see Preparation P29.1)<br>and<br>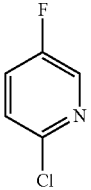 | K$_2$CO$_3$, i-PrOH, MW, 160° C. | 8.01-7.96 (m, 2H); 7.66-7.63 (m, 1H); 7.57-7.54 (m, 1H); 7.16-7.12 (m, 1H); 6.94-6.91 (m, 1H); 5.39-5.37 (m, 1H); 4.04-4.00 (m, 2H); 3.88-3.83 (m, 2H); 3.62-3.51 (m, 4H); 3.13-3.04 (m, 1H); 2.15-2.12 (m, 2H); 1.94-1.80 (m, 2H); 1.78-1.75 (m, 4H). |
| 27.50 | 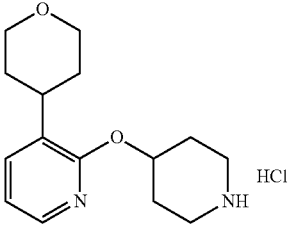<br>(see Preparation P29.1)<br>and<br>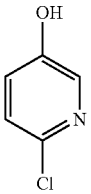 | K$_2$CO$_3$, i-PrOH, MW, 160° C. | (CDCl$_3$) 8.02-8.01 (m, 1H); 7.72 (s, 1H); 7.62 (d, J = 9.2 Hz, 1H); 7.51 (d, J = 7.2 Hz, 1H); 6.96-6.91 (m, 2H); 5.41 (d, J = 3.2 Hz, 1H); 4.06 (d, J = 11.2 Hz, 2H); 3.80-3.76 (m, 2H); 3.62-3.50 (m, 4H); 3.04-3.00 (m, 1H); 2.19-2.18 (m, 2H); 2.16-2.15 (m, 2H); 1.75-1.72 (m, 4H). |

TABLE 18B-continued
PREPARATION AND NMR DATA OF EXAMPLES 27.1-27.84
| Ex. # | Starting material (1) and (2) | Reaction condition | $^1$H NMR (CD$_3$OD, 400 MHz) δ (ppm) |
|---|---|---|---|
| 27.51 | 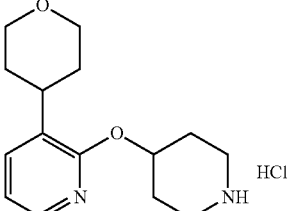 (see Preparation P29.1) and | K$_2$CO$_3$, i-PrOH, MW, 160° C. | 8.39 (dd, J = 0.8 Hz, J = 2.4 Hz, 1H); 7.97 (dd, J = 2 Hz, J = 5.2 Hz, 1H); 7.74 (dd, J = 2.4 Hz, J = 9.2 Hz, 1H); 7.58-7.56 (m, 1H); 6.95-6.92 (m, 2H); 5.40-5.38 (m, 1H); 4.04-3.97 (m, 4H); 3.75-3.69 (m, 2H); 3.57-3.50 (m, 2H); 3.13-3.04 (m, 1H); 2.12-2.07 (m, 2H); 1.88-1.86 (m, 2H); 1.80-1.74 (m, 4H). |
| 27.52 | 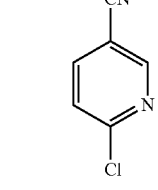 (see Preparation P29.1) and | K$_2$CO$_3$, i-PrOH, MW, 160° C. | 8.32 (s, 1H); 7.98 (dd, J = 1.6 Hz, J = 4.8 Hz, 1H); 7.85 (dd, J = 2.4 Hz, J = 9.6 Hz, 1H); 7.57-7.55 (m, 1H); 7.13 (d, J = 9.6 Hz, 1H); 6.93 (dd, J = 5.2 Hz, J = 7.2 Hz, 1H); 5.42-5.00 (m, 1H); 4.01-3.96 (m, 4H); 3.77-3.70 (m, 2H); 3.57-3.51 (m, 2H); 3.13-2.98 (m, 1H); 2.17-2.12 (m, 2H); 1.94-1.89 (m, 2H); 1.80-1.75 (m, 4H). |

TABLE 18B-continued

PREPARATION AND NMR DATA OF EXAMPLES 27.1-27.84

| Ex. # | Starting material (1) and (2) | Reaction condition | $^1$H NMR (CD$_3$OD, 400 MHz) δ (ppm) |
|---|---|---|---|
| 27.53 | 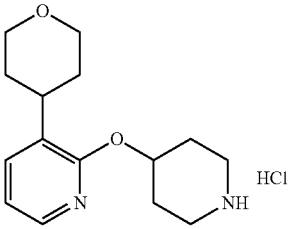 (see Preparation P29.1) and | K$_2$CO$_3$, i-PrOH, MW, 160° C. | 8.74 (d, J = 2 Hz, 1H); 8.05 (dd, J = 2.8 Hz, J = 6.8 Hz, 1H); 7.97 (dd, J = 1.6 Hz, J = 4.8 Hz, 1H); 7.56-7.54 (m, 1H); 6.96-6.86 (m, 2H); 5.41-5.39 (m, 1H); 4.07-4.00 (m, 4H); 3.76-3.70 (m, 2H); 3.58-3.51 (m, 2H); 3.16-3.05 (m, 1H); 2.50 (s, 3H); 2.09-2.07 (m, 2H); 1.87-1.75 (m, 6H). |
| 27.54 | 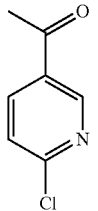 (see Preparation P29.1) and | K$_2$CO$_3$, i-PrOH, MW, 160° C. | (CDCl$_3$) 8.33-8.07 (m, 1H); 7.97-7.93 (m, 2H); 7.54 (d, J = 5.6 Hz, 1H); 7.24 (d, J = 6.8 Hz, 1H); 7.13 (d, J = 9.2 Hz, 1H); 7.14-7.02 (m, 1H); 6.87-6.85 (m, 1H); 5.47 (s, 1H); 4.04-4.04 (m, 6H); 3.51-3.49 (m, 2H); 3.00-2.98 (m, 1H); 2.58-2.46 (m, 3H); 2.19-2.10 (m, 4H); 1.72 (s, 4H). |
| 27.55 | 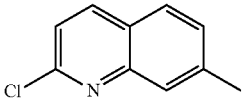 (see Preparation P29.1) and | K$_2$CO$_3$, i-PrOH, MW, 160° C. | (CDCl$_3$) 8.08-7.99 (m, 2H); 7.52-7.43 (m, 3H); 7.31-7.10 (m, 2H); 6.89-6.86 (m, 1H); 5.47 (s, 1H); 4.05-3.94 (m, 6H); 3.54-3.48 (m, 2H); 3.06-2.98 (m, 1H); 2.68 (s, 3H); 2.19-1.74 (m, 8H). |

TABLE 18B-continued

PREPARATION AND NMR DATA OF EXAMPLES 27.1-27.84

| Ex. # | Starting material (1) and (2) | Reaction condition | $^1$H NMR (CD$_3$OD, 400 MHz) δ (ppm) |
|---|---|---|---|
| 27.56 | (see Preparation P29.1) and [structure] | K$_2$CO$_3$, i-PrOH, MW, 160° C. | (CDCl$_3$) 8.74 (d, J = 2.4 Hz, 1H); 7.96-7.93 (m, 2H); 7.38-7.35 (m, 1H); 6.81-6.78 (m, 1H); 6.59-6.56 (m, 1H); 5.37-5.35 (m, 1H); 4.02-3.94 (m, 4H); 3.80 (s, 3H); 3.65-3.59 (m, 2H); 3.49-3.43 (m, 2H); 2.97-2.95 (m, 1H); 2.06-2.00 (m, 2H); 1.85-1.79 (m, 2H); 1.72-1.66 (m, 4H). |
| 27.57 | (see Preparation P29.3) and [structure] | K$_2$CO$_3$, i-PrOH, MW, 160° C. | (CDCl$_3$) 8.31-8.04 (m, 1H); 8.07-8.03 (m, 1H); 7.97-7.91 (m, 1H); 7.86 (d, J = 2.4 Hz, 1H); 7.55-7.51 (m, 1H); 7.22-7.20 (m, 1H); 7.09-6.97 (m, 1H); 5.41 (s, 1H); 4.02-3.99 (m, 6H); 3.48 (t, J = 10.8 Hz, 2H); 3.19-3.13 (m, 1H); 2.56-2.44 (m, 3H); 2.19-1.95 (m, 4H); 1.93-1.68 (m, 4H). |
| 27.58 | (see Preparation P29.3) and [structure] | K$_2$CO$_3$, i-PrOH, MW, 160° C. | (CDCl$_3$) 8.08-8.04 (m, 2H); 7.92 (d, J = 2.4 Hz, 1H); 7.53-7.51 (m, 2H); 7.31-7.24 (m, 1H); 7.10 (d, J = 8.8 Hz, 1H); 5.43 (s, 1H); 4.07-4.05 (m, 4H); 3.91 (s, 2H); 3.53 (t, J = 11.6 Hz, 2H); 3.25-3.19 (m, 1H); 2.70 (s, 3H); 2.21-1.90 (m, 6H); 1.74-1.72 (m, 2H). |

TABLE 18B-continued

PREPARATION AND NMR DATA OF EXAMPLES 27.1-27.84

| Ex. # | Starting material (1) and (2) | Reaction condition | $^1$H NMR (CD$_3$OD, 400 MHz) δ (ppm) |
|---|---|---|---|
| 27.59 | 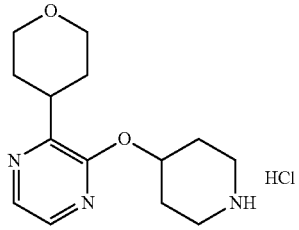<br>(see Preparation P29.3)<br>and<br>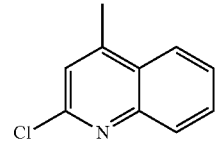 | K$_2$CO$_3$, i-PrOH, MW, 160° C. | (CDCl$_3$) 8.00 (d, J = 2.8 Hz, 1H); 7.86 (d, J = 2.8 Hz, 1H); 7.71 (d, J = 8.4 Hz, 1H); 7.65 (d, J = 8 Hz, 1H); 7.47 (t, J = 7.6 Hz, 1H); 7.20-7.17 (m, 2H); 6.83 (s, 1H); 5.34-5.31 (m, 1H); 4.07-3.98 (m, 4H); 3.64-3.59 (m, 2H); 3.50-3.44 (m, 2H); 3.19-3.14 (m, 1H); 2.54 (s, 3H); 2.10-2.05 (m, 2H); 1.97-1.82 (m, 3H); 1.74-1.70 (m, 2H). |
| 27.60 | 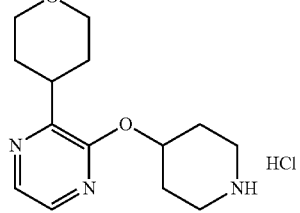<br>(see Preparation P29.3)<br>and<br>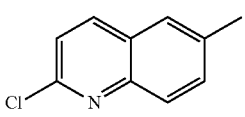 | K$_2$CO$_3$, i-PrOH, MW, 160° C. | 8.35 (d, J = 9.6 Hz, 1H); 8.09 (d, J = 2.8 Hz, 1H); 8.01 (d, J = 2.8 Hz, 1H); 7.83-7.65 (m, 3H); 7.52 (d, J = 9.6 Hz, 1H); 5.54-5.53 (m, 1H); 4.14-3.99 (m, 6H); 3.56-3.53 (m, 2H); 3.36-3.32 (m, 1H); 2.50 (s, 3H); 2.35-2.29 (m, 2H); 2.15-2.10 (m, 2H); 1.96-1.92 (m, 2H); 1.81-1.77 (m, 2H). |
| 27.61 | 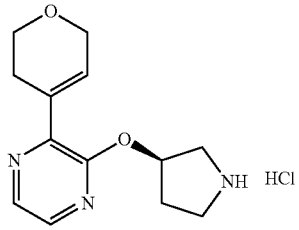<br>(see Preparation P26.5)<br>and<br>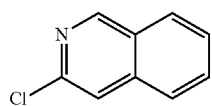 | Pd$_2$(dba)$_3$, BINAP, NaOtBu, Toluene | (CDCl$_3$) 8.93 (s, 1H); 8.10-8.09 (m, 1H); 7.96-7.95 (m, 1H); 7.77-7.74 (m, 1H); 7.56-7.53 (m, 1H); 7.49-7.45 (m, 1H); 7.20-7.17 (m, 1H); 6.53 (s, 1H); 5.78-5.77 (m, 1H); 4.05-3.96 (m, 3H); 3.83-3.71 (m, 3H); 3.52-3.46 (m, 2H); 3.17-3.14 (m, 1H); 2.47-2.42 (m, 2H); 1.95-1.82 (m, 2H); 1.76-1.63 (m, 2H). |

TABLE 18B-continued

PREPARATION AND NMR DATA OF EXAMPLES 27.1-27.84

| Ex. # | Starting material (1) and (2) | Reaction condition | $^1$H NMR (CD$_3$OD, 400 MHz) δ (ppm) |
|---|---|---|---|
| 27.62 | (see Preparation P27.2) and | i-PrOH, H$_2$O, K$_2$CO$_3$, MW | 8.13-8.12 (m, 1H); 8.04-8.03 (m, 1H); 7.41-7.39 (m, 2H); 7.38-7.28 (m, 2H); 5.86-5.84 (m, 1H); 4.15-4.10 (m, 1H); 4.00-3.88 (m, 5H); 3.56-3.50 (m, 2H); 3.27-3.21 (m, 1H); 2.60-2.50 (m, 2H); 1.93-1.87 (m, 2H); 1.77-1.68 (m, 2H). |
| 27.63 | (see Preparation P29.1) and | i-PrOH, H$_2$O, K$_2$CO$_3$, MW | (CDCl$_3$) 8.10-7.99 (m, 3H); 7.56-7.54 (m, 1H); 7.47-7.45 (m, 2H); 7.10-7.08 (m, 1H); 6.91-6.88 (m, 1H); 5.50 (s, 1H); 4.07-4.04 (m, 6H); 3.56-3.50 (m, 2H); 3.06-2.99 (m, 1H); 2.46 (s, 3H); 2.26-2.21 (m, 4H); 1.76-1.75 (m, 4H). |
| 27.64 | (see Preparation P29.1) and | i-PrOH, H$_2$O, K$_2$CO$_3$, MW | (CDCl$_3$) 8.17-8.15 (m, 1H); 7.99-7.98 (m, 1H); 7.81-7.79 (m, 1H); 7.68-7.64 (m, 1H); 7.46-7.42 (m, 2H); 7.00 (s, 1H); 6.90-6.87 (m, 1H); 5.49 (s, 1H); 4.05-4.02 (m, 6H); 3.54-3.48 (m, 2H); 3.05-2.97 (m, 1H); 2.69 (s, 3H); 2.21-2.10 (m, 4H); 1.75-1.73 (m, 4H). |

TABLE 18B-continued

PREPARATION AND NMR DATA OF EXAMPLES 27.1-27.84

| Ex. # | Starting material (1) and (2) | Reaction condition | $^1$H NMR (CD$_3$OD, 400 MHz) δ (ppm) |
|---|---|---|---|
| 27.65 | 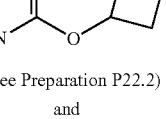 (see Preparation P22.2) and | K$_2$CO$_3$, i-PrOH, water MW, 160° C. | (CDCl$_3$) 8.50-8.49 (m, 1H); 8.04-8.02 (m, 1H); 7.84-7.82 (m, 1H); 7.69-7.66 (m, 1H); 7.15-7.13 (m, 1H); 6.87-6.84 (m, 1H); 5.59-5.56 (m, 1H); 4.84-4.80 (m, 2H); 4.46-4.42 (m, 2H). |
| 27.66 | 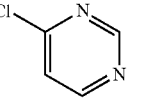 (see Preparation P22.2) and | K$_2$CO$_3$, i-PrOH, water MW, 160° C. | (CDCl$_3$) 8.52 (s, 1H); 8.12-8.11 (m, 1H); 7.99-7.98 (m, 1H); 7.78-7.76 (m, 1H); 6.79-6.75 (m, 1H); 6.16-6.14 (m, 1H); 5.48 (s, 1H); 4.49-4.45 (m, 2H); 4.13-4.11 (m, 2H). |
| 27.67 |  (see Preparation P29.6) and | Cs$_2$CO$_3$, MeCN, MW, 120° C. | 8.07 (d, J = 2.8 Hz, 1H); 8.02-7.94 (m, 3H); 7.42-7.39 (m, 1H); 6.98-6.94 (m, 1H); 5.54-5.48 (m, 1H); 4.62-4.58 (m, 1H); 4.11-.3.98 (m, 1H); 3.93-3.90 (m, 2H); 3.80-.3.77 (m, 2H); 3.34-3.31 (m, 1H); 3.20-3.26 (m, 1H); 2.82-2.78 (m, 1H); 2.25-2.22 (m, 2H), 2.13 (s, 3H); 2.06-2.02 (m, 2H); 1.92-1.90 (m, 3H); 1.90-1.68 (m, 1H). |

TABLE 18B-continued
PREPARATION AND NMR DATA OF EXAMPLES 27.1-27.84
| Ex. # | Starting material (1) and (2) | Reaction condition | $^1$H NMR (CD$_3$OD, 400 MHz) δ (ppm) |
|---|---|---|---|
| 27.68 | 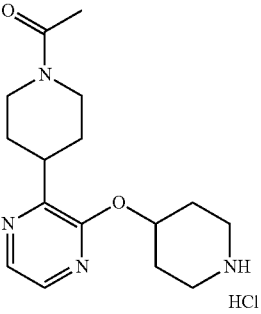 (see Preparation P29.6) and 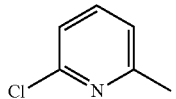 | Cs$_2$CO$_3$, MeCN, MW, 120° C. | 8.07 (d, J = 2.8 Hz, 1H); 8.00 (d, J = 2.8 Hz, 1H); 7.92 (dd, J = 7.2 Hz, 9.2 Hz, 1H); 7.23 (d, J = 9.2 Hz, 1H); 6.81 (d, J = 8.8 Hz, 1H), 5.54-5.48 (m, 1H); 4.62-4.58 (m, 1H); 4.11-.3.98 (m, 1H); 3.93-3.90 (m, 2H); 3.80-.3.77 (m, 2H); 3.40-3.25 (m, 2H) 2.82-2.78 (m, 1H); 2.57 (s, 3H), 2.28-2.22 (m, 2H), 2.13 (s, 3H); 2.08-2.02 (m, 2H); 1.92-1.90 (m, 3H); 1.90-1.70 (m, 1H). |
| 27.69 | 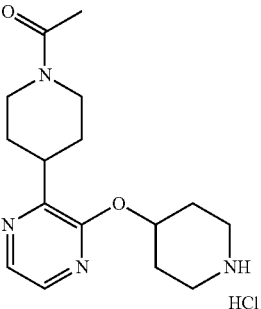 (see Preparation P29.6) and 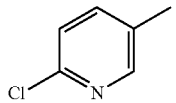 | Cs$_2$CO$_3$, MeCN, MW, 120° C. | 8.06 (d, J = 2.8 Hz, 1H); 8.00 (d, J = 2.8 Hz, 1H); 7.94-7.91 (m, 1H); 7.75 (s, 1H); 7.38 (d, J = 9.2 Hz, 1H), 5.54-5.48 (m, 1H); 4.62-4.58 (m, 1H); 4.11-.3.98 (m, 1H); 3.92-.390 (m, 2H); 3.80-3.72 (m, 2H); 3.40-3.31 (m, 2H) 2.82-2.78 (m, 1H); 2.30 (s, 3H), 2.29-2.21 (m, 2H), 2.11 (s, 3H); 2.06-2.02 (m, 2H), 1.92-1.89 (m, 3H); 1.89-1.71 (m, 1H). |

TABLE 18B-continued

PREPARATION AND NMR DATA OF EXAMPLES 27.1-27.84

| Ex. # | Starting material (1) and (2) | Reaction condition | $^1$H NMR (CD$_3$OD, 400 MHz) δ (ppm) |
|---|---|---|---|
| 27.70 | (see Preparation P29.6) and [2-chloro-4-methylpyridine] | Cs$_2$CO$_3$, MeCN, MW, 120° C. | 8.07 (d, J = 2.8 Hz, 1H); 8.00 (d, J = 2.8 Hz, 1H); 7.81 (d, J = 6.4 Hz, 1H); 7.29 (s, 1H); 6.87 (dd, J = 1.2 Hz, 6.4 Hz, 1H); 5.54-5.48 (m, 1H); 4.62-4.58 (m, 1H); 4.11-.3.98 (m, 1H); 3.93-3.90 (m, 2H); 3.80-3.77 (m, 2H); 3.34-3.26 (m, 2H) 2.82-2.78 (m, 1H); 2.50 (s, 3H), 2.25-2.22 (m, 2H), 2.13 (s, 3H); 2.06-2.02 (m, 2H), 1.92-1.90 (m, 3H); 1.89-1.68 (m, 1H). |
| 27.71 | (see Preparation P29.6) and [2-chloro-3-methylpyridine] | Cs$_2$CO$_3$, MeCN, MW, 120° C. | 8.11-8.04 (m, 3H); 8.00 (d, J = 2.8 Hz, 1H); 7.28 (dd, J = 6.0 Hz, 7.6 Hz, 1H); 5.54-5.48 (m, 1H); 4.62-4.58 (m, 1H); 4.10-4.01 (m, 1H); 3.73-.3.67 (m, 2H); 3.55-3.50 (m, 2H); 3.40-3.29 (m, 2H) 2.82-2.78 (m, 1H); 2.48 (s, 3H), 2.32-2.26 (m, 2H), 2.12-2.08 (m, 5H), 1.95-1.89 (m, 3H); 1.89-1.68 (m, 1H). |

TABLE 18B-continued
PREPARATION AND NMR DATA OF EXAMPLES 27.1-27.84
| Ex. # | Starting material (1) and (2) | Reaction condition | $^1$H NMR (CD$_3$OD, 400 MHz) δ (ppm) |
|---|---|---|---|
| 27.72 | 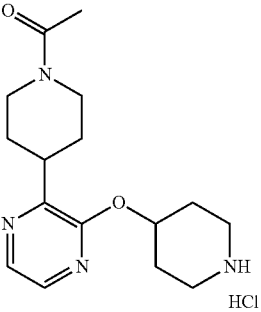<br>(see Preparation P29.6)<br>and<br>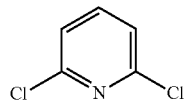 | Cs$_2$CO$_3$, MeCN, MW, 120° C. | 8.03 (d, J = 2.8 Hz, 1H); 7.98 (d, J = 2.8 Hz, 1H); 7.47 (dd, J = 7.2 Hz, 8.4 Hz, 1H); 6.72 (d, J = 8.4 Hz, 1H); 6.58 (d, J = 7.2 Hz, 1H), 5.40-5.37 (m, 1H); 4.62-4.58 (m, 1H); 4.04-4.00 (m, 1H); 3.93-.3.87 (m, 2H); 3.56-3.49 (m, 2H); 3.34-3.26 (m, 2H) 2.78-2.77 (m, 1H); 2.12-2.07 (m, 5H), 1.93-1.72 (m, 6H). |
| 27.73 | 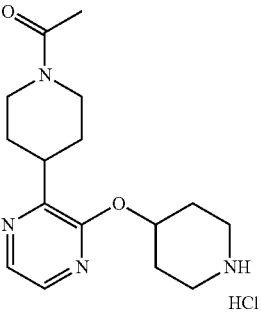<br>(see Preparation P29.6)<br>and<br>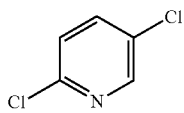 | Cs$_2$CO$_3$, MeCN, MW, 120° C. | 8.05-8.03 (m, 2H); 7.99 (d, J = 2.8 Hz, 1H); 7.75 (dd, J = 2.4 Hz, 9.6 Hz, 1H); 7.14 (dd, J = 0.8 Hz, 9.6 Hz, 1H); 5.44-5.42 (m, 1H); 4.62-4.58 (m, 1H); 4.04-4.00 (m, 1H); 3.93-.3.87 (m, 2H); 3.67-3.61 (m, 2H); 3.34-3.26 (m, 2H) 2.78-2.77 (m, 1H); 2.02-2.15 (m, 2H), 2.11 (s, 3H), 1.97-1.68 (m, 6H). |

TABLE 18B-continued
PREPARATION AND NMR DATA OF EXAMPLES 27.1-27.84
| Ex. # | Starting material (1) and (2) | Reaction condition | $^1$H NMR (CD$_3$OD, 400 MHz) δ (ppm) |
|---|---|---|---|
| 27.74 | 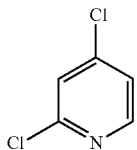<br>(see Preparation P29.6)<br>and<br>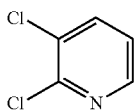 | Cs$_2$CO$_3$, MeCN, MW, 120° C. | 8.04 (d, J = 2.8 Hz, 1H); 7.98 (d, J = 2.8 Hz, 1H); 7.90 (d, J = 6.0 Hz, 1H); 6.88 (d, J = 2.4 Hz, 1H); 6.85-6.82 (m, 1H), 5.42-5.40 (m, 1H); 4.62-4.58 (m, 1H); 4.04-4.00 (m, 1H); 3.76-.3.71 (m, 2H); 3.50-3.44 (m, 2H); 3.33-3.22 (m, 2H) 2.78-2.77 (m, 1H); 2.16-2.11 (m, 5H), 1.93-1.68 (m, 6H). |
| 27.75 | (see Preparation P29.6)<br>and | Cs$_2$CO$_3$, MeCN, MW, 120° C. | 8.24-8.22 (m, 1H); 8.04 (d, J = 2.8 Hz, 1H); 7.94 (d, J = 2.8 Hz, 1H), 7.00 (d, J = 1.6 Hz, 1H); 6.93-6.89 (m, 1H), 5.39-5.35 (m, 1H); 4.72-4.58 (m, 1H); 3.97-3.94 (m, 1H); 3.69-.3.63 (m, 2H); 3.41-3.31 (m, 2H); 3.29-3.24 (m, 2H) 2.78-2.77 (m, 1H); 2.22-2.15 (m, 5H), 2.05-1.73 (m, 6H). |

TABLE 18B-continued
PREPARATION AND NMR DATA OF EXAMPLES 27.1-27.84
| Ex. # | Starting material (1) and (2) | Reaction condition | $^1$H NMR (CD$_3$OD, 400 MHz) δ (ppm) |
|---|---|---|---|
| 27.76 | 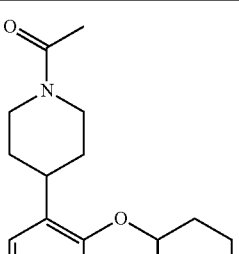 (see Preparation P29.7) and 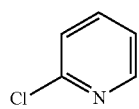 | Pd$_2$(dba)$_3$, BINAP, Cs$_2$CO$_3$, 1,4-dioxane, 120° C. | 8.06-7.98 (m, 2H); 7.94-7.91 (m, 1H); 7.57-7.55 (m, 1H); 7.46-7.43 (m, 1H); 7.00-6.92 (m, 2H), 5.54-5.48 (m, 1H); 4.68-4.62 (m, 1H); 4.08-.4.02 (m, 1H); 3.91-.3.88 (m, 2H); 3.83-3.79 (m, 2H); 3.30-3.06 (m, 2H) 2.72-2.68 (m, 1H); 2.30-2.20 (m, 2H), 2.11 (s, 3H), 2.10-2.00 (m, 2H); 2.00-1.60 (m, 4H). |
| 27.77 | (see Preparation P29.7) and 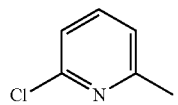 | Pd$_2$(dba)$_3$, BINAP, Cs$_2$CO$_3$, 1,4-dioxane, 120° C. | 8.00-7.98 (m, 1H); 7.92 (dd, J = 7.2 Hz, 9.2 Hz, 1H); 7.58-7.55 (m, 1H); 7.23(d, J = 9.2 Hz, 1H); 6.95-6.92 (m, 1H), 6.81-6.80 (m, 1H), 5.54-5.48 (m, 1H); 4.68-4.62 (m, 1H); 4.08-4.02 (m, 1H); 3.95-.3.89 (m, 2H); 3.83-3.77 (m, 2H); 3.30-3.06 (m, 2H) 2.72-2.68 (m, 1H); 2.57 (s, 3H), 2.25-2.19 (m, 2H), 2.12 (s, 3H), 2.04-2.00 (m, 2H), 1.89-1.60 (m, 4H). |

TABLE 18B-continued
PREPARATION AND NMR DATA OF EXAMPLES 27.1-27.84
| Ex. # | Starting material (1) and (2) | Reaction condition | $^1$H NMR (CD$_3$OD, 400 MHz) δ (ppm) |
|---|---|---|---|
| 27.78 | 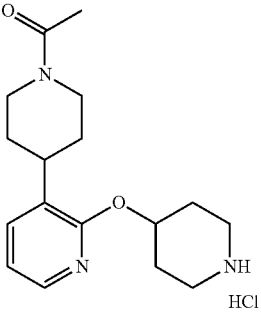<br>(see Preparation P29.7)<br>and<br>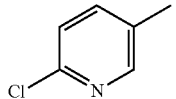 | Cs$_2$CO$_3$, MeCN, MW, 120° C. | 7.98 (dd, J = 4.0 Hz, 4.8 Hz, 1H); 7.84 (d, J = 1.2 Hz, 1H); 7.63 (dd, J = 4.0 Hz, 8.8 Hz, 1H); 7.54 (dd, J = 1.6 Hz, 7.6 Hz, 1H); 7.05 (d, J = 5.2 Hz, 1H), 6.93-6.89 (m, 1H), 5.40-5.37 (m, 1H); 4.68-4.62 (m, 1H); 4.08-4.02 (m, 1H); 3.85-.3.79 (m, 2H); 3.60-3.52 (m, 2H); 3.31-3.08 (m, 2H), 2.72-2.68 (m, 1H); 2.23 (s, 3H), 2.17-2.10 (m, 5H), 1.94-1.88 (m, 4H), 1.72-1.61 (m, 2H). |
| 27.79 | 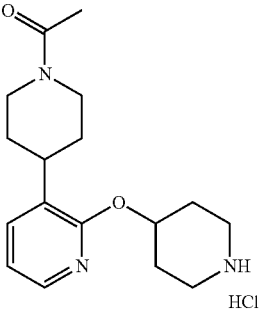<br>(see Preparation P29.7)<br>and<br>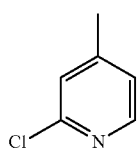 | Cs$_2$CO$_3$, MeCN, MW, 120° C. | 8.00-7.98 (m, 1H); 7.80 (d, J = 6.8 Hz, 1H); 7.57-7.55 (m, 1H); 7.28 (s, 1H); 6.95-6.91 (m, 1H), 6.87-6.84 (m, 1H), 5.47-5.45 (m, 1H); 4.66-4.62 (m, 1H); 4.08-4.02 (m, 1H); 3.92-.3.86 (m, 2H); 3.80-3.73 (m, 2H); 3.31-3.09 (m, 2H), 2.72-2.68 (m, 1H); 2.47 (s, 3H), 2.25-2.19 (m, 2H), 2.12 (s, 3H), 2.04-1.99 (m, 2H), 1.89-1.85 (m, 2H), 1.80-1.55 (m, 2H). |

TABLE 18B-continued
PREPARATION AND NMR DATA OF EXAMPLES 27.1-27.84
| Ex. # | Starting material (1) and (2) | Reaction condition | $^1$H NMR (CD$_3$OD, 400 MHz) δ (ppm) |
|---|---|---|---|
| 27.80 | 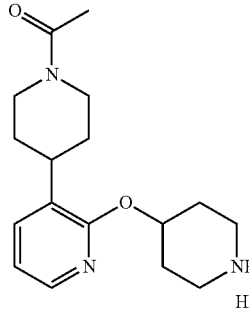<br>(see Preparation P29.7)<br>and<br>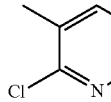 | Cs$_2$CO$_3$, MeCN, MW, 120° C. | 8.07-8.05 (m, 1H); 7.97 (dd, J = 2.0 Hz, 4.8 Hz, 1H); 7.55-7.51 (m, 2H); 6.95-6.88 (m, 2H); 5.38-5.32 (m, 1H); 4.68-4.62 (m, 1H); 4.08-4.02 (m, 1H); 3.40-.3.30 (m, 2H); 3.30-3.10 (m, 4H); 2.76-2.70 (m, 1H); 2.32 (s, 3H), 2.22-2.12 (m, 2H), 2.11 (s, 3H), 1.99-1.94 (m, 4H), 1.80-1.60 (m, 2H). |
| 27.81 | 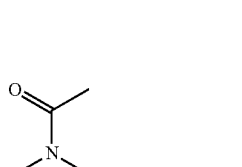<br>(see Preparation P29.7)<br>and<br>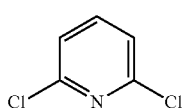 | Pd$_2$(dba)$_3$, BINAP, Cs$_2$CO$_3$, 1,4-dioxane, 120° C. | 7.97 (dd, J = 1.6 Hz, 4.8 Hz, 1H); 7.55-7.52 (m, 1H); 7.49-7.44 (m, 1H); 6.92-6.89 (m, 1H); 6.71 (d, J = 8.4 Hz, 1H); 6.58 (d, J = 7.2 Hz, 1H), 5.37-5.35 (m, 1H); 4.68-4.62 (m, 1H); 4.06-4.02 (m, 1H); 3.89-.3.84 (m, 2H); 3.52-3.52 (m, 2H); 3.30-3.05 (m, 2H); 2.72-2.68 (m, 1H), 2.11-2.04 (m, 5H), 1.93-1.81 (m, 4H), 1.70-1.60 (m, 2H). |

TABLE 18B-continued

PREPARATION AND NMR DATA OF EXAMPLES 27.1-27.84

| Ex. # | Starting material (1) and (2) | Reaction condition | $^1$H NMR (CD$_3$OD, 400 MHz) δ (ppm) |
|---|---|---|---|
| 27.82 | 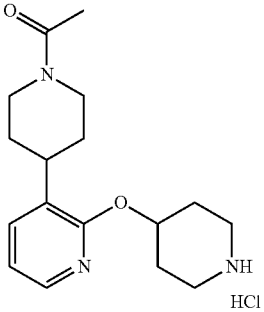 (see Preparation P29.7) and 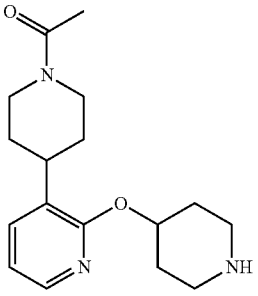 | Cs$_2$CO$_3$, MeCN, MW, 120° C. | 8.03 (d, J = 2.0 Hz, 1H); 7.98 (dd, J = 2.0 Hz, 4.2 Hz, 1H); 7.76 (dd, J = 2.8 Hz, 9.6 Hz, 1H); 7.55 (dd, J = 1.6 Hz, 7.6 Hz, 1H); 7.16 (d, J = 9.6 Hz, 1H); 6.91 (dd, J = 4.2 Hz, 7.6 Hz, 1H); 5.45-5.38 (m, 1H); 4.68-4.62 (m, 1H); 4.08-4.02 (m, 1H); 3.89-.3.85 (m, 2H); 3.69-3.63 (m, 2H); 3.30-3.08 (m, 2H); 2.72-2.68 (m, 1H), 2.18-2.11 (m, 6H), 1.96-1.85 (m, 4H), 1.73-1.60 (m, 1H). |
| 27.83 | 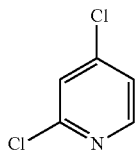 (see Preparation P29.7) and | Pd$_2$(dba)$_3$, BINAP, Cs$_2$CO$_3$, 1,4-dioxane, 120° C. | 7.99 (dd, J = 1.6 Hz, 4.8 Hz, 1H); 7.93 (dd, J = 0.4 Hz, 6.8 Hz, 1H); 7.57-7.54 (m, 2H); 6.99 (dd, J = 2.0 Hz, 6.8 Hz, 1H); 6.93 (dd, J = 1.2 Hz, 7.6 Hz, 1H) 5.48-5.46 (m, 1H); 4.68-4.62 (m, 1H); 4.08-4.02 (m, 1H); 3.92-3.80 (m, 2H); 3.79-3.75 (m, 2H); 3.30-3.08 (m, 2H); 2.72-2.68 (m, 1H), 2.22-2.18 (m, 2H), 2.12 (s, 3H), 2.04-2.01 (m, 2H), 1.98-1.90 (m, 2H), 1.80-1.60 (m, 2H). |

TABLE 18B-continued

PREPARATION AND NMR DATA OF EXAMPLES 27.1-27.84

| Ex. # | Starting material (1) and (2) | Reaction condition | $^1$H NMR (CD$_3$OD, 400 MHz) δ (ppm) |
|---|---|---|---|
| 27.84 | 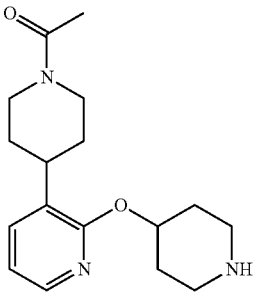 (see Preparation P29.7) and | Cs$_2$CO$_3$, MeCN, MW, 120° C. | 8.16 (dd, J = 1.6 Hz, 4.8 Hz, 1H); 7.97 (dd, J = 2.0 Hz, 5.2 Hz, 1H); 7.72 (dd, J = 1.6 Hz, 8.0 Hz, 1H); 7.53 (dd, J = 1.6 Hz, 7.2 Hz, 1H); 6.96-6.88 (m, 2H), 5.35-5.33 (m, 1H); 4.68-4.62 (m, 1H); 4.05-4.01 (m, 1H); 3.58-.3.53 (m, 2H); 3.33-3.11 (m, 4H); 2.72-2.70 (m, 1H); 2.19-2.16 (m, 2H), 2.11 (s, 3H), 1.99-1.87 (m, 4H), 1.78-1.60 (m, 2H). |

SCHEME 28

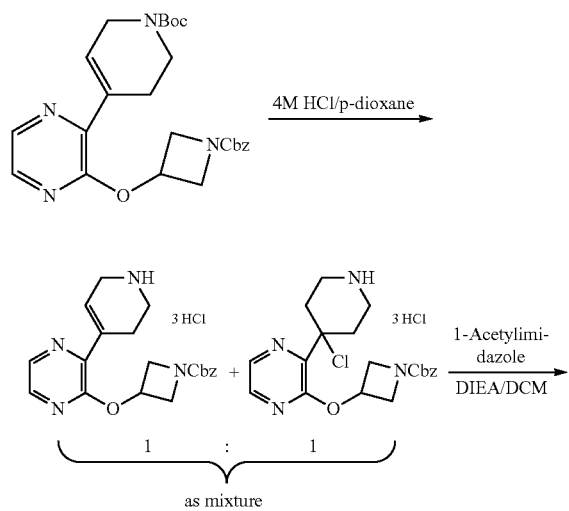

Note:
——Cbz is ——COOCH$_2$——C$_6$H$_5$

Example 28.1

Benzyl 3-(3-(1-Acetyl-4-Hydroxypiperidin-4-yl) Pyrazin-2-yloxy)Azetidine-1-Carboxylate Step1: Benzyl 3-((3-(4-Chloropiperidin-4-yl) Pyrazin-2-yl)Oxy)Azetidine-1-Carboxylate Trihydrochloride Salt To a stirred solution of tert-butyl 4-(3-(1-(benzyloxycarbonyl) azetidin-3-yloxy)pyrazin-2-yl)-5,6-dihydropyridine-1(2H)-carboxylate (see PREPARATION P28.3; 0.72 g, 1.543 mmol) in DCM (5 ml) was added hydrogen chloride (3.09 mL, 12.35 mmol). The reaction mixture was stirred for 3 hours, concentrated to dryness and used in the next step. The mixture also contained 1:1 ratio of benzyl 3-((3-(1,2,3,6-tetrahydropyridin-4-yl)pyrazin-2-yl)oxy)azetidine-1-carboxylate trihydrochloride salt. MS (m+2): 404.

Step 2: Benzyl 3-((3-(1-Acetyl-4-Hydroxypiperidin-4-yl)Pyrazin-2-yl)Oxy)Azetidine-1-Carboxylate

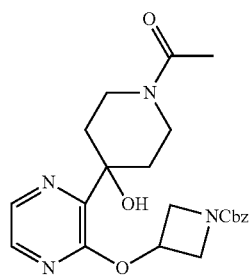

A mixture of benzyl 3-((3-(4-chloropiperidin-4-yl) pyrazin-2-yl)oxy)azetidine-1-carboxylate trihydrochloride salt, 1-acetylimidazole (0.204 g, 1.851 mmol), DIEA (1.58 mL, 9.25 mmol), and 1-acetylimidazole (0.204 g, 1.851 mmol) in DCM (10 mL) was stirred at room temperature for 16 hours. H$_2$O was added, and layers were separated. The organic extracts were dried over Na$_2$SO$_4$, concentrated and purified by silica gel chromatography using ISCO™ (0-60% EtOAc/Hexanes) to give the title compound. MS (M+1): 427 calc.

IC$_{50}$ (uM): 0.083; $^1$H NMR (CD$_3$OD, 400 MHz) δ (ppm): 7.59 (1H, br. s.), 7.17-7.50 (6H, m), 5.09 (2H, s), 4.14-4.38 (3H, m), 4.01 (1H, m), 3.61-3.84 (3H, m), 3.23-3.34 (4H, m), 2.71 (1H, br. s.), 2.62 (1H, br. s.), 2.14 (3H, s).

SCHEME 29

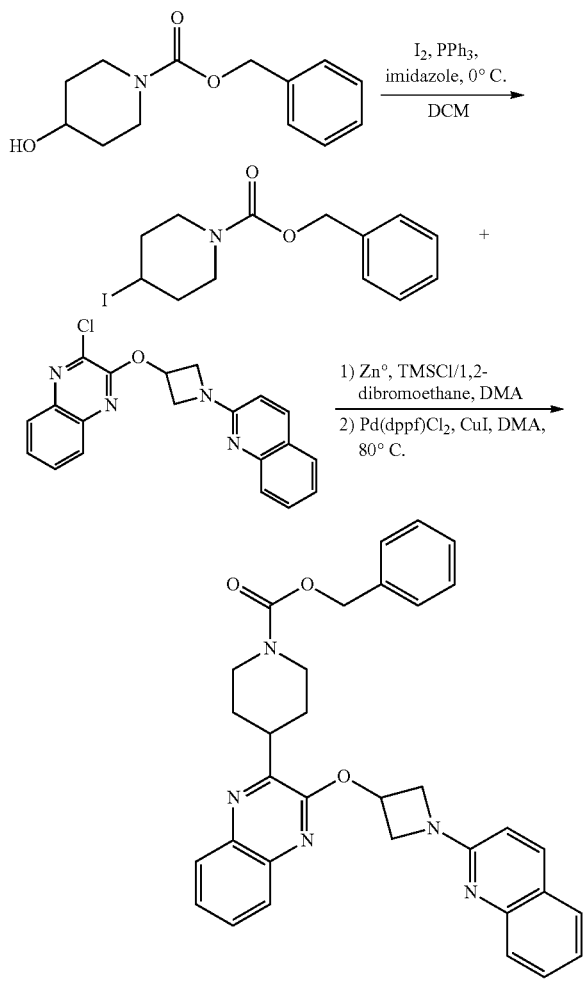

Example 29.1

Benzyl 4-(3-((1-(Quinolin-2-yl)Azetidin-3-yl)Oxy)Quinoxalin-2-yl)Piperidine-1-Carboxylate Step 1: Benzyl 4-Iodopiperidine-1-Carboxylate Iodine (17.6 g, 69.2 mmol) was added dropwise as a solution in THF (40 mL) over 1 hour to an ice cold solution of benzyl 4-hydroxypiperidine-1-carboxylate (15.5 g, 65.9 mmol), imidazole (4.71 g, 69.2 mmol), and triphenylphosphine (18.2 g, 69.2 mmol) in THF (40 mL). This resulting red solution was stirred overnight with warming to room temperature, then cooled back to 0° C. before being quenched with 10% aqueous sodium sulfite. The resulting biphasic mixture was separated and the aqueous layer was extracted with ethyl acetate (1×). The combined extracts were dried over magnesium sulfate (MgSO$_4$), filtered, and concentrated in vacuo to give an oil that was purified by silica gel chromatography (10% EtOAc/hexane) to give benzyl 4-iodopiperidine-1-carboxylate as a colorless oil (9.50 g, 42% yield).

Step 2: Benzyl 4-(3-((1-(Quinolin-2-yl)Azetidin-3-yl)Oxy)Quinoxalin-2-yl)Piperidine-1-Carboxylate A premixed mixture of TMSCl and 1,2-dibromoethane (7:5, v/v, 0.80 mL total volume added) was added dropwise over 5 minutes to a suspension of zinc (1.62 g, 24.8 mmol) in DMA (12 mL) under argon atmosphere. The mixture was stirred for 15 minutes before benzyl 4-iodopiperidine-1-carboxylate (7.13 g, 20.67 mmol) was added dropwise over 15 minutes as a solution in DMA (6 mL). This mixture was stirred for an additional 15 min before it was added slowly to a suspension of 2-chloro-3-((1-(quinolin-2-yl)azetidin-3-yl)oxy)quinoxaline (see PREPARATION P2.8; 5.0 g, 13.8 mmol), copper(I) iodide (0.26 g, 1.38 mmol), and Pd(dppf)Cl$_2$ dichloromethane adduct (0.56 g, 0.69 mmol) in DMA (15 mL) under argon. This mixture was stirred at 80° C. for 2 hours, then cooled to room temperature. Ethyl acetate was added and the suspension was filtered through CELITE® to remove insoluble material. The filtrate was diluted with more ethyl acetate and then washed with water (3×), brine(1×), dried (MgSO$_4$), filtered, and concentrated in vacuo to give an oil. This oil was purified by silica gel chromatography (0 to 100% EtOAc/hexane gradient) to give benzyl 4-(3-(1-(quinolin-2-yl)azetidin-3-yl)oxy)quinoxalin-2-yl)piperidine-1-carboxylate as an off-white solid (6.93 g, 92% yield).

TABLE 19A

EXAMPLES 29.1-29.2 PREPARED ANALOGOUS TO SCHEME 29

| Ex. # | Structure | Chemical Name | M + 1 | IC$_{50}$ (uM) |
|---|---|---|---|---|
| 29.1 | 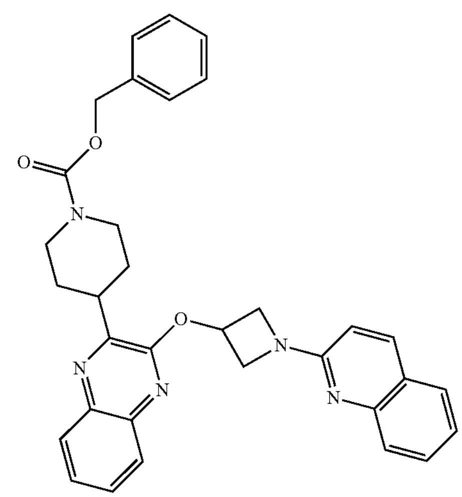 [SMILES: O=C(OCc1ccccc1)N1CCC(c2nc3ccccc3nc2OC2CN(c3ccc4ccccc4n3)C2)CC1] | benzyl 4-(3-((1-(quinolin-2-yl)azetidin-3-yl)oxy)quinoxalin-2-yl)piperidine-1-carboxylate | 546.2 | 0.05110 |

TABLE 19A-continued

EXAMPLES 29.1-29.2 PREPARED ANALOGOUS TO SCHEME 29

| Ex. # | Structure | Chemical Name | M + 1 | IC$_{50}$ (uM) |
|---|---|---|---|---|
| 29.2 | 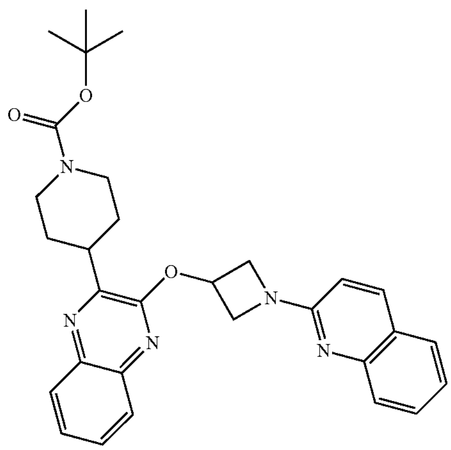 [SMILES: CC(C)(C)OC(=O)N1CCC(c2nc3ccccc3nc2OC2CN(c3ccc4ccccc4n3)C2)CC1] | tert-butyl 4-(3-((1-(quinolin-2-yl)azetidin-3-yl)oxy)quinoxalin-2-yl)piperidine-1-carboxylate | 512.2 | 0.115 |

TABLE 19B

PREPARATION AND NMR DATA OF EXAMPLES 29

| Ex. # | Starting material (1) and (2) | Reaction Condition | $^1$H NMR (CD$_3$OD, 400 MHz) δ (ppm) |
|---|---|---|---|
| 29.1 | (see Preparation P2.8) | Zn, TMSCl, 1,2-dibromoethane, DMA; Pd(dppf)Cl$_2$, CuI, DMA, 80° C. | (DMSO-d$_6$) 1.66-1.81 (m, 2H) 1.94-2.03 (m, 2H) 3.05 (br. s, 2H) 3.47 (s, 1H) 4.18 (d, J = 13.11 Hz, 2H) 4.25 (dd, J = 9.88, 4.01 Hz, 2H) 4.67 (dd, J = 9.68, 6.55 Hz, 2H) 5.12 (s, 2H) 5.71-5.79 (m, 1H) 6.85 (d, J = 8.80 Hz, 1H) 7.25 (td, J = 7.34, 1.37 Hz, 1H) 7.30-7.37 (m, 1H) 7.37-7.42 (m, 4H) 7.52-7.58 (m, 1H) 7.59-7.63 (m, 1H) 7.63-7.69 (m, 1H) 7.71-7.78 (m, 2H) 7.85 (dd, J = 8.22, 1.17 Hz, 1H) 7.99 (dd, J = 8.22, 1.17 Hz, 1H) 8.08 (d, J = 8.80 Hz, 1H) |

TABLE 19B-continued

PREPARATION AND NMR DATA OF EXAMPLES 29

| Ex. # | Starting material (1) and (2) | Reaction Condition | ¹H NMR (CD₃OD, 400 MHz) δ (ppm) |
|---|---|---|---|
| 29.2 | 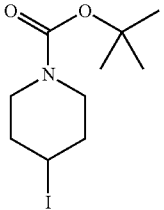 and 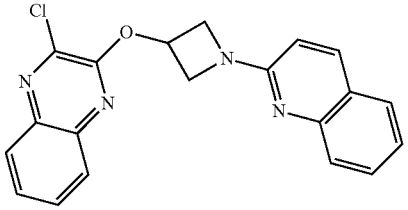 (see Preparation P2.8) | Zn, TMSCl, 1,2-dibromoethane, DMA; Pd(dppf)Cl$_2$, CuI, DMA, 80° C. | (DMSO-d$_6$) 1.42 (s, 9H) 1.62-1.76 (m, 2H) 1.90-1.98 (m, 2H) 2.93 (br. s., 2H) 3.38-3.47 (m, 1H) 4.09 (d, J = 11.54 Hz, 2H) 4.23 (dd, J = 9.98, 4.11 Hz, 2H) 4.66 (dd, J = 9.49, 6.75 Hz, 2H) 5.69-5.78 (m, 1H) 6.84 (d, J = 8.80 Hz, 1H) 7.20-7.28 (m, 1H) 7.50-7.57 (m, 1H) 7.58-7.62 (m, 1H) 7.62-7.68 (m, 1H) 7.70-7.77 (m, 2H) 7.84 (dd, J = 8.22, 0.98 Hz, 1H) 7.98 (dd, J = 8.22, 0.98 Hz, 1H) 8.07 (d, J = 8.80 Hz, 1H) |

The following examples nos. 30.1 to 30.29 can be prepared by those skilled in the art according to the above preparations and schemes by using commercially available starting materials.

TABLE 20

EXAMPLES 30.1-30.29

| Ex. # | Structure | Chemical Name |
|---|---|---|
| 30.1 | 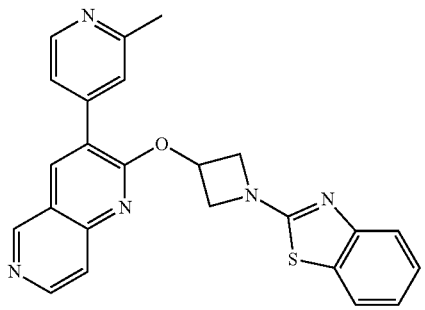 [SMILES: Cc1cc(-c2cc3cnccc3nc2OC2CN(c3nc4ccccc4s3)C2)ccn1] | 2-(3-((3-(2-methylpyridin-4-yl)-1,6-naphthyridin-2-yl)oxy)azetidin-1-yl)benzo[d]thiazole |
| 30.2 | 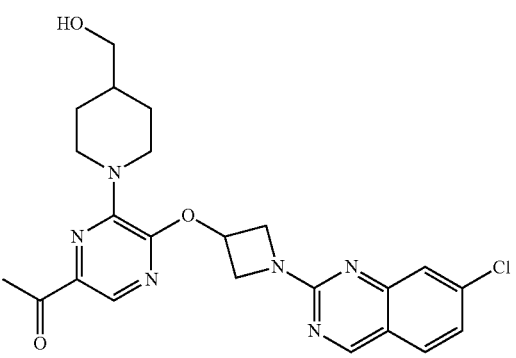 [SMILES: CC(=O)c1cnc(OC2CN(c3ncc4ccc(Cl)cc4n3)C2)c(N2CCC(CO)CC2)n1] | 1-(5-((1-(7-chloroquinazolin-2-yl)azetidin-3-yl)oxy)-6-(4-(hydroxymethyl)piperidin-1-yl)pyrazin-2-yl)ethanone |

TABLE 20-continued

EXAMPLES 30.1-30.29

| Ex. # | Structure | Chemical Name |
|---|---|---|
| 30.3 | 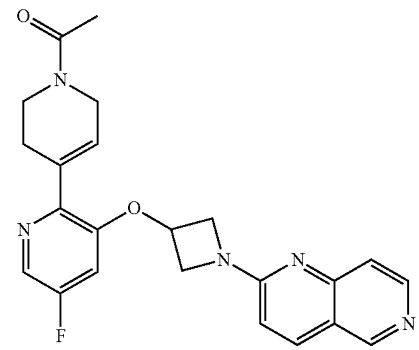 [SMILES: CC(=O)N1CC=C(c2ncc(F)cc2OC2CN(c3ccc4cnccc4n3)C2)CC1] | 1-(3-((1-(1,6-naphthyridin-2-yl)azetidin-3-yl)oxy)-5-fluoro-5',6'-dihydro-[2,4'-bipyridin]-1'(2'H)-yl)ethanone |
| 30.4 | 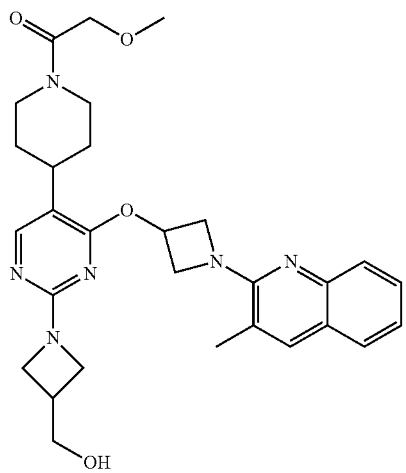 [SMILES: COCC(=O)N1CCC(c2cnc(N3CC(CO)C3)nc2OC2CN(c3nc4ccccc4cc3C)C2)CC1] | 1-(4-(2-(3-(hydroxymethyl)azetidin-1-yl)-4-((1-(3-methylquinolin-2-yl)azetidin-3-yl)oxy)pyrimidin-5-yl)piperidin-1-yl)-2-methoxyethanone |
| 30.5 | 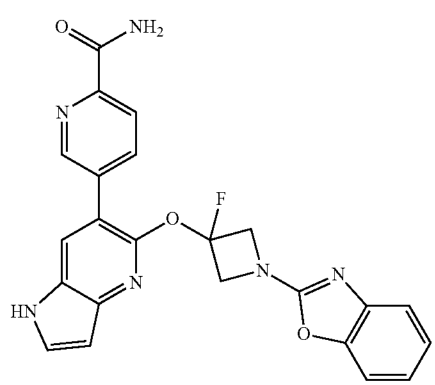 [SMILES: NC(=O)c1ccc(-c2cc3[nH]ccc3nc2OC2(F)CN(c3nc4ccccc4o3)C2)cn1] | 5-(5-((1-(benzo[d]oxazol-2-yl)-3-fluoroazetidin-3-yl)oxy)-1H-pyrrolo[3,2-b]pyridin-6-yl)picolinamide |
| 30.6 | 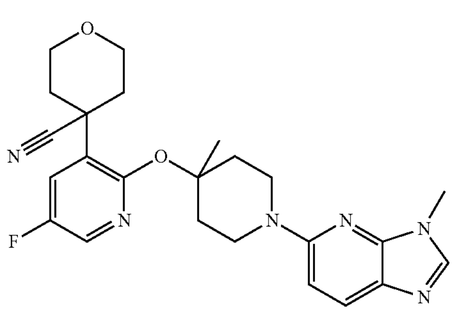 [SMILES: Cn1cnc2ccc(N3CCC(C)(Oc4ncc(F)cc4C4(C#N)CCOCC4)CC3)nc21] | 4-(5-fluoro-2-((4-methyl-1-(3-methyl-3H-imidazo[4,5-b]pyridin-5-yl)piperidin-4-yl)oxy)pyridin-3-yl)tetrahydro-2H-pyran-4-carbonitrile |

TABLE 20-continued

EXAMPLES 30.1-30.29

| Ex. # | Structure | Chemical Name |
|---|---|---|
| 30.7 | 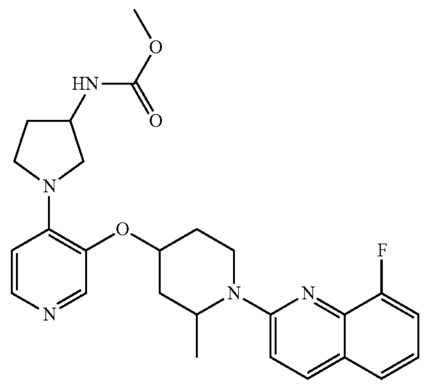 [SMILES: COC(=O)NC1CCN(c2ccncc2OC2CCN(c3ccc4cccc(F)c4n3)C(C)C2)C1] | methyl (1-(3-((1-(8-fluoroquinolin-2-yl)-2-methylpiperidin-4-yl)oxy)pyridin-4-yl)pyrrolidin-3-yl)carbamate |
| 30.8 | 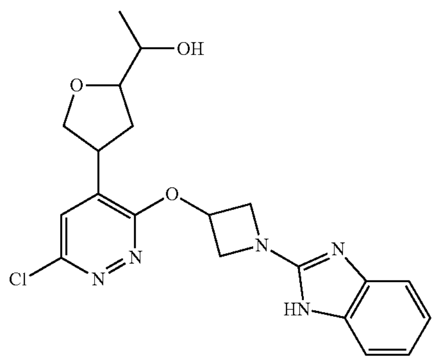 [SMILES: CC(O)C1CC(c2cc(Cl)nnc2OC2CN(c3nc4ccccc4[nH]3)C2)CO1] | 1-(4-(3-((1-(1H-benzo[d]imidazol-2-yl)azetidin-3-yl)oxy)-6-chloropyridazin-4-yl)tetrahydrofuran-2-yl)ethanol |
| 30.9 | 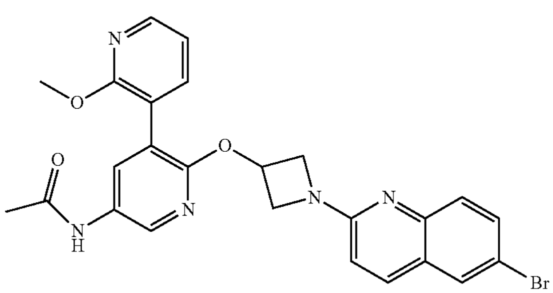 [SMILES: COc1ncccc1-c1cc(NC(C)=O)cnc1OC1CN(c2ccc3cc(Br)ccc3n2)C1] | N-(2-((1-(6-bromoquinolin-2-yl)azetidin-3-yl)oxy)-2'-methoxy-[3,3'-bipyridin]-5-yl)acetamide |
| 30.10 | 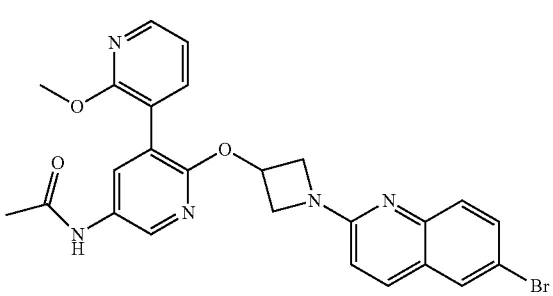 [SMILES: COc1ncccc1-c1cc(NC(C)=O)cnc1OC1CN(c2ccc3cc(Br)ccc3n2)C1] | 1-(3-(4-((1-(7,8-dihydro-6H-cyclopenta[g]quinolin-2-yl)azetidin-3-yl)oxy)-2-(4-(hydroxymethyl)piperidin-1-yl)pyrimidin-5-yl)-3-hydroxypyrrolidin-1-yl)ethanone |

TABLE 20-continued

EXAMPLES 30.1-30.29

| Ex. # | Structure | Chemical Name |
|---|---|---|
| 30.11 | 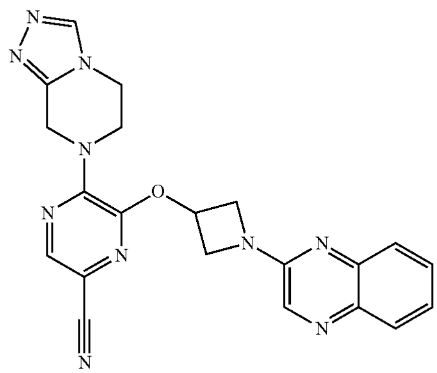 [SMILES: N#Cc1cnc(N2CCn3cnnc3C2)c(OC2CN(c3cnc4ccccc4n3)C2)n1] | 5-(5,6-dihydro-[1,2,4]triazolo[4,3-a]pyrazin-7(8H)-yl)-6-((1-(quinoxalin-2-yl)azetidin-3-yl)oxy)pyrazine-2-carbonitrile |
| 30.12 | 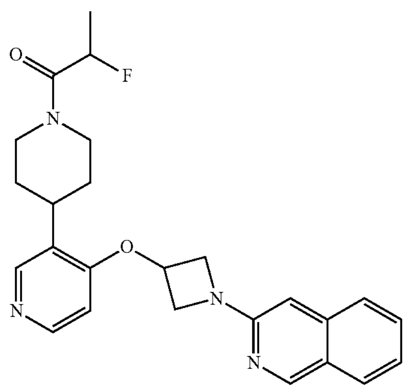 [SMILES: CC(F)C(=O)N1CCC(c2cnccc2OC2CN(c3cc4ccccc4cn3)C2)CC1] | 2-fluoro-1-(4-(4-((1-(isoquinolin-3-yl)azetidin-3-yl)oxy)pyridin-3-yl)piperidin-1-yl)propan-1-one |
| 30.13 | 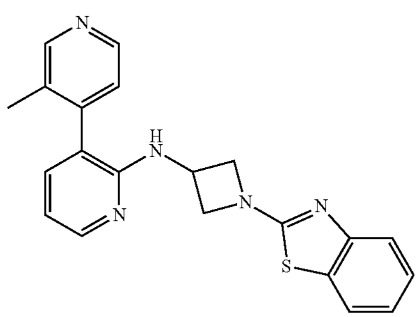 [SMILES: Cc1cnccc1-c1cccnc1NC1CN(c2nc3ccccc3s2)C1] | N-(1-(benzo[d]thiazol-2-yl)azetidin-3-yl)-3'-methyl-[3,4'-bipyridin]-2-amine |
| 30.14 | 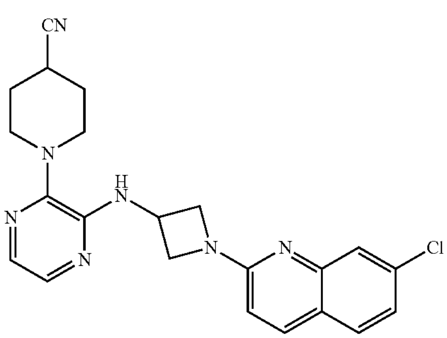 [SMILES: N#CC1CCN(c2nccnc2NC2CN(c3ccc4ccc(Cl)cc4n3)C2)CC1] | 1-(3-((1-(7-chloroquinolin-2-yl)azetidin-3-yl)amino)pyrazin-2-yl)piperidine-4-carbonitrile |

TABLE 20-continued

EXAMPLES 30.1-30.29

| Ex. # | Structure | Chemical Name |
|---|---|---|
| 30.15 | 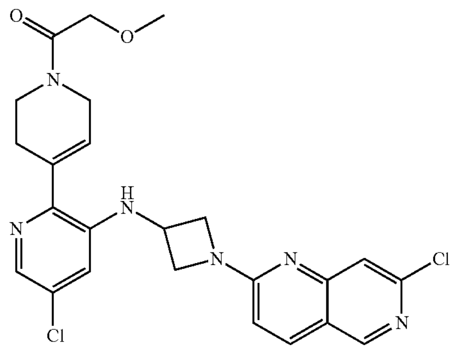 [SMILES: COCC(=O)N1CC=C(c2ncc(Cl)cc2NC2CN(c3ccc4cnc(Cl)cc4n3)C2)CC1] | 1-(5-chloro-3-((1-(7-chloro-1,6-naphthyridin-2-yl)azetidin-3-yl)amino)-5',6'-dihydro-[2,4'-bipyridin]-1'(2'H)-yl)-2-methoxyethanone |
| 30.16 | 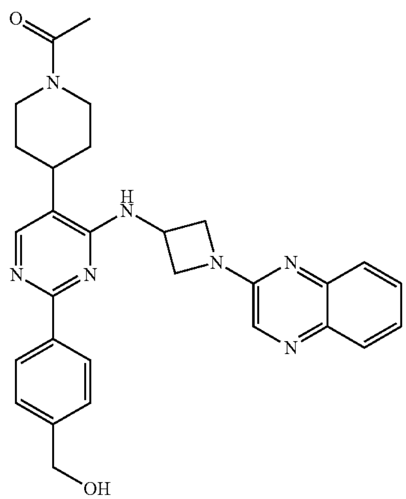 [SMILES: CC(=O)N1CCC(c2cnc(-c3ccc(CO)cc3)nc2NC2CN(c3cnc4ccccc4n3)C2)CC1] | 1-(4-(2-(4-(hydroxymethyl)phenyl)-4-((1-(quinoxalin-2-yl)azetidin-3-yl)amino)pyrimidin-5-yl)piperidin-1-yl)ethanone |
| 30.17 | 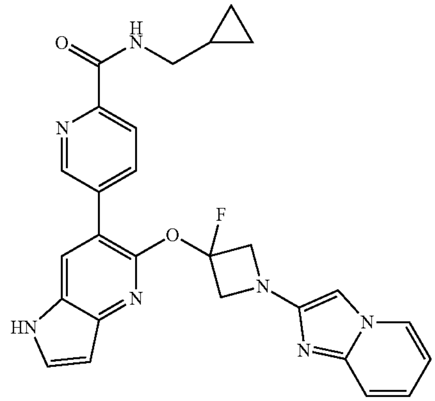 [SMILES: O=C(NCC1CC1)c1ccc(-c2cc3[nH]ccc3nc2OC2(F)CN(c3cn4ccccc4n3)C2)cn1] | N-(cyclopropylmethyl)-5-(5-((3-fluoro-1-(imidazo[1,2-a]pyridin-2-yl)azetidin-3-yl)oxy)-1H-pyrrolo[3,2-b]pyridin-6-yl)picolinamide |
| 30.18 | 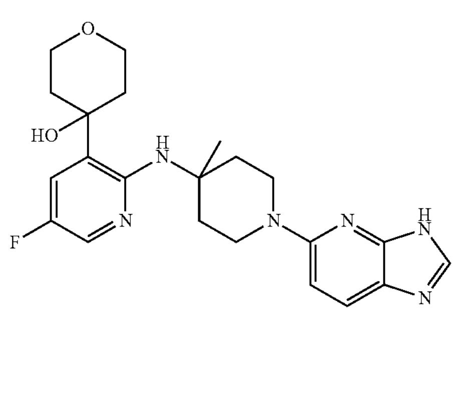 [SMILES: CC1(Nc2ncc(F)cc2C2(O)CCOCC2)CCN(c2ccc3nc[nH]c3n2)CC1] | 4-(2-((1-(3H-imidazo[4,5-b]pyridin-5-yl)-4-methylpiperidin-4-yl)amino)-5-fluoropyridin-3-yl)tetrahydro-2H-pyran-4-ol |

TABLE 20-continued

EXAMPLES 30.1-30.29

| Ex. # | Structure | Chemical Name |
|---|---|---|
| 30.19 | 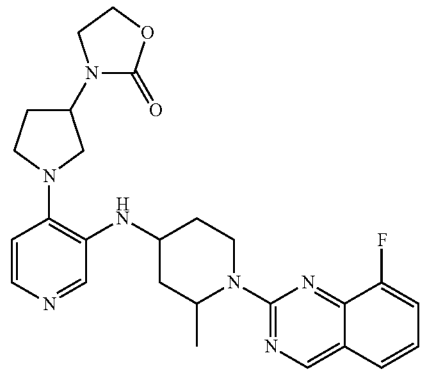 [SMILES: CC1CC(Nc2cnccc2N2CCC(N3CCOC3=O)C2)CCN1c1ncc2cccc(F)c2n1] | 3-(1-(3-((1-(8-fluoroquinazolin-2-yl)-2-methylpiperidin-4-yl)amino)pyridin-4-yl)pyrrolidin-3-yl)oxazolidin-2-one |
| 30.20 | 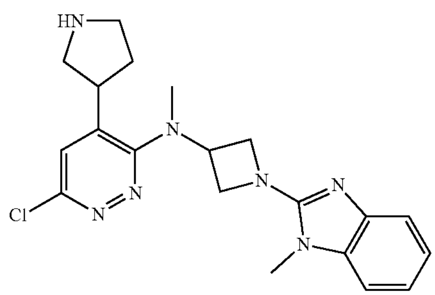 [SMILES: CN(c1nnc(Cl)cc1C1CCNC1)C1CN(c2nc3ccccc3n2C)C1] | 6-chloro-N-methyl-N-(1-(1-methyl-1H-benzo[d]imidazol-2-yl)azetidin-3-yl)-4-(pyrrolidin-3-yl)pyridazin-3-amine |
| 30.21 | 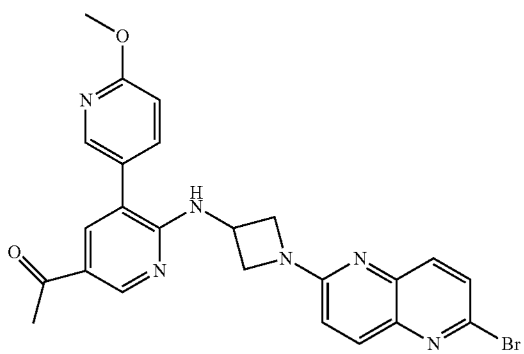 [SMILES: COc1ccc(-c2cc(C(C)=O)cnc2NC2CN(c3ccc4nc(Br)ccc4n3)C2)cn1] | 1-(2-((1-(6-bromo-1,5-naphthyridin-2-yl)azetidin-3-yl)amino)-6'-methoxy-[3,3'-bipyridin]-5-yl)ethanone |
| 30.22 | 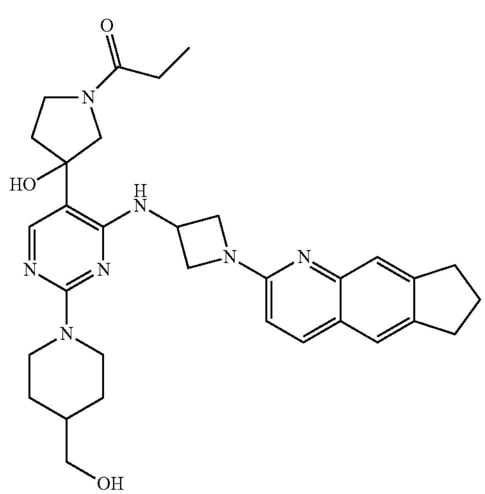 [SMILES: CCC(=O)N1CCC(O)(c2cnc(N3CCC(CO)CC3)nc2NC2CN(c3ccc4cc5c(cc4n3)CCC5)C2)C1] | 1-(3-(4-((1-(7,8-dihydro-6H-cyclopenta[g]quinolin-2-yl)azetidin-3-yl)amino)-2-(4-(hydroxymethyl)piperidin-1-yl)pyrimidin-5-yl)-3-hydroxypyrrolidin-1-yl)propan-1-one |

TABLE 20-continued

EXAMPLES 30.1-30.29

| Ex. # | Structure | Chemical Name |
|---|---|---|
| 30.23 | 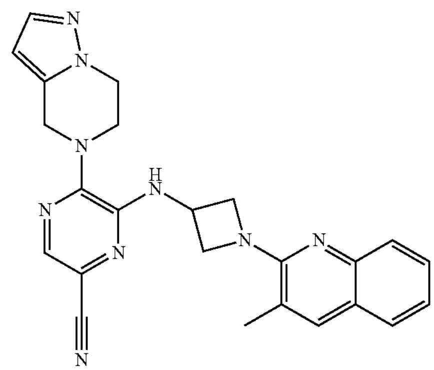 [SMILES: Cc1cc2ccccc2nc1N1CC(Nc2nc(C#N)cnc2N2CCn3nccc3C2)C1] | 5-(6,7-dihydropyrazolo[1,5-a]pyrazin-5(4H)-yl)-6-((1-(3-methylquinolin-2-yl)azetidin-3-yl)amino)pyrazine-2-carbonitrile |
| 30.24 | 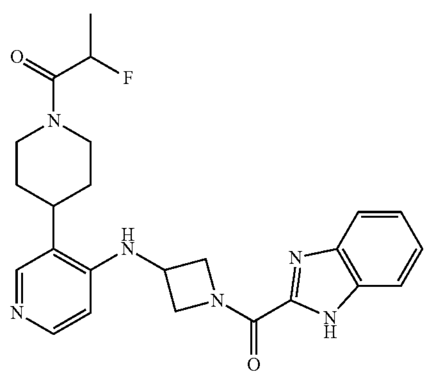 [SMILES: CC(F)C(=O)N1CCC(c2cnccc2NC2CN(C(=O)c3nc4ccccc4[nH]3)C2)CC1] | 1-(4-(4-((1-(1H-benzo[d]imidazole-2-carbonyl)azetidin-3-yl)amino)pyridin-3-yl)piperidin-1-yl)-2-fluoropropan-1-one |
| 30.25 | 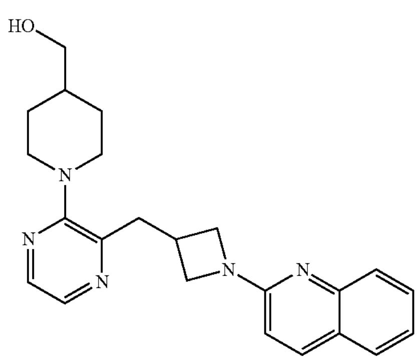 [SMILES: OCC1CCN(c2nccnc2CC2CN(c3ccc4ccccc4n3)C2)CC1] | (1-(3-((1-(quinolin-2-yl)azetidin-3-yl)methyl)pyrazin-2-yl)piperidin-4-yl)methanol |
| 30.26 | 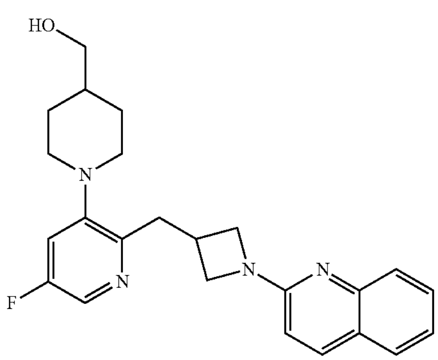 [SMILES: OCC1CCN(c2cc(F)cnc2CC2CN(c3ccc4ccccc4n3)C2)CC1] | (1-(5-fluoro-2-((1-(quinolin-2-yl)azetidin-3-yl)methyl)pyridin-3-yl)piperidin-4-yl)methanol |

TABLE 20-continued

EXAMPLES 30.1-30.29

| Ex. # | Structure | Chemical Name |
|---|---|---|
| 30.27 | 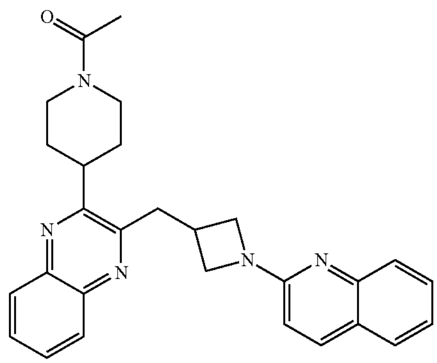 [SMILES: CC(=O)N1CCC(c2nc3ccccc3nc2CC2CN(c3ccc4ccccc4n3)C2)CC1] | 1-(4-(3-((1-(quinolin-2-yl)azetidin-3-yl)methyl)quinoxalin-2-yl)piperidin-1-yl)ethanone |
| 30.28 | 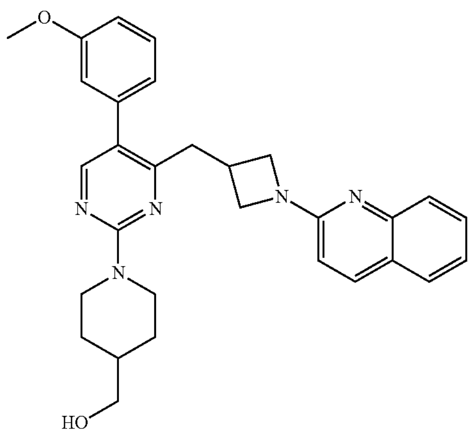 [SMILES: COc1cccc(-c2cnc(N3CCC(CO)CC3)nc2CC2CN(c3ccc4ccccc4n3)C2)c1] | (1-(5-(3-methoxyphenyl)-4-((1-(quinolin-2-yl)azetidin-3-yl)methyl)pyrimidin-2-yl)piperidin-4-yl)methanol |
| 30.29 | 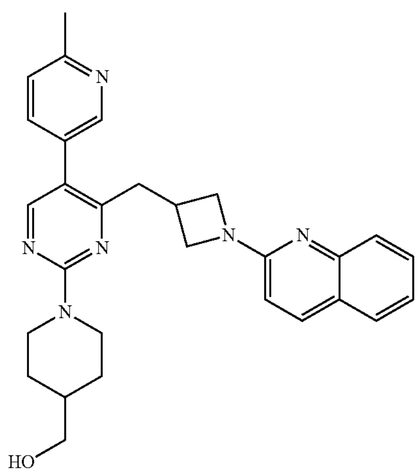 [SMILES: Cc1ccc(-c2cnc(N3CCC(CO)CC3)nc2CC2CN(c3ccc4ccccc4n3)C2)cn1] | (1-(5-(6-methylpyridin-3-yl)-4-((1-(quinolin-2-yl)azetidin-3-yl)methyl)pyrimidin-2-yl)piperidin-4-yl)methanol |

BIOLOGICAL EXAMPLES

Example A

MPDE10A7 Enzyme Activity and Inhibition

Enzyme Activity. An IMAP TR-FRET assay was used to analyze the enzyme activity (Molecular Devices Corp., Sunnyvale Calif.). 5 μL, of serial diluted PDE10A (BPS Bioscience, San Diego, Calif.) or tissue homogenate was incubated with equal volumes of diluted fluorescein labeled cAMP or cGMP for 60 min in 384-well polystyrene assay plates (Corning, Corning, N.Y.) at room temperature. After incubation, the reaction was stopped by adding 60 μL, of diluted binding reagents and was incubated for 3 hours to overnight at room temperature. The plates were read on an Envision (Perkin Elmer, Waltham, Mass.) for time resolved fluorescence resonance energy transfer. The data were analyzed with GraphPad Prism (La Jolla, Calif.).

Enzyme Inhibition. To check the inhibition profile, 5 μL of serial diluted compounds were incubated with 5 μL of diluted PDE10 enzyme (BPS Bioscience, San Diego, Calif.) or tissue homogenate in a 384-well polystyrene assay plate (Corning, Corning, N.Y.) for 30 min at room temperature. After incubation, 10 µL of diluted fluorescein labeled cAMP or cGMP substrate were added and incubated for 60 min at room temperature. The reaction was stopped by adding 60 µL of diluted binding reagents and plates were read on an Envision (Perkin Elmer, Waltham, Mass.) for time resolved fluorescence resonance energy transfer. The data were analyzed with GraphPad Prism (La Jolla, Calif.).

Example B

Apomorphine Induced Deficits in Prepulse Inhibition of the Startle Response in Rats, an In Vivo Test for Antipsychotic Activity The thought disorders that are characteristic of schizophrenia may result from an inability to filter, or gate, sensorimotor information. The ability to gate sensorimotor information can be tested in many animals as well as in humans. A test that is commonly used is the reversal of apomorphine-induced deficits in the prepulse inhibition of the startle response. The startle response is a reflex to a sudden intense stimulus such as a burst of noise. In this example, rats can be exposed to a sudden burst of noise, at a level of 120 db for 40 msec, e.g., the reflex activity of the rats can be measured. The reflex of the rats to the burst of noise may be attenuated by preceding the startle stimulus with a stimulus of lower intensity, at 3 db to 12 db above background (65 db), which attenuates the startle reflex by 20% to 80%.

The prepulse inhibition of the startle reflex, described above, may be attenuated by drugs that affect receptor signaling pathways in the CNS. One commonly used drug is the dopamine receptor agonist apomorphine. Administration of apomorphine reduces the inhibition of the startle reflex produced by the prepulse. Antipsychotic drugs such as haloperidol prevents apomorphine from reducing the prepulse inhibition of the startle reflex. This assay can be used to test the antipsychotic efficacy of PDE10 inhibitors, as they reduce the apomorphine-induced deficit in the prepulse inhibition of startle.

Example C

Conditioned Avoidance Responding (Car) in Rats, an In Vivo Test for Antipsychotic Activity Conditioned avoidance responding (CAR) occurs, for instance, when an animal learns that a tone and light predict the onset of a mild foot shock. The subject learns that when the tone and light are on, it must leave the chamber and enter a safe area. All known antipsychotic drugs reduce this avoidance response at doses which do not cause sedation. Examining the ability of test compounds to suppress the conditioned avoidance has been widely used for close to fifty years to screen for drugs with useful antipsychotic properties.

In this example, an animal can be placed in a two-chambered shuttle box and presented with a neutral conditioned stimulus (CS) consisting of a light and tone, followed by an aversive unconditioned stimulus (US) consisting of a mild foot shock through a floor grid in the shuttle box chamber. The animal can be free to escape the US by running from one chamber to the other, where the grid is not electrified. After several presentations of the CS-US pair, the animal typically learns to leave the chamber during the presentation of the CS and avoid the US altogether. Animals treated with clinically-relevant doses of antipsychotic drugs have a suppression of their rate of avoidances in the presence of the CS even though their escape response to the shock itself is unaffected.

Specifically, conditioned avoidance training can be conducted using a shuttle box (Med Associates, St. Albans, Vt.). The shuttle box is typically divided into 2 equal compartments that each contain a light source, a speaker that emits an 85 dB tone when activated and an electrified grid that can deliver a scrambled foot shock. Sessions can consist of 20 trials per day (intertrial interval of 25-40 sec) during which a 10 sec illumination and a concurrent 10 sec tone signals the subsequent delivery of a 0.5 mA shock applied for a maximum of 10 sec. Active avoidance, defined as the crossing into the opposite compartment during the 10 sec conditioning stimuli (light and tone) prevents the delivery of the shock. Crossing over to the other compartment after the delivery of the shock terminates shock delivery and may be recorded as an escape response. If an animal does not leave the conditioning chamber during the delivery of the shock it is recorded as an escape failure. Training can be continued daily until the avoidance of 16 or more shocks out of 20 trials (80% avoidance) on 2 consecutive days is achieved. After this criterion is reached the rats may be given one day of pharmacological testing. On test day, rats can be randomly assigned to experimental groups, weighed and injected intraperitoneally (i.p.) (1 cc tuberculin syringe, 26⅜ gauge needle) or per os (p.o.) (18 gauge feeding needle) with either control or compound solutions. Compounds can be injected at 1.0 ml/kg for i.p. and 10 mL/kg for p.o. administration. Compounds can be administered either acutely or chronically. For testing, each rat may be placed in the shuttle box, and given 20 trials with the same parameters as described above for training trials. The number of avoidances, escapes, and escape failures can be recorded.

Example D

PCP-Induced Hyperactivity (PCP-LMA)

Equipment Used: 4×8 home cage photobeam activity system (PAS) frame from San Diego Instruments. Open PAS program and prepare an experimental session using the following variables:
Multiphase Experiment
300 sec/interval (5 min)
12 intervals (1 h)
Individual on screen switches.
Start recording after first beam break.
End session after end of interval.
Cage Preparation:
Techniplast™ rat cage with filter top, but no wire lid. Place ~400 mL bedding and one food pellet in cage and place 250 mL techniplast water bottle in holder on filter top. Place the prepped cage in the PAS frame. Make sure bedding or pellet doesn't block the photobeams.
Animal Preparation:
Mark rats and record their weights. Bring rats to testing room.
Phase I: Habituation
Start the experiment session. Place the rat in the enclosure. The computer should start recording when it detects the rat breaking the beam. The computer will record for 1 h. During the habituation phase, prepare risperidone (positive control): Measure out risperidone, calculate final volume at 1 mg/mL concentration and add 1% glacial acetic acid of the final volume to dissolve risperidone. When risperidone is dissolved, add saline to final volume to make a concentration of 1 mg/mL. Fill syringes (3 mL syringes with 23 g½ needle or oral gavage needle) with Amgen compound solution (5 mL/kg) or risperidone (1 mL syringe with 23 g½ needle) control (1 mL/kg) s.c.

Phase II: Compound Pre-Treatment

Make sure Phase I has ended. Remove rat from enclosure, start the next phase using on-screen individual switch, administer compound p.o or i.p. and control s.c. and place rat back in the enclosure. The computer should start recording when it detects the rat breaking the beam. The computer will record for 1 h.

During phase II, prepare pcp: Dissolve pcp in saline to a concentration of 5 mg/mL.

Fill syringes (1 mL syringes with 26 g⅜ needle) with pcp solution (1 mL/kg).

Phase III: Pcp Administration.

Make sure phase II is ended. Remove rat from enclosure, start the next phase using on-screen individual switch, administer pcp s.c. and place rat back in the enclosure. The computer will record for 1 h.

Clean-Up:

End-session to terminate experiment and so that computer will compile data. Export raw data to excel file for data analysis. Euthanize rats and take necessary tissue/sample for PK.

Data Generation:

Export raw data to excel file for data analysis. Total time of movement is recorded as the number of photobeam breaks by the computer. Total time of movement (seconds) is combined into 5 minute bins and averaged for each treatment group for an N of 7-10 animals. Data are analyzed for statistical significance using a two-way ANOVA followed by a Bonferroni's post-hoc test for multiple comparisons.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

The compounds of the present invention may be administered orally, parentally, by inhalation spray, rectally, or topically in dosage unit formulations containing conventional pharmaceutically acceptable carriers, adjuvants, and vehicles, for the treatment of PDE10-related diseases, such as acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders. The term parenteral as used herein includes, subcutaneous, intravenous, intramuscular, intrasternal, infusion techniques or intraperitoneally.

Treatment of diseases and disorders herein is intended to also include the prophylactic administration of a compound of the invention, a pharmaceutical salt thereof, or a pharmaceutical composition of either to a subject (i.e., an animal, preferably a mammal, most preferably a human) believed to be in need of preventative treatment, such as, for example, pain, inflammation and the like.

The dosage regimen for treating PDE10-receptor-mediated diseases, cancer, and/or hyperglycemia with the compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, preferably from about 0.1 mg to 10 mg/kg, more preferably from about 0.25 mg to 1 mg/kg are useful for all methods of use disclosed herein.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

Injectable preparations, such as sterile injectable aqueous or oleaginous suspensions, may be formulated according to the known are using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

Formulations suitable for topical administration include liquid or semi-liquid preparations suitable for penetration through the skin (e.g., liniments, lotions, ointments, creams, or pastes) and drops suitable for administration to the eye, ear, or nose.

For administration, the compounds of this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulfuric acids, acacia, gelatin, sodium alginate, polyvinyl-pyrrolidine, and/or polyvinyl alcohol, and tableted or encapsulated for conventional administration. Alternatively, the compounds of this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

Compounds of the present invention can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using active starting materials. These isomers may be in the form of a free acid, a free base, an ester or a salt.

Likewise, the compounds of this invention may exist as isomers, that is compounds of the same molecular formula but in which the atoms, relative to one another, are arranged differently. In particular, the alkylene substituents of the compounds of this invention, are normally and preferably arranged and inserted into the molecules as indicated in the definitions for each of these groups, being read from left to right. However, in certain cases, one skilled in the art will appreciate that it is possible to prepare compounds of this invention in which these substituents are reversed in orientation relative to the other atoms in the molecule. That is, the substituent to be inserted may be the same as that noted above except that it is inserted into the molecule in the reverse orientation. One skilled in the art will appreciate that these isomeric forms of the compounds of this invention are to be construed as encompassed within the scope of the present invention.

The compounds of the present invention can be used in the form of salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methansulfonate, nicotinate, 2-naphthalenesulfonate, oxalate, palmoate, pectinate, persulfate, 2-phenylpropionate, picrate, pivalate, propionate, succinate, tartrate, thiocyanate, tosylate, mesylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to from pharmaceutically acceptable acid addition salts include such inorganic acids as hydrochloric acid, sulfuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

Also encompassed in the scope of the present invention are pharmaceutically acceptable esters of a carboxylic acid or hydroxyl containing group, including a metabolically labile ester or a prodrug form of a compound of this invention. A metabolically labile ester is one which may produce, for example, an increase in blood levels and prolong the efficacy of the corresponding non-esterified form of the compound. A prodrug form is one which is not in an active form of the molecule as administered but which becomes therapeutically active after some in vivo activity or biotransformation, such as metabolism, for example, enzymatic or hydrolytic cleavage. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl) Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use. Esters of a compound of this invention, may include, for example, the methyl, ethyl, propyl, and butyl esters, as well as other suitable esters formed between an acidic moiety and a hydroxyl containing moiety. Metabolically labile esters, may include, for example, methoxymethyl, ethoxymethyl, isopropoxymethyl, α-methoxyethyl, groups such as α-(($C_1$-$C_4$) alkyloxy)ethyl, for example, methoxyethyl, ethoxyethyl, propoxyethyl, iso-propoxyethyl, etc.; 2-oxo-1,3-dioxolen-4-ylmethyl groups, such as 5-methyl-2-oxo-1,3,dioxolen-4-ylmethyl, etc.; $C_1$-$C_3$ alkylthiomethyl groups, for example, methylthiomethyl, ethylthiomethyl, isopropylthiomethyl, etc.; acyloxymethyl groups, for example, pivaloyloxymethyl, α-acetoxymethyl, etc.; ethoxycarbonyl-1-methyl; or α-acyloxy-α-substituted methyl groups, for example α-acetoxyethyl.

Further, the compounds of the invention may exist as crystalline solids which can be crystallized from common solvents such as ethanol, N,N-dimethyl-formamide, water, or the like. Thus, crystalline forms of the compounds of the invention may exist as polymorphs, solvates and/or hydrates of the parent compounds or their pharmaceutically acceptable salts. All of such forms likewise are to be construed as falling within the scope of the invention.

While the compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

What is claimed is:
1. A compound of formula I:

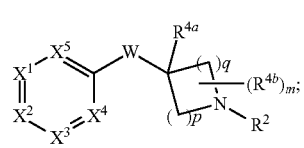

$X^1$ is N;
$X^2$ is $CR^6$;
$X^3$ is $CR^3$;
$X^4$ is N;
$X^5$ is $CR^6$;
2 of $X^1$, $X^2$, $X^3$, $X^4$ and $X^5$ are N;
the ring containing $X^1$, $X^2$, $X^3$, $X^4$, and $X^5$ can be fused to ring A, ring B, or ring C; each having the formula:

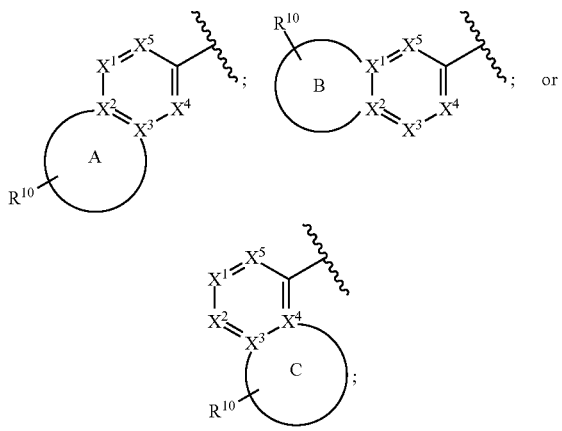

wherein each said ring A, ring B, or ring C is a fused 4- to 6-membered-saturated, -partially saturated, or -unsaturated-carbocyclic or -heterocyclic ring containing 0, 1, 2, or 3 heteroatoms; and is substituted by 0, 1, or 2 $R^{10}$ groups; which are oxo, $C_{1-6}$alkyl, $C_{1-3}$haloalkyl, —OH, —$OC_{1-4}$alkyl, —$NH_2$, —$NHC_{1-4}$alkyl, —OC(=O)$C_{1-4}$alkyl, or —N($C_{1-4}$alkyl,)$C_{1-4}$alkyl;
W is —O—; —NH—; —$NC_{1-6}$alkyl; —$CH_2$—; —CH($CH_3$)—; or C($CH_3$)$_2$—;
m is 0, 1, 2, 3, or 4;
each of p and q is independently 0, 1, 2, 3, 4, 5, or 6; wherein the sum of p and q is 2 to 6;
the ring containing p and q contains 0 or 1 double bond;
$R^1$ is —$OR^c$, —N($R^a$)C(=O)$R^b$, —C(=O)$R^a$, —C(=O)$R^c$, —C(=O)—O—$R^a$, —$NR^aR^c$, —N($R^c$)C(=O)$R^b$, —N($R^a$)C(=O)$R^c$, —C(=O)$NR^aR^b$, —C(=O)$NR^aR^c$, or $C_{0-4}$alkyl-$L^1$; wherein said $C_{1-8}$alkyl group is substituted by 0, 1, 2 or 3 groups which are halo, $C_{1-3}$haloalkyl, —OH, —$OC_{1-4}$alkyl, —$NH_2$, —$NHC_{1-4}$alkyl, —OC(=O)$C_{1-4}$alkyl, or —N($C_{1-4}$-alk)$C_{1-4}$alkyl;
$R^2$ is quinolinyl independently substituted by 0, 1, 2 or 3 $R^7$ groups which are independently F, Cl, Br, $C_{1-6}$alkyl, $C_{1-4}$-haloalkyl, —$OR^a$, —$OC_{1-4}$haloalkyl, CN, —C(=O)$R^b$, —C(=O)$OR^a$, —C(=O)$NR^aR^a$, —C(=$NR^a$)$NR^aR^a$, —OC(=O)$R^b$, —OC(=O) $NR^aR^a$, —$OC_{1-6}$alkyl$NR^aR^a$, —$OC_{1-6}$alkyl$OR^a$, —$SR^a$, —S(=O)$R^b$, —S(=O)$_2R^b$, —S(=O)$_2NR^aR^a$, —$NR^aR^a$, —$NR^aR^c$, —N($R^a$)C(=O)$R^b$, —N($R^a$)C (=O)OR$^b$, —N(R$^a$)C(=O)NR$^a$R$^a$, —N(R$^a$)C(=NR$^a$) NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{1-6}$alkylOR$^a$, —C$_{1-6}$alkylNR$^a$R$^a$, —C$_{1-6}$alkylOR$^a$, —C$_{1-6}$alkylN(R$^a$)C(=O)R$^b$, —C$_{1-6}$alkylOC(=O)R$^b$, —C$_{1-6}$alkylC(=O)NR$^a$R$^a$, —C$_{1-6}$alkylC(=O)OR$^a$, or oxo;

each of R$^3$ and R$^6$ is independently R$^1$, H, halo, CN, OH, OC$_{1-4}$alkyl, C$_{1-4}$-alkyl, or C$_{1-4}$haloalkyl; wherein 1 or 2 of R$^3$ and R$^6$ must be R$^1$;

R$^{4a}$ is H, C$_{1-4}$-alkyl, or C$_{1-4}$haloalkyl;

each R$^{4b}$ is independently F, Cl, Br, CN, OH, OC$_{1-4}$alkyl, C$_{1-4}$alkyl, or C$_{1-4}$haloalkyl;

R$^5$ is H, C$_{1-8}$alkyl, or C$_{0-8}$alkyl-L$^3$;

R$^a$ is independently H or R$^b$;

R$^b$ is independently phenyl, benzyl, or C$_{1-6}$alkyl, wherein said phenyl, benzyl, and C$_{1-6}$alkyl are being substituted by 0, 1, 2 or 3 substituents selected from halo, C$_{1-4}$alkyl, C$_{1-3}$haloalkyl, —OH, —OC$_{1-4}$alkyl, —NH$_2$, —NHC$_{1-4}$alkyl, —OC(=O)C$_{1-4}$alkyl, or —N(C$_{1-4}$alkyl)C$_{1-4}$alkyl;

R$^c$ is C$_{0-4}$alkyl-L$^4$; and each of L$^1$, L$^3$, and L$^4$ is independently a carbon-linked or nitrogen-linked saturated, partially-saturated or unsaturated 3-, 4-, 5-, 6-, or 7-membered monocyclic ring or a saturated, partially-saturated or unsaturated 8-, 9-, 10-, 11-, or 12-membered bicyclic ring; each said ring contains 0, 1, 2, 3, or 4 N atoms and 0, 1, or 2 atoms which are O or S; each L$^1$, L$^3$, and L$^4$ is independently substituted by 0, 1, 2 or 3 R$^7$ groups which are independently F, Cl, Br, C$_{1-6}$alkyl, C$_{1-4}$haloalkyl, —OR$^a$, —OC$_{1-4}$haloalkyl, CN, —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —OC$_{1-6}$alkylNR$^a$R$^a$, —OC$_{1-6}$alkylOR$^a$, —SR$^a$, —S(=O)R$^b$, —S(=O)$_2$R$^b$, —S(=O)$_2$NR$^a$R$^a$, —NR$^a$R$^a$, —NR$^a$R$^c$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{1-6}$alkylOR$^a$, —C$_{1-6}$alkylNR$^a$R$^a$, —C$_{1-6}$alkylOR$^a$, —C$_{1-6}$alkylN(R$^a$)C(=O)R$^b$, —C$_{1-6}$alkylOC(=O)R$^b$, —C$_{1-6}$alkylC(=O)NR$^a$R$^a$, —C$_{1-6}$alkylC(=O)OR$^a$, or oxo.

2. The compound as in claim 1, or a pharmaceutically acceptable salt thereof, wherein W is —O—.

3. The compound according to claim 1, or a pharmaceutically acceptable salt thereof, wherein R$^1$ is a saturated, partially-saturated or unsaturated 4-, 5-, 6-, or 7-membered monocyclic ring, wherein each said ring contains 0, 1, 2, or 3 N atoms and 0, 1, or 2 O atoms, and wherein each said ring is substituted by 0, 1, 2 or 3 R$^7$ groups which are independently F, Cl, Br, C$_{1-6}$alkyl, C$_{1-4}$haloalkyl, —OR$^a$, —OC$_{1-4}$haloalkyl, CN, —C(=O)R$^b$, —C(=O)OR$^a$, —C(=O)NR$^a$R$^a$, —NR$^a$R$^a$, —NR$^a$R$^c$, or —C$_{1-6}$alkylOR$^a$.

4. The compound according to claim 1, or a pharmaceutically acceptable salt thereof, wherein R$^1$ is a saturated, partially-saturated or unsaturated 5- or 6-membered monocyclic ring, wherein each said ring contains 0, 1, 2, or 3 N atoms and 0, 1, or 2 O atoms, and wherein each said ring is substituted by 0, 1, 2 or 3 R$^7$ groups which are independently F, Cl, Br, C$_{1-6}$alkyl, C$_{1-4}$haloalkyl, —OR$^a$, —OC$_{1-4}$haloalkyl, CN, —C(=O)R$^b$, —C(=O)OR$^a$, —C(=O)NR$^a$R$^a$, —NR$^a$R$^a$, —NR$^a$R$^c$, or —C$_{1-6}$alkylOR$^a$.

5. The compound according to claim 1, or a pharmaceutically acceptable salt thereof, wherein R$^1$ is azepanyl, phenyl, 2-pyridyl, 3-pyridyl, 4-pyridyl, morpholinyl, piperidinyl, piperazinyl, dihydropyranyl dihydropyridyl, tetrahydropyranyl, benzothiazolinyl, quinolinyl, or quinazolinyl; each R$^1$ is independently substituted by 0, 1, or 2 R$^7$ groups which are independently F, Cl, Br, methyl, methoxy, —CN, —C(=O)CH$_3$, —C(=O)OC(CH$_3$)$_3$, —C(=O)NH(CH$_3$), —C(=O)N(CH$_3$)$_2$, —NH$_2$, —CH$_2$OH, or —CH$_2$CH$_2$OH.

6. The compound according to claim 1, or a pharmaceutically acceptable salt thereof, wherein R$^3$ is R$^1$ or H.

7. The compound as in claim 1, or a pharmaceutically acceptable salt thereof, wherein the ring containing X$^1$, X$^2$, X$^3$, X$^4$, and X$^5$ is pyrazin, or quinoxalinyl.

8. The compound as in claim 1, or a pharmaceutically acceptable salt thereof, wherein the ring containing X$^1$, X$^2$, X$^3$, X$^4$, and X$^5$ is

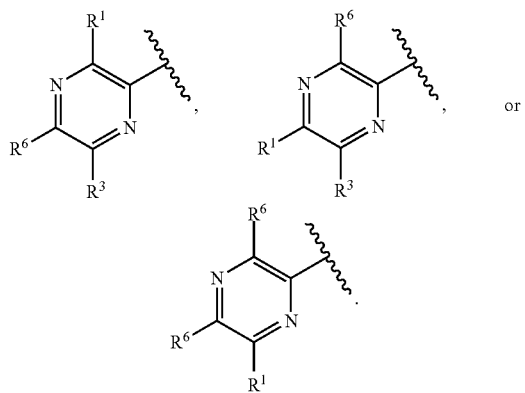

9. The compound according to claim 1, or a pharmaceutically acceptable salt thereof, wherein each of p and q is independently 1.

10. The compound according to claim 1, or a pharmaceutically acceptable salt thereof, wherein m is 0.

11. The compound according to claim 1, or a pharmaceutically acceptable salt thereof, wherein the group

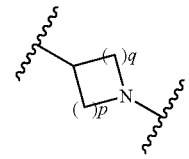

is azetidinyl, pyrrolidinyl, piperidinyl, or azepanyl.

12. The compound according to claim 1, or a pharmaceutically acceptable salt thereof, wherein R$^{4a}$ is H or C$_{1-4}$alkyl; and m is 0.

13. The compound according to claim 1, or a pharmaceutically acceptable salt thereof, wherein R$^2$ is

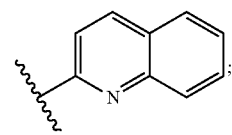

wherein each R$^2$ is substituted by 0, 1 or 2 R$^7$ groups.

14. The compound according to claim 1, or a pharmaceutically acceptable salt thereof, wherein W is —O—; R$^1$ is azepanyl, phenyl, 2-pyridyl, 3-pyridyl, 4-pyridyl, morpholinyl, piperidinyl, piperazinyl, dihydropyranyl dihydropyridyl, tetrahydropyranyl, benzothiazolinyl, quinolinyl, or quinazolinyl; each R$^1$ is independently substituted by 0, 1, or 2 R⁷ groups which are independently F, Cl, Br, methyl, methoxy, —CN, —C(=O)CH₃, —C(=O)OC(CH₃)₃, —C(=O)NH(CH₃), —C(=O)N(CH₃)₂, —NH₂, —CH₂OH, or —CH₂CH₂OH; R² is quinolinyl, or; each of p and q is independently 1 or 2; and R³ is R¹ or H.

15. A pharmaceutical composition comprising a compound according to claim 1, or a pharmaceutically acceptable salt thereof, and a pharmaceutically acceptable excipient.

16. The compound according to claim 1, or a pharmaceutically acceptable salt thereof, which is:

1-(4-(3-(1-(quinolin-2-yl)azetidin-3-yloxy)pyrazin-2yl)-5,6-dihydropyridin-1(2H)-yl)ethanone;
1-(4-(3-1-(quinolin-2-yl)azetidin-3yloxy)pyrazin-2-yl)piperidin-1-yl)ethanone;
2-(4-(3-(tetrahydro-2H-pyran-4-yl)pyrazin-2-yloxy)piperidin-1-yl)quinoline;
(R)-2-(3-(3-(tetrahydro-2H-pyran-4-yl)pyrazin-2-yloxy)pyrrolidin-1-yl)quinoline;
(S)-2-(3-(3-(tetrahydro-2H-pyran-4-yl)pyrazin-2-yloxy)pyrrolidin-1-yl)quinoline;
2-(4-((3-(2-methoxypyridin-3yl)pyrazin-2yl)oxy)piperidin-1-yl)quinoline;
2-(4-((3-(pyridin-3-yl)pyrazin-2yl)oxy)piperidin-1-yl)quinoline;
2-(4-((3-(pyridin-4-yl)pyrazin-2yl)oxy)piperidin-1-yl)quinoline;
1-(3-((1-(quinolin-2-yl)piperidin-4-yl)oxy)pyrazin-2-yl)piperidin-4-ol;
2-(4-((3-(4-methoxypiperidin-1-yl)pyrazin-2-yl)oxy)piperidin-1-yl)quinoline;
1-methyl-4-(3-((1-(quinolin-2-yl)azetidin-3-yl)oxy)pyrazin-2-yl)piperazin-2-one;
(1-(3-((1-(quinolin-2-yl)azetidin-3-yl)oxy)pyrazin-2-yl)piperidin-3-yl)methanol;
(1-(3-((1-(quinolin-2-yl)azetidin-3-yl)oxy)pyrazin-2-yl)piperidin-4-yl)methanol;
2-(1-(3-((1-(2-quinolinyl)-3-azetidinyl)oxy)-2-pyrazinyl)-4-piperidinyl)ethanol;
1-(3-((1-(quinolin-2-yl)azetidin-3-yl)oxy)pyrazin-2-yl)piperidine-4-carbonitrile;
((2S)-1-(3-((1-(2-quinolinyl)-3-azetidinyl)oxy)-2-pyrazinyl)-2-pyrrolidinyl)methanol;
1-(3-((1-(quinolin-2-yl)azetidin-3-yl)oxy)pyrazin-2-yl)pyrrolidin-3-ol;
2-(4-(3-((1-(2-quinolinyl)-3-azetidinyl)oxy)-2-pyrazinyl)-1-piperazinyl)ethanol;
2-(3-((3-(4-(1-pyrrolidinyl)-1-piperidinyl)-2-pyrazinyl)oxy)-1-azetidinyl)quinoline;
N,N-dimethyl-1-(3-((1-(2-quinolinyl)-3-azetidinyl)oxy)-2-pyrazinyl)-4-piperidinamine;
2-methyl-4-(3-((1-(quinolin-2-yl)azetidin-3-yl)oxy)pyrazin-2-yl)morpholine;
(4-(3-((1-(quinolin-2-yl)azetidin-3-yl)oxy)pyrazin-2-yl)morpholin-2-yl)methanol;
2-(3-((3-(4-(trifluoromethyl)piperidin-1-yl)pyrazin-2-yl)oxy)azetidin-1-yl)quinoline;
1-(3-((1-(2-quinolinyl)-3-azetidinyl)oxy)-2-pyrazinyl)-3-azetidinol;
quinolin-2-yl(4-((3-(tetrahydro-2H-pyran-4-yl)oxy)piperidin-1-yl)methanone;
(S)-1-(3-((1-(quinolin-2-yl)piperidin-4-yl)oxy)pyrazin-2-yl)pyrrolidin-3-ol;
(R)-1-(3-((1-(quinolin-2-yl)piperidin-4-yl)oxy)pyrazin-2-yl)pyrrolidin-3-ol;
2-{4-[3-(2-Methyl-pyridin-4-yl)-pyrazin-2-yloxy]-piperidin-1-yl}-quinoline;
2-(3-((3-(3,6-dihydro-2H-pyran-4-yl)pyrazin-2-yl)oxy)azetidin-1-yl)quinoline;
2-(3-((3-(5-benzyl-1-benzofuran-2-yl)-2-pyrazinyl)oxy)-1-azetidinyl)quinoline;
6-(3-((1-(2-quinolinyl)-3-azetidinyl)oxy)-2-pyrazinyl)-2-quinazolinamine;
2-(3-((3-(6-methoxy-3-pyridinyl)-2-pyrazinyl)oxy)-1-azetidinyl)quinoline;
2-(3-((3-(1,3-benzothiazol-5-yl)-2-pyrazinyl)oxy)-1-azetidinyl)quinoline;
2-(3-((3-(6-chloro-3-pyridinyl)-2-pyrazinyl)oxy)-1-azetidinyl)quinoline;
2-(3-((3-(3-bromophenyl)-2-pyrazinyl)oxy)-1-azetidinyl)quinoline;
(3-(3-((1-(2-quinolinyl)-3-azetidinyl)oxy)-2-pyrazinyl)phenyl)methanol;
(4-(3-((1-(2-quinolinyl)-3-azetidinyl)oxy)-2-pyrazinyl)phenyl)methanol;
2-(3-((3-(5-quinolinyl)-2-pyrazinyl)oxy)-1-azetidinyl)quinoline;
2-(3-((3-(5-phenyl-2-thiophenyl)-2-pyrazinyl)oxy)-1-azetidinyl)quinoline;
2-(3-((3-(3-pyridinyl)-2-pyrazinyl)oxy)-1-azetidinyl)quinoline;
2-(3-((3-(3-quinolinyl)-2-pyrazinyl)oxy)-1-azetidinyl)quinoline;
methyl 4-(3-((1-(2-quinolinyl)-3-azetidinyl)oxy)-2-pyrazinyl)benzoate;
2-(3-((3-(3-fluoro-5-(1-methylethoxy)phenyl)-2-pyrazinyl)oxy)-1-azetidinyl)quinoline;
2-(3-((3-(5-pyrimidinyl)-2-pyrazinyl)oxy)-1-azetidinyl)quinoline;
2-(3-((3-(2-methylpyridin-4-yl)pyrazin-2-yl)oxy)azetidin-1-yl)quinoline;
2-(3-((3-(2-methyl-4-pyridinyl)-2-pyrazinyl)oxy)-1-azetidinyl)quinoline;
2-(3-((3-(6-(cyclopropylmethoxy)-3-pyridinyl)-2-pyrazinyl)oxy)-1-azetidinyl)quinoline;
2-(3-((3-(6-methyl-3-pyridinyl)-2-pyrazinyl)oxy)-1-azetidinyl)quinoline;
2-(3-(3-((3-methyloxetan-3-yl)ethynyl)pyrazin-2-yloxy)azetidin-1-yl)quinoline;
4-(3-((1-(quinolin-2-yl)piperidin-4-yl)oxy)pyrazin-2-yl)morpholine;
2-(4-((3-(azetidin-1-yl)pyrazin-2-yl)oxy)piperidin-1-yl)quinoline;
4-methyl-2-(4-((3-(tetrahydro-2H-pyran-4-yl)pyrazin-2-yl)oxy)piperidin-1-yl)quinoline;
1-(4-(3-((1-(quinolin-2-yl)piperidin-4-yl)oxy)pyrazin-2-yl)piperazin-1-yl)ethanone;
2-(4-((3-(piperidin-1-yl)pyrazin-2-yl)oxy)piperidin-1-yl)quinoline;
2-(4-((3-(pyrrolidin-1-yl)pyrazin-2-yl)oxy)piperidin-1-yl)quinoline;
2-(4-((3-(3-methylpyridin-4-yl)pyrazin-2-yl)oxy)piperidin-1-yl)quinoline;
6-methyl-2-(4-((3-(tetrahydro-2H-pyran-4-yl)pyrazin-2-yl)oxy)piperidin-1-yl)quinoline;
1-(3-((1-(quinolin-2-yl)piperidin-4-yl)oxy)pyrazin-2-yl)azetidin-3-ol;
2-(4-((3-(3-chloropyridin-4-yl)pyrazin-2-yl)oxy)piperidin-1-yl)quinoline;
6-((1-(quinolin-2-yl)piperidin-4-yl)oxy)pyrazin-2-yl)-2-oxa-6-azaspiro[3.3]heptane;
(1-(3-((1-(quinolin-2-yl)piperidin-4-yl)oxy)pyrazin-2-yl)piperidin-4-yl)methanol;

1-(4-(3-((1-(quinolin-2-yl)azetidin-3-yl)oxy)pyrazin-2-yl)piperazin-1-yl)ethanone;
1-(3-((1-(quinolin-2-yl)azetidin-3-yl)oxy)pyrazin-2-yl)piperidin-4-ol;
2-(3-((3-(piperidin-1-yl)pyrazin-2-yl)oxy)azetidin-1-yl)quinoline;
4-(3-((1-(quinolin-2-yl)azetidin-3-yl)oxy)pyrazin-2-yl)morpholine;
7-methyl-2-(4-((3-(tetrahydro-2H-pyran-4-yl)pyrazin-2-yl)oxy)piperidin-1-yl)quinoline;
8-methyl-2-(4-((3-(tetrahydro-2H-pyran-4-yl)pyrazin-2-yl)oxy)piperidin-1-yl)quinoline;
(4-((3-morpholinopyrazin-2-yl)oxy)piperidin-1-yl)(quinolin-2-yl)methanone;
(4-((3-(2-methylpyridin-4-yl)pyrazin-2-yl)oxy)piperidin-1-yl)(quinolin-2-yl)methanone;
1-(6-(3-((1-(quinolin-2-yl)piperidin-4-yl)oxy)pyrazin-2-yl)-2,6-diazaspiro[3.3]heptan-2-yl)ethanone;
1-(3-((1-(quinolin-2-yl)piperidin-4-yl)oxy)pyrazin-2-yl)piperidin-4-one;
1-(3-((1-(quinolin-2-yl)azetidin-3-yl)oxy)pyrazin-2-yl)piperidin-4-one;
2-(3-((3-(p-tolyl)pyrazin-2-yl)oxy)azetidin-1-yl)quinoline;
2-(1-(3-((1-(quinolin-2-yl)piperidin-4-yl)oxy)pyrazin-2-yl)piperidin-4-yl)propan-2-ol;
2-(1-(3-((1-(quinolin-2-yl)azetidin-3-yl)oxy)pyrazin-2-yl)piperidin-4-yl)propan-2-ol;
2-(3-((3-(4-(methoxymethyl)piperidin-1-yl)pyrazin-2-yl)oxy)azetidin-1-yl)quinoline;
2-(3-((3-(4,4-difluoropiperidin-1-yl)pyrazin-2-yl)oxy)azetidin-1-yl)quinoline;
2-(3-((3-(2-methoxypyridin-3-yl)pyrazin-2-yl)oxy)azetidin-1-yl)quinoline;
2-(3-((3-(o-tolyl)pyrazin-2-yl)oxy)azetidin-1-yl)quinoline;
2-(3-((3-(2-methoxyphenyl)pyrazin-2-yl)oxy)azetidin-1-yl)quinoline;
2-(4-(3-(4-(methoxymethyl)piperidin-1-yl)pyrazin-2-yl)oxy)piperidin-1-yl)quinoline;
2-(3-((3-(pyridin-4-yl)pyrazin-2-yl)oxy)azetidin-1-yl)quinoline;
2-(3-((3-(4-fluoro-2-methylphenyl)pyrazin-2-yl)oxy)azetidin-1-yl)quinoline;
2-(3-((3-phenylpyrazin-2-yl)oxy)azetidin-1-yl)quinoline;
2-(3-((3-(3-chloropyridin-4-yl)pyrazin-2-yl)oxy)azetidin-1-yl)quinoline;
2-(3-((1-(quinolin-2-yl)azetidin-3-yl)oxy)pyrazin-2-yl)benzonitrile;
2-(3-((3-(m-tolyl)pyrazin-2-yl)oxy)azetidin-1-yl)quinoline;
4-(3-((1-(quinolin-2-yl)azetidin-3-yl)oxy)pyrazin-2-yl)benzonitrile;
2-(3-((3-(3-methylpyridin-4-yl)pyrazin-2-yl)oxy)azetidin-1-yl)quinoline;
2-(3-((3-(pyridin-2-yl)pyrazin-2-yl)oxy)azetidin-1-yl)quinoline;
2-(3-((3-(2-fluoropyridin-4-yl)pyrazin-2-yl)oxy)azetidin-1-yl)quinoline;
3-(3-((1-(quinolin-2-yl)azetidin-3-yl)oxy)pyrazin-2-yl)benzonitrile;
N,N-dimethyl-4-(3-((1-(quinolin-2-yl)azetidin-3-yl)oxy)pyrazin-2-yl)benzamide;
2-(3-((3-(4-methylpiperidin-1-yl)pyrazin-2-yl)oxy)azetidin-1-yl)quinoline;
2-(3-((3-(5,6-dihydropyridin-1(2H)-yl)pyrazin-2-yl)oxy)azetidin-1-yl)quinoline;
7-(3-((1-(quinolin-2-yl)azetidin-3-yl)oxy)pyrazin-2-yl)-2-oxa-7-azaspiro[3.5]nonane;
2-methoxy-1-(4-(3-((1-(quinolin-2-yl)azetidin-3-yl)oxy)pyrazin-2-yl)piperidin-1-yl)ethanone;
2-(3-((3-(2-azabicyclo[2.2.1]heptan-2-yl)pyrazin-2-yl)oxy)azetidin-1-yl)quinoline;
2-(3-((3-(3,3-difluoropyrrolidin-1-yl)pyrazin-2-yl)oxy)azetidin-1-yl)quinoline;
2-(3-((3-(azetidin-1-yl)pyrazin-2-yl)oxy)azetidin-1-yl)quinoline;
2-(3-((3-(azepan-1-yl)pyrazin-2-yl)oxy)azetidin-1-yl)quinoline;
2-(3-((3-(pyrrolidin-1-yl)pyrazin-2-yl)oxy)azetidin-1-yl)quinoline;
(R)-(1-(3-((1-(quinolin-2-yl)azetidin-3-yl)oxy)pyrazin-2-yl)pyrrolidin-2-yl)methanol;
2-(3-((3-(3,3-difluoropiperidin-1-yl)pyrazin-2-yl)oxy)azetidin-1-yl)quinoline;
1-(3-(3-((1-(quinolin-2-yl)azetidin-3-yl)oxy)pyrazin-2-yl)phenyl)ethanone;
(S)-(1-(3-((1-(quinolin-2-yl)pyrrolidin-3-yl)oxy)pyrazin-2-yl)piperidin-4-yl)methanol;
(R)-(1-(3-((1-(quinolin-2-yl)pyrrolidin-3-yl)oxy)pyrazin-2-yl)piperidin-4-yl)methanol;
1-(4-(3-((1-(quinolin-2-yl)azetidin-3-yl)oxy)pyrazin-2-yl)phenyl)ethanone;
N,N-dimethyl-3-(3-((1-(quinolin-2-yl)azetidin-3-yl)oxy)pyrazin-2-yl)benzamide;
2-(3-((3-(1-(methylsulfonyl)piperidin-4-yl)pyrazin-2-yl)oxy)azetidin-1-yl)quinoline;
methyl 4-(3-((1-(quinolin-2-yl)azetidin-3-yl)oxy)pyrazin-2-yl)piperidine-1-carboxylate;
1-(3-(3-((1-(quinolin-2-yl)azetidin-3-yl)oxy)pyrazin-2-yl)phenyl)ethanol;
4-(3-((1-(quinolin-2-yl)azetidin-3-yl)oxy)pyrazin-2-yl)-1,4-oxazepane;
(1-(3-((1-(quinolin-2-yl)azetidin-3-yl)oxy)pyrazin-2-yl)pyrrolidin-3-yl)methanol;
2-(3-((3-(3-(methoxymethyl)phenyl)pyrazin-2-yl)oxy)azetidin-1-yl)quinoline;
N-methyl-4-(3-((1-(quinolin-2-yl)azetidin-3-yl)oxy)pyrazin-2-yl)benzamide;
(S)-(1-(3-((1-(quinolin-2-yl)piperidin-3-yl)oxy)pyrazin-2-yl)piperidin-4-yl)methanol;
(R)-(1-(3-((1-(quinolin-2-yl)piperidin-3-yl)oxy)pyrazin-2-yl)piperidin-4-yl)methanol;
2-(3-((3-(4-methyl-1,4-diazepan-1-yl)pyrazin-2-yl)oxy)azetidin-1-yl)quinoline;
1-(4-(3-((1-(quinolin-2-yl)azetidin-3-yl)oxy)pyrazin-2-yl)-1,4-diazepan-1-yl)ethanone;
1-(4-(3-((1-(quinolin-2-yl)azetidin-3-yl)oxy)pyrazin-2-yl)phenyl)ethanol;
(S)-2-(3-((3-(2-methylpyridin-4-yl)pyrazin-2-yl)oxy)piperidin-1-yl)quinoline;
(R)-2-(3-((3-(2-methylpyridin-4-yl)pyrazin-2-yl)oxy)piperidin-1-yl)quinoline-;
2-(3-((3-chloropyrazin-2-yl)oxy)azetidin-1-yl)quinoline;
2-(3-((3-chloropyrazin-2-yl)oxy)piperidin-1-yl)quinoline;
1-(3-((1-(quinolin-2-yl)azetidin-3-yl)oxy)pyrazin-2-yl)azepan-4-ol;
(R)-2-(3-((3-(2-methylpyridin-4-yl)pyrazin-2-yl)oxy)pyrrolidin-1-yl)quinoline;
(S)-2-(3-((3-(2-methylpyridin-4-yl)pyrazin-2-yl)oxy)pyrrolidin-1-yl)quinoline;
4-(3-((1-(quinolin-2-yl)azetidin-3-yl)oxy)pyrazin-2-yl)but-3-yn-2-ol;

2-(3-((3-(3-methoxyprop-1-yn-1-yl)pyrazin-2-yl)oxy) azetidin-1-yl)quinoline;

3-(3-((1-(quinolin-2-yl)azetidin-3-yl)oxy)pyrazin-2-yl) prop-2-yn-1-ol;

(1-(6-((1-(quinolin-2-yl)azetidin-3-yl)oxy)pyrazin-2-yl) piperidin-4-yl)methanol;

(1-(3-((1-(quinolin-2-yl)azetidin-3-yl)amino)pyrazin-2-yl)piperidin-4-yl)methanol;

5-(3-((1-(quinolin-2-yl)azetidin-3-yl)oxy)pyrazin-2-yl) picolinonitrile;

1-(3-((1-(quinolin-2-yl)azetidin-3-yl)oxy)pyrazin-2-yl) piperidine-4-carboxamide;

1-(1-(3-((1-(quinolin-2-yl)azetidin-3-yl)oxy)pyrazin-2-yl)piperidin-4-yl)ethanol;

2-(3-((3-(4-methylpiperazin-1-yl)pyrazin-2-yl)oxy)azetidin-1-yl)quinoline;

2-(3-((3-(6-fluoropyridin-3-yl)pyrazin-2-yl)oxy)azetidin-1-yl)quinoline;

2-(3-((3-(2-methylpyridin-3-yl)pyrazin-2-yl)oxy)azetidin-1-yl)quinoline;

2-(3-((3-(3-methoxyphenyl)pyrazin-2-yl)oxy)azetidin-1-yl)quinoline; or 2-(3-((3-(4-methylpyridin-3-yl)pyrazin-2-yl)oxy)azetidin-1-yl)quinoline.

* * * * *